(12) United States Patent
Kelner

(10) Patent No.: US 12,280,021 B2
(45) Date of Patent: Apr. 22, 2025

(54) AFFINITY MEDICANT CONJUGATE

(71) Applicant: Califia Pharma Inc., San Diego, CA (US)

(72) Inventor: Michael Kelner, La Jolla, CA (US)

(73) Assignee: AF CHEMICALS, LLC, San Diego, CA (US)

( * ) Notice: Subject to any disclaimer, the term of this patent is extended or adjusted under 35 U.S.C. 154(b) by 0 days.

(21) Appl. No.: 18/365,920

(22) Filed: Aug. 4, 2023

(65) Prior Publication Data

US 2023/0372267 A1 Nov. 23, 2023

Related U.S. Application Data

(60) Continuation of application No. 17/576,767, filed on Jan. 14, 2022, now abandoned, which is a continuation of application No. 17/482,242, filed on Sep. 22, 2021, now Pat. No. 11,241,398, which is a division of application No. 17/035,529, filed on Sep. 28, 2020, now Pat. No. 11,135,182, which is a continuation-in-part of application No. 15/986,727, filed on May 22, 2018, now Pat. No. 10,806,708, which is a continuation of application No. 15/201,301, filed on Jul. 1, 2016, now Pat. No. 9,980,926, which is a continuation of application No. 14/684,218, filed on Apr. 10, 2015, now Pat. No. 9,381,178.

(60) Provisional application No. 61/978,195, filed on Apr. 10, 2014.

(51) Int. Cl.
| | | |
|---|---|---|
| *A61K 31/122* | (2006.01) | |
| *A61K 31/19* | (2006.01) | |
| *A61K 47/54* | (2017.01) | |
| *A61K 47/55* | (2017.01) | |
| *A61K 47/58* | (2017.01) | |
| *A61K 47/59* | (2017.01) | |
| *A61K 47/62* | (2017.01) | |
| *A61K 47/64* | (2017.01) | |
| *A61K 47/65* | (2017.01) | |
| *A61K 47/68* | (2017.01) | |

(52) U.S. Cl.
CPC ............ *A61K 31/122* (2013.01); *A61K 31/19* (2013.01); *A61K 47/55* (2017.08); *A61K 47/551* (2017.08); *A61K 47/554* (2017.08); *A61K 47/58* (2017.08); *A61K 47/59* (2017.08); *A61K 47/593* (2017.08); *A61K 47/62* (2017.08); *A61K 47/64* (2017.08); *A61K 47/6415* (2017.08); *A61K 47/642* (2017.08); *A61K 47/65* (2017.08); *A61K 47/68* (2017.08); *A61K 47/6803* (2017.08); *A61K 47/6889* (2017.08)

(58) Field of Classification Search
CPC ........ A61K 47/55; A61K 47/58; A61K 47/59; A61K 47/62; A61K 47/6803
See application file for complete search history.

(56) References Cited

U.S. PATENT DOCUMENTS

| | | |
|---|---|---|
| 3,230,201 A | 1/1966 | Hart |
| 5,439,936 A | 8/1995 | Kelner |
| 5,439,942 A | 8/1995 | Kelner |
| 5,523,490 A | 6/1996 | Kelner |
| 5,563,176 A | 10/1996 | Kelner |
| 5,723,632 A | 3/1998 | McMorris |
| 5,932,553 A | 8/1999 | McMorris |
| 6,025,328 A | 2/2000 | McMorris |
| 6,069,283 A | 5/2000 | McMorris |
| 6,160,184 A | 12/2000 | McMorris |
| 6,252,093 B1 | 6/2001 | McMorris |
| 6,323,181 B1 | 11/2001 | McMorris |
| 6,380,403 B1 | 4/2002 | McMorris |
| 6,469,184 B2 | 10/2002 | McMorris |
| 6,548,679 B1 | 4/2003 | McMorris |
| 6,639,105 B2 | 10/2003 | McMorris |
| 6,717,017 B2 | 4/2004 | McMorris |
| 6,855,696 B2 | 2/2005 | McMorris |
| 6,908,918 B2 | 6/2005 | McMorris |
| 6,987,193 B2 | 1/2006 | McMorris |
| 7,141,603 B2 | 11/2006 | McMorris |

(Continued)

FOREIGN PATENT DOCUMENTS

| | | |
|---|---|---|
| WO | PCT/US2005/017804 | 12/2005 |
| WO | PCT/US2015/025208 | 10/2015 |

(Continued)

OTHER PUBLICATIONS

A. Annamalai et al., Reaction of the Adenine Nucleotide Analogue W-p-Fluorosulfonylbenzoyl Adenosine at Distinct Tyrosine and Cysteine Residues of Rabbit Muscle Pyruvate Kinase, J. Biol. Chem., 256, 10276-10283, 1981.

(Continued)

*Primary Examiner* — Pancham Bakshi
(74) *Attorney, Agent, or Firm* — SCI-LAW STRATEGIES, PC

(57) ABSTRACT

In an embodiment of the invention, a composition for treating a cell population comprises an Affinity Medicant Conjugate (AMC). The medicant moiety can be a toxin including an acylfulvene or a drug moiety. The affinity moiety can be an antibody, a binding protein, a steroid, a lipid, a growth factor, a protein, a peptide or non peptidic. The affinity moiety can be covalently bound to the medicant via a linker. Novel linkers that can be directed to cysteine, arginine or lysine residues based on solution pH allow greater flexibility in preserving and/or generating specific epitopes in the AMC.

20 Claims, 26 Drawing Sheets

Specification includes a Sequence Listing.

(56) References Cited

U.S. PATENT DOCUMENTS

| | | | |
|---|---|---|---|
| 7,329,759 B2 | 2/2008 | McMorris | |
| 7,629,380 B2 | 12/2009 | McMorris | |
| 7,655,695 B2 | 2/2010 | McMorris | |
| 7,713,939 B2 | 5/2010 | McMorris | |
| 7,855,275 B2 | 12/2010 | Eigenbrot | |
| 8,937,161 B2 | 1/2015 | Mao | |
| 9,381,178 B2* | 7/2016 | Kelner | A61K 47/64 |
| 9,725,769 B1 | 8/2017 | Knudsen | |
| 9,980,926 B1* | 5/2018 | Kelner | C07C 247/18 |
| 10,285,955 B2 | 5/2019 | Kelner | |
| 10,806,708 B2* | 10/2020 | Kelner | A61P 5/26 |
| 11,135,182 B2* | 10/2021 | Kelner | A61K 47/68 |
| 11,160,807 B1 | 11/2021 | Kelner | |
| 11,241,398 B2* | 2/2022 | Kelner | A61K 31/19 |
| 11,591,295 B2 | 2/2023 | Kelner | |
| 2005/0250675 A1 | 11/2005 | McMorris | |
| 2007/0072790 A1* | 3/2007 | McMorris | C07K 5/0812 514/23 |
| 2007/0092940 A1 | 4/2007 | Eigenbrot | |
| 2008/0306147 A1 | 12/2008 | McMorris | |
| 2011/0033378 A1 | 2/2011 | Dimasi | |
| 2018/0100197 A1 | 4/2018 | Knudsen | |
| 2019/0231795 A1 | 8/2019 | Knudsen | |
| 2020/0340067 A1 | 10/2020 | Knudsen | |
| 2021/0155583 A1 | 5/2021 | Kelner | |
| 2021/0198191 A1 | 7/2021 | Tobin | |
| 2021/0222252 A1 | 7/2021 | Knudsen | |
| 2021/0230662 A1 | 7/2021 | Kulkarni | |
| 2022/0226454 A1 | 7/2022 | Nara | |

FOREIGN PATENT DOCUMENTS

| | | |
|---|---|---|
| WO | PCT/US2019/056039 | 4/2020 |
| WO | PCT/US2021/072496 | 5/2022 |
| WO | PCT/US2021/070126 | 7/2022 |

OTHER PUBLICATIONS

E. Brandsteterova, M.J. Kelner, T.C. McMorris, W. Wang, and R. Bagnell. HPLC analysis of novel anticancer agents Illudins and analogs. *J. Liquid Chromatography*. 16:115-126, 1993.

E. Brandsteterova, M.J. Kelner, T.C. McMorris, L. Estes, R. Bagnell, and M. Montoya.HPLC determination of a new anticancer agent (acylfulvene).in serum. *Neoplasma* 39:369-373, 1992.

R.F. Colman, Affinity Labelling of Purine Nucleotide Sites in proteins, 52, 67-91, 1983.

SR Demeade et al., Prostate-Specific Antigen-Activated Thapsigargin Prodrug as Targeted Therapy for Prostate Cancer, JNCI 95, 990, 2003.

R.P.M. Dings, et al., Chapter 18: Non-peptidic mimietics as cancer-sensitizing agents. In: Sensitization of cancer cells for Chemo/Immuno/Radiotherapy, 305-325.Editor Benjamin Bonavida, Human Press, 2008.

R.P. M. Dings, et al., Inhibiting Tumor Growth by Targeting Tumor Vasculature with Galectin-1 Antagonist Anginex Conjugated to the Cytotoxic Acylfulvene, 6-Hydroxylpropylacylfulvene. Bioconjugate Chemistry 21:20-27, 2010.

R.P. M. Dings, et al., Ovarian tumor growth regression using a combination of vascular targeting agents anginex or topomimetic 0118 and the chemotherapeutic irofulven. Cancer Letters 265: 270-280, 2008.

K.E. Dombrowski, et al., 5'-p-(Fluorosulfonyl)benzoyl-8-azidoadenosine: A New Bifunctional Affinity Label for Nucleotide Binding Sites in Proteins, Arch. Biochem. Biophys. 275, 302-308, 1989.

F.S. Esch et al., A procedure for the synthesis of p-Fluorosulfonyl[14C]benzoyl-5'-Adenosine with [14C] in the benzoyl moiety, Anal Biochem., 84, 642-645, 1978.

F.S. Esch et al., Identification of a tyrosine residue at a nucleotide binding site in the B subunit of the mitochondrial ATPase with p-Fluorosulfonyl[14C]benzoyl-5'-Adenosine, J. Biol. Chem., 253, 6100-6106, 1978.

VM Garsky, The Synthesis of a Prodrug of Doxorubicin Designed to Provide Reduced Systemic Toxicity and Greater Target Efficacy, J. Med. Chem. 44, 4216-4224, 2001.

M. Jaffe et al., Use of 5'-[p-Fluorosulfonylbenzoyl] guanosine as an affinity probe for the Guanine Nucleotide Binding Site of Transducin, The Prot. Journal, 26, 125-133, 2007.

N.G.J. Jaspers, et al., Anti-tumor compounds illudin S and Irofulven induce DNA lesions ignored by global repair and exclusively processed by transcription- and replication-coupled repair pathways. *DNA Repair* 1:1027-1038, 2002.

M.J. Kelner, et al., Preclinical evaluations of Illudins as anticancer agents. *Cancer Res*. 47:3186-9, 1987.

M.J. Kelner, et al., Preclinical evaluation of Illudins as anti-cancer agents. Basis for selective cytotoxicity. *J. Natl. Cancer Inst*. 82:1562-1565, 1990.

M.J. Kelner, et al., Characterization of Illudin S sensitivity of DNA repair-deficient Chinese Hamster cells: unusually high sensitivity of ERCC2 and ERCC3 DNA-helicase deficient mutants in comparison to other chemotherapeutic agents. *Biochem. Pharmacol*. 48:403-409, 1994.

M.J. Kelner, et al., Nonresponsiveness of the metastatic human lung carcinoma MV522 xenograft to conventional anticancer agents. *Anticancer Res*. 15:867-872, 1995.

M.J. Kelner, et al., In vitro and In vivo studies on the anticancer activity of dehydroilludin M. *Anticancer Res*. 15:873-878, 1995.

M.J. Kelner, et al., Efficacy of Acylfulvene Illudin analogs against a metastatic lung carcinoma MV522 xenograft nonresponsive to traditional anticancer agents retention of activity against various mdr phenotypes and unusual cytotoxicity against ERCC2 and ERCC3 DNA helicase-deficient cells. *Cancer Res*. 55:4936-4940, 1995.

M.J. Kelner, et al., Efficacy of HMAF (MGI-114) in the MV522 metastatic lung carcinoma xenograft model nonresponsive to traditional anticancer agents. *Invest. New Drugs* 14:161-167, 1996.

M.J. Kelner, et al., Characterization of cellular accumulation and toxicity of Illudin S in sensitive and non-sensitive tumor cells. *Cancer Chemother. Pharmacol*. 40:65-71, 1997.

M.J. Kelner, et al., Characterization of Acylfulvene histiospecific toxicity in human tumor cell lines. *Cancer Chemother. Pharmacol*. 41:237-242, 1998.

M.J. Kelner, et al., Efficacy of MGI 114 (6-hydroxymethylacylfulvene, HMAF) against the mdr1/gp170 Metastatic MV522 lung carcinoma xenograft. *Eur. J. Cancer*. 34:908-913, 1998.

M.J. Kelner, et al., Characterization of MGI 114 (HMAF): Histiospecific toxicity in human tumor cell lines. *Cancer Chemother. Pharmacol*. 44:235-240, 1999.

M.J. Kelner, et al., Anti-leukemic action of the novel agent MGI 114 (HMAF) and synergistic action with Topotecan. *Leukemia* 14:136-141, 2000.

M.J. Kelner, et al., Efficacy of MGI 114 against the MRP-positive metastatic MV522 lung carcinoma Xenograft. *Anti-Cancer Drugs* 11: 217-224, 2000.

M.J. Kelner, et al., Enhanced antitumor activity of irofulven in combination with thiotepa or mitomycin C. *Cancer Chemother. Pharmacol*. 49:412-8, 2002.

M.J. Kelner, et al., Enhanced antitumor activity of Irofulven in combination with antimitotic agents.*Invest New Drugs* 20:271-279, 2002.

M.J. Kelner, et al., Synergy of Irofulven in combination with other DNA damaging Agents: synergistic interaction with altretamine, alkylating, and platinum-derived agents in the MV522 lung tumor model. *Cancer Chemotherap Pharmacol*. 63:19-26, 2008.

M.J. Kelner, et al., Synergy of Irofulven in combination with various anti-metabolites, enzyme inhibitors, and miscellaneous agents in MV522 lung carcinoma cells: marked interaction with gemcitabine and 5-fluorouracil. *Invest. New Drugs*. 26:407-415, 2008.

J.J. Likos et al., Affinity labelling of the active site of yeast Pyruvate Kinase by 5'-p-Fluorosulfonyl benzoyl Adenosine, *J. Biol. Chem.*, 255, 9388-9398, 1980.

J.R. MacDonald, et al., Preclinical antitumor activity of 6-Hydroxymethylacylfulvene, a semisynthetic derivative of the mushroom toxin Illudin S. *Cancer Res*. 57:279-283, 1997.

(56) References Cited

OTHER PUBLICATIONS

T.C. McMorris, et al., Structure and reactivity of Illudins. *Tetrahedron* 45:5433-5440, 1989.
T.C. McMorris, et al., On the mechanism of toxicity of Illudins. The role of glutathione. *Chem. Res. Toxicol.* 3:574-579, 1990.
T.C. McMorris, et al., Structure activity-relationships of Illudins Analogs with improved therapeutic index. *J. Org. Chem.* 57:6876-6883, 1992.
T.C. McMorris, et al., Acylfulvenes, a new class of potent antitumor agents. *Experientia* 52:75-80, 1996.
T.C. McMorris, et al., (Hydroxymethyl)acylfulvene: an Illudin derivative with superior antitumor properties. *J. Natural Products* 59:896-899, 1996.
T.C. McMorris, et al., Total synthesis of Hydroxymethylacylfulvene; an antitumor derivative of Illudin S. *Chem. Commun.* 3:315-316, 1997.
T.C. McMorris, et al., An Acetal derivative of Illudin S with improved tumor activity. *Tetrahedron Lett.* 38:1697-1698, 1997.
T.C. McMorris, et al., The design and total synthesis of antitumor acylfulvenes. *J. Organic Chem.* 62:3015-3018, 1997.
T.C. McMorris, et al., Reaction of antitumor hydroxymethylacylfulvene (HMAF) with thiols. *Tetrahedron*.53: 14579-90, 1997.
T.C. McMorris, et al., Synthesis of [$^3$H]-Illudin S, [$^3$H]-Acylfulvene, [$^3$H] & [$^{14}$C]-Hydroxymethylacylfulvene (MGI 114). *J. Labelled Cpd. Radiopharm.* XLI: 279-285, 1998.
T.C. McMorris, et al., Metabolism of antitumor Acylfulvene by rat liver cytosol. *Biochem. Pharmacol.* 57:83-88, 1999.
T.C. McMorris, et al., Metabolism of antitumor hydroxymethylacylfulvene by rat liver cytosol. *Drug Metab. Dispos.* 27:983-985, 1999.
T.C. McMorris, et al., Preparation and biological activity of amino acid and peptide conjugates of antitumor hydroxymethylacylfulvene. *J. Med. Chem.* 43: 3577-3580, 2000.
T.C. McMorris, et al., Sequiterpenes from the Basidiomycete *Omphalotus illudens*. *J. Nat. Prod.* 63:1557-1559, 2000.
T.C. McMorris, et al., Structure-activity studies of antitumor agent irofulven (hydroxymethylacylfulvene) and related analogues. *J. Org. Chem.* 66:6158-6163, 2001.
T.C. McMorris, et al., Sesquiterpenes from Omphalotus illudens. *Phytochemistry* 61:395-398, 2002.
T.C. McMorris, et al., Reaction of Irofulven with Zinc and Acid. *J Nat Products.* 66:310-312, 2003.
T.C. McMorris, et al., Structure-activity relationship studies of Illudins: Analogues possessing a spiro-cyclobutane ring. *J. Org. Chem.* 68:9648-53, 2003.
T.C. McMorris, et al., Synthesis and biological activity of enantiomers of antitumor Irofulven. *J. Org. Chem* 69:619-623, 2004.
T.C. McMorris, et al., Synthesis and Antitumor Activity of Amine Analogs of Irofulven *Bioorganic & Medicinal Chemistry Letters.* 17: 6770-72, 2007.
T.C. McMorris, et al., Structure-Activity Studies of Urea, Carbamate and Sulfonamide Derivatives of Acylfulvene. *J. Med. Chem.* 53: 1109-16, 2010.
Narayanan, A. and Jones, L.H. Sulfonyl fluorides as privileged warheads in chemical biology, Chem Sci., 6, 2650, 2015.
P.K. Pal et al, Affinity Labeling of a Regulatory Site of Bovine Liver Glutamate Dehydrogenase, Biochem., 14, 707-714, 1975.
P.K. Pal et al, Affinity Labeling of a inhibitory DPNH Site of Bovine Liver Glutamate Dehydrogenase by 5'-Fluorosulfonylbenzoyl Adenosine, J.Biol. Chem. 250, 8140-8147, 1975.
T.L. Poulos, The involvement of serine and carboxyl groups in the activity of Bovine Pancreatic Deoxyribonuclease A, J. Biol. Chem. 249, 1453-1457, 1974.
S. Roy et al., Affinity Labeling of a Lysine Residue in the Coenzyme Binding Site of Pig Heart Mitochondrial Malate Dehydrogenase, Biochemistry, 18, 4683-4690, 1979.
K.V. Saradambal ey al., Lysine and Tyrosine in the NADH Inhibitory Site of Bovine Liver Glutamate Dehydrogenase, J. Biol. Chem. 256, 11866-11872, 1981.
R. Schobert, et al., Conjugates of the fungal cytotoxin illudin M with improved tumour specificity. Biorg Med Chem 16:8592-97, 2008.
R. Schobert, et al., Cancer selective metallocenedicarboxylates of the fungal cytotoxin Illudin M. J Med Chem. 54: 6177-82, 2011.
R. Schobert, et al., Anticancer Active Illudins: Recent developments of a potent alkylating compound class. Current Medicinal Chemistry 18:790-807, 2011.
M.D. Staake, et al., Hydroxyurea derivatives of irofulven with improved antitumor efficacy. *Bioorg. Med. Chem. Lett.* 26: 2836-38, 2016.2010.
M. Tanasova, S.J. Sturla. "Chemistry and Biology of Acylfulvenes: Sesquiterpene-derived antitumor agents" (2012) Chemical Reviews. 112, 3578-3610.
C.T. Togashi et al., 5'-p-Fluorosulfonylbenzoyladenosine: Inactivatio of myosine subfragment I and a model reaction with Cysteine (1981) J Biol. Chem. 257, 10112-10118.
J.M. Tomich et al., Modification of two essential cysteines in rabbit muscle pyruvate kinase by the guanosine nucleotide analogue 5'-[p-(Fluorosulfonyl)benzoyl] guanosine, 1981 Biochem, 20, 6711-6720.
PCT/US2015/025208, ISR dated Oct. 23, 2015, 26 pages.
A. Narayanan et al., Sulfonyl fluorides as privileged warheads in chemical biology, Chem Sci, 2650, 6 (2015).
A Paci et al., "Pharmacokinetics, Metabolism, and Routes of Excretion of Intravenous Irofulven in Patients with Advanced Solid Tumors", Drug Metabolism and Disposition, vol. 34, No. 11, Aug. 16, 2006.
J. Gong et al., "Depurinating Acylfulvene-DNA Adducts: Characterizing Cellular Chemical Reactions of a Selective Antitumor Agent", Journal Ofthe American Chemical Society, vol. 129, No. 7, Feb. 1, 2007, pp. 2101-2111.
Partial Supplementary eSR 15776253.5 PCT/US2015/025208, dated Feb. 5, 2018 (stamped by foreign associate as incoming on Jan. 31, 2018), 18 pages.
A. Stornetta, "DNA Adducts from Anticancer Drugs as Candidate Predictive Markers for Precision Medicine", (2017) Chemical Research in Toxicology, 30, 388-409.
A. Intra, "Regioselective Enzymatic Acylation of Polyhydroxylated Sesquiterpenoids" (2004) J. Molecular Catalysis B: Enzymatic 29, 95-98.
C. Nord, "Cytotoxic Illudane Sesquiterpenes from the Fungus Granulobasidium vellereum (Ellis and Cragin) Jülich", J. of Natural Products (2015) 78, 2559-2564.
T. Horn et al., "High-Order Drug Combinations Are Required to Effectively Kill Colorectal Cancer Cells", (2016) Cancer Res. 76, 6950-6963.
K. Mouw, "Improving Methods to Detect and Target Nucleotide Excision Repair (NER) Deficiency in Bladder Cancer" (2020) IBCN, https://www.urotoday.com/conference-highlights/ibcn-2020/125289-ibcn-2020-improving-methods-to-detect-and-target-nucleotide-excision-repair-deficiency-in-bladder-cancer.html, last visited Feb. 25, 2021.
European Search Report, Application 3667323, Feb. 11, 2020, 4 pages.
C. McCann et al., "Molecular Targets and Cancer Therapeutics" (2015) Poster Abstract, htpps://www.aacr.org/Documents/Targets15_AbstractsPosterC.pdf.
K. E. Pietsch et al., "Quantification of Acylfulvene- and Illudin S-DNA Adducts in Cells with Variable Bioactivation Capacities" (2013) Chemical Res. in Toxicology, 26 146-155.
W. Yang et al., "Genomics of Drug Sensitivity in Cancer (GDSC): a resource for therapeutic biomarker discovery in cancer cells" (2013) Nucleic Acids Res. 41 D955-D961.
McMorris et al., Synthesis and Biological Activity of Enantiomers of Antitumor Irofulven, J. Org. Chem. 69 (2004) 619-623.
EP 20209541.0, eESR dated Jun. 15, 2022, 9 pages.
Le Philllipe et al., A Chemical Proteomic Analysis of Illudin-Interacting Proteins, 25 (2019) 12644-12651.
J. Pan et al., Sparse dictionary learning recovers pleiotropy from human cell fitness screens, Cell Systems, 13 (2022) 1-18.
U. Kathad et al., Expanding the repertoire of Antibody Drug Conjugate (ADC) targets with improved tumor selectivity and range

(56) References Cited

OTHER PUBLICATIONS of potent payloads through in-silico analysis, PLOS ONE https://doi.org/10.1371/journal.pone.0308604 Aug. 26, (2024) 1-25.

* cited by examiner (H)

(I)

Figure 2P
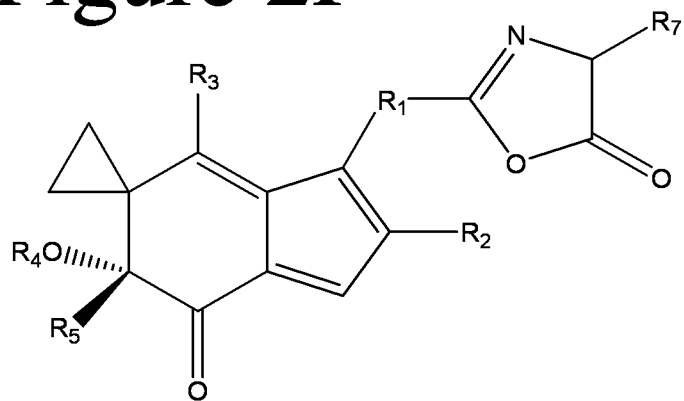
Figure 2Q
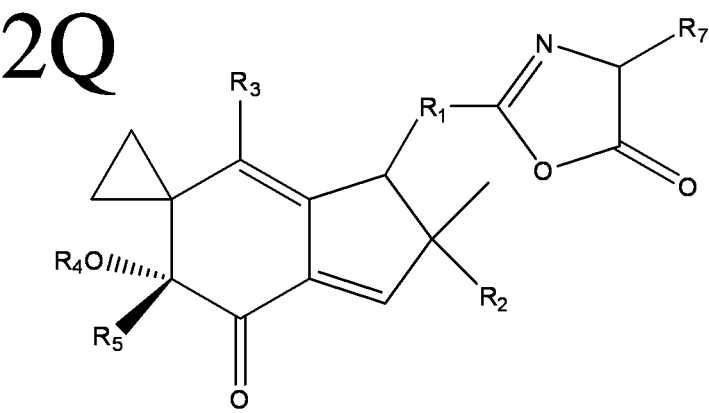
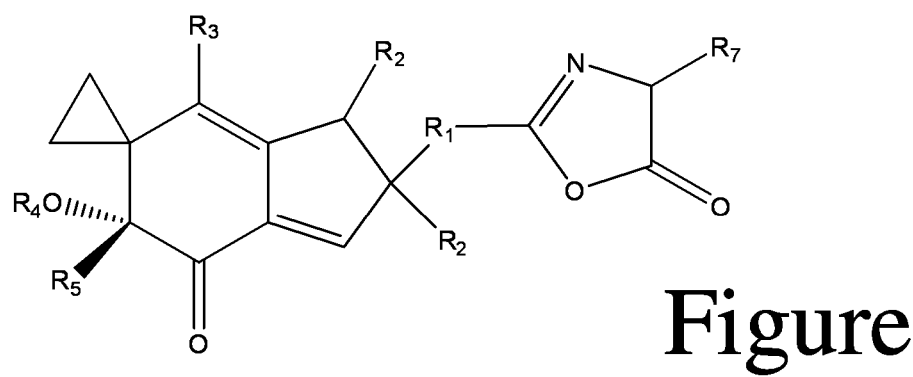
Figure 2R

Figure 2S
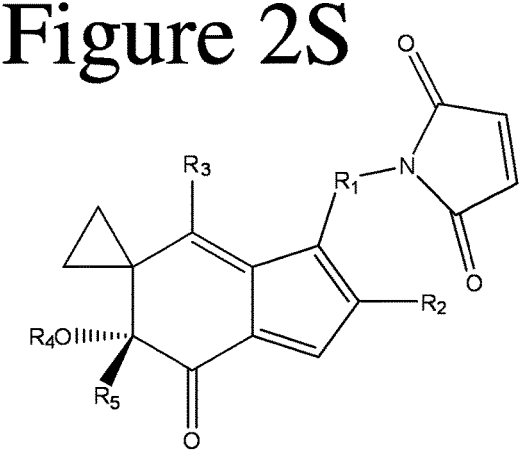
Figure 2T
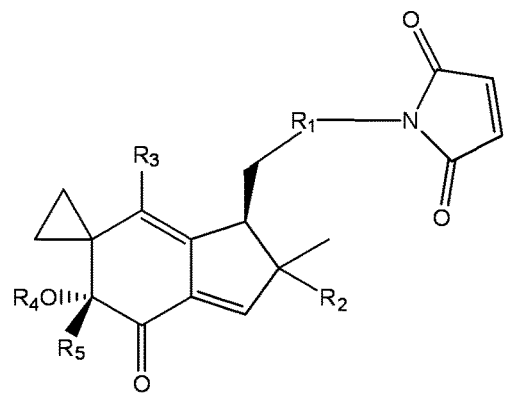
Figure 2U
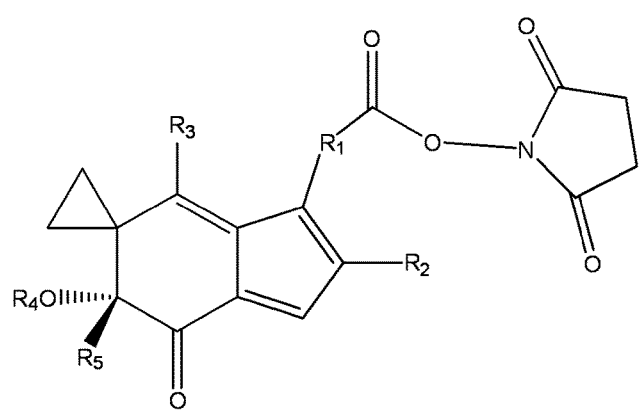
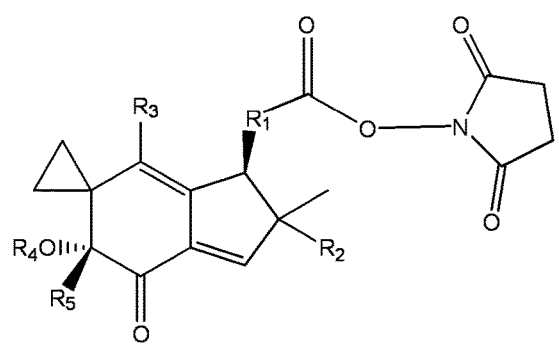
Figure 2V

Figure 4

| Tumor cell line | 2 hr | 48 hr |
|---|---|---|
| Myeloid leukemias | Yes | Yes |
| Breast carcinomas | Yes | Yes |
| Epidermoid | Yes | Yes |
| Ovarian | Yes | Yes |
| Lung carcinomas | Yes | Yes |
| Prostate carcinomas | Yes | Yes |
| B cell leukemias | No | Yes |
| T cell leukemias | No | Yes |
| Fibroblasts (normal) | No | Yes |

Figure 5

Unique DNA Damage Profile

|        | Other Drugs | UV | Illudin S |
|--------|-------------|----|-----------|
| XP-A   | +           | +  | +         |
| XP-B   | 0           | +  | +         |
| XP-C   | +           | +  | 0         |
| XP-D   | 0           | +  | +         |
| XP-E   | +           | +  | 0         |
| XP-F   | +           | +  | +         |
| CS-A   | +/-         | +  | ++        |
| CS-B   | +/-         | +  | ++        |
| ERCC1  | +           | +  | +         |
| ERCC5  | +           | +  | +         |

Indicates novel mechanism of action versus other chemotherapeutic agents

Figure 7

| Mechanism | Resistance to Irofulven |
|---|---|
| Gp170/MDR1 | No |
| Gp180/MRP | No |
| Topoisomerase I | No |
| Topoisomerase II | No |
| LRP(vault) | No |
| Thiol Content | No |
| DNA repair (?) | No |
| Myc expression | No |
| Bcl-2 expression | No |
| BRCA status | No |
| p53 status | No |
| p21 status | No |

Figure 14A
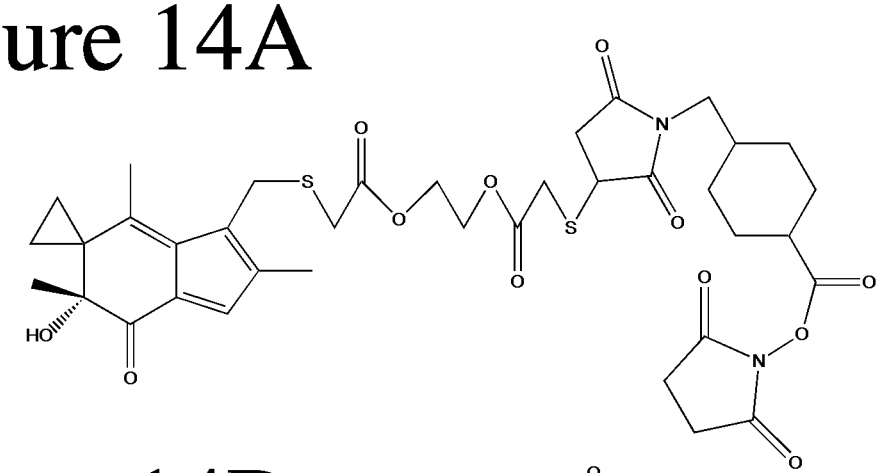
Figure 14B
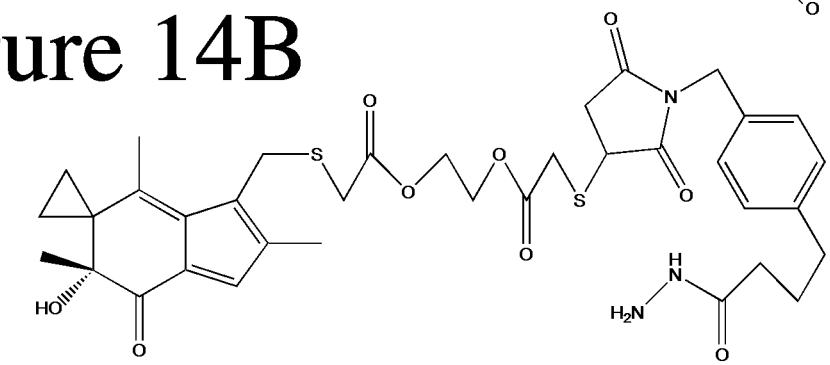
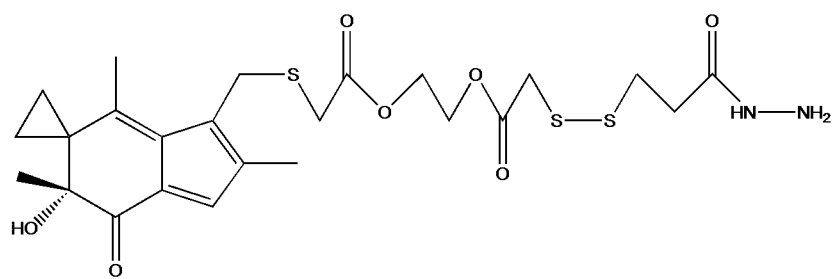
Figure 14C

Figure 20A
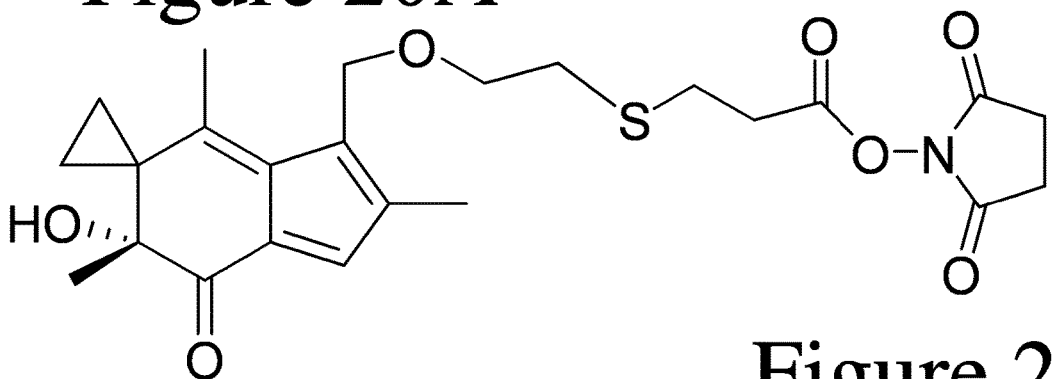
Figure 20B
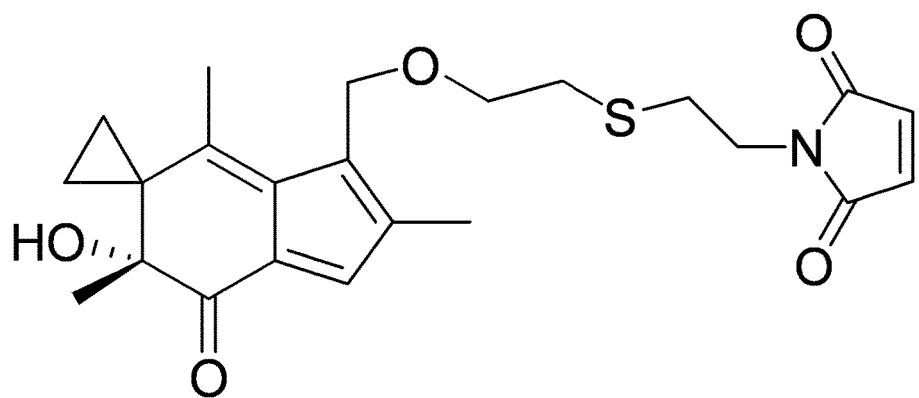
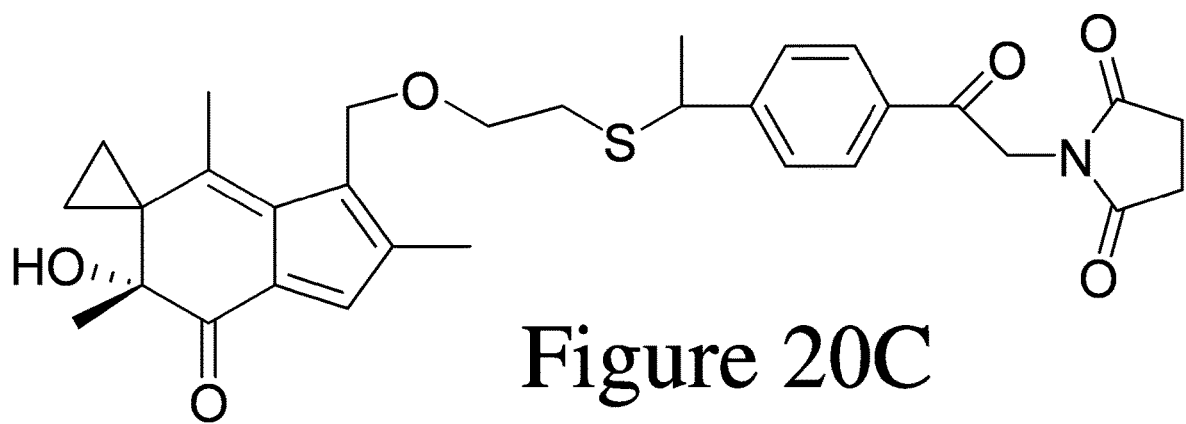
Figure 20C

AFFINITY MEDICANT CONJUGATE

PRIORITY CLAIM

This application is a continuation of and claims priority to (1) U.S. patent application Ser. No. 17/576,767 entitled "AFFINITY MEDICANT CONJUGATES", inventor: Michael J. Kelner, filed Jan. 14, 2022, which is a continuation of and claims priority to (2) U.S. patent application Ser. No. 17/482,242 entitled "AFFINITY MEDICANT CONJUGATES", inventor: Michael J. Kelner, filed Sep. 22, 2021, which issued as U.S. Pat. No. 11,241,398 on Feb. 8, 2022, which is a divisional of and claims priority to (3) U.S. patent application Ser. No. 17/035,529 entitled "AFFINITY MEDICANT CONJUGATES", inventor: Michael J. Kelner, filed Sep. 28, 2020, which issued as U.S. Pat. No. 11,135,182 on Oct. 5, 2021, which is a continuation in part of and claims priority to (4) U.S. patent application Ser. No. 15/986,727 entitled "AFFINITY MEDICANT CONJUGATES", inventor: Michael J. Kelner, filed May 22, 2018, which issued as U.S. Pat. No. 10,806,708 on Oct. 20, 2020, which is a continuation of (5) U.S. patent application Ser. No. 15/201,301 entitled "AFFINITY MEDICANT CONJUGATES", inventor: Michael J. Kelner, filed Jul. 1, 2016, which issued as U.S. Pat. No. 9,980,926 on May 29, 2018, which is a continuation of (6) U.S. patent application Ser. No. 14/684,218 entitled "AFFINITY MEDICANT CONJUGATES", inventor: Michael J. Kelner, filed Apr. 10, 2015, which issued as U.S. Pat. No. 9,381,178 on Jul. 5, 2016 and which claims priority to (7) the U.S. Provisional Application No. 61/978,195 entitled "AFFINITY MEDICANT CONJUGATES", inventor: Michael J. Kelner filed Apr. 10, 2014, which applications (1)-(7) are herein expressly incorporated by reference in their entireties and for all purposes.

REFERENCE TO A "SEQUENCE LISTING," A TABLE, OR A COMPUTER PROGRAM LISTING APPENDIX SUBMITTED AS AN ASCII TEXT FILE

The Sequence Listing written in file MKEL-01047US9_ST26.xml, created Jul. 15, 2023, 441,274 bytes, machine format IBM-PC, MS-Windows operating system, is hereby incorporated by reference.

TECHNICAL FIELD

The present invention relates to compositions and methods for treating target molecules including cell populations with an affinity medicant conjugate such as an antibody drug conjugate.

BACKGROUND

The present invention is directed to Affinity Medicant Conjugates (AMC) including acylfulvene, Illudin and Syn-Illudin based conjugates, Affinity Medicant Linker Conjugates (AMLC), antibody-drug conjugates (ADC) and medicant-linker (ML) compounds, as well as to compositions of the same, and to methods for their use in treating cancer, an autoimmune to methods of using Ligand Linker Medicant (LLM) conjugates and ML compounds in vitro, in situ, and in vivo for the detection, diagnosis or treatment of cells and associated pathological conditions.

SUMMARY OF INVENTION

There exists a continuing need for delivery of chemotherapeutic agents for which tumors do not have a medicant resistant phenotype and which inhibit tumor growth, especially solid tumor growth, and which have an adequate therapeutic index to be effective for in vivo treatment. The antibody medicant conjugates of the present invention can have utility in a wide range of therapeutic applications in humans as well as in animals in general. For example, such therapeutic applications can include: cancer, adenocarcinoma, carcinoma, breast cancer, prostate cancer, ovarian cancer, endometrial cancer, neuroendocrine tumors, infertility, polycystic ovary syndrome, endometriosis, and precocious puberty. For example, veterinary and agricultural applications can include treatment of cancer, adenocarcinoma, carcinoma, ovarian cancer, endometrial cancer, neuroendocrine tumors, and endometriosis in farmyard and/or companion animals.

The methods of this invention include administration of an effective amount of an antibody medicant conjugate, preferably in the form of a pharmaceutical composition, to an animal in need thereof. In a further embodiment, pharmaceutical compositions are disclosed containing an antibody medicant conjugate of the present invention in combination with a pharmaceutically acceptable carrier.

In various embodiments of the present invention, an affinity medicant conjugate is made up of an antibody 1110 linked to an illudin1 moiety 1301. Various embodiments of the invention, are directed to the methods for the preparation, use, and to pharmaceutical compositions containing an illudin1 moiety 1301 linked to an antibody 1110 to form an antibody medicant conjugate (AMC). In various embodiments the compounds of the present invention, the AMC can have the general formula shown in FIG. 3A, where the antibody 1110 is bound to a linker 1200 which is bound to an illudin1 moiety 1301. In other various embodiments of the present invention, the compounds of the present AMC invention can have the general formula shown in FIG. 3B, where a growth factor 1120 is bound to a linker 1200 which is bound to an illudin1 moiety 1301. In various embodiments the compounds of the present invention include stereoisomers, solvates, and pharmaceutically acceptable salts thereof, where the linker 1200 is as defined in Table X, and the illudin1 1301 is as defined below in Table XI.

In various embodiment of the present invention, an antibody linked to an acylfulvene moiety acts as a ligand for an Epidermal Growth Factor (EGF) receptor (EGF-R) (SEQ. ID. 143) and directs the acylfulvene to cell populations expressing the EGF-R. These compounds are useful as a means of treating cell populations expressing the EGF-R. In an embodiment of the present invention, these compounds are useful in treatment of tumors in which the EGF-R is over expressed. In an embodiment of the present invention, these compounds are useful in treatment of cells in which the EGF-R acts as a marker. In various embodiment of the present invention, these compounds are useful in agricultural applications in which the EGF-R acts as a marker of cell populations involved in agricultural production. In various embodiment of the present invention, these compounds are useful in veterinary medicine in which the EGF-R acts as a marker of cell populations involved in pet reproduction. In various embodiments of the present invention, pharmaceutical compositions comprising these compounds are used in the treatment of tumors in which the EGF-R is involved. In various embodiments of the present invention, methods of using the pharmaceutical compositions comprise these compounds to treat tumors in which the GH-R is involved.

BRIEF DESCRIPTION OF THE DRAWINGS

This invention is described with respect to specific embodiments thereof. Additional features can be appreciated from the Figures in which:

FIG. 2P shows the structure of azlactone acylfulvene medicant moiety (where $R_2$=H, $CH_3$, $CH_2OH$), according to an embodiment of the invention; FIG. 2Q shows the structure of azlactone secondary hydroxyl illudin2 linkage medicant moiety (where $R_2$=H, $CH_3$, $CH_2OH$), according to an embodiment of the invention; FIG. 2R shows the structure of azlactone primary hydroxyl linkage illudin2 medicant moiety (where $R_2$=H, $CH_3$, $CH_2OH$), according to an embodiment of the invention; FIG. 2S and FIG. 2T show the structures of the maleimide acylfulvene and maleimide illudin medicant moieties, respectively; FIG. 2U shows the structure of the maleic acylfulvene medicant moiety, according to an embodiment of the invention; FIG. 2V shows the structure of the maleic illudin medicant moiety, according to an embodiment of the invention;

FIG. 4 shows the selective toxicity of an acylfulvene analog, according to various embodiments of the invention;

FIG. 5 shows the unique deoxynucleic acid (DNA) damage profile of an acylfulvene analog, according to an embodiment of the invention;

FIG. 7 shows the multidrug resistance studies of an acylfulvene analog, according to an embodiment of the invention;

FIG. 14A shows the structure of the analog 051 attached via the sulfhydryl group using SMCC linking reagent according to an embodiment of the invention; FIG. 14B shows the structure of the analog 051 attached via the sulfhydryl group using MPBH linking reagent according to an embodiment of the invention; FIG. 14C shows the structure of the analog 051 attached via the sulfhydryl group using PDPH linking reagent according to an embodiment of the invention;

FIG. 20A shows analog 20 linked to DSP according to an embodiment of the invention;

FIG. 20B shows analog 20 linked to DTME according to an embodiment of the invention; and FIG. 20C shows analog 20 linked to SMPT according to an embodiment of the invention.

DETAILED DESCRIPTION OF THE INVENTION

Definitions

Figure 1A:
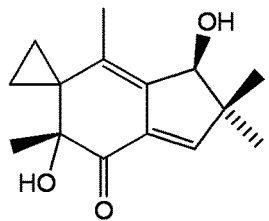
FIG. 1A shows the structure of Illudin M.
Figure 1B:
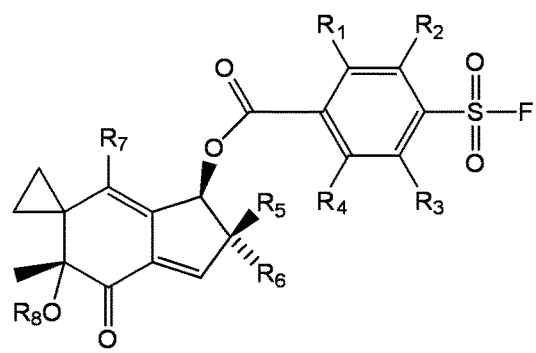
FIG. 1B shows a mono-substituted product formed by reacting Illudin M on the secondary hydroxyl to form 4-FSB linking reagent according to an embodiment of the invention.
Figure 1C:
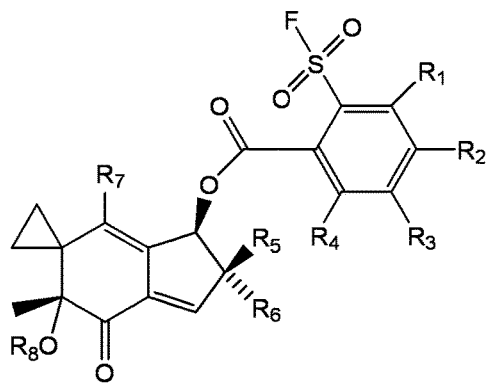
FIG. 1C shows a mono-substituted product formed by reacting Illudin M on the secondary hydroxyl to form 2-FSB linking reagent according to an embodiment of the invention.
Figure 1D:
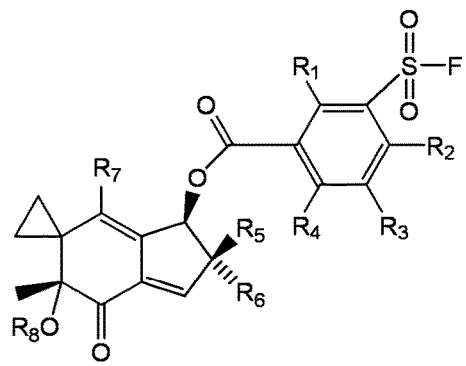
FIG. 1D a mono-substituted product formed by reacting Illudin M on the secondary hydroxyl to form 3-FSB linking reagent according to an embodiment of the invention.

As used herein, the term "receptor for a biologically active polypeptide" means a receptor which can bind a biologically active peptide conjugate.

As used herein, the term "cell population" is used to describe a set or subset of cells expressing a receptor.

As used herein, the terms "analog", "medicant" and "medicant moiety" are used interchangeably and comprise synthetic and naturally occurring drugs, toxins, nutraceuticals and other cytoactive, anti-inflammatory and bioactive molecules including Doxorubicin (Immunomedics), auristatins E (Seattle Genetics), auristatins F (Celdex), monomethyl auristatin E (MMAE) (Amgen), monomethyl auristatin F (MMAF) (Astelles), maytanasines (Immunogen), DM1 (Biotest), DM4 (Amgen), calicheamicin (CellTech), irinotecan, folate, SN38 (Immunomedics), Pyrrolobenzodiazepines (Seattle Genetics), MGBA a duocarmycin derivative (Medarex), thalidomides, taxanes, penicillins, Trastuzumab emtansine (Genentech for Breast cancer uses maytanasine derive DM-1). A medicant includes analogs 192, 197, 272, 273, 274, 290, 291, 292, 293 (i.e., acylfulvenes linked to thalidomide, cephalosporin or colchicines derivatives). Some of the above analogs are stand alone drugs, but can be used as a medicant moiety in an affinity drug conjugate according to various embodiments of the invention.

As used herein, the phrase "peptide receptor" includes peptide hormone receptors, protein hormone receptors, chemotactic receptors and chemokine receptors.

As used herein, the term "receptor" includes growth factor receptors, peptide hormone receptors, peptide receptors, steroid hormone receptors, steroid receptors and lipid receptors.

As used herein, phrase "affinity medicant conjugate" is an Affinity Moiety covalently bound to a medicant moiety, and includes antibody medicant conjugates, where the antibody is directed to a specific receptor. As used herein the phrase 'Affinity Moiety' includes antibodies, antibody fragments, peptides, proteins, growth factors, steroids, and lipids, where the antibodies, antibody fragments, peptides, proteins, growth factors, steroids, folate or lipids have an affinity for a specific receptor, receptors, is processed by an enzyme to produce a ligand that has an affinity for a specific receptor or otherwise directs the Affinity Moiety to a specific subset of cells. A 'medicant moiety' includes a group bound to an Affinity Moiety, which when released acts as a medicant.

As used herein, the term "Affinity Moiety" (AM) is used to describe a chemical group or molecule that can bind a receptor or proteins. An AM is understood to have a minimum binding affinity greater than approximately $1\times10^{-3}$ M affinity. As used herein, the term AM includes "ligands", "ligand moieties", "affinity unit" and an AM modified to include a linker. As used herein, the phrase "an affinity moiety directed to a peptide receptor" is used to describe a molecule or a portion of a molecule which has a binding affinity to the peptide receptor greater than approximately $1\times10^{-10}$ M. In this range approximately means $1\times10^{-9}$ M to $1\times10^{-11}$ M. In an embodiment of the invention, an AM directed to a peptide receptor has a binding affinity to the peptide receptor greater than approximately $1\times10^{-12}$ M. In this range approximately means $1\times10^{-11}$ M to $1\times10^{-13}$ M.

As used herein, the term "linker" is used to describe one or more covalently bonded groups of atoms that are covalently bonded to a medicant moiety and an AM. For example a linker can be covalently bound to both an acylfulvene moiety and to an antibody or other ligand moiety with an affinity for a receptor.

As used herein, the term "non releasable linker" is used to describe a linker covalently bound to an AM and a medicant moiety in which the AM and the medicant moiety remain covalently bound to the linker after internalization and exposure to both reducing and acidic environments of vesicles within the cell. As used herein, the term "membrane permeability" is used to describe a compound comprising a linker covalently bound to an AM and an acylfulvene moiety, where the compound can diffuse across membranes within the cell.

As used herein, the term "transmembrane receptor" means a protein that spans the plasma membrane of a cell with the extracellular domain of the protein having the ability to bind an AM and the intracellular domain having an activity such as activation of G protein signaling which is induced upon the AM binding.

As used herein, the term "seven transmembrane receptor" is a transmembrane receptor including a transmembrane domain where the protein spans the cell membrane in seven (7) regions.

As used herein, the term "G-protein coupled receptor" means a seven transmembrane domain receptor which transduces a biological signal via G-protein coupling.

As used herein, the term "conjugated" or "conjugate" means a chemical compound that is formed by joining two or more compounds with one or more chemical bonds or linkers. In an embodiment of the invention, an antibody and a medicant form a conjugate.

As used herein, the term "antibody" herein is used in the broadest sense and specifically covers intact antibodies, monoclonal antibodies, polyclonal antibodies, mono-specific antibodies, multi-specific antibodies (e.g., bi-specific antibodies), and antibody fragments that exhibit the desired biological activity, including those antibodies directed against Alk, Alk fusion proteins, CD 2 (SEQ. ID. 001), CD3epsilon (SEQ. ID. 002), CD5 (SEQ. ID. 003), CD7 (SEQ. ID. 004), CD19 (SEQ. ID. 005), CD20 (SEQ. ID. 006), CD22 (SEQ. ID. 007), CD25 (SEQ. ID. 008), CD30 (SEQ. ID. 009), CD33 (SEQ. ID. 010), CD37 (SEQ. ID. 011), CD44 (SEQ. ID. 012), CD44v6 (SEQ. ID. 013), CD56 (SEQ. ID. 014), CD70 (SEQ. ID. 015), CD74 (SEQ. ID. 016), CD79 (SEQ. ID. 017), CD79b (SEQ. ID. 018), CD 80 (SEQ. ID. 019), CD 86 (SEQ. ID. 020), CD138 (syndecan 1) (SEQ. ID. 021), CAIX (SEQ. ID. 022), Integrin alphaV-beta 3 (SEQ. ID. 023), EphA2 (SEQ. ID. 024), Crypto 1 (SEQ. ID. 025), CanAg (SEQ. ID. 026), ENPP3 (SEQ. ID. 027), Nectin-4 (SEQ. ID. 028), Mesothelin (SEQ. ID. 029), Lewis Y (SEQ. ID. 030), EGFRvIII (SEQ. ID. 031), SLC44A4 (SEQ. ID. 032), EBTR (endothelin) (SEQ. ID. 033), erbB2/neu/HER2 (SEQ. ID. 034), Transferrin receptor (SEQ. ID. 035), 55 kDa breast cancer antigen, 72 kDa TAA, GPNMB (osteoactivin) (SEQ. ID. 038), CA-IX (SEQ. ID. 039), CEA (CD66e) (SEQ. ID. 040), CEACAMS (SEQ. ID. 041), PSMA (SEQ. ID. 042), CA125 (MUC16) (SEQ. ID. 043), Muc1 (CA6) (SEQ. ID. 044), Melanoma glycoprotein NMB (SEQ. ID. 045), IL-2R (SEQ. ID. 166 and 046), IL13R (SEQ. ID. 047), TACSTD2 (TROP2 or EGP1) (SEQ. ID. 048), Folate receptor 1 (SEQ. ID. 049), Mucin 16 (SEQ. ID. 050), Endothelin receptor ETB (SEQ. ID. 051), STEAP1 (SEQ. ID. 052), SLC44A4 (AGS-5) (SEQ. ID. 053), AGS-16 (SEQ. ID. 054), and Guanylyl cyclase C (SEQ. ID. 055). An intact antibody has primarily two regions: a variable region and a constant region. The variable region binds to and interacts with a target antigen. The variable region includes a complementary determinusng region (CDR) that recognizes and binds to a specific binding site on a particular antigen. The constant region may be recognized by and interact with the immune system. An antibody can be of any type or class (e.g., IgG, IgE, IgM, IgD, and IgA) or subclass (e.g., IgG1, IgG2, IgG3, IgG4, IgA1 and IgA2). The antibody can be derived from any suitable species. In some embodiments, the antibody is of human or murine origin. An antibody can be, for example, human, humanized or chimeric.

As used herein, the terms "specifically binds" and "specific binding" refer to antibody binding to a predetermined antigen. Typically, the antibody binds with an affinity of at least about $1 \times 10^7$ M, and binds to the predetermined antigen with an affinity that is at least two-fold greater than its affinity for binding to a non-specific antigen (e.g., Bovine Serum Albumin, casein) other than the predetermined antigen or a closely-related antigen.

As used herein, "isolated" means separated from other components of (a) a natural source, such as a plant or animal cell or cell culture, or (b) a synthetic organic chemical reaction mixture. As used herein, "purified" means that when isolated, the isolate contains at least 95%, and in another aspect at least 98%, of a compound (e.g., a conjugate) by weight of the isolate.

As used herein, the term "therapeutically effective amount" refers to an amount of a medicant effective to treat a disease or disorder in a mammal. In the case of cancer, the therapeutically effective amount of the medicant may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. To the extent the medicant may inhibit the growth of and/or kill existing cancer cells, it may be cytostatic and/or cytotoxic. For cancer therapy, efficacy can, for example, be measured by assessing the time to disease progression (TTP) and/or determining the response rate (RR).

As used herein, the term "substantial amount" refers to a majority, i.e. greater than approximately fifty percent (50%) of a population, of a mixture or a sample. In this range approximately means plus or minus ten percent (10%).

As used herein, the term "intracellular metabolite" refers to a compound resulting from a metabolic process or reaction inside a cell on an Affinity Medicant Linker conjugate (e.g., an Antibody Drug Conjugate (AMC)). The metabolic process or reaction may be an enzymatic process such as proteolytic cleavage of a peptide linker of the AMC. Intracellular metabolites include, but are not limited to, antibodies and free medicant which have undergone intracellular cleavage after entry, diffusion, uptake or transport into a cell.

As used herein, the terms "intracellularly cleaved" and "intracellular cleavage" refer to a metabolic process or reaction inside a cell on an Affinity Medicant Linker conjugate (e.g., an Antibody Medicant conjugate (AMC) or the like), whereby the covalent attachment, e.g., the linker, between the Medicant moiety (M) and the Affinity unit (e.g., an antibody (Ab)) is broken, resulting in the free Medicant, or other metabolite of the conjugate dissociated from the antibody inside the cell. The cleaved moieties of the Affinity Medicant Linker conjugate are thus intracellular metabolites.

As used herein, the term "bioavailability" refers to the systemic availability (i.e., blood/plasma levels) of a given amount of a medicant administered to a patient. Bioavailability is an absolute term that indicates measurement of both the time (rate) and total amount (extent) of medicant that reaches the general circulation from an administered dosage form.

As used herein, the term "cytotoxic activity" refers to a cell-killing, a cytostatic or an anti-proliferative effect of an Affinity Medicant Linker conjugate or an intracellular metabolite of an Affinity Medicant Linker conjugate. Cytotoxic activity may be expressed as the $IC_{50}$ value, which is the concentration (molar or mass) per unit volume at which half the cells survive.

As used herein, the term "cytotoxic agent" as used herein refers to a substance that inhibits or inhibits the function of cells and/or causes destruction of cells. The term is intended to include radioactive isotopes (e.g., $^{211}$At, $^{131}$I, $^{125}$I, $^{90}$Y, $^{186}$Re, $^{188}$Re, $^{153}$Sm, $^{212}$Bi, $^{32}$P, $^{60}$C, and radioactive isotopes of Lu), chemotherapeutic agents, and toxins such as small molecule toxins or enzymatically active toxins of bacterial, fungal, plant or animal origin, including synthetic analogs and derivatives thereof. In one aspect, the term does not include a radioactive isotope(s).

As used herein, an example of a "patient" includes, but is not limited to, a human, rat, mouse, guinea pig, monkey, pig, goat, cow, horse, dog, cat, bird and fowl. In an exemplary embodiment, the patient is a human.

As used herein, the terms "treat" or "treatment," unless otherwise indicated by context, refer to therapeutic treatment and prophylactic measures to prevent relapse, wherein the object is to inhibit or slow down (lessen) an undesired physiological change or disorder, such as the development or spread of cancer. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already having the condition or disorder as well as those prone to have the condition or disorder.

As used herein, in the context of cancer, the term "treating" includes any or all of inhibiting growth of tumor cells, cancer cells, or of a tumor; inhibiting replication of tumor cells or cancer cells, lessening of overall tumor burden or decreasing the number of cancerous cells, and ameliorating one or more symptoms associated with the disease.

As used herein, the term "chiral" refers to molecules which have the property of non-superimposability of the mirror image partner, while the term "achiral" refers to molecules which are superimposable on their mirror image partner.

As used herein, the term "stereoisomers" refers to compounds which have identical chemical constitution, but differ with regard to the arrangement of the atoms or groups in space.

As used herein, "diastereomer" refers to a stereoisomer with two or more centers of chirality and whose molecules are not mirror images of one another. Diastereomers have different physical properties, e.g., melting points, boiling points, spectral properties, and reactivities. Mixtures of diastereomers may separate under high resolution analytical procedures such as electrophoresis and chromatography.

The abbreviations used herein have their conventional meaning within the chemical and biological arts. The chemical structures and formulae set forth herein are constructed according to the standard rules of chemical valency known in the chemical arts.

Where substituent groups are specified by their conventional chemical formulae, written from left to right, they equally encompass the chemically identical substituents that would result from writing the structure from right to left, e.g., —CH$_2$O— is equivalent to —OCH$_2$—.

The term "alkyl," by itself or as part of another substituent, means, unless otherwise stated, a straight (i.e., unbranched) or branched chain, or combination thereof, which may be fully saturated, mono- or polyunsaturated and can include di- and multivalent radicals, having the number of carbon atoms designated (i.e., C$_1$-C$_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, (cyclohexyl)methyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. An alkoxy is an alkyl attached to the remainder of the molecule via an oxygen linker (—O—).

The term "alkylene," by itself or as part of another substituent, means, unless otherwise stated, a divalent radical derived from an alkyl, as exemplified, but not limited by, —CH$_2$CH$_2$CH$_2$CH$_2$—. Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms.

The term "heteroalkyl," by itself or in combination with another term, means, unless otherwise stated, a stable straight or branched chain, or combinations thereof, consisting of at least one carbon atom and at least one heteroatom selected from the group consisting of O, N, P, Si, and S, and wherein the nitrogen and sulfur atoms may optionally be oxidized, and the nitrogen heteroatom may optionally be quaternized. The heteroatom(s) O, N, P, S, and Si may be placed at any interior position of the heteroalkyl group or at the position at which the alkyl group is attached to the remainder of the molecule. Examples include, but are not limited to: —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH=CH—O—CH$_3$, —Si(CH$_3$)$_3$, —CH$_2$—CH=N—OCH$_3$, —CH=CH—N(CH$_3$)—CH$_3$, —O—CH$_3$, —O—CH—$_2$—CH$_3$, and —CN. Up to two heteroatoms may be consecutive, such as, for example, —CH$_2$—NH—OCH$_3$.

Similarly, the term "heteroalkylene," by itself or as part of another substituent, means, unless otherwise stated, a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—. As described above, heteroalkyl groups, as used herein, include those groups that are attached to the remainder of the molecule through a heteroatom, such as —C(O)R', —C(O)NR', —NR'R", —OR', —SR', and/or —SO$_2$R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl," by themselves or in combination with other terms, mean, unless otherwise stated, cyclic versions of "alkyl" and "heteroalkyl," respectively. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively.

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo($C_1$-$C_4$) alkyl" includes, but is not limited to, fluoromethyl, difluoromethyl, trifluoromethyl, 2,2,2-trifluoroethyl, 4-chlorobutyl, and 3-bromopropyl.

The term "acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently. A fused ring aryl refers to multiple rings fused together wherein at least one of the fused rings is an aryl ring. The term "heteroaryl" refers to aryl groups (or rings) that contain from one to four heteroatoms selected from N, O, and S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl, and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

The term "oxo," as used herein, means an oxygen that is double bonded to a carbon atom.

The term "alkylsulfoxide" as used herein, means a moiety having the formula R—S(O)—R', where R and R' are alkyl groups as defined above. R and R' may have a specified number of carbons (e.g., "$C_1$-$C_4$ alkylsulfoxide").

Each of the above terms (e.g., "alkyl," "heteroalkyl," "aryl," and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', =O, =NR', =N—OR', —NR'R", —SR', -halogen, —SiR'R"R"', —OC(O)R', —C(O)R', —$CO_2$R', —CONR'R", —OC(O)NR'R", —NR"C(O)R', —NR'—C(O)NR"R"', —NR"C(O)$_2$R', —NR—C(NR'R"R"')=NR—, —NR—C(NR'R")=NR—, —S(O)R', —S(O)$_2$R', —S(O)$_2$NR'R", —NRSO$_2$R', —CN, and —NO$_2$ in a number ranging from zero to (2m'+1), where m' is the total number of carbon atoms in such radical. R', R", R"', and R"" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted alkyl, alkoxy, or thioalkoxy groups, or arylalkyl groups. When a compound of the invention includes more than one R group, for example, each of the R groups is independently selected as are each R', R", R", and R"" group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are varied and are selected from, for example: —OR', —NR'R", —SR', -halogen, —SiR'R"R"', —OC(O)R', —C(O)R', —$CO_2$R', —CONR'R", —OC(O)NR'R", —NR"C(O)R', —NR'—C(O)NR"R"', —NR"C(O)$_2$R', —NR—C(NR'R"R"')=NR"", —NR—C(NR'R")=NR"', —S(O)R', —S(O)$_2$R', —S(O)$_2$NR'R", —NRSO$_2$R', —CN, —NO$_2$, —R', —N$_3$, —CH(Ph)$_2$, fluoro($C_1$-$C_4$)alkoxy, and fluoro($C_1$-$C_4$)alkyl, in a number ranging from zero to the total number of open valences on the aromatic ring system; and where R', R", R"', and R"" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound of the invention includes more than one R group, for example, each of the R groups is independently selected as are each R', R", R'", and R"" groups when more than one of these groups is present.

Two or more substituents may optionally be joined to form aryl, heteroaryl, cycloalkyl, or heterocycloalkyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

Two of the substituents on adjacent atoms of the aryl or heteroaryl ring may optionally form a ring of the formula -T-C(O)—(CRR')$_q$—U—, wherein T and U are independently —NR—, —O—, —CRR'—, or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'—, or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X'—(C"R"')$_d$—, where s and d are independently integers of from 0 to 3, and X' is —O—, —NR'—, —S—, —S(O)—, —S(O)$_2$—, or —S(O)$_2$NR'—. The substituents R, R', R", and R'" are preferably independently selected from hydrogen, substituted or unsubstituted alkyl, substituted or unsubstituted cycloalkyl, substituted or unsubstituted heterocycloalkyl, substituted or unsubstituted aryl, and substituted or unsubstituted heteroaryl.

As used herein, the terms "heteroatom" or "ring heteroatom" are meant to include oxygen (O), nitrogen (N), sulfur (S), phosphorus (P), and silicon (Si).

A "substituent group," as used herein, means a group selected from the following moieties: (A) —OH, —NH$_2$, —SH, —CN, —CF$_3$, —NO$_2$, oxo, halogen, unsubstituted alkyl, unsubstituted heteroalkyl, unsubstituted cycloalkyl, unsubstituted heterocycloalkyl, unsubstituted aryl, unsubstituted heteroaryl, and (B) alkyl, heteroalkyl, cycloalkyl, heterocycloalkyl, aryl, and heteroaryl, substituted with at least one substituent selected from: (i) oxo, —OH, —NH$_2$, —SH, —CN, —CF$_3$, —NO$_2$, halogen, unsubstituted alkyl, unsubstituted heteroalkyl, unsubstituted cycloalkyl, unsubstituted heterocycloalkyl, unsubstituted aryl, unsubstituted heteroaryl, and (ii) alkyl, heteroalkyl, cycloalkyl, heterocycloalkyl, aryl, and heteroaryl, substituted with at least one substituent selected from: (a) oxo, —OH, —NH$_2$, —SH, —CN, —CF$_3$, —NO$_2$, halogen, unsubstituted alkyl, unsubstituted heteroalkyl, unsubstituted cycloalkyl, unsubstituted heterocycloalkyl, unsubstituted aryl, unsubstituted heteroaryl, and (b) alkyl, heteroalkyl, cycloalkyl, heterocycloalkyl, aryl, or heteroaryl, substituted with at least one substituent selected from: oxo, —OH, —NH$_2$, —SH, —CN, —CF$_3$, —NO$_2$, halogen, unsubstituted alkyl, unsubstituted heteroalkyl, unsubstituted cycloalkyl, unsubstituted heterocycloalkyl, unsubstituted aryl, and unsubstituted heteroaryl.

A "size-limited substituent" or "size-limited substituent group," as used herein, means a group selected from all of the substituents described above for a "substituent group," wherein each substituted or unsubstituted alkyl is a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_4$-$C_8$ cycloalkyl, and each substituted or unsubstituted heterocycloalkyl is a substituted or unsubstituted 4 to 8 membered heterocycloalkyl.

A "lower substituent" or "lower substituent group," as used herein, means a group selected from all of the substituents described above for a "substituent group," wherein each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_5$-$C_7$ cycloalkyl, and each substituted or unsubstituted heterocycloalkyl is a substituted or unsubstituted 5 to 7 membered heterocycloalkyl.

The term "pharmaceutically acceptable salts" is meant to include salts of the active compounds that are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, oxalic, methanesulfonic, and the like. Also included are salts of amino acids such as arginate, and salts of organic acids like glucuronic or galacturonic acids. Certain specific compounds of the present invention contain both basic and acidic functionalities that allow the compounds to be converted into either base or acid addition salts.

Thus, the compounds of the present invention may exist as salts, such as with pharmaceutically acceptable acids. The present invention includes such salts. Examples of such salts include hydrochlorides, hydrobromides, sulfates, methanesulfonates, nitrates, maleates, acetates, citrates, fumarates, tartrates (e.g., (+)-tartrates, (−)-tartrates, or mixtures thereof including racemic mixtures), succinates, benzoates, and salts with amino acids such as glutamic acid. These salts may be prepared by methods known to those skilled in the art.

The neutral forms of the compounds are preferably regenerated by contacting the salt with a base or acid and isolating the parent compound in the conventional manner. The parent form of the compound differs from the various salt forms in certain physical properties, such as solubility in polar solvents.

In addition to salt forms, the present invention provides compounds in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, tautomers, geometric isomers, and individual isomers are encompassed within the scope of the present invention. The compounds of the present invention do not include those that are known in the art to be too unstable to synthesize and/or isolate.

The compounds of the present invention may also contain unnatural proportions of atomic isotopes at one or more of the atoms that constitute such compounds. For example, the compounds may be radiolabeled with radioactive isotopes, such as for example tritium ($^3H$), iodine-125 ($^{125}I$), carbon-13 ($^{12}C$), or carbon-14 ($^{14}C$). All isotopic variations of the compounds of the present invention, whether radioactive or not, are encompassed within the scope of the present invention.

Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

As used herein, an amino acid "derivative" includes an amino acid having substitutions or modifications by covalent attachment of a parent amino acid, such as, e.g., by alkylation, glycosylation, acetylation, phosphorylation, and the like. Further included within the definition of "derivative" is, for example, one or more analogs' of an amino acid with substituted linkages, as well as other modifications known in the art.

As used herein, a "natural amino acid" refers to arginine, glutamine, phenylalanine, tyrosine, tryptophan, lysine, glycine, alanine, histidine, serine, proline, glutamic acid, aspartic acid, threonine, cysteine, methionine, leucine, asparagine, isoleucine, and valine, unless otherwise indicated by context.

As used herein, a "protecting group" refers to a moiety that when attached to a reactive group in a molecule masks, reduces or prevents that reactivity. Representative hydroxy protecting groups include acyl groups, benzyl and trityl ethers, tetrahydropyranyl ethers, trialkylsilyl ethers and allyl ethers. Representative amino protecting groups include formyl, acetyl, trifluoroacetyl, benzyl, benzyloxycarbonyl (CBZ), tert-butoxycarbonyl (Boc), trimethyl silyl (TMS), 2-trimethylsilyl-ethanesulfonyl (SES), trityl and substituted trityl groups, allyloxycarbonyl, 9-fluorenylmethyloxycarbonyl (FMOC), nitro-veratryloxycarbonyl (NVOC), and the like. Examples of a "hydroxyl protecting group" include, but are not limited to, methoxymethyl ether, 2-methoxyethoxymethyl ether, tetrahydropyranyl ether, benzyl ether, p-methoxybenzyl ether, trimethylsilyl ether, triethylsilyl ether, triisopropyl silyl ether, t-butyldimethyl silyl ether, triphenylmethyl silyl ether, acetate ester, substituted acetate esters, pivaloate, benzoate, methanesulfonate and p-toluenesulfonate.

Abbreviations used include: DMAP=4-dimethylaminopyridine; DCC=N,N'-dicyclohexylcarbodiimide; ODHBt=3,4,-dihydroxy-4-oxo-1,2,3-benzo-triazine-3-yl ester; NMM=N-methylmorpholin; EDC=1-(3-dimethylaminopropyl)-3-ethylcarbodiimide hydrochloride; DIAD=diisopropyl azodicarboxylate; DEAD=diethyl azodicarboxylate; and DIPC=N,N'-diisopropylcarbodiimide.

As used herein, a "leaving group" refers to a functional group that can be substituted by another functional group. Such leaving groups are well known in the art, and examples include, but are not limited to, a halide (e.g., chloride, bromide, and iodide), methanesulfonyl (mesyl), p-toluenesulfonyl (tosyl), trifluoromethylsulfonyl (triflate), and trifluoromethylsulfonate.

The phrase "pharmaceutically acceptable salt," as used herein, refers to pharmaceutically acceptable organic or inorganic salts of a compound (e.g., a Medicant Linker compound, or an Affinity Medicant Linker conjugate). The compound typically contains at least one amino group, and accordingly acid addition salts can be formed with this amino group. Exemplary salts include, but are not limited to, sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate, ethanesulfonate, benzenesulfonate, p-toluenesulfonate, and palmoate (i.e., 1,1'-methylene-bis-(2-hydroxy-3-naphthoate)) salts. A pharmaceutically acceptable salt may involve the inclusion of another molecule such as an acetate ion, a succinate ion or other counter ion. The counter ion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counter ion.

As used herein, a "pharmaceutically acceptable solvate" or "solvate" refer to an association of one or more solvent molecules and a compound of the invention, e.g., an Affinity Medicant Linker conjugate or a Medicant Linker compound. Examples of solvents that form pharmaceutically acceptable solvates include, but are not limited to, water, isopropanol, ethanol, methanol, DMSO, ethyl acetate, acetic acid, and ethanolamine.

The following abbreviations are used herein and have the indicated definitions: Boc is N-(t-butoxycarbonyl), cit is citrulline, dap is dolaproine, DCM is dichloromethane, DIEA is N,N-diisopropylethylamine, dil is dolaisoleuine, DMF is N,N-dimethylformamide, DMSO is dimethylsulfoxide, doe is dolaphenine, dov is N,N-dimethylvaline, DTNB is 5,5'-dithiobis(2-nitrobenzoic acid), DTPA is diethylenetriaminepentaacetic acid, DTT is dithiothreitol, Fmoc is N-(9-fluorenylmethoxycarbonyl), gly is glycine, HATU is O-(7-azabenzotriazol-1-yl)-N,N,N',N'-tetramethyluronium hexafluorophosphate, HBTU is 2-[1H-benzotriazole-1-yl]-1,1,3,3-tetramethylaminium hexafluorophosphate; HOBt is 1-hydroxybenzotriazole, HPLC is high pressure liquid chromatography, ile is isoleucine, lys is lysine, MeOH is methanol, MeVal is N-methyl-valine, PAB is p-aminobenzyl, PBS is phosphate-buffered saline (pH 7.4), Ph is phenyl, phe is L-phenylalanine, PyBrop is bromo tris-pyrrolidino phosphonium hexafluorophosphate, TFA is trifluoroacetic acid, UV is ultraviolet, and val is valine.

The following LU abbreviations are used herein and have the indicated definitions: Val Cit or vc is a valine-citrulline dipeptide site in protease cleavable linker; PABC is p-aminobenzylcarbamoyl; (Me)vc is N-methyl-valine citrulline, where the linker peptide bond has been modified to prevent its cleavage by cathepsin B; and MC(PEG)$_6$-OH is maleimidocaproyl-polyethylene glycol.

As used herein, a "pegylated compound" refers to a compound conjugated with two or more polyethylene glycol moieties or two or more polypropylene glycol moieties or a combination thereof.

As used herein, a "pro-peptide" includes pro-peptide, pre-peptide, pro-protein and pre-protein amino acid sequences including those amino acid sequences cleaved by enzymes disclosed in Table IX.

As used herein, "Illudin1" or "illudin-1" means those analogs disclosed in Table XI. As used herein "Illudin2" or "illudin2" means those analogs disclosed in Table XI and Table XII. As used herein, "acylfulvene" means "illudin2" and any analog derived therefrom.

Malignant neoplasia is the second most common cause of death in the United States behind cardiovascular disease. Chemotherapy has exerted a predominant role in increasing life spans for patients with a variety of tumors including Burkitt's lymphoma, acute lymphocytic leukemia and Hodgkin's disease. Further, new cancer chemotherapeutic agents and methods of care combined with early detection and treatment have resulted in decreases in the overall incidence of cancer and decreases in the death rates from all cancers combined. Responsive tumors represent only a small fraction of the various types of cancer. Further, agents such as cyclophosphamide, adriamycin, 5-fluorouracil and hexamethylmelamine, which are highly active against clinical solid tumors, are limited. Thus, patients with many types of malignancies remain at significant risk for relapse and mortality. After relapse, some patients can be re-induced into remission with their initial treatment regimen. However, higher doses of the initial chemotherapeutic agent or the use of additional agents are frequently required, indicating the development of at least partial medicant resistance. Evidence indicates medicant resistance can develop simultaneously to several agents, including medicant resistance to treatments to which the patient was not exposed. The development of multiple-medicant resistant tumors may be a function of tumor mass and constitutes a major cause of treatment failure. To overcome this medicant resistance, high-dose chemotherapy with or without radiation and allogenic or autologous bone marrow transplantation can be employed. The high-dose chemotherapy may employ the original medicant(s) or be altered to include additional agents. As a result, there remain many cancer patients for whom no or minimally effective therapy exists. Accordingly, there is a need for the development of novel chemotherapeutics with greater efficacy or safety, either as monotherapy or in combination with other chemotherapeutic agents, and such agents with the potential to overcome medicant resistance in cancer cells.

Figure 19A:
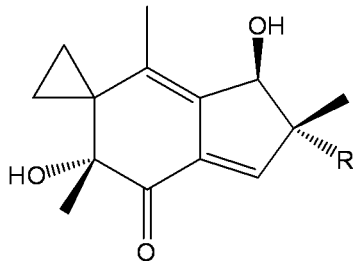
FIG. 19A shows an illudin analog according to various embodiments of the invention.
Figure 19B:
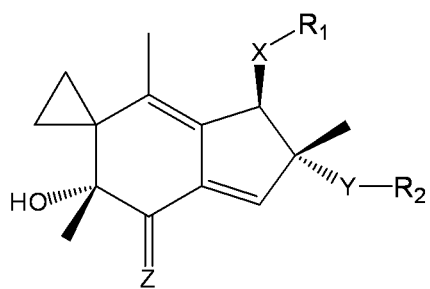
FIG. 19B shows a syn-illudin analog according to various embodiments of the invention.
Figure 19C:
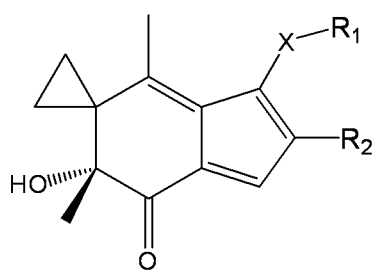
FIG. 19C and FIG. 19D show acylfulvene analogs according to various embodiments of the invention.
Figure 19D:
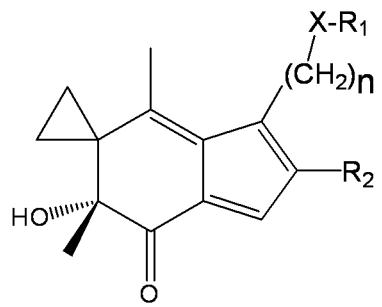

Illudins are toxic natural products produced by mushrooms of the genus *Omphalotus* (FIG. 19A). Syn-Illudins are semi-synthetic derivatives of Illudins. Acylfulvenes are also semi-synthetic derivatives of Illudins. Syn-Illudins and Acylfulvenes have each been chemically modified at select sites to allow their use as medicants. The modifications in the Syn-Illudins do not alter any of the cyclic rings (cyclopropane, cyclopentane, cyclohexane) of the basic Illudin chemical structure (FIG. 19B). The modifications of Acylfulvenes differ from Syn-Illudins in that an additional double bond (an unsaturated bond) has been created in the 5 membered (cyclopentane) ring (FIG. 19C, FIG. 19D).

Figure 6:
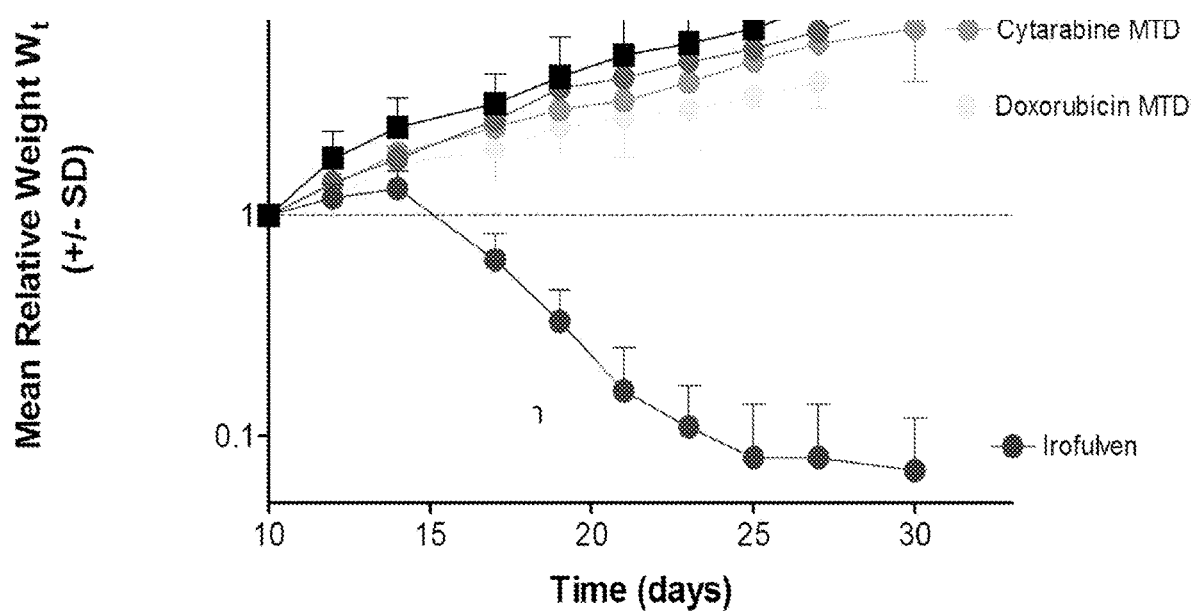
FIG. 6 shows the tumor regression of an acylfulvene analog, according to an embodiment of the invention.

Illudins function as alkylating agents that damage DNA and thereby block transcription. The blockage can be repaired through nucleotide excision. The toxicity of the illudins has prevented any applications in human tumor therapy. Acylfulvenes have been developed which exhibit promising antitumor activity with a better safety profile, as described in U.S. Pat. Nos. 5,439,936; 5,523,490 and 6,380,403 which are each herein expressly incorporated by reference in their entireties. Irofulven or 6-hydroxymethylacylfulvene (see FIG. 6) is an analog of illudin S which has demonstrated clinical activity with an acceptable safety profile in hormone-refractory prostate cancer. Most relevant to clinical applications, irofulven activity is independent of common resistance mechanisms such as the multi-medicant resistance phenotype, anti-apoptotic B-cell lymphoma 2 (Bcl-2) (SEQ. ID. 056) over expression, as well as tumor protein 53 (p53) (SEQ. ID. 057) and cyclin dependent kinase inhibitor 1 (p21/WAF1) (SEQ. ID. 058) mutations (see FIG. 7 and Table XIV).

Growth factors, including peptides and proteins are critical mediators of a wide range of cell-cell communication. They are important endocrine, paracrine and autocrine messengers. Growth factors function as neurotransmitters and neuromodulators, regulate chemotaxis, immune function, development, cell growth, and can influence tumor cells. The receptors that recognize growth factors are highly selective and define specific cell populations. As a result, growth factor receptors are a large and important class of medicant (including drug) targets. In addition to physiologic noncancerous cell populations, these receptors can also be expressed in various cancer cell populations.

A polypeptide is a long, continuous, and unbranched chain of amino acids. A glycol-peptide is a peptide that contains one or more carbohydrate moieties covalently attached to the side chains of specific amino acids. A pro-peptide, is an inactive peptide that can be turned into an active form through a post translational modification that enzymatically cleaves the pro-peptide. Examples include pro-insulin (SEQ. ID. 059) and pro-opiomelanocortin (SEQ. ID. 060). Enzymatically cleaving the pro-peptide, allows for the peptide to be available on short notice and/or in large quantities. Some pro-peptides are secreted from the cell. Many of these are synthesized with an N-terminal signal peptide that targets the pro-peptide for secretion.

Cytokines are small proteins (approximately 5 to 20 kDa) that affect the behavior of other cells, and sometimes the releasing cell itself and are thereby important in cell signaling (see Table XIV). Many specific cytokines can be released by a variety of different kinds of cells, e.g., macrophages, B lymphocytes, T lymphocytes, mast cells, endothelial cells, fibroblasts, and various stromal cells. Cytokines act through specific receptors, and are important in the humoral and cell-based immune responses. Cytokines also regulate the maturation, growth, and responsiveness of specific cell populations. Cytokines circulate in much higher concentrations than hormones and in contrast with hormones are made by a variety of different kinds of cells. Cytokines are important in host responses to infection, immune responses, inflammation, trauma, sepsis, cancer, and reproduction. As a result, cytokine receptors are upregulated in many forms of cancers.

A steroid is an organic compound that contains four cycloalkane rings joined to each other. Examples of steroids include the dietary lipid cholesterol and the sex hormones estradiol and testosterone. The core of a steroid molecule is composed of seventeen carbon atoms bonded together that take the form of four fused rings: three six-carbon atom rings and one five-carbon atom ring. A variety of functional groups can be attached to the four-ring core. Steroids can also vary depending on the oxidation state of the rings. A steroid hormone is a steroid that acts as a hormone. Steroid hormones can be grouped into five groups (glucocorticoids, mineralocorticoids, androgens, estrogens, and progesterones) based on the receptors to which they bind. Steroid hormones, particularly androgens, are essential not only for growth and development but also in the progression of many forms of cancer. As a result, steroid hormone receptors are upregulated in many forms of cancers.

The retinoic acid receptor (RAR) is a nuclear receptor which can also act as a transcription factor. The RAR can be activated by either all-trans retinoic acid or 9-cis retinoic acid. There are three RAR isoforms (alpha (SEQ. ID. 061), beta (SEQ. ID. 062), and gamma (SEQ. ID. 063)), each encoded by separate genes, where splice variants generate still further diversity in the expressed receptor. The retinoid X receptor (RXR) is a nuclear receptor activated by 9-cis retinoic acid. There are also three RXR isoforms (alpha (SEQ. ID. 064), beta (SEQ. ID. 065), and gamma (SEQ. ID. 066)), each encoded by separate genes. RXR hetero-dimerizes with subfamily 1 nuclear receptors including RAR. In the absence of ligand, the RAR/RXR dimer binds to retinoic acid response elements complexes with a co-repressor protein. Binding of agonist ligands to RAR results in dissociation of the co-repressor and recruitment of a co-activator protein that, in turn, promotes transcription of the downstream target gene into mRNA and thereby protein or other RNA signaling mechanisms.

Lipid metabolism is altered in many forms of cancer, including upregulation of de novo lipid synthesis. Cancer cells can also use alternative enzymes and pathways to facilitate the production of fatty acids. These newly synthesized lipids may support a number of cellular processes to promote cancer cell proliferation and survival. Elaidic acid or (E)-octadec-9-enoic acid is the trans isomer of oleic acid and is found in small quantities in caprine milk, bovine milk and some meats. It increases Cholesteryl Ester Transfer Protein (CETP) (SEQ. ID. 067) activity, which in turn raises levels of very low density lipoprotein and lowers levels of high density lipoprotein (HDL) cholesterol. CETP is found in plasma, where it is involved in the transfer of cholesteryl ester from HDL to other lipoproteins. Defects in the CETP gene are a cause of hyperalphalipoproteinemia 1.

An antibody is a protein made up of four peptide chains disulfide linked together to form a "Y"-shape. Antibodies are produced by plasma cells and are used by the immune system to identify and neutralize foreign antigens such as bacteria and viruses. The antibody recognizes a unique part of the antigen using each FAB portion of the protein (i.e., the tip of the "Y" portion of the antibody), allowing a specific high affinity binding interaction to occur. The binding interaction of different antibodies can target specific antigen epitopes. An antibody fragment containing one or both FAB portions can also target specific antigen epitopes.

The ability of the Illudin, Syn-Illudin and Acylfulvene analogs to inhibit tumor cell growth is shown in Table XV. The MV522 cell line is a lung-derived adenocarcinoma cell line. In various embodiments of the invention, the MV522 cell line represents a "target" cell line. That is an Illudin, Syn-Illudin or Acylfulvene analog that exhibits toxicity against this solid tumor cell line shows a desirable result. The 8392B cell line represents a hematopoietic (non-solid) cell line. In various embodiments of the invention, the 8392B cell line is considered a "nontarget" cell line. The two hour toxicity data represents the concentration of a given analog for which a two hour exposure will inhibit 50% of the DNA synthesis activity in a given cell line. The 48 hour exposure data represents the concentration at which a given analog with a 48 hour exposure will inhibit the growth or viability in a given cell line as defined by the standard Trypan Blue Exclusion assay. As an example, analog 002 will inhibit the target MV522 cell line at 110 nM with only a 2 hour exposure but has no inhibitory effect on the nontarget 8392B cell line at 26,000 nM (26 µM). Analog 002 with a prolonged exposure period (e.g. 48 hours) can eventually inhibit the nontarget cell line. In contrast, Analog 201 will inhibit the target MV522 cell line with only a 2 hour exposure (IC50=360 nM) but has minimal effect on the 8392B cell nontarget line with even a 48 hour exposure (IC50=26,000 nM) indicating, superior anticancer activity as a monotherapeutic agent. In contrast to these two analogs, analog 224 displayed minimal toxicity as well as no differential toxicity between the target and nontarget cell line indicating it would have minimal properties as a monotherapeutic anticancer agent.

As used herein, a "growth factor" or an "anti-angiogenic protein" includes Adrenomedullin (SEQ. ID. 068), Angiopoietin (Ang) (SEQ. ID. 069, 106, 111, and 145), Autocrine motility factor (SEQ. ID. 070), Bone morphogenetic proteins (BMPs) (SEQ. ID. 071), Brain-derived neurotrophic factor (BDNF) (SEQ. ID. 072), Endostatin (SEQ. ID. 073), Endostar (SEQ. ID. 074), Epidermal growth factor (EGF) (SEQ. ID. 075), Erythropoietin (EPO) (SEQ. ID. 076), Fibroblast growth factor (FGF) (SEQ. ID. 077), Glial cell line-derived neurotrophic factor (GDNF) (SEQ. ID. 078), Granulocyte colony-stimulating factor (G-CSF) (SEQ. ID. 079), Granulocyte macrophage colony-stimulating factor (GM-CSF) (SEQ. ID. 080), Growth differentiation factor-9 (GDF9) (SEQ. ID. 081), Hepatocyte growth factor (HGF) (SEQ. ID. 082), Hepatoma-derived growth factor (HDGF) (SEQ. ID. 083), Insulin-like growth factor (IGF) (SEQ. ID. 084), Migration-stimulating factor (SEQ. ID. 085), Myostatin (GDF-8) (SEQ. ID. 086), Nerve growth factor (NGF) (SEQ. ID. 087) and other neurotrophins (SEQ. ID. 144), Platelet-derived growth factor (PDGF A) (SEQ. ID. 088), PDGF B (SEQ. ID 168), PDGF C (SEQ. ID. 036), PDGF D (SEQ. ID. 037), Thrombopoietin (TPO) (SEQ. ID. 089), Transforming growth factor alpha(TGF-α) (SEQ. ID. 090), Transforming growth factor beta(TGF-β) (SEQ. ID. 091), Tumor necrosis factor-alpha(TNF-α) (SEQ. ID. 092), Vascular endothelial growth factor (VEGF) (SEQ. ID. 093), and placental growth factor (P1GF) (SEQ. ID. 094).

As used herein, a "protein toxin" includes ricin A chain (SEQ. ID. 095), ricin B chain (SEQ. ID. 096), diphtheria toxin (SEQ. ID. 097), *Pseudomonas aeurginosa* exotoxin A (SEQ. ID. 098), r-gelonin (SEQ. ID. 099), saporin (SEQ. ID. 100), glycosylated protein toxins, deglcosylated protein toxins and protein toxin fragments which includes deglycosylated ricin A, deglycosylated ricin B, *Pseudomonas aeurginosa* exotoxin A PE40 fragment (SEQ. ID. 101) and *Pseudomonas aeurginosa* exotoxin A PE38 fragment (SEQ. ID. 102).

As used herein, a "steroid" includes cholesterol (5-cholesten-3beta-ol), pregnenolone (3beta-hydroxy-5-pregnen-20-one), 17-hydroxyprenenolone (3-beta,17-dihydroxy-5-pregnen-20-one), progesterone (4-pregnene-3,20-dione), 17-hydroxyprogesterone (17-hydroxy-4-pregnene-3,20-dione), androstenedione (4-androstene-3,17-dione), 4-hydroxyandrostenedione (4-hydroxy-4-androstene-3,17-dione), 11-beta-hydroxyandostenedione (11beta-4-androstene-3,17-dione), androstanediol (3-beta,17-beta-Androstanediol), androsterone (3-alpha-hydroxy-5alpha-androstan-17-one), epiandrosterone (3-beta-hydroxy-5alpha-androstan-17-one), adrenosterone (4-androstene-3,11,17-trione), dehydroepiandrosterone (3beta-hydroxy-5-androsten-17-one), dehydroepiandrosterone sulfate (3-beta-sulfooxy-5-androsten-17-one), testosterone (17beta-hydroxy-4-androsten-3-one), epitestosterone (17-alpha-hydroxy-4-androsten-3-one), 5-alpha-dihydrotesterone (17-beta-hydroxy-5alpha-androstan-3-one), 5-beta-dihydrotestosterone (17-beta-hydroxy-5beta-androstan-3-one), 11-beta-hydroxytesosterone (11-beta,17beta-dihydroxy-4-androsten-3-one), 11-ketotesosterone (17-beta-hydroxy-4-androsten-3,17-dione), estrogen (including: estrone (3-hydroxy-1,3,5(10)-estratrien-17-one), estradiol (1,3,5(10)-estratriene-3,17beta-diol), and estriol (1,3,5(10)-estratriene-3,16alpha,17beta-triol)), corticosterone (11-beta,21-dihydroxy-4-pregnene-3,20-dione), deoxycorticosterone (21-hydroxy-4-pregnene-3,20-dione), cortisol (11-beta,17,21-trihydroxy-4-pregnene-3,20-dione), 11-deoxycortisol (17,21-dihydroxy-4-pregnene-3,20-dione), cortisone (17, 21-dihydroxy-4-pregnene-3,11,20-trione), 18-hydroxycorticosterone (11-beta,18,21-trihydroxy-4-pregnene-3,20-dione), 1-alpha-hydroxycorticosterone (1-alpha,11-beta,21-trihydroxy-4-pregnene-3,20-dione), and aldosterone (18,11-hemiacetal of 11beta,21-dihydroxy-3,20-dioxo-4-pregnen-18-al).

As used herein, a "Specific Binding Peptide" includes an "anti-angiogenic peptide" (SEQ. ID. 146) and an "integrin binding peptide" (SEQ. ID. 147). A "Specific Binding Peptide" includes integrin binding peptide RGD4C=CDCRGDFC (SEQ. ID. 147), integrin binding peptide RGD10 (SEQ. ID. 148), c(RGDyK) (SEQ. ID. 149), integrin binding peptide c(RGDfK) (SEQ. ID. 150), integrin binding peptide [c(RGDyK)]2 (SEQ. ID. 151), integrin binding peptide CAGKNFFWKTFTSC (SEQ. ID. 152), cilengitide (cyclic RGD pentapeptide) (SEQ. ID. 153), ATN-161 (peptide antagonist of integrin alpha5beta1) (SEQ. ID. 154), ATN-454 (Ac—PHSCN—NH$_2$) (peptide antagonist of integrin alpha5beta1) (SEQ. ID. 155), tumstatin T7 peptide TMPFLFCNVNDVCNFASRNDYSYWL (SEQ. ID. 156), tumstatin sequence 1 YSNS (SEQ. ID. 157), tumstatin sequence 2 YSNSG (SEQ. ID. 158), endostatin motif FLSSRLQDLYSIVRRADRAA (SEQ. ID. 159), endostatin motif IVRRADRAAVP (SEQ. ID. 160), laminin peptide A13 (RQVFQVAYIIKA) (SEQ. ID. 161), laminin peptide C$_{16}$ (KAFDITYVRLKF) (SEQ. ID. 162), laminin peptide C16S (DFKLFAVTIKYR) (SEQ. ID. 163), and VEGFR1 peptide (CPQPRPLC) (SEQ. ID. 164).

As used herein, a traditional linker includes linkers that can be formed from those reagents disclosed in Tables IA-ID, IIA-IID, IIIA-IIIC, IVA-IVC, VA-VB, and VIA-VID.

Figure 15A:
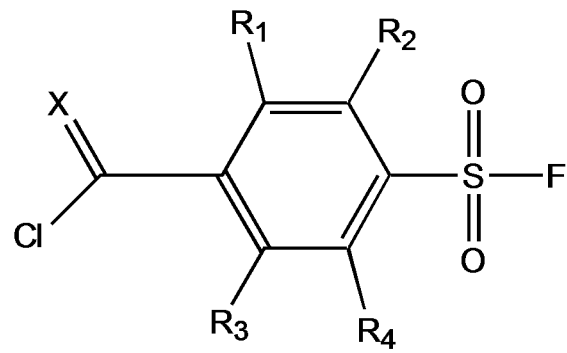
FIG. 15A shows the structures of 4-fluorosulfonyl benzoyl.
Figure 15B:
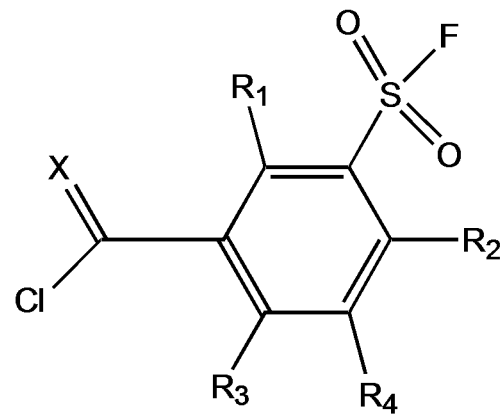
FIG. 15B shows the structure of 4-fluorosulfonyl benzoyl, 3-fluorosulfonyl benzoyl.
Figure 15C:
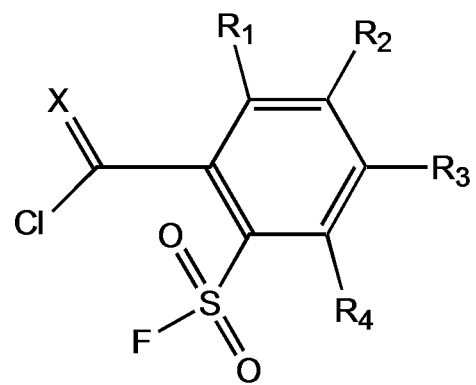
FIG. 15C show the structures of 2-fluorosulfonyl benzoyl where $R_1$, $R_2$, $R_3$, and $R_4$ independently denote H, F, Cl, Br and I.
Figure 16A:
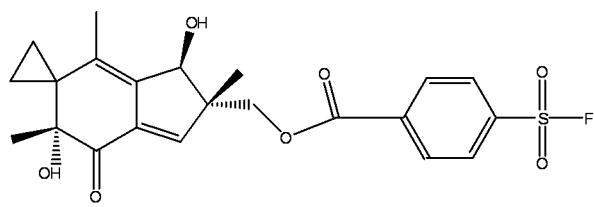
FIG. 16A shows the structure of the Illudin S FSB mono-substituted on the primary hydroxy reagent according to an embodiment of the invention.
Figure 16B:
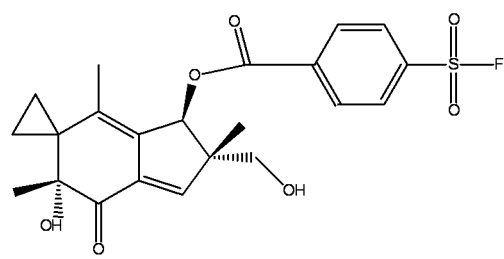
FIG. 16B shows the structure of the Illudin S FSB mono-substituted on the secondary hydroxy reagent according to an embodiment of the invention.
Figure 16C:
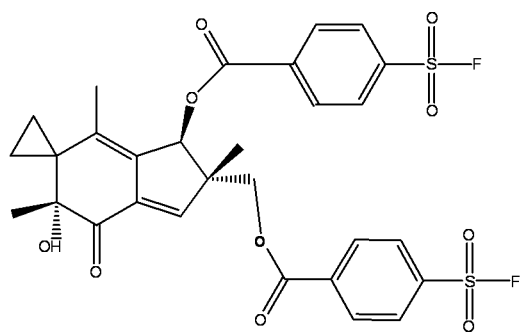
FIG. 16C shows the structure of the Illudin S FSB di-substituted reagent according to an embodiment of the invention.
Figure 17:
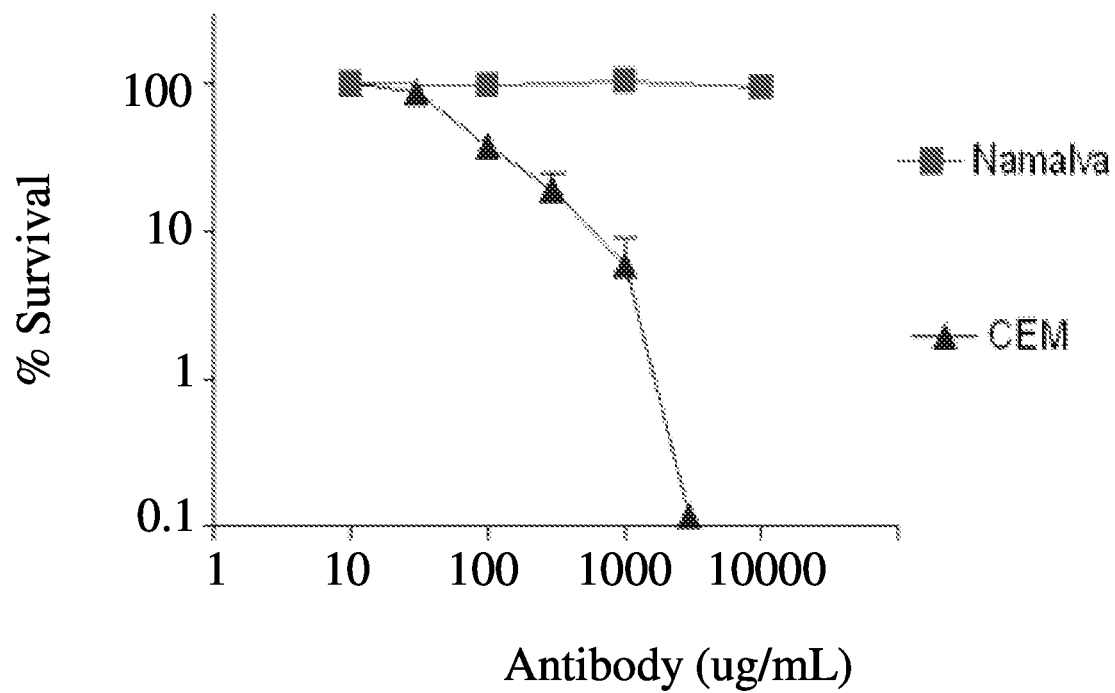
FIG. 17 shows the response of an ADC made by combining analog 316 with the T101 antibody according to an embodiment of the invention, where the percent of control is plotted versus the concentration of Namalva, a negative control (i.e., a cell line not expressing T101) where the $IC_{50}$>1000 ng/mL and CEM, a positive control (i.e., a cell line expressing T101) where the $IC_{50}$<5 ng/mL, after a four (4) hour exposure and then eighteen (18) hour recovery, where the toxin to antibody ratio is 5:1 (as determined using a radiolabelled toxin) and where the concentration is in Illudin equivalents (ng of Illudin attached to antibody per mL of cell culture media), which demonstrates the ability of T101-316 ADC to kill cells expressing T101 antigen on their surface but not cells that fail to express the T101 antigen.
Figure 18A:
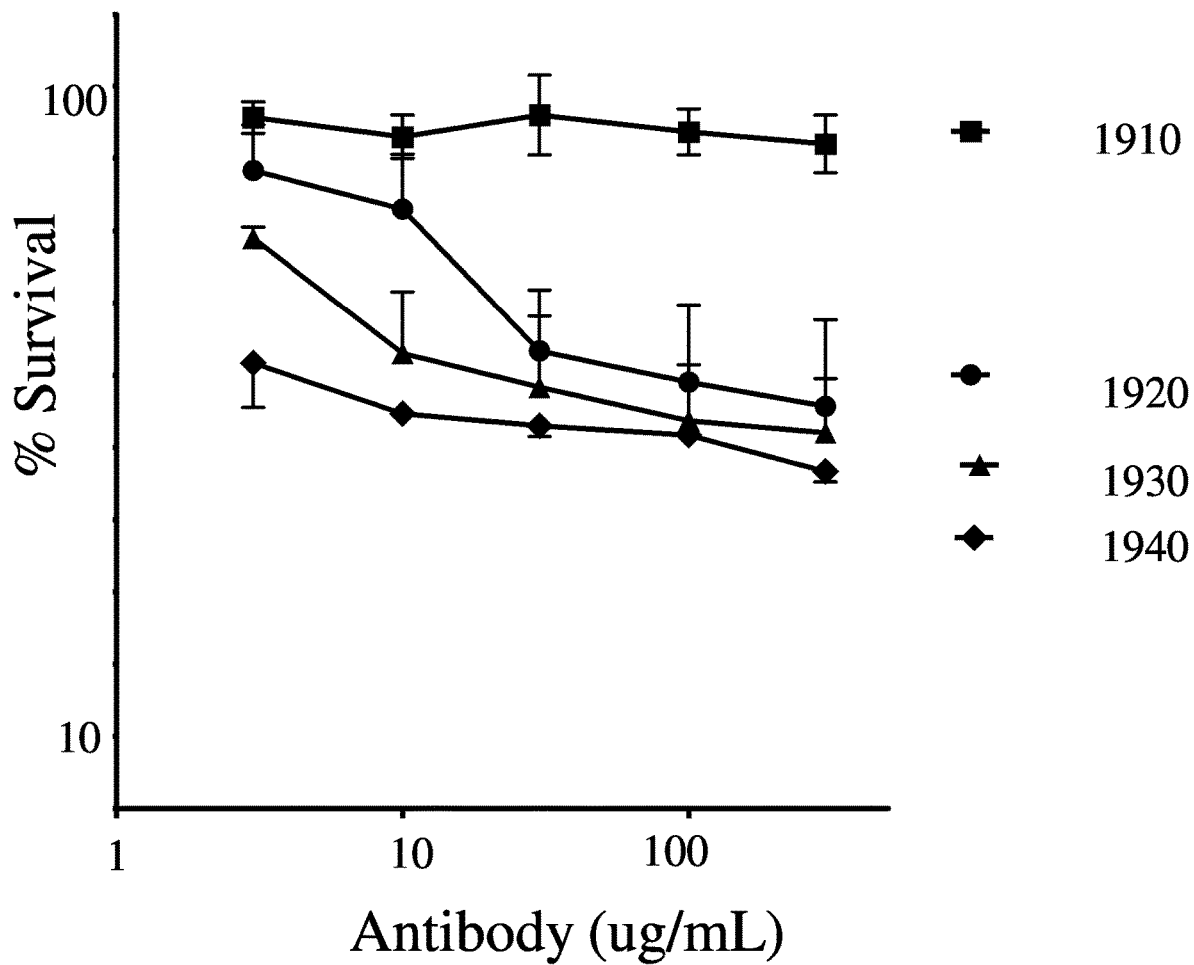
FIG. 18A shows the activity (percent survival of the Rituxin antibody alone is proportional to CD20 expression on B cells (where MV522 cells are CD20 negative 1910, 8392 cells express low numbers of CD20 1920, Raji express medium numbers of CD20 1930 and Ramos express high numbers of CD20 molecules) 1940, and where B cells are relatively resistant to Illudins and irofulvens (48 hr $IC_{50}$>7,000 nM)
Figure 18B:
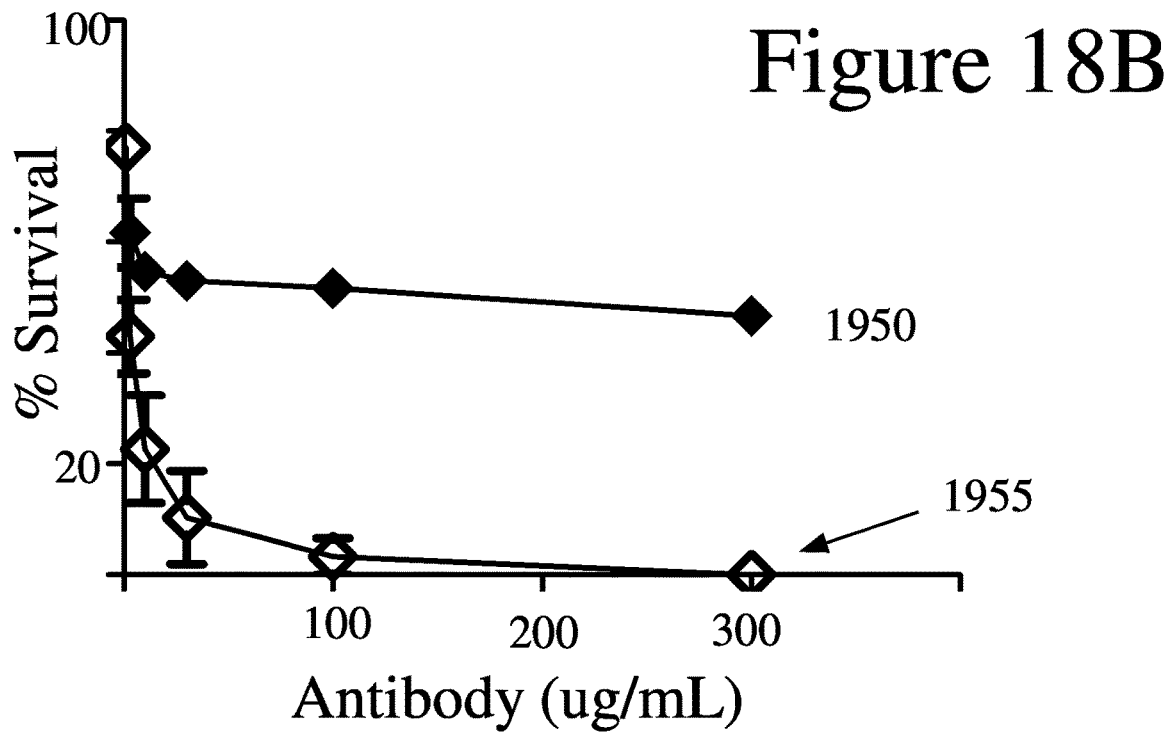
FIG. 18B shows the activity of the Rituxin antibody alone 1950 compared with an ADC of Rituxin with analog 218 on Ramos cells 1955.
Figure 18C:
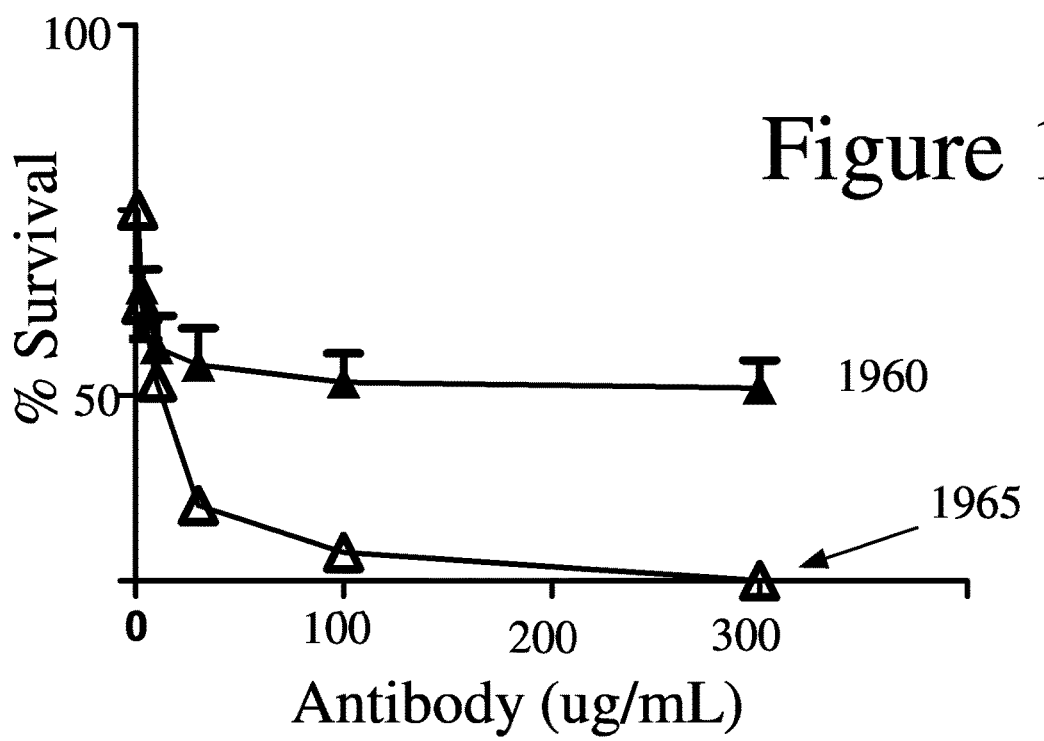
FIG. 18C shows the activity of the Rituxin antibody alone 1960 compared with an ADC of Rituxin with analog 218 on Raji cells 1965.
Figure 18D:
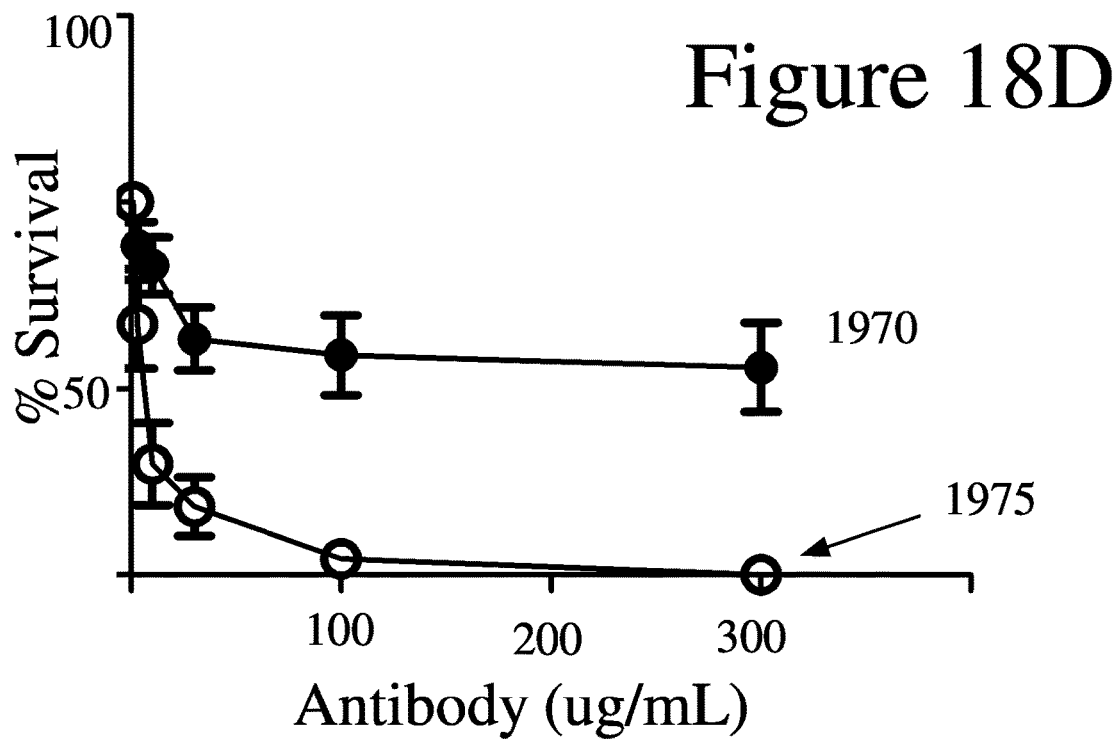
FIG. 18D shows the activity of the Rituxin antibody alone 1970 compared with an ADC of Rituxin with analog 218 on 8392 cells 1975.
Figure 18E:
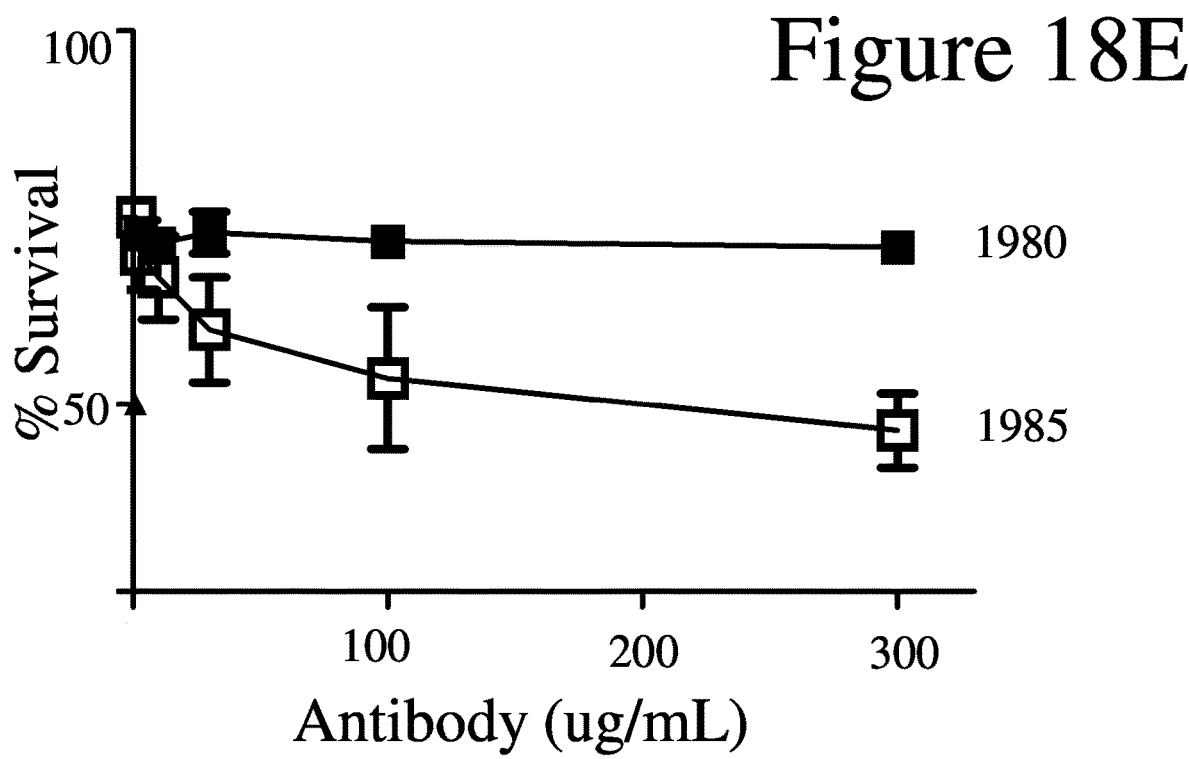
FIG. 18E shows the activity of the Rituxin antibody alone 1980 compared with an ADC of Rituxin with analog 218 on MV522 cells (where MV522 cells grew in the presence of the Rituxan-analog 218 ADC but at a slower rate than in the absence of analog 218 ADC) 1985).

As used herein, a "FSB linker" includes those linkers selected from the group consisting of 4-fluorosulfonyl benzoyl, 3-fluorosulfonyl benzoyl and 2-fluorosulfonyl benzoyl as depicted in FIG. 15.

As used herein, a "Mall" linker includes a malonic linker and a maleimide linker covalently attached to an Illudin, Syn-Illudin, or Acylfulvene.

As used herein, a "protease" includes those enzymes disclosed in Table IX.

As used herein, a "cytokine" includes chemokines, interferons, interleukins, lymphokines, tumor necrosis factor, neutrophil activating protein-2, and monocyte chemotactic protein-1 and those compounds disclosed in Table XIV.

Despite recent advances in therapy, many patients with cancer invariably relapse and require additional treatments. Most of these patient's cancers become refractory to standard chemotherapy and/or radiation treatment regimens. The prognosis for these patients is poor and long term survival rates for metastatic solid tumor cancers remain very low. Thus, there is a need for the development of novel agents and treatment regimens that specifically target these recurring tumor cells and also produce less systemic toxicity. Target therapies, such as monoclonal antibodies, now provide a promising alternative to the conventional cytotoxic chemotherapy approach.

Monoclonal antibody based therapy has recently achieved considerable success in oncology and there are currently nine monoclonal antibodies (without a medicant attached) approved by the FDA as cancer therapeutics. As an example, HERCEPTIN® and RITUXAN® (both produced by Genentech, South San Francisco, California), are used to successfully treat breast cancer and non-Hodgkin's lymphoma, respectively. HERCEPTIN® is a recombinant DNA-derived humanized monoclonal antibody selectively binding to the extracellular domain of the Human Epidermal growth factor Receptor 2 (HER2) proto-oncogene whereas RITUXAN® is a genetically engineered chimeric murine/human monoclonal antibody directed against the CD20 antigen overexpressed on the surface of normal and malignant B lymphocytes.

Recent clinical evidence indicates that while the monoclonal antibody based therapies are effective at inducing remission, they do not always produce a complete cure, and relapses eventually occur in most patients. There is now a tremendous interest in the use of antibody medicant conjugates as a class of therapeutics that utilize the antigen-selectivity of monoclonal antibodies to deliver potent cytotoxic medicants to specific tumor cells. Antibody medicant conjugates are produced by attaching a cytotoxic agent to an antibody that binds specifically to a tumor-associated antigen.

In theory, antibody medicant conjugates can confer an increased therapeutic index to highly potent medicants by improving therapeutic efficacy and reducing systemic toxicity (by minimizing damage to normal tissues), although this goal has been elusive in achieving. The basis for the efficacy of antibody medicant conjugates is that they target tumor cells that preferentially express an antigen that is recognized by the associated antibody. In contrast, non-tumor cells either fail to express this antigen, or express the antigen at a very low level. In theory, only the tumor cells expressing the associated antibody are recognized and destroyed by the AMC, and other cells are left untouched and undamaged.

While different medicant classes have been tried for delivery via antibodies, only a few have proved efficacious for use as antibody medicant conjugates. The two main medicant classes used to date to produce antibody medicant conjugates are the auristatins (MMAE/N-methylvaline-valine-dolaisoleuine-dolaproine-norephedrine or MMAF/N-methylvaline-valine-dolaisoleuine-dolaproine-phenylalanine) and the maytansines (DM1 or DM4). Currently only two antibody medicant conjugates are approved by the U.S.F.D.A. and marketed; brentuximab vedotin (auristatin based) and ado-trastuzumab emtansine (maytansine based).

Illudins (see FIG. 19A, where R=$CH_3OH$ or OH), Syn-illudins (see FIG. 19B, where X or Y=C, N, S, O and Z=O or NH or NOH), and Acylfulvenes (see FIG. 19C and FIG. 19D, where X=C, N, S, O and n>1) have several unique properties over agents traditional used to make antibody drug conjugates (ADCs). Firstly, these are the only agents known to function by inhibition of the DNA transcription-coupled repair pathway (see FIG. 5). No other toxin, drug or medicant inhibits this pathway. The result is that Illudins, Syn-illudins, and Acylfulvenes are true cytotoxic agents whereas other agents traditionally used to produce ADCs (pyrrolobenzodiazepines, maytansines, fumagillols, dolstatins, auristatins, enadiynes, halichondrins, and tubulysins) are only cytostatic. In the NCI-DTP 60 cell line panel these other agents were capable of inhibiting tumor cell growth ($IC_{50}$ value), had some ability to block tumor cell growth (TGI value) but none were capable of actually causing tumor cell death or cytotoxicity (Table XIII). The illudin derivatives, however, are capable of killing tumor cells at nanomolar concentrations (Table XIII). This means that while ADCs developed using other toxins can stall tumor cell growth, they cannot actually kill the tumor cell. Once the effect of the drug has worn off the tumor cells will again grow and kill the patient. In contrast, the Illudins, Syn-illudins, and Acylfulvenes actually kill the tumor cell with as little as a 2 hour exposure (see FIG. 4). Secondly, whereas tumor cells will undergo apoptosis or cell death with hours once the DNA transcription-coupled repair pathway is blocked, normal diploid non-tumor cells can survive for hours. This translates into a wide therapeutic window for ADCs developed with Illudins, Syn-illudins, and Acylfulvenes. The two ADC agents currently FDA approved for administration deliver a dose of the associated toxin that is 300% higher than a lethal dose which is why these agents have severe systemic toxicity. In contrast, the comparable ADC developed with Illudins, Syn-illudins, or Acylfulvenes will deliver a dose of the associated toxin that is 40% of a known non-toxic dose (estimated at 28% of a toxic dose and only 12% of a lethal dose). Thus, ADCS developed with Illudins, Syn-illudins, and Acylfulvenes will have minimal systemic toxicity as compared to current agents. Thirdly, these agents are stable down to a pH of 2.0. An ADC is engulfed by a tumor cell, transported to the endosomes (pH<6.0) and then into the lysozomes (pH<4). Many agents used for ADCs will degrade in these low pH environment, whereas Illudins, Syn-illudins, and Acylfulvenes are stable. 4) Cancer cells can become resistant to various toxins and drugs through the development of what is termed multi-drug resistance. This process is known to occur through several different mechanisms. Whereas other toxins and drugs are substrates for the most common MDR mechanisms (MDR1/gp170 and MRP/gp180), and cancer cells can become resistant to these agents, the Illudins, Syn-illudins, and Acylfulvenes remain active against all MDR phenotypes regardless of the mechanism (see FIG. 7 and Table XIV). Hence, if tumor cells have already developed multi-drug resistance prior to ADC with a conventional toxin, or during the administration of a course of the ADC, the ADC will have no efficacy. In contrast, ADCs developed with Illudins, Syn-illudins, or Acylfulvenes will continue to kill cancer cells.

The present invention is based on the unexpected discovery that acylfulvenes, can be conjugated directly to a linker, via a variety of peptide or non-peptide bonds, and are active as medicant delivery agents in vitro and in vivo. Similar to other medicant classes used to produce antibody medicant conjugates, the acylfulvenes can be conjugated to a linker that allows subsequent coupling to a monoclonal antibody. Surprisingly, unlike previous medicant classes such as the auristatins (MMAE, MMAF, dolstatin-10), the maytansines (DM1 or DM4), the irinotecans and their metabolites (SN38), the calicheamicins (17-DMAG), the pyrrolobenzodiazepines (SJG-136), the duocarmycins (CC-1065), many of the acylfulvene compounds do not require a linker and can be directly attached to a monoclonal antibody or fragment thereof by a variety of simple chemical reactions. In this sense, the lack of requirement for a linker or a spacer, the acylfulvene compounds are unique. They will directly form covalent bonds with reactive groups on an AM such as a monoclonal antibody. In addition, because of their very small size and extreme cytotoxicity the acylfulvenes can be coupled directly to very small molecular weight entities (or affinity moieties) that allow tumor specific cytotoxicity without the concomitant requirement of use of a monoclonal antibody. Examples include the ability to link illudins/acylfulvenes directly to steroids which allow the medicant-affinity complex to kill cells overexpressing a specific steroid receptor (such as estrogen- or progesterone-positive breast cancer cells) or even to be chemically coupled to various lipids. The small size and extreme cytotoxicity acylfulvenes allows direct coupling to peptides which can preferentially bind to tumor cells (integrin binding peptides) or display anti-angiogenic properties to hinder tumor invasion. The illudins/acylfulvenes can also be coupled to specific peptides which actually renders the medicant-affinity complex non-toxic until the peptide is cleaved by a protease secreted by tumor cells. An example includes PSA (prostate specific antigen) secreted by prostate adenocarcinoma cells. Again, unlike previous medicant classes such as the auristatins (MMAE, MMAF, dolstatin-10), the maytansines (DM1 or DM4), the irinotecans and their metabolites (SN38), the calicheamicins (17-DMAG), the pyrrolobenzodiazepines (SJG-136), the duocarmycins (CC-1065), the acylfulvene compounds do not require a linker and can be directly attached to a steroid or a peptide that will subsequently function as an AM and direct the associated complex to specific tumor cells. An acylfulvene is attached to either a Specific Binding Peptide or a peptide which if cleaved by a specific protease (see Table IX) such as PSA generates an entity which is cytotoxic (see Table VIII).

Trastuzumab emtansine (Genentech for Breast cancer) uses maytanasine derive DM-1, a stable non-cleavable linker Brentuximab vedotin (Seattle Genetics/Takeda for Hodgkin's Lymphoma) uses auristatin MMAE to anti-CD30, an enzyme sensitive cleavable linker.

The malonic linker, maleimide linker and SMCC [succinimidyl 4-(N-maleimidomethyl)-cyclohexane-1-carboxylate] linker can form active intermediates that react with sulfhydryl groups on an antibody. SMCC has been used to bind maytansine derivative DM1 to the monoclonal antibody Herceptin. The AMC was internalized where the Herceptin was degraded by proteases and DM1 was released into the cytosol. Further, Sulfo-SMCC [sulfosuccinimidyloxycarbonyl-α-methyl-α-(2-pyridyldithio)toluene] forms an active intermediate that reacts with sulfhydryl groups on an antibody. The resulting Sulfo-SMCC AMC is more water soluble than the SMCC AMC.

Compounds and Conjugates. The present invention is drawn to a series of compounds and conjugates containing a Medicant moiety (M) linked via its C terminus to a LU (LU). The LU can operate to provide a suitable release of M.

In one group of embodiments, the invention provides Medicant Linker compounds having Formula I: LU-M (I) or a pharmaceutically acceptable salt or solvate thereof where the medicant loading is represented by p, the average number of medicant molecules per affinity (e.g., an antibody) (e.g. of Formula II, IIa, IIa'). Medicant loading may range from 1 to 20 Medicant units (M) per Affinity unit (e.g., Ab or in Ab). Compositions of Formula IIa and Formula IIa' include mixtures of antibodies conjugated with a range of medicants, from 1 to 20.

In some embodiments, p is from about 1 to about 8 Medicant units per Affinity unit. In some embodiments, p is 1. In some embodiments, p is from about 2 to about 8 Medicant units per Affinity unit. In some embodiments, p is from about 2 to about 6, 2 to about 5, or 2 to about 4 Medicant units per LU. In some embodiments, p is about 2, about 4, about 6 or about 8 Medicant units per Affinity unit.

The average number of Medicants units per Affinity unit in a preparation from a conjugation reaction may be characterized by conventional means such as mass spectroscopy, ELISA assay, and HPLC. The quantitative distribution of Affinity Medicant Linker conjugates in terms of p may also be determined. In some instances, separation, purification, and characterization of homogeneous Affinity Medicant Linker conjugates, where p is a certain value from Affinity Medicant Linker conjugates with other medicant loadings may be achieved by means such as reverse phase HPLC or electrophoresis.

Returning to Formula IIa', the conjugates comprise an antibody covalently attached to one or more Medicant units (moieties) via a LU: A, a, W and w are as described above. The antibody medicant conjugate include pharmaceutically acceptable salts or solvates thereof.

The medicant loading is represented by p, the average number of Medicant units per antibody in a molecule of Formula II. Medicant loading may range from 1 to 20 medicants (M) per Ab or mAb. Compositions of the AMC of Formula IIa' include mixtures of antibodies conjugated with a range of medicants, from 1 to 20. In some embodiments, p is from about 1 to about 8 Medicant units per antibody. In some embodiments, p is 1. In some embodiments, p is from about 2 to about 8 Medicant units per antibody. In some embodiments, p is from about 2 to about 6, 2 to about 5, or 2 to about 4 Medicant units per antibody. In some embodiments, p is about 2, about 4, about 6 or about 8 Medicant units per antibody.

The average number of medicants per antibody in preparations of AMCs from conjugation reactions may be characterized by conventional means such as UV/visible spectroscopy, mass spectrometry, ELISA assay, and HPLC. The quantitative distribution of AMCs in terms of p may also be determined. In some instances, separation, purification, and characterization of homogeneous AMCs where p is a certain value from AMC with other medicant loadings may be achieved by means such as reverse phase HPLC or electrophoresis.

For some antibody medicant conjugates, p may be limited by the number of attachment sites on the antibody. For example, where the attachment is a cysteine thiol, an antibody may have only one or several cysteine thiol groups, or may have only one or several sufficiently reactive thiol groups through which a LU may be attached. In some embodiments, the cysteine thiol is a thiol group of a cysteine residue that forms an interchain disulfide bond. In some embodiments, the cysteine thiol is a thiol group of a cysteine residue that does not form an interchain disulfide bond.

Typically, less than the theoretical maximums of medicant moieties are conjugated to an antibody during a conjugation reaction. An antibody may contain, for example, many lysine residues that do not react with the Medicant Linker compound intermediate or LU reagent. Only the most reactive lysine groups may react with an amine-reactive LU reagent. Generally, antibodies do not contain many, if any, free and reactive cysteine thiol groups which may be linked to a Medicant moiety via a LU. Most cysteine thiol residues in the antibodies exist as disulfide bridges and must be reduced with a reducing agent such as dithiothreitol (DTT). The antibody may be subjected to denaturing conditions to reveal reactive nucleophilic groups such as lysine or cysteine. The loading (medicant/antibody ratio) of an AMC may be controlled in several different manners, including: (i) limiting the molar excess of Medicant Linker compound intermediate or LU reagent relative to antibody, (ii) limiting the conjugation reaction time or temperature, and (iii) partial or limiting reductive conditions for cysteine thiol modification.

Where more than one nucleophilic group reacts with a Medicant Linker compound intermediate, or LU reagent followed by Medicant moiety reagent, then the resulting product is a mixture of Affinity Medicant Linker Conjugates (e.g., AMCs) with a distribution of one or more Medicant moieties per Affinity unit (e.g., an antibody). The average number of medicants per Affinity unit (e.g., antibody) may be calculated from the mixture by, for example, dual enzyme linked immune serum assay (ELISA) antibody assay, specific for antibody and specific for the medicant. Individual Affinity Medicant Linker Conjugate molecules may be identified in the mixture by mass spectroscopy, and separated by high performance liquid chromatography (HPLC), e.g., hydrophobic interaction chromatography. Thus, a homogeneous conjugate with a single loading value may be isolated from the conjugation mixture by electrophoresis or chromatography.

A "Linker Unit" (LU) is a bifunctional compound which can be used to link a Medicant unit and/or an Affinity unit to form an Affinity Medicant Linker conjugate. Such conjugates are useful, for example, in the formation of immuno conjugates directed against tumor associated antigens. Such conjugates allow the selective delivery of cytotoxic drugs to tumor cells. A LU includes a traditional linker, a 4-fluorosulfonyl benzoyl (4-FSB) linker, a 3-fluorosulfonyl benzoyl (3-FSB) linker a 2-fluorosulfonyl benzoyl (2-FSB) linker, a maleimide (Mall) linker, an azlactone linker and a bridging amino acid.

A traditional linker is a linker as defined in Table I through Table VI, where the reagent column identifies various traditional linkers. A Stretcher Unit includes two or more Linker Units.

A bridging amino acid means —NH—C(R')H—CO— or —N(R")—C(R')H—CO— including glycine, L-alanine, L-serine, L-threonine, L-cysteine, L-valine, L-leucine, L-isoleucine, L-methionine, L-proline, L-phenylalanine, L-tyrosine, L-tryptophan, L-aspartic acid, L-glutamic acid, L-asparagine, L-glutamine, L-histidine, L-lysine, L-arginine, L-homocysteine, L-selenocysteine, L-pyrrolysine, L-carnitine, L-hypusine, 2-aminoisobutyric acid, dehydroalanine, L-gamma-aminobutyric acid, L-ornithine, L-citrulline, L-α-Amino-n-butyric acid, L-Norvaline, L-Norleucine, L-Pipecolic acid, L-Alloisoleucine, L-α,β-diaminopropionic acid, L-α,γ-diaminobutyric acid, L-Allothreonine, L-α-Amino-n-heptanoic acid, L-Homoserine, β-Amino-n-butyric acid, β-Aminoisobutyric acid, γ-Aminobutyric acid, L-isovaline, L-Sarcosine, N-ethyl glycine, N-propyl glycine, N-isopropyl glycine, L-N-methyl alanine, L-N-ethyl alanine, N-methyl β-alanine, N-ethyl β-alanine, Isoserine, L-α-hydroxy-γ-aminobutyric acid, L-diaminopimelic acid, cystathione, L-aminoisobutyric acid, dehydroalanine, delta-aminolevulinic acid, 4-aminobenzoic acid, L-Hydroxyproline, Formylmethioinine, L-lanthionine, djenkolic acid, L-Pyroglutamic acid, Hypusine, L-carboxyglutamic acid, penicillamine, L-thialysine, quisqualic acid, L-canavine, L-azetidine-2-carboxylic acid, D-alanine, D-serine, D-threonine, D-cysteine, D-valine, D-leucine, D-isoleucine, D-methionine, D-proline, D-phenylalanine, D-tyrosine, D-tryptophan, D-aspartic acid, D-glutamic acid, D-asparagine, D-glutamine, D-histidine, D-lysine, D-arginine, D-homocysteine, D-selenocysteine, D-pyrrolysine, D-carnitine, D-hypusine, D-gamma-aminobutyric acid, D-ornithine, D-citrulline, D-α-Amino-n-butyric acid, D-Norvaline, D-Norleucine, D-Pipecolic acid, D-Alloisoleucine, D-α,β-diaminopropionic acid, D-α,γ-diaminobutyric acid, D-Allothreonine, D-α-Amino-n-heptanoic acid, D-Homoserine, D-isovaline, D-Sarcosine, D-N-methyl alanine, D-N-ethyl alanine, D-α-hydroxy-γ-aminobutyric acid, D-diaminopimelic acid, D-aminoisobutyric acid, D-Hydroxyproline, D-lanthionine, D-Pyroglutamic acid, D-carboxyglutamic acid, D-thialysine, quisqualic acid, D-canavine, D-azetidine-2-carboxylic acid. A 'modified bridging amino acid' means a bridging amino acid with R' including a hydroxyl group that has been esterified, a bridging amino acid with R' including a sulphur atom where the sulphur atom has been reacted with an alkyl or other organic group and/or a bridging amino acid with R' including a primary amino group that has been converted into a secondary or tertiary amino group.

In one embodiment, the LU of the Medicant Linker compound and Affinity Medicant Linker conjugate has the formula: —$W_w$-$A_a$ wherein -A- is a Stretcher Unit; a is 1 or 2; each —W— is independently an Amino Acid unit; w is independently an integer ranging from 1 to 20. In the Affinity Medicant Linker conjugate, the LU serves to attach the Medicant moiety and the AM.

The Affinity Moiety (AM) includes within its scope an Affinity Unit (AU) that specifically binds or reactively associates or complexes with a receptor, antigen or other receptive moiety associated with a given target-cell population. An AU is a molecule that binds to, complexes with, or reacts with a receptor, antigen or other receptive moiety of a cell population sought to be therapeutically or otherwise biologically modified. In one aspect, the AM acts to deliver the Medicant unit to the particular target cell population with which the AM interacts. Such AM's include, but are not limited to, proteins, polypeptides and peptides and include, antibodies, binding proteins, smaller molecular weight proteins, polypeptides, peptides, lectins, glycoproteins, non-peptides, vitamins, nutrient-transport molecules (such as, but not limited to, transferrin), or any other cell binding molecule or substance.

In an embodiment of the invention, an AM can form a bond to a Stretcher Unit. In an alternative embodiment of the invention, an AM can form a bond to the Stretcher Unit of the LU via a heteroatom of the AM. Heteroatoms that may be present on an AM include sulfur (in one embodiment, from a sulfhydryl group of an AM), oxygen (in one embodiment, from a carbonyl, carboxyl or hydroxyl group of an AM) and nitrogen (in one embodiment, from a primary or secondary amino group of an AM). These hetero atoms can be present on the AM in the AM's natural state, for example a naturally-occurring antibody, or can be introduced into the AM via chemical modification.

In one embodiment, an AM unit has a sulfhydryl group and the AM bonds to the LU via the sulfhydryl group's sulfur atom. In another embodiment, the AM has lysine residues that can react with activated esters (such esters include, but are not limited to, N-hydroxysuccinimide, pentafluorophenyl, and p-nitrophenyl esters) of the Stretcher Unit of the AM and thus form an amide bond consisting of the primary nitrogen atom of the AM and the carboxyl group of the AM. In yet another aspect, the AM has one or more lysine residues that can be chemically modified to introduce one or more sulfhydryl groups. The AM bonds to the LU via the sulfhydryl group's sulfur atom. The reagents that can be used to modify lysines include, but are not limited to, N-succinimidyl S-acetylthioacetate (SATA) and 2-Iminothiolane hydrochloride (Traut's Reagent).

In another embodiment, the AM can have one or more carbohydrate groups that can be chemically modified to have one or more sulfhydryl groups. The AM bonds to the LU (or a Stretcher Unit) via the sulfhydryl group's sulfur atom. In yet another embodiment, the AM can have one or more carbohydrate groups that can be oxidized to provide an aldehyde (—CHO) group. The corresponding aldehyde can form a bond with a reactive site on a Stretcher Unit. Reactive sites on a Stretcher Unit that can react with a carbonyl group on an AM include, but are not limited to, hydrazine and hydroxylamine.

Useful non-immunoreactive protein, polypeptide, or peptide affinity moieties include, but are not limited to, transferrin, epidermal growth factors ("EGF"), bombesin, gastrin, gastrin-releasing peptide, platelet-derived growth factor, IL-2, IL-6, transforming growth factors ("TOP"), such as TGF-.alpha. and TGF-.beta., vaccinia growth factor ("VGF"), insulin and insulin-like growth factors I and II, somatostatin, lectins and apoprotein from low density lipoprotein.

Useful polyclonal antibodies are heterogeneous populations of antibody molecules derived from the sera of immunized animals. Useful monoclonal antibodies are homogeneous populations of antibodies to a particular antigenic determinant (e.g., a cancer cell antigen, a viral antigen, a microbial antigen, a protein, a peptide, a carbohydrate, a chemical, nucleic acid, or fragments thereof). A monoclonal antibody (mAb) to an antigen-of-interest can be prepared by using any technique known in the art which provides for the production of antibody molecules by continuous cell lines in culture.

Useful monoclonal antibodies include, but are not limited to, human monoclonal antibodies, humanized monoclonal antibodies, antibody fragments, or chimeric monoclonal antibodies. Human monoclonal antibodies may be made by any of numerous techniques known in the art.

The antibody can also be a bispecific antibody. Methods for making bispecific antibodies are known in the art and are discussed infra.

The antibody can be a functionally active fragment, derivative or analog of an antibody that immunospecifically binds to target cells (e.g., cancer cell antigens, viral antigens, or microbial antigens) or other antibodies that bind to tumor cells or matrix. In this regard, "functionally active" means that the fragment, derivative or analog is able to elicit anti-anti-idiotype antibodies that recognize the same antigen that the antibody from which the fragment, derivative or analog is derived recognized. Specifically, in an exemplary embodiment the antigenicity of the idiotype of the immunoglobulin molecule can be enhanced by deletion of framework and CDR sequences that are C-terminal to the CDR sequence that specifically recognizes the antigen. To determine which CDR sequences bind the antigen, synthetic peptides containing the CDR sequences can be used in binding assays with the antigen by any binding assay method known in the art (e.g., the BIA core assay).

Other useful antibodies include fragments of antibodies such as, but not limited to, F(ab')$_2$ fragments, Fab fragments, Fvs, single chain antibodies, diabodies, triabodies, tetrabodies, scFv, scFv-FV, or any other molecule with the same specificity as the antibody.

Additionally, recombinant antibodies, such as chimeric and humanized monoclonal antibodies, comprising both human and non-human portions, which can be made using standard recombinant DNA techniques, are useful antibodies. A chimeric antibody is a molecule in which different portions are derived from different animal species, such as for example, those having a variable region derived from a murine monoclonal and human immunoglobulin constant regions. Humanized antibodies are antibody molecules from non-human species having one or more complementarity determining regions (CDRs) from the non-human species and a framework region from a human immunoglobulin molecule. Such chimeric and humanized monoclonal antibodies can be produced by recombinant DNA techniques known in the art.

Completely human antibodies are particularly desirable and can be produced using transgenic mice that are incapable of expressing endogenous immunoglobulin heavy and light chains genes, but which can express human heavy and light chain genes. The transgenic mice are immunized in the normal fashion with a selected antigen, e.g., all or a portion of a polypeptide of the invention. Monoclonal antibodies directed against the antigen can be obtained using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. Other human antibodies can be obtained commercially from, for example, Abgenix, Inc. (now Amgen, Freemont, Calif.) and Medarex (Princeton, N.J.).

Completely human antibodies that recognize a selected epitope can be generated using a technique referred to as "guided selection." In this approach a selected non-human monoclonal antibody, e.g., a mouse antibody, is used to guide the selection of a completely human antibody recognizing the same epitope. Human antibodies can also be produced using various techniques known in the art, including phage display libraries.

In other embodiments, the antibody is a fusion protein of an antibody, or a functionally active fragment thereof, for example in which the antibody is fused via a covalent bond (e.g., a peptide bond), at either the N-terminus or the C-terminus to an amino acid sequence of another protein (or portion thereof, preferably at least 10, 20 or 50 amino acid portion of the protein) that is not from an antibody. Preferably, the antibody or fragment thereof is covalently linked to the other protein at the N-terminus of the constant domain.

Antibodies include analogs and derivatives that are either modified, i.e., by the covalent attachment of any type of molecule as long as such covalent attachment permits the antibody to retain its antigen binding immunospecificity. For example, but not by way of limitation, derivatives and analogs of the antibodies include those that have been further modified, e.g., by glycosylation, acetylation, pegylation, phosphorylation, amidation, derivatization by known protecting/blocking groups, proteolytic cleavage, linkage to a cellular antibody unit or other protein, etc. Any of numerous chemical modifications can be carried out by known techniques including, but not limited to, specific chemical cleavage, acetylation, formylation, metabolic synthesis in the presence of tunicamycin, etc. Additionally, the analog or derivative can contain one or more unnatural amino acids.

Antibodies can have modifications (e.g., substitutions, deletions or additions) in amino acid residues that interact with Fc receptors. In particular, antibodies can have modifications in amino acid residues identified as involved in the interaction between the anti-Fc domain and the FcRn receptor.

Antibodies immunospecific for a cancer cell antigen can be obtained commercially or produced by any method known to one of skill in the art such as, e.g., chemical synthesis or recombinant expression techniques. The nucleotide sequence encoding antibodies immunospecific for a cancer cell antigen can be obtained, e.g., from the GenBank database or a database like it, literature publications, or by routine cloning and sequencing.

In a specific embodiment, known antibodies for the treatment of cancer can be used. Antibodies immunospecific for a cancer cell antigen can be obtained commercially or produced by any method known to one of skill in the art such as, e.g., recombinant expression techniques. The nucleotide sequence encoding antibodies immunospecific for a cancer cell antigen can be obtained, e.g., from the GenBank database or a database like it, the literature publications, or by routine cloning and sequencing. Examples of antibodies available for the treatment of cancer include, but are not limited to, RITUXAN® (rituximab; Genentech) which is a chimeric anti-CD20 monoclonal antibody for the treatment of patients with non-Hodgkin's lymphoma; OVAREX which is a murine antibody for the treatment of ovarian cancer; PANOREX (Glaxo Wellcome, N.C.) which is a murine IgG$_{2a}$ antibody for the treatment of colorectal cancer; Cetuximab ERBITUX (Imclone Systems Inc., NY) which is an anti-EGFR IgG chimeric antibody for the treatment of epidermal growth factor positive cancers, such as head and neck cancer; Vitaxin (MedImmune, Inc., MD) which is a humanized antibody for the treatment of sarcoma; CAMPATH I/H (Leukosite, MA) which is a humanized IgG$_1$ antibody for the treatment of chronic lymphocytic leukemia (CLL); SMART MI95 (Protein Design Labs, Inc., CA) and SGN-33 (Seattle Genetics, Inc., WA) which is a humanized anti-CD33 IgG antibody for the treatment of acute myeloid leukemia (AML); LYMPHOCIDE (Immunomedics, Inc., NJ) which is a humanized anti-CD22 IgG antibody for the treatment of non-Hodgkin's lymphoma; SMART ID10 (Protein Design Labs, Inc., CA) which is a humanized anti-HLA-DR antibody for the treatment of non-Hodgkin's lymphoma; ONCOLYM (Techniclone, Inc., CA) which is a radiolabeled murine anti-HLA-Dr10 antibody for the treatment of non-Hodgkin's lymphoma; ALLOMUNE (BioTransplant, CA) which is a humanized anti-CD2 mAb for the treatment of Hodgkin's Disease or non-Hodgkin's lymphoma; AVASTIN (Genentech, Inc., CA) which is an anti-VEGF humanized antibody for the treatment of lung and colorectal cancers; Epratuzamab (Immunomedics, Inc., NJ and Amgen, Calif.) which is an anti-CD22 antibody for the treatment of non-Hodgkin's lymphoma; and CEACIDE (Immunomedics, N.J.) which is a humanized anti-CEA antibody for the treatment of colorectal cancer.

Other antibodies useful in the treatment of cancer include, but are not limited to, antibodies against the following antigens (where exemplary cancers that can be treated with the antibody are in parentheses): Alk (adrenocarcinomas) (SEQ. ID. 103), CA125 (ovarian) (SEQ. ID. 104), CA15-3 (carcinomas) (SEQ. ID. 105), CA19-9 (carcinomas), L6 (carcinomas) (SEQ. ID. 107), Lewis Y (carcinomas) (SEQ. ID. 108), Lewis X (carcinomas) (SEQ. ID. 109), alpha fetoprotein (carcinomas) (SEQ. ID. 110), CA 242 (colorectal), placental alkaline phosphatase (carcinomas) (SEQ. ID. 112), prostate specific antigen (prostate) (SEQ. ID. 113), prostate specific membrane antigen (prostate) (SEQ. ID. 114), prostatic acid phosphatase (prostate) (SEQ. ID. 115), epidermal growth factor (carcinomas), MAGE-1 (carcinomas) (SEQ. ID. 117), MAGE-2 (carcinomas) (SEQ. ID. 118), MAGE-3 (carcinomas) (SEQ. ID. 119), MAGE-4 (carcinomas) (SEQ. ID. 120), anti-transferrin receptor (carcinomas) (SEQ. ID. 121), p97 (melanoma) (SEQ. ID. 122), MUC1 (breast cancer) (SEQ. ID. 123), CEA (colorectal) (SEQ. ID. 124), gp100 (melanoma) (SEQ. ID. 125), MART-1 (melanoma) (SEQ. ID. 126), IL-2 receptor (T-cell leukemia and lymphomas), CD2 (buccal mucosa) (SEQ. ID. 128), CD20 (non-Hodgkin's lymphoma) (SEQ. ID. 129), CD52 (leukemia) (SEQ. ID. 130), CD33 (leukemia), CD22 (lymphoma), beta human chorionic gonadotropin (carcinoma) (SEQ. ID. 133), CD38 (multiple myeloma) (SEQ. ID. 134), CD40 (lymphoma) (SEQ. ID. 135), CD80 (colorectal), CD86 (colorectal), mucin (carcinomas), P21 (carcinomas), MPG (melanoma) (SEQ. ID. 140), Neu oncogene product (carcinomas) and STEAP-1 (prostate).

Compositions and Methods of Administration. In other embodiments, described is a pharmaceutical composition including an effective amount of an Affinity Medicant Linker conjugate and/or a Medicant Linker compound and a pharmaceutically acceptable carrier or vehicle. The compositions are suitable for veterinary or human administration.

The present pharmaceutical compositions can be in any form that allows for the composition to be administered to a patient. For example, the composition can be in the form of a solid or liquid. Typical routes of administration include, without limitation, parenteral, ocular and intra-tumor. Parenteral administration includes subcutaneous injections, intravenous, intramuscular or intrasternal injection or infusion techniques. In one aspect, the compositions are administered parenterally. In a specific embodiment, the compositions are administered intravenously.

Pharmaceutical compositions can be formulated so as to allow an Affinity Medicant Linker conjugate and/or a Medicant Linker compound to be bioavailable upon administration of the composition to a patient. Compositions can take the form of one or more dosage units, where for example, a tablet can be a single dosage unit, and a container of an Affinity Medicant Linker conjugate and/or a Medicant Linker compound in liquid form can hold a plurality of dosage units.

Materials used in preparing the pharmaceutical compositions can be non-toxic in the amounts used. It will be evident to those of ordinary skill in the art that the optimal dosage of the active ingredient(s) in the pharmaceutical composition will depend on a variety of factors. Relevant factors include, without limitation, the type of animal (e.g., human), the particular form of the Affinity Medicant Linker conjugate and/or a Medicant Linker compound, the manner of administration, and the composition employed.

The pharmaceutically acceptable carrier or vehicle can be solid or particulate, so that the compositions are, for example, in tablet or powder form. The carrier(s) can be liquid. In addition, the carrier(s) can be particulate.

The composition can be in the form of a liquid, e.g., a solution, emulsion or suspension. In a composition for administration by injection, one or more of a surfactant, preservative, wetting agent, dispersing agent, suspending agent, buffer, stabilizer and isotonic agent can also be included.

The liquid compositions, whether they are solutions, suspensions or other like form, can also include one or more of the following: sterile diluents such as water for injection, saline solution, preferably physiological saline, Ringer's solution, isotonic sodium chloride, fixed oils such as synthetic mono or digylcerides which can serve as the solvent or suspending medium, polyethylene glycols, glycerin, cyclodextrin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates, phosphates or amino acids and agents for the adjustment of tonicity such as sodium chloride or dextrose. A parenteral composition can be enclosed in ampoule, a disposable syringe or a multiple-dose vial made of glass, plastic or other material. Physiological saline is an exemplary adjuvant. An injectable composition is preferably sterile.

The amount of the Affinity Medicant Linker conjugate and/or a Medicant Linker compound that is effective in the treatment of a particular disorder or condition will depend on the nature of the disorder or condition, and can be determined by standard clinical techniques. In addition, in vitro or in vivo assays can optionally be employed to help identify optimal dosage ranges. The precise dose to be employed in the compositions will also depend on the route of administration, and the seriousness of the disease or disorder, and should be decided according to the judgment of the practitioner and each patient's circumstances.

The compositions comprise an effective amount of an Affinity Medicant Linker conjugate and/or a Medicant Linker compound such that a suitable dosage will be obtained. Typically, this amount is at least about 0.01% of an Affinity Medicant Linker conjugate and/or a Medicant Linker compound by weight of the composition. In an exemplary embodiment, pharmaceutical compositions are prepared so that a parenteral dosage unit contains from about 0.01% to about 2% by weight of the Affinity Medicant Linker conjugate and/or a Medicant Linker compound.

For intravenous administration, the composition can comprise from about 0.01 to about 100 mg of an Affinity Medicant Linker conjugate and/or a Medicant Linker compound per kg of the patient's body weight. In one aspect, the composition can include from about 1 to about 100 mg of an Affinity Medicant Linker conjugate and/or a Medicant Linker compound per kg of the patient's body weight. In another aspect, the amount administered will be in the range from about 0.1 to about 25 mg/kg of body weight of the Affinity Medicant Linker conjugate and/or a Medicant Linker compound.

Prior art ADC's such as Kadcyla or Adcetris deliver a dose of the associated toxin (auristatins MMAE or emtansine DM-1) that is three or more times the lethal dose (for that toxin) which results in severe systemic (or non-target) toxicity. In contrast, Illudin and Acylfulvene ADC's (such as analog 189, analog 190), analog 217, analog 218, analog 219, analog 222, or analog 316 deliver less than one third (i.e., <⅓) of a lethal dose, minimizing the risk and severity of systemic toxicity. Illudins and Acylfulvenes are true cytotoxic agents whereas other toxic agents used in prior art ADC's (e.g., pyrrolobenzodiazepines, maytansines, fumagillols, dolstatins, auristatins, enadiynes, halichondrins, and tubulysins) are only cytostatic. See Table XIII (the NCI-DTP 60 cell line table). Hence, other payloads, such as those used in Herceptin, Adcetris or Rituxin only stall tumor cell growth and do not actually kill the tumor cells. Other payloads (e.g., pyrrolobenzodiazepines, maytansines, fumagillols, dolstatins, auristatins, enadiynes, halichondrins, and tubulysins) are not active against multidrug phenotypes, notably the MDR1/GP170 and MRP/GP180 transport mechanisms (see Table XIV). Illudins and Acylfulvenes show the excellent effect of remaining active against all MDR phenotypes known regardless of the mechanism of resistance (see Table XIV). Hence, if tumor cells have already developed multi-drug resistance to a prior art ADC with a prior art toxin, or develop multi-drug resistance during the administration of a course of the prior art ADC with a prior art toxin, then the ADC will have no efficacy. In contrast, ADCs developed with Illudins, Syn-illudins, or Acylfulvenes have the advantageous effect that they will continue to kill cancer cells.

Generally, the dosage of an Affinity Medicant Linker conjugate and/or a Medicant Linker compound administered to a patient is typically about 0.01 mg/kg to about 20 mg/kg of the patient's body weight. In one aspect, the dosage administered to a patient is between about 0.01 mg/kg to about 10 mg/kg of the patient's body weight. In another aspect, the dosage administered to a patient is between about 0.1 mg/kg and about 10 mg/kg of the patient's body weight. In yet another aspect, the dosage administered to a patient is between about 0.1 mg/kg and about 5 mg/kg of the patient's body weight. In yet another aspect the dosage administered is between about 0.1 mg/kg to about 3 mg/kg of the patient's body weight. In yet another aspect, the dosage administered is between about 1 mg/kg to about 3 mg/kg of the patient's body weight.

The Affinity Medicant Linker conjugate and/or a Medicant Linker compound can be administered by any convenient route, for example by infusion or bolus injection. Administration can be systemic or local. Various delivery systems are known, e.g., encapsulation in liposomes, microparticles, microcapsules, capsules, etc., and can be used to administer an Affinity Medicant Linker conjugate and/or a Medicant Linker compound. In certain embodiments, more than one Affinity Medicant Linker conjugate and/or a Medicant Linker compound is administered to a patient.

In specific embodiments, it can be desirable to administer one or more Affinity Medicant Linker conjugates and/or a Medicant Linker compound locally to the area in need of treatment. This can be achieved, for example, and not by way of limitation, by local infusion during surgery; topical application, e.g., in conjunction with a wound dressing after surgery; by injection; by means of a catheter; or by means of an implant, the implant being of a porous, non-porous, or gelatinous material, including membranes, such as sialastic membranes, or fibers. In one embodiment, administration can be by direct injection at the site (or former site) of a cancer, tumor or neoplastic or pre-neoplastic tissue. In another embodiment, administration can be by direct injection at the site (or former site) of a manifestation of an autoimmune disease.

In yet another embodiment, the Affinity Medicant Linker conjugate and/or a Medicant Linker compound can be delivered in a controlled release system, such as but not limited to, a pump or various polymeric materials can be used. In yet another embodiment, a controlled-release system can be placed in proximity of the target of the Linker Affinity conjugate and/or a Medicant Linker compound, e.g., the liver, thus requiring only a fraction of the systemic dose.

The term "carrier" refers to a diluent, adjuvant or excipient, with which an Affinity Medicant Linker conjugate and/or a Medicant Linker compound is administered. Such pharmaceutical carriers can be liquids, such as water and oils, including those of petroleum, animal, vegetable or synthetic origin. The carriers can be saline, and the like. In addition, auxiliary, stabilizing and other agents can be used. In one embodiment, when administered to a patient, the Affinity Medicant Linker conjugate and/or the Medicant Linker compound and pharmaceutically acceptable carriers are sterile. Water is an exemplary carrier when the Affinity Medicant Linker conjugate and/or a Medicant Linker compound are administered intravenously. Saline solutions and aqueous dextrose and glycerol solutions can also be employed as liquid carriers, particularly for injectable solutions. The present compositions, if desired, can also contain minor amounts of wetting or emulsifying agents, or pH buffering agents.

The present compositions can take the form of solutions, pellets, powders, sustained-release formulations, or any other form suitable for use.

In an embodiment, the Affinity Medicant Linker conjugates and/or Medicant Linker compounds are formulated in accordance with routine procedures as a pharmaceutical composition adapted for intravenous administration to animals, particularly human beings. Typically, the carriers or vehicles for intravenous administration are sterile isotonic aqueous buffer solutions. Where necessary, the compositions can also include a solubilizing agent. Compositions for intravenous administration can optionally comprise a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where an Affinity Medicant Linker conjugate and/or Medicant Linker compound is to be administered by infusion, it can be dispensed, for example, with an infusion bottle containing sterile pharmaceutical grade water or saline. Where the Affinity Medicant Linker conjugate and/or Medicant Linker compound is administered by injection, an ampoule of sterile water for injection or saline can be provided so that the ingredients can be mixed prior to administration.

The composition can include various materials that modify the physical form of a solid or liquid dosage unit. For example, the composition can include materials that form a coating shell around the active ingredients. The materials that form the coating shell are typically inert, and can be selected from, for example, sugar, shellac, and other enteric coating agents. Alternatively, the active ingredients can be encased in a gelatin capsule.

Whether in solid or liquid form, the present compositions can include a pharmacological agent used in the treatment of cancer, an autoimmune disease or an infectious disease.

Treatment of Cancer. The Affinity Medicant Linker conjugates and Medicant Linker compounds are useful for inhibiting the multiplication of a tumor cell or cancer cell, causing apoptosis in a tumor or cancer cell, or for treating cancer in a patient. The Affinity Medicant Linker conjugates and/or Medicant Linker compounds can be used accordingly in a variety of settings for the treatment of animal cancers. The Affinity Medicant Linker Conjugates can be used to deliver a Medicant or Medicant unit to a tumor cell or cancer cell. Without being bound by theory, in one embodiment, the AM of an Affinity Medicant Linker conjugate binds to or associates with a cancer-cell or a tumor-cell-associated antigen, and the Affinity Medicant Linker conjugate can be taken up (internalized) inside a tumor cell or cancer cell through receptor-mediated endocytosis or other internalization mechanism. The antigen can be attached to a tumor cell or cancer cell or can be an extracellular matrix protein associated with the tumor cell or cancer cell. Once inside the cell, one or more specific peptide sequences within or at the Medicant unit's proximal end of the LU are hydrolytically cleaved by one or more tumor cell or cancer cell-associated proteases, resulting in release of the Medicant unit. The released Medicant unit is then free to migrate within the cell and induce cytotoxic or cytostatic activities. The Affinity Medicant Linker conjugate also can be cleaved by an intracellular protease to release the Medicant moiety. In an alternative embodiment, the Medicant or Medicant unit is cleaved from the Affinity Medicant Linker conjugate outside the tumor cell or cancer cell, and the Medicant or Medicant unit subsequently penetrates the cell.

The Affinity Medicant Linker conjugates provide conjugation-specific tumor or cancer medicant targeting, thus reducing general toxicity of the Medicant. The LUs stabilize the Affinity Medicant Conjugates in blood, yet are cleavable by tumor-specific proteases within the cell, liberating a Medicant unit.

In one embodiment, the AM binds to the tumor cell or cancer cell. In another embodiment, the AM binds to a tumor cell or cancer cell antigen which is on the surface of the tumor cell or cancer cell. In another embodiment, the AM binds to a tumor cell or cancer cell antigen which is an extracellular matrix protein associated with the tumor cell or cancer cell.

The specificity of the AM for a particular tumor cell or cancer cell can be important for determining those tumors or cancers that are most effectively treated. For example, an Affinity Medicant Linker conjugate and/or Medicant Linker compound having a BR96 AM can be useful for treating antigen positive carcinomas including those of the lung, breast, colon, ovaries, and pancreas. Affinity Medicant Linker conjugates having an anti-CD30 or an anti-CD70 binding affinity moiety can be useful for treating hematologic malignancies.

Other particular types of cancers that can be treated with an Affinity Medicant Linker conjugate and/or a Medicant Linker compound include, but are not limited to fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon cancer, colorectal cancer, kidney cancer, pancreatic cancer, bone cancer, breast cancer, ovarian cancer, prostate cancer, esophageal cancer, stomach cancer, oral cancer, nasal cancer, throat cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, uterine cancer, testicular cancer, small cell lung carcinoma, bladder carcinoma, lung cancer, epithelial carcinoma, glioma, glioblastoma multiforme, astrocytoma, medulloblastoma, craniopharyngioma, ependymoma, pinealoma, hemangioblastoma, acoustic neuroma, oligodendroglioma, meningioma, skin cancer, melanoma, neuroblastoma, retinoblastoma blood-borne cancers, including but not limited to: acute lymphoblastic leukemia "ALL", acute lymphoblastic B-cell leukemia, acute lymphoblastic T-cell leukemia, acute myeloblastic leukemia "AML", acute promyelocytic leukemia "APL", acute monoblastic leukemia, acute erythroleukemic leukemia, acute megakaryoblastic leukemia, acute myelomonocytic leukemia, acute nonlymphocytic leukemia, acute undifferentiated leukemia, chronic myelocytic leukemia "CML", chronic lymphocytic leukemia "CLL", hairy cell leukemia, multiple myeloma acute and chronic leukemias: lymphoblastic, myelogenous, lymphocytic, myelocytic leukemias Lymphomas: Hodgkin's disease, non-Hodgkin's Lymphoma, Multiple myeloma, Waldenstrom's macroglobulinemia, Heavy chain disease, Polycythemia vera.

Multi-Modality Therapy for Cancer. Cancers, including, but not limited to, a tumor, metastasis, or other disease or disorder characterized by uncontrolled cell growth, can be treated or inhibited by administration of an Affinity Medicant Linker conjugate or Medicant Linker compound.

In other embodiments, methods for treating cancer are provided, including administering to a patient in need thereof an effective amount of an Affinity Medicant Linker conjugate and a chemotherapeutic agent. In one embodiment the chemotherapeutic agent is that with which treatment of the cancer has not been found to be refractory. In another embodiment, the chemotherapeutic agent is that with which the treatment of cancer has been found to be refractory. The Affinity Medicant Linker conjugates can be administered to a patient that has also undergone surgery as treatment for the cancer.

In some embodiments, the patient also receives an additional treatment, such as radiation therapy. In a specific embodiment, the Affinity Medicant Linker conjugate is administered concurrently with the chemotherapeutic agent or with radiation therapy. In another specific embodiment, the chemotherapeutic agent or radiation therapy is administered prior or subsequent to administration of an Affinity Medicant Linker conjugate.

A chemotherapeutic agent can be administered over a series of sessions. Any one or a combination of the chemotherapeutic agents, such a standard of care chemotherapeutic agent(s), can be administered.

Additionally, methods of treatment of cancer with an Affinity Medicant Linker conjugate and/or a Medicant Linker compound are provided as an alternative to chemotherapy or radiation therapy where the chemotherapy or the radiation therapy has proven or can prove too toxic, e.g., results in unacceptable or unbearable side effects, for the subject being treated. The patient being treated can, optionally, be treated with another cancer treatment such as surgery, radiation therapy or chemotherapy, depending on which treatment is found to be acceptable or bearable.

The Affinity Medicant Linker (AML) conjugates and/or Medicant Linker (ML) compounds can also be used in an in vitro or ex vivo fashion, such as for the treatment of certain cancers, including, but not limited to leukemia and lymphomas, such treatment involving autologous stem cell transplants. This can involve a multi-step process in which the animal's autologous hematopoietic stein cells are harvested and purged of all cancer cells, the animal's remaining bone-marrow cell population is then eradicated via the administration of a high dose of an AML conjugates and/or ML compound with or without accompanying high dose radiation therapy, and the stem cell graft is infused back into the animal. Supportive care is then provided while bone marrow function is restored and the patient recovers.

Treatment of Autoimmune Diseases. The Affinity Medicant Linker conjugates and Medicant Linker compounds are useful for killing or inhibiting the replication of a cell that produces an autoimmune disease or for treating an autoimmune disease. The Affinity Medicant Linker conjugates and Medicant Linker compounds can be used accordingly in a variety of settings for the treatment of an autoimmune disease in a patient. The Affinity Medicant Linker conjugates can be used to deliver a Medicant unit to a target cell. Without being bound by theory, in one embodiment, the Affinity Medicant Linker conjugate associates with an antigen on the surface of a target cell, and the Affinity Medicant Linker conjugate is then taken up inside a target-cell through receptor-mediated endocytosis. Once inside the cell, one or more specific peptide sequences within and/or Medicant unit proximal to the LU are enzymatically or hydrolytically cleaved, resulting in release of the Medicant or Medicant unit. The released Medicant or Medicant unit is then free to migrate in the cytosol and induce cytotoxic or cytostatic activities. The Affinity Medicant Linker conjugate also can be cleaved by an intracellular protease to release the Medicant or Medicant moiety. In an alternative embodiment, the Medicant is cleaved from the Affinity Medicant Linker conjugate outside the target cell, and the Medicant or Medicant unit subsequently penetrates the cell.

In an embodiment of the present invention, the AM binds to an autoimmune antigen. In one aspect, the antigen is on the surface of a cell involved in an autoimmune condition. In another embodiment, the AM binds to an autoimmune antigen which is on the surface of a cell. In one embodiment, the AM binds to activated lymphocytes that are associated with the autoimmune disease state.

In a further embodiment, the Affinity Medicant Linker conjugate or Medicant Linker compound kills or inhibit the multiplication of cells that produce an autoimmune antibody associated with a particular autoimmune disease.

In various embodiments of the present invention, the AML or AM conjugates can be used to treat particular types of autoimmune diseases including, but not limited to, Th2 lymphocyte related disorders (e.g., atopic dermatitis, atopic asthma, rhinoconjunctivitis, allergic rhinitis, Omenn's syndrome, systemic sclerosis, and graft versus host disease); Thi lymphocyte-related disorders (e.g., rheumatoid arthritis, multiple sclerosis, psoriasis, Sjorgren's syndrome, Hashimoto's thyroiditis, Grave's disease, primary biliary cirrhosis, Wegener's granulomatosis, and tuberculosis); activated B lymphocyte-related disorders (e.g., systemic lupus erythematosus, Goodpasture's syndrome, rheumatoid arthritis, and type I diabetes); and Active Chronic Hepatitis, Addison's Disease, Allergic Alveolitis, Allergic Reaction, Allergic Rhinitis, Alport's Syndrome, Anaphlaxis, Ankylosing Spondylitis, Anti-phosholipid Syndrome, Arthritis, Ascariasis, Aspergillosis, Atopic Allergy, Atropic Dermatitis, Atropic Rhinitis, Behcet's Disease, Bird-Fancier's Lung, Bronchial Asthma, Caplan's Syndrome, Cardiomyopathy, Celiac Disease, Chagas' Disease, Chronic Glomerulonephritis, Cogan's Syndrome, Cold Agglutinin Disease, Congenital Rubella Infection, CREST Syndrome, Crohn's Disease, Cryoglobulinemia, Cushing's Syndrome, Dermatomyositis, Discoid Lupus, Dressler's Syndrome, Eaton-Lambert Syndrome, Echovirus Infection, Encephalomyelitis, Endocrine opthalmopathy, Epstein-Barr Virus Infection, Equine Heaves, Erythematosis, Evan's Syndrome, Felty's Syndrome, Fibromyalgia, Fuch's Cyclitis, Gastric Atrophy, Gastrointestinal Allergy, Giant Cell Arteritis, Glomerulonephritis, Goodpasture's Syndrome, Graft v. Host Disease, Graves' Disease, Guillain-Barre Disease, Hashimoto's Thyroiditis, Hemolytic Anemia, Henoch-Schonlein Purpura, Idiopathic Adrenal Atrophy, Idiopathic Pulmonary Fibrosis, IgA Nephropathy, Inflammatory Bowel Diseases, Insulin-dependent Diabetes Mellitus, Juvenile Arthritis, Juvenile Diabetes Mellitus (Type I), Lambert-Eaton Syndrome, Laminitis, Lichen Planus, Lupoid Hepatitis, Lupus, Lymphopenia, Meniere's Disease, Mixed Connective Tissue Disease, Multiple Sclerosis, Myasthenia Gravis, Pernicious Anemia, Polyglandular Syndromes, Presenile Dementia, Primary Agammaglobulinemia, Primary Biliary Cirrhosis, Psoriasis, Psoriatic Arthritis, Raynauds Phenomenon, Recurrent Abortion, Reiter's Syndrome, Rheumatic Fever, Rheumatoid Arthritis, Sampter's Syndrome, Schistosomiasis, Schmidt's Syndrome, Scleroderma, Shulman's Syndrome, Sjorgen's Syndrome, Stiff-Man Syndrome, Sympathetic Ophthalmia, Systemic Lupus Erythematosis, Takayasu's Arteritis, Temporal Arteritis, Thyroiditis, Thrombocytopenia, Thyrotoxicosis, Toxic Epidermal Necrolysis, Type B Insulin Resistance, Type I Diabetes Mellitus, Ulcerative Colitis, Uveitis, Vitiligo, Waldenstrom's Macroglobulemia, Wegener's Granulomatosis.

Multi-Medicant Therapy of Autoimmune Diseases. Methods for treating an autoimmune disease are also disclosed including administering to a patient in need thereof an effective amount of an Affinity Medicant Linker conjugates or Medicant Linker compound and another therapeutic agent known for the treatment of an autoimmune disease.

Treatment of Infectious Diseases. The Affinity Medicant Linker conjugates and Medicant Linker compounds are useful for killing or inhibiting the multiplication of a cell that produces an infectious disease or for treating an infectious disease. The Affinity Medicant Linker conjugates and Medicant Linker compounds can be used accordingly in a variety of settings for the treatment of an infectious disease in a patient. The Affinity Medicant Linker conjugates can be used to deliver a Medicant unit to a target cell. In an embodiment of the present invention, AM binds to the infectious disease cell.

In various embodiments of the present invention, the AML or AM conjugates kill or inhibit the multiplication of cells that produce a particular infectious disease including, but not limited to, Diphtheria, Pertussis, Occult Bacteremia, Urinary Tract Infection, Gastroenteritis, Cellulitis, Epiglottitis, Tracheitis, Adenoid Hypertrophy, Retropharyngeal Abcess, Impetigo, Ecthyma, Pneumonia, Endocarditis, Septic Arthritis, Pneumococca, Peritonitis, Bactermia, Meningitis, Acute Purulent Meningitis, Urethritis, Cervicitis, Proctitis, Pharyngitis, Salpingitis, Epididymitis, Gonorrhea, Syphilis, Listeriosis, Anthrax, Nocardiosis, *Salmonella*, Typhoid Fever, Dysentery, Conjunctivitis, Sinusitis, Brucellosis, Tullaremia, Cholera, Bubonic Plague, Tetanus, Necrotizing Enteritis, Actinomycosis, Mixed Anaerobic Infections, Syphilis, Relapsing Fever, Leptospirosis, Lyme Disease, Rat Bite Fever, Tuberculosis, Lymphadenitis, Leprosy, *Chlamydia*, Chlamydial Pneumonia, Trachoma, Inclusion Conjunctivitis Systemic Fungal Diseases: Histoplamosis, Coccidiodomycosis, Blastomycosis, Sporotrichosis, Cryptococcsis, Systemic Candidiasis, Aspergillosis, Mucormycosis, Mycetoma, Chromomycosis Rickettsial Diseases: Typhus, Rocky Mountain Spotted Fever, Ehrlichiosis, Eastern Tick-Borne Rickettsioses, Rickettsialpox, Q Fever, Bartonellosis Parasitic Diseases: Malaria, Babesiosis, African Sleeping Sickness, Chagas' Disease, Leishmaniasis, Dum-Dum Fever, Toxoplasmosis, Meningoencephalitis, Keratitis, Entamebiasis, Giardiasis, Cryptosporidiasis, Isosporiasis, Cyclosporiasis, Microsporidiosis, Ascariasis, Whipworm Infection, Hookworm Infection, Threadworm Infection, Ocular Larva Migrans, Trichinosis, Guinea Worm Disease, Lymphatic Filariasis, Loiasis, River Blindness, Canine Heartworm Infection, Schistosomiasis, Swimmer's Itch, Oriental Lung Fluke, Oriental Liver Fluke, Fascioliasis, Fasciolopsiasis, Opisthorchiasis, Tapeworm Infections, Hydatid Disease, Alveolar Hydatid Disease Viral Diseases: Measles, Subacute sclerosing panencephalitis, Common Cold, Mumps, Rubella, Roseola, Fifth Disease, Chickenpox, Respiratory syncytial virus infection, Croup, Bronchiolitis, Infectious Mononucleosis, Poliomyelitis, Herpangina, Hand-Foot-and-Mouth Disease, Bornholm Disease, Genital Herpes, Genital Warts, Aseptic Meningitis, Myocarditis, Pericarditis, Gastroenteritis, Acquired Immunodeficiency Syndrome (AIDS), Human Immunodeficiency Virus (HIV), Reye's Syndrome, Kawasaki Syndrome, Influenza, Bronchitis, Viral "Walking" Pneumonia, Acute Febrile Respiratory Disease, Acute pharyngoconjunctival fever, Epidemic keratoconjunctivitis, Herpes Simplex Virus 1 (HSV-1), Herpes Simplex Virus 2 (HSV-2), Shingles, Cytomegalic Inclusion Disease, Rabies, Progressive Multifocal Leukoencephalopathy, Kuru, Fatal Familial Insomnia, Creutzfeldt-Jakob Disease, Gerstmann-Straussler-Scheinker Disease, Tropical Spastic Paraparesis, Western Equine Encephalitis, California Encephalitis, St. Louis Encephalitis, Yellow Fever, Dengue, Lymphocytic choriomeningitis, Lassa Fever, Hemorrhagic Fever, Hantvirus Pulmonary Syndrome, Marburg Virus Infections, Ebola Virus Infections, Smallpox.

Synthesis of AMCs with SMCC and Sulfo-SMCC linkers. In an embodiment of the present invention, an affinity medicant conjugate (AMC) 1000 is formed between an AM 1100 and a medicant 1350 by reacting the medicant 1350 with succinimidyl 4-(N-maleimidomethyl)-cyclohexane-1-carboxylate (SMCC) which forms an active intermediate that reacts with a sulfhydryl groups on the AM 1100. In an embodiment of the present invention, the resulting AMC includes one or more molecules of the medicant 1350 bound to the AM 1100. In an embodiment of the present invention, the resulting AMC is not cleaved in the cytosol, but internalized and the AM 1100 degraded by proteases in the cytosol until the medicant 1350 is released.

In an alternative embodiment of the present invention, an AMC 1000 is formed between an AM 1100 and a medicant 1350 by reacting the medicant 1350 with sulfosuccinimidyloxycarbonyl-α-methyl-α-(2-pyridyldithio)toluene (Sulfo-SMCC) which forms an active intermediate that reacts with a sulfhydryl groups on the AM 1100 to form a more water soluble AMC. In an embodiment of the present invention, the resulting AMC includes one or more molecules of the medicant 1350 bound to the AM 1100. In an embodiment of the present invention, the resulting AMC is not cleaved in the cytosol, but internalized and the AM 1100 degraded by proteases in the cytosol until the medicant 1350 is released.

In an embodiment of the present invention, an AMC 1000 comprises an AM 1100 bound to a medicant 1350 through an optional linker as illustrated in FIG. 1. In an embodiment of the present invention, an antibody 1110 is bound to a linker 1200 which is bound to the medicant 1350. In an unexpected result, an AMC 1000 can retain both the receptor binding activity of the AM 1100 and the intracellular cytoactivity of the medicant 1350 in a single compound. In an embodiment of the present invention, an antibody 1110 is bound to a linker 1200 which is bound to the medicant 1350. In an unexpected result, an antibody medicant conjugate can retain both the receptor binding activity of the antibody 1110 and the intracellular cytoactivity of an acylfulvene in a single compound. Surprisingly, the antibody is capable of binding to a polypeptide receptor on cell populations thereby bringing the acylfulvene in contact with the cell population.

In an embodiment of the present invention, the medicant moiety is an acylfulvene moiety. An acylfulvene moiety includes irofulven derivatives (see FIGS. 2A, 2C, 2F, 2H, 2I, 2L, 2M, 2P, 2S and 2U) and illudin derivatives (see FIGS. 2B, 2D, 2E, 2G, 2J, 2K, 2N, 2O, 2Q, 2R, 2T, and 2V).

Amine Derivative. In an embodiment of the present invention, the acylfulvene structures shown in FIGS. 2A, 2C, 2F, 2H, 2I, 2L and 2M and illudin structures shown in FIGS. 2B, 2D, 2E, 2G, 2J, 2K, 2N and 2O, where $R_1$ denotes independently a carbon or a heteroatom containing nitrogen (N), oxygen (O) or sulphur (S); where $R_6$ denotes including —H, —CN, —CF$_3$, —O, —NH$_2$, —SO$_3$, —COOH—, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl in which incorporated heteroatoms can be halogens (F, Cl, Br, I); nitrogen (N) functional groups including primary amines (—NH$_2$), secondary amines (—NH—), tertiary amines (—NR$_A$R$_B$), imine (—C(=N)H—), (—C(=N)R$_A$—), Azo (—N=N—), Cyanate (—C=N), isocyanate (—N=(C=O), amide (—C(=O)NR$_A$R$_B$) or (—C(=O)NR$_A$H) or (—C(=O)NH$_2$); sulfur (S) functional groups including thioethers (—S—), thiones (—C(=S)—, sulfoxides (—S(=O)—, sulfones (—S(=O)$_2$—), sulfoximes (—S(=O)(=NR$_A$)— or (—S(=O)(=NH)—, sulfhydryls (—SH), thiocyanate (—S—C(=N)—, isothiocyanate (—N=C(=S); oxygen (O) functional groups including hydroxyl (—OH), carbonyl (—C(=O)—, aldehyde (—C(=O)H, carboxylate (COOH), ethers (—O—), esters (—OC(=O)—), carbonate (—O(C=O)O—); and $R_2$, $R_3$, $R_4$, $R_5$ denote either H, CH$_3$, or CH$_2$OH and where $R_6$ is NH$_2$ (an amino group) for an acylfulvene derivative shown in FIGS. 2A, 2C, 2F, 2H, 2I, 2L and 2M and illudin derivative shown in FIGS. 2B, 2D, 2E, 2G, 2J, 2K, 2N and 2O.

Table IA shows acylfulvene amine analogs which can be attached to a bi-functional linker which can then be attached to a sulfhydryl reacting group of the AM using the reagent. In an embodiment of the present invention, the acylfulvene amino derivative shown in the first column of Table IA is linked to the AM through the free sulfhydryl group of the AM using the reagent identified in the second column of Table IA to form the AMC.

Figure 8A:
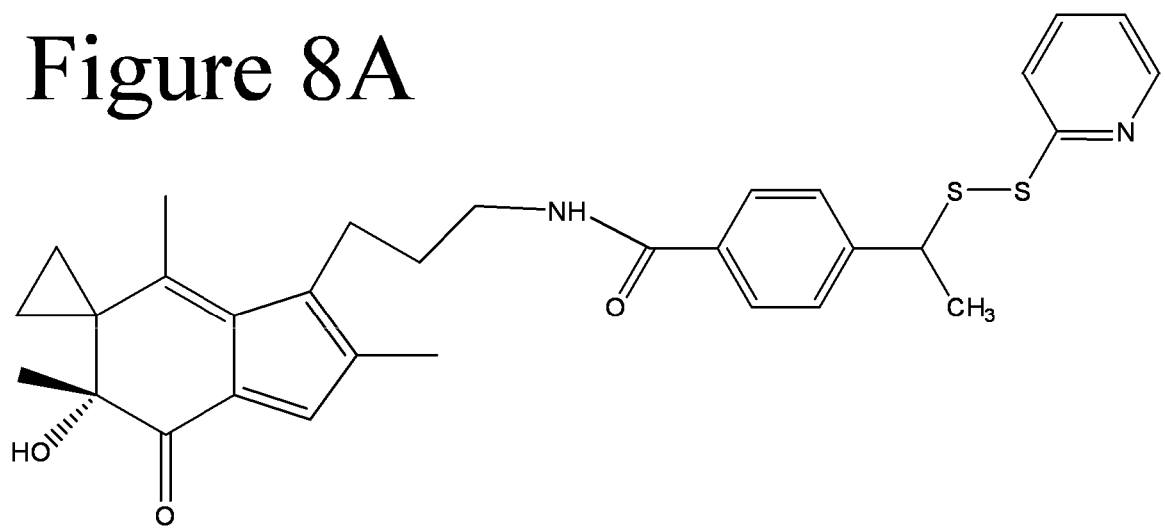
FIG. 8A shows the structure of the analog 211 attached via the amino group using the sulfosuccinimidyl 6-(alpha-methyl-alpha-(2-[pyridyldithio)-toluamido)hexanoate (SMPT) linking reagent according to an embodiment of the invention.
Figure 8B:
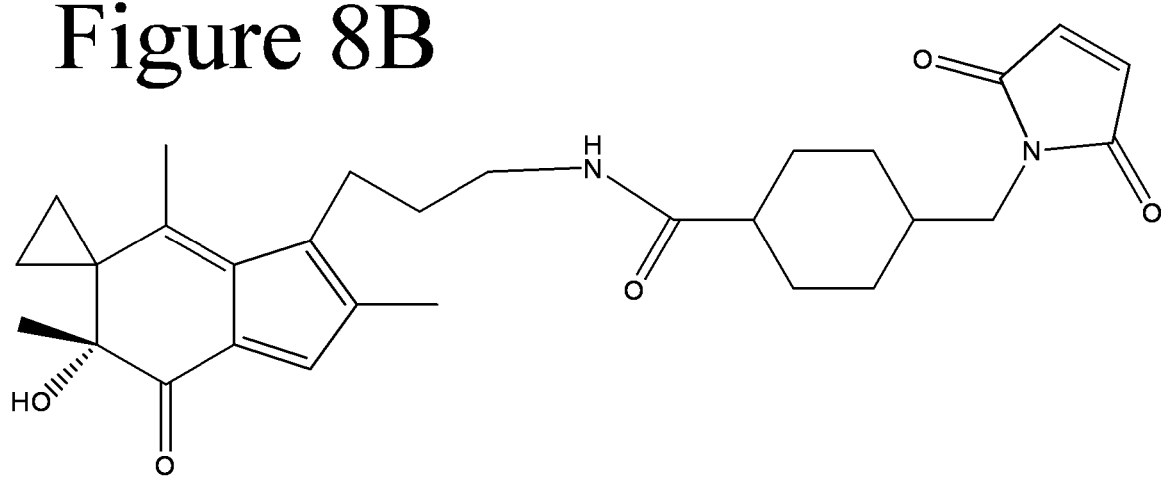
FIG. 8B shows the structure of the analog 211 attached via the amino group using the sulfosuccimidyl 4-(N-maleimido-methyl)cyclohexane-1-carboxylate (SMCC) linking reagent according to an embodiment of the invention.
Figure 8C:
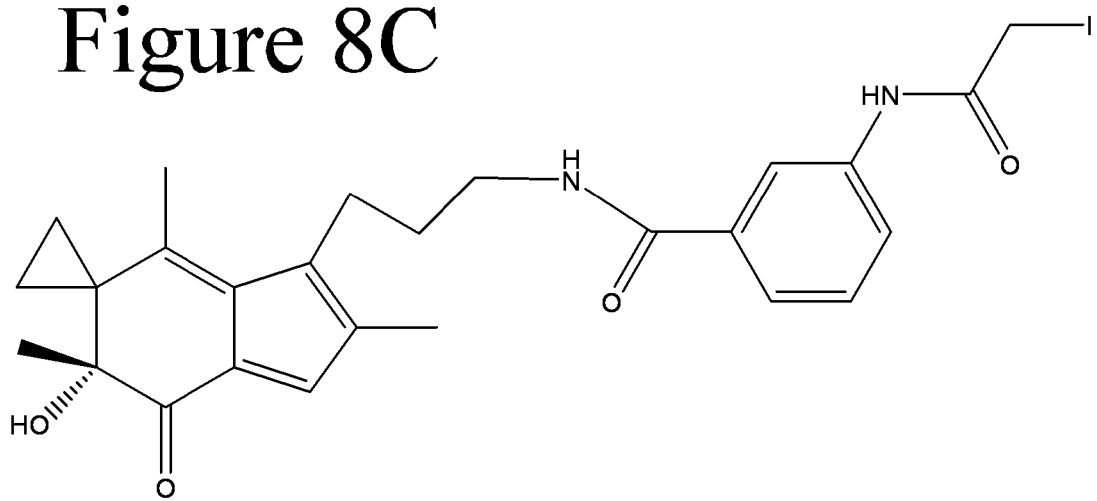
FIG. 8C shows the structure of the analog 211 attached via the amino group using the sulfosuccimidyl(4-iodo-acetyl)aminobenzoate (SIAB) linking reagent according to an embodiment of the invention.

FIG. 8A shows the structure of the analog 211 attached via the amino group using the SMPT linking reagents. FIG. 8B shows the structure of the analog 211 attached via the amino group using the SMCC linking reagent. FIG. 8C shows the structure of the analog 211 attached via the amino group using the SIAB linking reagent.

Table IB shows acylfulvene amine analogs which can be attached to a bi-functional linker which can then be attached to the AM via a photoactivatable group at the other terminus using the reagent. In an embodiment of the present invention, the acylfulvene amino derivative shown in the first column of Table IB is linked to the AM to the AM through the photoactivatable group at the other terminus using the reagent identified in the second column of Table IB to form the AMC.

Table IC shows acylfulvene amine analogs which can be attached to a bi-functional linker which can then be attached to the AM through a reactive amine group at the other terminus using the reagent. In an embodiment of the present invention, the acylfulvene amino derivative shown in the first column of Table IC is linked to the AM through an amine reactive group using the reagent identified in the second column of Table IC to form the AMC.

Table ID shows acylfulvene amine analogs which can be attached to a bi-functional linker which can then be attached to the AM through an aldehyde, carbonyl or carboxylate group at the other terminus using the reagent. In an embodiment of the present invention, the acylfulvene amino derivative shown in the first column of Table ID is linked to the AM through an aldehyde, carbonyl or carboxylate group at the other terminus using the reagent identified in the second column of Table ID to form AMC.

Figure 9A:
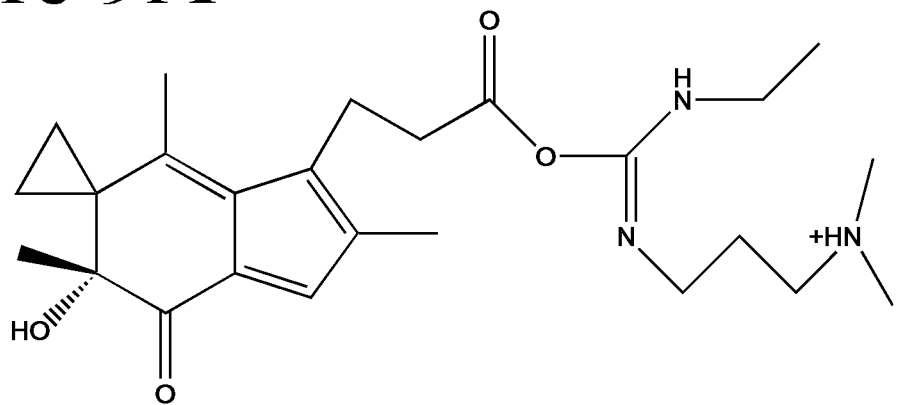
FIG. 9A shows the structure of the analog 038 attached via the carboxyl group using 1-ethyl-3-(3-dimethylamino-propyl) carbodiimide hydrochloride (EDC) linking reagent according to an embodiment of the invention.
Figure 9B:
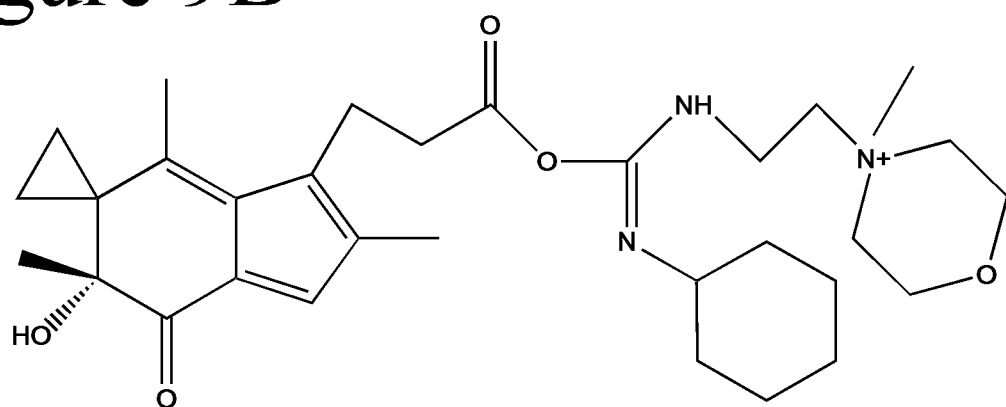
FIG. 9B shows the structure of the analog 038 attached via the carboxyl group using the 1-cyclohexyl-3-2(2-morpholino-ethyl)carbodiimide (CMC) linking reagent according to an embodiment of the invention.
Figure 9C:
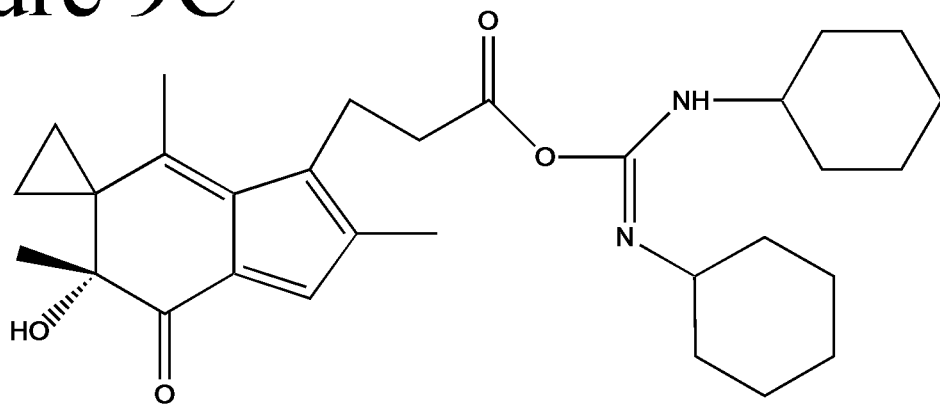
FIG. 9C shows the structure of the analog 038 attached via the carboxyl group using the N,N'-dicyclohexylcarbodiimide (DCC) linking reagent according to an embodiment of the invention.

Carboxyl Derivative. In an embodiment of the present invention, the acylfulvene structures shown FIGS. 2A, 2C, 2F, 2H, 2I, 2L and 2M and illudin structures shown in FIGS. 2B, 2D, 2E, 2G, 2J, 2K, 2N and 2O, where $R_1$ denotes substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl in which incorporated heteroatoms can be halogens (F, Cl, Br, I); nitrogen (N) functional groups including primary amines (—NH$_2$), secondary amines (—NH—), tertiary amines (—NR$_A$R$_B$), imine (—C(=N)H—), (—C(=N)R$_A$—), Azo (—N=N—), Cyanate (—C=N), isocyanate (—N=C=O), amide (—C(=O)NR$_A$R$_B$) or (—C(=O)NR$_A$H) or (—C(=O)NH$_2$); sulfur (S) functional groups including thioethers (—S—), thiones (—C(=S)—, sulfoxides (—S(=O)—, sulfones (—S(=O)$_2$—), sulfoximes (—S(=O)(=NR$_A$)— or (—S(=O)(=NH)—, sulfhydryls (—SH), thiocyanate (—S—C(=N)—, isothiocyanate (—N=C(=S); oxygen (O) functional groups including hydroxyl (—OH), carbonyl (—C(=O)—), aldehyde (—C(=O)H, carboxylate (COOH), ethers (—O—), esters (—OC(=O)—), carbonate (—O(C=O)O—); and R$_2$, R$_3$, R$_4$, R$_5$ denote either H, CH$_3$, or CH$_2$OH and where R$_6$ is CO$_2$H (a carboxyl group) for an acylfulvene derivative shown in FIGS. 2A, 2C, 2F, 2H, 2I, 2L and 2M and illudin derivative shown in FIGS. 2B, 2D, 2E, 2G, 2J, 2K, 2N and 2O. $R_5$ is glycine or either an L or D amino acid including alanine, serine, threonine, cysteine, valine, leucine, isoleucine, methionine, proline, phenylalanine, tyrosine, tryptophan, aspartic acid, glutamic acid, asparagine, glutamine, histidine, lysine, arginine, alpha-methyl glycine or 2-dimethylglycine. $R_5$ can also comprise nonstandard amino acids to reduce nonspecific esterase activity present in blood and cells including homocysteine, selenocysteine, pyrrolysine, carnitine, hypusine, lanthionine, 2-aminoisobutyric acid, dehydroalanine, gamma-aminobutyric acid, ornithine, citrulline, α-Amino-n-butyric acid, Norvaline, Norleucine, Pipecolic acid, Alloisoleucine, α,β-diaminopropionic acid, α,γ-diaminobutyric acid, Allothreonine, α-Amino-n-heptanoic acid, Homoserine, β-Amino-n-butyric acid, β-Aminoisobutyric acid, γ-Aminobutyric acid, isovaline, Sarcosine, N-ethyl glycine, N-propyl glycine, N-isopropyl glycine, N-methyl alanine, N-ethyl alanine, N-methyl β-alanine, N-ethyl β-alanine, Isoserine, α-hydroxy-γ-aminobutyric acid, diaminopimelic acid, cystathione, aminoisobutyric acid, dehydroalanine,delta-aminolevulinic acid, 4-aminobenzoic acid, Hydroxyproline, Formylmethioinine, lanthionine, djenkolic acid, Pyroglutamic acid, Hypusine, carboxyglutamic acid, penicillamine, thialysine, quisqualic acid, canavine, azetidine-2-carboxylic acid. FIG. 9A shows the structure of the analog 038 attached via the carboxyl group using the EDC linking reagent. FIG. 9B shows the structure of the analog 038 attached via the carboxyl group using the CMC linking reagent. FIG. 9C shows structure of the analog 038 attached via the carboxyl group using DCC linking reagent.

Table IIA shows acylfulvene carboxylate analogs which can be attached to a bi-functional linker which can then be attached to a sulfhydryl reacting group of the AM. In an embodiment of the present invention, the acylfulvene carboxylate derivative shown in the first column of Table IIA is linked to the AM through the free sulfhydryl group of the AM using the reagent identified in the second column of Table IIA to form the AMC.

Table IIB shows acylfulvene carboxylate analogs which can be attached to a bi-functional linker, where the linker also contains a photoactivatable reactive group which can attach to the AM. In an embodiment of the present invention, the acylfulvene carboxylate derivative shown in the first column of Table IIB is linked to the AM through the photoactivatable reactive group using the reagent identified in the second column of Table IIB to form the AMC.

Table IIC shows acylfulvene carboxylate analogs which can be attached to a bi-functional linker, where the linker also contains an amino reactive group which can attach to the AM. In an embodiment of the present invention, the acylfulvene carboxylate derivative shown in the first column of Table IIC is linked to the AM through the amino group using the reagent identified in the second column of Table IIC to form the AMC.

Figure 10A:
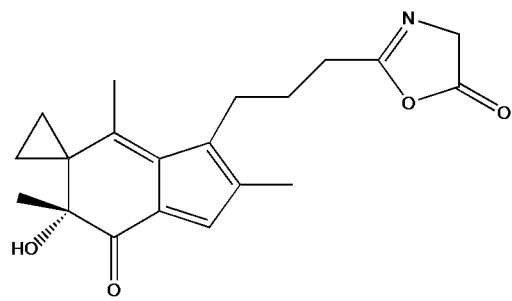
FIG. 10A shows the structure of the analog 038 attached via the carboxyl group using DCC or N,N'-diisopropylcarbodiimide (DIC) linking reagents in the presence of glycine according to various embodiments of the invention.
Figure 10B:
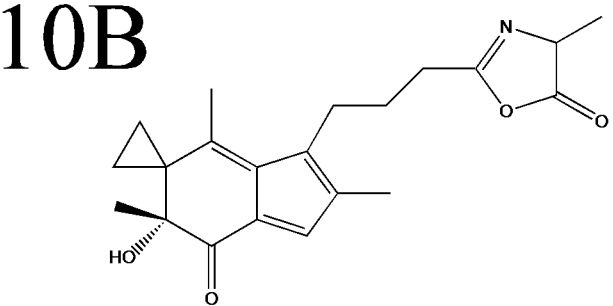
FIG. 10B shows the structure of the analog 038 attached via the carboxyl group using DCC or DIC linking reagents in the presence of alanine according to various embodiments of the invention.
Figure 10C:
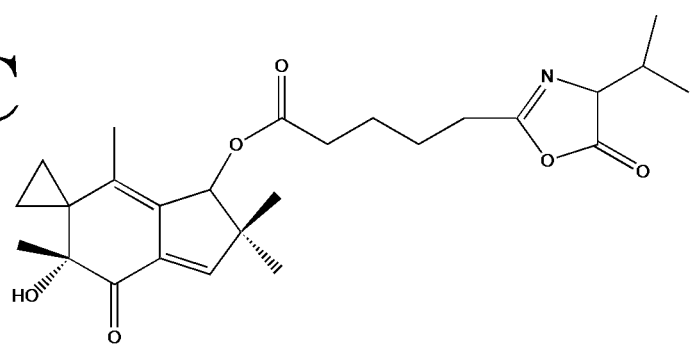
FIG. 10C shows the structure of the analog 106 attached via the carboxyl group using DCC or DIC linking reagents in the presence of valine according to various embodiments of the invention.

Azlactone Derivative. FIG. 10A shows the structure of the analog 038 attached via the carboxyl group using DCC or DIC linking reagents in the presence of glycine. FIG. 10B shows the structure of the analog 038 attached via the carboxyl group using DCC or DIC linking reagents in the presence of alanine. FIG. 10C shows the structure of the analog 106 attached via the carboxyl group using DCC or DIC linking reagents in the presence of valine.

Table IID shows acylfulvene carboxylate analogs which can be reacted to form acylfulvene azlactone derivatives where the azlactone reactive group can be used to attach to the AM. In an embodiment of the present invention, the acylfulvene derivative shown in the first column of Table IID is converted to the acylfulvene azlactone derivative (see FIG. 2P) using the reagent identified in the second column of Table IID to form the AMC.

Carbonyl Derivative. In an embodiment of the present invention, the acylfulvene structures shown in FIGS. 2A, 2C, 2F, 2H, 2I, 2L and 2M and illudin structures shown in FIGS. 2B, 2D, 2E, 2G, 2J, 2K, 2N and 2O, where $R_1$ and $R_7$ denote independently substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl in which incorporated heteroatoms can be halogens (F, Cl, Br, I); nitrogen (N) functional groups including primary amines (—NH$_2$), secondary amines (—NH—), tertiary amines (—NR$_A$R$_B$), imine (—C(=N)H—), (—C(=N)R$_A$—), Azo (—N=N—), Cyanate (—C=N), isocyanate (—N=(C=O), amide (—C(=O)NR$_A$R$_B$) or (—C(=O)NR$_A$H) or (—C(=O)NH$_2$); sulfur (S) functional groups including thioethers (—S—), thiones (—C(═S)—), sulfoxides (—S(═O)—), sulfones (—S(═O)$_2$—), sulfoximes (—S(═O)(═NR$_A$)— or (—S(═O)(═NH)—), sulfhydryls (—SH), thiocyanate (—S—C(═N)—), isothiocyanate (—N═C(═S); oxygen (O) functional groups including hydroxyl (—OH), carbonyl (—C(═O)—), aldehyde (—C(═O)H, carboxylate (COOH), ethers (—O—), esters (—OC(═O)—), carbonate (—O(C═O)O—); and R$_2$, R$_3$, R$_4$, R$_5$ denote either H, CH$_3$, or CH$_2$OH and where R$_6$ is CO—R$_2$ (a carbonyl linking group) for an acylfulvene derivative shown in FIGS. 2A, 2C, 2F, 2H, 2I, 2L and 2M and illudin derivative shown in FIGS. 2B, 2D, 2E, 2G, 2J, 2K, 2N and 2O.

Figure 11A:
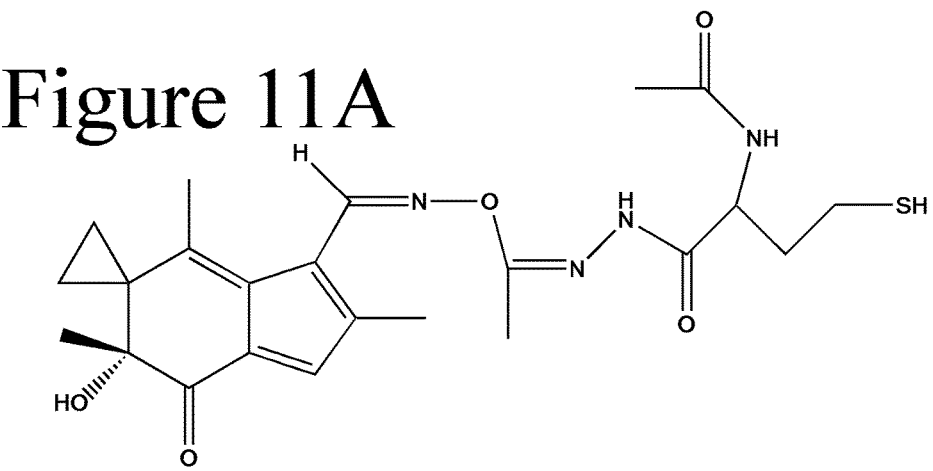
FIG. 11A shows the structure of the analog 124 attached via the carbonyl group using the 2-acetamido-4-mercaptobutyric acid hydrazide (AMBH) linking reagent according to an embodiment of the invention.
Figure 11B:
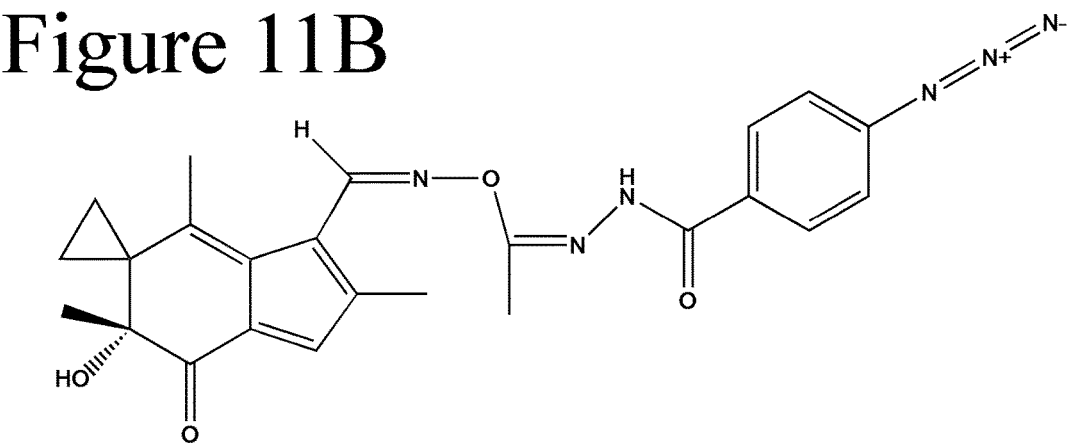
FIG. 11B shows the structure of the analog 124 attached via the carbonyl group using the p-azidobenzoyl hydrazide (ABH) linking reagent according to an embodiment of the invention.
Figure 11C:
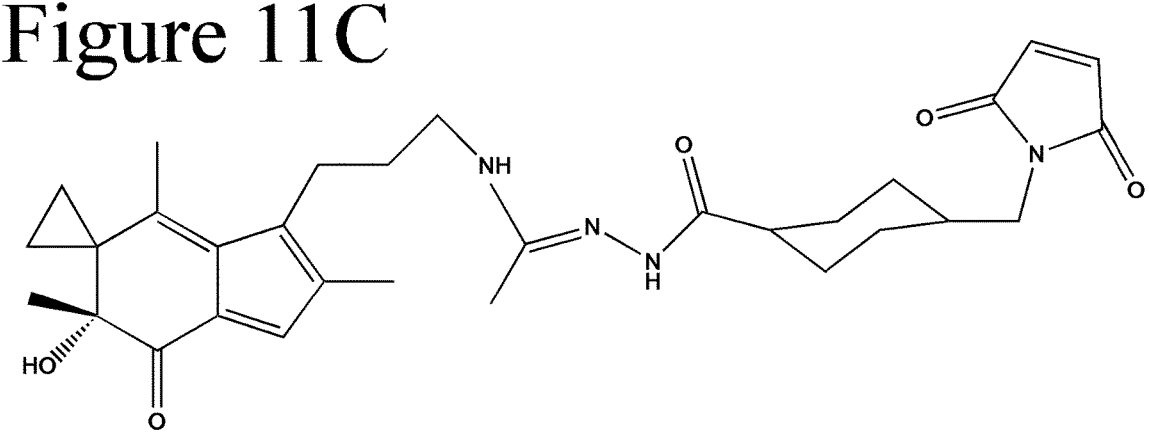
FIG. 11C shows the structure of the analog 201 attached via the 4-(N-maleimidomethyl) cyclohexane-1-1carboxyl-hydrazide ($M_2C_2H$) linking reagent according to an embodiment of the invention.

FIG. 11A shows the structure of the analog 124 attached via the carbonyl group using the AMBH linking reagent. FIG. 11B shows the structure of the analog 124 attached via the carbonyl group using the ABH linking reagent. FIG. 11C shows the structure of the analog 201 attached via the M$_2$C$_2$H linking reagent.

Table IIIA shows acylfulvene carbonyl analogs which can be attached to a bi-functional linker which can be attached to a sulfhydryl reacting group of the AM using the reagent. In an embodiment of the present invention, the acylfulvene carbonyl derivative shown in the first column of Table IIIA is linked to the AM through the free sulfhydryl group of the AM using the reagent identified in the second column of Table IIIA to form the AMC.

Table IIIB shows acylfulvene carbonyl analogs which can be attached to a bi-functional linker, where the linker also contains a photoactivatable reactive group which can attach to the AM using the reagent. In an embodiment of the present invention, the acylfulvene carbonyl derivative shown in the first column of Table IIIB is linked to the AM through the photoactivatable reactive group using the reagent identified in the second column of Table IIIB to form the AMC.

Table IIIC shows acylfulvene carbonyl analogs which can be attached to a bi-functional linker, where the linker also contains an amine reactive group which can attach to the AM using the reagent. In an embodiment of the present invention, the acylfulvene carbonyl derivative shown in the first column of Table IIIC is linked to the AM through the amino group using the reagent identified in the second column of Table IIIC to form the AMC.

Aldehyde Derivative. In an embodiment of the present invention, the acylfulvene structures shown in FIGS. 2A, 2C, 2F, 2H, 2I, 2L and 2M and illudin structures shown in FIGS. 2B, 2D, 2E, 2G, 2J, 2K, 2N and 2O, where R$_1$ denotes substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl in which incorporated heteroatoms can be halogens (F, Cl, Br, I); nitrogen (N) functional groups including primary amines (—NH$_2$), secondary amines (—NH—), tertiary amines (—NR$_A$R$_B$), imine (—C(═N)H—), (—C(═N)R$_A$—), Azo (—N═N—), Cyanate (—C═N), isocyanate (—N═C═O), amide (—C(═O)NR$_A$R$_B$) or (—C(═O)NR$_A$H) or (—C(═O)NH$_2$); sulfur (S) functional groups including thioethers (—S—), thiones (—C(═S)—), sulfoxides (—S(═O)—), sulfones (—S(═O)$_2$—), sulfoximes (—S(═O)(═NR$_A$)— or (—S(═O)(═NH)—), sulfhydryls (—SH), thiocyanate (—S—C(═N)—), isothiocyanate (—N═C(═S); oxygen (O) functional groups including hydroxyl (—OH), carbonyl (—C(═O)—), aldehyde (—C(═O)H, carboxylate (COOH), ethers (—O—), esters (—OC(═O)—), carbonate (—O(C═O)O—); and R$_2$, R$_3$, R$_4$, R$_5$ denote either H, CH$_3$, or CH$_2$OH and where R$_6$ is HCO (an aldehyde group) for an acylfulvene derivative shown in FIGS. 2A, 2C, 2F, 2H, 2I, 2L and 2M and illudin derivative shown in FIGS. 2B, 2D, 2E, 2G, 2J, 2K, 2N and 2O.

Figure 12A:
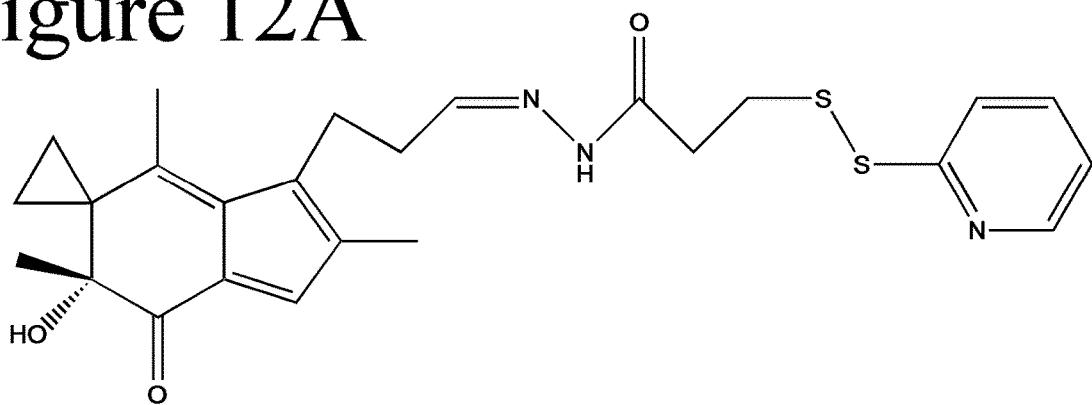
FIG. 12A shows the structure of the analog 010 attached via the aldehyde group using the 3-(2-pyridyldithio) propionyl hydrazide (PDPH) linking reagent according to an embodiment of the invention.
Figure 12B:
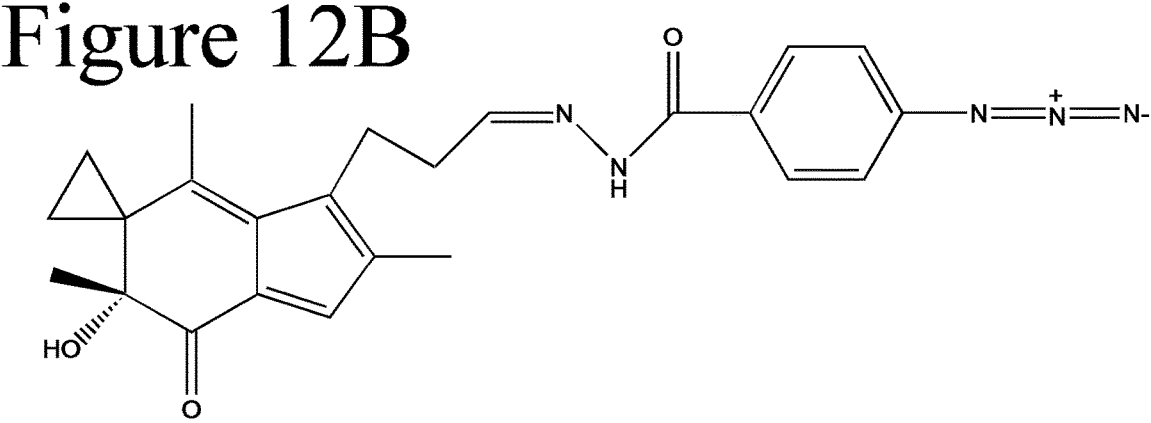
FIG. 12B shows the structure of the analog 010 attached via the aldehyde group using the ABH linking reagent according to an embodiment of the invention.
Figure 12C:
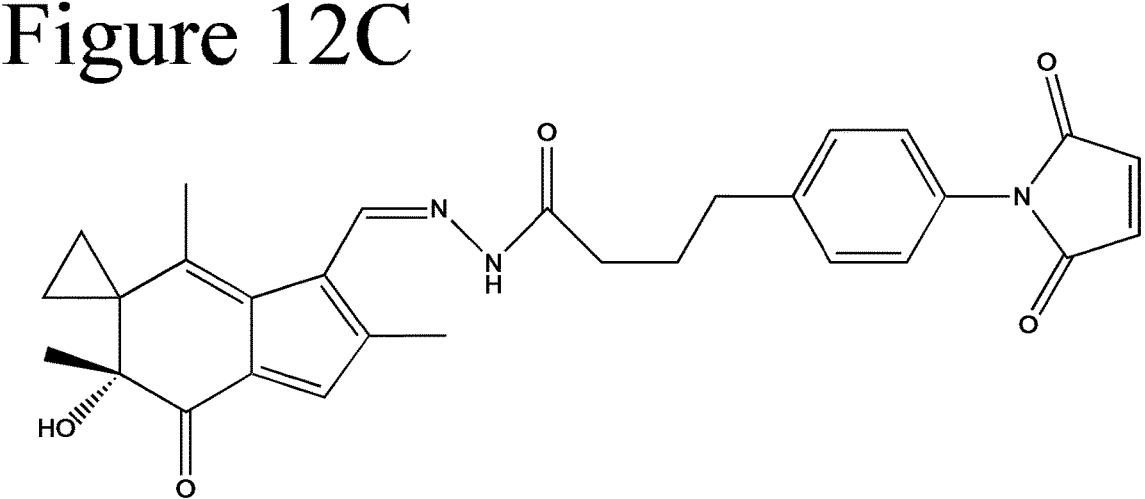
FIG. 12C shows the structure of the analog 011 attached via 4-(4-N-maleimidophenyl)-butyric acid hydrazide (MPBH) linking reagent according to an embodiment of the invention.

FIG. 12A shows the structure of the analog 010 attached via the aldehyde group using the PDPH linking reagent. FIG. 12B shows the structure of the analog 010 attached via the aldehyde group using the ABH linking reagent. FIG. 12C shows the structure of the analog 011 attached via MPBH linking reagent.

Table IVA shows acylfulvene aldehyde analogs which can be attached to a bi-functional linker which can be attached to a sulfhydryl reacting group of the AM using the reagent. In an embodiment of the present invention, the acylfulvene aldehyde derivative shown in the first column of Table IVA is linked to the AM through the free sulfhydryl group of the AM using the reagent identified in the second column of Table IVA to form the AMC.

Table IVB shows acylfulvene aldehyde analogs which can be attached to a bi-functional linker, where the linker also contains a photoactivatable reactive group which can attach to the AM using the reagent. In an embodiment of the present invention, the acylfulvene aldehyde derivative shown in the first column of Table IVB is linked to the AM through the photoactivatable reactive group using the reagent identified in the second column of Table IVB to form the AMC.

Table IVC shows acylfulvene aldehyde analogs which can be attached to a bi-functional linker, where the linker also contains an amine reactive group which can attach to the AM using the reagent. In an embodiment of the present invention, the acylfulvene aldehyde derivative shown in the first column of Table IVC is linked to the AM through the amino group using the reagent identified in the second column of Table IVC to form the AMC.

Figure 2A:
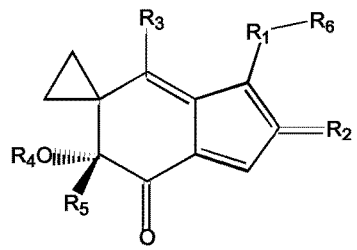
FIGS. 2A, 2C, 2F, 2H, 2I, 2L and 2M show the structures of acylfulvene medicant moieties, according to various embodiments of the invention.
Figure 2B:
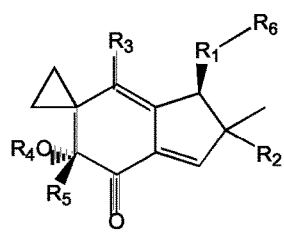
FIGS. 2B, 2D, 2E, 2G, 2J, 2K, 2N and 2O show the structures of illudin medicant moieties, according to various embodiments of the invention.
Figure 2C:
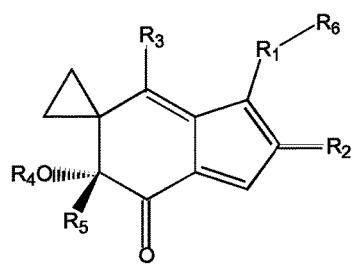
Figure 2D:
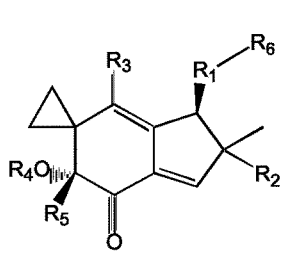
Figure 2E:
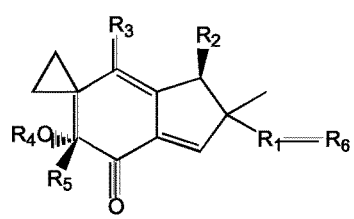
Figure 2F:
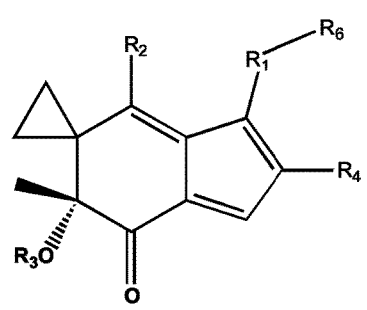
Figure 13A:
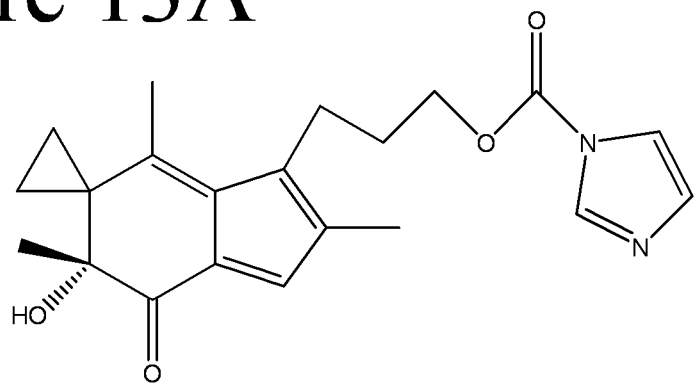
FIG. 13A shows the structure of the analog 009 attached via the alcohol group using the N,N'-carbonyldiimidazole (CDI) linking reagent according to an embodiment of the invention.
Figure 13B:
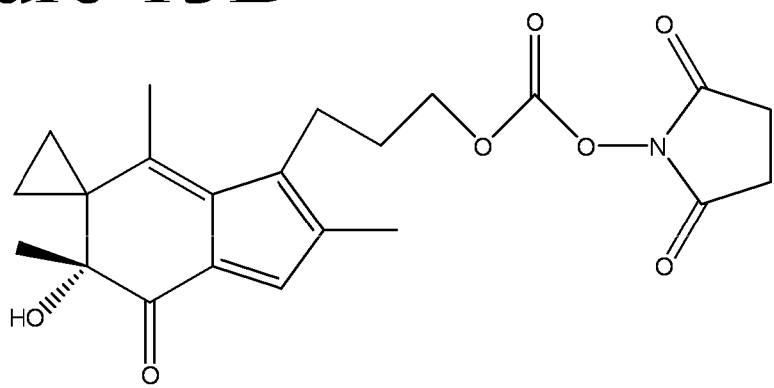
FIG. 13B shows the structure of the analog 009 attached via the alcohol group using the N-hydroxysuccinimidyl chloroformate (HSC) linking reagent according to an embodiment of the invention.
Figure 13C:
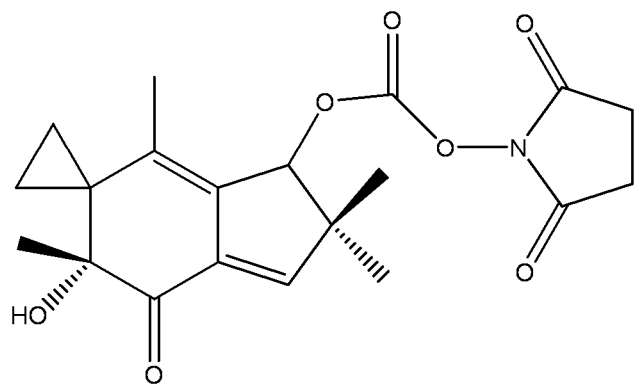
FIG. 13C shows the structure of the medicant moiety Illudin M (FIG. 1A) attached via the N,N'-disuccinimidyl carbonate (DSC) linking reagent according to an embodiment of the invention.

Alcohol Derivative. In an embodiment of the present invention, the structures shown in FIG. 2C, FIG. 2D, and FIG. 2E, R$_1$ denotes substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl in which incorporated heteroatoms can be halogens (F, Cl, Br, I); nitrogen (N) functional groups including primary amines (—NH$_2$), secondary amines (—NH—), tertiary amines (—NR$_A$R$_B$), imine (—C(═N)H—), (—C(═N)R$_A$—), Azo (—N═N—), Cyanate (—C═N), isocyanate (—N═C═O), amide (—C(═O)NR$_A$R$_B$) or (—C(═O)NR$_A$H) or (—C(═O)NH$_2$); sulfur (S) functional groups including thioethers (—S—), thiones (—C(═S)—), sulfoxides (—S(═O)—), sulfones (—S(═O)$_2$—), sulfoximes (—S(═O)(═NR$_A$)— or (—S(═O)(═NH)—), sulfhydryls (—SH), thiocyanate (—S—C(═N)—), isothiocyanate (—N═C(═S); oxygen (O) functional groups including hydroxyl (—OH), carbonyl (—C(═O)—), aldehyde (—C(═O)H, carboxylate (COOH), ethers (—O—), esters (—OC(═O)—), carbonate (—O(C═O)O—); and R$_2$, R$_3$, R$_4$, R$_5$ denote either H, CH$_3$, or CH$_2$OH for an irofulven derivative (FIG. 2C), an illudin ring derivative (FIG. 2D) or an illudin alkyl derivative (FIG. 2E). FIG. 13A shows the structure of the analog 009 attached via the alcohol group using the CDI linking reagent. FIG. 13B shows the structure of the analog 009 attached via the alcohol group using the HSC linking reagent. FIG. 13C shows the structure of the medicant moiety Illudin M attached via the DSC linking reagent.

Table VA shows acylfulvene alcohol analogs which can be attached to a bi-functional linker which can be attached to a sulfhydryl reacting group of the AM using the reagent. In an embodiment of the present invention, the acylfulvene alcohol derivative shown in the first column of Table VA is linked to the AM through the free sulfhydryl group of the AM using the reagent identified in the second column of Table VA to form the AMC.

Table VB shows acylfulvene alcohol analogs which can be attached to a bi-functional linker, where the linker also contains an amine reactive group which can attach to the AM using the reagent. In an embodiment of the present invention, the acylfulvene alcohol derivative shown in the first column of Table VB is linked to the AM through the amino group using the reagent identified in the second column of Table VB to form the AMC.

Sulfhydryl Derivative. In an embodiment of the present invention, the structures shown in FIG. 2C, FIG. 2D, and FIG. 2E, $R_1$ and $R_6$ denote independently substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl in which incorporated heteroatoms can be halogens (F, Cl, Br, I); nitrogen (N) functional groups including primary amines (—$NH_2$), secondary amines (—NH—), tertiary amines (—$NR_AR_B$), imine (—C(=N)H—), (—C(=N)$R_A$—), Azo (—N=N—), Cyanate (—C≡N), isocyanate (—N=(C=O), amide (—C(=O)$NR_AR_B$) or (—C(=O)$NR_AH$) or (—C(=O)$NH_2$); sulfur (S) functional groups including thioethers (—S—), thiones (—C(=S)—, sulfoxides (—S(=O)—, sulfones (—S(=O)$_2$—), sulfoximes (—S(=O)(=$NR_A$)— or (—S(=O)(=NH)—, sulfhydryls (—SH), thiocyanate (—S—C(=N)—, isothiocyanate (—N=C(=S); oxygen (O) functional groups including hydroxyl (—OH), carbonyl (—C(=O)—), aldehyde (—C(=O)H, carboxylate (COOH), ethers (—O—), esters (—OC(=O)—), carbonate (—O(C=O)O—); and $R_2$, $R_3$, $R_4$, $R_5$ denote either H, $CH_3$, or $CH_2OH$, and $R_2$, $R_3$, $R_4$, $R_5$ denote either H, $CH_3$, or $CH_2OH$ and $R_7$ is SH or SS—$R_8$ for an irofulven derivative (FIG. 2C), an illudin ring derivative (FIG. 2D) or an illudin alkyl derivative (FIG. 2E). FIG. 14A shows the structure of the analog 051 attached via the sulfhydryl group using SMCC linking reagent. FIG. 14B shows the structure of the analog 051 attached via the sulfhydryl group using MPBH linking reagent. FIG. 14C shows structure of the analog 051 attached via sulfhydryl group using PDPH linking reagent.

In an embodiment of the present invention, analog 051 can be attached to an AM by attaching a disulfide bridge at 6' position, a terminal cysteine or n-acetylcysteine group. Analog 051 has a free sulfhydryl group which can react with other sulfhydryl groups to produce a disulfide bond or alternatively react with specific sulfhydryl-reacting groups such as malonic acid derivatives. The other sulfhydryl groups can be on a linker, where the free sulfhydryl group will react with sulfhydryl reactive groups on the linkers, e.g., malonic acid derivatives such as SMCC. Alternatively a medicant with a free sufhydryl can directly react with free sulfhydryl groups on an AM (such as are present in cysteine residues).

Table VIA shows acylfulvene sulfhydryl analogs which can be attached to a bi-functional linker, where the linker also contains an amine reactive group which can attach to the AM using the reagent (a reducing agent can be used to reduce the disulfide and generate a sulfhydryl group). In an embodiment of the present invention, the acylfulvene sulfhydryl derivative shown in the first column of Table VIA is linked to the AM through the free amino group of the bi-functional linker using the reagent identified in the second column of Table VIA to form the AMC.

Table VIB shows acylfulvene sulfhydryl analogs which can be attached to a bi-functional linker, where the linker also contains a sulfhydryl reacting group which can attach to the AM using the reagent (a reducing agent can be used to reduce the disulfide and generate a sulfhydryl group). In an embodiment of the present invention, the acylfulvene sulfhydryl derivative shown in the first column of Table VIB is linked to the AM through the free sulfhydryl group of the bi-functional linker using the reagent identified in the second column of Table VIB to form the AMC.

Table VIC shows acylfulvene sulfhydryl analogs which can be attached to a bi-functional linker, where the linker also contains a photoactivatable reactive group which can attach to the AM using the reagent (a reducing agent can be used to reduce the disulfide and generate a sulfhydryl group). In an embodiment of the present invention, the acylfulvene sulfhydryl derivative shown in the first column of Table VIC is linked to the AM through the photoactivatable reactive group of the bi-functional linker using the reagent identified in the second column of Table VIC to form the AMC.

Table VID shows acylfulvene sulfhydryl analogs which can be attached to a bi-functional linker, where the linker also contains a carboxylate reactive group which can attach to the AM using the reagent (a reducing agent can be used to reduce the disulfide and generate a sulfhydryl group). In an embodiment of the present invention, the acylfulvene sulfhydryl derivative shown in the first column of Table VID is linked to the AM through the carboxylate reactive group of the bi-functional linker using the reagent identified in the second column of Table VID to form the AMC.

Halide Derivative. In an embodiment of the present invention, the structures shown in FIG. 2C, FIG. 2D, and FIG. 2E, $R_1$ denotes substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl in which incorporated heteroatoms can be halogens (F, Cl, Br, I); nitrogen (N) functional groups including primary amines (—$NH_2$), secondary amines (—NH—), tertiary amines (—$NR_AR_B$), imine (—C(=N)H—), (—C(=N)$R_A$—), Azo (—N=N—), Cyanate (—C≡N), isocyanate (—N=(C=O), amide (—C(=O)$NR_AR_B$) or (—C(=O)$NR_AH$) or (—C(=O)$NH_2$); sulfur (S) functional groups including thioethers (—S—), thiones (—C(=S)—, sulfoxides (—S(=O)—, sulfones (—S(=O)$_2$—), sulfoximes (—S(=O)(=$NR_A$)— or (—S(=O)(=NH)—, sulfhydryls (—SH), thiocyanate (—S—C(=N)—, isothiocyanate (—N=C(=S); oxygen (O) functional groups including hydroxyl (—OH), carbonyl (—C(=O)—), aldehyde (—C(=O)H, carboxylate (COOH), ethers (—O—), esters (—OC(=O)—), carbonate (—O(C=O)O—); and $R_2$, $R_3$, $R_4$, $R_5$ denote either H, $CH_3$, or $CH_2OH$ and X is a halogen for an irofulven derivative (FIG. 2C), an illudin ring derivative (FIG. 2D) or an illudin alkyl derivative (FIG. 2E).

In an embodiment of the present invention, the medicant moieties 4, 5, 20, 53, 237 which contain halide groups can react in one of two ways. They will react directly with free sulfhydryl groups present on antibodies/proteins (e.g., on cysteine residues) or they can react with sulfhydryl groups on linkers (e.g., such as malonic acid derivatives such as SMCC). FIG. 20 shows analog 20 linked to DSP (FIG. 20A), DTME (FIG. 20B) and SMPT (FIG. 20C).

Figure 2G:
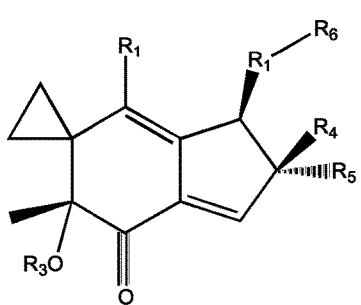
Figure 2H:
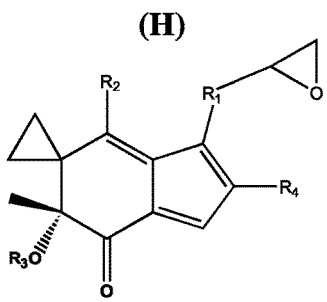
Figure 2I:
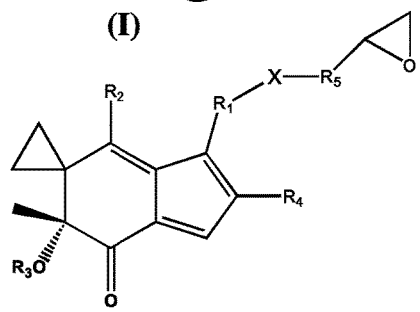

Acyl azide or Azide Derivative. In an embodiment of the present invention, the structures shown in FIG. 2F and FIG. 2G, $R_1$ denotes independently substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl in which incorporated heteroatoms can be halogens (F, Cl, Br, I); nitrogen (N) functional groups including primary amines (—$NH_2$), secondary amines (—NH—), tertiary amines (—$NR_AR_B$), imine (—C(=N)H—), (—C(=N)$R_A$—), Azo (—N=N—), Cyanate (—C=N), isocyanate (—N=(C=O), amide (—C(=O)$NR_AR_B$) or (—C(=O)$NR_A$H) or (—C(=O)$NH_2$); sulfur (S) functional groups including thioethers (—S—), thiones (—C(=S)—), sulfoxides (—S(=O)—), sulfones (—S(=O)$_2$—), sulfoximes (—S(=O)(=$NR_A$)— or (—S(=O)(=NH)—), sulfhydryls (—SH), thiocyanate (—S—C(=N)—), isothiocyanate (—N=C(=S); oxygen (O) functional groups including hydroxyl (—OH), carbonyl (—C(=O)—), aldehyde (—C(=O)H, carboxylate (COOH), ethers (—O—), esters (—OC(=O)—), carbonate (—O(C=O)O—); and $R_2$, $R_3$, $R_4$, $R_5$ denote either H, $CH_3$, OH, $OCH_3$, $CH_2OH$, $CH_2CH_3$, $OCH_2CH_3$ for an irofulven derivative (FIG. 2F) or an illudin derivative (FIG. 2G).

In an embodiment of the present invention, the medicant moieties 193, 195, 299, 300, 307 can be photoactivated, with UV radiation. The acyl azides and phenylazides do not need linkers, forming a reactive nitrene group that reacts with primary amines on proteins. The only caveat is the reaction of the drug and protein must be carried out in the absence of thiol reducing agents.

The azide must be on a ring system like a benzene or phenyl group, see analogs 193, 195, 300), 307 and 309.

Figure 2J:
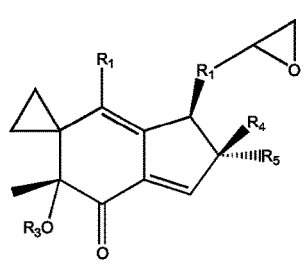
Figure 2K:
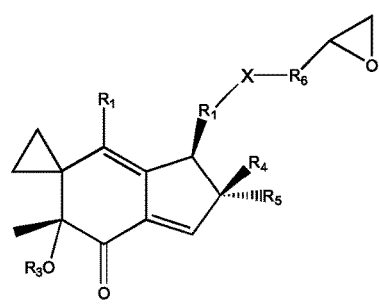
Figure 2L:
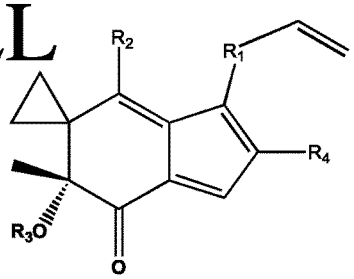
Figure 2M:
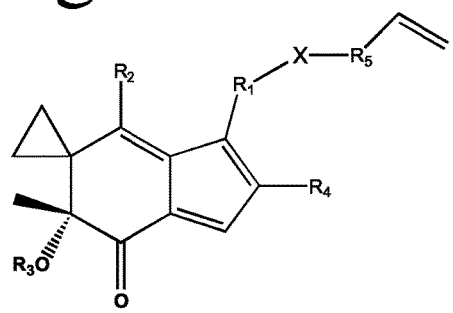

Epoxide Derivative. In an embodiment of the present invention, the structures shown in FIG. 2H, FIG. 2I, FIG. 2J and FIG. 2K, where $R_1$ substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl in which incorporated heteroatoms can be halogens (F, Cl, Br, I); nitrogen (N) functional groups including primary amines (—$NH_2$), secondary amines (—NH—), tertiary amines (—$NR_AR_B$), imine (—C(=N)H—), (—C(=N)$R_A$—), Azo (—N=N—), Cyanate (—C=N), isocyanate (—N=(C=O), amide (—C(=O)$NR_AR_B$) or (—C(=O)$NR_A$H) or (—C(=O)$NH_2$); sulfur (S) functional groups including thioethers (—S—), thiones (—C(=S)—), sulfoxides (—S(=O)—), sulfones (—S(=O)$_2$—), sulfoximes (—S(=O)(=$NR_A$)— or (—S(=O)(=NH)—), sulfhydryls (—SH), thiocyanate (—S—C(=N)—), isothiocyanate (—N=C(=S); oxygen (O) functional groups including hydroxyl (—OH), carbonyl (—C(=O)—), aldehyde (—C(=O)H, carboxylate (COOH), ethers (—O—), esters (—OC(=O)—), carbonate (—O(C=O)O—); and $R_2$, $R_3$, $R_4$, $R_5$ denote either H, $CH_3$, or $CH_2OH$, $R_6$ denotes independently halogen, —CN, —$CF_3$, —OH, —$NH_2$, —$SO_2$, —COOH, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and $R_2$, $R_3$, $R_4$, $R_5$ denote either H, $CH_3$, OH, $OCH_3$, $CH_2OH$, $CH_2CH_3$, $OCH_2CH_3$ and X denotes a heteroatom including oxygen (O), sulfur (S), and nitrogen (N) for irofulven derivatives (FIG. 2H and FIG. 2I) or illudin derivatives (FIG. 2J and FIG. 2K).

In an embodiment of the present invention, the medicant moieties 114 epoxides react with carboxyl groups, thiols, amines and hydroxyl groups. For example, analog 114 can be linked to ABH, BMPA, or PDPH.

Example 1. Synthesis of Medicant 113. The Wittig reaction was performed on analog 10. First 65 mg $CH_3PPh_3Br$ (0.185 mmol) in anhydrous THF was cooled to −75° C. and stirred for 1 hour. Then 200 μL of n-butyl lithium (0.183 mmol) was added very slowly to the flask while maintaining temperature at −75° C., and a yellow precipitate formed. It was stirred for another 1.5 hours then analog 10 (50 mg, 0.183 mmol) was slowly added while maintaining temperature at −75° C., followed by stirring for 2.0 hours. The reaction was quenched with ammonium chloride, extracted with $CH_2Cl_2$, washed with water, $NaHCO_3$, and saline. Dried over $Na_2SO_4$ and concentrated. The residue was eluted through a column (10% ethyl acetate in hexane) to give analog 113 as a solid.

Figure 2N:
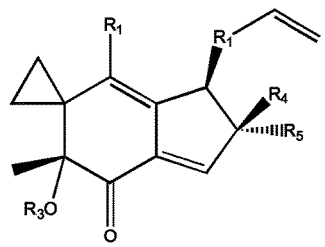
Figure 2O:
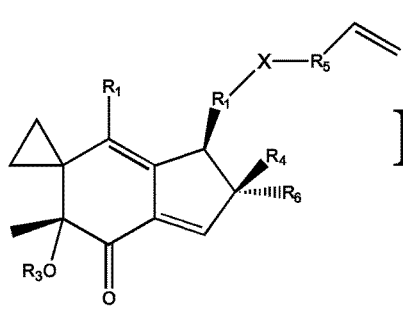

Acroyl Derivative. In an embodiment of the present invention, the structures shown in FIG. 2L, FIG. 2M, and FIG. 2N and FIGS. 2O, $R_1$ and $R_6$ denote independently substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl in which incorporated heteroatoms can be halogens (F, Cl, Br, I); nitrogen (N) functional groups including primary amines (—$NH_2$), secondary amines (—NH—), tertiary amines (—$NR_AR_B$), imine (—C(=N)H—), (—C(=N)$R_A$—), Azo (—N=N—), Cyanate (—C=N), isocyanate (—N=(C=O), amide (—C(=O)$NR_AR_B$) or (—C(=O)$NR_A$H) or (—C(=O)$NH_2$); sulfur (S) functional groups including thioethers (—S—), thiones (—C(=S)—), sulfoxides (—S(=O)—), sulfones (—S(=O)$_2$—), sulfoximes (—S(=O)(=$NR_A$)— or (—S(=O)(=NH)—), sulfhydryls (—SH), thiocyanate (—S—C(=N)—), isothiocyanate (—N=C(=S); oxygen (O) functional groups including hydroxyl (—OH), carbonyl (—C(=O)—), aldehyde (—C(=O)H, carboxylate (COOH), ethers (—O—), esters (—OC(=O)—), carbonate (—O(C=O)O—); and $R_2$, $R_3$, $R_4$, $R_5$ denote independently either H, $CH_3$, OH, $OCH_3$, $CH_2OH$, $CH_2CH_3$, $OCH_2CH_3$ and X denotes a heteroatom including oxygen (O), sulfur (S), and nitrogen (N) for irofulven derivatives (FIG. 2L and FIG. 2M) or illudin derivatives (FIG. 2N and FIG. 2O).

In an embodiment of the present invention, the medicant moieties 1300 react predominately with sulfhydryl groups. Acroyl derivatives can react in one of two ways. They will react directly with free sulfhydryl groups present on antibodies and proteins (e.g., on cysteine residues) or they will react with sulfhydryl groups on linkers (e.g., such as malonic acid derivatives such as SMCC).

Figure 3A:
FIG. 3A shows a schematic descriptions of an AMC 1001 where an Antibody (Ab) 1110 bound to a LU 1200 is bound to a medicant moiety (MM) 1300, according to various embodiments of the invention.
Figure 3B:
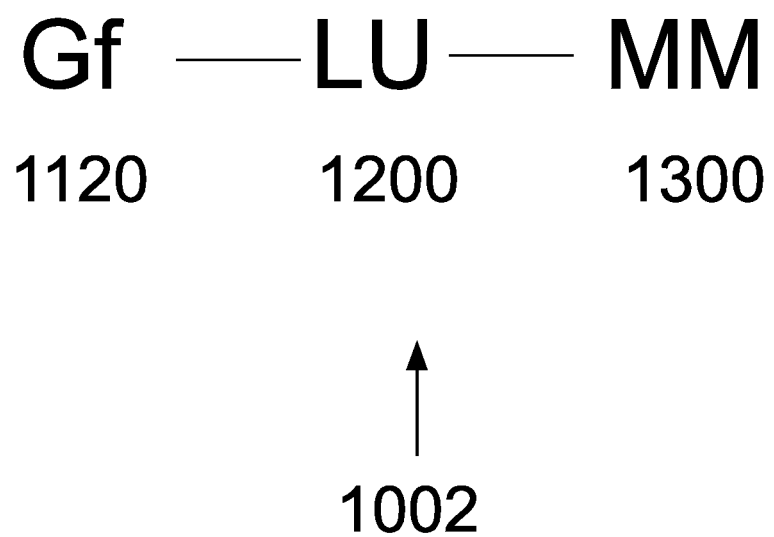
FIG. 3B shows a schematic descriptions of an AMC 1002 where a Growth factor (Gf) 1120 bound to a LU 1200 is bound to a medicant moiety (MM) 1300, according to various embodiments of the invention.

Illudin1 linked to an Antibody. In various embodiments of the present invention, an AMC is made up of an antibody 1110 linked to an illudin1 moiety 1301. Various embodiments of the invention, are directed to the methods for the preparation, use, and to pharmaceutical compositions containing an illudin1 moiety 1301 linked to an antibody 1110 to form an antibody medicant conjugate (AMC). In various embodiments the compounds of the present invention, the AMC can have the general formula shown in FIG. 3A, where the antibody 1110 is bound to a linker 1200 which is bound to an illudin1 moiety 1301. In other various embodiments of the present invention, the compounds of the present AMC invention can have the general formula shown in FIG. 3B, where a growth factor 1120 is bound to a linker 1200 which is bound to an illudin1 moiety 1301. In various embodiments the compounds of the present invention include stereoisomers, solvates, and pharmaceutically acceptable salts thereof, where the linker 1200 is as defined in Table X, and the illudin1 1301 is as defined below in Table XI.

Linker to bind Illudin to an Antibody. In an embodiment of the present invention, an antibody 1110 with a traditional linker 1240 to an illudin1 moiety 1301 binds to a receptor to which the antibody 1110 was prepared and directs the illudin1 moiety 1301 to cell populations expressing the receptor. In an embodiment of the present invention, an antibody 1110 bound with a traditional linker 1240 to an illudin1 moiety 1301 acts as an AM for a receptor and directs the illudin1 moiety 1301 to tissues containing cells expressing the receptor. In an embodiment of the present invention, an antibody 1110 with a traditional linker 1240 bound to an illudin1 moiety 1301 acts as an AM for a receptor and directs the illudin1 moiety 1301 to tumors containing cells expressing the receptor. In an embodiment of the present invention, an antibody 1110 with a traditional linker 1240 bound to an illudin1 moiety 1301 acts as an AM for a receptor and directs the illudin1 moiety 1301 to tumors containing cells over-expressing the receptor compared to non tumor cells.

Linker to bind Illudin to Growth Factor. In an embodiment of the present invention, an illudin1 moiety 1301 linked via a traditional linker 1240 to a growth factor 1120 binds to the growth factor receptor and direct the illudin1 moiety 1301 to cell populations expressing the receptor. In an embodiment of the present invention, a growth factor 1120 linked via a traditional linker 1240 to an illudin1 moiety 1301 acts as an AM for the growth factor receptor and directs the illudin1 moiety 1301 to tissues containing cells expressing the receptor. In an embodiment of the present invention, a growth factor 1120 linked via a traditional linker 1240 to an illudin1 moiety 1301 acts as an AM for the growth factor receptor and directs the illudin1 moiety 1301 to tumors containing cells expressing the receptor. In an embodiment of the present invention, a growth factor 1120 linked via a traditional linker 1240 to an illudin1 moiety 1301 acts as an AM for the growth factor receptor and directs the illudin1 moiety 1301 to tumors containing cells over-expressing the receptor compared to non tumor cells.

Linker to bind Illudin to Steroid. Whereby Illudin S, Illudin M, or one of analogs 001 through 316 can be attached, either directly or with a linker, to a steroid which allows preferential binding to a cell overexpressing that particular receptor for that steroid and subsequent killing of the cell (see e.g., Table VII).

Example 2. Synthesis of Medicant-Estrone 107. Analog 106 (see Example 13) (139 mg 0.384 mmol, 1 equiv.), DMAP (4 mg, 0.03 mmol, 0.08 equiv.) and estrone (104.4 mg, 0.384 mmol, 1 equiv.) were dissolved in $CH_2Cl_2$ (14 mL) at 0° C. To this solution was added $CH_2Cl_2$ solution of DCC (460 μL, 1 M, 0.46 mmol, 1.2 equiv.) through a syringe. After 0.5 hours the solution was raised to room temperature. After 2 hours the mixture was filtered and the filtrate was washed with dilute HCl (1.5%), saturated $NaHCO_3$ and brine in sequence. The organic phase was then dried and evaporated. The residue was eluted through a column ($CH_2Cl_2$/Methanol, 10:0.25) to give analog 107 (100 mg, 42%) as semisolid. Analog 107 can be subsequently linked to estrone.

Example 3. Preparation of Medicant-Estradiol 108. Analog 038 (58.5 mg, 0.2035 mmol), beta-estradiol (58.0 mg, 0.2150 mmol) and DMAP (5 mg. 0.048 mmol) were dissolved in $CH_2Cl_2$ (5.6 mL) at 0° C. To this solution was added $CH_2Cl_2$ solution of DCC (250 μL, 1 M, 0.244 mmol), stirred for 30 minutes, allowed to warm to room temperature then stirred for 1.5 hours. The filtrate was washed with dilute HCl (1.5%), saturated $NaHCO_3$ and brine in sequence. The organic phase was dried over $Na_2SO_4$, and evaporated. The residue was eluted through a column (100% $CH_2Cl_2$), fractions collected then eluted through a second column ($CH_2Cl_2$ plus 0.5% methanol), to give analog 108 (45 mg) as a solid.

Table VII shows the cytotoxic data $IC_{50}$ values (micromolar, 2 hour exposure, N=3, mean±SD) for 108. MCF7 over express estrogen alpha-receptors. MCF7 cells are preferentially killed by 110 the acylfulvene-estrone analog and to a lesser extent 108 the acylfulvene-estradiol analog because estrone preferentially binds to alpha-receptor.

Example 4. Preparation of Medicant-Estradiol 109. Analog 106 (54.5 mg, 0.15 mmol, 1 equiv.), β-estradiol (40.5 mg, 0.15 mmol), and DMAP (1.8 mg, 0.015 mmol, 0.1 equiv.) were dissolved in $CH_2Cl_2$(5 mL) at 0° C. To this solution was added $CH_2Cl_2$ solution of DCC (165 μL, 1 M, 0.165 mmol, 1.1 equiv.). The mixture was raised to room temperature after 0.5 h. After another 2 h, the mixture was filtered. The filtrate was washed with dilute HCl (1.5%), saturated $NaHCO_3$ and brine in sequence. The organic phase was dried and evaporated. The residue was eluted through a column ($CH_2Cl_2$/Methanol 10:0.25) to give analog 109 (55 mg, 60%) as semisolid.

Example 5. Preparation of Medicant-Estrone 110. Analog 038 (68 mg, 0.2365 mmol), estrone (68.0 mg, 0.2160 mmol) and DMAP (5 mg. 0.048 mmol) were dissolved in $CH_2Cl_2$ (8.0 mL) at 0° C. To this solution was added $CH_2Cl_2$ solution of DCC (300 μL, 1 M, 0.283 mmol), stirred for 30 minutes, allowed to warm to room temperature then stirred for 0.5 hours. The filtrate was washed with dilute HCl (1.5%), saturated $NaHCO_3$ and brine in sequence. The organic phase was dried over $Na_2SO_4$, and evaporated. The residue was eluted through a column (100% $CH_2Cl_2$), fractions collected then eluted through a second column ($CH_2Cl_2$ plus 0.5% methanol), to give analog 110 (40 mg) as a solid.

Table VII shows the cytotoxic data $IC_{50}$ values (micromolar, 2 hour exposure, N=3, mean+SD) for 110. MCF7 cells over express estrogen alpha-receptors. MCF7 cells are preferentially killed by the acylfulvene-estrone analog 110 and to a lesser extent by the acylfulvene-estradiol analog 108 because estrone preferentially binds to alpha-receptor. In contrast, illudin M killed both ER negative and ER positive cells to the same extent. The data in Table VII demonstrates that compounds 108 and 110 are preferentially cytotoxic to cells expressing large numbers of estrogen receptors on their surface.

Example 6. Preparation of Medicant-Testosterone 111. Analog 038 (52.5 mg, 0.182 mmol), testosterone (50.0 mg, 0.173 mmol) and DMAP (5 mg. 0.048 mmol) were dissolved in $CH_2Cl_2$ (8.0 mL) at 0° C. To this solution was added $CH_2Cl_2$ solution of DCC (250 μL, 1 M), stirred for 30 minutes, allowed to warm to room temperature then stirred for 2 hours. The filtrate was washed with dilute HCl (1.5%), saturated $NaHCO_3$ and brine in sequence. The organic phase was dried over $Na_2SO_4$, and evaporated. The residue was eluted through a column (100% $CH_2Cl_2$ plus 0.5% methanol), to give analog 111 (15 mg) as a solid.

Example 7. Preparation of Medicant-Androsterone 112. Analog 038 (29 mg), androsterone (25.0 mg) and DMAP (5 mg. 0.048 mmol) were dissolved in $CH_2Cl_2$ (5.0 mL) at 0° C. To this solution was added $CH_2Cl_2$ solution of DCC (150 μL, 1 M), stirred for 30 minutes, allowed to warm to room temperature then stirred for 2 hours. The filtrate was washed with dilute HCl (1.5%), saturated $NaHCO_3$ and brine in sequence. The organic phase was dried over $Na_2SO_4$, and evaporated. The residue was eluted through a column (2:3 ethyl acetate:hexane) to give analog 112 (15 mg) as a solid.

In an embodiment of the present invention, an illudin2 moiety 1302 linked via a traditional linker 1240 to a steroid 1140 bind to receptors for the steroid and directs the illudin2 moiety 1302 to cell populations expressing the receptor. In an embodiment of the present invention, a steroid 1140 linked via a traditional linker 1240 to an illudin2 moiety 1302 acts as an AM for the steroid hormone receptor and directs the illudin2 moiety 1302 to tissues containing cells expressing the receptor. In an embodiment of the present invention, a steroid 1140 linked via a traditional linker 1240 to an illudin2 moiety 1302 acts as an AM for the steroid hormone receptor and directs the illudin2 moiety 1302 to tumors containing cells over-expressing the receptor compared to non tumor cells.

Example 4. Preparation of Medicant-Estradiol 109. Analog 106 (54.5 mg, 0.15 mmol, 1 equiv.), β-estradiol (40.5 mg, 0.15 mmol), and DMAP (1.8 mg, 0.015 mmol, 0.1 equiv.) were dissolved in $CH_2Cl_2$(5 mL) at 0° C. To this solution was added $CH_2Cl_2$ solution of DCC (165 μL, 1 M, 0.165 mmol, 1.1 equiv.). The mixture was raised to room temperature after 0.5 h. After another 2 h, the mixture was filtered. The filtrate was washed with dilute HCl (1.5%), saturated $NaHCO_3$ and brine in sequence. The organic phase was dried and evaporated. The residue was eluted through a column ($CH_2Cl_2$/Methanol 10:0.25) to give analog 109 (55 mg, 60%) as semisolid.

Example 5. Preparation of Medicant-Estrone 110. Analog 038 (68 mg, 0.2365 mmol), estrone (68.0 mg, 0.2160 mmol) and DMAP (5 mg. 0.048 mmol) were dissolved in $CH_2Cl_2$ (8.0 mL) at 0° C. To this solution was added $CH_2Cl_2$ solution of DCC (300 μL, 1 M, 0.283 mmol), stirred for 30 minutes, allowed to warm to room temperature then stirred for 0.5 hours. The filtrate was washed with dilute HCl (1.5%), saturated $NaHCO_3$ and brine in sequence. The organic phase was dried over $Na_2SO_4$, and evaporated. The residue was eluted through a column (100% $CH_2Cl_2$), fractions collected then eluted through a second column ($CH_2Cl_2$plus 0.5% methanol), to give analog 110 (40 mg) as a solid.

Table VII shows the cytotoxic data $IC_{50}$ values (micromolar, 2 hour exposure, N=3, mean+SD) for 110. MCF7 cells over express estrogen alpha-receptors. MCF7 cells are preferentially killed by the acylfulvene-estrone analog 110 and to a lesser extent by the acylfulvene-estradiol analog 108 because estrone preferentially binds to alpha-receptor. In contrast, illudin M killed both ER negative and ER positive cells to the same extent. The data in Table VII demonstrates that compounds 108 and 110 are preferentially cytotoxic to cells expressing large numbers of estrogen receptors on their surface.

Example 6. Preparation of Medicant-Testosterone 111. Analog 038 (52.5 mg, 0.182 mmol), testosterone (50.0 mg, 0.173 mmol) and DMAP (5 mg. 0.048 mmol) were dissolved in $CH_2Cl_2$ (8.0 mL) at 0° C. To this solution was added $CH_2Cl_2$ solution of DCC (250 μL, 1 M), stirred for 30 minutes, allowed to warm to room temperature then stirred for 2 hours. The filtrate was washed with dilute HCl (1.5%), saturated $NaHCO_3$ and brine in sequence. The organic phase was dried over $Na_2SO_4$, and evaporated. The residue was eluted through a column (100% $CH_2Cl_2$ plus 0.5% methanol), to give analog 111 (15 mg) as a solid.

Example 7. Preparation of Medicant-Androsterone 112. Analog 038 (29 mg), androsterone (25.0 mg) and DMAP (5 mg. 0.048 mmol) were dissolved in $CH_2Cl_2$ (5.0 mL) at 0° C. To this solution was added $CH_2Cl_2$ solution of DCC (150 μL, 1 M), stirred for 30 minutes, allowed to warm to room temperature then stirred for 2 hours. The filtrate was washed with dilute HCl (1.5%), saturated $NaHCO_3$ and brine in sequence. The organic phase was dried over $Na_2SO_4$, and evaporated. The residue was eluted through a column (2:3 ethyl acetate:hexane) to give analog 112 (15 mg) as a solid.

In an embodiment of the present invention, an illudin2 moiety 1302 linked via a traditional linker 1240 to a steroid 1140 bind to receptors for the steroid and directs the illudin2 moiety 1302 to cell populations expressing the receptor. In an embodiment of the present invention, a steroid 1140 linked via a traditional linker 1240 to an illudin2 moiety 1302 acts as an AM for the steroid hormone receptor and directs the illudin2 moiety 1302 to tissues containing cells expressing the receptor. In an embodiment of the present invention, a steroid 1140 linked via a traditional linker 1240 to an illudin2 moiety 1302 acts as an AM for the steroid hormone receptor and directs the illudin2 moiety 1302 to tumors containing cells over-expressing the receptor compared to non tumor cells factor receptor and directs the illudin2 moiety 1302 to tissues containing cells expressing the receptor. In an embodiment of the present invention, a growth factor 1120 linked via a FSB linker 1220 to an illudin2 moiety 1302 acts as an AM for the growth factor receptor and directs the illudin2 moiety 1302 to tumors containing cells expressing the receptor. In an embodiment of the present invention, a growth factor 1120 linked via a FSB linker 1220 to an illudin2 moiety 1302 acts as an AM for the growth factor receptor and directs the illudin2 moiety 1302 to tumors containing cells over-expressing the receptor compared to non tumor cells.

FSB Linker to bind Illudin to a Steroid. In an embodiment of the present invention, an illudin2 moiety 1302 linked via a FSB linker 1220 to a steroid 1140 binds to receptors for the steroid and direct the illudin2 moiety 1302 to cell populations expressing the receptor. In an embodiment of the present invention, a steroid 1140 linked via a FSB linker 1220 to an illudin2 moiety 1302 acts as a ligand for the steroid hormone receptor and directs the illudin2 moiety 1302 to tissues containing cells expressing the receptor. In an embodiment of the present invention, a steroid 1140 linked via a FSB linker 1220 to an illudin2 moiety 1302 acts as a ligand for the steroid hormone receptor and directs the illudin2 moiety 1302 to tumors containing cells expressing the receptor. In an embodiment of the present invention, a steroid 1140 linked via a FSB linker 1220 to an illudin2 moiety 1302 acts as an AM for the steroid hormone receptor and directs the illudin2 moiety 1302 to tissues containing cells expressing the receptor. In an embodiment of the present invention, a steroid 1140 linked via a FSB linker 1220 to an illudin2 moiety 1302 acts as an AM for the steroid hormone receptor and directs the illudin2 moiety 1302 to tumors containing cells expressing the receptor. In an embodiment of the present invention, a steroid 1140 linked via a FSB linker 1220 to an illudin2 moiety 1302 acts as an AM for the steroid hormone receptor and directs the illudin2 moiety 1302 to tumors containing cells over-expressing the receptor compared to non tumor cells.

FSB Linker to bind Illudin to an Anti-angiogenic peptide. In an embodiment of the present invention, an illudin2 moiety 1302 linked via a FSB linker 1220 to an anti-angiogenic peptide 1130 binds to receptors for the anti-angiogenic peptide and directs the illudin2 moiety 1302 to cell populations expressing the receptor. In an embodiment of the present invention, an anti-angiogenic peptide 1130 linked via a FSB linker 1220 to an illudin2 moiety 1302 acts as a ligand for the anti-angiogenic peptide receptor and directs the illudin2 moiety 1302 to tissues containing cells expressing the receptor. In an embodiment of the present invention, an anti-angiogenic peptide 1130 linked via a FSB linker 1220 to an illudin2 moiety 1302 acts as a ligand for the peptide receptor and directs the illudin2 moiety 1302 to tumors containing cells expressing the receptor. In an embodiment of the present invention, an anti-angiogenic peptide 1130 linked via a FSB linker 1220 to an illudin2 moiety 1302 acts as an AM for the anti-angiogenic peptide receptor and directs the illudin2 moiety 1302 to tissues containing cells expressing the receptor. In an embodiment of the present invention, an anti-angiogenic peptide 1130 linked via a FSB linker 1220 to an illudin2 moiety 1302 acts as an AM for the peptide receptor and directs the illudin2 moiety 1302 to tumors containing cells expressing the receptor. In an embodiment of the present invention, an anti-angiogenic peptide 1130 linked via a FSB linker 1220 to an illudin2 moiety 1302 acts as an AM for the peptide receptor and directs the illudin2 moiety 1302 to tumors containing cells over-expressing the receptor compared to non tumor cells.

FSB Linker to bind Illudin to an Integrin binding peptide. In an embodiment of the present invention, an illudin2 moiety 1302 linked via a FSB linker 1220 to an integrin binding peptide 1150 binds to receptors for the integrin binding peptide and directs the illudin2 moiety 1302 to cell populations expressing the receptor. In an embodiment of the present invention, an integrin binding peptide 1150 linked via a FSB linker 1220 to an illudin2 moiety 1302 acts as a ligand for the integrin binding peptide receptor and directs the illudin2 moiety 1302 to tissues containing cells expressing the receptor. In an embodiment of the present invention, an integrin binding peptide 1150 linked FSB linker 1220 to an illudin2 moiety 1302 acts as a ligand for the integrin binding peptide receptor and directs the illudin2 moiety 1302 to tumors containing cells expressing the receptor. In an embodiment of the present invention, an integrin binding peptide 1150 linked via a FSB linker 1220 to an illudin2 moiety 1302 acts as an AM for the integrin binding peptide receptor and directs the illudin2 moiety 1302 to tissues containing cells expressing the receptor. In an embodiment of the present invention, an integrin binding peptide 1150 linked FSB linker 1220 to an illudin2 moiety 1302 acts as an AM for the integrin binding peptide receptor and directs the illudin2 moiety 1302 to tumors containing cells expressing the receptor. In an embodiment of the present invention, an integrin binding peptide 1150 linked FSB linker 1220 to an illudin2 moiety 1302 acts as an AM for the integrin binding peptide receptor and directs the illudin2 moiety 1302 to tumors containing cells over-expressing the receptor compared to non tumor cells.

FSB Linker to bind Illudin to a Pro-peptide. In an embodiment of the present invention, an illudin2 moiety 1302 linked via a FSB linker 1220 to a pro-peptide 1160 is cleaved by an enzyme 1165 to generate the peptide 1161 and thereafter binds to receptors for the peptide and directs the illudin2 moiety 1302 to cell populations expressing the receptor. In an embodiment of the present invention, a pro-peptide 1160 linked via a FSB linker 1220 to an illudin2 moiety 1302 is cleaved by an enzyme 1165 and thereafter the peptide 1161 acts as a ligand for the peptide receptor and directs the illudin2 moiety 1302 to tissues containing cells expressing the receptor. In an embodiment of the present invention, a pro-peptide 1160 linked via a FSB linker 1220 to an illudin2 moiety 1302 is cleaved by an enzyme 1165 and thereafter the peptide 1161 acts as an AM for the peptide receptor and directs the illudin2 moiety 1302 to tissues containing cells expressing the receptor. In an embodiment of the present invention, a pro-peptide 1160 linked via a FSB linker 1220 to an illudin2 moiety 1302 is cleaved by an enzyme 1165 and thereafter the peptide 1161 directs the illudin2 moiety 1302 to tumors containing cells expressing the receptor. In an embodiment of the present invention, a pro-peptide 1160 linked via a FSB linker 1220 to an illudin2 moiety 1302 is cleaved by an enzyme 1165 and thereafter the peptide 1161 directs the illudin2 moiety 1302 to tumors containing cells over-expressing the receptor compared to non tumor cells.

FSB Linker to bind Illudin to a Glycopeptide. In an embodiment of the present invention, an illudin2 moiety 1302 linked via a FSB linker 1220 to a glycopeptide 1170 with biological activity binds to receptors for the glycopeptide 1170 and directs the illudin2 moiety 1302 to cell populations expressing the receptor. In an embodiment of the present invention, a glycopeptide 1170 linked via a FSB linker 1220 to an illudin2 moiety 1302 acts as a ligand for the glycopeptide receptor and directs the illudin2 moiety 1302 to tissues containing cells expressing the receptor. In an embodiment of the present invention, a glycopeptide 1170 linked via a FSB linker 1220 to an illudin2 moiety 1302 acts as a ligand for the glycopeptide receptor and directs the illudin2 moiety 1302 to tumors containing cells expressing the receptor. In an embodiment of the present invention, a glycopeptide 1170 linked via a FSB linker 1220 to an illudin2 moiety 1302 acts as an AM for the glycopeptide receptor and directs the illudin2 moiety 1302 to tissues containing cells expressing the receptor. In an embodiment of the present invention, a glycopeptide 1170 linked via a FSB linker 1220 to an illudin2 moiety 1302 acts as an AM for the glycopeptide receptor and directs the illudin2 moiety 1302 to tumors containing cells expressing the receptor. In an embodiment of the present invention, a glycopeptide 1170 linked via a FSB linker 1220 to an illudin2 moiety 1302 acts as an AM for the glycopeptide receptor and directs the illudin2 moiety 1302 to tumors containing cells over-expressing the receptor compared to non tumor cells.

FSB Linker to bind Illudin to a Lipid. In an embodiment of the present invention, an illudin2 moiety 1302 linked via a FSB linker 1220 to a lipid 1180 with biological activity binds to receptors for the lipid 1180 and directs the illudin2 moiety 1302 to cell populations expressing the lipid. In an embodiment of the present invention, a lipid 1180 linked via a FSB linker 1220 to an illudin2 moiety 1302 acts as a ligand for the lipid receptor and directs the illudin2 moiety 1302 to tissues containing cells expressing the receptor. In an embodiment of the present invention, a lipid 1180 linked via a FSB linker 1220 to an illudin2 moiety 1302 acts as a ligand for the lipid receptor and directs the illudin2 moiety 1302 to tumors containing cells expressing the receptor. In an embodiment of the present invention, a lipid 1180 linked via a FSB linker 1220 to an illudin2 moiety 1302 acts as an AM for the lipid receptor and directs the illudin2 moiety 1302 to tissues containing cells expressing the receptor. In an embodiment of the present invention, a lipid 1180 linked via a FSB linker 1220 to an illudin2 moiety 1302 acts as an AM for the lipid receptor and directs the illudin2 moiety 1302 to tumors containing cells over-expressing the receptor compared to non tumor cells.

FSB Linker to bind Illudin to a Peptide. In an embodiment of the present invention, an illudin2 moiety 1302 linked via a FSB linker 1220 to a peptide 1190 with biological activity binds to the peptide receptor and directs the illudin2 moiety 1302 to cell populations expressing the receptor. In an embodiment of the present invention, a peptide 1190 linked via a FSB linker 1220 to an illudin2 moiety 1302 acts as a ligand for the peptide receptor and directs the illudin2 moiety 1302 to tissues containing cells expressing the receptor. In an embodiment of the present invention, a peptide 1190 linked via a FSB linker 1220 to an illudin2 moiety 1302 acts as a ligand for the peptide receptor and directs the illudin2 moiety 1302 to tumors containing cells expressing the receptor. In an embodiment of the present invention, a peptide 1190 linked via a FSB linker 1220 to an illudin2 moiety 1302 acts as an AM for the peptide receptor and directs the illudin2 moiety 1302 to tissues containing cells expressing the receptor. In an embodiment of the present invention, a peptide 1190 linked via a FSB linker 1220 to an illudin2 moiety 1302 acts as an AM for the peptide receptor and directs the illudin2 moiety 1302 to tumors containing cells expressing the receptor. In an embodiment of the present invention, a peptide 1190 linked via a FSB linker 1220 to an illudin2 moiety 1302 acts as an AM for the peptide receptor and directs the illudin2 moiety 1302 to tumors containing cells over-expressing the receptor compared to non tumor cells.

Linker to bind Illudin2 to a Glycopeptide. In an embodiment of the present invention, an illudin2 moiety 1302 linked via a traditional linker 1240 to a glycopeptide 1170 with biological activity binds to receptors for the glycopeptide 1170 and directs the illudin2 moiety 1302 to cell populations expressing the receptor. In an embodiment of the present invention, a glycopeptide 1170 linked via a traditional linker 1240 to an illudin2 moiety 1302 acts as a ligand for the glycopeptide receptor and directs the illudin2 moiety 1302 to tissues containing cells expressing the receptor. In an embodiment of the present invention, a glycopeptide 1170 linked via a traditional linker 1240 to an illudin2 moiety 1302 acts as a ligand for the glycopeptide receptor and directs the illudin2 moiety 1302 to tumors containing cells expressing the receptor.

Linker to bind Illudin2 to a Lipid. In an embodiment of the present invention, an illudin2 moiety 1302 linked via a traditional linker 1240 to a lipid 1180 with biological activity binds to receptors for the lipid 1180 and directs the illudin2 moiety 1302 to cell populations expressing the lipid receptor or lipid binding protein. In an embodiment of the present invention, a lipid 1180 linked via a traditional linker 1240 to an illudin2 moiety 1302 acts as a ligand for the lipid receptor and directs the illudin2 moiety 1302 to tissues containing cells expressing the receptor. In an embodiment of the present invention, a lipid 1180 linked via a traditional linker 1240 to an illudin2 moiety 1302 acts as a ligand for the lipid receptor and directs the illudin2 moiety 1302 to tumors containing cells expressing the receptor.

Linker to bind Illudin2 to a Growth Factor. In an embodiment of the present invention, an illudin2 moiety 1302 linked via a traditional linker 1240 to a growth factor 1120 with biological activity binds to receptors for the growth factor 1120 and directs the illudin2 moiety 1302 to cell populations expressing the growth factor receptor. In an embodiment of the present invention, a growth factor 1120 linked via a traditional linker 1240 to an illudin2 moiety 1302 acts as a ligand for the growth factor receptor and directs the illudin2 moiety 1302 to tissues containing cells expressing the receptor. In an embodiment of the present invention, a growth factor 1120 linked via a traditional linker 1240 to an illudin2 moiety 1302 acts as a ligand for the growth factor receptor and directs the illudin2 moiety 1302 to tumors containing cells expressing the receptor.

Linker to bind Illudin2 to an anti-angiogenic peptide. In an embodiment of the present invention, an illudin2 moiety 1302 linked via a traditional linker 1240 to an anti-angiogenic peptide 1130 with biological activity binds to receptors for the anti-angiogenic peptide 1130 and directs the illudin2 moiety 1302 to cell populations expressing the anti-angiogenic peptide receptor. In an embodiment of the present invention, an anti-angiogenic peptide 1130 linked via a traditional linker 1240 to an illudin2 moiety 1302 acts as a ligand for the anti-angiogenic peptide receptor and directs the illudin2 moiety 1302 to tissues containing cells expressing the receptor. In an embodiment of the present invention, an anti-angiogenic peptide 1130 linked via a traditional linker 1240 to an illudin2 moiety 1302 acts as a ligand for the anti-angiogenic peptide receptor and directs the illudin2 moiety 1302 to tumors containing cells expressing the receptor.

Linker to bind Illudin2 to a Steroid. In an embodiment of the present invention, an illudin2 moiety 1302 linked via a traditional linker 1240 to a steroid 1140 with biological activity binds to receptors for the steroid 1140 and directs the illudin2 moiety 1302 to cell populations expressing the steroid receptor. In an embodiment of the present invention, a steroid 1140 linked via a traditional linker 1240 to an illudin2 moiety 1302 acts as a ligand for the steroid receptor and directs the illudin2 moiety 1302 to tissues containing cells expressing the receptor. In an embodiment of the present invention, a steroid 1140 linked via a traditional linker 1240 to an illudin2 moiety 1302 acts as a ligand for the steroid receptor and directs the illudin2 moiety 1302 to tumors containing cells expressing the receptor.

Linker to bind Illudin2 to an Integrin binding protein. In an embodiment of the present invention, an illudin2 moiety 1302 linked via a traditional linker 1240 to an integrin binding protein 1150 with biological activity binds to receptors for the integrin binding protein 1150 and directs the illudin2 moiety 1302 to cell populations expressing the integrin binding protein receptor. In an embodiment of the present invention, an integrin binding protein 1150 linked via a traditional linker 1240 to an illudin2 moiety 1302 acts as a ligand for the integrin binding protein receptor and directs the illudin2 moiety 1302 to tissues containing cells expressing the receptor. In an embodiment of the present invention, an integrin binding protein 1150 linked via a traditional linker 1240 to an illudin2 moiety 1302 acts as a ligand for the integrin binding protein receptor and directs the illudin2 moiety 1302 to tumors containing cells expressing the receptor.

Linker to bind Illudin2 to Folate. In an embodiment of the present invention, an illudin2 moiety 1302 linked via a traditional linker 1240 to folate 1185 binds to receptors for the folate 1185 and directs the illudin2 moiety 1302 to cell populations expressing the folate receptor. In an embodiment of the present invention, folate 1185 linked via a traditional linker 1240 to an illudin2 moiety 1302 acts as a ligand for the folate receptor and directs the illudin2 moiety 1302 to tissues containing cells expressing the receptor. In an embodiment of the present invention, folate 1185 linked via a traditional linker 1240 to an illudin2 moiety 1302 acts as a ligand for the folate receptor and directs the illudin2 moiety 1302 to tumors containing cells expressing the receptor.

Linker to bind Illudin2 to a Peptide. In an embodiment of the present invention, an illudin2 moiety 1302 linked via a traditional linker 1240 to a peptide 1190 with biological activity binds to the peptide receptor and directs the illudin2 moiety 1302 to cell populations expressing the receptor. In an embodiment of the present invention, a peptide 1190 linked via a traditional linker 1240 to an illudin2 moiety 1302 acts as a ligand for the peptide receptor and directs the illudin2 moiety 1302 to tissues containing cells expressing the receptor. In an embodiment of the present invention, a peptide 1190 linked via a traditional linker 1240 to an illudin2 moiety 1302 acts as a ligand for the peptide receptor and directs the illudin2 moiety 1302 to tumors containing cells expressing the receptor.

Mall linker 1211. Synthesis of mono-protected linkers. Maleimide or Maleic derivatives of acylfulvenes, Illudins and Syn-illudins can react directly with thiol groups on antibodies, proteins or with primary amines. When the Mall linker is used there is no need to attach the acylfulvene or illudin analog to linker as it is already incorporated into the analog (see FIG. 2S, FIG. 2T, FIG. 2U, and FIG. 2V). Both Illudin and Acylfulvene derivatives have been synthesized (e.g., analog 189, analog 190, analog 217, and analog 218, see also FIG. 18), and data demonstrating their in vitro activity and selectivity towards cells expressing a specific surface antigen are shown in FIG. 18.

Example 12. In an embodiment of the present invention, AMC's 189, 190, 217, 218 incorporating Mall linkers were synthesized. Unexpectedly, the AMC 189, 190, 217, 218 were found to be cytotoxic with nM activity (see Table XV).

In an embodiment of the present invention, an AMC in which analog 218 bound to an antibody using the Mall linker (FIG. 18) shows superior activity compared to current antibodies medicinally used (e.g. Herceptin). Table XV shows the cytotoxicity data for AMC's 189, 190, 217, 218 incorporating the Mall linker.

In an embodiment of the present invention, the Mall linker was attached to the acylfulvene. In this manner, the medicant-linker will bind directly to sulfhydryl groups on an AM, e.g., antibody or peptides containing a cysteine (with a sulfhydryl group). This novel medicant-linker allows the generation of toxin-peptide conjugates that can be cleaved by enzymes. Alternatively toxin-peptide conjugates can be prepared that will bind directly to tumor associated antigens (PMSA), specific integrins, or anti-angiogenic peptides.

Synthesis of Linkers. The synthesis of medicant moieties bound to linkers can be carried out using the following strategies: React R—$NH_2$ with H—N=C=S to form isothiourea R—NH—C(=S)—$NH_2$. React R—$NH_2$ with H—N=C=O to form isourea R—NH—C(=O)—$NH_2$. React R—$NH_2$ with acyl azide to form RC(=0)NHR. React R—$NH_2$ with NHS ester to form RC(=O)NHR. React amine with sulfonyl chloride to form sulfonamide bond R(S(=O)(=O)NHR. React amine with imidoester to form amidine linkage $RCH_2$C(=$NH_2$)NHR. React amine with succinic acid to make amide bond with carboxylate ion. React imidoester with amine to form amidine bond $RCH_2$C(=$NH_2$+)NHR (see also Table X).

Azlactone linker Reactions of carbodiimides such as dicyclohexylcarbodiimide (DCC) or diisopropylcarbodiimide (DIC) with a carboxylic acid yields a highly reactive O-acylisourea. During artificial protein synthesis (such as Fmoc solid-state synthesizers), the C-terminus is often used as the attachment site on which the amino acid monomers are added. To enhance the electrophilicity of carboxylate group, the negatively charged oxygen must first be "activated" into a better leaving group and carbodiimides can be used for this purpose. The negatively charged oxygen will act as a nucleophile, attacking the central carbon in DCC. DCC is temporarily attached to the former carboxylate group (which is now an ester group), making nucleophilic attack by an amino group (on the attaching amino acid) to the former C-terminus (carbonyl group) more efficient.

When the Illudin, Syn-Illudin, or Acylfulvene carboxylic acid analog is activated by DCC or DIC in the presence of an amino acid the DCC-activated carboxylate will react with the amino acid to form an azlactone (FIG. 2P, FIG. 2Q, FIG. 2R, and FIG. 10). This amino acid-derived azlactone will react with primary amines, undergo ring opening, and forms an amide bond.

Example 13. Synthesis of Medicant 106. Illudin M (450 mg, 1.845 mmol, 1 equiv.), glutaric anhydride (2.10 g, 18.45 mmol, 10 equiv.) and DMAP (171 mg, 1.4 mmol, 0.76 equiv.) were dissolved in $CH_2Cl_2$ (5 mL) at room temperature. After 3.5 hours the mixture was taken up by $CH_2Cl_2$, which was washed with water, and brine in sequence. It was then dried and evaporated. The residue was eluted through a column (Hexane/EtOAc 4:1) to give analog 106 (365 mg, 55%) as a liquid. UV ($CHCl_3$) λ nm (ε): 309 (3387).

Analog 106 was generated from illudin M as outlined in Example 13. The carboxylic acid derivative was activated using DCC/DMAP to synthesize steroid AFC's 107 and 109. In addition, Irofulven carboxylic acid derivative, analog 038 was activated using DCC/DMAP to produce analogs 108, 110, 111, and 112. In general, carboxylate group containing compounds can be activated using a carbodiimide in the presence of an amino acid to form an azlactone. The azlactone formed will react spontaneously with primary amine groups on an amino acid, a peptide, an antibody, a protein, or another drug, and undergo ring opening with the formation of an amide bond. For proteins, antibodies and peptides the amino acids capable of reacting with the azlactone derivative includes arginine and lysine.

To form an Illudin derived azlactone active drug-linker moiety, either analog 106 or analog 038 can be activated by DCC/DMAP in the presence of a small amino acid such as glycine to form the azlactone. DCC cannot be added without the presence of an amine containing target (such as the glycine) or the activated carboxylate reacts with another carboxylate to form a symmetrical anhydride. The azlactone formed will react spontaneously with primary amine groups on a peptide, an antibody, a protein, or a medicant.

Example 14. Activation of analog 038 by DCC to form medicant-azlactone. Part A: Production of Azlactone from carboxylate Acylfulvene analog: Analog 038 (58.5 mg, 0.2035 mmol), and DMAP (5 mg. 0.048 mmol) were dissolved in $CH_2Cl_2$ (5.6 mL) at 0° C. The desired amino acid (such as glycine) is added in an equimolar amount. Note that amino acids having substitutions on the C4 carbon (such as alpha-methyl glycine or 2-dimethylglycine) are preferred over conventional amino acids as substitution cannot occur at the C4 position after ring-opening and all nucleophilic coupling reactions must occur at the C5 position, resulting only in the desired amide-bond formation with the amine-containing molecule. To this solution was added $CH_2Cl_2$ solution of DCC (250 µL, 1 M, 0.244 mmol), stirred for 30 minutes, allowed to warm to room temperature then stirred for 1.5 hours. The filtrate was washed with dilute HCl (1.5%), saturated $NaHCO_3$ and brine in sequence. The organic phase was dried over $Na_2SO_4$, and evaporated. The residue was eluted through a column (100% $CH_2Cl_2$ plus 0.5% methanol), to give the desired azlactone analog as a solid. Part B: Coupling of Azlactone to the protein component (reacting with primary amines on amino acids such as the one on lysine): The typical protein coupling reaction consists of the Azlactone suspended in buffer [25 mM sodium phosphate, 150 mM NaCl (pH 7.5)] and the desired amount of protein (20 µg to 5.0 mg) is added. The mixture is gently rocked for 60 minutes, then the reaction terminated by the addition of the blocking reagent, 1.0 ml of 1.0 M ethanolamine in 25 mM sodium pyrophosphate (titrated to pH 9.0 with HCl) Sample rocked gently for 5 minutes then the residual ethanolamine removed by dialysis or chromatography using pH 7.5 phosphate-NaCl buffer.

Example 15. Reaction of the medicant-azlactone product with an antibody. The azlactone derivative generated in Example 14 (note that other amino acids can be used in place of glycine) is then reacted with the desired peptide or protein or other compound containing a primary amino group at a 1:1 ratio in buffer (25 mM sodium phosphate, 150 mM sodium chloride, pH 7.5) with gentle rocking at room temperature for 60 minutes. The reaction is terminated by the addition of 1.0 mL of 25 mM ethanolamine (titrated to pH 9.00) with rocking for 5 minutes at room temperature). The drug-azlactone-ligand product can be purified by column chromatography or dialysis to remove the ethanolamine by-product.

Azlactone linker to bind Illudin2 to a Glycopeptide. In an embodiment of the present invention, an illudin2 moiety 1302 linked via an azlactone linker 1230 to a glycopeptide 1170 with biological activity binds to receptors for the glycopeptide 1170 and directs the illudin2 moiety 1302 to cell populations expressing the receptor. In an embodiment of the present invention, a glycopeptide 1170 linked via an azlactone linker 1230 to an illudin2 moiety 1302 acts as an AM for the glycopeptide receptor and directs the illudin2 moiety 1302 to tissues containing cells expressing the receptor. In an embodiment of the present invention, a glycopeptide 1170 linked via an azlactone linker 1230 to an illudin2 moiety 1302 acts as an AM for the glycopeptide receptor and directs the illudin2 moiety 1302 to tumors containing cells expressing the receptor. In an embodiment of the present invention, a glycopeptide 1170 linked via an azlactone linker 1230 to an illudin2 moiety 1302 acts as an AM for the glycopeptide receptor and directs the illudin2 moiety 1302 to tumors containing cells over-expressing the receptor compared to non tumor cells Azlactone linker to bind Illudin2 to a Lipid. In an embodiment of the present invention, an illudin2 moiety 1302 linked via an azlactone linker 1230 to a lipid 1180 with biological activity binds to receptors for the lipid 1180 and directs the illudin2 moiety 1302 to cell populations expressing the lipid. In an embodiment of the present invention, a lipid 1180 linked via an azlactone linker 1230 to an illudin2 moiety 1302 acts as an AM for the lipid receptor and directs the illudin2 moiety 1302 to tissues containing cells expressing the receptor. In an embodiment of the present invention, a lipid 1180 linked via an azlactone linker 1230 to an illudin2 moiety 1302 acts as an AM for the lipid receptor and directs the illudin2 moiety 1302 to tumors containing cells over-expressing the receptor compared to non tumor cells.

Azlactone linker to bind Illudin2 to a Peptide. In an embodiment of the present invention, an illudin2 moiety 1302 linked via an azlactone linker 1230 to a peptide 1190 with biological activity binds to the peptide receptor and directs the illudin2 moiety 1302 to cell populations expressing the receptor. In an embodiment of the present invention, a peptide 1190 linked via an azlactone linker 1230 to an illudin2 moiety 1302 acts as an AM for the peptide receptor and directs the illudin2 moiety 1302 to tissues containing cells expressing the receptor. In an embodiment of the present invention, a peptide 1190 linked via an azlactone linker 1230 to an illudin2 moiety 1302 acts as an AM for the peptide receptor and directs the illudin2 moiety 1302 to tumors containing cells expressing the receptor. In an embodiment of the present invention, a peptide 1190 linked via an azlactone linker 1230 to an illudin2 moiety 1302 acts as an AM for the peptide receptor and directs the illudin2 moiety 1302 to tumors containing cells over-expressing the receptor compared to non tumor cells.

Azlactone linker to bind Illudin2 to a Steroid. In an embodiment of the present invention, an illudin2 moiety 1302 linked via an azlactone linker 1230 to a steroid 1140 binds to receptors for the steroid and directs the illudin2 moiety 1302 to cell populations expressing the receptor. In an embodiment of the present invention, a steroid 1140 linked via an azlactone linker 1230 to an illudin2 moiety 1302 acts as an AM for the steroid hormone receptor and directs the illudin2 moiety 1302 to tissues containing cells expressing the receptor. In an embodiment of the present invention, a steroid 1140 linked via an azlactone linker 1230 to an illudin2 moiety 1302 acts as an AM for the steroid hormone receptor and directs the illudin2 moiety 1302 to tumors containing cells expressing the receptor. In an embodiment of the present invention, a steroid 1140 linked via an azlactone linker 1230 to an illudin2 moiety 1302 acts as an AM for the steroid hormone receptor and directs the illudin2 moiety 1302 to tumors containing cells over-expressing the receptor compared to non tumor cells.

Azlactone linker to bind an Antibody to a Protein Toxin. In an embodiment of the present invention, an antibody 1110 is bound to a protein toxin 1330 with an azlactone linker 1230. In an embodiment of the present invention, an antibody 1110 directs the protein toxin 1330 to cell populations expressing the receptor. In an embodiment of the present invention, the antibody 1110 with an azlactone linker 1230 to a protein toxin 1330 acts as an AM for a receptor and directs the protein toxin 1330 to tissues containing cells expressing the receptor. In an embodiment of the present invention, an antibody 1110 with an azlactone linker 1230 to the protein toxin 1330 acts as an AM for a receptor and directs the protein toxin 1330 to tumors containing cells expressing the receptor. In an embodiment of the present invention, an antibody 1110 with an azlactone linker 1230 to the protein toxin 1330 acts as an AM for a receptor and directs the protein toxin 1330 to tumors containing cells over-expressing the receptor compared to non tumor cells.

Azlactone linker to bind an Growth Factor to a Protein Toxin. In an embodiment of the present invention, a growth factor 1120 is bound to a protein toxin 1330 with an azlactone linker 1230. In an embodiment of the present invention, the growth factor 1120 directs the protein toxin 1330 to cell populations expressing the receptor to the growth factor 1120. In an embodiment of the present invention, the growth factor 1120 with an azlactone linker 1230 to a protein toxin 1330 acts as an AM for a receptor to the growth factor 1120 and directs the protein toxin 1330 to tissues containing cells expressing the receptor. In an embodiment of the present invention, the growth factor 1120 with an azlactone linker 1230 to the protein toxin 1330 acts as an AM for the growth factor receptor and directs the protein toxin 1330 to tumors containing cells over-expressing the receptor compared to non tumor cells.

Azlactone linker to bind an Antibody to a Medicant. In an embodiment of the present invention, an antibody 1110 is bound to a medicant 1350 with an azlactone linker 1230. In an embodiment of the present invention, an antibody 1110 directs the medicant 1350 to cell populations expressing the receptor. In an embodiment of the present invention, the antibody 1110 with an azlactone linker 1230 to the medicant 1350 acts as an AM for a receptor and directs the medicant 1350 to tissues containing cells expressing the receptor. In an embodiment of the present invention, an antibody 1110 with an azlactone linker 1230 to the medicant 1350 acts as an AM for a receptor and directs the medicant 1350 to tumors containing cells expressing the receptor. In an embodiment of the present invention, an antibody 1110 with an azlactone linker 1230 to the medicant 1350 acts as an AM for a receptor and directs the medicant 1350 to tumors containing cells over-expressing the receptor compared to non tumor cells.

Azlactone linker to bind an Growth Factor to a Medicant. In an embodiment of the present invention, a growth factor 1120 is bound to a medicant 1350 with an azlactone linker 1230. In an embodiment of the present invention, the growth factor 1120 directs the medicant 1350 to cell populations expressing the receptor to the growth factor 1120. In an embodiment of the present invention, the growth factor 1120 with an azlactone linker 1230 to a medicant 1350 acts as an AM for a receptor to the growth factor 1120 and directs the medicant 1350 to tissues containing cells expressing the receptor. In an embodiment of the present invention, the growth factor 1120 with an azlactone linker 1230 to the medicant 1350 acts as an AM for a receptor and directs the medicant 1350 to tumors containing cells expressing the receptor for the growth factor 1120. In an embodiment of the present invention, the growth factor 1120 with an azlactone linker 1230 to the medicant 1350 acts as an AM for a receptor and directs the medicant 1350 to tumors containing cells over-expressing the receptor compared to non tumor cells.

Example 16. Synthesis of Medicant 114. $(CH_3)_3S(O)I$ (110 mg, 0.4 mmol) and tBuOK(50 mg, 0.4 mmol) were dissolved in anhydrous DMSO (1 mL) and stirred at room temperature for 40 minutes at room temperature. Then analog 10 (50 mg, 0.2 mmol) in 1.0 mL of DMSO was added via syringe, and stirred for 3 hours. Reaction quenched with saturated $NH_4Cl$ (1 mL), extracted with $CH_2Cl_2$, dried over $Na_2SO_4$, concentrated then chromatographed (2:3 hexane: ethyl acetate) to yield analog 114 (20 mg., 50% yield).

Example 17. Synthesis of Medicant 115. Analog 10 (40 mg) and $NAHCO_3$ (50 mg) are dissolved in 10 mL of 1:1 Ethanol and water mixture, then hydroxylamine hydrochloride (20 mg) is added, stirred for 30 minutes at room temperature. Water and ethyl acetate (1:1 mixture) is added, stirred, the organic layer is recovered, washed with saturated $NaHCO_3$ and then brine, dried over $Na_2SO_4$, concentrated then chromatographed (2:3 ethyl acetate:hexane) to yield analog 115.

Example 18. Synthesis of Medicant 116. $SeO_2$ (45 mg) and 500 mg $SiO_2$ transferred into a dried RB flask, 5 mL of $CH_2Cl_2$ added, and stirred for 1 hour under nitrogen. Then 250 µL of $tBuO_2H$ added and stirred for 15 minutes. Then 100 mg of Irofulven in 1 mL $CH_2Cl_2$ is added, and stirred for 3 hours at room temperature under a nitrogen atmosphere. Product is filtered, wash twice with water (25 mL), twice with brine (25 mL), dried over $Na_2SO_4$ and concentrated then chromatographed (4:1 hexane:ethyl acetate) to yield analog 116.

Example 19. Synthesis of Medicant 116. Analog 117: Illudin S (100 mg, 0.378 mmol) and glutaric anhydride (215.46 mg, 1.89 mmol) are dissolved in 5 mL of $CH_2Cl_2$, and DMAP added (92.23 mg, 0.756 mmol), and stirred for 2 hours at room temperature. The $CH_2Cl_2$ is evaporated, 5 mL of water is added, and stirred for 1 hour. The solution is extracted with 10 mL of $CH_2Cl_2$, washed with water, dried over $Na_2SO_4$ and concentrated to yield analog 117 (120 mg).

Example 20. Synthesis of Analog 118: Analog 302 (75 mg), glutaric anhydride (20 mg) are dissolved in 5 mL of $CH_2Cl_2$, and DMAP added (42 mg), and stirred for 2 hours at room temperature. The $CH_2Cl_2$ is evaporated, 5 mL of water added, and stirred for 1 hour. Solution is extracted with 10 mL of $CH_2Cl_2$, washed with water, dried over $Na_2SO_4$ and concentrated to yield analog 118 (120 mg).

Example 21. Synthesis of Analog 119: Analog 114 (10 mg) is dissolved in 1.5 mL of acetone with 1.0 mL of 4N $H_2SO_4$, and contents stirred for 1.5 hours at room temperature. Then 10 mL of $CH_2Cl_2$ and 10 mL of water are added, extracted, and the organic layer recovered which is then washed with saturated $NaHCO_3$ and saline, dried over $Na_2SO_4$ and concentrated, and analog 119 recovered (analog 128 is a byproduct).

Example 22. Synthesis of Analog 120: Analog 10 (50 mg), $NaHCO_3$ are dissolved in 10 mL of 1:1 mixture of water and ethanol, then $NH_2NH_2$ (0.5 mL added with stirring at room temperature for one hour. The solution is extracted with $CH_2Cl_2$ twice, the organic layer recovered, washed with water, then $NaHCO_3$ solution, dried over $Na_2SO_4$, and evaporated to yield analog 120 (30 mg).

Example 23. Synthesis of Analog 121: Analog 10 (50 mg) and $NaCO_2CH_3$ (75 mg) are dissolved in 10 mL of 1:1 mixture of water and ethanol 1:1, then semicarbazide hydrochloride salt ($H_2NNHCONH_2HCl$, 50 mg) added, and stirred for 2 hours at room temperature. The solution is extracted with $CH_2Cl_2$ twice, the organic layer recovered, washed with water, then $NaHCO_3$ solution, dried over $Na_2SO_4$, and evaporated then chromatographed (5% methanol in ethyl acetate) to yield analog 121.

Example 24. Synthesis of Analog 122: Analog 10 (50 mg) and $NaCO_2CH_3$ (75 mg) are dissolved in 5 mL of ethanol, then phenylhydrazide (50 mg) is added, stirred for 1 hour at room temperature. Then 5 mL of water is added, followed by extraction with ethyl acetate, washed with water, dried over $Na_2SO_4$ and concentrated and chromatographed (5% methanol in ethyl acetate) to yield analog 122.

Example 25. Synthesis of Analog 123: Analog 10 (50 mg) and $NaCO_2CH_3$ (75 mg) are dissolved in 10 mL of 1:1 water and ethanol, then $H_2NNHTS$ ($H_2NNHS(=O)_2$(phenyl) methyl, 50 mg) is added, stirred for 2 hour at room temperature. Then 5 mL of water is added, followed by extraction with ethyl acetate, washed with water, dried over $Na_2SO_4$ and concentrated and chromatographed (5% methanol in ethyl acetate) to yield analog 123.

Example 26. Synthesis of Analog 124: Analog 115 (15 mg) and NaOAc (15 mg) are dissolved in acetic anhydride (1 mL) and stirred for 2 hours, then sodium acetate (300 mg) is added with stirring for 1 hour. Then the mixture is chromatographed (10% ethyl acetate in hexane) to give analog 124.

Example 27. Synthesis of Analog 125: Analog 10 (50 mg) and $NaCO_2CH_3$ (75 mg) are dissolved in 5 mL of ethanol, then the dinitrophenylhydrazide (50 mg) is added, stirred for 1 hour at room temperature. Then 5 mL of water is added, followed by extraction with ethyl acetate, washed with water, dried over $Na_2SO_4$ and concentrated and chromatographed (5% methanol in ethyl acetate) to yield analog 125.

Example 28. Synthesis of Analog 126: Analog 11 (40 mg), hydroxylamine (20 mg), $NaHCO_3$ (50 mg) are dissolved in 10 mL of ethanol and water (1:1) then stirred at room temperature for 90 minutes. Then the mixture is extracted with water (10 mL) and ethyl acetate (20 mL), the organic layer washed with saturated $NaHCO_3$ then brine, dried over $Na_2SO_4$ and concentrated, then chromatographed (2:3 ethyl acetate:hexane) to give analog 126.

Example 29. Synthesis of Analog 127: Analog 10 (100 mg) and NH$_4$Cl (1.5 equivalent) are dissolved in 1,4-dioxane (5 mL) and water (0.2 mL), then NaCN added (1.3 equivalents), stirred for 1 hour at room temperature. Then ethyl ether (20 mL) was added, the organic layer recovered, washed with water, washed with brine, then dried over Na$_2$SO$_4$, then chromatographed (2:3 ethyl acetate:hexane) to yield analog 127.

Example 30. Synthesis of Analog 128: Analog 114 (10 mg) is dissolved in 1.5 mL of acetone with 1.0 mL of 4N H$_2$SO$_4$, and contents stirred for 1.5 hours at room temperature. Then 10 mL of CH$_2$Cl$_2$ and 10 mL of water are added, extracted, and the organic layer recovered which is then washed with saturated NaHCO$_3$ and saline, dried over Na$_2$SO$_4$ and concentrated, and analog 128 recovered (analog 119 is a byproduct).

Example 31. Synthesis of Analog 129: Acylfulvene (200 mg) is dissolved in anhydrous THF (10 mL) at room temperature then NaBH$_4$ (100 mg) is added slowly for 30 minutes. Reaction is quenched with 1 mL of water then extracted with ethyl acetate (10 mL), washed with saturated NaHCO$_3$, and dried over Na$_2$SO$_4$, then concentrated to yield analog 129. If need be the compound can be purified by chromatography (1:1 ethyl acetate:hexane).

Example 32. Analog 141: Analog 129 (200 mg) is dissolved in CH$_2$Cl$_2$ at room temperature, then 1,4-dimethyl but-2-ynedioate (1.1 equivalent) is added slowly and mixture allowed to react for one hour, then evaporated to yield analog 141. If need be the compound can be purified by chromatography (1:1 ethyl acetate:hexane).

Example 33. Synthesis of Analog 42 Analog 141 (100 mg) is dissolved in CH$_2$Cl$_2$ at room temperature then Dess-Martin Periodinane reagent (200 mg) added with stirring for 1 hour to yield analog 142. If need be the compound can be purified by chromatography (1:1 ethyl acetate:hexane).

Example 34. Synthesis of Analog 146: Analog 127 (35 mg, 0.117 mmol), DMAP (5 mg), and diimidazole (22 mg, 1.2 eq) were dissolved in anhydrous CH$_2$Cl$_2$ under an argon atmosphere, and stirred for 30 minutes. The solution was cooled to 20° C. then tributyl tin hydride (Bu$_3$SnH, 0.6 mL) and azobis isobutylnitrite (4 mg) were added with stirring for 30 minutes. The mixture was filtered then chromatographed (1:10 ethyl acetate: hexane) to remove impurities and starting materials, then chromatographed (2:3 ethyl acetate:hexane) to yield analog 146.

Example 35. Synthesis of Analog 147: Irofulven (10 mg) is dissolved in 3 mL of acetone and 1 M H$_2$SO$_4$ solution (1:1) with stirring at room temperature and 2-Mercaptobenzothiazole (1 equivalent) is added, stirred for 2 hours, then partitioned between ethyl acetate and water. The organic extract is washed with saturated NaHCO$_3$ and saline until neutral, dried over MgSO$_4$, concentrated then chromatographed (1:1 ethyl acetate:hexane) to give analog 147.

Example 36. Synthesis of Analog 148: Irofulven (10 mg) is dissolved in 3 mL of acetone and 1 M H$_2$SO$_4$ solution (1:1) with stirring at room temperature and 2-Mercaptobenzoxazole (1 equivalent) is added, stirred for 2 hours, then partitioned between ethyl acetate and water. The organic extract is washed with saturated NaHCO$_3$ and saline until neutral, dried over MgSO$_4$, concentrated then chromatographed (1:1 Ethyl acetate:hexane) to give analog 148.

Example 37. Synthesis of Analog 149: Irofulven (10 mg) is dissolved in 4 mL of acetone and 1 M H$_2$SO$_4$ solution (1:1) with stirring at room temperature and thiol-imidazole (1 equivalent) is added, stirred for 24 hours, then partitioned between ethyl acetate and water. The organic extract is washed with saturated NaHCO$_3$ and saline until neutral, dried over MgSO$_4$, concentrated then chromatographed (1:1 ethyl acetate:hexane) to give analog 149.

Example 38. Synthesis of Analog 150: Irofulven (10 mg) is dissolved in 4 mL of acetone and 1 M H$_2$SO$_4$ solution (1:1) with stirring at room temperature and 2-mercapto-5-methylbenzimidazole (1 equivalent) is added, stirred for 12 hours, then partitioned between ethyl acetate and water. The organic extract is washed with saturated NaHCO$_3$ and saline until neutral, dried over MgSO$_4$, concentrated then chromatographed (1:1 ethyl acetate:hexane) to give analog 150.

Example 39. Synthesis of Analog 151: Irofulven (10 mg) is dissolved in 3 mL of acetone and 1 M H$_2$SO$_4$ solution (1:1) with stirring at room temperature and 1-phenyl-1,2,3,4-tetraazole-5-thiol (1 equivalent) is added, stirred for 2 hours, then partitioned between ethyl acetate and water. The organic extract is washed with saturated NaHCO$_3$ and saline until neutral, dried over MgSO$_4$, concentrated then chromatographed (1:1 ethyl acetate:hexane) to give analog 151.

Example 40. Synthesis of Analog 152: Irofulven (10 mg) is dissolved in 3 mL of acetone and 1 M H$_2$SO$_4$ solution (1:1) with stirring at room temperature and 2-mercapto-5-nitro benzimidazole (1 equivalent) is added, stirred for 2 hours, then partitioned between ethyl acetate and water. The organic extract is washed with saturated NaHCO$_3$ and saline until neutral, dried over MgSO$_4$, concentrated then chromatographed (1:1 ethyl acetate:hexane) to give analog 152.

Example 41. Synthesis of Analog 153: Irofulven (10 mg) is dissolved in 3 mL of acetone and 1 M H$_2$SO$_4$ solution (1:1) with stirring at room temperature and 1, 2, 4-Triazole-3-thiol (1 equivalent) is added, stirred for 2 hours, then partitioned between ethyl acetate and water. The organic extract is washed with saturated NaHCO$_3$ and saline until neutral, dried over MgSO$_4$, concentrated then chromatographed (1:1 ethyl acetate:hexane) to give analog 153.

Example 42. Synthesis of Analog 154: Irofulven (10 mg) is dissolved in 3 mL of acetone and 1 M H$_2$SO$_4$ solution (1:1) with stirring at room temperature and 2-sulfanylpteridin-4-ol (1 equivalent) is added, stirred for 2 hours, then partitioned between ethyl acetate and water. The organic extract is washed with saturated NaHCO$_3$ and saline until neutral, dried over MgSO$_4$, concentrated then chromatographed (1:1 ethyl acetate:hexane) to give analog 154.

Example 43. Synthesis of Analog 155: Irofulven (10 mg) is dissolved in 3 mL of acetone and 1 M H$_2$SO$_4$ solution (1:1) with stirring at room temperature and 4-(5-sulfanyl-1H-1,2,3,4-tetrazol-1-yl)phenol (1 equivalent) is added, stirred for 2 hours, then partitioned between ethyl acetate and water. The organic extract is washed with saturated NaHCO$_3$ and saline until neutral, dried over MgSO$_4$, concentrated then chromatographed (1:1 ethyl acetate:hexane) to give analog 155.

Example 44. Synthesis of Analog 156: Irofulven (10 mg) is dissolved in 3 mL of acetone and 1 M H$_2$SO$_4$ solution (1:1) with stirring at room temperature and 4-(5-sulfanyl-1H-1,2,3,4-tetrazol-1-yl)benzoic acid (1 equivalent) is added, stirred for 2 hours, then partitioned between ethyl acetate and water. The organic extract is washed with saturated NaHCO$_3$ and saline until neutral, dried over MgSO$_4$, concentrated then chromatographed (1:1 ethyl acetate:hexane) to give analog 156.

Example 45. Synthesis of Analog 159: Illudin S (300 mg) is dissolved acetic anhydride (6 mL) and stirred for 15 minutes, then sodium acetate (300 mg) is added with stirring for 1 hour. Water (6 mL) is added, ethyl acetate extraction performed, washed with sodium bicarbonate solution, dried over Na$_2$SO$_4$, concentrated then chromatographed (2:3 ethyl acetate:hexane) to give analog 159.

Example 46. Synthesis of Analog 160: Analog 159 (60 mg) is dissolved in dry $CH_2Cl_2$ (6 mL) under nitrogen at room temperature and glutaric anhydride (100 mg) with DMAP (20 mg) is added with stirring for 30 minutes. The solvent is removed, water added, extracted with $CH_2Cl_2$, washed with water, dried over $Na_2SO_4$, concentrated then chromatographed (2:3 ethyl acetate:hexane) to give analog 160.

Example 47. Synthesis of Analog 161: Dehydroilludin S (300 mg) is dissolved acetic anhydride (6 mL) and stirred for 15 minutes, then sodium acetate (300 mg) is added with stirring for 1 hour. Water (6 mL) is added, ethyl acetate extraction performed, washed with sodium bicarbonate solution, dried over $Na_2SO_4$, concentrated then chromatographed (2:3 ethyl acetate:hexane) to give analog 161.

Example 48. Synthesis of Analog 162: Dehydroilludin S (60 mg) is dissolved in dry $CH_2Cl_2$ (6 mL) under nitrogen at room temperature and glutaric anhydride (150 mg) with DMAP (50 mg) is added with stirring for 30 minutes. The solvent is removed, water added, extracted with $CH_2Cl_2$, washed with water, dried over $Na_2SO_4$, concentrated then chromatographed (2:3 ethyl acetate:hexane) to give analog 162.

Example 49. Synthesis of Analog 163: Analog 159 (20.25 mg), DMAP (20 mg) are dissolved in dry $CH_2Cl_2$ (6 mL) at 0° C. under nitrogen atmosphere and stirred for 10 minutes. Then chloroacetyl chloride (0.2 mL) is added slowly and the mixture stirred for 30 minutes, warmed to room temperature with stirring over 1 5 minutes. Then water (6 mL) is added, mixed, and then extracted with $CH_2Cl_2$. The organic layer is washed with saturated $NaHCO_3$ followed by a saline wash, dried over $Na_2SO_4$ then chromatographed (2:3 ethyl acetate:hexane) to yield analog 163 (60% yield).

Example 50. Synthesis of Analog 164: Irofulven (50 mg), DMAP (40 mg) are dissolved in dry $CH_2Cl_2$ (6 mL) at 0° C. under nitrogen atmosphere and stirred for 10 minutes. Then chloroacetyl chloride (0.2 mL) is added slowly and the mixture stirred for 30 minutes, warmed to room temperature with stirring over 1 5 minutes. Then water (6 mL) is added, mixed, and then extracted with $CH_2Cl_2$. The organic layer is washed with saturated $NaHCO_3$ followed by a saline wash, dried over $Na_2SO_4$ then chromatographed (2:3 ethyl acetate:hexane) to yield analog 164 (60% yield).

Example 51. Synthesis of Analog 165: Analog 164 (40 mg) is dissolved in dry $CH_2Cl_2$ (6 mL) at room temperature under nitrogen atmosphere and stirred for 10 minutes. Then 1 mL of morpholine is added drop wise, with stirring for 30 minutes. The reaction is diluted with water (6 mL), extracted with $CH_2Cl_2$ (12 mL). The organic layer is washed with saturated $NaHCO_3$ then washed with saline, dried over $Na_2SO_4$ and chromatographed (2:3 ethyl acetate:hexane) to yield 165 (35% yield).

Example 52. Synthesis of Analog 166 and analog 167 (prepared together): Analog 160 (30 mg) is dissolved in methanol (4 mL) at 0° C., and 1N $H_2SO_4$ (1 mL) is added with stirring for 1 hour. Water (6 mL) is added, extracted with ethyl acetate, washed with $NaHCO_3$ then a brine solution, dried over $MgSO_4$, concentrated and then chromatographed (1:1 ethyl acetate:hexane) to yield analogs 166 and 167 in equal amounts.

Example 53. Synthesis of Analog 168: Analog 162 (20 mg) is dissolved in methanol (5 mL) at 0° C. and stirred for 10 minutes, then 1 mL of 1N $H_2SO_4$ in methanol is slowly added, followed by stirring for 30 minutes. Water is added, followed by an ethyl acetate extraction, washed with $NaHCO_3$ then a brine solution, dried over $Na_2SO_4$, concentrated then chromatographed (1:1 ethyl acetate:hexane) to yield analog 168.

Example 54. Synthesis of Analog 169: Dehydroilludin S (20 mg), DMAP (20 mg) are dissolved in dry $CH_2Cl_2$ (6 mL) at 0° C. under nitrogen atmosphere and stirred for 10 minutes. Then chloroacetyl chloride (0.2 mL) is added slowly and the mixture stirred for 30 minutes, warmed to room temperature with stirring over 15 minutes. Then water (6 mL) is added, mixed, then extracted with $CH_2Cl_2$. The organic layer is washed with saturated $NaHCO_3$ followed by a saline wash, dried over $Na_2SO_4$ then chromatographed (2:3 ethyl acetate:hexane) to yield analog 169 (60% yield).

Example 55. Synthesis of Analog 176: To a solution of analog 9 (266 umol), Boc protected leucine amino acid (300 umol) and DMAP (dimethylaminopyridine, 110 umol) in $CH_2Cl_2$ (2.5 mL) at 0° C. is added DCC (dicyclohexylcarbodiimide; 1.0M in $CH_2Cl_2$, 300 umol). The mixture is stirred for 35 minutes then 5 μL of water added to quench the reaction. The mixture is diluted with hexane and precipitate filtered off, solvent evaporated off and crude product chromatographed (2:1 hexanes-ethyl acetate) to give the desired Boc-protected derivative of 176 at 80% yield. The Boc group is removed by dissolving the Boc-protected derivative in a 1:1 mixture (2.0 mL) of 1,4-dioxane and 2M $H_2SO_4$, stirred for 18 hours, then partitioned between ethyl acetate and water. Aqueous layer is extracted with ethyl acetate and extracts discarded. Aqueous layer is neutralized with saturated $NaHCO_3$ and extracted again with ethyl acetate. Organic layer is washed with brine, dried with $MgSO_3$, solvent evaporated to yield the analog 9 amino acid derivative. As the amine derivative is unstable over prolonged periods of time it can be converted to the very stable trifluoroacetate salt by dissolving in $CH_2Cl_2$ adding the equal molar amount of trifluoroacetic acid and concentrating to dryness.

Example 56. Synthesis of Analog 178: Analog 9 (15 mg) is dissolved in $CH_2Cl_2$ (2.0 mL) under a nitrogen atmosphere at room temperature, succinic anhydride (1 equivalent) is added, followed by DMAP (10 mg) and stirring for 30 minutes. Solvent is removed and product recrystallized to give analog 178.

Example 57. Synthesis of Analog 179: To a solution of Analog 9 (266 μmol), Boc protected glycine amino acid (300 umol) and DMAP (dimethylaminopyridine, 110 umol) in $CH_2Cl_2$ (2.5 mL) at 0° C. is added DCC (dicyclohexylcarbodiimide; 1.0M in $CH_2Cl_2$, 300 umol). The mixture is stirred for 35 minutes then 5 μL of water added to quench the reaction. The mixture is diluted with hexane and precipitate filtered off, solvent evaporated off and crude product chromatographed (2:1 hexanes-ethyl acetate) to give the desired Boc-protected derivative of 179 at 80% yield. The Boc group is removed by dissolving the Boc-protected derivative in a 1:1 mixture (2.0 mL) of 1,4-dioxane and 2M $H_2SO_4$, stirred for 18 hours, then partitioned between ethyl acetate and water. Aqueous layer is extracted with ethyl acetate and extracts discarded. Aqueous layer is neutralized with saturated $NaHCO_3$ and extracted again with ethyl acetate. Organic layer is washed with brine, dried with $MgSO_3$, solvent evaporated to yield the analog 9 amino acid derivative. As the amine derivative is unstable over prolonged periods of time it can be converted to the very stable trifluoroacetate salt by dissolving in $CH_2Cl_2$ adding the equal molar amount of trifluoroacetic acid and concentrating to dryness.

Example 58. Synthesis of Analog 180: Illudin M (50 mg) is dissolved in dry benzene (10 mL) under a nitrogen atmosphere, and vanadyl acetylacetonate (VO(acac)$_2$, 1.2 mg) is added. Then t-butyl hydroperoxide (t-BuO$_2$H, 0.5 mL) in benzene is added drop wise with stirring for 30 minutes. A saturated solution of Na$_2$S$_2$O$_3$ is added (10 mL), then extraction with ethyl acetate, and the organic layer is dried over Na$_2$SO$_4$, concentrated then chromatographed) (1:1 ethyl acetate:hexane) to give analog 180.

Example 59. Synthesis of Analog 181: Analog 159 (40 mg) was dissolved in dry benzene (8 mL) under a nitrogen atmosphere, and vanadyl acetylacetonate (VO(acac)$_2$, 2 mg) was added. Then t-butyl hydroperoxide (t-BuO$_2$H, 0.5 mL) in benzene was added drop wise with stirring for 30 minutes. A saturated solution of Na$_2$S$_2$O3 is added (10 mL), then extraction with ethyl acetate, followed by a brine wash, and the organic layer was then dried over Na$_2$SO$_4$, concentrated then chromatographed) (1:1 ethyl acetate:hexane) to give analog 181.

Example 60. Synthesis of Analog 189: To a solution of Irofulven (1.00 equivalent), maleimide (1.71 equivalent), triphenylphosphine (PPh$_3$, 1.71 equivalent) in 1.5 mL of THF at −40° C., is added DEAD (diethylazodicarboxylate; 1.68 equivalent). The mixture is stirred for 30 minutes then water (20 μL) added to quench the reaction. The mixture is concentrated on a rotary evaporator and crude product is chromatographed on a silica column (10:3 hexanes:ethyl acetate) to yield an orange compound (20% yield).

Example 61. Synthesis of Analog 190: To a solution of analog 9 (6-hydroxy-n-propylacylfulvene—structure below, 1.00 equivalent), maleimide (1.23 equivalent), triphenylphosphine (PPh$_3$, 1.13 equivalent) in 2.5 mL, of THF at −40° C., is added DIAD (diisopropylcarbodiimide; 1.44 equivalent). The mixture is stirred for 1 hour then water (10 μL) added to quench the reaction. The mixture is concentrated on a rotary evaporator and crude product is chromatographed on a silica column (5:1→10:3 hexanes:ethyl acetate) to yield an orange compound (15% yield).

Example 62. Synthesis of Analog 196: To a solution of analog 9 (266 umol), Boc protected proline amino acid (300 umol) and DMAP (dimethylaminopyridine, 110 umol) in CH$_2$Cl$_2$ (2.5 mL) at 0° C. is added DCC (dicyclohexylcarbodiimide; 1.0M in CH$_2$Cl$_2$, 300 umol). The mixture is stirred for 35 minutes then 5 μL of water added to quench the reaction. The mixture is diluted with hexane and precipitate filtered off, solvent evaporated off and crude product chromatographed (2:1 hexanes-ethyl acetate) to give the desired Boc-protected derivative of 196 at 80% yield. The Boc group is removed by dissolving the Boc-protected derivative in a 1:1 mixture (2.0 mL) of 1,4-dioxane and 2M H$_2$SO$_4$, stirred for 18 hours, then partitioned between ethyl acetate and water. Aqueous layer is extracted with ethyl acetate and extracts discarded. Aqueous layer is neutralized with saturated NaHCO$_3$ and extracted again with ethyl acetate. Organic layer is washed with brine, dried with MgSO$_3$, solvent evaporated to yield the analog 9 amino acid derivative. As the amine derivative is unstable over prolonged periods of time it can be converted to the very stable trifluoroacetate salt by dissolving in CH$_2$Cl$_2$ adding the equal molar amount of trifluoroacetic acid and concentrating to dryness.

Example 63. Synthesis of Analog 198: Irofulven (26.3 mg, 107 umol), p-nitrophenol (16.2 mg, 116 umol) and PPh$_3$ (30.8 mg, 117 umol) were dissolved in anhydrous THF (1.5 mL) at −40° C., the DEAD (25 μL, 160 umol) was added, followed by stirring for 30 minutes, then diluted with hexane. The precipitate was filtered off, solvent evaporated, and crude product chromatographed (6:1→2:1 hexane:ethyl acetate) to give analog 198 as a yellow product (18.5 mg, 47%).

Example 64. Analogs 199 and 200 (prepared together): Irofulven (25.2 mg, 102 umol), phenol (11.5 mg, 122 umol) and PPh$_3$ (29.1 mg, 117 μmol) were dissolved in anhydrous THF (1.0 mL) at −40° C., the DEAD (25 μL, 192 μmol) was added, followed by stirring for 30 minutes, then diluted with hexane. The precipitate was filtered off, solvent evaporated, and crude product chromatographed (6:1→3:1 hexane:ethyl acetate) to give analog 199 (8.2 mg, 25%) and analog 200 (14.6 mg, 44%) as a yellow products.

Example 65. Synthesis of Analog 201 [6-(acetamidopropyl)acylfulvene]: To a solution of analog 195 (49.1 umol) and water (20 μL in THF (0.5 ml) was added a solution of O-acetyl-2-(diphenylphosphino)phenol (39.0 umol) in THF (0.5 mL). The mixture was stirred for 3 days at room temperature then concentrated. The crude product was chromatographed (100% ethyl acetate) to yield 8.2 mg of analog 201.

Example 66. Synthesis of Analog 202 (i.e., analog 211 linked to proline): Prepared via Staudinger ligation. To a solution of analog 195 (94 umol) in THF (1.2 mL), water (40 μL) was added, the was added N-Boc-proline, 2-(diphenylphosphino)phenyl ester (101 μmol) in THF (0.8 mL). The mixture was stirred for 3 days at room temperature then concentrated. The crude product was chromatographed (5:1→1:2 hexanes-ethyl acetate) to yield 31.4 mg (66.7 umol) of analog 202-Boc (71%). The analog 202-Boc was dissolved (66.7 umol) in dioxane (2.0 mL) and 2.0 mL of 2M H$_2$SO$_4$ was added, and the mixture was stirred overnight. Water and ethyl acetate was added, orange color appeared in the aqueous. The aqueous was extracted again with ethyl acetate and organic layer discarded. Sodium bicarbonate was added to aqueous until basic, re-extracted with ethyl acetate. The solution was dried with magnesium sulphate, concentrated to dryness, dissolved in CH$_2$Cl$_2$ and 8 mg of TFA added (1 drop). Analog 202 was obtained in an amount of 22.2 mg (69%).

Example 67. Synthesis of Analog 203: Synthesis of Analog 208 (9.2 mg, 16.5 umol) is dissolved in CH$_2$Cl$_2$ (1.5 mL), 1 drop of anisole added, then 0.5 mL of trifluro acetic acid for 15 minutes. The mixture is concentrated, dissolved in water, then re-extracted with CH$_2$Cl$_2$, and the orange color remains in the aqueous phase, which is concentrated to give analog 203 as the orange colored TFA salt (10.0 mg).

Example 68. Synthesis of Analog 204: Although the Fmoc-Pro-OH would preferentially react with the primary hydroxyl group on Illudin S, the resulting ester linkage is not stable, as illudin S was recovered after storage in CDCl$_3$ for several days at room temperature. The secondary hydroxy group of illudin S was therefore used for coupling with peptides. The primary hydroxy group of illudin S first protected with a TBS group (TBSCl, Imidazole, and DMF, 92%) to produce analog 204.

Example 69. Synthesis of Analog 205 Analog 309 (20 mg, 0.050 mmol, 1 equiv.), triphenylphosphine (40 mg, 0.1525 mmol, 3 equiv.) was dissolved in THF (1 mL) at room temperature. After 20 hours a few drops of water was added and the mixture was heated up at 70° C. After 5 hours the solution was cooled down and evaporated. The residue was chromatographed (hexane/EtOAc/Et$_3$N 4:1:0.1) to give analog 205 (5.3 mg, 29%) as an oil.

Example 70. Synthesis of Analog 206: Analog 205 (14 mg, 0.037 mmol, 1 equiv.) was dissolved in CH$_3$CN (0.5 mL) and pyridine (0.1 mL) at 0° C. To this solution was added HF·Pyridine (7 μL, 0.245 mmol, 35 M, 6.6 equiv.).

After 10 min K$_2$CO$_3$ (0.5 mL, 0.5 M) was added and this mixture was chromatographed (CH$_2$Cl$_2$/Methanol/Et$_3$N 5:0.5:0.1) to give analog 206 (10 mg, 68%) as an oil.

Example 71. Synthesis of Analog 207 (211-leucine): Prepared via Staudinger ligation. To a solution of analog 195 (101 umol) in THF (1.0 mL), water (40 μL) was added, then was added N-Boc-leucine,2-(diphenylphosphino)phenyl ester (95.9 μmol) in THF (1.2 mL). The mixture was stirred for 6 days at room temperature then concentrated. The crude product was chromatographed (1:1 hexanes-ethyl acetate) to yield 27.3 mg of analog 207-Boc. The analog 207-Boc was dissolved (16 μmol) in CH$_2$Cl$_2$ with 3 drops of anisole, TFA was added (0.3 mL), and the mixture was stirred for 15 minutes then concentrated. The crude material was dissolved in water then extracted with CH$_2$Cl$_2$. The aqueous layer was recovered and concentrated to yield 17.4 mg of the analog 207 TFA salt (87%).

Example 72. Analog 208: The TFA salt of analog 196 (13.7 mg, 28.2 μmol) was dissolved in anhydrous DMF (2.5 mL), Boc-Serine-OH (9.6 mg, 47 umol) was added, ODHBT (13.0 mg, 79.4 umol), cooled to 0° C. under a nitrogen atmosphere. Next EDC (15.1 mg) was added followed by NMM (10 μL) to adjust pH, and the mixture stirred at 0° C. for 3 hours. The reaction was added to ethyl acetate/water mixture, and the orange product appeared in the organic layer. The aqueous layer was re-extracted with ethyl acetate, organic layers combined, washed with dilute NaHSO$_4$, water, saturated NaHCO$_3$, brine, then dried with MgSO$_4$. The organic layer was concentrated then chromatographed (1:3 hexane:ethyl acetate) to yield analog 208 as an orange residue (63% yield).

Example 73. Synthesis of Analog 209: The TFA salt of analog 196 (12.5 mg, 25.7 μmol) was dissolved in anhydrous DMF (2.5 mL), Boc-Serine-Ser OH (88.6 umol) was added, ODHBT (33.9 mg, 205 umol), cooled to 0° C. under a nitrogen atmosphere. Next EDC (142 umol) was added followed by NMM (10 μL) to adjust pH, and the mixture stirred at 0° C. but allowed to gradually warm as the ice melts. The mixture was stirred a total of 16 hour then 1 mL water added followed by stirring for 50 minutes. The reaction was added to ethyl acetate/water mixture, and the orange product appeared in the organic layer. The aqueous layer was re-extracted with ethyl acetate, organic layers combined, washed with dilute NaHSO$_4$, water, saturated NaHCO$_3$, brine, and then dried with MgSO$_4$. The organic layer was concentrated then chromatographed (10:1 ethyl acetate:methanol) to give analog 209 as an orange residue (5.9 mg, 36% yield).

Example 74. Synthesis of Analog 210 (Ac-Hyp-Ser-Ser-Chg-Gln-Ser-Ser-Pro-O—(CH$_2$)$_3$-acylfulvene): To a mixture of Analog 196 TFA salt (21.6 umol), the peptide Ac-Hyp-Ser-Ser-Chg-Gln-Ser-Ser-OH (30.3 umol), ODHBt (3,4,-dihydroxy-4-oxo-1,2,3-benzo-triazine-3-yl ester, 71.7 μmol) and NMM (N-methylmorpholine; 7.5 ul) in DMF (2.0 ml) at room temperature is added EDC (1-(3-dimethylaminopropyl)-3-ethylcarbodiimide hydrochloride, 68 μmol), the mixture stirred for 2 hours at room temperature, then diluted with 10 mL of water. Solution is directly chromatographed on a reverse phase C18 column (4:1→2:1, water/acetonitrile gradient) to yield 69% of analog 210.

Example 75. Synthesis of Analog 212 (Illudin M-proline) Illudin M (20 mg, 0.081 mmol, 1 equivalent), DMAP (1 mg, 0.008 mmol, 0.1 equiv.) and Fmoc-Pro-OH (33 mg, 0.097 mmol, 1.2 equiv.) were dissolved in CH$_2$Cl$_2$ (1 mL) at 0° C., to which was added a CH$_2$Cl$_2$ solution of DCC (100 μL, 0.1 mmol, 1 M, 1.2 equiv.). The temperature of the mixture gradually rose to 5° C. in 1.5 hours and then the mixture was filtered through a pad of Celite. The filtrate was concentrated and the residue was chromatographed (CH$_2$Cl$_2$/EtOAc 5:0.1-5:0.4) to give Illudin-M-proline-Fmoc protected analog (36 mg, 79%) as oil. The proton spectra of this oil showed that it was a mixture of two isomers (rotamers). And then this oil was dissolved in CH$_2$Cl$_2$ (4 mL) and treated with piperidine (1 mL) at 0° C. After 0.5 hours the solution was concentrated and the concentrate was chromatographed (CH$_2$Cl$_2$/Methanol 5:0.4) to give analog 212 (15 mg, 54%) as oil.

Example 76. Synthesis of Analog 213: Analog 204 is coupled with Fmoc-Pro-H (DMAP, CH$_2$Cl$_2$, DCC, 0° C., 85%), followed by deprotection of Fmoc group with 20% piperidine in CH$_2$Cl$_2$ to produce analog 213 in 78% yield.

Example 77. Synthesis of Analog 214 (Illudin S-Pro-Ser-Ser-HHOAc): The Fmoc protected peptide of H-Ser-Ser-OH was prepared by taking H-Ser-Ser-OH (50 mg, 0.26 mmol, 1 equiv.) and K$_2$CO$_3$ (89.7 mg, 0.65 mmol, 2.5 equiv.), dissolving in a mixture of water (4 mL) and dioxane (3 mL) at 0° C. To this solution FmoCl (67.3 mg, 0.26 mmol, 1 equiv.) was added in several portions. After 18 hours the mixture was acidified by KHSO$_4$ and the pH raised to 2.5. Then this mixture was taken up by ethyl acetate, which was washed with brine, dried, filtered and evaporated. The residue was chromatographed (CH$_2$Cl$_2$/Methanol/HOAc 5:1:0.1) to give 3.27 (75 mg, 70%) as a white solid. The analog 212 (Illudin S tosylate-Pro) (42.8 mg 0.09 mmol, 0.9 equiv.), and the Fmoc protected H-Ser-Ser-OH peptide (41.2 mg, 0.1 mmol, 1 equiv.) were dissolved in DMF (1.5 mL) at 0° C. To this solution was added NMM (22 μL, 0.2 mmol, 2 equiv.), ODHBt (29.4 mg, 0.18 mmol, 1.8 equiv.), and EDC (31.1 mg, 0.16 mmol, 1.6 equiv.). The solution temperature was then raised to room temperature and kept for 3 hours before it was taken up by ethyl acetate. The mixture was then washed with saturated sodium bicarbonate and brine. It was then dried, filtered and evaporated. The residue was chromatographed (CH$_2$Cl$_2$/Methanol 5:0.3) to give analog 214 (50.5 mg, 67%) as an oil.

Example 78. Synthesis of Analog 215: (Illudin S-Pro-Ser-Ser-Gln-Chg-Ser-Ser-Hyp-Ac) Analog 204 is coupled with Fmoc-Pro-H (DMAP, CH$_2$Cl$_2$, DCC, 0° C., 85%), followed by deprotection of Fmoc group with 20% piperidine in CH$_2$Cl$_2$ to produce analog 213 in 78% yield. Peptide conjugate, analog 215 was obtained from further coupling with hepta-peptide Ac-Hyp-Ser-Ser-Chg-Gln-Ser-Ser-OH (ODHBt, NMM, DMF, 0° C., 47%).

Example 79. Synthesis of Analog 216: (Illudin M-Pro-Ser-Ser-Gln-Chg-Ser-Ser-Hyp-Ac). Analog 212 was further coupled with the commercially available hepta-peptide Ac-Hyp-Ser-Ser-Chg-Gln-Ser-Ser-OH (ODHBt, NMM, DMF, EDC, 0° C.) to yield analog 216 at 33%. The low yield resulted from repeated chromatographic purification as the purity of the final raw product was estimated by HPLC to be only 70%.

Example 80. Synthesis of Analog 217: To a solution of Irofulven (1.00 equivalent), epsilon-maleimidocaproic acid (1.27 equivalent), DMAP (0.15 equivalent) in 1.0 mL of methylene chloride (CH$_2$Cl$_2$) at 0° C., is added DCC (dicyclohexylcarbodiimide; 1.27 equivalent) in methylene chloride (CH$_2$Cl$_2$). The mixture is stirred for 1.25 hours, diluted with hexane and precipitated is filtered. Residual solvent is evaporated off, and oil residue is chromatographed on a silica column (2:1 hexanes:ethyl acetate) to yield analog 217, an orange compound (77% yield).

Example 81. Synthesis of Analog 218: To a solution of Illudin M (1.00 equivalent), epsilon-maleimidocaproic acid (1.33 equivalent), DMAP (0.18 equivalent) in 1.0 mL of methylene chloride (CH$_2$Cl$_2$) at 0° C., is added DCC (dicyclohexylcarbodiimide; 1.33 equivalent) in methylene chloride (CH$_2$Cl$_2$). The mixture is stirred for 2.25 hours, diluted with hexane and precipitated is filtered. Residual solvent is evaporated off, and oil residue is chromatographed on a silica column (2:1 hexane:ethyl acetate) to yield analog 218, an orange compound (83% yield).

Example 82. Synthesis of Analog 219: Analog 204 (33.4 mg) is dissolved in 1.0 mL of anhydrous pyridine under a nitrogen atmosphere, then DMAP (5.1 mg) is added, followed by 4-fluorosulfonyl-benzoyl chloride (86.1 mg). The mixture is stirred for 90 minutes at room temperature The mixture is diluted with ethyl acetate, washed once with saturated copper sulfate solution, washed twice with water, then dried over MgSO$_4$, concentrated then chromatographed (20% ethyl acetate:hexane) to give analog 219.

Example 83. Synthesis of Analog 221: Prepared from Analog 207 by coupling with Mu-His-Ser-Ser-Lys(Fmoc)-Leu-Gln-OH in DIC/HOBt for 5 minutes, then 5% piperidine/DMF for 1 minute. Followed by TFA quenching to yield analog 221 at 21% yield.

Example 84. Synthesis of Analog 222: Illudin M (63 mg) is dissolved in 1.0 mL of anhydrous pyridine under a nitrogen atmosphere, then DMAP (6.4 mg) is added, followed by 4-fluorosulfonyl-benzoyl chloride (86 mg). The mixture is stirred for 35 minutes at room temperature then chromatographed (20% ethyl acetate:hexane) to give analog (70.9 mg).

Example 85. Synthesis of Analog 223: The disulfhydryl peptide CNGRC is first converted to a cyclic disulfide peptide by dissolving 355 mg in 3.0 mL DMSO, adding 9 mL of water, allowing to sit overnight at room temperature, followed by water removal on a rotoevaporator then DMSO removal under high vacuum. The TFA salt of analog 179 (14.5 mg) is dissolved in DMF (2.0 mL) and the CNGRC disulfide peptide added (19.0 mg), 60 µL of DIPEA is added, followed by gradual addition of a solution of Py-BOP (19.6 mg) and HOBt (8.9 mg) in DMF (2.0 mL) over 150 minutes at room temperature. The reaction is stopped by adding two drops of TFA and water. The mixture is applied to a reverse phase column and analog 223 is eluted with acetonitrile:water (1:4).

Example 86. Synthesis of Analog 224: Acylfulvene (116 mg) is dissolved in ethanol (4.0 mL) with stirring, hydroxylamine hydrochloride (84.2 mg) added, Sodium acetate (233 mg) added, then refluxed for 70 minutes at 85° C. The ethanol is removed, then ethyl acetate (10 mL) added to dissolve crude product, then water (10 mL) added, the organic layer is washed with brine, dried over Na$_2$SO$_4$, concentrated then chromatographed (20% ethyl acetate: hexane) to give analog 224 (63.7 mg, 54% yield).

Example 87. Synthesis of Analog 225: Illudin S (439 mg) is dissolved in ethanol (15 mL) with stirring, hydroxylamine hydrochloride (233 mg) added, sodium acetate (933 mg) added, then refluxed for 130 minutes at 85° C. The solution is cooled to room temperature, filtered, ethanol is removed, then ethyl acetate (30 mL) added to dissolve crude product, then water (30 mL) added, the organic layer is washed with brine, dried over Na$_2$SO$_4$, concentrated then chromatographed (30%→50%, acetone:hexane) to give analog 225 (372 mg, 80% yield).

Example 88. Synthesis of Analog 226: Irofulven (37.6 mg) is dissolved with stirring in CH$_2$Cl$_2$, elaidic acid (180 mg. 1.3 equivalents) added, DMAP (15 mg) added, cooled to 0° C., then DCC (180 µL) in CH$_2$Cl$_2$ (640 µL) added. Reaction mixture stirred at 0° C. for 1 hour, then additional DCC (120 µL) added, and stirred for 2 more hours. Mixture chromatographed (20% ethyl acetate:hexane) to give analog 226 as a yellow oil (50.5 mg, 48% yield).

Example 89. Synthesis of Analog 227: Analog 009 (87 mg) is dissolved with stirring in CH$_2$Cl$_2$, elaidic acid (108 mg) added, DMAP (15.4 mg) added, cooled to 0° C., then DCC (0.5 mL) in CH$_2$Cl$_2$ (1.5 mL) added. Reaction mixture stirred at 0° C. for 3 hours, then the mixture directly chromatographed (20% ethyl acetate:hexane) to give analog 227 as a yellow oil (105 mg, 61% yield).

Example 90. Synthesis of Analog 228: Illudin S (86 mg) is dissolved with stirring in CH$_2$Cl$_2$, elaidic acid (202 mg) added, DMAP (15.4 mg) added, cooled to 0° C., then DCC (1.0 mL) in CH$_2$Cl$_2$ (3.0 mL) added. Reaction mixture stirred at 0° C. for 3 hours, then the mixture directly chromatographed (20% ethyl acetate:hexane) to give analog 228 as a yellow oil (198 mg, 77% yield).

Example 91. Synthesis of Analog 229: The elaidic ester of 0-diphenylphosphine phenol is first prepared by dissolving with stirring in 3.0 mL of CH$_2$Cl$_2$ the O-diphenylphosphine phenol (91.3 mg), elaidic acid (94.5 mg, 1 equivalent), DMAP (9.4 mg). The solution is cooled to 0° C. then DDC (0.44 mL, 1.0 M in CH$_2$Cl$_2$) is added with stirring for 3.5 hours. The precipitate is filtered off and discarded. The elaidic ester is chromatographed and concentrated to dryness then dissolved in THF (1.0 mL). Analog 195 (26.1 mg) is dissolved in THF (1.0 mL) and water (80 µL) added. The elaidic ester solution is slowly added to the analog 195 solution with stirring, and reacted for 22 hours at room temperature. The mixture is directly chromatographed (30% acetone:hexane) to give analog 229 (22.2 mg, 47% yield).

Example 92. Synthesis of Analog 230: Analog 308 (22 mg) is dissolved in anhydrous CH$_2$Cl$_2$ (1.5 mL), diisopropylethylamine (20 µL) added, and the mixture cooled to 0° C., then methylsulfonyl chloride added (15 µL), mixture stirred at 0° C. for 1 hour, and allowed to warm to room temperature while being stirred for an additional hour. The mixture is chromatographed (30% ethyl acetate in hexane) to yield analog 230 (35% yield).

Example 93. Synthesis of Analog 231: Analog 308 (16 mg) is dissolved in anhydrous CH$_2$Cl$_2$ (1.5 mL), diisopropylethylamine (20 µL) added, and the mixture cooled to 0° C., then tosyl chloride added (18.4 mg), mixture stirred at 0° C. for 1 hour, and allowed to warm to room temperature while being stirred for an additional 3 hours. The mixture is chromatographed (30% ethyl acetate in hexane) to yield analog 231 (8.6 mg).

Example 94. Synthesis of Analog 240: Analog 232 (25.1 mg) is dissolved in anhydrous CH$_2$Cl$_2$ (2.0 mL), 15 µL of acetic anhydride added, and the mixture cooled to room temperature, then DMAP added (5 mg), and stirred for 25 minutes. The mixture is partially concentrated then chromatographed (30% ethyl acetate in hexane) to yield analog 240 (26.6 mg, 93% yield).

Example 95. Synthesis of Analog 254: Analog 009 (51.4 mg), 4-carboxybenzene sulfonamide (59.4 mg), and DCC (39.6 mg) were dissolved in anhydrous DMF (1.0 mL) at room temperature, stirred, then DMAP (15 mg) added. The mixture was stirred for 2 hours at room temperature then solid material was filtered off. The mixture was then chromatographed (1:1 ethyl acetate:hexane) to give analog 254 (38.6 mg, 45% yield).

Example 96. Synthesis of Analog 255: Analog 009 (244.3 mg) and sulfamoyl chloride (157 mg) were dissolved in anhydrous DMAP (2.0 mL) at room temperature, and stirred for 3.5 hours. The mixture was concentrated under high vacuum then chromatographed (30% ethyl acetate in hexane) to give analog 255.

Example 97. Synthesis of Analog 259: Analog 255 (64.7 mg), (diacetoxyiodo)benzene (64.7 mg), dirhodiumtetraacetate or $Rh_2(OAc)_4$ and magnesium (16.8) dissolved in 5.0 mL of $CH_2Cl_2$ are heated to 70° C. and stirred for 7 hours. The mixture is filtered, concentrated, then chromatographed (1:1 ethyl acetate:hexane) to give analog 259.

Example 98. Synthesis of Analog 262 and 263 (prepared together): Analog 25 (44.7 mg) is dissolved in methanol (1.0 mL), Oxone® reagent (246 mg, 3 equivalents) is dissolved in water (1.0 mL). The oxone solution is slowly added to the methanol solution with stirring at room temperature for 3.5 hours, then an additional amount of Oxone reagent added followed by stirring for 1.5 hours. Then 2 mL of saturated sodium sulfite solution was added, followed by ethyl acetate extraction, dried over $Na_2SO_4$, concentrated then chromatographed (1:1 Ethyl acetate:hexane) to yield first analog 263 (21.4 mg) and then analog 262 (14.3 mg).

Example 99. Synthesis of Analog 284 and 289 (prepared together): Analog 34 (174 mg) and uracil (227 mg) are dissolved in $CH_2Cl_2$ with stirring and the mixture cooled to 0° C. Then $SnCL_4$ (148.8 µL) is slowly added. The mixture is stirred at 0° C. for 80 minutes, then concentrated, chromatographed (2→5% methanol:$CH_2Cl_2$) to give analog 284 (68.9 mg, 33% yield) and analog 289 (21.6 mg, 10% yield).

Example 100. Synthesis of Analog 285: Analog 34 (25 mg) is dissolved in ethanol, and O-(tert-Butyldimethylsilyl) hydroxylamine (25 mg) is added followed by stirring for 2 hours at room temperature. The secondary amine intermediate (9 mg) is recovered by chromatography (30% ethyl acetate:hexane), dissolved in $CH_2Cl_2$, and reacted with sulfamoil chloride ($ClSO_2NH_2$, 5 mg) and DABCO (2 mg) with stirring for one hour, then additional sulfamoil chloride (6 mg) was added with stirring for another 1.5 hours. The TPS blocked product was recovered by chromatography (30% ethyl acetate:hexane), and the TPS group was removed in THF by adding TBAF (Tetra-n-butylammonium fluoride). The TPS group can also be removed by dissolving the TPS product in pyridine and THF at 0° C., then adding HF-pyridine overnight. After TPS deblocking the mixture is chromatographed (50% ethyl acetate:hexane) to give analog 285.

Example 101. Synthesis of Analog 286 and 287 (prepared together): The ketone groups on 5-fluorouracil are first blocked with TMS groups by dissolving 5-fluorouracil (610 mg) and $(NH_4)_2SO_4$ in HMDS (10 mL) under a nitrogen atmosphere. The solution is refluxed at 142° C. for 2.5 hours, cooled to 60° C. and excess HMDS distilled off, then concentrated to dryness under high vacuum. Analog 34 (180 mg) and the di-TMS 5-fluorouracil are dissolved in $CH_2Cl_2$ (5.0 mL) with stirring and the mixture cooled to 0° C. Then $SnCL_4$ (120 µL) is slowly added drop wise. The mixture is stirred at 0° C. for 3.5 hours, then concentrated, chromatographed (80% ethyl acetate:hexane) to give analog 286 (18.9 mg, 9% yield) and analog 287 (84 mg, 38% yield).

Example 102. Synthesis of Analog 289: See the preparation of analog 284 for the preparation of analog 289 (284 and 289 prepared simultaneously then separated by chromatography).

Example 103. Analogs 299 and 300 (prepared together): Analogs 299 and 300 are prepared in equal amounts from Illudin S using the Mitsunobu reaction. Illudin S is directly reacted with $HN_3$ ($PPh_3$, DEAD, benzene) at 0° C. under nitrogen for 45 minutes. Mitsunobu, 0. Synthesis 1:1-28, 1981.

Example 104. Synthesis of Analog 301: Irofulven (31.6 mg, 0.128 mmol), 5-benzoylvaleric acid (35.8 mg, 0.174 mmol) and DMAP (4.7 mg) is dissolved in $CH_2Cl_2$ (2 mL) under a nitrogen atmosphere, cooled to 0° C., the DCC added (170 µL of 1.0M solution in $CH_2Cl_2$). The mixture is stirred for 60 minutes then diluted with hexane (10 mL) and filtered. The organic layer is further diluted with $CH_2Cl_2$, washed with water, then saturated $NaHCO_3$ then brine, dried with $MgSO_4$, concentrated, then dissolved in $CH_2Cl_2$, filtered and chromatographed (10:3 hexane:ethyl acetate), appropriate fractions collected, pooled, concentrated then chromatographed (3:1 hexane:ethyl acetate) to give analog 301 (23.2 mg, 42% yield).

Example 105. Analogs 302 and 303 (prepared together): Illudin S (100 mg, 0.378 mmol) is benzoylated by dissolving in pyridine (1.0 mL) then adding 3, 5-dintirobenzoyl chloride (110 mg, 0.5 mmol) at room temperature and stirring for 24 hours. The mixture is poured onto crushed ice then extracted with $CH_2Cl_2$ (10 mL), which is washed twice with water (20 mL). The organic layer is dried over $Na_2SO_4$ and concentrated to yield analogs 302 and 303. The two analogs can be separated by column chromatography (1:1 hexane: ethyl acetate).

Example 106. Synthesis of Analog 304: Analog 009 (84.6 mg) is dissolved in anhydrous $CH_2Cl_2$ (3.0 mL), DCC added (81.2 mg), mixture cooled to 0° C., propiolic acid (35 µL) added, then the reaction started with DMAP (15 mg), stirred and allowed to warm to room temperature over 1 hour. The mixture was filtered to remove solids then chromatographed (30% ethyl acetate in hexane) to give analog 304 (60% yield).

Example 107. Synthesis of Analog 305: Analog 009 (99.1 mg) is dissolved in anhydrous $CH_2Cl_2$ (3.0 mL), pyridine (150 µL) added, then p-nitrophenylchloroformate and stirred for 3.5 hours at room temperature. The mixture was concentrated, hexane (20 mL) added, and precipitate filtered before chromatographing (50% ethyl acetate in hexane) to give analog 305 (50% yield).

Example 108. Synthesis of Analog 306: Analog 009 (244 mg) is dissolved in anhydrous $CH_2Cl_2$ (4.0 mL), tosyl chloride (181 mg) added, the mixture cooled to 0° C., to which an aliquot of pyridine (80 µL) is added. The mixture stirred at 0° C. for 1 hour, and allowed to warm to room temperature while being stirred for an additional 20 hours. The mixture is concentrated then chromatographed (50% ethyl acetate in hexane) to yield analog 306.

Example 109. Synthesis of Analog 307: A solution of 1.0 M $N_3H$ in benzene is first prepared by mixing 654 mg $N_3H$, 0.65 mL water, in 10 mL of benzene. The mixture is cooled to 0° C., 0.5 mL of concentrated $H_{2SO4}$ added, and allowed to warm slowly to room temperature and then stirred for 80 minutes. Next $PPh_3$ (590 mg) is dissolved in anhydrous THF (1.5 mL) and cooled to 0° C. Then 2.1 mL of $N_3H$ 1.0 M solution is added, followed by DEAD (0.475 mL) then Illudin S (282 mg in 1.0 mL anhydrous THF). The mixture is stirred for 3 hours at 0° C., warmed, concentrated, followed by chromatography (30% ethyl acetate in hexane) to give analog 307.

Example 110. Synthesis of Analog 308: Analog 307 (100 mg) is dissolved in anhydrous THF (3.0 mL) at room temperature and PPH3 added (306 mg, 3 equivalents). The mixture is stirred for 5 hours at room temperature, then the reaction stooped by adding water (0.15 mL). The mixture is heated to 85° C. for 30 minutes, then concentrated and chromatographed (20% methanol in ethyl acetate) to give analog 308.

Example 111. Synthesis of Analog 309: Analog 204 was reacted with $HN_3$ (DEAD, THF) to yield the azide analog 309 at 68% yield.

Example 112. Synthesis of Analog 310: Irofulven (42.9 mg), 4-carboxybenzene sulfonamide (41.4 mg), and DCC (38.4 mg) were dissolved in anhydrous DMF (1.0 mL) at room temperature, stirred and then DMAP (10 mg) added. The mixture was stirred for 75 minutes at room temperature then solid material was filtered off. The mixture was then chromatographed (1:1 ethyl acetate:hexane) to give analog 310 (40% yield).

Example 113. Synthesis of Analog 311: Illudin M (32.4 mg), 4-carboxybenzene sulfonamide (39.7 mg), and DCC (24.4 mg) were dissolved in anhydrous DMF (1.0 mL) at room temperature, stirred, then DMAP (15 mg) added. The mixture was stirred for 75 minutes at room temperature, allowed to warm to room temperature, then stirred for 22 hours. The solid material was filtered off and the mixture was then chromatographed (1:1 ethyl acetate:hexane) to give analog 311 (35% yield).

Example 114. Synthesis of Analog 312: Irofulven (1.18 grams) is dissolved in anhydrous $CH_2Cl_2$ (4.0 mL), tosyl chloride (1.1 equivalent) added, the mixture cooled to 0° C., then pyridine (0.4 mL) added. The mixture stirred at 0° C. for 1 hour, and allowed to warm to room temperature while being stirred for an additional 3 hours. The mixture is concentrated then chromatographed (50% ethyl acetate in hexane) to yield analog 312.

Example 115. Synthesis of Analog 313: Analog 308 (31 mg) is dissolved in anhydrous $CH_2Cl_2$, cooled to 0° C., with stirring then diisopropylethylamine added (45 µL), then fluorophenylsulfonyl chloride added (36 µL) for 3 hours at 0° C. Mixture is directly chromatographed (20% ethyl acetate:hexane) to give analog 313 (23.3 mg).

Example 116. Synthesis of Analog 314: Analog 009 is dissolved in anhydrous $CH_2Cl_2$ (4.0 mL), tosyl chloride (1.1 equivalent) added, the mixture cooled to 0° C., then pyridine (0.4 mL) added. The mixture stirred at 0° C. for 1 hour, and allowed to warm to room temperature while being stirred for an additional 3 hours. The mixture is concentrated then chromatographed (50% ethyl acetate in hexane) to yield analog 314.

Example 117. Synthesis of Analog 315: Irofulven was dissolved in a solution of 2,5 dimethylpyrrole (4 fold excess molar solution) in 5 mL of dry $CH_2Cl_2$ at −78° C. Boron trifluoride (equivalent molar amount to the irofulven) was slowly added with stirring. The reaction was allowed to stir for 2 more hours at −78° C., then water slowly added. The mixture was extracted twice with 2 fold equivalent volumes of ethyl acetate, the organic extracts combined, washed with saturated $NaHCO_3$, water, brine, then dried over $MgSO_4$. The solution was concentrated under vacuum until a red residue remained, which was chromatographed on silica gel (50% ethyl acetate in hexane) to yield analog 315 (30% yield).

Example 118. Synthesis of Analog 316: Analog 316 was prepared by dissolving Illudin S (20 mg) in pyridine (0.5 mL) and then 4-fluorosulfonylbenzoly chloride (equivalent molar amount) was added to the mixture in an ice bath. The solution is allowed to warm slowly and then react overnight. The liquid was then removed under reduced pressure until a crude residue remained. Rather than recrystallize from chloroform, the residue was instead chromatographed on a standard silica gel column using hexane-ethylacetate (1:1). The mono-adduct (analog 316), a di-adduct and a small amount of unreacted Illudin S were recovered in separate eluates.

Example 119. $N_3H$ 1.0 M Solution: A solution of 1.0 M $N_3H$ in benzene is first prepared by mixing 654 mg $N_3H$, 0.65 mL water, in 10 mL of benzene. The mixture is cooled to 0° C., 0.5 mL of concentrated $H_2SO_4$ added, and allowed to warm slowly to room temperature and then stirred for 80 minutes.

Example 120. Synthesis of Analog 193: Irofulven (221 mg, 0.897 umol) is dissolved in anhydrous THF (1.5 mL), then $PPh_3$ (261 mg, 0.995 umol) is added, then 1.0 M $N_3H$ solution (1.0 mL, 1.0 mmol) under nitrogen atmosphere. The solution is cooled to −40° C., and then DIAD (0.21 mL, 1.013 umol) added and stirred for 30 minutes at 0° C. then diluted with hexane, and filtered to remove precipitate. The mixture is concentrated then chromatographed (30% ethyl acetate:hexane) to give analog 193 (171 mg, 71%).

Example 121. Synthesis of Analog 195: Analog 009 (31.9 mg, 116 umol) is dissolved in anhydrous THF (3.0 mL), then $PPh_3$ (33 mg, 126 umol) is added, then 1.0 M $N_3H$ solution (0.3061 mL) under nitrogen atmosphere. The solution is cooled to 0° C., DIAD (30 µL, 145 umol) added and stirred for 30 minutes at 0° C. then water (5 µL) is added to destroy the $PPh_3$. The mixture is concentrated then chromatographed (30% ethyl acetate:hexane) to give analog 195 (24.9 mg, 72%).

Example 122. Synthesis of Analog 441: 27 mg (0.095 mmol) of analog 022 is dissolved in 5.0 ml of anhydrous pyridine under nitrogen atmosphere, 20 µL of triethylamine is added to help dissolve analog 022 in the pyridine, then a catalytic amount of DMAP (2.2 mg) is added followed by the 4-(fluorosulfonyl)benzoyl chloride (25 mg). The mixture is stirred for one hour at room temperature then purified by chromatography (30% ethyl acetate:hexane) to yield analog 441 (17 mg).

Example 123. Synthesis of Analog: xx mg of analog 127 is dissolved in 5.0 ml of anhydrous pyridine under nitrogen atmosphere, 20 µL of triethylamine is added to help dissolve analog 127 in the pyridine, then a catalytic amount of DMAP (2.2 mg) is added followed by the 4-(fluorosulfonyl) benzoyl chloride (25 mg). The mixture is stirred for one hour at room temperature then purified by chromatography (30% ethyl acetate:hexane) to yield analog xxx (xx mg).

The foregoing description of embodiments of the methods, systems, and components of the present invention has been provided for the purposes of illustration and description. It is not intended to be exhaustive or to limit the invention to the precise forms disclosed. Many modifications and variations will be apparent to one of ordinary skill in the relevant arts. For example, steps performed in the embodiments of the invention disclosed can be performed in alternate orders, certain steps can be omitted, and additional steps can be added. The embodiments were chosen and described in order to best explain the principles of the invention and its practical application, thereby enabling others skilled in the art to understand the invention for various embodiments and with various modifications that are suited to the particular used contemplated. Other embodiments are possible and are covered by the invention. Such embodiments will be apparent to persons skilled in the relevant art(s) based on the teachings contained herein. The breadth and scope of the present invention should not be limited by any of the above-described exemplary embodiments, but should be defined only in accordance with the following claims and their equivalents.

Table IA shows acylfulvene amine analogs which can be attached to a bi-functional linker which can then be attached to a sulfhydryl reacting group of the AM using the reagent.

| Amine analog | Reagent |
|---|---|
| 97, 121, 176, 179, 184, 203, 205, 206, 207, 211, 220, 244, 245, 254, 255, 264, 266, 267, 270, 276, 283, 285, 294, 295, 296, 297, 308, 310, 311 | 2IT [2-iminothiolane (generated from) methyl 4-mercaptobutyrimidate], AMAS [N-(α-maleimidoacetoxy)-succinimide ester], BMPA [N-β-malemidopropionic acid], BMPS [N-β-malemidopropyloxy)succinimide ester], C6-SFB [C6-succinimidyl 4-formylbenzoate], Citiolone [N-acetylhomocysteinethiolactone], DST [disuccinimidyl tartrate], EMCH [N-(epsilon-maleimidocaproic acid) hydrazide], EMCS [N-(episilon-maleimideocaproyloxy)succinimide ester], GMBS [N-(gamma-maleimideobutyrloxy)succinimide ester], KMUA [N-kappa-maleimidoundecanoic acid], KMUH [N-(kappa-maleimidoundecanoic acid) hydrazide], LC-SMCC [succinimidyl 4-(N-maleimidomethyl)cyclohexane-1-carboxy-(6-amidocaproate)], LC-SDPD [succinimidyl 6-(3'-(2-pyridyl-dithio)propionamido)hexanoate], MBS [m-maleimidobenzoyl-N-hydroxysuccinimide ester], MCP [methyl 3-mercaptopropionimidate], MPBH [4-(4-N-maleimidophenyl)-butyric acid hydrazide], M2C2H [4-(N-maleimidomethyl)cyclohexanee-1-1carboxyl-hydrazide], NPIA [p-nitrophenyl iodoacetate], PDPH [3-(2-pyridyldithio)propionyl hydrazide], PDTP [3-2(pyridyldithio)propionate], PMPI [N-(p-maleimidophenyl)isocyanate], SATA [succinimidyl S-acetylthioacetate], SATP [succinimidyl acetylthiopropionate], SFB [succinimidyl p-formylbenzoate], SFPA [succinimidyl p-formylphneoxyacetate], SHTH [succinimidyl 4-hydrazidoterephthalate], SIAB [N-succinimidyl(4-iodoacetyl)-aminobenzoate], SIAC [succinimidyl 4-(((iodoacetyl)amino)methyl)-cyclohexane-1-caroxylate], SIACX [succinimidyl 6-((((4(iodoacetyl)amino)methyl) cyclohexane-1-carbonyl)aminohexanoate], SIAX [succinimidyl 6-((iodoacetyl)amino)hexanoate], SIAXX [succinimidyl 6-(6-(((iodoacetyl)amino)-hexanoyl)aminohexanoate], SAMSA [S-acetylmercaptosuccinic anhydride], SMCC [succinimidyl 4-(N-maleimidomethyl)-cyclohexane-1-carboxylate], SM(PEG)2 [NHS-PEO2-maleimide or maleimide PEG2 N-hydroxysuccinimide], SM(PEG)4 [NHS-PEO4-maleimide or maleimide PEG4 N-hydroxysuccinimide], SM(PEG)8 [NHS-PEO8-maleimide or maleimide PEG6 N-hydroxysuccinimide], SM(PEG)12 [NHS-PEO12-mleimide or maleimide PEG8 N-hydroxysuccinimide], SMPB [succinimidyl 4-(para-maleimido-phenyl)butyrate], SMPH [succinimidyl-6-(beta-maleimidopropionamido)hexanoate], SMPT [4-succinimidyloxycarbonyl-methyl-alpha-(2-pyridyldithio)toluene], SPDP [N-succinimidyl 3-(2-pyridyldithio)propionate], Sulfo-DST [sulfo-disuccinimidyl tartrate], Sulfo-EMCS [N-(episilon-maleimidocaproyloxy)sulfosuccinimide], Sulfo-GMBS [N-(gamma-maleimidobutyrloxy)sulfosuccinimide ester], Sulfo-KMUS [N-(kappa-maleimidoundecanoyloxy)sulfosuccinimide ester], Sulfo-LC-SMPT [sulfosuccinimidyl 6-(alpha-methyl-alpha-(2-[pyridyldithio)-toluamido)hexanoate], Sulfo-LC-SPDP [sulfosuccinimidyl 6-(3'-(2-pyridyl-dithio)propionamido)hexanoate], Sulfo-MBS [m-maleimidobenzoyl-N-hydroxysulfosuccinimide ester], Sulfo-SIAB [sulfo-succinimidyl(4-iodoacetyl)-aminobenzoate], Sulfo-SMCC [sulfosuccinimidyl 4-(N-maleimido-methyl)cyclohexane-1-carboxylate], Sulfo-SMPB [sulfosuccimidyl 4-(p-maleimidophenyl)butyrate] |

TABLE IB

Acylfulvene amine analogs attached to a linker which is attached to a photoactivatable group at the other terminus.

| Amine analog | Reagent |
|---|---|
| 97, 121, 176, 179, 184, 203, 205, 206, 207, 211, 220, 244, 245, 254, 255, 264, 266, 267, 270, 276, 283, 285, 294, 295, 296, 297, 308, 310, 311 | ANB-NOS [N-5-azido-2-nitrobenzyloxy-succinimide], NHS-ASA [N-hydroxysuccinimidyl-4-azidosalicylic acid], SADPH [N-succinimidyl (4'-azidophenyl)1,3'-dithiopropionate], SANPAH [N-succinimidyl 6-(4'azido-2'-nitrophenylamino)hexanoate], SPB [succinimidyl-(4-psoralen-8y; oxy)butyrate], Sulfo-HSAB [N-hydroxysulfosuccinimidyl-4-azidobenzoate], Sulfo-NHS-LC-ASA [sulfosuccinimidyl(4-azido-salicylamido)hexanoate], Sulfo-SADP [sulfosuccinimidyl(4-azido-phenyldithio)propionate], Sulfo-SAED [sulfosuccinimidyl 2-(7-azido-4-methylcoumarin-3-acetamido)ethyl-1,3'-dithiopropionate], Sulfo-SASD [sulfosuccinimidyl 2-(p-azido-salicylamido)ethyl 1,3'-dithiopropionate], Sulfo-SFAD [sulfosuccinimidyl(perfluoroazidobenzamido)ethyl 1,3'-dithiopropionate], Sulfo-SAND [sulfosuccinimidyl-2-(m-azido-o-nitrobenzamido)ethyl 1,3'-dithiopropionate], Sulfo-SANPAH [sulfosuccinimidyl 6-(4'-azido-2'-nitrophenylamino)hexanoate] |

TABLE IC

Acylfulvene amine analogs attached to a linker which is attached to an amine reactive group at the other terminus.

| Amine analog | Reagent |
| --- | --- |
| 97, 121, 176, 179, 184, 203, 205, 206, 207, 211, 220, 244, 245, 254, 255, 264, 266, 267, 270, 276, 283, 285, 294, 295, 296, 297, 308, 310, 311 | BS2G-do [bis(sulfosuccinimidyl)glutarate-d0], BS2G-d4 [bis(sulfosuccinimidyl)2,2,4,4,glutarate-d4], BS3 (or Sulfo-DSS) [bis(sulfosuccinimidyl)suberate], BS3do [bis(sulfosuccinimidyl)suberate], BS3d4 [bis(sulfosuccinimidyl)2,2,7,7-suberate-d4], BS(PEG)5 [bis(NHS)PEO5], BSOCOES [bis(2-(succininidoxycarbonyloxy)ethyl)sulfone], DMA [dimethyl adipimidate], DMP [dimethyl pimelimidate], DMS [dimethyl suberimidate], DFDNB [1,5,-difluoro-2,4-dinitrobenzene], DFDNPS [4,4'-difluoro-3,3'-dinitrophenylsulfone], DSG [disuccinimidyl glutarate], DSS [disuccinimidyl suberate], DST [disuccinimidyl tartarate], DSP or Lomant's reagent [dithiobis(succimidylpropionate)], DTBP [dimethyl 3,3'-dithiobispropionimidate], DTSSP (sulfo-DSP) = [3,3'-dithio-bis(sulfosuccinimidylpropionate)], EGS [ethylene glycol bis(succinimidylsuccinate)], PMPI [N-(4-Isocyanatophenyl)maleimide], Sulfo-EGS [ethylene glycol bis(sulfo-succinimidylsuccinate)] |

TABLE ID

Acylfulvene amine analogs attached to a linker which is attached to a reactive group capable of reacting with an aldehyde, carbonyl or carboxylate group at the other terminus.

| Amine analog | Reagent |
| --- | --- |
| 97, 121, 176, 179, 184, 203, 205, 206, 207, 211, 220, 244, 245, 254, 255, 264, 266, 267, 270, 276, 283, 285, 294, 295, 296, 297, 308, 310, 311 | C6-SANH [C6-succinimidyl 4-hydraznonicotinate acetone hydrazone] SANH [succinimidyl 4-hydraznonicotinate acetone hydrazone] EDC [1-ethyl-3-(3-dimethylaminopropyl) carbodiimide hydrochloride] |

Table IIA shows acylfulvene carboxylate analogs which can be attached to a bi-functional linker which can be attached to a sulfhydryl reacting group of the AM.

| Carboxylate analog | Reagent |
| --- | --- |
| 29, 37, 38, 64, 97, 98, 106, 117, 118, 145, 160, 162, 177, 178, 181, 258 | BMPH [N-β-maleimidopropionic acid) hydrazide-trifluoroacetic acid salt], EMCH [N-(episilon-maleimidocaproic acid) hydrazide] KMUH [N-(kappa-maleimidoundecanoic acid)hydrazide], MPBH [4-(4-N-maleimidophenyl)-butyric acid hydrazide], PDPH [3-(2-pyridyldithio)propionylhydrazide], SHTH [succinimidyl 4-hydrazidoterephthalate], M2C2H [4-(N-maleimidomethyl)cyclohexanee-1-1carboxyl-hydrazide], PMPI [N-(4-Isocyanatophenyl)maleimide], AMBH [2-acetamido-4-mercaptobutyric acid hydrazide] |

Table IIB shows acylfulvene carboxylate analogs which can be attached to a bi-functional linker, where the linker also contains a photoactivatable reactive group which can attach to the AM.

| Carboxylate analog | Reagent |
| --- | --- |
| 29, 37, 38, 64, 97, 98, 106, 117, 118, | ABH [p-azidobenzoyl hydrazide] ASBA [4-(p-azidosalicylamido)-butylamine] |
| 145, 160, 162, 177, 178, 181, 258 | |

Table IIC shows acylfulvene carboxylate analogs which can be attached to a bi-functional linker, where the linker also contains an amino reactive group which can attach to the AM.

| Carboxylate analog | Reagent |
|---|---|
| 29, 37, 38, 64, 97, 98, 106, 117, 118, 145, 160, 162, 177, 178, 181, 258 | EDC [1-ethyl-3-(3-dimethylaminopropyl) carbodiimide hydrochloride<br>CMC [1-cyclohexyl-3-2(2-morpholinoethyl)carbodiimide]<br>AADH [adipic acid dihydrazide]<br>Woodward's Reagent K [N-ethyl-3-phenylisoxazolium-3'sulfonate] |

TABLE IID

Acylfulvene carboxylate analog attached through carboxylate group to a linker where the linker also contains an azlactone reactive group to attach to the AM.

| Carboxylate analog | Reagent |
|---|---|
| 29, 37, 38, 64, 97, 98, 106, 117, 118, 145, 160, 162, 177, 178, 181, 258 | glycine or either an L or D amino acid including alanine, serine, threonine, cysteine, valine, leucine, isoleucine, methionine, proline, phenylalanine, tyrosine, tryptophan, aspartic acid, glutamic acid, asparagine, glutamine, histidine, lysine, arginine, or nonstandard amino acids including homocysteine, selenocysteine, pyrrolysine, carnitine, hypusine, lanthionine, 2-aminoisobutyric acid, dehydroalanine, gamma-aminobutyric acid, ornithine, citrulline, α-Amino-n-butyric acid, Norvaline, Norleucine, Pipecolic acid, Alloisoleucine, α,β-diaminopropionic acid, α,γ-diaminobutyric acid, Allothreonine, α-Amino-n-heptanoic acid, Homoserine, β-Amino-n-butyric acid, β-Aminoisobutyric acid, γ-Aminobutyric acid, isovaline, Sarcosine, N-ethyl glycine, N-propyl glycine, N-isopropyl glycine, N-methyl alanine, N-ethyl alanine, N-methyl β-alanine, N-ethyl β-alanine, Isoserine, α-hydroxy-γ-aminobutyric acid, diaminopimelic acid, cystathione, aminoisobutyric acid, dehydroalanine, delta-aminolevulinic acid, 4-aminobenzoic acid, Hydroxyproline, Formylmethioinine, lanthionine, djenkolic acid, Pyroglutamic acid, Hypusine, carboxyglutamic acid, penicillamine, thialysine, quisqualic acid, canavine, azetidine-2-carboxylic acid, 2-dimethylglycine. |

Table IIIA shows acylfulvene carbonyl analogs which can be attached to a bi-functional linker which can be attached to a sulfhydryl reacting group of the AM using the reagent.

| Carbonyl analog | Reagent |
|---|---|
| 13, 27, 28, 51, 83, 84, 124, 131, 144, 167, 184, 201, 207, 232, 233, 234, 235, 237, 238, 239, 240, 243, 276, 277, 278, 279, 280, 281, 282, 286, 287, 288, 289, 294, 295, 296, 297, 298, 301, 302, 303, | AMBH [2-acetamido-4-mercaptobutyric acid hydrazide, BMPH [N-β-maleimidopropionic acid) hydrazide-trifluoroacetic acid salt], EMCH [N-(episilon-maleimidocaproic acid) hydrazide], KMUH [N-(kappa-maleimidoundecanoic acid)hydrazide], MPBH [4-(4-N-maleimidophenyl)-butyric acid hydrazide], PDPH [3-(2-pyridyldithio)propionylhydrazide], SHTH [succinimidyl 4-hydrazidoterephthalate] |

Table IIIB shows acylfulvene carbonyl analogs which can be attached to a bi-functional linker, where linker also contains photoactivatable reactive group which can attach to AM using reagent.

| Carbonyl analog | Reagent |
|---|---|
| 13, 27, 28, 51, 83, 84, 124, 131, 144, 167, 184, 201, 207, 232, 233, 234, 235, 237, 238, 239, 240, 243, 276, 277, 278, 279, 280, 281, 282, 286, 287, 288, 289, 294, 295, 296, 297, 298, 301, 302, 303 | ABH [p-azidobenzoyl hydrazide]<br>ASBA [4-(p-azidosalicylamido)-butylamine] |

Table IIIC shows acylfulvene carbonyl analogs which can be attached to a bi-functional linker, where linker also contains an amine reactive group which can attach to the AM using the reagent.

| Carbonyl analog | Reagent |
|---|---|
| 13, 27, 28, 51, 83, 84, 124, 131, 144, 167, 184, 201, 207, 232, 233, 234, 235, 237, 238, 239, 240, 243, 276, 277, 278, 279, 280, 281, 282, | EDC [1-ethyl-3-(3-dimethylaminopropyl) carbodiimide hydrochloride<br>CMC [1-cyclohexyl-3-2(2-morpholinoethyl)carbodiimide]<br>C6-SANH [C6-succinimidyl 4-hydraznonicotinate acetone hydrazone] |

-continued

| Carbonyl analog | Reagent |
|---|---|
| 286, 287, 288, 289, 294, 295, 296, 297, 298, 301, 302, 303 | SANH [succinimidyl 4-hydraznonicotinate acetone hydrazone] |

Table IVA shows acylfulvene aldehyde analogs which can be attached to a bi-functional linker which can be attached to a sulfhydryl reacting group of the AM using the reagent.

| Aldehyde analog | Reagent |
|---|---|
| 8, 10, 11, 13, 41, 144, 156, 201 | BMPH [N-β-maleimidopropionic acid) hydrazide-trifluoroacetic acid salt], EMCH [N-(episilon-maleimidocaproic acid) hydrazide], KMUH [N-(kappa-maleimidoundecanoic acid)hydrazide], MPBH [4-(4-N-maleimidophenyl)-butyric acid hydrazide], PDPH [3-(2-pyridyldithio)propionylhydrazide], SHTH [succinimidyl 4-hydrazidoterephthalate], AMBH [2-acetamido-4-mercaptobutyric acid hydrazide], PMPI [N-(4-Isocyanatophenyl)maleimide], AMBH [2-acetamido-4-mercaptobutyric acid hydrazide] |

Table IVB shows acylfulvene aldehyde analogs which can be attached to a bi-functional linker, where the linker also contains a photoactivatable reactive group which can attach to the AM using the reagent.

| Aldehyde analog | Reagent |
|---|---|
| 8, 10, 11, 13, 41, 144, 156, 201 | ABH [p-azidobenzoyl hydrazide] ASBA [4-(p-azidosalicylamido)-butylamine] |

Table IVC shows acylfulvene aldehyde analogs which can be attached to a bi-functional linker, where the linker also contains an amine reactive group which can attach to the AM using the reagent.

| Aldehyde analog | Reagent |
|---|---|
| 8, 10, 11, 13, 41, 144, 156, 201 | EDC [1-ethyl-3-(3-dimethylaminopropyl) carbodiimide hydrochloride] CMC [1-cyclohexyl-3-2(2-morpholinoethyl)carbodiimide] AADH [adipic acid dihydrazide] C6-SANH [C6-succinimidyl 4-hydraznonicotinate acetone hydrazone] SANH [succinimidyl 4-hydraznonicotinate acetone hydrazone] Carbohydrazide [1,3-diamonourea] |

Table VA shows acylfulvene alcohol analogs which can be attached to a bi-functional linker which can be attached to a sulfhydryl reacting group of the AM using the reagent.

| Alcohol analog | Reagent |
|---|---|
| Illudin S, Illudin M, 2, 6, 9, 15, 19, 22, 23, 32, 42, 56, 62, 63, 77, 78, 81, 90, 99, 103, 117, 118, 119, 127, 128, 135, 136, 145, 155, 159, 162, 187, 200, 204, 208, 277 & 279 & 280, 299, 300, 307, 308 | PMPI [N-(p-maleimidophenyl)isocyanate] |

Table VB shows acylfulvene alcohol analogs which can be attached to a bi-functional linker, where the linker also contains an amine reactive group which can attach to the AM using the reagent.

| Alcohol analog | Reagent |
|---|---|
| Illudin S, Illudin M, 2, 6, 9, 15, 19, 22, 23, 32, 42, 56, 62, 63, 77, 78, 81, 90, 99, 103, 117, 118, 119, | CDI [N,N'-carbonyldiimidazole], DSC [N,N'-disuccinimidyl carbonate], HSC [N- |

-continued

| Alcohol analog | Reagent |
| --- | --- |
| 127, 128, 135, 136, 145, 155, 159, 162, 187, 200, 204, 208, 277 & 279 & 280, 299, 300, 307, 308 | hydroxysuccinimidyl chloroformate] |

Table VIA shows acylfulvene sulfhydryl analogs which can be attached to a bi-functional linker, where the linker also contains an amine reactive group which can attach to the AM using the reagent.

| Sulfhydryl analog | Reagent |
| --- | --- |
| Analog 51 Terminal cysteine or reagent acetyl cysteine | AMAS [N-(α-maleimidoacetoxy)-succinimide ester]BMPA [N-β-malemidopropionic acid] <br> BMPS [N-β-(malemidopropyloxy)succinimide ester] <br> EMCH [N-(episilon-maleimidocaproic acid) hydrazide] <br> EMCS [N-(episilon-maleimideocaproyloxy)succinimide ester] <br> GMBS [N-(gamma-maleimideobutyrloxy)succinimide ester] <br> KMUA [N-kappa-maleimidoundecanoic acid] <br> KMUH [N-(kappa-maleimidoundecanoic acid) hydrazide] <br> LC-SMCC [sucinimidyl 4-(N-maleimidomethyl)cyclohexane-1-carboxy-(6-amidocaproate)] <br> LC-SDPD [succinimidyl 6-(3'-(2-pyridyl-dithio)propionamido)hexanoate] <br> MBS [m-maleimidobenzoyl-N-hydroxysuccinimide ester] <br> M2C2H [4-(N-maleimidomethyl)cyclohexanee-1-1carboxyl-hydrazide] <br> MPBH [4-(4-N-maleimidophenyl)-butyric acid hydrazide] <br> PDPH [3-(2-pyridyldithio)propionylhydrazide] <br> PMPI [N-(p-maleimidophenyl)isocyanate] <br> SBAP [succinimidyl 3-bromoacetamido)propionate] <br> SHTH [succinimidyl 4-hydrazidoterephthalate] <br> SIA [N-succinimidyl iodacetate] <br> SLAB [N-succinimidyl(4-iodacetyl)aminobenzoate] <br> SMCC [succinimidyl 4-(N-maleimidomethyl)-cyclohane-1-carboxylate] <br> SMPB [succinimidyl 4-(para-maleimido-phenyl)butyrate] <br> SMPH [succinimidyl-6-(beta-maleimidopropionamido)hexanoate] <br> SM(PEG)2 [NHS-PEO$_2$-maleimide or maleimide PEG2 N-hydroxysuccinimide] <br> SM(PEG)4 [NHS-PEO$_4$-maleimide or maleimide PEG4 N-hydroxysuccinimide] <br> SM(PEG)8 [NHS-PEO$_8$-maleimide or maleimide PEG6 N-hydroxysuccinimide] <br> SM(PEG)12 [NHS-PEO$_{12}$-mleimide or maleimide PEG8 N-hydroxysuccinimide] <br> SMPH [succinimidyl-6-(beta-maleimidopropionamido)hexanoate] <br> SMPT [4-succinimidyloxycarbonyl-methyl-alpha-(2-pyridyldithio)toluene] <br> SPDP [N-succinimidyl 3-(2-pyridyldithio)propionate] <br> Sulfo-EMCS [N-(episilon-maleimidocaproyloxy)sulfosuccinimide] <br> Sulfo-GMBS [N-(gamma-maleimidobutyrloxy)sulfosuccinimide ester] <br> Sulfo-KMUS [N-(kappa-maleimidoundecanoyloxy)sulfosuccinimide ester] <br> Sulfo-LC-SMPT [sulfosuccinimidyl 6-(alpha-methyl-alpha-(2-[pyridyldithio)-toluamido)hexanoate], Sulfo-LC-SPDP [sulfosuccinimidyl 6-(3'-(2-pyridyl-dithio)propionamido)hexanoate], Sulfo-MBS [m-maleimidobenzoyl-N-hydroxysulfosuccinimide ester], Sulfo-SIAB [sulfosuccimidyl(4-iodo-acetyl)aminobenzoate], Sulfo-SMCC [sulfosuccimidyl 4-(N-maleimido-methyl)cyclohexane-1-carboxylate], Sulfo-SMPB [sulfosuccimidyl 4-(p-maleimidophenyl)butyrate] |

Table VIB shows acylfulvene sulfhydryl analogs which can be attached to a bi-functional linker, where the linker also contains a sulfhydryl reacting group which can attach to AM using reagent.

| Sulfhydryl analog | Reagent |
| --- | --- |
| Analog 51, Terminal cysteine or n-acetyl cysteine | BMB [1,4-bis-maleimidobutane], BMDB [1,4-bis-maleimidyl-2,3-hydroxybutyrate], BMH [bis-maleimidehexane], BMOE [bis-maleimideetha], BM[PEO]2 [1,8-bis-malemidodiethyene-glycol], BM[PEO]3 [1,11-bis-malemidotriethyene-glycol], DPDPB [1,4-di(3'-(2'pyridyldithio)propionamido)butane], DTME [dithio-bis-(sulfosuccinimidylpropionate)], HBVS [1,6-hexane-bis-vinylsulfone] |

Table VIC shows acylfulvene sulfhydryl analogs which can be attached to a bi-functional linker, where linker also contains photoactivatable reactive group which can attach to AM using reagent.

| Sulfhydryl analog | Reagent |
|---|---|
| Analog 51, Terminal cysteine or n-acetyl cysteine | APDP [N-(4-(p-azidosalicylamido)butyl)-3'-(2'-pyridyldithio)propionamide] |

Table VID shows acylfulvene sulfhydryl analogs which can be attached to a bi-functional linker, where the linker also contains a carboxylate reactive group which can attach to AM using reagent.

| Sulfhydryl analog | Reagent |
|---|---|
| Analog 51, Terminal cysteine or reagent acetyl cysteine | EMCA [N-(episilon-maleimidocaproic acid)] |

Table VII shows the cytotoxic data $IC_{50}$ values (micromolar, 2 hour exposure, N=3, mean±SD) for Illudin M, analog 108 and analog 110 for cells expressing the estrogen receptor (ER) (MCF7) and cells not expressing the ER (HT29).

| Analog | HT29 (ER Negative) | MCF7 (ER positive) |
|---|---|---|
| Illudin M | 0.52 ± 0.10 | 0.48 ± 0.13 |
| 108 | >55 | 14.1 ± 2.8 |
| 110 | >19 | 2.0 ± 0.1 |

Table VIII shows the activity of PSA cleavable acylfulven analogs (210, 215, 216, 221) and precursor analogs against PSA negative and PSA positive cell line (48 hour exposure, N=3; mean±SD; $IC_{50}$ values in nM).

| Analog | Prostate PC3 (negative PSA) | Prostate DuPro (trace PSA) | Prostate LnCAP (positive PSA) |
|---|---|---|---|
| Illudin S | 16 ± 5 | 11 ± 3 | 15 ± 3 |
| 204 (Illudin S tosylate) | n.t. | n.t. | 3,300 ± 1,000 |
| 207 (9-amine-leucine) | 880 ± 330 | 450 ± 40 | 560 ± 60 |
| 211 (9-amine) | 350 ± 80 | 280 ± 20 | 270 ± 50 |
| 212 (Illudin M-proline) | 120 ± 20 | 20 ± 2 | 120 ± 30 |
| 213 (Illudin S-tosylate-proline) | 2,200 ± 100 | 360 ± 80 | 900 ± 200 |
| 214 (Illudin S-Pro-Ser-Ser-HOAc) | 300 ± 50 | 90 ± 10 | 190 ± 30 |
| 210 (9-ester linkage/Ac-Hyp-Ser-Ser-Chg-Gly-Gln-Ser-Pro) | 4,700 ± 500 | 3,500 ± 400 | 810 ± 130 |
| 215 (Illudin S-tosylate ester/Ac-Hyp-Ser-Ser-Chg-Gln-Gln-Ser-Pro) | n.t. | n.t. | >20,000 |
| 216 (Illudin M/ester/Ac-Hyp-Ser-Ser-Chg-Gly-Gln-Ser-Pro) | 190 ± 10 | 280 ± 60 | 190 ± 30 |
| 221 (211/amide or nonester) Mu-His-Ser-Ser-Lys(Fmoc)-Leu-Gln-Leu | >21,000 | 13,000 ± 1,000 | 800 ± 100 | n.t. denotes not tested n.t. denotes not tested
Table IX showing peptides cleaved by proteases.

| Protease | Peptide | SEQ. ID's |
|---|---|---|
| PSA | His-Ser-Ser-Lys-Leu-Gln-X | SEQ. ID. 104 |
| | Mu-His-Ser-Ser-Lys-Leu-Gln-X | |
| | Mu-His-Ser-Ser-Lys-Leu-Gln-Lys-X | SEQ. ID. 106 |
| | Mu-His-Ser-Ser-Lys-Leu-EDA-Lys-X | SEQ. ID. 108 |
| | Mc-His-Ser-Ser-Lys-Leu-Gln-X | |
| | Mc-His-Ser-Ser-Lys-Leu-Gln-X | |
| | Hyp-Ala-Ser-Chg-Gln-Ser-X | SEQ. ID. 111 |
| | Hyp-Ala-Ser-Chg-Gln-Ser-Leu-X | SEQ. ID. 116 |
| | Mu-Hyp-Ala-Ser-Chg-Gln-Ser-X | |
| | Mu-Hyp-Ala-Ser-Chg-Gln-Ser-Leu-X | |
| | Mc-Hyp-Ala-Ser-Chg-Gln-Ser-X | |
| | Mc-Hyp-Ala-Ser-Chg-Gln-Ser-Leu-X | |
| | Hyp-Ser-Ser-Chg-Gln-Ser-Ser-Pro-X | SEQ. ID. 127 |
| | Mu-Hyp-Ser-Ser-Chg-Gln-Ser-Ser-Pro-X | |
| | Mc-Hyp-Ser-Ser-Chg-Gln-Ser-Ser-Pro-X | |
| | 4-O-Ac-Hyp-Ser-Ser-Chg-Gln-Ser-Ser-Pro-X | SEQ. ID. 131 |
| | Arg-Arg-Ser-Ser-Tyr-Tyr-Ser-Gly-X | SEQ. ID. 132 |
| | Mu-Arg-Arg-Ser-Ser-Tyr-Tyr-Ser-Gly-X | |
| | Mc-Arg-Arg-Ser-Ser-Tyr-Tyr-Ser-Gly-X | |
| | Mc-Ser-Ser-Lys-Tyr-Gln-Leu-X | SEQ. ID. 136 |
| | Mu-Ser-Ser-Lys-Tyr-Gln-Leu-X | |
| | N-glutaryl-Hyp-Ala-Ser-chGly-Gln-Ser-Leu | SEQ. ID. 137 |
| | Mu-N-glutaryl-Hyp-Ala-Ser-chGly-Gln-Ser-Leu | |
| | Mc-N-glutaryl-Hyp-Ala-Ser-chGly-Gln-Ser-Leu | |

-continued

| Protease | Peptide | SEQ. ID's |
|---|---|---|
| Caspase-3 | Asp-Glu-Val-Asp-Pro-X<br>Mu-Asp-Glu-Val-Asp-Pro-X<br>Mc-Asp-Glu-Val-Asp-Pro-X<br>Lys-Gly-Ser-Gly-Asp-Val-Glu-Gly-X<br>Mu-Lys-Gly-Ser-Gly-Asp-Val-Glu-Gly-X<br>Mc-Lys-Gly-Ser-Gly-Asp-Val-Glu-Gly-X | SEQ. ID. 138<br><br><br>SEQ. ID. 139 |
| Cathepsin B | PLE-X<br>Gly-Phe-Leu-Gly-X<br>Lys-Lys-Phe-D-Ala-X<br>D-Ala-Phe-Lys-Lys-X<br>Mc-Poly-L-glutamic acid-X<br>Mc-Gly-Phe-Leu-Gly-X<br>Mc-Lys-Lys-Phe-D-Ala-X<br>Mc-D-Ala-Phe-Lys-Lys-X<br>Mu-Poly-L-glutamic acid-X<br>Mu-Gly-Phe-Leu-Gly-X<br>Mu-Lys-Lys-Phe-D-Ala-X<br>Mu-D-Ala-Phe-Lys-Lys-X<br>Val-Cit-X | <br>SEQ. ID. 141<br>SEQ. ID. 142<br>SEQ. ID. 144<br><br>SEQ. ID. 145 |
| FAP | Lys-Gln-Glu-Gln-Asn-Pro-Gly-Ser-Thr-X<br>Mu-Lys-Gln-Glu-Gln-Asn-Pro-Gly-Ser-Thr-X<br>Mc-Lys-Gln-Glu-Gln-Asn-Pro-Gly-Ser-Thr-X | SEQ. ID. 146 |
| Kallikrein 2 | Gly-Lys-Ala-Phe-Arg-Arg-X<br>Mu-Gly-Lys-Ala-Phe-Arg-Arg-X<br>Mc-Gly-Lys-Ala-Phe-Arg-Arg-X | SEQ. ID. 171 |
| MMP-2/-9/ | Glu-Pro-Cit-Gly-Hof-Tyr-Leu-X<br>Mu-Glu-Pro-Cit-Gly-Hof-Tyr-Leu-X<br>Mc-Glu-Pro-Cit-Gly-Hof-Tyr-Leu-X<br>Gly-Ile-Leu-Gly-Val-Pro-X<br>Mu-Gly-Ile-Leu-Gly-Val-Pro-X<br>Mc-Gly-Ile-Leu-Gly-Val-Pro-X<br>Gly-Pro-Leu-Gly-Ile-Ala-Gly-Gln-X<br>Mu-Gly-Pro-Leu-Gly-Ile-Ala-Gly-Gln-X<br>Mc-Gly-Pro-Leu-Gly-Ile-Ala-Gly-Gln-X | SEQ. ID. 172<br><br><br>SEQ. ID. 173<br><br><br>SEQ. ID. 174 |
| MMP-7 | Lys-Arg-Ala-Leu-Gly-Leu-Pro-Gly<br>Mu-Lys-Arg-Ala-Leu-Gly-Leu-Pro-Gly<br>Mc-Lys-Arg-Ala-Leu-Gly-Leu-Pro-Gly<br>Arg-Pro-Leu-Ala-Leu-Trp-Arg-Ser<br>Mu-Arg-Pro-Leu-Ala-Leu-Trp-Arg-Ser<br>Mc-Arg-Pro-Leu-Ala-Leu-Trp-Arg-Ser | SEQ. ID. 175<br><br><br>SEQ. ID. 176 |
| TOP | Ala-L-L-Ala-L-Ile<br>Mu-Ala-L-L-Ala-L-Ile<br>Mc-Ala-L-L-Ala-L-Ile | |
| uPA | D-Ala-Phe-Lys or<br>D-Ala-Phe-Lys-PABC | SEQ. ID. 177 |
| Cathepsin K | Gly-Gly-Pro-Nle-X<br>Mu-Gly-Gly-Pro-Nle-X<br>Mc-Gly-Gly-Pro-Nle-X | SEQ. ID. 178 |
| Plasmin | D-Ala-Phe-Lys-Lys-X<br>Mu-D-Ala-Phe-Lys-Lys-X<br>Mc-D-Ala-Phe-Lys-Lys-X<br><br>D-Ala-Phe-Lys-X<br>Mu-D-Ala-Phe-Lys-X<br>Mc-D-Ala-Phe-Lys-X | SEQ. ID. 179 |
| Thrombin | Poly-L-Lys-Gly-D-Phe-Pip-Arg-Ser-Gly-Gly-<br>Gly-Gly-Gly-X | SEQ. ID. 180 |
| Trypsin | Poly-L-Lysine-Gly-Ala-Ser-D-Arg-Phe-Thr-Gly-<br>X | SEQ. ID. 181 |

In Table IX, the letter 'X' denotes the end attached to the medicant, Chg denotes cyclohexyl glycine, Cit denotes citrulline, EDA denotes ethanyl-D-Alanine, Hof denotes homophenylalanine, Hyp denotes 4-hydroxyproline, Mc denotes morpholinocarbonyl (carboxy-terminal protecting group), Mu denotes 4-morpholine-carbonyl (amino-terminal protecting group), Nle denotes norleucine, PABC denotes para-aminobenzoylcarboxyl, PLE denotes Poly-L-glutamic acid, Pip denotes piperidine.

Table X shows different Linker Strategies.

| Linker Reactive Group* | IDer | Functional Group | Bond product |
|---|---|---|---|
| FSB | 1220 | Carboxylate | Ester |
| FSB | 1220 | Hydroxyl | Ether |
| Isothiocyanate | 1241 | Primary Amine | Isothiourea |
| Isocyanate | 1242 | Primary amine | Isourea |
| Cyanate ester | | Primary amine | Isourea |
| Acyl Azide | 1243 | Primary Amine | Amide |
| NHS Ester | 1244 | Primary Amine | Amide |
| Sulfonyl chloride | 1245 | Primary Amine | Sulfonamide |
| Tosylate Ester | | Thiol | Thioether |
| Tosylate Ester | | Primary Amine | Secondary Amine |
| Tosylate Ester | | Hydroxyl | Ether |
| Tresyl Ester | | Primary Amine | Sulfonamide |
| Aldehyde | | Primary Amine | Secondary Amine |
| Epoxide | | Primary Amine | Secondary Amine |
| Carboxylate | | Primary Amine | Carbamate |
| Aryl Halide (Like Fluorobenzene) | | Primary Amine | Arylamine |
| Imidoester | 1248 | Primary Amine | Amidine |
| Carbodiimides (eg EDC or CMC) | | Primary Amine | Amide |
| Diimidazoles (like CDI) | | Primary amine | Carbamate |
| Maleic anhydride | | Primary amine | Amide |
| Alkylphosphate | | Primary Amine | Phosphoramidate |
| Succinic anhydride (like DSC) | 1247 | Primary Amine | Amide |
| Fluorophenyl esters | | Primary Amine | Amide |
| N,N'-disuccinimidyl carbonate | | Primary Amine | Carbamate |
| N-hydroxylsuccinimidyl chloroformate | | Primary Amine | Carbamate |
| Haloalkyl (like Iodoacetyl) | | Sulfhydryl | Thioester |
| Maleimide (like NEM) | | Sulfhydryl | Thioether |
| MAL I | 1210 | Sulfhydryl | Thioether |
| MAL I | 1211 | Sulfhydryl | Thioether |
| Maleimide | | Hexadienes | 2 + 4 cycloaddition |
| Aziridine | | Sulfhydryl | Thioether |
| Acryloyl | | Sulfhydryl | Thioether |
| Flurobenzene | | Sulfhydryl | Aryl Thioether |
| Pyridyl disulfide | | Sulfhydryl | Disulfide bond |
| 5-thio-2-nitrobenzoic acid (TNB) | | Sulfhydryl | Disulfide bond |
| Vinylsulfone (like HBVS) | | Sulfhydryl | Beta-thiosulfonyl |
| Diazoalkane or Diazoacetate | | Carboxylate | Ester |
| N,N'-carbonyl diimidazole | | Hydroxyl | Carbamate |
| Isocyanate | | Hydroxyl | Carbamate |
| Haloacetyl or alkyl halide | | Hydroxyl | Ether |
| Aminooxy | | Aldehyde | Oxime |
| Hydroxylamine | | Aldehyde | Oxime |
| Photolysis | | Aryl Azide | Nucleophilic addition |
| Photolysis | | Halogenated Aryl Azide | Nucleophilic addition |
| Azide/copper catalyst | | Alkene | Triazoline |
| Azide/copper catalyst | | Alkyne | Triazole |
| Aldehyde/NaCNBH3 | | Primary Amine | Secondary Amine |
| Amino acid | 1230 | Carboxylate/DCC | Azlactone |
| Azlactone | | Primary Amine | Amide |
| Woodward's/Carboxylate | | Primary Amine | Amide |
| DSP or DTSSP | | Primary Amines | Disulfide |
| DSS | | Primary Amines | Amide |
| DST and sulfo-DST | | Primary Amines | Amide |
| BSOCOES and sulfo-BSOCOES | | Primary Amines | Amide |
| EGS and sulfo-EGS | | Primary Amines | Amide |
| DSG | | Primary Amines | Amide |
| DMA | | Primary Amines | Amidines |
| DMP | | Primary Amines | Amidines |
| DMS | | Primary Amines | Amidines |
| DTBP | | Primary Amines | Disulfide |
| Difluorobenzene derivatives (DFDNB or DFDNPS) | | Primary Amines | Aryl secondary amines |
| Epoxide | | Sulfhydryl | Thioether |
| Epoxide | | Hydroxyl | Ether |
| Carbohydrazide | | Aldehyde | Hydrazone-Hydrazine |
| SPDP or Sulfo-SPDP or LC-SDPDP or Sulfhydryl LC-SDPDP | | Primary Amine | Amide |
| SPDP or Sulfo-SPDP or LC-SDPDP or Sulfhydryl LC-SDPDP | | Sulfhydryl | Disulfide |
| SMPT or Sulfo-LC-SMPT | | Primary Amine | Amide |
| SMPT or Sulfo-LC-SMPT | | Sulfhydryl | Disulfide |

-continued

| Linker Reactive Group* | IDer Functional Group | Bond product |
|---|---|---|
| MCC or Sulfo-SMCC or LC-SMCC or Sulfhydryl LC-SMCC | Primary Amine | Amide |
| SMCC or Sulfo-SMCC or LC-SMCC or Sulfhydryl LC-SMCC | Sulfhydryl | Disulfide |
| MBS and sulfo-MBS | Primary Amine | Amide |
| MBS and sulfo-MBS | Sulfhydryl | Thioether |
| SIA/B and sulfo-SIA/B | Primary Amine | Amide |
| SIAB and sulfo-SIAB | Sulfhydryl | Thioether |
| SIAC or SIACX or SIAX or SIAXX | Primary Amine | Amide |
| SIAC or SIACX or SIAX or SIAXX | Sulfhydryl | Thioether |
| GMBS and sulfo-GMBS | Primary Amine | Amide |
| GMBS and sulfo-GMBS | Sulfhydryl | Thioether |
| MPBH | Sulfhydryl | Thioether |
| MPBH | Carbonyl | Amide/Hydrazone |
| M2C2H | Sulfhydryl | Thioether |
| M2C2H | Carbonyl | Amide |
| PDPH | Sulfhydryl | Disulfide |
| PDPH | Carbonyl | Amide/Hydrazone |
| NHS-ASA | Primary Amine | Photoreactive Aryl Azide |
| Sulfo-NHS-ASA | Primary Amine | Photoreactive Aryl Azide |
| Sulfo-NHS-LC-ASA | Primary Amine | Photoreactive Aryl Azide |
| HSAB and Sulfo-HSAB | Primary Amine | Photoreactive Azide with Amide |
| SANPAH and Sulfo-SANPAH | Primary Amine | Photoreactive Azide with Amide |
| ANB-NOS | Primary Amine | Photoreactive Azide with Amide |
| SAND and Sulfo-SAND | Primary Amine | Photoreactive Azide with Amide |
| SADP and Sulfo-SADP | Primary Amine | Photoreactive Azide with Amide |
| SAPB and Sulfo-SAPB | Primary Amine | Photoreactive Azide with Amide |
| SAED and Sulfo-SAED | Primary Amine | Photoreactive Azide with Amide |
| Sulfo-SAMCA | Primary Amine | Photoreactive Azide with Amide |
| Sulfo-SASD | Primary Amine | Photoreactive Azide with Amide |
| Sulfo-SFAD | Primary Amine | Photoreactive Azide with Amide |
| pNDPD | Primary Amine | Photoreactive Azide with Amide |
| PNP-DTP | Primary Amine | Photoreactive Diazo with Amide |
| APDP | Sulfhydryl | Photoreactive Azide with Thioether |
| ABH | Aldehyde | Photoreactive Azide with Hydrazone |
| ASBA | Carboxylate | Photoreactive Azide with Amide |
| SPB | Primary Amine | Photoreactive Psoralen group with Amide |
| PMPA or PMPS | Sulfyhydryl | Thioether |
| SANH or SHNH or SHTH | Primary Amine | Amide |
| SANH or SHNH or SHTH | Aldehyde | Hydrazone |
| BMPA or BMPS | Sulfhydryl | Thioether |
| BMPA or BMPS | Primary Amine | Amide |
| SATA or SATP or SAMSA | Primary Amine | Amide |
| SATA or SATP or SAMSA | Hydroxylamine | Sulfhydryl |
| AMBH | Aldehyde | Hydrazone |
| PMPI | Sulfhydryl | Thioether |
| PMPI | Hydroyxl | Carbamate |
| AADH | Aldehyde | Hydrazone |
| AMAS | Primary Amine | Amide |
| AMAS | Sulfhydryl | Thioether |
| KMUS or Sulfo-KMUS | Primary Amine | Amide |
| KMUS or Sulfo-KMUS | Sulfhydryl | Thioether |
| EMCH or EMCS or sulfo-EMCS | Primary Amine | Amide |
| EMCH or EMCS or sulfo-EMCS | Sulfhydryl | Thioether |
| BS2 or BS3 or BS(PEG)5 series | Amine | Amide |
| Citiolone | Primary Amine | Amide with free Sulfhydryl |
| SMPB or Sulfo-SMPB or SMPH or SBAP | Primary Amine | Amide |
| SMPB or Sulfo-SMPB or SMPH or SBAP | Sulfhydryl | Thioether |
| Woodward's Reagent K | Carboxylate | Enol Ester Intermediate |
| " " Enol Ester Intermediate | Primary Amine | Amide |
| KMUA | Sulfhydryl | Thioether |
| KMUA | Primary Amine in presence EDC | Amide |
| KMUH | Sulfhydryl | Thioether |
| KMUH | Aldehyde or Carboxylate | Hydrazone |
| BMPH | Sulfhydryl | Thioether |
| BMPH | Aldehyde or Carboxylate | Hydrazone |
| PDTP | Primary Amine | Amide |
| SFB or SFPA | Primary Amine | Amide with free aldehyde |
| SM(PEG)n Series | Primary Amine | Amide |
| SM(PEG)n Series | Sulfhydryl | Thioether |
| DPDPB | Two Sulfhydryls | Two Disulfides |
| BM[PEO]n series | Two Sulfhydryls | Two Thioethers |
| BMH or BMOE | Two Sulfhydryls | Two Thioethers |

-continued

| Linker Reactive Group* | IDer Functional Group | Bond product |
|---|---|---|
| BMB or BMDB | Two Sulfhydryls | Two Thioethers |
| DTME | Two Sulfhydryls | Two Thioethers with internal disulfide bond |
| NPIA | Primary Amine | Amide |
| NPIA | Sulfhydryl | Thioether |
| MCP | Primary Amine | Amidine |

Abbreviation in Table X have been defined previously in Tables I through Table VI.

Abbreviation in Table X have been defined previously in Tables I through Table VI.
Table XI shows Illudin1 analogs.

| | Analog | IUPAC Name of Illudofulvene Analog |
|---|---|---|
| 1 | 106 | 5-(((3'S,6'R)-6'-hydroxy-2',2',4',6'-tetramethyl-7'-oxo-2',3',6',7'-tetrahydrospiro[cyclopropane-1,5'-inden]-3'-yl)oxy)-5-oxopentanoic acid |
| 2 | 107 | (3'S,6'R)-6'-hydroxy-2',2',4',6'-tetramethyl-7'-oxo-2',3',6',7'-tetrahydrospiro[cyclopropane-1,5'-inden]-3'-yl ((13S)-13-methyl-17-oxo-7,8,9,11,12,13,14,15,16,17-decahydro-6H-cyclopenta[a]phenanthren-3-yl) glutarate |
| 3 | 108 | (13S)-17-hydroxy-13-methyl-7,8,9,11,12,13,14,15,16,17-decahydro-6H-cyclopenta[a]phenanthren-3-yl 3-((R)-6'-hydroxy-2',4',6'-trimethyl-7'-oxo-6',7'-dihydrospiro[cyclopropane-1,5'-inden]-3'-yl)propanoate |
| 4 | 109 | (13S)-17-hydroxy-13-methyl-7,8,9,11,12,13,14,15,16,17-decahydro-6H-cyclopenta[a]phenanthren-3-yl ((3'S,6'R)-6'-hydroxy-2',2',4',6'-tetramethyl-7'-oxo-2',3',6',7'-tetrahydrospiro[cyclopropane-1,5'-inden]-3'-yl) glutarate |
| 5 | 110 | (13S)-13-methyl-17-oxo-7,8,9,11,12,13,14,15,16,17-decahydro-6H-cyclopenta[a]phenanthren-3-yl 3-((R)-6'-hydroxy-2',4',6'-trimethyl-7'-oxo-6',7'-dihydrospiro[cyclopropane-1,5'-inden]-3'-yl)propanoate |
| 6 | 111 | (10R,13S)-10,13-dimethyl-3-oxo-2,3,6,7,8,9,10,11,12,13,14,15,16,17-tetradecahydro-1H-cyclopenta[a]phenanthren-17-yl 3-(6'-hydroxy-2',4'-dimethyl-7'-oxo-6',7'-dihydrospiro[cyclopropane-1,5'-inden]-3'-yl)propanoate |
| 7 | 112 | (13S)-10,13-dimethyl-17-oxohexadecahydro-1H-cyclopenta[a]phenanthren-3-yl 3-((R)-6'-hydroxy-2',4',6'-trimethyl-7'-oxo-6',7'-dihydrospiro[cyclopropane-1,5'-inden]-3'-yl)propanoate |
| 8 | 113 | (R)-3'-(but-3-en-1-yl)-6'-hydroxy-2',4',6'-trimethylspiro[cyclopropane-1,5'-inden]-7'(6'H)-one |
| 9 | 114 | (6'R)-6'-hydroxy-2',4',6'-trimethyl-3'-(2-(oxiran-2-yl)ethyl)spiro[cyclopropane-1,5'-inden]-7'(6'H)-one |
| 10 | 115 | (R)-3-(6'-hydroxy-2',4',6'-trimethyl-7'-oxo-6',7'-dihydrospiro[cyclopropane-1,5'-inden]-3'-yl)propanal oxime |
| 11 | 116 | (R)-3'-(tert-butoxymethyl)-6'-hydroxy-2',4',6'-trimethylspiro[cyclopropane-1,5'-inden]-7'(6'H)-one |
| 12 | 117 | 5-(((2'S,6'R)-3'-((4-carboxybutanoyl)oxy)-6'-hydroxy-2',4',6'-trimethyl-7'-oxo-2',3',6',7'-tetrahydrospiro[cyclopropane-1,5'-inden]-2'-yl)methoxy)-5-oxopentanoic acid |

-continued

| | Analog | IUPAC Name of Illudofulvene Analog |
|---|---|---|
| 13 | 118 | 5-(((2'S,6'R)-2'-(((3,5-dinitrobenzoyl)oxy)methyl)-6'-hydroxy-2',4',6'-trimethyl-7'-oxo-2',3',6',7'-tetrahydrospiro[cyclopropane-1,5'-inden]-3'-yl)oxy)-5-oxopentanoic acid |
| 14 | 119 | (6'R)-3'-(3,4-dihydroxybutyl)-6'-hydroxy-2',4',6'-trimethylspiro[cyclopropane-1,5'-inden]-7'(6'H)-one |
| 15 | 120 | (R)-6'-hydroxy-3'-(3-((S)-6'-hydroxy-2',4',6'-trimethyl-7'-oxo-6',7'-dihydrospiro[cyclopropane-1,5'-inden]-3'-yl)propylidene)hydrazineylidene)propyl)-2',4',6'-trimethylspiro[cyclopropane-1,5'-inden]-7'(6'H)-one |
| 16 | 121 | (R)-2-(3-(6'-hydroxy-2',4',6'-trimethyl-7'-oxo-6',7'-dihydrospiro[cyclopropane-1,5'-inden]-3'-yl)propylidene)hydrazine-1-carboxamide |
| 17 | 122 | (R)-6'-hydroxy-2',4',6'-trimethyl-3'-(3-(2-phenylhydrazineylidene)propyl)spiro[cyclopropane-1,5'-inden]-7'(6'H)-one |
| 18 | 123 | (R)-N'-(3-(6'-hydroxy-2',4',6'-trimethyl-7'-oxo-6',7'-dihydrospiro[cyclopropane-1,5'-inden]-3'-yl)propylidene)-4-methylbenzenesulfonohydrazide |
| 19 | 124 | (R)-3-(6'-hydroxy-2',4',6'-trimethyl-7'-oxo-6',7'-dihydrospiro[cyclopropane-1,5'-inden]-3'-yl)propanal O-acetyl oxime |
| 20 | 125 | (R)-3'-(3-(2-(2,4-dinitrophenyl)hydrazineylidene)propyl)-6'-hydroxy-2',4',6'-trimethylspiro[cyclopropane-1,5'-inden]-7'(6'H)-one |
| 21 | 126 | (R)-6'-hydroxy-2',4',6'-trimethyl-7'-oxo-6',7'-dihydrospiro[cyclopropane-1,5'-indene]-3'-carbaldehyde oxime |
| 22 | 127 | 2-hydroxy-4-((R)-6'-hydroxy-2',4',6'-trimethyl-7'-oxo-6',7'-dihydrospiro[cyclopropane-1,5'-inden]-3'-yl)butanenitrile |
| 23 | 128 | (6'R)-6'-hydroxy-3'-(3-hydroxybutyl)-2',4',6'-trimethylspiro[cyclopropane-1,5'-inden]-7'(6'H)-one |
| 24 | 129 | (6'R)-2',4',6'-trimethyl-6',7'-dihydrospiro[cyclopropane-1,5'-indene]-6',7'-diol |
| 25 | 130 | (R)-6'-hydroxy-3'-(3-(hydroxyamino)propyl)-2',4',6'-trimethylspiro[cyclopropane-1,5'-inden]-7'(6'H)-one |
| 26 | 131 | (R)-N-benzyl-3-(6'-hydroxy-2',4',6'-trimethyl-7'-oxo-6',7'-dihydrospiro[cyclopropane-1,5'-inden]-3'-yl)propanamide |
| 27 | 133 | (E)-7-(chloromethylene)-5-hydroxy-5,9-dimethylspiro[3.5]non-8-en-6-one |
| 28 | 134 | (E)-6-(chloromethylene)-4-hydroxy-4,8-dimethylspiro[2.5]oct-7-en-5-one |
| 29 | 135 | ((2'S,6'R)-3'-(3,6'-dihydroxy-2',4',6'-trimethyl-7'-oxo-2',3',6',7'-tetrahydrospiro[cyclopropane-1,5'-inden]-2'-yl)methyl 4-nitrobenzoate |
| 30 | 136 | ((2'S,6'R)-3',6'-dihydroxy-2',4',6'-trimethyl-7'-oxo-2',3',6',7'- |

| Analog | IUPAC Name of Illudofulvene Analog |
|---|---|
| 31 | 137 tetrahydrospiro[cyclopropane-1,5'-inden]-2'-yl)methyl 4-(N-acetoxyacetamido)benzoate ((2'S,6'R)-6'-hydroxy-2',4',6'-trimethyl-3',7'-dioxo-2',3',6',7'-tetrahydrospiro[cyclopropane-1,5'-inden]-2'-yl)methyl 4-nitrobenzoate |
| 32 | 138 ((2'S,6'R)-6'-hydroxy-2',4',6'-trimethyl-3',7'-dioxo-2',3',6',7'-tetrahydrospiro[cyclopropane-1,5'-inden]-2'-yl)methyl 4-(N-acetoxyacetamido)benzoate |
| 33 | 139 (2'S,6'R)-6'-hydroxy-2',4',6'-trimethyl-2'-(((4-nitrobenzoyl)oxy)methyl)-7'-oxo-2',3',6',7'-tetrahydrospiro[cyclopropane-1,5'-inden]-3'-yl 4-nitrobenzoate |
| 34 | 140 ((2'S,6'R)-3'-((4-(N-acetoxyacetamido)benzoyl)oxy)-6'-hydroxy-2',4',6'-trimethyl-7'-oxo-2',3',6',7'-tetrahydrospiro[cyclopropane-1,5'-inden]-2'-yl)methyl 4-(N-acetoxyacetamido)benzoate |
| 35 | 141 dimethyl (5'R)-4',5'-dihydroxy-5',7',9'-trimethyl-4',5'-dihydro-1'H-spiro[cyclopropane-1,6'-[1,3a]ethenoindene]-2',3'-dicarboxylate |
| 36 | 142 dimethyl (5'R)-5'-hydroxy-5',7',9'-trimethyl-4'-oxo-4',5'-dihydro-1'H-spiro[cyclopropane-1,6'-[1,3a]ethenoindene]-2',3'-dicarboxylate |
| 37 | 143 (R)-6'-hydroxy-1',2',4',6'-tetramethylspiro[cyclopropane-1,5'-inden]-7'(6'H)-one |
| 38 | 144 (R)-2-((2'-ethyl-6'-hydroxy-4',6'-dimethyl-7'-oxo-6',7'-dihydrospiro[cyclopropane-1,5'-inden]-3'-yl)methoxy)ethyl acetate |
| 39 | 145 (R)-5-((6'-hydroxy-2',4',6'-trimethyl-7'-oxo-6',7'-dihydrospiro[cyclopropane-1,5'-inden]-3'-yl)methoxy)-5-oxopentanoic acid |
| 40 | 146 (R)-4-(6'-hydroxy-2',4',6'-trimethyl-7'-oxo-6',7'-dihydrospiro[cyclopropane-1,5'-inden]-3'-yl)butanenitrile |
| 41 | 147 (R)-3'-((benzo[d]thiazol-2-ylthio)methyl)-6'-hydroxy-2',4',6'-trimethylspiro[cyclopropane-1,5'-inden]-7'(6'H)-one |
| 42 | 148 (R)-3'-((benzo[d]oxazol-2-ylthio)methyl)-6'-hydroxy-2',4',6'-trimethylspiro[cyclopropane-1,5'-inden]-7'(6'H)-one |
| 43 | 149 (R)-6'-hydroxy-2',4',6'-trimethyl-3'-(((1-methyl-1H-tetrazol-5-yl)thio)methyl)spiro[cyclopropane-1,5'-inden]-7'(6'H)-one |
| 44 | 150 (R)-6'-hydroxy-2',4',6'-trimethyl-3'-(((5-methyl-1H-benzo[d]imidazol-2-yl)thio)methyl)spiro[cyclopropane-1,5'-inden]-7'(6'H)-one |
| 45 | 151 (R)-6'-hydroxy-2',4',6'-trimethyl-3'-(((1-phenyl-1H-tetrazol-5-yl)thio)methyl)spiro[cyclopropane-1,5'-inden]-7'(6'H)-one |
| 46 | 152 (R)-6'-hydroxy-2',4',6'-trimethyl-3'-(((5-nitro-1H-benzo[d]imidazol-2-yl)thio)methyl)spiro[cyclopropane-1,5'-inden]-7'(6'H)-one |
| 47 | 153 (R)-3'-(((1H-1,2,4-triazol-3-yl)thio)methyl)-6'-hydroxy-2',4',6'-trimethylspiro[cyclopropane-1,5'-inden]-7'(6'H)-one |
| 48 | 154 (R)-6'-hydroxy-3'-(((4-hydroxypteridin-2-yl)thio)methyl)-2',4',6'-trimethylspiro[cyclopropane-1,5'-inden]-7'(6'H)-one |
| 49 | 155 (R)-6'-hydroxy-3'-(((1-(4-hydroxyphenyl)-1H-tetrazol-5-yl)thio)methyl)-2',4',6'-trimethylspiro[cyclopropane-1,5'-inden]-7'(6'H)-one |
| 50 | 156 (R)-4-(5-(((6'-hydroxy-2',4',6'-trimethyl-7'-oxo-6',7'-dihydrospiro[cyclopropane-1,5'-inden]-3'-yl)methyl)thio)-1H-tetrazol-1-yl)phenyl acetate |
| 51 | 157 7'-methyl-4'H-dispiro[cyclobutane-1,6'-indene-5',2''-[1,3]dioxolan]-4'-one |
| 52 | 158 5-hydroxy-2,2,6,8a-tetramethyl-2,3,3a,8,8a,8b-hexahydro-1H-cyclobuta[d]cyclopenta[b]oxepin-7(5H)-one |
| 53 | 159 ((6'R)-3',6'-dihydroxy-2',4',6'-trimethyl-7'-oxo-2',3',6',7'-tetrahydrospiro[cyclopropane-1,5'-inden]-2'-yl)methyl acetate |
| 54 | 160 5-(((6'R)-2'-(acetoxymethyl)-6'-hydroxy-2',4',6'-trimethyl-7'-oxo-2',3',6',7'-tetrahydrospiro[cyclopropane-1,5'-inden]-3'-yl)oxy)-5-oxopentanoic acid |
| 55 | 161 ((6'R)-6'-hydroxy-2',4',6'-trimethyl-3',7'-dioxo-2',3',6',7'-tetrahydrospiro[cyclopropane-1,5'-inden]-2'-yl)methyl acetate |
| 56 | 162 5-(((6'R)-6'-hydroxy-2',4',6'-trimethyl-3',7'-dioxo-2',3',6',7'-tetrahydrospiro[cyclopropane-1,5'-inden]-2'-yl)methoxy)-5-oxopentanoic acid |
| 57 | 163 (6'R)-2'-(acetoxymethyl)-6'-hydroxy-2',4',6'-trimethyl-7'-oxo-2',3',6',7'-tetrahydrospiro[cyclopropane-1,5'-inden]-3'-yl 2-chloroacetate |
| 58 | 164 (R)-(6'-hydroxy-2',4',6'-trimethyl-7'-oxo-6',7'-dihydrospiro[cyclopropane-1,5'-inden]-3'-yl)methyl 2-chloroacetate |
| 59 | 165 (R)-(6'-hydroxy-2',4',6'-trimethyl-7'-oxo-6',7'-dihydrospiro[cyclopropane-1,5'-inden]-3'-yl)methyl 2-morpholinoacetate |
| 60 | 166 (6'R)-2'-(acetoxymethyl)-6'-hydroxy-2',4',6'-trimethyl-7'-oxo-2',3',6',7'-tetrahydrospiro[cyclopropane-1,5'-inden]-3'-yl methyl glutarate |
| 61 | 167 (6'R)-6'-hydroxy-2'-(hydroxymethyl)-2',4',6'-trimethyl-7'-oxo-2',3',6',7'-tetrahydrospiro[cyclopropane-1,5'-inden]-3'-yl methyl glutarate |
| 62 | 168 ((6'R)-6'-hydroxy-2',4',6'-trimethyl-3',7'-dioxo-2',3',6',7'-tetrahydrospiro[cyclopropane-1,5'-inden]-2'-yl)methyl methyl glutarate |
| 63 | 169 ((6'R)-6'-hydroxy-2',4',6'-trimethyl-3',7'-dioxo-2',3',6',7'-tetrahydrospiro[cyclopropane-1,5'-inden]-2'-yl)methyl 2-chloroacetate |
| 64 | 171 6-(2-hydroxyethyl)-2,5,7-trimethyl-1-methylene-1H-inden-4-ol |
| 65 | 172 6-ethyl-2,5,7-trimethyl-1-methylene-1H-inden-4-ol |
| 66 | 173 2-(4-hydroxy-2,5,7-trimethyl-1-methylene-1H-inden-6-yl)ethyl acetate |
| 67 | 174 5-(2-hydroxyethyl)-3-(hydroxymethyl)-2,4,6-trimethyl-1H-indene-1,7-diol |
| 68 | 175 (2S,3S,4R,5S,6R)-2-(acetoxymethyl)-6-(((R)-6'-hydroxy-2',4',6'-trimethyl-7'-oxo-6',7'-dihydrospiro[cyclopropane-1,5'-inden]-3'-yl)methoxy)tetrahydro-2H-pyran-3,4,5-triyl triacetate |
| 69 | 177 (R)-5-(3-(6'-hydroxy-2',4',6'-trimethyl-7'-oxo-6',7'-dihydrospiro[cyclopropane-1,5'-inden]-3'-yl)propoxy)-5-oxopentanoic acid |
| 70 | 178 (R)-4-(3-(6'-hydroxy-2',4',6'-trimethyl-7'-oxo-6',7'-dihydrospiro[cyclopropane-1,5'-inden]-3'-yl)propoxy)-4-oxobutanoic acid |
| 71 | 179 (R)-3-(6'-hydroxy-2',4',6'-trimethyl-7'-oxo-6',7'-dihydrospiro[cyclopropane-1,5'-inden]-3'-yl)propyl glycinate |
| 72 | 180 (1a'R,3'R,7'S,7a'R)-3',7'-dihydroxy-3',6',6'-tetramethyl-6',7'-dihydro-1a'H-spiro[cyclopropane-1,2'-indeno[3a,4-b]oxiren]-4'(3'H)-one |
| 73 | 181 ((1a'R,3'R,6'S,7'S,7a'R)-3',7'-dihydroxy-1a',3',6'-trimethyl-4'-oxo-3',4',6',7'-tetrahydro-1a'H-spiro[cyclopropane-1,2'-indeno[3a,4-b]oxiren]-6'-yl)methyl acetate |
| 74 | 182 (2'R,7'S,7a'S)-2'-chloro-7'-hydroxy-2',4'-dimethyl-1',2',7',7a'-tetrahydrospiro[cyclopropane-1,5'-indene]-3',6'-dione |
| 75 | 183 (2'S,7'S,7a'S)-7'-hydroxy-2'-isopropoxy-2',4'-dimethyl-1',2',7',7a'-tetrahydrospiro[cyclopropane-1,5'-indene]-3',6'-dione |
| 76 | 188 (6'S,6'''S)-3',3'''-methylenebis(6'-hydroxy-2',4',6'-trimethylspiro[cyclopropane-1,5'-inden]-7'(6'H)-one) |
| 77 | 189 (R)-1-((6'-hydroxy-2',4',6'-trimethyl-7'-oxo-6',7'-dihydrospiro[cyclopropane-1,5'-inden]-3'-yl)methyl)-1H-pyrrole-2,5-dione |

-continued

| Analog | | IUPAC Name of Illudofulvene Analog |
|---|---|---|
| 78 | 190 | (R)-1-(3-(6'-hydroxy-2',4',6'-trimethyl-7'-oxo-6',7'-dihydrospiro[cyclopropane-1,5'-inden]-3'-yl)propyl)-1H-pyrrole-2,5-dione |
| 79 | 191 | 6'-hydroxy-4',6'-dimethylspiro[cyclobutane-1,5'-inden]-7'(6'H)-one |
| 80 | 192 | (R)-2-((6'-hydroxy-2',4',6'-trimethyl-7'-oxo-6',7'-dihydrospiro[cyclopropane-1,5'-inden]-3'-yl)methyl)isoindoline-1,3-dione |
| 81 | 193 | (R)-3'-(azidomethyl)-6'-hydroxy-2',4',6'-trimethylspiro[cyclopropane-1,5'-inden]-7'(6'H)-one |
| 82 | 194 | (R)-3'-(((R)-3'-(azidomethyl)-6'-hydroxy-2',4',6'-trimethyl-7'-oxo-6',7'-dihydrospiro[cyclopropane-1,5'-inden]-1'-yl)methyl)-6'-hydroxy-2',4',6'-trimethylspiro[cyclopropane-1,5'-inden]-7'(6'H)-one |
| 83 | 195 | (R)-3'-(3-azidopropyl)-6'-hydroxy-4',6'-dimethylspiro[cyclopropane-1,5'-inden]-7'(6'H)-one |
| 84 | 196 | 3-((R)-6'-hydroxy-2',4',6'-trimethyl-7'-oxo-6',7'-dihydrospiro[cyclopropane-1,5'-inden]-3'-yl)propyl L-prolinate |
| 85 | 197 | (R)-2-(3-(6'-hydroxy-2',4',6'-trimethyl-7'-oxo-6',7'-dihydrospiro[cyclopropane-1,5'-inden]-3'-yl)propyl)isoindoline-1,3-dione |
| 86 | 198 | (R)-6'-hydroxy-2',4',6'-trimethyl-3'-((4-nitrophenoxy)methyl)spiro[cyclopropane-1,5'-inden]-7'(6'H)-one |
| 87 | 199 | (R)-6'-hydroxy-2',4',6'-trimethyl-3'-(phenoxymethyl)spiro[cyclopropane-1,5'-inden]-7'(6'H)-one |
| 88 | 200 | (R)-6'-hydroxy-3'-(2-hydroxybenzyl)-2',4',6'-trimethylspiro[cyclopropane-1,5'-inden]-7'(6'H)-one |
| 89 | 201 | (R)-N-(3-(6'-hydroxy-2',4',6'-trimethyl-7'-oxo-6',7'-dihydrospiro[cyclopropane-1,5'-inden]-3'-yl)propyl)acetamide |
| 90 | 202 | (S)-N-(3-((R)-6'-hydroxy-2',4',6'-trimethyl-7'-oxo-6',7'-dihydrospiro[cyclopropane-1,5'-inden]-3'-yl)propyl)pyrrolidine-2-carboxamide |
| 91 | 203 | 3-((R)-6'-hydroxy-2',4',6'-trimethyl-7'-oxo-6',7'-dihydrospiro[cyclopropane-1,5'-inden]-3'-yl)propyl L-seryl-L-prolinate |
| 92 | 204 | 2'-(((tert-butyldimethylsilyl)oxy)methyl)-3',6'-dihydroxy-2',4',6'-trimethyl-2',3'-dihydrospiro[cyclopropane-1,5'-inden]-7'(6'H)-one |
| 93 | 205 | (2'R,3'S,6'R)-3'-amino-2'-(((tert-butyldimethylsilyl)oxy)methyl)-6'-hydroxy-2',4',6'-trimethyl-2',3'-dihydrospiro[cyclopropane-1,5'-inden]-7'(6'H)-one |
| 94 | 206 | (2'R,3'S,6'R)-3'-amino-6'-hydroxy-2'-(hydroxymethyl)-2',4',6'-trimethyl-2',3'-dihydrospiro[cyclopropane-1,5'-inden]-7'(6'H)-one |
| 95 | 207 | (S)-2-amino-N-(3-((R)-6'-hydroxy-2',4',6'-trimethyl-7'-oxo-6',7'-dihydrospiro[cyclopropane-1,5'-inden]-3'-yl)propyl)-4-methylpentanamide |
| 96 | 208 | 3-((R)-6'-hydroxy-2',4',6'-trimethyl-7'-oxo-6',7'-dihydrospiro[cyclopropane-1,5'-inden]-3'-yl)propyl (tert-butoxycarbonyl)-L-seryl-L-prolinate |
| 97 | 209 | 3-((R)-6'-hydroxy-2',4',6'-trimethyl-7'-oxo-6',7'-dihydrospiro[cyclopropane-1,5'-inden]-3'-yl)propyl L-seryl-L-seryl-L-prolinate |
| 98 | 210 | 3-((R)-6'-hydroxy-2',4',6'-trimethyl-7'-oxo-6',7'-dihydrospiro[cyclopropane-1,5'-inden]-3'-yl)propyl ((S)-2-((S)-2-((S)-2-((2S,4R)-1-acetyl-4-hydroxypyrrolidine-2-carboxamido)-3-hydroxypropanamido)-3-hydroxypropanamido)-2-cyclohexylacetyl)-L-glutaminyl-L-seryl-L-seryl-L-prolinate |
| 99 | 212 | (3'S,6'R)-6'-hydroxy-2',2',4',6'-tetramethyl-7'-oxo-2',3',6',7'-tetrahydrospiro[cyclopropane-1,5'-inden]-3'-yl L-prolinate |
| 100 | 213 | (2'S,3'R,6'R)-2'-(((tert-butyldimethylsilyl)oxy)methyl)-6'-hydroxy-2',4',6'-trimethyl-7'-oxo-2',3',6',7'-etrahydrospiro[cyclopropane-1,5'-inden]-3'-yl L-prolinate |
| 101 | 214 | (2'S,3'R,6'R)-2'-(((tert-butyldimethylsilyl)oxy)methyl)-6'-hydroxy-2',4',6'-trimethyl-7'-oxo-2',3',6',7'-tetrahydrospiro[cyclopropane-1,5'-inden]-3'-yl L-seryl-L-seryl-L-prolinate |
| 102 | 215 | (2'S,3'R,6'R)-2'-(((tert-butyldimethylsilyl)oxy)methyl)-6'-hydroxy-2',4',6'-trimethyl-7'-oxo-2',3',6',7'-tetrahydrospiro[cyclopropane-1,5'-inden]-3'-yl ((S)-2-((S)-2-((S)-2-((2S,4R)-1-acetyl-4-hydroxypyrrolidine-2-carboxamido)-3-hydroxypropanamido)-3-hydroxypropanamido)-2-cyclohexylacetyl)-L-glutaminyl-L-seryl-L-seryl-L-prolinate |
| 103 | 216 | (3'S,6'R)-6'-hydroxy-2',2',4',6'-tetramethyl-7'-oxo-2',3',6',7'-tetrahydrospiro[cyclopropane-1,5'-inden]-3'-yl ((S)-2-((S)-2-((S)-2-((2S,4R)-1-acetyl-4-hydroxypyrrolidine-2-carboxamido)-3-hydroxypropanamido)-3-hydroxypropanamido)-2-cyclohexylacetyl)-L-glutaminyl-L-seryl-L-seryl-L-prolinate |
| 104 | 217 | (R)-(6'-hydroxy-2',4',6'-trimethyl-7'-oxo-6',7'-dihydrospiro[cyclopropane-1,5'-inden]-3'-yl)methyl 6-(2,5-dioxo-2,5-dihydro-1H-pyrrol-1-yl)hexanoate |
| 105 | 218 | (3'S,6'R)-6'-hydroxy-2',2',4',6'-tetramethyl-7'-oxo-2',3',6',7'-tetrahydrospiro[cyclopropane-1,5'-inden]-3'-yl 6-(2,5-dioxo-2,5-dihydro-1H-pyrrol-1-yl)hexanoate |
| 106 | 219 | (2'S,3'R,6'R)-2'-(((tert-butyldimethylsilyl)oxy)methyl)-6'-hydroxy-2',4',6'-trimethyl-7'-oxo-2',3',6',7'-tetrahydrospiro[cyclopropane-1,5'-inden]-3'-yl 4-(fluorosulfonyl)benzoate |
| 107 | 221 | (S)-2-((3S,6S,9S,12S,15S)-3-((1H-imidazol-4-yl)methyl)-12-(4-aminobutyl)-6,9-bis(hydroxymethyl)-15-isobutyl-1-morpholino-1,4,7,10,13-pentaoxo-2,5,8,11,14-pentaazahexadecan-16-amido)-N1-((S)-1-((3-((R)-6'-hydroxy-2',4',6'-trimethyl-7'-oxo-6',7'-dihydrospiro [cyclopropane-1,5'-inden]-3'-yl)propyl)amino)-4-methyl-1-oxopentan-2-yl)pentanediamide |
| 108 | 222 | (3'S,6'R)-6'-hydroxy-2',2',4',6'-tetramethyl-7'-oxo-2',3',6',7'-tetrahydrospiro[cyclopropane-1,5'-inden]-3'-yl 4-(fluorosulfonyl)benzoate |
| 109 | 223 | 3-((R)-6'-hydroxy-2',4',6'-trimethyl-7'-oxo-6',7'-dihydrospiro[cyclopropane-1,5'-inden]-3'-yl)propyl ((4R,7S,13S)-13-(2-amino-2-oxoethyl)-7-(3-guanidinopropyl)-6,9,12,15-tetraoxo-1,2-dithia-5,8,14-triazacycloheptadecane-4-carbonyl)glycinate |
| 110 | 224 | (R,E)-6'-hydroxy-2',4',6'-trimethylspiro[cyclopropane-1,5'-inden]-7'(6'H)-one oxime |
| 111 | 225 | (2'R,3'R,6'R,E)-2',3',6'-trihydroxy-2',4',6'-trimethyl-2',3'-dihydrospiro[cyclopropane-1,5'-inden]-7'(6'H)-one oxime |
| 112 | 226 | (R)-(6'-hydroxy-2',4',6'-trimethyl-7'-oxo-6',7'-dihydrospiro[cyclopropane-1,5'-inden]-3'-yl)methyl (E)-octadec-9-enoate |
| 113 | 227 | (R)-3-(6'-hydroxy-2',4',6'-trimethyl-7'-oxo-6',7'-dihydrospiro[cyclopropane-1,5'-inden]-3'-yl)propyl (E)-octadec-9-enoate |
| 114 | 228 | (2'S,6'R)-6'-hydroxy-2',4',6'-trimethyl-2'-((((E)-octadec-9-enoyl)oxy)methyl)-7'-oxo-2',3',6',7'-tetrahydrospiro[cyclopropane-1,5'-inden]-3'-yl (E)-octadec-9-enoate |
| 115 | 229 | (R,E)-N-(3-(6'-hydroxy-2',4',6'-trimethyl-7'-oxo-6',7'-dihydrospiro[cyclopropane-1,5'-inden]-3'-yl)propyl)octadec-9-enamide |
| 116 | 230 | N-((3'R,6'R)-6'-hydroxy-2',4',6'-tetramethyl-7'-oxo-2',3',6',7'-tetrahydrospiro[cyclopropane-1,5'-inden]-3'-yl)methanesulfonamide |
| 117 | 231 | N-((3'R,6'R)-6'-hydroxy-2',4',6'-tetramethyl-7'-oxo-2',3',6',7'-tetrahydrospiro[cyclopropane-1,5'-inden]-3'-yl)-4-methylbenzenesulfonamide |
| 118 | 236 | (R)-6'-hydroxy-3'-(hydroxymethyl)-1',2',4',6'-tetramethylspiro[cyclopropane-1,5'-inden]-7'(6'H)-one |

-continued

| Analog | | IUPAC Name of Illudofulvene Analog |
|---|---|---|
| 119 | 240 | (R)-3-(6'-hydroxy-2',4',6'-trimethyl-7'-oxo-6',7'-dihydrospiro[cyclopropane-1,5'-inden]-3'-yl)propyl acetoxy(acetyl)carbamate |
| 120 | 249 | (R)-6'-hydroxy-2'-(hydroxymethyl)-3',4',6'-trimethylspiro[cyclopropane-1,5'-inden]-7'(6'H)-one |
| 121 | 250 | ((1a'R,2'S,3'R,6'R,7a'S)-3'-acetoxy-6'-hydroxy-2',4',6'-trimethyl-7'-oxo-1',1a',2',3',6',7'-hexahydrospiro[cyclopropane-1,5'-cyclopropa[c]inden]-2'-yl)methyl acetate |
| 122 | 251 | ((1a'S,2'S,3'R,6'R,7a'R)-3'-acetoxy-6'-hydroxy-2',4',6'-trimethyl-7'-oxo-1',1a',2',3',6',7'-hexahydrospiro[cclopropane-1,5'-cyclopropa[c]inden]-2'-yl)methyl acetate |
| 123 | 252 | (1a'R,3'S,6'R,7a'S)-3',6'-dihydroxy-2',2',4',6'-tetramethyl-1',1a',2',3'-tetrahydrospiro[cyclopropane-1,5'-cyclopropa[c]inden]-7'(6'H)-one |
| 124 | 253 | (1a'S,3'S,6'R,7a'R)-3',6'-dihydroxy-2',2',4',6'-tetramethyl-1',1a',2',3'-tetrahydrospiro[cyclopropane-1,5'-cyclopropa[c]inden]-7'(6'H)-one |
| 125 | 254 | (R)-3-(6'-hydroxy-2',4',6'-trimethyl-7'-oxo-6',7'-dihydrospiro[cyclopropane-1,5'-inden]-3'-yl)propyl 4-sulfamoylbenzoate |
| 126 | 255 | (R)-3-(6'-hydroxy-2',4',6'-trimethyl-7'-oxo-6',7'-dihydrospiro[cyclopropane-1,5'-inden]-3'-yl)propyl sulfamate |
| 127 | 256 | 3-((R)-6'-hydroxy-2',4',6'-trimethyl-7'-oxo-6',7'-dihydrospiro[cyclopropane-1,5'-inden]-3'-yl)propyl 1-(3-((R)-6'-hydroxy-2',4',6'-trimethyl-7'-oxo-6',7'-dihydrospiro[cyclopropane-1,5'-inden]-3'-yl)propyl)-1H-1,2,3-triazole-4-carboxylate |
| 128 | 257 | 3-((R)-6'-hydroxy-2',4',6'-trimethyl-7'-oxo-6',7'-dihydrospiro[cyclopropane-1,5'-inden]-3'-yl)propyl 1-(((R)-6'-hydroxy-2',4',6'-trimethyl-7'-oxo-6',7'-dihydrospiro[cyclopropane-1,5'-inden]-3'-yl)methyl)-1H-1,2,3-triazole-4-carboxylate |
| 129 | 258 | (4-carboxy-4-(4-carboxy-4-((3-((R)-6'-hydroxy-2',4',6'-trimethyl-7'-oxo-6',7'-dihydrospiro[cyclopropane-1,5'-inden]-3'-yl)propyl)amino)butanamido)butanoyl)glutamic acid |
| 130 | 259 | (R)-3'-((S)-2,2-dioxido-1,2,3-oxathiazinan-4-yl)-6'-hydroxy-2',4',6'-trimethylspiro[cyclopropane-1,5'-inden]-7'(6'H)-one |
| 131 | 262 | methyl (R)-2-(((6'-hydroxy-2',4',6'-trimethyl-7'-oxo-6',7'-dihydrospiro[cyclopropane-1,5'-inden]-3'-yl)methyl)sulfonyl)acetate |
| 132 | 263 | methyl 2-((((R)-6'-hydroxy-2',4',6'-trimethyl-7'-oxo-6',7'-dihydrospiro[cyclopropane-1,5'-inden]-3'-yl)methyl)sulfinyl)acetate |
| 133 | 267 | (R)-2-amino-N-((6'-hydroxy-2',4',6'-trimethyl-7'-oxo-6',7'-dihydrospiro[cyclopropane-1,5'-inden]-3'-yl)methyl)-N-methoxyacetamide |
| 134 | 268 | (R)-2,2,2-trifluoro-N-(3-(6'-hydroxy-2',4',6'-trimethyl-7'-oxo-6',7'-dihydrospiro[cyclopropane-1,5'-inden]-3'-yl)propyl)acetamide |
| 135 | 269 | (R)-(6'-hydroxy-2',4',6'-trimethyl-7'-oxo-6',7'-dihydrospiro[cyclopropane-1,5'-inden]-3'-yl)methyl (4-methoxyphenyl)sulfamate |
| 136 | 270 | (R)-3'-(aminomethyl)-6'-hydroxy-2',4',6'-trimethylspiro[cyclopropane-1,5'-inden]-7'(6'H)-one |
| 137 | 272 | (5S,6S,7S)-3-(((3-((R)-6'-hydroxy-2',4',6'-trimethyl-7'-oxo-6',7'-dihydrospiro[cyclopropane-1,5'-inden]-3'-yl)propanoyl)oxy)methyl)-8-oxo-7-(2-(thiophen-2-yl)acetamido)-5-thia-1-azabicyclo[4.2.0]oct-2-ene-2-carboxylic acid 5-oxide |
| 138 | 273 | (5S,6S,7S)-3-((((3-((R)-6'-hydroxy-2',4',6'-trimethyl-7'-oxo-6',7'-dihydrospiro[cyclopropane-1,5'-inden]-3'-yl)propyl)carbamoyl)oxy)methyl)-8-oxo-7-(2-(thiophen-2-yl)acetamido)-5-thia-1-azabicyclo[4.2.0]oct-2-ene-2-carboxylic acid 5-oxide |
| 139 | 274 | (6S,7S)-3-((((3-((R)-6'-hydroxy-2',4',6'-trimethyl-7'-oxo-6',7'-dihydrospiro[cyclopropane-1,5'-inden]-3'-yl)propyl)carbamoyl)oxy)methyl)-8-oxo-7-(2-(thiophen-2-yl)acetamido)-5-thia-1-azabicyclo[4.2.0]oct-2-ene-2-carboxylic acid 5,5-dioxide |
| 140 | 275 | N-(((R)-6'-hydroxy-2',4',6'-trimethyl-7'-oxo-6',7'-dihydrospiro[cyclopropane-1,5'-inden]-3'-yl)methyl)pyrrolidine-2-carboxamide |
| 141 | 276 | 2-amino-N-(((R)-6'-hydroxy-2',4',6'-trimethyl-7'-oxo-6',7'-dihydrospiro[cyclopropane-1,5'-inden]-3'-yl)methyl)-4-methylpentanamide |
| 142 | 284 | (R)-3-((6'-hydroxy-2',4',6'-trimethyl-7'-oxo-6',7'-dihydrospiro[cyclopropane-1,5'-inden]-3'-yl)methyl)pyrimidine-2,4(1H,3H)-dione |
| 143 | 285 | N-hydroxy-N-[(6'-hydroxy-2',6'-dimethyl-7'-oxo-6',7'-dihydrospiro[cyclopropane-1,5'-inden]-3'-yl)methyl]sulfuric diamide |
| 144 | 286 | (R)-5-fluoro-1-((6'-hydroxy-2',4',6'-trimethyl-7'-oxo-6',7'-dihydrospiro[cyclopropane-1,5'-inden]-3'-yl)methyl)pyrimidine-2,4(1H,3H)-dione |
| 145 | 287 | (R)-5-fluoro-3-((6'-hydroxy-2',4',6'-trimethyl-7'-oxo-6',7'-dihydrospiro[cyclopropane-1,5'-inden]-3'-yl)methyl)pyrimidine-2,4(1H,3H)-dione |
| 146 | 289 | (R)-1-((6'-hydroxy-2',4',6'-trimethyl-7'-oxo-6',7'-dihydrospiro[cyclopropane-1,5'-inden]-3'-yl)methyl)pyrimidine-2,4(1H,3H)-dione |
| 147 | 290 | ((S)-6'-hydroxy-2',4',6'-trimethyl-7'-oxo-6',7'-dihydrospiro[cyclopropane-1,5'-inden]-3'-yl)methyl 5-oxo-5-(((S)-1,2,3,10-tetramethoxy-9-oxo-5,6,7,9-tetrahydrobenzo[a]heptalen-7-yl)amino)pentanoate |
| 148 | 291 | 3-((S)-6'-hydroxy-2',4',6'-trimethyl-7'-oxo-6',7'-dihydrospiro[cyclopropane-1,5'-inden]-3'-yl)propyl 5-oxo-5-(((S)-1,2,3,10-tetramethoxy-9-oxo-5,6,7,9-tetrahydrobenzo[a]heptalen-7-yl)amino)pentanoate |
| 149 | 292 | N1-(((S)-6'-hydroxy-2',4',6'-trimethyl-7'-oxo-6',7'-dihydrospiro[cyclopropane-1,5'-inden]-3'-yl)methyl)-N5-((S)-1,2,3,10-tetramethoxy-9-oxo-5,6,7,9-tetrahydrobenzo[a]heptalen-7-yl)glutaramide |
| 150 | 293 | 3-((S)-6'-hydroxy-2',4',6'-trimethyl-7'-oxo-6',7'-dihydrospiro[cyclopropane-1,5'-inden]-3'-yl)-N-((S)-1,2,3,10-tetramethoxy-9-oxo-5,6,7,9-tetrahydrobenzo[a]heptalen-7-yl)propanamide |
| 151 | 294 | 2-amino-N-(((R)-6'-hydroxy-2',4',6'-trimethyl-7'-oxo-6',7'-dihydrospiro[cyclopropane-1,5'-inden]-3'-yl)methyl)-N-methoxypropanamide |
| 152 | 295 | 2-amino-N-(((R)-6'-hydroxy-2',4',6'-trimethyl-7'-oxo-6',7'-dihydrospiro[cyclopropane-1,5'-inden]-3'-yl)methyl)-N-methoxy-4-methylpentanamide |
| 153 | 296 | 2-amino-N-(((R)-6'-hydroxy-2',4',6'-trimethyl-7'-oxo-6',7'-dihydrospiro[cyclopropane-1,5'-inden]-3'-yl)methyl)-N-methoxy-4-(methylthio)butanamide |
| 154 | 297 | 2-amino-N-(((R)-6'-hydroxy-2',4',6'-trimethyl-7'-oxo-6',7'-dihydrospiro[cyclopropane-1,5'-inden]-3'-yl)methyl)-3-(1H-indol-3-yl)-N-methoxypropanamide |
| 155 | 298 | (R)-3-(6'-hydroxy-2',4',6'-trimethyl-7'-oxo-6',7'-dihydrospiro[cyclopropane-1,5'-inden]-3'-yl)propyl (tert-butoxycarbonyl)glycinate |
| 156 | 299 | (2'S,3'R,6'R)-2'-(azidomethyl)-3',6'-dihydroxy-2',4',6'-trimethyl-2',3'-dihydrospiro[cyclopropane-1,5'-inden]-7'(6'H)-one |
| 157 | 300 | (2'R,3'R,6'R)-3'-azido-6'-hydroxy-2'-(hydroxymethyl)-2',4',6'-trimethyl-2',3'-dihydrospiro[cyclopropane-1,5'-inden]-7'(6'H)-one |
| 158 | 301 | (R)-6'-hydroxy-2',4',6'-trimethyl-7'-oxo-6',7'-dihydrospiro[cyclopropane-1,5'-inden]-3'-yl 6-oxo-6-phenylhexanoate |
| 159 | 302 | ((2'S,3'R,6'R)-3',6'-dihydroxy-2',4',6'-trimethyl-7'-oxo-2',3',6',7'-tetrahydrospiro[cyclopropane-1,5'-inden]-2'-yl)methyl 3,5-dinitrobenzoate |
| 160 | 303 | (2'S,3'R,6'R)-2'-(((3,5-dinitrocyclohexa-2,4-diene-1-carbonyl)oxy)methyl)-6'-hydroxy-2',4',6'-trimethyl-7'-oxo-2',3',6',7'-tetrahydrospiro[cyclopropane-1,5'-inden]-3'-yl 3,5-dinitrobenzoate |

| | Analog | IUPAC Name of Illudofulvene Analog |
|---|---|---|
| 161 | 304 | (R)-3-(6'-hydroxy-2',4',6'-trimethyl-7'-oxo-6',7'-dihydrospiro[cyclopropane-1,5'-inden]-3'-yl)propyl propiolate |
| 162 | 305 | (R)-3-(6'-hydroxy-2',4',6'-trimethyl-7'-oxo-6',7'-dihydrospiro[cyclopropane-1,5'-inden]-3'-yl)propyl (4-nitrophenyl) carbonate |
| 163 | 306 | (R)-3-(6'-hydroxy-2',4',6'-trimethyl-7'-oxo-6',7'-dihydrospiro[cyclopropane-1,5'-inden]-3'-yl)propyl 4-methylbenzenesulfonate |
| 164 | 307 | (3'R,6'R)-3'-azido-6'-hydroxy-2',2',4',6'-tetramethyl-2',3'-dihydrospiro[cyclopropane-1,5'-inden]-7'(6'H)-one |
| 165 | 308 | (3'R,6'R)-3'-amino-6'-hydroxy-2',2',4',6'-tetramethyl-2',3'-dihydrospiro[cyclopropane-1,5'-inden]-7'(6'H)-one |
| 166 | 309 | (2'R,3'S,6'R)-3'-azido-2'-(((tert-butyldimethylsilyl)oxy)methyl)-6'-hydroxy-2',4',6'-trimethyl-2',3'-dihydrospiro[cyclopropane-1,5'-inden]-7'(6'H)-one |
| 167 | 310 | (R)-(6'-hydroxy-2',4',6'-trimethyl-7'-oxo-6',7'-dihydrospiro[cyclopropane-1,5'-inden]-3'-yl)methyl 4-sulfamoylbenzoate |
| 168 | 311 | (3'S,6'R)-6'-hydroxy-2',2',4',6'-tetramethyl-7'-oxo-2',3',6',7'-tetrahydrospiro[cyclopropane-1,5'-inden]-3'-yl 4-sulfamoylbenzoate |
| 169 | 312 | (R)-(6'-hydroxy-2',4',6'-trimethyl-7'-oxo-6',7'-dihydrospiro[cyclopropane-1,5'-inden]-3'-yl)methyl 4-methylbenzenesulfonate |
| 170 | 313 | 2,3,4,5,6-pentafluoro-N-((3'R,6'R)-6'-hydroxy-2',2',4',6'-tetramethyl-7'-oxo-2',3',6',7'-tetrahydrospiro[cyclopropane-1,5'-inden]-3'-yl)benzenesulfonamide |
| 171 | 314 | (R)-3-(6'-hydroxy-2',4',6'-trimethyl-7'-oxo-6',7'-dihydrospiro[cyclopropane-1,5'-inden]-3'-yl)propyl 4-methylbenzenesulfonate |
| 172 | 315 | (R)-3'-((2,5-dimethyl-1H-pyrrol-3-yl)methyl)-6'-hydroxy-2',4',6'-trimethylspiro[cyclopropane-1,5'-inden]-7'(6'H)-one |
| 173 | 316 | ((2'S,3'R,6'R)-3',6'-dihydroxy-2',4',6'-trimethyl-7'-oxo-2',3',6',7'-tetrahydrospiro[cyclopropane-1,5'-inden]-2'-yl)methyl 4-(fluorosulfonyl)benzoate |
| 174 | 441 | (R)-2-((6'-hydroxy-2',4',6'-trimethyl-7'-oxo-6',7'-dihydrospiro[cyclopropane-1,5'-inden]-3'-yl)methoxy)ethyl 4-(fluorosulfonyl)benzoate |
| 175 | xxx | 4-[(1-cyano-3-{6'-hydroxy-2',4',6'-trimethyl-7'-methylidene-6',7'-dihydrospiro[cyclopropane-1,5'-inden]-3'-yl}propoxy)methyl]cyclohexane-1-sulfonyl fluoride |

Table XII shows previously identified Illudin analogs.

| # | Analog | IUPAC Name of Illudofulvene Analog |
|---|---|---|
| 1 | 001 | (R)-6'-hydroxy-2',4',6'-trimethylspiro[cyclopropane-1,5'-inden]-7'(6'H)-one |
| 2 | 002 | (6'R)-6'-hydroxy-3'-(hydroxymethyl)-2',4',6'-trimethylspiro[cyclopropane-1,5'-inden]-7'(6'H)-one |
| 3 | 003 | (6'R,6'''R)-3',3'''-methylenebis(6'-hydroxy-2',4',6'-trimethylspiro[cyclopropane-1,5'-inden]-7'(6'H)-one) |
| 4 | 004 | (R)-3'-bromo-6'-hydroxy-2',4',6'-trimethylspiro[cyclopropane-1,5'-inden]-7'(6'H)-one |
| 5 | 005 | (R)-6'-hydroxy-3'-iodo-2',4',6'-trimethylspiro[cyclopropane-1,5'-inden]-7'(6'H)-one |
| 6 | 006 | (R)-6'-hydroxy-3'-(4-hydroxybenzyl)-2',4',6'-trimethylspiro[cyclopropane-1,5'-inden]-7'(6'H)-one |
| 7 | 007 | (R)-6'-hydroxy-3'-(4-methoxybenzyl)-2',4',6'-trimethylspiro[cyclopropane-15'-inden]-7'(6'H)-one |
| 8 | 008 | (R)-((6'-hydroxy-2',4',6'-trimethyl-7'-oxo-6',7'-dihydrospiro[cyclopropane-1,5'-inden]-3 '-yl)methoxy)methyl acetate |
| 9 | 009 | (R)-6'-hydroxy-3'-(3-hydroxypropyl)-2',4',6'-trimethylspiro[cyclopropane-1,5'-inden]-7'(6'H)-one |
| 10 | 010 | (R)-3-(6'-hydroxy-2',4',6'-trimethyl-7'-oxo-6',7'-dihydrospiro[cyclopropane-1,5'-inden]-3'-yl)propanal |
| 11 | 011 | (R)-6'-hydroxy-2',4',6'-trimethyl-7'-oxo-6',7'-dihydrospiro[cyclopropane-1,5'-indene]-3'-carbaldehyde |
| 12 | 012 | (R)-6'-hydroxy-2',4',6'-trimethyl-3'-nitrospiro[cyclopropane-1,5'-inden]-7'(6'H)-one |
| 13 | 013 | 4-hydroxy-5-(((R)-6'-hydroxy-2',4',6'-trimethyl-7'-oxo-6',7'-dihydrospiro[cyclopropane-1,5'-inden]-3'-yl)methyl)cyclohexane-1,3-dicarbaldehyde |
| 14 | 014 | (4a'S,7'R,9b'S)-7'-hydroxy-4a',7',9'-trimethyl-4a',9b'-dihydro-4'H-spiro[cyclopropane-1,8'-indeno[1,2-d][1,3]dioxin]-6'(7'H)-one |
| 15 | 015 | (R)-3'-(hydroxymethyl)-2',4',6'-trimethyl-7'-oxo-6',7'-dihydrospiro[cyclopropane-1,5'-inden]-6'-yl acetate |
| 16 | 016 | (R)-3'-(ethoxymethyl)-6'-hydroxy-2',4',6'-trimethylspiro[cyclopropane-1,5'-inden]-7'(6'H)-one |
| 17 | 017 | (6'R,6'''R)-3',3'''-(oxybis(methylene))bis(6'-hydroxy-2',4',6'-trimethylspiro[cyclopropane-1,5'-inden]-7'(6'H)-one) |
| 18 | 018 | (R)-6'-hydroxy-2',4',6'-trimethyl-3'-(((((2R,3S,4R,5R,6S)-3,4,5-trihydroxy-6-(hydroxymethyl)tetrahydro-2H-pyran-2-yl)oxy)methyl)spiro[cyclopropane-1,5'-inden]-7'(6'H)-one |
| 19 | 019 | (6'R)-3'-((2,3-dihydroxypropoxy)methyl)-6'-hydroxy-2',4',6'-trimethylspiro[cyclopropane-1,5'-inden]-7'(6'H)-one |
| 20 | 020 | (R)-3'-((2-bromoethoxy)methyl)-6'-hydroxy-2',4',6'-trimethylspiro[cyclopropane-1,5'-inden]-7'(6'H)-one |
| 21 | 021 | (R)-6'-hydroxy-3'-(((2-methoxypropan-2-yl)oxy)methyl)-2',4',6'-trimethylspiro [cyclopropane-1,5'-inden]-7'(6'H)-one |
| 22 | 022 | (R)-6'-hydroxy-3'-((2-hydroxyethoxy)methyl)-2',4',6'-trimethylspiro[cyclopropane-1,5'-inden]-7'(6'H)-one |
| 23 | 023 | (R)-6'-hydroxy-3'-(((4-hydroxyphenyl)thio)methyl)-2',4',6'-trimethylspiro[cyclopropane-1,5'-inden]-7'(6'H)-one |
| 24 | 024 | (R)-3'-((benzylthio)methyl)-6'-hydroxy-2',4',6'-trimethylspiro[cyclopropane-1,5'-inden]-7'(6'H)-one |

| # | Analog | IUPAC Name of Illudofulvene Analog |
|---|---|---|
| 25 | 025 | methyl (R)-2-(((6'-hydroxy-2',4',6'-trimethyl-7'-oxo-6',7'-dihydrospiro[cyclopropane-1,5'-inden]-3'-yl)methyl)thio)acetate |
| 26 | 026 | (R)-6'-hydroxy-2',4',6'-trimethyl-3'-((p-tolylthio)methyl)spiro[cyclopropane-1,5'-inden]-7'(6'H)-one |
| 27 | 027 | (R)-(6'-hydroxy-2',4',6'-trimethyl-7'-oxo-6',7'-dihydrospiro[cyclopropane-1,5'-inden]-3'-yl)methyl phenyl carbonate |
| 28 | 028 | (R)-(6'-hydroxy-2',4',6'-trimethyl-7'-oxo-6',7'-dihydrospiro[cyclopropane-1,5'-inden]-3'-yl)methyl benzoate |
| 29 | 029 | (R)-2-(((6'-hydroxy-2',4',6'-trimethyl-7'-oxo-6',7'-dihydrospiro[cyclopropane-1,5'-inden]-3'-yl)methyl)thio)acetic acid |
| 30 | 030 | methyl (R)-2-(((6'-hydroxy-1'-((2-methoxy-2-oxoethyl)thio)-2',4',6'-trimethyl-7'-oxo-6',7'-dihydrospiro[cyclopropane-1,5'-inden]-3'-yl)methyl)thio)acetate |
| 31 | 031 | methyl 2-(((((6'R)-6',7a'-dihydroxy-1'-((2-methoxy-2-oxoethyl)thio)-2',4',6'-trimethyl-7'-oxo-1',6',7',7a'-tetrahydrospiro[cyclopropane-1,5'-inden]-3'-yl)methyl)thio)acetate |
| 32 | 032 | (6'R)-3'-(((2,3-dihydroxypropyl)thio)methyl)-6'-hydroxy-2',4',6'-trimethylspiro[cyclopropane-1,5'-inden]-7'(6'H)-one |
| 33 | 033 | 7'-methyl-4'H-dispiro[cyclopropane-1,6'-indene-5',2''-[1,3]dioxolan]-4'-one |
| 34 | 034 | (R)-(6'-hydroxy-2',4',6'-trimethyl-7'-oxo-6',7'-dihydrospiro[cyclopropane-1,5'-inden]-3'-yl)methyl acetate |
| 35 | 035 | 6'-hydroxy-4'-methylspiro[cyclopropane-1,5'-inden]-7'(6'H)-one |
| 36 | 036 | (R)-3'-((1H-imidazol-1-yl)methyl)-6'-hydroxy-2',4',6'-trimethylspiro[cyclopropane-1,5'-inden]-7'(6'H)-one |
| 37 | 037 | 1-carboxy-2-((((R)-6'-hydroxy-2',4',6'-trimethyl-7'-oxo-6',7'-dihydrospiro[cyclopropane-1,5'-inden]-3'-yl)methyl)thio)ethan-1-aminium |
| 38 | 038 | (R)-3-(6'-hydroxy-2',4',6'-trimethyl-7'-oxo-6',7'-dihydrospiro[cyclopropane-1,5'-inden]-3'-yl)propanoic acid |
| 39 | 039 | (R)-3'-(3,3-dimethoxypropyl)-6'-hydroxy-2',4',6'-trimethylspiro[cyclopropane-1,5'-inden]-7'(6'H)-one |
| 40 | 040 | (R)-3'-(3,3-diethoxypropyl)-6'-hydroxy-2',4',6'-trimethylspiro[cyclopropane-1,5'-inden]-7'(6'H)-one |
| 41 | 041 | (R,Z)-3-(6'-hydroxy-2',4',6'-trimethyl-7'-oxo-6',7'-dihydrospiro[cyclopropane-1,5'-inden]-3'-yl)acrylaldehyde |
| 42 | 042 | (R)-3'-(hydroxymethyl)-4',6'-dimethyl-6'-((triethylsilyl)oxy)spiro[cyclopropane-1,5'-inden]-7'(6'H)-one |
| 43 | 043 | (R)-6'-hydroxy-2',4',6'-trimethyl-3'-(((triethylsilyl)oxy)methyl)spiro[cyclopropane-1,5'-inden]-7'(6'H)-one |
| 44 | 044 | (R)-2',4',6'-trimethyl-6'-((triethylsilyl)oxy)-3'-(((triethylsilyl)oxy)methyl)spiro[cyclopropane-1,5'-inden]-7'(6'H)-one |
| 45 | 045 | methyl 2-((7-hydroxy-5-(2-hydroxyethyl)-3-(hydroxymethyl)-2,4,6-trimethyl-1H-inden-1-yl)thio)acetate |
| 46 | 046 | (R)-3-(6'-hydroxy-2',4',6'-trimethyl-7'-oxo-6',7'-dihydrospiro[cyclopropane-1,5'-inden]-3'-yl)propyl acetate |
| 47 | 047 | (6'R)-3'-(2-(1,7-dihydroxy-2,4,6-trimethyl-1H-inden-5-yl)ethyl)-6'-hydroxy-2',4',6'-trimethylspiro[cyclopropane-1,5'-inden]-7'(6'H)-one |
| 48 | 048 | (R)-6'-hydroxy-2',4',6'-trimethyl-1'-(p-tolylthio)-3'-((p-tolylthio)methyl)spiro[cyclopropane-1,5'-inden]-7'(6'H)-one |
| 49 | 049 | (R)-6'-hydroxy-2',4',6'-trimethyl-3'-(p-tolylthio)spiro[cyclopropane-1,5'-inden]-7'(6'H)-one |
| 50 | 050 | (R)-6'-hydroxy-2',4',6'-trimethyl-1',3'-bis(p-tolylthio)spiro[cyclopropane-1,5'-inden]-7'(6'H)-one |
| 51 | 051 | (R)-2-(2-(((6'-hydroxy-2',4',6'-trimethyl-7'-oxo-6',7'-dihydrospiro[cyclopropane-1,5'-inden]-3'-yl)methyl)thio)acetoxy)ethyl 2-mercaptoacetate |
| 52 | 052 | ethane-1,2-diyl bis(2-(((((R)-6'-hydroxy-2',4',6'-trimethyl-7'-oxo-6',7'-dihydrospiro[cyclopropane-1,5'-inden]-3'-yl)methyl)thio)acetate) |
| 53 | 053 | (R)-3'-((2-(2-bromoethoxy)ethoxy)methyl)-6'-hydroxy-2',4',6'-trimethylspiro[cyclopropane-1,5'-inden]-7'(6'H)-one |
| 54 | 054 | (R)-6'-hydroxy-1'-(((R)-6'-hydroxy-2',4',6'-trimethyl-7'-oxo-6',7'-dihydrospiro[cyclopropane-1,5'-inden]-3'-yl)methyl)-3'-(hydroxymethyl)-2',4',6'-trimethylspiro[cyclopropane-1,5'-inden]-7'(6'H)-one |
| 55 | 055 | 5-(2-hydroxyethyl)-1-((4-hydroxyphenyl)thio)-3-(((4-hydroxyphenyl)thio)methyl)-2,4,6-trimethyl-1H-inden-7-ol |
| 56 | 056 | (R)-6'-hydroxy-3'-((4-hydroxyphenyl)thio)-2',4',6'-trimethylspiro[cyclopropane-1,5'-inden]-7'(6'H)-one |
| 57 | 057 | (R)-6'-hydroxy-1'-((4-hydroxyphenyl)thio)-2',4',6'-trimethylspiro[cyclopropane-1,5'-inden]-7'(6'H)-one |
| 58 | 058 | (R)-6'-hydroxy-1',3'-bis((4-hydroxyphenyl)thio)-2',4',6'-trimethylspiro[cyclopropane-1,5'-inden]-7'(6'H)-one |
| 59 | 059 | (6'S,7'R)-4'-methyl-6'-((triethylsilyl)oxy)-6',7'-dihydrospiro[cyclopropane-1,5'-inden]-7'-ol |
| 60 | 060 | (R)-7'-methyl-4'H-dispiro[cyclopropane-1,6'-indene-5',2''-[1,3]dioxolan]-4'-ol |
| 61 | 061 | (S)-4'-methyl-6'-((triethylsilyl)oxy)spiro[cyclopropane-1,5'-inden]-7'(6'H)-one |
| 62 | 062 | (R)-6'-hydroxy-2'-(hydroxymethyl)-4',6'-dimethylspiro[cyclopropane-1,5'-inden]-7'(6'H)-one |
| 63 | 063 | (R)-6'-hydroxy-2',3'-bis(hydroxymethyl)-4',6'-dimethylspiro[cyclopropane-1,5'-inden]-7'(6'H)-one |

-continued

| # | Analog | IUPAC Name of Illudofulvene Analog |
|---|--------|-------------------------------------|
| 64 | 064 | N-acetyl-S-(((R)-6'-hydroxy-2',4',6'-trimethyl-7'-oxo-6',7'-dihydrospiro[cyclopropane-1,5'-inden]-3'-yl)methyl)-L-cysteine |
| 65 | 065 | (R)-2-acetamido-3-((((R)-6'-hydroxy-4',6'-dimethyl-7'-oxo-6',7'-dihydrospiro[cyclopropane-1,5'-inden]-3'-yl)methyl)thio)-N-((S)-1-phenylethyl)propanamide |
| 66 | 066 | (S)-2-acetamido-3-((((R)-6'-hydroxy-2',4',6'-trimethyl-7'-oxo-6',7'-dihydrospiro[cyclopropane-1,5'-inden]-3'-yl)methyl)thio)-N-((S)-1-phenylethyl)propanamide |
| 67 | 067 | 4-methyl-2,3-dihydro-5H-indeno[5,6-b]furan-5-one |
| 68 | 068 | 5-hydroxy-6-(2-hydroxyethyl)-7-methyl-1H-inden-1-one |
| 69 | 069 | 5-(2-hydroxyethoxy)-6-(2-hydroxyethyl)-7-methyl-1H-inden-1-one |
| 70 | 070 | (3a'R,4'R)-4'-hydroxy-7'-methyl-3a',4'-dihydro-1'H-dispiro[cyclopropane-1,6'-indene-5',2''-[1,3]dioxolan]-1'-one |
| 71 | 071 | (3a'R,4'R)-7'-methyl-4'-((triethylsilyl)oxy)-3a',4'-dihydro-1'H-dispiro[cyclopropane-1,6'-indene-5',2''-[1,3]dioxolan]-1'-one |
| 72 | 072 | (7'R,7a'R)-7'-hydroxy-4'-methyl-7',7a'-dihydrospiro[cyclopropane-1,5'-indene]-3',6'-dione |
| 73 | 073 | (7'R,7a'R)-4'-methyl-7'-((triethylsilyl)oxy)-7',7a'-dihydrospiro[cyclopropane-1,5'-indene]-3',6'-dione |
| 74 | 074 | (6'R)-3'-((((2,2-dimethyl-1,3-dioxolan-4-yl)methyl)thio)methyl)-6'-hydroxy-2',4',6'-trimethylspiro[cyclopropane-1,5'-inden]-7'(6'H)-one |
| 75 | 075 | (R)-(6'-hydroxy-4',6'-dimethyl-7'-oxo-6',7'-dihydrospiro[cyclopropane-1,5'-inden]-2'-yl)methyl acetate |
| 76 | 076 | (R)-(6'-hydroxy-4',6'-dimethyl-7'-oxo-6',7'-dihydrospiro[cyclopropane-1,5'-indene]-2',3'-diyl)bis(methylene) diacetate |
| 77 | 077 | (R)-(6'-hydroxy-3'-(hydroxymethyl)-4',6'-dimethyl-7'-oxo-6',7'-dihydrospiro[cyclopropane-1,5'-inden]-2'-yl)methyl acetate |
| 78 | 078 | (R)-(6'-hydroxy-2'-(hydroxymethyl)-4',6'-dimethyl-7'-oxo-6',7'-dihydrospiro[cyclopropane-1,5'-inden]-3'-yl)methyl acetate |
| 79 | 079 | (R)-6'-hydroxy-2'-(methoxymethyl)-4',6'-dimethylspiro[cyclopropane-1,5'-inden]-7'(6'H)-one |
| 80 | 080 | (R)-6'-hydroxy-3'-(methoxymethyl)-2',4',6'-trimethylspiro[cyclopropane-1,5'-inden]-7'(6'H)-one |
| 81 | 081 | (R)-6'-hydroxy-2'-(hydroxymethyl)-3'-(methoxymethyl)-4',6'-dimethylspiro[cyclopropane-1,5'-inden]-7'(6'H)-one |
| 82 | 082 | (R)-6'-hydroxy-2',3'-bis(methoxymethyl)-4',6'-dimethylspiro[cyclopropane-1,5'-inden]-7'(6'H)-one |
| 83 | 083 | (R)-2-acetamido-3-((((R)-6'-hydroxy-2',4',6'-trimethyl-7'-oxo-6',7'-dihydrospiro[cyclopropane-1,5'-inden]-3'-yl)methyl)thio)-N-((S)-1-((2-(((S)-4-methyl-1-oxopentan-2-yl)amino)-2-oxoethyl)amino)-1-oxo-3-phenylpropan-2-yl)propanamide |
| 84 | 084 | (S)-2-((R)-2-acetamido-3-((((R)-6'-hydroxy-2',4',6'-trimethyl-7'-oxo-6',7'-dihydrospiro[cyclopropane-1,5'-inden]-3'-yl)methyl)thio)propanamido)-4-methyl-N-(2-oxo-2-(((R)-1-oxo-3-phenylpropan-2-yl)amino)ethyl)pentanamide |
| 85 | 085 | (S)-2-((R)-2-acetamido-3-((((R)-6'-hydroxy-2',4',6'-trimethyl-7'-oxo-6',7'-dihydrospiro[cyclopropane-1,5'-inden]-3'-yl)methyl)thio)propanamido)-4-methyl-N-((S)-4-methyl-1-oxo-1-(((R)-1-oxo-3-phenylpropan-2-yl)amino)pentan-2-yl)pentanamide |
| 86 | 086 | (R)-2-acetamido-3-((((R)-6'-hydroxy-2',4',6'-trimethyl-7'-oxo-6',7'-dihydrospiro[cyclopropane-1,5'-inden]-3'-yl)methyl)thio)-N-(2-oxo-2-(((R)-1-oxo-3-phenylpropan-2-yl)amino)ethyl)propanamide |
| 87 | 087 | (S)-2-((R)-2-acetamido-3-((((R)-6'-hydroxy-2',4',6'-trimethyl-7'-oxo-6',7'-dihydrospiro[cyclopropane-1,5'-inden]-3'-yl)methyl)thio)propanamido)-4-methyl-N-((R)-4-methyl-1-(((S)-4-methyl-1-oxopentan-2-yl)amino)-1-oxopentan-2-yl)pentanamide |
| 88 | 088 | (R)-(6'-acetoxy-2',4',6'-trimethyl-7'-oxo-6',7'-dihydrospiro[cyclopropane-1,5'-inden]-3'-yl)methyl acetate |
| 89 | 089 | N5-((R)-1-((carboxymethyl)amino)-3-((((R)-6'-hydroxy-2',4',6'-trimethyl-7'-oxo-6',7'-dihydrospiro[cyclopropane-1,5'-inden]-3'-yl)methyl)thio)-1-oxopropan-2-yl)-D-glutamine |
| 90 | 090 | (R)-2'-(hydroxymethyl)-4',6'-dimethyl-7'-oxo-6',7'-dihydrospiro[cyclopropane-1,5'-inden]-6'-yl acetate |
| 94 | 094 | (R)-3-(6'-hydroxy-2',4',6'-trimethyl-7'-oxo-6',7'-dihydrospiro[cyclopropane-1,5'-inden]-3'-yl)propyl acetate |
| 95 | 095 | (R)-6'-hydroxy-3'-(3-methoxypropyl)-2',4',6'-trimethylspiro[cyclopropane-1,5'-inden]-7'(6'H)-one |
| 96 | 096 | (R)-6'-hydroxy-2',4',6'-trimethyl-3'-(((1-methyl-1H-imidazol-2-yl)thio)methyl)spiro[cyclopropane-1,5'-inden]-7'(6'H)-one |
| 97 | 097 | S-(((R)-6'-hydroxy-2',4',6'-trimethyl-7'-oxo-6',7'-dihydrospiro[cyclopropane-1,5'-inden]-3'-yl)methyl)homocysteine |
| 98 | 098 | ((S)-3-((((R)-6'-hydroxy-2',4',6'-trimethyl-7'-oxo-6',7'-dihydrospiro[cyclopropane-1,5'-inden]-3'-yl)methyl)thio)-2-methylpropanoyl)proline |
| 99 | 099 | (2'S,6'R)-6'-hydroxy-2'-(hydroxymethyl)-2',4',6'-trimethylspiro[cyclopropane-1,5'-indene]-3',7'(2'H,6'H)-dione |
| 100 | 100 | S-(((R)-6'-hydroxy-2',4',6'-trimethyl-7'-oxo-6',7'-dihydrospiro[cyclopropane-1,5'-inden]-3'-yl)methyl)-N-S-(((R)-6'-hydroxy-2',4',6'-trimethyl-7'-oxo-6',7'- |

-continued

| # | Analog | IUPAC Name of Illudofulvene Analog |
|---|---|---|
| | | dihydrospiro[cyclopropane-1,5'-inden]-3'-yl)methyl)cystemyl-L-asparaginylglycyl-L-arginylcysteine |
| 101 | 101 | S-(((R)-6'-hydroxy-2',4',6'-trimethyl-7'-oxo-6',7'-dihydrospiro[cyclopropane-1,5'-inden]-3'-yl)methyl)-N-S-(((R)-6'-hydroxy-2',4',6'-trimethyl-7'-oxo-6',7'-dihydrospiro[cyclopropane-1,5'-inden]-3'-yl)methyl)cysteinyl-L-arginylglycyl-L-asparaginylcysteine |
| 102 | 102 | S-(((R)-6'-hydroxy-2',4',6'-trimethyl-7'-oxo-6',7'-dihydrospiro[cyclopropane-1,5'-inden]-3'-yl)methyl)cysteinyl-L-asparaginylglycyl-L-arginylcysteine |
| 103 | 103 | (R)-(6'-acetoxy-2'-(hydroxymethyl)-4',6'-dimethyl-7'-oxo-6',7'-dihydrospiro[cyclopropane-1,5'-inden]-3'-yl)methyl acetate |
| 104 | 104 | (R)-8'-hydroxy-6',8'-dimethyl-1',5'-dihydrospiro[cyclopropane-1,7'-indeno[1,2-e][1,3]dioxepin]-9'(8'H)-one |
| 105 | 105 | (E)-2-((2R,4S)-4-hydroxy-2-((1R,2S)-2-hydroxy-4,4-dimethylcyclopentyl)-2-methylcyclobutylidene)propanal |
| 106 | 132 | (E)-7-(chloromethylene)-5-hydroxy-5,9-dimethylspiro[3.5]non-8-en-6-one |
| 107 | 170 | 5-(2-hydroxyethyl)-3-(hydroxymethyl)-2,4,6-trimethyl-1H-inden-7-ol |
| 108 | 176 | 3-((R)-6'-hydroxy-2',4',6'-trimethyl-7'-oxo-6',7'-dihydrospiro[cyclopropane-1,5'-inden]-3'-yl)propyl leucinate |
| 109 | 184 | (R)-1-hydroxy-1-((6'-hydroxy-2',4',6'-trimethyl-7'-oxo-6',7'-dihydrospiro[cyclopropane-1,5'-inden]-3'-yl)methyl)urea |
| 110 | 185 | (S)-6'-hydroxy-2',4',6'-trimethylspiro[cyclopropane-1,5'-inden]-7'(6'H)-one |
| 111 | 186 | (6'S,7'R)-6',7'-dihydroxy-2',4',6'-trimethyl-7',7a'-dihydrospiro[cyclopropane-1,5'-inden]-3'(6'H)-one |
| 112 | 187 | (S)-6'-hydroxy-3'-(hydroxymethyl)-2',4',6'-trimethylspiro[cyclopropane-1,5'-inden]-7'(6'H)-one |
| 113 | 211 | (R)-3'-(3-aminopropyl)-6'-hydroxy-2',4',6'-trimethylspiro[cyclopropane-1,5'-inden]-7'(6'H)-one |
| 114 | 220 | (R)-1-acetoxy-1-((6'-hydroxy-2',4',6'-trimethyl-7'-oxo-6',7'-dihydrospiro[cyclopropane-1,5'-inden]-3'-yl)methyl)ur |
| 115 | 232 | (R)-3-(6'-hydroxy-2',4',6'-trimethyl-7'-oxo-6',7'-dihydrospiro[cyclopropane-1,5'-inden]-3'-yl)propyl hydroxycarbamate |
| 116 | 233 | ethyl(R)-hydroxy((6'-hydroxy-2',4',6'-trimethyl-7'-oxo-6',7'-dihydrospiro[cyclopropane-1,5'-inden]-3'-yl)methyl)carbamate |
| 117 | 234 | benzyl (R)-hydroxy((6'-hydroxy-2',4',6'-trimethyl-7'-oxo-6',7'-dihydrospiro[cyclopropane-1,5'-inden]-3'-yl)methyl)carbamate |
| 118 | 235 | tert-butyl (R)-hydroxy((6'-hydroxy-2',4',6'-trimethyl-7'-oxo-6',7'-dihydrospiro[cyclopropane-1,5'-inden]-3'-yl)methyl)carbamate |
| 119 | 237 | (R)-3-(6'-hydroxy-2',4',6'-trimethyl-7'-oxo-6',7'-dihydrospiro[cyclopropane-1,5'-inden]-3'-yl)propyl(2-bromoethyl)carbamate |
| 120 | 238 | (R)-3-(6'-hydroxy-2',4',6'-trimethyl-7'-oxo-6',7'-dihydrospiro[cyclopropane-1,5'-inden]-3'-yl)propyl(2-chloroethyl)carbamate |
| 121 | 239 | (R)-3-(6'-hydroxy-2',4',6'-trimethyl-7'-oxo-6',7'-dihydrospiro[cyclopropane-1,5'-inden]-3'-yl)propyl(2-hydroxyethyl)carbamate |
| 122 | 241 | (R)-N-(3-(6'-hydroxy-2',4',6'-trimethyl-7'-oxo-6',7'-dihydrospiro[cyclopropane-1,5'-inden]-3'-yl)propyl)methanesulfonamide |
| 123 | 242 | (R)-N-(3-(6'-hydroxy-2',4',6'-trimethyl-7'-oxo-6',7'-dihydrospiro[cyclopropane-1,5'-inden]-3'-yl)propyl)-4-methylbenzenesulfonamide |
| 124 | 243 | (R)-3-(6'-hydroxy-2',4',6'-trimethyl-7'-oxo-6',7'-dihydrospiro[cyclopropane-1,5'-inden]-3'-yl)propyl(2-fluoroethyl)carbamate |
| 125 | 244 | (R)-1-hydroxy-1-(3-(6'-hydroxy-2',4',6'-trimethyl-7'-oxo-6',7'-dihydrospiro[cyclopropane-1,5'-inden]-3'-yl)propyl)urea |
| 126 | 245 | (R)-1-hydroxy-1-(3-(6'-hydroxy-2',4',6'-trimethyl-7'-oxo-6',7'-dihydrospiro[cyclopropane-1,5'-inden]-3'-yl)propyl)thiourea |
| 127 | 246 | (R)-3-(6'-hydroxy-2',4',6'-trimethyl-7'-oxo-6',7'-dihydrospiro[cyclopropane-1,5'-inden]-3'-yl)propyl morpholme-4-carboxylate |
| 128 | 247 | (R)-3-(6'-hydroxy-2',4',6'-trimethyl-7'-oxo-6',7'-dihydrospiro[cyclopropane-1,5'-inden]-3'-yl)propyl morpholine-4-carboxylate |
| 129 | 248 | (R)-3-(6'-hydroxy-2',4',6'-trimethyl-7'-oxo-6',7'-dihydrospiro[cyclopropane-1,5'-inden]-3'-yl)propyl[1,4'-bipiperidme]-1'-carboxylate |
| 130 | 260 | (R)-N-(3-(6'-hydroxy-2',4',6'-trimethyl-7'-oxo-6',7'-dihydrospiro[cyclopropane-1,5'-inden]-3'-yl)propyl)-[1,4'-bipiperidine]-1'-carboxamide |
| 131 | 261 | (R)-3-(6'-hydroxy-2',4',6-trimethyl-7'-oxo-6',7'-dihydrospiro[cyclopropane-1,5'-inden]-3'-yl)propyl 1H-imidazole-1-carboxylate |
| 132 | 264 | N-[3-(6'-hydroxy-2',6'-dimethyl-7'-oxo-6',7'-dihydrospiro[cyclopropane-1,5'-inden]-3'-yl)propyl]sulfuric diamide |
| 133 | 265 | N-hydroxy-N'-[3-(6'-hydroxy-2',6'-dimethyl-7'-oxo-6',7'-dihydrospiro[cyclopropane-1,5'-inden]-3'-yl)propyl]sulfuric diamide |
| 134 | 266 | N-[3-(6'-hydroxy-2',6'-dimethyl-7'-oxo-6',7'-dihydrospiro[cyclopropane-1,5'-inden]-3'-yl)propyl]-N-methoxysulfuric diamide |
| 135 | 271 | (R)-N-((6'-hydroxy-2',4',6'-trimethyl-7'-oxo-6',7'-dihydrospiro[cyclopropane-1,5'-inden]-3'-yl)methyl)methanesulfonamide |
| 136 | 277 | (R)-1-hydroxy-3-((6'-hydroxy-2',4',6'-trimethyl-7'-oxo-6',7'-dihydrospiro[cyclopropane-1,5'-inden]-3'-yl)methyl)urea |
| 137 | 278 | (R)-1-((6'-hydroxy-2',4',6'-trimethyl-7'-oxo-6',7'-dihydrospiro[cyclopropane-1,5'-inden]-3'-yl)methyl)-3-methoxyurea |
| 138 | 279 | (R)-1-((6'-hydroxy-2',4',6'-trimethyl-7'-oxo-6',7'-dihydrospiro[cyclopropane-1,5'-inden]-3'-yl)methyl)-3-(2-hydroxyethyl)urea |

-continued

| # | Analog | IUPAC Name of Illudofulvene Analog |
|---|--------|-----------------------------------|
| 139 | 280 | (R)-1-(3-(6'-hydroxy-2',4',6'-trimethyl-7'-oxo-6',7'-dihydrospiro[cyclopropane-1,5'-inden]-3'-yl)propyl)-3-(2-hydroxyethyl)urea |
| 140 | 281 | (R)-1-(2-chloroethyl)-3-(3-(6'-hydroxy-2',4',6'-trimethyl-7'-oxo-6',7'-dihydrospiro[cyclopropane-1,5'-inden]-3'-yl)propyl)urea |
| 141 | 282 | (R)-1-(2-chloroethyl)-3-((6'-hydroxy-2',4',6'-trimethyl-7'-oxo-6',7'-dihydrospiro[cyclopropane-1,5'-inden]-3'-yl)methyl)urea |
| 142 | 283 | N-[(6'-hydroxy-2',6'-dimethyl-7'-oxo-6',7'-dihydrospiro[cyclopropane-1,5'-inden]-3'-yl)methyl]sulfuric diamide |
| 143 | 288 | (R)-1-hydroxy-3-(3-(6'-hydroxy-2',4',6'-trimethyl-7'-oxo-6',7'-dihydrospiro[cyclopropane-1,5'-inden]-3'-yl)propyl)urea |

TABLE XIII

Summary NCI DTP 60 Cell Line Data.

| NAME/NSC | Mean GI50 inhibition | Mean TGI cytostatic | Mean LD50 cytotoxic |
|---|---|---|---|
| Pyrrolobenzodiazepines 694501 | 7 nM | 302 nM | >23,000 nM* |
| Maytansine** 153858 | 19 nM | 318 nM | 49,200 nM |
| Fumagillol 642492 | 6,130 nM | 9,850 nM | >50,000 nM |
| Dolstatin-10 376128 | 17 nM | 2,680 nM | >50,000 nM |
| Auristatins 654663 | 1.4 nM | 902** nM | >5,000 nM** |
| Enadiyne 157365 | 2,900 nM | >100,000 nM | >100,000 nM |
| Halichondrin B 609395 | 1.2 nM | 199 nM | >1,000 nM |
| Tubulysin A | 12 nM | 1,318 nM | >10,000 nM |
| Illudin S | 10 nM | 64 nM | 511 nM |
| Illudin M | 3 nM | 20 nM | 291 nM |

TABLE XIV

Mechanisms of Drug Resistance.

| Mechanism of Multi-drug Resistance | Resistance to Illudins, Syn-illudins, and Acylfulvenes |
|---|---|
| Gp170/MDR1 | No |
| Gp180/MRP | No |
| Topoisomerase I | No |
| Topoisomerase II | No |
| MVP/LRP (vault) | No |
| Thiol content/GST pi | No |
| DNA repair | No |
| Myc expression | No |
| Bcl-2 expression | No |
| BRCA status | No |
| P53 status | No |
| P21 status | No |
| MGMT expression | No |
| Microtubulin alteration | No |

TABLE XV ability of Illudin, Syn-Illudin & Acylfulvene to inhibit tumor cell growth.

Mean IC50 value (nM) ± SD, N = 3 unless otherwise indicated

| Analog Number | MV522 Target Cell Line | | 8392B Nontarget Cell Line | |
|---|---|---|---|---|
| | 2 hr exposure | 48 hr exposure | 2 hr exposure | 48 hr exposure |
| 001 | 2200 ± 100 | 350 ± 20 | | 830 ± 100 |
| 002 | 110 ± 40 | 70 ± 10 | 26000 ± 4500 | 800 ± 100 |
| 004 | 4200 | 600 | | |
| 008 | 870 ± 90 | 630 ± 80 | 12200 ± 700 | 15100 ± 2200 |
| 009 | 500 ± 30 | 850 ± 180 | 47100 ± 11000 | 43200 ± 2300 |
| 010 | 8900 ± 1500 | 170 ± 60 | 29400 ± 1600 | 14500 ± 1700 |
| 011 | 4900 ± 900 | 1200 (N = 2) | >100000 | 40400 ± 6700 |
| 012 | 5150 ± 1350 | 320 ± 90 | 42200 ± 5000 | 18800 ± 2800 |
| 013 | 5100 ± 700 | 270 ± 130 | 11900 ± 1300 | 4200 ± 400 |
| 014 | 115 ± 30 | 460 ± 120 | 9650 ± 200 | 1100 ± 300 |
| 015 | 1800 ± 200 | 480 ± 110 | 810 ± 260 | 1300 ± 150 |
| 016 | 490 ± 130 | 440 ± 90 | >100000 | 870 ± 60 |
| 017 | 2400 ± 360 | 320 ± 60 | 14700 ± 900 | |
| 018 | 8800 ± 2900 | | 4200 ± 1300 | |
| 019 | 470 ± 60 | 660 ± 80 | >75000 | |
| 020 | 530 ± 140 | 230 ± 10 | 25000 ± 3100 | |
| 021 | 2400 ± 1000 | 930 ± 250 | 34400 ± 9400 | |
| 022 | 700 ± 200 | 680 ± 180 | 31700 ± 1400 | |
| 023 | 2900 ± 1140 | 2750 ± 500 | >138000 | |
| 024 | 1800 ± 200 | 1200 ± 300 | 12800 ± 2100 | |
| 025 | 1300 ± 310 | 1200 ± 100 | >25000 | |
| 030 | | >3000 | | |
| 031 | | >3000 | | |
| 032 | 600 ± 190 | 210 ± 30 | >30000 | |
| 033 | 10000 ± 1100 | 4600 ± 200 | 29900 ± 3300 | |
| 034 | 1400 ± 170 | 490 ± 40 | >100000 | 4400 ± 200 |
| 035 | 5600 ± 600 | | >150000 | |
| 037 | 26000 ± 5000 | 29200 ± 2300 | >85000 | |

TABLE XV-continued ability of Illudin, Syn-Illudin & Acylfulvene to inhibit tumor cell growth.

Mean IC50 value (nM) ± SD, N = 3 unless otherwise indicated

| Analog Number | MV522 Target Cell Line | | 8392B Nontarget Cell Line | |
|---|---|---|---|---|
| | 2 hr exposure | 48 hr exposure | 2 hr exposure | 48 hr exposure |
| 038 | 750 ± 60 | | 24900 ± 8000 | |
| 039 | 1500 ± 240 | 600 ± 40 | 24600 ± 2400 | 820 ± 250 |
| 040 | 3400 ± 360 | 700 ± 90 | 24000 ± 3300 | 5200 ± 470 |
| 060 | 19400 ± 1800 | | 27600 ± 3000 | |
| 062 | 2600 ± 300 | 660 ± 200 | 37100 ± 2300 | |
| 063 | 43000 ± 5700 | 580 ± 250 | | |
| 064 | 28000 ± 4600 | 1200 ± 300 | | |
| 065 | 6200 ± 1100 | 2500 ± 1200 | | |
| 075 | 19600 ± 9700 | | 62000 ± 3600 | |
| 076 | 24000 ± 6100 | | 39500 ± 7200 | |
| 077 | 9200 ± 1200 | | | |
| 078 | 20400 ± 6300 | | >100000 | |
| 079 | 7700 ± 3500 | | >100000 | |
| 080 | 8800 ± 2400 | | >100000 | |
| 081 | >80000 | | >80000 | |
| 082 | 50600 ± 7100 | | >100000 | |
| 083 | | 37200 ± 2900 | | >42000 |
| 084 | | 28200 ± 1400 | | >42000 |
| 085 | >40000 | >40000 | | |
| 086 | | | | |
| 087 | >40000 | 24700 ± 3900 | >40000 | |
| 088 | | | | |
| 089 | 19300 ± 5700 | 15500 ± 2800 | >60000 | |
| 090 | 2500 ± 400 | 2900 ± 400 | 1600 ± 200 | 3800 ± 300 |
| 094 | 800 ± 100 | 210 ± 20 | 9000 ± 1700 | 110 ± 10 |
| 096 | 2700 ± 400 | 6200 ± 600 | >88000 | >3000 |
| 097 | 2900 ± 100 | | >82000 | |
| 098 | 18800 ± 2500 | 4600 ± 250 | >65000 | 11700 ± 1800 |
| 099 | 8400 ± 1100 | 1800 ± 200 | 4000 ± 400 | 300 ± 20 |
| 100 | >10000 | 1700 ± 500 | | |
| 101 | >8000 | >7500 | | |
| 102 | >13000 | 1300 ± 100 | | |
| 103 | 31800 ± 4900 | 5900 ± 400 | 12100 ± 2000 | 2300 ± 200 |
| 104 | 6300 ± 400 | 6000 ± 500 | 36400 ± 6500 | 2700 ± 600 |
| 105 | 7300 ± 1200 | 2100 ± 400 | >100000 | |
| 106 | 5200 ± 1000 | | >83000 | |
| 107 | >50000 | 1600 ± 100 | >50000 | |
| 108 | 12300 ± 2300 | 520 ± 50 | >55000 | 6000 ± 1600 |
| 109 | >50000 | | >50000 | |
| 110 | >55000 | 1400 ± 100 | >55000 | 25300 ± 2100 |
| 111 | 16700 ± 2100 | 11900 ± 2800 | 34600 ± 2100 | 10200 ± 1000 |
| 112 | 10000 ± 2000 | 6700 ± 1200 | 14900 ± 100 | 5200 ± 300 |
| 113 | 85000 ± 700 | 14100 ± 3000 | >93000 | 7800 ± 1000 |
| 114 | 1500 ± 100 | 260 ± 70 | 25100 ± 1000 | 700 ± 100 |
| 115 | 1500 ± 100 | 70 ± 5 | 1600 ± 700 | 630 ± 60 |
| 116 | 400 ± 100 | 1000 ± 50 | 7000 ± 400 | 170 ± 30 |
| 117 | 1100 ± 100 | 100 ± 30 | 7900 ± 1600 | 10 ± 2 |
| 118 | 14000 ± 2000 | 740 ± 120 | 24500 ± 4500 | 2000 ± 400 |
| 119 | 1100 ± 70 | 270 ± 40 | >33000 | >10000 |
| 120 | 2800 ± 900 | 600 ± 100 | 19100 ± 4600 | 510 ± 110 |
| 121 | 300 ± 10 | 90 ± 10 | 15200 ± 6000 | 1300 ± 500 |
| 122 | 6400 ± 300 | 2400 ± 300 | 14500 ± 1200 | 1100 ± 300 |
| 123 | 1900 ± 400 | 600 ± 60 | 450 ± 30 | 2400 ± 500 |
| 124 | 2800 ± 700 | 870 ± 350 | >30000 | 2400 ± 550 |
| 125 | 3700 ± 600 | 1200 ± 200 | 15500 ± 1400 | 600 ± 100 |
| 126 | 2100 ± 500 | 900 ± 100 | >30000 | 330 ± 80 |
| 127 | 870 ± 30 | 340 ± 90 | >30000 | 100 ± 40 |
| 128 | 840 ± 230 | 370 ± 50 | >35000 | 800 ± 70 |
| 129 | >136000 | 19700 ± 1900 | >136000 | 39400 ± 9200 |
| 130 | 700 ± 100 | 130 ± 40 | 27,000 ± 7000 | 4400 ± 500 |
| 133 | 58800 ± 6600 | 15800 ± 2600 | 12200 ± 2300 | 2700 ± 400 |
| 134 | 50000 ± 6000 | 28000 ± 4000 | 43900 ± 5100 | 8500 ± 2000 |
| 135 | 1600 ± 300 | 22 ± 4 | 70 ± 20 | 22 ± 2 |
| 136 | 430 ± 10 | 130 ± 10 | >6200 | 25 ± 2 |
| 137 | 850 ± 110 | 1200 ± 100 | 8500 ± 1200 | 710 ± 60 |
| 138 | 2100 ± 200 | 1000 ± 200 | 5400 ± 200 | 820 ± 230 |
| 139 | 6400 ± 900 | 3400 ± 500 | 11600 ± 900 | 2600 ± 1000 |
| 140 | 17100 ± 5100 | >14000 | 12700 ± 300 | >14000 |
| 141 | 11400 ± 1000 | 3700 ± 800 | 13700 ± 1900 | 1100 ± 140 |
| 142 | 90 ± 10 | 24 ± 7 | 6400 ± 1100 | 80 ± 6 |
| 143 | 43500 ± 11300 | 11400 ± 1800 | 56500 ± 20000 | 3600 ± 700 |
| 146 | 2500 ± 400 | 740 ± 280 | 13,000 ± 1200 | |

TABLE XV-continued ability of Illudin, Syn-Illudin & Acylfulvene to inhibit tumor cell growth.

| | Mean IC50 value (nM) ± SD, N = 3 unless otherwise indicated | | | |
|---|---|---|---|---|
| Analog | MV522 Target Cell Line | | 8392B Nontarget Cell Line | |
| Number | 2 hr exposure | 48 hr exposure | 2 hr exposure | 48 hr exposure |
| 147 | >76000 | 26100 ± 12900 | >76000 | 43800 ± 3000 |
| 148 | 17100 ± 1100 | 6800 ± 1100 | 61000 ± 11600 | 6700 ± 1600 |
| 149 | 2900 ± 1000 | 1500 500 | 44600 ± 1400 | 4100 ± 900 |
| 150 | 9500 ± 1600 | 1400 ± 400 | 59000 ± 5500 | 10600 ± 800 |
| 151 | 7900 ± 400 | 4200 ± 1600 | 25500 ± 1200 | 6600 ± 2300 |
| 152 | | 6400 ± 1200 | 49000 ± 7700 | 9100 ± 100 |
| 153 | 8700 ± 2700 | 10900 ± 3400 | >90000 | 15800 ± 9600 |
| 154 | >70000 | 61300 ± 10000 | >70000 | 46,700 ± 13100 |
| 155 | 8200 ± 1200 | 3600 ± 400 | 17,000 ± 4000 | 9100 ± 1100 |
| 156 | 7200 ± 500 | 3100 ± 100 | 32,300 ± 9,400 | 5500 ± 1200 |
| 157 | >400,000 | >123,000 | >350,000 | 13100 ± 1600 |
| 158 | >175,000 | >175,000 | >200,000 | 61,000 ± 9,000 |
| 159 | 2700 ± 400 | 120 ± 10 | 13,700 ± 4,200 | <10 nM |
| 160 | 1900 ± 200 | 500 ± 200 | 52,400 ± 17,800 | 3200 ± 1100 |
| 161 | 2800 ± 500 | 3300 ± 700 | 13,800 ± 3,400 | >10,000 |
| 163 | 3500 ± 800 | 820 ± 40 | 18600 ± 800 | 910 ± 100 |
| 164 | | 70 ± 10 | 3500 ± 1600 | 130 ± 40 |
| 165 | 7700 ± 1100 | 290 ± 40 | 11000 ± 3300 | 11000 ± 1000 |
| 166 | 6500 ± 600 | 7200 ± 1900 | 6500 ± 2100 | 6000 ± 1500 |
| 167 | 14800 ± 2200 | | 18500 ± 2300 | |
| 169 | 7100 ± 600 | | 2300 ± 600 | |
| 177 | 7500 ± 800 | 1900 ± 800 | 73000 ± 5000 | 4100 ± 1300 |
| 178 | 21000 ± 4000 | 1000 ± 100 | 32000 ± 9000 | >8000 |
| 180 | 19900 ± 300 | >4000 | 5200 ± 1800 | 660 ± 50 |
| 182 | 99000 ± 12000 | 38000 ± 8200 | 39000 ± 7000 | 18700 ± 2700 |
| 183 | >120,000 | >275,000 | >120,000 | >235,000 |
| 184 | 800 ± 300 | 210 ± 20 | >100,000 | >10000 |
| 185 | 1700 ± 600 | 1900 ± 100 | | |
| 186 | 144000 ± 32000 | 70000 ± 16000 | 79000 ± 24000 | 48000 ± 2000 |
| 187 | 1300 ± 400 | 900 ± 200 | 3200 ± 800 | 3200 ± 700 |
| 189 | 8900 ± 2500 | 6100 ± 2600 | 41,000 ± 3700 | |
| 190 | 19,000 ± 4000 | >9,000 | 56,000 ± 2000 | >9,000 |
| 191 | >140,000 | 49,000 ± 13000 | >140,000 | 15000 ± 4000 |
| 192 | 1,600 ± 200 | 700 ± 100 | 8700 ± 1700 | 200 ± 30 |
| 193 | 1400 ± 400 | 2500 ± 600 | 48,000 ± 7000 | >11,000 |
| 195 | 1400 ± 200 | 390 ± 120 | 21,000 ± 6000 | 4300 ± 1200 |
| 196 | 840 ± 100 | 450 ± 120 | 80,000 ± 5000 | >9,200 |
| 197 | 950 ± 70 | 500 ± 100 | 9500 ± 400 | 11,300 ± 100 |
| 198 | 700 ± 100 | 2800 ± 600 | >8,200 | >82,000 |
| 199 | 4700 ± 600 | 2500 ± 1100 | >93,000 | >9,300 |
| 201 | 360 ± 110 | 260 ± 70 | 13,000 ± 1700 | 26,000 ± 7000 |
| 202 | 1200 ± 100 | 650 ± 100 | >62,000 | >6200 |
| 203 | 760 ± 170 | 940 ± 330 | 48,000 ± 6000 | >5500 |
| 204 | 220 ± 40 | 1600 ± 300 | 4100 ± 800 | 8600 ± 800 |
| 205 | 8400 ± 2200 | 1200 ± 400 | >185,000 | >2,600 |
| 206 | 610 ± 40 | 230 ± 20 | 20,000 ± 1000 | 8200 ± 200 |
| 207 | 570 ± 60 | 410 ± 60 | | |
| 208 | 1200 ± 100 | 930 ± 160 | 25,000 ± 3000 | |
| 209 | 3900 ± 1100 | 610 ± 100 | >90,000 | |
| 210 | 40,000 ± 4000 | 5500 ± 600 | | |
| 211 | 470 ± 120 | 430 ± 100 | 59,000 ± 9000 | |
| 212 | 80 ± 10 | 55 ± 5 | | |
| 213 | 2300 ± 700 | 1700 ± 700 | | |
| 214 | 2900 ± 800 | 360 ± 30 | | |
| 215 | 26,000 ± 3000 | 490 ± 120 | | |
| 216 | 460 ± 60 | 150 ± 40 | | |
| 217 | 2,200 ± 100 | 2,200 ± 100 | 43,000 ± 4,000 | >7,000 |
| 218 | 10,000 ± 3,000 | 600 ± 200 | 15,000 ± 6,000 | 600 ± 100 |
| 219 | >52,000 | >52,00 | >52,000 | >52,000 |
| 220 | 90 ± 10 | 130 ± 10 | 101,000 ± 18,000 | 40,000 ± 3,000 |
| 221 | >21,000 | 2,500 ± 200 | >21,000 | >21,000 |
| 222 | 5,000 ± 100 | 1,100 ± 100 | 9,300 ± 200 | 330 ± 60 |
| 223 | 20,000 ± 3,700 | 2,700 ± 300 | >185,000 | >55,000 |
| 224 | >200,000 | >130,000 | >200,000 | >130,000 |
| 225 | 47,000 ± 4,000 | 55,000 ± 11,000 | >350,000 | 33,000 ± 13,000 |
| 226 | >59,000 | >59,000 | >59,000 | >59,000 |
| 227 | >57,000 | 4,400 ± 700 | >57,000 | 16,000 ± 4,000 |
| 228 | >38,000 | >38,000 | 24,000 ± 3,000 | >38,000 |
| 229 | >56,000 | >2,000 | >56,000 | >2,000 |
| 230 | 620 ± 80 | 100 ± 10 | 38,000 ± 5,000 | 1,000 ± 200 |
| 231 | 1,500 ± 100 | 280 ± 10 | 14,000 ± 4,000 | |
| 232 | 700 ± 100 | 460 ± 60 | 42,000 ± 6,000 | 3,300 ± 600 |

TABLE XV-continued ability of Illudin, Syn-Illudin & Acylfulvene to inhibit tumor cell growth.

Mean IC50 value (nM) ± SD, N = 3 unless otherwise indicated

| Analog Number | MV522 Target Cell Line | | 8392B Nontarget Cell Line | |
|---|---|---|---|---|
| | 2 hr exposure | 48 hr exposure | 2 hr exposure | 48 hr exposure |
| 233 | 3,200 ± 300 | 350 ± 80 | >150,000 | 2,400 ± 700 |
| 234 | 3,000 ± 300 | 1,100 ± 400 | 24,000 ± 6,000 | 9,000 ± 1,000 |
| 235 | 3,500 ± 400 | 2,200 ± 400 | 49,000 ± 6,000 | 6,500 ± 1,600 |
| 236 | 49,000 ± 11,000 | 29,000 ± 5,000 | 48,000 ± 10,000 | |
| 237 | 1,200 ± 300 | 730 ± 140 | 22,000 ± 1,000 | 6,600 ± 900 |
| 238 | 780 ± 190 | 57 ± 8 | 23,000 ± 2,000 | 4,700 ± 1,200 |
| 239 | 420 ± 60 | 70 ± 20 | 39,000 ± 3,000 | 28,000 ± 4,000 |
| 240 | 2,900 ± 100 | 1,300 ± 200 | >24,000 | 1,300 ± 100 |
| 241 | 560 ± 90 | 110 ± 20 | >28,000 | 18,000 ± 4,000 |
| 242 | 2,400 ± 400 | 580 ± 150 | 18,000 ± 2,000 | 2,900 ± 600 |
| 243 | 2,200 ± 500 | 670 ± 240 | 64,000 ± 10,000 | 26,000 ± 6,000 |
| 244 | 1,600 ± 400 | 150 ± 10 | 87,000 ± 11,000 | 35,000 ± 7,000 |
| 245 | 3,400 ± 1000 | 440 ± 90 | 79,000 ± 7,000 | 14,000 ± 1,700 |
| 246 | 2,800 ± 260 | 1,900 ± 450 | 14,000 ± 2,000 | 6,200 ± 1,300 |
| 247 | 6,100 ± 2,000 | 1,200 ± 250 | 10,000 ± 1,400 | 7,100 ± 1,700 |
| 248 | 830 ± 100 | 200 ± 25 | 23,000 ± 1,000 | 610 ± 120 |
| 249 | 4,100 ± 820 | 420 ± 100 | 18,000 ± 3,500 | 19,000 ± 3,800 |
| 250 | 99,000 ± 21,000 | 137,000 ± 14,000 | >275,000 | 137,000 ± 10,000 |
| 251 | 128,000 ± 4,000 | 51,000 ± 1,000 | >275,000 | 82,000 ± 8,000 |
| 252 | >380,000 | 33,000 ± 3,000 | >380,000 | >380,000 |
| 253 | >380,000 | >38,000 | >380,000 | >380,000 |
| 254 | 2,700 ± 800 | 1,100 ± 100 | 43,000 ± 6,000 | >65,000 |
| 255 | 2,900 ± 500 | 55 ± 2 | 119,000 ± 15,000 | 99,000 ± 4,000 |
| 256 | 1,500 ± 200 | 880 ± 200 | 7,500 ± 800 | 7,100 ± 300 |
| 257 | 2,800 ± 600 | 320 ± 30 | 25,000 ± 2,000 | 26,000 ± 3,000 |
| 258 | >45,000 | >45,000 | >45,000 | >45,000 |
| 259 | 16000 ± 3000 | 2400 ± 200 | >85,000 | 4700 ± 400 |
| 260 | 1600 ± 500 | 150 ± 20 | >64,000 | 19000 ± 4500 |
| 261 | 6300 ± 1100 | 1000 ± 150 | 64000 ± 2000 | 38000 ± 2100 |
| 262 | 8700 ± 1300 | 3900 ± 570 | 287000 ± 14000 | 73000 ± 17000 |
| 263 | 2000 ± 300 | 1400 ± 200 | 124000 ± 18000 | 39000 ± 7000 |
| 264 | 1400 ± 100 | 76 ± 17 | >85,000 | 54000 ± 20000 |
| 265 | 810 ± 20 | 8 ± 1 | 1100 ± 200 | 250 ± 80 |
| 266 | 140 ± 20 | 70 ± 18 | 56000 ± 15000 | 32000 ± 7000 |
| 267 | 900 ± 160 | 160 ± 20 | >90,000 | 28000 ± 8000 |
| 268 | 2100 ± 200 | 330 ± 90 | 54,000 ± 16000 | >8,000 |
| 269 | 11000 ± 3000 | 850 ± 320 | 52000 ± 4000 | >7,000 |
| 270 | 8000 ± 1500 | 1300 ± 100 | >84,000 | 7100 ± 700 |
| 271 | 1700 ± 200 | 200 ± 90 | >93,000 | >9,300 |
| 272 | >46,000 | >4,700 | >47,000 | >4,700 |
| 273 | 30000 ± 5000 | >1,500 | >45,000 | >4,500 |
| 274 | 39000 ± 3000 | 1200 ± 300 | >46,000 | >4,500 |
| 275 | 1500 ± 300 | 370 ± 40 | >62,000 | >6,200 |
| 276 | 1500 ± 200 | 760 ± 100 | >61,000 | >6,100 |
| 277 | 760 ± 70 | 190 ± 20 | 31,000 ± 6000 | 9,800 ± 1000 |
| 278 | 1000 ± 200 | 270 ± 10 | >94000 | >9,400 |
| 279 | 1700 ± 400 | 190 ± 20 | >90000 | >9,000 |
| 280 | 2400 ± 800 | <80 | >83000 | >2,800 |
| 281 | 1800 ± 700 | 170 ± 10 | 27000 ± 2000 | 5000 ± 700 |
| 282 | 680 ± 60 | 110 ± 10 | >85000 | >8,500 |
| 283 | 2900 ± 1200 | 300 ± 20 | 40000 ± 4000 | >9,300 |
| 284 | 13,600 (N = 2) | 340 ± 20 | | >8,800 |
| 285 | 3800 ± 1100 | 310 ± 20 | 84000 ± 9000 | 2000 ± 100 |
| 286 | 48000 ± 10000 | 6300 ± 200 | 51000 ± 1700 | >8,800 |
| 287 | 455000 ± 22000 | 1100 ± 100 | 567000 ± 17000 | 4700 ± 400 |
| 288 | 1800 ± 600 | 150 ± 20 | 11000 ± 3200 | ~9,000 |
| 289 | 51 ± 4 | 530 ± 150 | >290000 | >8,800 |
| 294 | 960 ± 170 | | | |
| 295 | 200 ± 44 | | | |
| 296 | 250 (N = 2) | | | |
| 297 | 2200 (N = 1) | | | |
| 298 | >7000 | | | |

SEQUENCE LISTING

Sequence total quantity: 181
SEQ ID NO: 1        moltype = AA  length = 351

```
FEATURE                 Location/Qualifiers
source                  1..351
                        mol_type = protein
                        organism = Homo sapiens
SEQUENCE: 1
MSFPCKFVAS FLLIFNVSSK GAVSKEITNA LETWGALGQD INLDIPSFQM SDDIDDIKWE   60
KTSDKKKIAQ FRKEKETFKE KDTYKLFKNG TLKIKHLKTD DQDIYKVSIY DTKGKNVLEK  120
IFDLKIQERV SKPKISWTCI NTTLTCEVMN GTDPELNLYQ DGKHLKLSQR VITHKWTTSL  180
SAKFKCTAGN KVSKESSVEP VSCPEKGLDI YLIIGICGKG SLLMVFVALL VPYITKRKKQ  240
RSRRNDEELE TRAHRVATEE RGRKPHQIPA STPQNPATSQ HPPPPPGHRS QAPSHRPPPP  300
GHRVQHQPQK RPPAPSGTQV HQQKGPPLPR PRVQPKPPHG AAENSLSPSS N          351

SEQ ID NO: 2            moltype = AA  length = 209
FEATURE                 Location/Qualifiers
source                  1..209
                        mol_type = protein
                        organism = Homo sapiens
SEQUENCE: 2
CDMQSGTHWR VLGLCLLSVG VWGQDGNEEM GGITQTPYKV SISGTTVILT CPQYPGSEIL   60
WQHNDKNIGG DEDDKNIGSD EDHLSLKEFS ELEQSGYYVC YPRGSKPEDA NFYLYLRARV  120
CENCMEMDVM SVATIVIVDI CITGLLLLV YYWSKNRKAK AKPVTRGAGA GGRQRGQNKE  180
RPPPVPNPDY EPIRKGQRDL YSGLNQRRI                                   209

SEQ ID NO: 3            moltype = AA  length = 495
FEATURE                 Location/Qualifiers
source                  1..495
                        mol_type = protein
                        organism = Homo sapiens
SEQUENCE: 3
MPMGSLQPLA TLYLLGMLVA SCLGRLSWYD PDFQARLTRS NSKCQGQLEV YLKDGWHMVC   60
SQSWGRSSKQ WEDPSQASKV CQRLNCGVPL SLGPFLVTYT PQSSIICYGQ LGSFSNCSHS  120
RNDMCHSLGL TCLEPQKTTP PTTRPPPTTT PEPTAPPRLQ LVAQSGGQHC AGVVEFYSGS  180
LGGTISYEAQ DKTQDLENFL CNNLQCGSFL KHLPETEAGR AQDPGEPREH QPLPIQWKIQ  240
NSSCTSLEHC FRKIKPQKSG RVLALLCSGF QPKVQSRLVG GSSICEGTVE VRQGAQWAAL  300
CDSSSARSSL RWEEVCREQQ CGSVNSYRVL DAGDPTSRGL FCPHQKLSQC HELWERNSYC  360
KKVFVTCQDP NPAGLAAGTV ASIILALVLL VVLLVVCGPL AYKKLVKKFR QKKQRQWIGP  420
TGMNQNMSFH RNHTATVRSH AENPTASHVD NEYSQPPRNS HLSAYPALEG ALHRSSMQPD  480
NSSDSDYDLH GAQRL                                                  495

SEQ ID NO: 4            moltype = AA  length = 240
FEATURE                 Location/Qualifiers
source                  1..240
                        mol_type = protein
                        organism = Homo sapiens
SEQUENCE: 4
MAGPPRLLLL PLLLALARGL PGALAAQEVQ QSPHCTTVPV GASVNITCST SGGLRGIYLR   60
QLGPQPQDII YYEDGVVPTT DRRFRGRIDF SGSQDNLTIT MHRLQLSDTG TYTCQAITEV  120
NVYGSGTLVL VTEEQSQGWH RCSDAPPRAS ALPAPPTGSA LPDPQTASAL PDPPAASALP  180
AALAVISFLL GLGLGVACVL ARTQIKKLCS WRDKNSAACV VYEDMSHSRC NTLSSPNQYQ  240

SEQ ID NO: 5            moltype = AA  length = 556
FEATURE                 Location/Qualifiers
source                  1..556
                        mol_type = protein
                        organism = Homo sapiens
SEQUENCE: 5
MPPPRLLFFL LFLTPMEVRP EEPLVVKVEE GDNAVLQCLK GTSDGPTQQL TWSRESPLKP   60
FLKLSLGLPG LGIHMRPLAS WLFIFNVSQQ MGGFYLCQPG PPSEKAWQPG WTVNVEGSGE  120
LFRWNVSDLG GLGCGLKNRS SEGPSSPSGK LMSPKLYVWA KDRPEIWEGE PPCVPPRDSL  180
NQSLSQDLTM APGSTLWLSC GVPPDSVSRG PLSWTHVHPK GPKSLLSLEL KDDRPARDMW  240
VMETGLLLPR ATAQDAGKYY CHRGNLTMSF HLEITARPVL WHWLLRTGGW KVSAVTLAYL  300
IFCLCSLVGI LHLQRALVLR RKRKRMTDPT RRFFKVTPPP GSGPQNQYGN VLSLPTPTSG  360
LGRAQRWAAG LGGTAPSYGN PSSDVQADGA LGSRSPPGVG PEEEEGEGYE EPDSEEDSEF  420
YENDSNLGQD QLSQDGSGYE NPEDEPLGPE DEDSFSNAES YENEDEELTQ PVARTMDFLS  480
PHGSAWDPSR EATSLGSQSY EDMRGILYAA PQLRSIRGQP GPNHEEDADS YENMDNPDGP  540
DPAWGGGGRM GTWSTR                                                 556

SEQ ID NO: 6            moltype = AA  length = 297
FEATURE                 Location/Qualifiers
source                  1..297
                        mol_type = protein
                        organism = Homo sapiens
SEQUENCE: 6
MTTPRNSVNG TFPAEPMKGP IAMQSGPKPL FRRMSSLVGP TQSFFMRESK TLGAVQIMNG   60
LFHIALGGLL MIPAGIYAPI CVTVWYPLWG GIMYIISGSL LAATEKNSRK CLVKGKMIMN  120
SLSLFAAISG MILSIMDILN IKISHFLKME SLNFIRAHTP YINIYNCEPA NPSEKNSPST  180
QYCYSIQSLF LGILSVMLIF AFFQELVIAG IVENEWKRTC SRPKSNIVLL SAEEKKEQTI  240
EIKEEVVGLT ETSSQPKNEE DIEIIPIQEE EEEETETNFP EPPQDQESSP IENDSSP    297
```

```
SEQ ID NO: 7                moltype = AA  length = 847
FEATURE                     Location/Qualifiers
source                      1..847
                            mol_type = protein
                            organism = Homo sapiens
SEQUENCE: 7
MHLLGPWLLL LVLEYLAFSD SSKWVFEHPE TLYAWEGACV WIPCTYRALD GDLESFILFH    60
NPEYNKNTSK FDGTRLYEST KDGKVPSEQK RVQFLGDKNK NCTLSIHPVH LNDSGQLGLR   120
MESKTEKWME RIHLNVSERP FPPHIQLPPE IQESQEVTLT CLLNFSCYGY PIQLQWLLEG   180
VPMRQAAVTS TSLTIKSVFT RSELKFSPQW SHHGKIVTCQ LQDADGKFLS NDTVQLNVKH   240
TPKLEIKVTP SDAIVREGDS VTMTCEVSSS NPEYTTVSWL KDGTSLKKQN TFTLNLREVT   300
KDQSGKYCCQ VSNDVGPGRS EEVFLQVQYA PEPSTVQILH SPAVEGSQVE FLCMSLANPL   360
PTNYTWYHNG KEMQGRTEEK VHIPKILPWH AGTYSCVAEN ILGTGQRGPG AELDVQYPPK   420
KVTTVIQNPM PIREGDTVTL SCNYNSSNPS VTRYEWKPHG AWEEPSLGVL KIQNVGWDNT   480
TIACAACNSW CSWASPVALN VQYAPRDVRV RKIKPLSEIH SGNSVSLQCD FSSSHPKEVQ   540
FFWEKNGRLL GKESQLNFDS ISPEDAGSYS CWVNNSIGQT ASKAWTLEVL YAPRRLVSM   600
SPGDQVMEGK SATLTCESDA NPPVSHYTWF DWNNQSLPYH SQKLRLEPVK VQHSGAYWCQ   660
GTNSVGKGRS PLSTLTVYYS PETIGRRVAV GLGSCLAILI LAICGLKLQR RWKRTQSQQG   720
LQENSSGQSF FVRNKKVRRA PLSEGPHSLG CYNPMMEDGI SYTTLRFPEM NIPRTGDAES   780
SEMQRPPPDC DDTVTYSALH KRQVGDYENV IPDFPEDEGI HYSELIQFGV GERPQAQENV   840
DYVILKH                                                             847

SEQ ID NO: 8                moltype = AA  length = 272
FEATURE                     Location/Qualifiers
source                      1..272
                            mol_type = protein
                            organism = Homo sapiens
SEQUENCE: 8
MDSYLLMWGL LTFIMVPGCQ AELCDDDPPE IPHATFKAMA YKEGTMLNCE CKRGFRRIKS    60
GSLYMLCTGN SSHSSWDNQC QCTSSATRNT TKQVTPQPEE QKERKTTEMQ SPMQPVDQAS   120
LPGHCREPPP WENEATERIY HFVVGQMVYY QCVQGYRALH RGPAESVCKM THGKTRWTQP   180
QLICTGEMET SQFPGEEKPQ ASPEGRPESE TSCLVTTTDF QIQTEMAATM ETSIFTTEYQ   240
VAVAGCVFLL ISVLLLSGLT WQRRQRKSRR TI                                 272

SEQ ID NO: 9                moltype = AA  length = 594
FEATURE                     Location/Qualifiers
source                      1..594
                            mol_type = protein
                            organism = Homo sapiens
SEQUENCE: 9
RVLLAALGLL FLGALRAFPQ DRPFEDTCHG NPSHYYDKAV RRCCYRCPMG LFPTQQCPQR    60
PTDCRKQCEP DYYLDEADRC TACVTCSRDD LVEKTPCAWN SSRVCECRPG MFCSTSAVNS   120
CARCFFHSVC PAGMIVKFPG TAQKNTVCEP ASPGVSPACA SPENCKEPSS GTIPQAKPTP   180
VSPATSSAST MPVRGGTRLA QEAASKLTRA PDSPSSVGRP SSDPGLSPTQ PCPEGSGDCR   240
KQCEPDYYLD EAGRCTACVS CSRDDLVEKT PCAWNSSRTC ECRPGMICAT SATNSCARCV   300
PYPICAAETV TKPQDMAEKD TTFEAPPLGT QPDCNPTPEN GEAPASTSPT QSLLVDSQAS   360
KTLPIPTSAP VALSSTGKPV LDAGPVLFWV ILVLVVVVGS SAFLLCHRRA CRKRIRQKLH   420
LCYPVQTSQP KLELVDSRPR RSSTQLRSGA SVTEPVAEER GLMSQPLMET CHSVGAAYLE   480
SLPLQDASPA GGPSSPRDLP EPRVSTEHTN NKIEKIYIMK ADTVIVGTVK AELPEGRGLA   540
GPAEPELEEE LEADHTPHYP EQETEPPLGS CSDVMLSVEE EGKEDPLPTA ASGK         594

SEQ ID NO: 10               moltype = AA  length = 364
FEATURE                     Location/Qualifiers
source                      1..364
                            mol_type = protein
                            organism = Homo sapiens
SEQUENCE: 10
MPLLLLLPLL WAGALAMDPN FWLQVQESVT VQEGLCVLVP CTFFHPIPYY DKNSPVHGYW    60
FREGAIISRD SPVATNKLDQ EVQEETQGRF RLLGDPSRNN CSLSIVDARR RDNGSYFFRM   120
ERGSTKYSYK SPQLSVHVTD LTHRPKILIP GTLEPGHSKN LTCSVSWACE QGTPPIFSWL   180
SAAPTSLGPR TTHSSVLIIT PRPQDHGTNL TCQVKFAGAG VTTERTIQLN VTYVPQNPTT   240
GIFPGDGSGK QETRAGVVHG AIGGAGVTAL LALCLCLIFF IVKTHRRKAA RTAVGRNDTH   300
PTTGSASPKH QKKSKLHGPT ETSSCSGAAP TVEMDEELHY ASLNFHGMNP SKDTSTEYSE   360
VRTQ                                                                364

SEQ ID NO: 11               moltype = AA  length = 281
FEATURE                     Location/Qualifiers
source                      1..281
                            mol_type = protein
                            organism = Homo sapiens
SEQUENCE: 11
MSAQESCLSL IKYFLFVFNL FFFVLGSLIF CFGIWILIDK TSFVSFVGLA FVPLQIWSKV    60
LAISGIFTMG IALLGCVGAL KELRCLLGLY FGMLLLLFAT QITLGILIST QRAQLERSLR   120
DVVEKTIQKY GTNPEETAAE ESWDYVQFQL RCCGWHYPQD WFQVLILRIS GSEAHRVPCS   180
CYNLSATNDS TILDKVILPQ LSRLGHLARS RHSADICAVP AESHIYREGC AQGLQKWLHN   240
NLISIVGICL GVGLLELGFM TLSIFLCRNL DHVYNRLARY R                       281

SEQ ID NO: 12               moltype = AA  length = 742
FEATURE                     Location/Qualifiers
```

```
source                     1..742
                           mol_type = protein
                           organism = Homo sapiens
SEQUENCE: 12
MDKFWWHAAW GLCLVPLSLA QIDLNITCRF AGVFHVEKNG RYSISRTEAA DLCKAFNSTL    60
PTMAQMEKAL SIGFETCRYG FIEGHVVIPR IHPNSICAAN NTGVYILTSN TSQYDTYCFN   120
ASAPPEEDCT SVTDLPNAFD GPITITIVNR DGTRYVQKGE YRTNPEDIYP SNPTDDDVSS   180
GSSSERSSTS GGYIFYTFST VHPIPDEDSP WITDSTDRIP ATTLMSTSAT ATETATKRQE   240
TWDWFSWLFL PSESKNHLHT TTQMAGTSSN TISAGWEPNE ENEDERDRHL SFSGSGIDDD   300
EDFISSTIST TPRAFDHTKQ NQDWTQWNPS HSNPEVLLQT TTRMTDVDRN GTTAYEGNWN   360
PEAHPPLIHH EHHEEEETPH STSTIQATPS STTEETATQK EQWFGNRWHE GYRQTPKEDS   420
HSTTGTAAAS AHTSHPMQGR TTPSPEDSSW TDFFNPISHP MGRGHQAGRR MDMDSSHSIT   480
LQPTANPNTG LVEDLDRTGP LSMTTQQSNS QSFSTSHEGL EEDKDHPTTS TLTSSNRNDV   540
TGGRRDPNHS EGSTTLLEGY TSHYPHTKES RTFIPVTSAK TGSFGVTAVT VGDSNSNVNR   600
SLSGDQDTFH PSGGSHTTHG SESDGHSHGS QEGGANTTSG PIRTPQIPEW LIILASLLAL   660
ALILAVCIAV NSRRRCGQKK KLVINSGNGA VEDRKPSGLN GEASKSQEMV HLVNKESSET   720
PDQFMTADET RNLQNVDMKI GV                                           742

SEQ ID NO: 13              moltype = AA  length = 429
FEATURE                    Location/Qualifiers
source                     1..429
                           mol_type = protein
                           organism = Homo sapiens
SEQUENCE: 13
MDKFWWHAAW GLCLVPLSLA QIDLNITCRF AGVFHVEKNG RYSISRTEAA DLCKAFNSTL    60
PTMAQMEKAL SIGFETCRYG FIEGHVVIPR IHPNSICAAN NTGVYILTSN TSQYDTYCFN   120
ASAPPEEDCT SVTDLPNAFD GPITITIVNR DGTRYVQKGE YRTNPEDIYP SNPTDDDVSS   180
GSSSERSSTS GGYIFYTFST VHPIPDEDSP WITDSTDRIP ATNRNDVTGG RRDPNHSEGS   240
TTLLEGYTSH YPHTKESRTF IPVTSAKTGS FGVTAVTVGD SNSNVRSLS GDQDTFHPSG    300
GSHTTHGSES DGHSHGSQEG GANTTSGPIR TPQIPEWLII LASLLALALI LAVCIAVNSR   360
RRCGQKKKLV INSGNGAVED RKPSGLNGEA SKSQEMVHLV NKESSETPDQ FMTADETRNL   420
QNVDMKIGV                                                          429

SEQ ID NO: 14              moltype = AA  length = 848
FEATURE                    Location/Qualifiers
source                     1..848
                           mol_type = protein
                           organism = Homo sapiens
SEQUENCE: 14
MLQTKDLIWT LFFLGTAVSL QVDIVPSQGE ISVGESKFFL CQVAGDAKDK DISWFSPNGE    60
KLTPNQQRIS VVWNDDSSST LTIYNANIDD AGIYKCVVTG EDGSESEATV NVKIFQKLMF   120
KNAPTPQEFR EGEDAVIVCD VVSSLPPTII WKHKGRDVIL KKDVRFIVLS NNYLQIRGIK   180
KTDEGTYRCE GRILARGEIN FKDIQVNVNV PPTIRARQNI VNATANLGQS VTLVCDAERF   240
PEPTMSWTKD GEQIEQEEDD EKYIFSDDSS QLTIKKVDKN DEAEYICIAE NKAGEQDATI   300
HLKVFAKPKI TYVENQTAME LEEQVTLTCE ASGDPIPSIT WRTSTRNISS EEKTLDGHMV   360
VRSHARVSSL TLKSIQYTDA GEYICTASNT IGQDSQSMYL EVQYAPKLQG PVAVYTWEGN   420
QVNITCEVFA YPSATISWFR DGQLLPSSNY SNIKIYNTPS ASYLEVTPDS ENDFGNYNCT   480
AVNRIGQESF EFILVQADTP SSPSIDQVEP YSSTAQVQFD EPEATGGVPI LKYKAEWRAV   540
GEEVWHSKWY DAKEASMEGI VTIVGLKPET TYAVRLAALN GKGLGEISAA SEFKTQPVQG   600
EPSAPKLEGQ MGEDGNSIKV NLIKQDDGGS PIRHYLVRYR ALSSEWKPEI RLPSGSDHVM   660
LKSLDWNAEY EVYVVAENQQ GKSKAAHFVF RTSAQPTAIP ANGSPTSGLS TGAIVGILIV   720
IFVLLLVVVD ITCYFLNKCG LFMCIAVNLC GKAGPGAKGK DMEEGKAAFS KDESKEPIVE   780
VRTEEERTPN HDGGKHTEPN ETTPLTEPEK GPVEAKPECQ ETETKPAPAE VKTVPNDATQ   840
TKENESKA                                                           848

SEQ ID NO: 15              moltype = AA  length = 193
FEATURE                    Location/Qualifiers
source                     1..193
                           mol_type = protein
                           organism = Homo sapiens
SEQUENCE: 15
MPEEGSGCSV RRRPYGCVLR AALVPLVAGL VICLVVCIQR FAQAQQQLPL ESLGWDVAEL    60
QLNHTGPQQD PRLYWQGGPA LGRSFLHGPE LDKGQLRIHR DGIYMVHIQV TLAICSSTTA   120
SRHHPTTLAV GICSPASRSI SLLRLSFHQG CTIASQRLTP LARGDTLCTN LTGTLLPSRN   180
TDETFFGVQW VRP                                                     193

SEQ ID NO: 16              moltype = AA  length = 296
FEATURE                    Location/Qualifiers
source                     1..296
                           mol_type = protein
                           organism = Homo sapiens
SEQUENCE: 16
MHRRRSRSCR EDQKPVMDDQ RDLISNNEQL PMLGRRPGAP ESKCSRGALY TGFSILVTLL    60
LAGQATTAYF LYQQQGRLDK LTVTSQNLQL ENLRMKLPKP PKPVSKMRMA TPLLMQALPM   120
GALPQGMQN  ATKYGNMTED HVMHLLQNAD PLKVYPPLKG SFPENLRHLK NTMETIDWKV   180
FESWMHHWLL FEMSRHSLEQ KPTDAPPKVL TKCQEEVSHI PAVHPGSFRP KCDENGNYLP   240
LQCYGSIGYC WCVFPNGTEV PNTRSRGHHN CSESLELEDP SSGLGVTKQD LGPVPM       296

SEQ ID NO: 17              moltype = AA  length = 226
```

```
FEATURE                Location/Qualifiers
source                 1..226
                       mol_type = protein
                       organism = Homo sapiens
SEQUENCE: 17
MPGGPGVLQA LPATIFLLFL LSAVYLGPGC QALWMHKVPA SLMVSLGEDA HFQCPHNSSN    60
NANVTWWRVL HGNYTWPPEF LGPGEDPNGT LIIQNVNKSH GGIYVCRVQE GNESYQQSCG   120
TYLRVRQPPP RPFLDMGEGT KNRIITAEGI ILLFCAVVPG TLLLFRKRWQ NEKLGLDAGD   180
EYEDENLYEG LNLDDCSMYE DISRGLQGTY QDVGSLNIGD VQLEKP                  226

SEQ ID NO: 18          moltype = AA   length = 229
FEATURE                Location/Qualifiers
source                 1..229
                       mol_type = protein
                       organism = Homo sapiens
SEQUENCE: 18
MARLALSPVP SHWMVALLLL LSAEPVPAAR SEDRYRNPKG SACSRIWQSP RFIARKRGFT    60
VKMHCYMNSA SGNVSWLWKQ EMDENPQQLK LEKGRMEESQ NESLATLTIQ GIRFEDNGIY   120
FCQQKCNNTS EVYQGCGTEL RVMGFSTLAQ LKQRNTLKDG IIMIQTLLII LFIIVPIFLL   180
LDKDDSKAGM EEDHTYEGLD IDQTATYEDI VTLRTGEVKW SVGEHPGQE               229

SEQ ID NO: 19          moltype = AA   length = 288
FEATURE                Location/Qualifiers
source                 1..288
                       mol_type = protein
                       organism = Homo sapiens
SEQUENCE: 19
MGHTRRQGTS PSKCPYLNFF QLLVLAGLSH FCSGVIHVTK EVKEVATLSC GHNVSVEELA    60
QTRIYWQKEK KMVLTMMSGD MNIWPEYKNR TIFDITNNLS IVILALRPSD EGTYECVVLK   120
YEKDAFKREH LAEVTLSVKA DFPTPSISDF EIPTSNIRRI ICSTSGGFPE PHLSWLENGE   180
ELNAINTTVS QDPETELYAV SSKLDFNMTT NHSFMCLIKY GHLRVNQTFN WNTTKQEHFP   240
DNLLPSWAIT LISVNGIFVI CCLTYCFAPR CRERRRNERL RRESVRPV                288

SEQ ID NO: 20          moltype = AA   length = 329
FEATURE                Location/Qualifiers
source                 1..329
                       mol_type = protein
                       organism = Homo sapiens
SEQUENCE: 20
MDPQCTMGLS NILFVMAFLL SGAAPLKIQA YFNETADLPC QFANSQNQSL SELVVFWQDQ    60
ENLVLNEVYL GKEKFDSVHS KYMGRTSFDS DSWTLRLHNL QIKDKGLYQC IIHHKKPTGM   120
IRIHQMNSEL SVLANFSQPE IVPISNITEN VYINLTCSSI HGYPEPKKMS VLLRTKNSTI   180
EYDGVMQKSQ DNVTELYDVS ISLSVSFPDV TSNMTIFCIL ETDKTRLLSS PFSIELEDPQ   240
PPPDHIPWIT AVLPTVIICV MVFCLILWKW KKKKRPRNSY KCGTNTMERE ESEQTKKREK   300
IHIPERSDEA QRVFKSSKTS SCDKSDTCF                                     329

SEQ ID NO: 21          moltype = AA   length = 310
FEATURE                Location/Qualifiers
source                 1..310
                       mol_type = protein
                       organism = Homo sapiens
SEQUENCE: 21
MRRAALWLWL CALALSLQPA LPQIVATNLP PEDQDGSGDD SDNFSGSGAG ALQDITLSQQ    60
TPSTWKDTQL LTAIPTSPEP TGLEATAAST STLPAGEGPK EGEAVVLPEV EPGLTAREQE   120
ATPRPRETTQ LPTTHQASTT TATTAQEPAT SHPHRDMQPG HHETSTPAGP SQADLHTPHT   180
EDGGPSATER AAEDGASSQL PAAEGSGEQD FTFETSGENT AVVAVEPDRR NQSPVDQGAT   240
GASQGLLDRK EVLGGVIAVG LVGLIFAVCL VGFMLYRMKK KDEGSYSLEE PKQANGGAYQ   300
KPTKQEEFYA                                                          310

SEQ ID NO: 22          moltype = AA   length = 459
FEATURE                Location/Qualifiers
source                 1..459
                       mol_type = protein
                       organism = Homo sapiens
SEQUENCE: 22
MAPLCPSPWL PLLIPAPAPG LTVQLLLSLL LLVPVHPQRL PRMQEDSPLG GGSSGEDDPL    60
GEEDLPSEED SPREEDPPGE EDLPGEEDLP GEEDLPEVKP KSEEEGSLKL EDLPTVEAPG   120
DPQEPQNNAH RDKEGDDQSH WRYGGDPPWP RVSPACAGRF QSPVDIRPQL AAFCPALRPL   180
ELLGFQLPPL PELRLRNNGH SVQLTLPPGL EMALGPGREY RALQLHLHWG AAGRPGSEHT   240
VEGHRFPAEI HVVHLSTAFA RVDEALGRPG GLAVLAAFLE EGPEENSAYE QLLSRLEEIA   300
EEGSETQVPG LDISALLPSD FSRYFQYEGS LTTPPCAQGV IWTVFNQTVM LSAKQLHTLS   360
DTLWGPGDSR LQLNFRATQP LNGRVIEASF PAGVDSSPRA AEPVQLNSCL AAGDILALVF   420
GLLFAVTSVA FLVQMRRQHR RGTKGGVSYR PAEVAETGA                          459

SEQ ID NO: 23          moltype = AA   length = 1048
FEATURE                Location/Qualifiers
source                 1..1048
                       mol_type = protein
                       organism = Homo sapiens
```

```
SEQUENCE: 23
MAFPPRRRLR LGPRGLPLLL SGLLLPLCRA FNLDVDSPAE YSGPEGSYFG FAVDFFVPSA     60
SSRMFLLVGA PKANTTQPGI VEGGQVLKCD WSSTRRCQPI EFDATGNRDY AKDDPLEFKS    120
HQWFGASVRS KQDKILACAP LYHWRTEMKQ EREPVGTCFL QDGTKTVEYA PCRSQDIDAD    180
GQGFCQGGFS IDFTKADRVL LGGPGSFYWQ GQLISDQVAE IVSKYDPNVY SIKYNNQLAT    240
RTAQAIFDDS YLGYSVAVGD FNGDGIDDFV SGVPRAARTL GMVYIYDGKN MSSLYNFTGE    300
QMAAYFGFSV AATDINGDDY ADVFIGAPLF MDRGSDGKLQ EVGQVSVSLQ RASGDFQTTK    360
LNGFEVFARF GSAIAPLGDL DQDGFNDIAI AAPYGGEDKK GIVYIFNGRS TGLNAVPSQI    420
LEGQWAARSM PPSFGYSMKG ATDIDKNGYP DLIVGAFGVD RAILYRARPV ITVNAGLEVY    480
PSILNQDNKT CSLPGTALKV SCFNVRFCLK ADGKGVLPRK LNFQVELLLD KLKQKGAIRR    540
ALFLYSRSPS HSKNMTISRG GLMQCEELIA YLRDESEFRD KLTPITIFME YRLDYRTAAD    600
TTGLQPILNQ FTPANISRQA HILLDCGEDN VCKPKLEVSV DSDQKKIYIG DDNPLTLIVK    660
AQNQGEGAYE AELIVSIPLQ ADFIGVVRRN EALARLSCAF KTENQTRQVV CDLGNPMKAG    720
TQLLAGLRFS VHQQSEMDTS VKFDLQIQSS NLFDKVSPVV SHKVDLAVLA AVEIRGVSSP    780
DHIFLPIPNW EHKENPETEE DVGPVVQHIY ELRNNGPSSF SKAMLHLQWP YKYNNNTLLY    840
ILHYDIDGPM NCTSDMEINP LRIKISSLQT TEKNDTVAGQ GERDHLITKR DLALSEGDIH    900
TLGCGVAQCL KIVCQVGRLD RGKSAILYVK SLLWTETFMN KENQNHSYSL KSSASFNVIE    960
FPYKNLPIED ITNSTLVTTN VTWGIQPAPM PVPVWVIILA VLAGLLLLAV LVFVMYRMGF   1020
FKRVRPPQEE QEREQLQPHE NGEGNSET                                      1048

SEQ ID NO: 24         moltype = AA  length = 976
FEATURE               Location/Qualifiers
source                1..976
                      mol_type = protein
                      organism = Homo sapiens
SEQUENCE: 24
MELQAARACF ALLWGCALAA AAAAQGKEVV LLDFAAAGGE LGWLTHPYGK GWDLMQNIMN     60
DMPIYMYSVC NVMSGDQDNW LRTNWVYRGE AERIFIELKF TVRDCNSFPG GASSCKETFN    120
LYYAESDLDY GTNFQKRLFT KIDTIAPDEI TVSSDFEARH VKLNVEERSV GPLTRKGFYL    180
APQDIGACVA LLSVRVYYKK CPELLQGLAH FPETIAGSDA PSLATVAGTC VDHAVVPPGG    240
EEPRMHCAVD GEWLVPIGQC LCQAGYEKVE DACQACSPGF FKFEASESPC LECPEHTLPS    300
PEGATSCECE EGFFRAPQDP ASMPCTRPPS APHYLTAVGM GAKVELRWTP PQDSGGREDI    360
VYSVTCEQCW PESGECGPCE ASVRYSEPPH GLTRTSVTVS DLEPHMNYTF TVEARNGVSG    420
LVTSRSFRTA SVSINQTEPP KVRLEGRSTT SLSVSWSIPP PQQSRVWKYE VTYRKKGDSN    480
SYNVRRTEGF SVTLDDLAPD TTYLVQVQAL TQEGQGAGSK VHEFQTLSPE GSGNLAVIGG    540
VAVGVVLLLV LAGVGFFIHR RRKNQRARQS PEDVYFSKSE QLKPLKTYVD PHTYEDPNQA    600
VLKFTTEIHP SCVTRQKVIG AGEFGEVYKG MLKTSSGKKE VPVAIKTLKA GYTEKQRVDF    660
LGEAGIMGQF SHHNIIRLEG VISKYKPMMI ITEYMENGAL DKFLREKDGE FSVLQLVGML    720
RGIAAGMKYL ANMNYVHRDL AARNILVNSN LVCKVSDFGL SRVLEDDPEA TYTTSGGKIP    780
IRWTAPEAIS YRKFTSASDV WSFGIVMWEV MTYGERPYWE LSNHEVMKAI NDGFRLPTPM    840
DCPSAIYQLM MQCWQQERAR RPKFADIVSI LDKLIRAPDS LKTLADFDPR VSIRLPSTSG    900
SEGVPFRTVS EWLESIKMQQ YTEHFMAAGY TAIEKVVQMT NDDIKRIGVR LPGHQKRIAY    960
SLLGLKDQVN TVGIPI                                                    976

SEQ ID NO: 25         moltype = AA  length = 188
FEATURE               Location/Qualifiers
source                1..188
                      mol_type = protein
                      organism = Homo sapiens
SEQUENCE: 25
MDCRKMARFS YSVIWIMAIS KVFELGLVAG LGHQEFARPS RGYLAFRDDS IWPQEEPAIR     60
PRSSQRVPPM GIQHSKELNR TCCLNGGTCM LGSFCACPPS FYGRNCEHDV RKENCGSVPH    120
DTWLPKKCSL CKCWHGQLRC FPQAFLPGCD GLVMDEHLVA SRTPELPPSA RTTTFMLVGI    180
CLSIQSYY                                                             188

SEQ ID NO: 26         moltype = AA  length = 264
FEATURE               Location/Qualifiers
source                1..264
                      mol_type = protein
                      organism = Homo sapiens
SEQUENCE: 26
MTPGTQSPFF LLLLLTVLTA TTAPKPATVV TGSGHASSTP GGEKETSATQ RSSVPSSTEK     60
NAFNSSLEDP STDYYQELQR DISEMFLQIY KQGGFLGLSN IKFRPGSVVV QLTLAFREGT    120
INVHDVETQF NQYKTEAASR YNLTISDVSV SDVPFPFSAQ SGAGVPGWGI ALLVLVCVLV    180
ALAIVYLIAL AVCQCRRKNY GQLDIFPARD TYHPMSEYPT YHTHGRYVPP SSTDRSPYEK    240
VSAGNGGSSL SYTNPAVAAT SANL                                           264

SEQ ID NO: 27         moltype = AA  length = 875
FEATURE               Location/Qualifiers
source                1..875
                      mol_type = protein
                      organism = Homo sapiens
SEQUENCE: 27
MESTLTLATE QPVKKNTLKK YKIACIVLLA LLVIMSLGLG LGLGLRKLEK QGSCRKKCFD     60
ASFRGLENCR CDVACKDRGD CCWDFEDTCV ESTRIWMCNK FRCGETRLEA SLCSCSDDCL    120
QRKDCCADYK SVCQGETSWL EENCDTAQQS QCPEGFDLPP VILFSMDGFR AEYLYTWDTL    180
MPNINKLKTC GIHSKYMRAM YPTKTFPNHY TIVTGLYPES HGIIDNNMYD VNLNKNFSLS    240
SKEQNNPAWW HGQPMWLTAM YQGLKAATYF WPGSEVAING SFPSIYMPYN GSVPFEERIS    300
TLLKWLDLPK AERPRFYTMY FEEPDSSGHA GGPVSARVIK ALQVVDHAFG MLMEGLKQRN    360
```

```
LHNCVNIIL    ADHGMDQTYC  NKMEYMTDYF  PRINFFYMYE  GPAPRIRAHN  IPHDFFSFNS    420
EEIVRNLSCR   KPDQHFKPYL  TPDLPKRLHY  AKNVRIDKVH  LFVDQQWLAV  RSKSNTNCGG    480
GNHGYNNEFR   SMEAIFLAHG  PSFKEKTEVE  PFENIEVYNL  MCDLLRIQPA  PNNGTHGSLN    540
HLLKVPFYEP   SHAEEVSKFS  VCGFANPLPT  ESLDCFCPHL  QNSTQLEQVN  QMLNLTQEEI    600
TATVKVNLPF   GRPRVLQKNV  DHCLLYHREY  VSGFGKAMRM  PMWSSYTVPQ  LGDTSPLPPT    660
VPDCLRADVR   VPPSESQKCS  FYLADKNITH  GFLYPPASNR  TSDSQYDALI  TSNLVPMYEE    720
FRKMWDYFHS   VLLIKHATER  NGVNVVSGPI  FDYNYDGHFD  APDEITKHLA  NTDVPIPTHY    780
FVVLTSCKNK   SHTPENCPGW  LDVLPFIIPH  RPTNVESCPE  GKPEALWVEE  RFTAHIARVR    840
DVELLTGLDF   YQDKVQPVSE  ILQLKTYLPT  FETTI                                 875

SEQ ID NO: 28            moltype = AA   length = 510
FEATURE                  Location/Qualifiers
source                   1..510
                         mol_type = protein
                         organism = Homo sapiens
SEQUENCE: 28
MPLSLGAEMW   GPEAWLLLLL  LLASFTGRCP  AGELETSDVV  TVVLGQDAKL  PCFYRGDSGE     60
QVGQVAWARV   DAGEGAQELA  LLHSKYGLHV  SPAYEGRVEQ  PPPPRNPLDG  SVLLRNAVQA    120
DEGEYECRVS   TFPAGSFQAR  LRLRVLVPPL  PSLNPGPALE  EGQGLTLAAS  CTAEGSPAPS    180
VTWDTEVKGT   TSSRSFKHSR  SAAVTSEFHL  VPSRSMNGQP  LTCVVSHPGL  LQDQRITHIL    240
HVSFLAEASV   RGLEDQNLWH  IGREGAMLKC  LSEGQPPPSY  NWTRLDGPLP  SGVRVDGDTL    300
GFPPLTTEHS   GIYVCHVSNE  FSSRDSQVTV  DVLDPQGDLS  KQVDLVSASV  VVVGVIAALL    360
FCLLVVVVVL   MSRYHRRKAQ  QMTQKYEEEL  TLTRENSIRR  LHSHHTDPRS  QPEESVGLRA    420
EGHPDSLKDN   SSCSVMSEEP  EGRSYSTLTT  VREIETQTEL  LSPGSGRAEE  EEDQDEGIKQ    480
AMNHFVQENG   TLRAKPTGNG  IYINGRGHLV                                        510

SEQ ID NO: 29            moltype = AA   length = 622
FEATURE                  Location/Qualifiers
source                   1..622
                         mol_type = protein
                         organism = Homo sapiens
SEQUENCE: 29
MALPTARPLL   GSCGTPALGS  LLFLLFSLGW  VQPSRTLAGE  TGQEAAPLDG  VLANPPNISS     60
LSPRQLLGFP   CAEVSGLSTE  RVRELAVALA  QKNVKLSTEQ  LRCLAHRLSE  PPEDLDALPL    120
DLLLFLNPDA   FSGPQACTHF  FSRITKANVD  LLPRGAPERQ  RLLPAALACW  GVRGSLLSEA    180
DVRALGGLAC   DLPGRFVAES  AEVLLPRLVS  CPGPLDQDQQ  EEAARAALQGG  GPPYGPPSTW   240
SVSTMDALRG   LLPVLGQPII  RSIPQGIVAA  WRQRSSRDPS  WRQPERTILR  PRFRREVEKT    300
ACPSGKKARE   IDESLIFYKK  WELEACVDAA  LLATQMDRVN  AIPFTYEQLD  VLKHKLDELY    360
PQGYPESVIQ   HLGYLFLKMS  PEDIRKWNVT  SLETKALLE   VNKGHEMSPQ  VATLIDRFVK    420
GRGQLDKDTL   DTLTAFYPGY  LCSLSPEELS  SVPPSSIWAV  RPQDLDTCDP  RQLDVLYPKA    480
RLAFQNMNGS   EYFVKIQSFL  GGAPTEDLKA  LSQQNVSMDL  ATFMKLRTDA  VLPLTVAEVQ    540
KLLGPHVEGL   KAEERHRPVR  DWILRQRQDD  LDTLGLGLQG  GIPNGYLVLD  LSVQEALSGT    600
PCLLGPGPVL   TVLALLLAST  LA                                                622

SEQ ID NO: 30            moltype = AA   length = 360
FEATURE                  Location/Qualifiers
source                   1..360
                         mol_type = protein
                         organism = Homo sapiens
SEQUENCE: 30
DPLGAAKPQW   PWRRCLAALL  FQLLVAVCFF  SYLRVSRDDA  TGSPRAPSGS  SRQDTTPTRP     60
TLLILLWTWP   FHIPVALSRC  SEMVPGTADC  HITADRKVYP  QADTVIVHHW  DIMSNPKSRL    120
PPSPRPQGQR   WIWFNLEPPP  NCQHLEALDR  YFNLTMSYRS  DSDIFTPYGW  LEPWSGQPAH    180
PPLNLSAKTE   LVAWAVSNWK  PDSARVRYYQ  SLQAHLKVDV  YGRSHKPLPK  GTMMETLSRY    240
KFYLAFENSL   HPDYITEKLW  RNALEAWAVP  VVLGPSRSNY  ERFLPPDAFI  HVDDFQSPKD    300
LARYLQELDK   DHARYLSYFR  WRETLRPRSF  SWALDFCKAC  WKLQQESRYQ  TVRSIAAWFT    360

SEQ ID NO: 31            moltype = AA   length = 1210
FEATURE                  Location/Qualifiers
source                   1..1210
                         mol_type = protein
                         organism = Homo sapiens
SEQUENCE: 31
MRPSGTAGAA   LLALLAALCP  ASRALEEKKV  CQGTSNKLTQ  LGTFEDHFLS  LQRMFNNCEV     60
VLGNLEITYV   QRNYDLSFLK  TIQEVAGYVL  IALNTVERIP  LENLQIIRGN  MYYENSYALA    120
VLSNYDANKT   GLKELPMRNL  QEILHGAVRF  SNNPALCNVE  SIQWRDIVSS  DFLSNMSMDF    180
QNHLGSCQKC   DPSCPNGSCW  GAGEENCQKL  TKIICAQQCS  GRCRGKSPSD  CCHNQCAAGC    240
TGPRESDCLV   CRKFRDEATC  KDTCPPLMLY  NPTTYQMDVN  PEGKYSFGAT  CVKKCPRNYV    300
VTDHGSCVRA   CGADSYEMEE  DGVRKCKKCE  GPCRKVCNGI  GIGEFKDSLS  INATNIKHFK    360
NCTSISGDLH   ILPVAFRGDS  FTHTPPLDPQ  ELDILKTVKE  ITGFLLIQAW  PENRTDLHAF    420
ENLEIIRGRT   KQHGQFSLAV  VSLNITSLGL  RSLKEISDGD  VIISGNKNLC  YANTINWKKL    480
FGTSGQKTKI   ISNRGENSCK  ATGQVCHALC  SPEGCWGPEP  RDCVSCRNVS  RGRECVDKCK    540
LLEGEPREFV   ENSECIQCHP  ECLPQAMNIT  CTGRGPDNCI  QCAHYIDGPH  CVKTCPAGVM    600
GENNTLVWKY   ADAGHCHLC   HPNCTYGCTG  PGLEGCPTNG  PKIPSIATGM  VGALLLLLVV    660
ALGIGLFMRR   RHIVRKRTLR  RLLQERELVE  PLTPSGEAPN  QALLRILKET  EFKKIKVLGS    720
GAFGTVYKGL   WIPEGEKVKI  PVAIKELREA  TSPKANKEIL  DEAYVMASVD  NPHVCRLLGI    780
CLTSTVQLIT   QLMPFGCLLD  YVREHKDNIG  SQYLLNWCVQ  IAKGMNYLED  RRLVHRDLAA    840
RNVLVKTPQH   VKITDFGLAK  LLGAEEKEYH  AEGGKVPIKW  MALESILHRI  YTHQSDVWSY    900
GVTVWELMTF   GSKPYDGIPA  SEISSILEKG  ERLPQPPICT  IDVYMIMVKC  WMIDADSRPK    960
```

```
FRELIIEFSK MARDPQRYLV IQGDERMHLP SPTDSNFYRA LMDEEDMDDV VDADEYLIPQ    1020
QGFFSSPSTS RTPLLSSLSA TSNNSTVACI DRNGLQSCPI KEDSFLQRYS SDPTGALTED    1080
SIDDTFLPVP EYINQSVPKR PAGSVQNPVY HNQPLNPAPS RDPHYQDPHS TAVGNPEYLN    1140
TVQPTCVNST FDSPAHWAQK GSHQISLDNP DYQQDFFPKE AKPNGIFKGS TAENAEYLRV    1200
APQSSEFIGA                                                          1210

SEQ ID NO: 32           moltype = AA   length = 710
FEATURE                 Location/Qualifiers
source                  1..710
                        mol_type = protein
                        organism = Homo sapiens
SEQUENCE: 32
MGGKQRDEDD EAYGKPVKYD PSFRGPIKNR SCTDVICCVL FLLFILGYIV VGIVAWLYGD     60
PRQVLYPRNS TGAYCGMGEN KDKPYLLYFN IFSCILSSNI ISVAENGLQC PTPQVCSSSC    120
PEDPWTVGKN EFSQTVGEVF YTKNRNFCLP GVPNMTVIT SLQQELCPSF LLPSAPALGR     180
CFPWTNVTPP ALPGITNDTT IQQGISGLID SLNARDISVK IFEDFAQSWY WILVALGVAL    240
VLSLLFILLL RLVAGPLVLV LILGVLGVLA YGIYYCWEEY RVLRDKGASI SQLGFTTNLS    300
AYQSVQETWL AALIVLAVLE AILLLMLIFL RQRIRIAIAL LKEASKAVGQ MMSTMFYPLV    360
TFVLLLICIA YWAMTALYLA TSGQPQYVLW ASNISSPGCE KVPINTSCNP TAHLVNSSCP    420
GLMCVFQGYS SKGLIQRSVF NLQIYGVLGL FWTLNWVLAL GQCVLAGAFA SFYWAPHKPQ    480
DIPTFPLISA FIRTLRYHTG SLAFGALILT LVQIARVILE YIDHKLRGVQ NPVARCIMCC    540
FKCCLWCLEK PIKFLNRNAY IMIAIYGKNF CVSAKNAFML LMRNIVRVVV LDKVTDLLLF    600
FGKLLVVGGV GVLSFFFFSG RIPGLGKDFK SPHLNYYWLP IMTSILGAYV IASGFFSVFG    660
MCVDTLFLCF LEDLERNNGS LDRPYYMSKS LLKILGKKNE APPDNKKRKK              710

SEQ ID NO: 33           moltype = AA   length = 442
FEATURE                 Location/Qualifiers
source                  1..442
                        mol_type = protein
                        organism = Homo sapiens
SEQUENCE: 33
MQPPPSLCGR ALVALVLACG LSRIWGEERG FPPDRATPLL QTAEIMTPPT KTLWPKGSNA     60
SLARSLAPAE VPKGDRTAGS PPRTISPPPC QGPIEIKETF KYINTVVSCL VFVLGIIGNS    120
TLLRIIYKNK CMRNGPNILI ASLALGDLLH IVIDIPINYV LLAEDWPFG AEMCKLVPFI     180
QKASVGITVL SLCALSIDRY RAVASWSRIK GIGVPKWTAV EIVLIWVVSV VLAVPEAIGF    240
DIITMDYKGS YLRICLLHPV QKTAFMQFYK TAKDWWLFSF YFCLPLAITA FFYTLMTCEM    300
LRKKSGMQIA LNDHLKQRRE VAKTVFCLVL VFALCWLPLH LSRILKLTLY NQNDPNRCEL    360
LSFLLVLDYI GINMASLNSC INPIALYLVS KRFKNCFKSC LCCWCQSFEE KQSLEEKQSC    420
LKFKANDHGY DNFRSSNKYS SS                                            442

SEQ ID NO: 34           moltype = AA   length = 1255
FEATURE                 Location/Qualifiers
source                  1..1255
                        mol_type = protein
                        organism = Homo sapiens
SEQUENCE: 34
MELAAALCRWG LLLALLPPGA ASTQVCTGTD MKLRLPASPE THLDMLRHLY QGCQVVQGNL     60
ELTYLPTNAS LSFLQDIQEV QGYVLIAHNQ VRQVPLQRLR IVRGTQLFED NYALAVLDNG    120
DPLNNTTPVT GASPGGLREL QLRSLTEILK GGVLIQRNPQ LCYQDTILWK DIFHKNNQLA    180
LTLIDTNRSR ACHPCSPMCK GSRCWGESSE DCQSLTRTVC AGGCARCKGP LPTDCCHEQC    240
AAGCTGPKHS DCLACLHFNH SGICELHCPA LVTYNTDTFE SMPNPEGRYT FGASCVTACP    300
YNYLSTDVGS CTLVCPLHNQ EVTAEDGTQR CEKCSKPCAR VCYGLGMEHL REVRAVTSAN    360
IQEFAGCKKI FGSLAFLPES FDGDPASNTA PLQPEQLQVF ETLEEITGYL YISAWPDSLP    420
DLSVFQNLQV IRGRILHNGA YSLTLQGLGI SWLGLRSLRE LGSGLALIHH NTHLCFVHTV    480
PWDQLFRNPH QALLHTANRP EDECVGEGLA CHQLCARGHC WGPGPTQCVN CSQFLRGQEC    540
VEECRVLQGL PREYVNARHC LPCHPECQPQ NGSVTCFGPE ADQCVACAHY KDPPFCVARC    600
PSGVKPDLSY MPIWKFPDEE GACQPCPINC THSCVDLDDK GCPAEQRASP LTSIISAVVG    660
ILLVVVLGVV FGILIKRRQQ KIRKYTMRRL LQETELVEPL TPSGAMPNQA QMRILKETEL    720
RKVKVLGSGA FGTVYKGIWI PDGENVKIPV AIKVLRENTS PKANKEILDE AYVMAGVGSP    780
YVSRLLGICL TSTVQLVTQL MPYGCLLDHV RENRGRLGSQ DLLNWCMQIA KGMSYLEDVR    840
LVHRDLAARN VLVKSPNHVK ITDFGLARLL DIDETEYHAD GGKVPIKWMA LESILRRRFT    900
HQSDVWSYGV TVWELMTFGA KPYDGIPARE IPDLLEKGER LPQPPICTID VYMIMVKCWM    960
IDSECRPRFR ELVSEFSRMA RDPQRFVVIQ NEDLGPASPL DSTFYRSLLE DDDMGDLVDA   1020
EEYLVPQQGF FCPDPAPGAG GMVHHRHRSS STRSGGGDLT LGLEPSEEEA PRSPLAPSEG   1080
AGSDVFDGDL GMGAAKGLQS LPTHDPSPLQ RYSEDPTVPL PSETDGYVAP LTCSPQPEYV   1140
NQPDVRPQPP SPREGPLPAA RPAGATLERP KTLSPGKNGV VKDVFAFGGA VENPEYLTPQ   1200
GGAAPQPHPP PAFSPAFDNL YYWDQDPPER GAPPSTFKGT PTAENPEYLG LDVPV        1255

SEQ ID NO: 35           moltype = AA   length = 760
FEATURE                 Location/Qualifiers
source                  1..760
                        mol_type = protein
                        organism = Homo sapiens
SEQUENCE: 35
MMDQARSAFS NLFGGEPLSY TRFSLARQVD GDNSHVEMKL AVDEEENADN NTKANVTKPK     60
RCSGSICYGT IAVIVFFLIG FMIGYLGYCK GVEPKTECER LAGTESPVRE EPGEDFPAAR    120
RLYWDDLKRK LSEKLDSTDF TGTIKLLNEN SYVPREAGSQ KDENLALYVE NQFREFKLSK    180
VWRDQHFVKI QVKDSAQNSV IIVDKNGRLV YLVENPGGYV AYSKAATVTG KLVHANFGTK    240
KDFEDLYTPV NGSIVIVRAG KITFAEKVAN AESLNAIGVL IYMDQTKFPI VNAELSFFGH    300
```

```
AHLGTGDPYT PGFPSFNHTQ FPPSRSSGLP NIPVQTISRA AAEKLFGNME GDCPSDWKTD   360
STCRMVTSES KNVKLTVSNV LKEIKILNIF GVIKGFVEPD HYVVVGAQRD AWGPGAAKSG   420
VGTALLLKLA QMFSDMVLKD GFQPSRSIIF ASWSAGDFGS VGATEWLEGY LSSLHLKAFT   480
YINLDKAVLG TSNFKVSASP LLYTLIEKTM QNVKHPVTGQ FLYQDSNWAS KVEKLTLDNA   540
APPFLAYSGI PAVSFCFCED TDYPYLGTTM DTYKELIERI PELNKVARAA AEVAGQPVIK   600
LTHDVELNLD YERYNSQLLS FVRDLNQYRA DIKEMGLSLQ WLYSARGDFF RATSRLTTDF   660
GNAEKTDRFV MKKLNDRVMR VEYHFLSPYV SPKESPFRHV FWGSGSHTLP ALLENLKLRK   720
QNNGAFNETL FRNQLALATW TIQGAANALS GDVWDIDNEF                        760

SEQ ID NO: 36         moltype = AA   length = 334
FEATURE               Location/Qualifiers
source                1..334
                      mol_type = protein
                      organism = Homo sapiens
SEQUENCE: 36
MPLLPVLLVG TISKHLDWHR KEEKEHLKGV QDPQHERIIT VSTNGSIHSP RFPHTYPRNT    60
VLVWRLVAVE ENVWIQLTFD ERFGLEDPED DICKYDFVEV EEPSDGTILG RWCGSGTVPG   120
KQISKGNQIR IRFVSDEYFP SEPGFCIHYN IVMPQFTEAV SPSVLPPSAL PLDLLNNAIT   180
AFSTLEDLIR YLEPERWQLD LEDLYRPTWQ LLGKAFVFGR KSRVVDLNLL TEEVRLYSCT   240
PRNFSVSIRE ELKRTDTIFW PGCLLVKRCG GNCACCLHNC NECQCVPSKV TKKYHEVLQL   300
RPKTGVRGLH KSLTDVALEH HEECDCVCRG STGG                              334

SEQ ID NO: 37         moltype = AA   length = 370
FEATURE               Location/Qualifiers
source                1..370
                      mol_type = protein
                      organism = Homo sapiens
SEQUENCE: 37
MHRLIFVYTL ICANFCSCRD TSATPQSASI KALRNANLRR DESNHLTDLY RRDETIQVKG    60
NGYVQSPRFP NSYPRNLLLT WRLHSQENTR IQLVFDNQFG LEEAENDICR YDFVEVEDIS   120
ETSTIIRGRW CGHKEVPPRI KSRTNQIKIT FKSDDYFVAK PGFKIYYSLL EDFQPAAASE   180
TNWESVTSSI SGVSYNSPSV TDPTLIADAL DKKIAEFDTV EDLLKYFNPE SWQEDLENMY   240
LDTPRYRGRS YHDRKSKVDL DRLNDDAKRY SCTPRNYSVN IREELKLANV VFFPRCLLVQ   300
RCGGNCGCGT VNWRSCTCNS GKTVKKYHEV LQFEPGHIKR RGRAKTMALV DIQLDHHERC   360
DCICSSRPPR                                                         370

SEQ ID NO: 38         moltype = AA   length = 572
FEATURE               Location/Qualifiers
source                1..572
                      mol_type = protein
                      organism = Homo sapiens
SEQUENCE: 38
MECLYYFLGF LLLAARLPLD AAKRFHDVLG NERPSAYMRE HNQLNGWSSD ENDWNEKLYP    60
VWKRGDMRWK NSWKGGRVQA VLTSDSPALV GSNITFAVNL IFPRCQKEDA NGNIVYEKNC   120
RNEAGLSADP YVYNWTAWSE DSDGENGTGQ SHHNVFPDGK PFPHHPGWRR WNFIYVFHTL   180
GQYFQKLGRC SVRVSNTAN VTLGPQLMEV TVYRRHGRAY VPIAQVKDVY VVTDQIPVFV   240
TMFQKNDRNS SDETFLKDLP IMFDVLIHDP SHFLNYSTIN YKWSFGDNTG LFVSTNHTVN   300
HTYVLNGTFS LNLTVKAAAP GPCPPPPPPP RPSKPTPSLA TTLKSYDSNT PGPAGDNPLE   360
LSRIPDENCQ INRYGHFQAT ITIVEGILEV NIIQMTDVLM PVPWPESSLI DFVVTCQGSI   420
PTEVCTIISD PTCEITQNTV CSPVDVDEMC LLTVRRTFNG SGTYCVNLTL GDDTSLALTS   480
TLISVPDRDP ASPLRMANSA LISVGCLAIF VTVISLLVYK KHKEYNPIEN SPGNVVRSKG   540
LSVFLNRAKA VFFPGNQEKD PLLKNQEFKG VS                                572

SEQ ID NO: 39         moltype = AA   length = 701
FEATURE               Location/Qualifiers
source                1..701
                      mol_type = protein
                      organism = Homo sapiens
SEQUENCE: 39
MESPSAPPHR WCIPWQRLLL TASLLTFWNP PTTAKLTIES TPFNVAEGKE VLLLVHNLPQ    60
HLFGYSWYKG ERVDGNRQII GYVIGTQQAT PGPAYSGREI IYPNASLLIQ NIIQNDTGFY   120
TLHVIKSDLV NEEATGQFRV YPELPKPSIS SNNSKPVEDK DAVAFTCEPE TQDATYLWWV   180
NNQSLPVSPR LQLSNGNRTL TLFNVTRNDT ASYKCETQNP VSARRSDSVI LNVLYGPDAP   240
TISPLNTSYR SGENLNLSCH AASNPPAQYS WFVNGTFQQS TQELFIPNIT VNNSGSYTCQ   300
AHNSDTGLNR TTVTTITVYA EPPKPFITSN NSNPVEDEDA VALTCEPEIQ NTTYLWWVNN   360
QSLPVSPRLQ LSNDNRTLTL LSVTRNDVGP YECGIQNELS VDHSDPVILN VLYGPDDPTI   420
SPSYTYYRPG VNLSLSCHAA SNPPAQYSWL IDGNIQQHTQ ELFISNITEK NSGLYTCQAN   480
NSASGHSRTT VKTITVSAEL PKPSISSNNS KPVEDKDAVA FTCEPEAQNT TYLWWVNGQS   540
LPVSPRLQLS NGNRTLTLFN VTRNDARAYV CGIQNSVSAN RSDPVTLDVL YGPDTPIISP   600
PDSSYLSGAN LNLSCHSASN PSPQYSWRIN GIPQQHTQVL FIAKITPNNN GTYACFVSNL   660
ATGRNNSIVK SITVSASGTS PGLSAGATVG IMIGVLVGVA L                      701

SEQ ID NO: 40         moltype = AA   length = 702
FEATURE               Location/Qualifiers
source                1..702
                      mol_type = protein
                      organism = Homo sapiens
SEQUENCE: 40
MESPSAPPHR WCIPWQRLLL TASLLTFWNP PTTAKLTIES TPFNVAEGKE VLLLVHNLPQ    60
```

```
HLFGYSWYKG ERVDGNRQII GYVIGTQQAT PGPAYSGREI IYPNASLLIQ NIIQNDTGFY    120
TLHVIKSDLV NEEATGQFRV YPELPKPSIS SNNSKPVEDK DAVAFTCEPE TQDATYLWWV    180
NNQSLPVSPR LQLSNGNRTL TLFNVTRNDT ASYKCETQNP VSARRSDSVI LNVLYGPDAP    240
TISPLNTSYR SGENLNLSCH AASNPPAQYS WFVNGTFQQS TQELFIPNIT VNNSGSYTCQ    300
AHNSDTGLNR TTVTTITVYA EPPKPFITSN NSNPVEDEDA VALTCEPEIQ NTTYLWWVNN    360
QSLPVSPRLQ LSNDNRTLTL LSVTRNDVGP YECGIQNELS VDHSDPVILN VLYGPDDPTI    420
SPSYTYYRPG VNLSLSCHAA SNPPAQYSWL IDGNIQQHTQ ELFISNITEK NSGLYTCQAN    480
NSASGHSRTT VKTITVSAEL PKPSISSNNS KPVEDKDAVA FTCEPEAQNT TYLWWVNGQS    540
LPVSPRLQLS NGNRTLTLFN VTRNDARAYV CGIQNSVSAN RSDPVTLDVL YGPDTPIISP    600
PDSSYLSGAN LNLSCHSASN PSPQYSWRIN GIPQQHTQVL FIAKITPNNN GTYACFVSNL    660
ATGRNNSIVK SITVSASGTS PGLSAGATVG IMIGVLVGVA LI                      702

SEQ ID NO: 41          moltype = AA  length = 701
FEATURE                Location/Qualifiers
source                 1..701
                       mol_type = protein
                       organism = Homo sapiens
SEQUENCE: 41
MESPSAPPHR WCIPWQRLLL TASLLTFWNP PTTAKLTIES TPFNVAEGKE VLLLVHNLPQ     60
HLFGYSWYKG ERVDGNRQII GYVIGTQQAT PGPAYSGREI IYPNASLLIQ NIIQNDTGFY    120
TLHVIKSDLV NEEATGQFRV YPELPKPSIS SNNSKPVEDK DAVAFTCEPE TQDATYLWWV    180
NNQSLPVSPR LQLSNGNRTL TLFNVTRNDT ASYKCETQNP VSARRSDSVI LNVLYGPDAP    240
TISPLNTSYR SGENLNLSCH AASNPPAQYS WFVNGTFQQS TQELFIPNIT VNNSGSYTCQ    300
AHNSDTGLNR TTVTTITVYA EPPKPFITSN NSNPVEDEDA VALTCEPEIQ NTTYLWWVNN    360
QSLPVSPRLQ LSNDNRTLTL LSVTRNDVGP YECGIQNELS VDHSDPVILN VLYGPDDPTI    420
SPSYTYYRPG VNLSLSCHAA SNPPAQYSWL IDGNIQQHTQ ELFISNITEK NSGLYTCQAN    480
NSASGHSRTT VKTITVSAEL PKPSISSNNS KPVEDKDAVA FTCEPEAQNT TYLWWVNGQS    540
LPVSPRLQLS NGNRTLTLFN VTRNDARAYV CGIQNSVSAN RSDPVTLDVL YGPDTPIISP    600
PDSSYLSGAN LNLSCHSASN PSPQYSWRIN GIPQQHTQVL FIAKITPNNN GTYACFVSNL    660
ATGRNNSIVK SITVSASGTS PGLSAGATVG IMIGVLVGVA L                       701

SEQ ID NO: 42          moltype = AA  length = 750
FEATURE                Location/Qualifiers
source                 1..750
                       mol_type = protein
                       organism = Homo sapiens
SEQUENCE: 42
MWNLLHETDS AVATARRPRW LCAGALVLAG GFFLLGFLFG WFIKSSNEAT NITPKHNMKA     60
FLDELKAENI KKFLYNFTQI PHLAGTEQNF QLAKQIQSQW KEFGLDSVEL AHYDVLLSYP    120
NKTHPNYISI INEDGNEIFN TSLFEPPPPG YENVSDIVPP FSAFSPQGMP EGDLVYVNYA    180
RTEDFFKLER DMKINCSGKI VIARYGKVFR GNKVKNAQLA GAKGVILYSD PADYFAPGVK    240
SYPDGWNLPG GGVQRGNILN LNGAGDPLTP GYPANEYAYR RGIAEAVGLP SIPVHPIGYY    300
DAQKLLEKMG GSAPPDSSWR GSLKVPYNVG PGFTGNFSTQ KVKMHIHSTN EVTRIYNVIG    360
TLRGAVEPDR YVILGGHRDS WVFGGIDPQS GAAVVHEIVR SFGTLKKEGW RPRRTILFAS    420
WDAEEFGLLG STEWAEENSR LLQERGVAYI NADSSIEGNY TLRVDCTPLM YSLVHNLTKE    480
LKSPDEGFEG KSLYESWTKK SPSPEFSGMP RISKLGSGND FEVFFQRLGI ASGRARYTKN    540
WETNKFSGYP LYHSVYETYE LVEKFYDPMF KYHLTVAQVR GGMVFELANS IVLPFDCRDY    600
AVVLRKYADK IYSISMKHPQ EMKTYSVSFD SLFSAVKNFT EIASKFSERL QDFDKSNPIV    660
LRMMNDQLMF LERAFIDPLG LPDRPFYRHV IYAPSSHNKY AGESFPGIYD ALFDIESKVD    720
PSKAWGEVKR QIYVAAFTVQ AAAETLSEVA                                    750

SEQ ID NO: 43          moltype = AA  length = 22152
FEATURE                Location/Qualifiers
REGION                 13877..13878
                       note = misc_feature - Xaa can be any naturally occurring
                        amino acid
SITE                   13880
                       note = misc_feature - Xaa can be any naturally occurring
                        amino acid
SITE                   13887
                       note = misc_feature - Xaa can be any naturally occurring
                        amino acid
REGION                 13890..13891
                       note = misc_feature - Xaa can be any naturally occurring
                        amino acid
SITE                   13893
                       note = misc_feature - Xaa can be any naturally occurring
                        amino acid
SITE                   13903
                       note = misc_feature - Xaa can be any naturally occurring
                        amino acid
REGION                 13913..13914
                       note = misc_feature - Xaa can be any naturally occurring
                        amino acid
SITE                   13916
                       note = misc_feature - Xaa can be any naturally occurring
                        amino acid
REGION                 13928..13929
                       note = misc_feature - Xaa can be any naturally occurring
```

-continued

```
                          amino acid
SITE                      13938
                          note = misc_feature - Xaa can be any naturally occurring
                          amino acid
REGION                    13940..13941
                          note = misc_feature - Xaa can be any naturally occurring
                          amino acid
REGION                    14569..14571
                          note = misc_feature - Xaa can be any naturally occurring
                          amino acid
SITE                      14575
                          note = misc_feature - Xaa can be any naturally occurring
                          amino acid
SITE                      14579
                          note = misc_feature - Xaa can be any naturally occurring
                          amino acid
SITE                      14581
                          note = misc_feature - Xaa can be any naturally occurring
                          amino acid
REGION                    14587..14591
                          note = misc_feature - Xaa can be any naturally occurring
                          amino acid
REGION                    14593..14594
                          note = misc_feature - Xaa can be any naturally occurring
                          amino acid
REGION                    14725..14727
                          note = misc_feature - Xaa can be any naturally occurring
                          amino acid
SITE                      14731
                          note = misc_feature - Xaa can be any naturally occurring
                          amino acid
SITE                      14735
                          note = misc_feature - Xaa can be any naturally occurring
                          amino acid
SITE                      14737
                          note = misc_feature - Xaa can be any naturally occurring
                          amino acid
REGION                    14743..14747
                          note = misc_feature - Xaa can be any naturally occurring
                          amino acid
REGION                    14749..14750
                          note = misc_feature - Xaa can be any naturally occurring
                          amino acid
REGION                    15661..15663
                          note = misc_feature - Xaa can be any naturally occurring
                          amino acid
SITE                      15667
                          note = misc_feature - Xaa can be any naturally occurring
                          amino acid
SITE                      15671
                          note = misc_feature - Xaa can be any naturally occurring
                          amino acid
SITE                      15673
                          note = misc_feature - Xaa can be any naturally occurring
                          amino acid
REGION                    15679..15683
                          note = misc_feature - Xaa can be any naturally occurring
                          amino acid
REGION                    15685..15686
                          note = misc_feature - Xaa can be any naturally occurring
                          amino acid
REGION                    15972..15974
                          note = misc_feature - Xaa can be any naturally occurring
                          amino acid
SITE                      15978
                          note = misc_feature - Xaa can be any naturally occurring
                          amino acid
SITE                      15982
                          note = misc_feature - Xaa can be any naturally occurring
                          amino acid
SITE                      15984
                          note = misc_feature - Xaa can be any naturally occurring
                          amino acid
REGION                    15990..15994
                          note = misc_feature - Xaa can be any naturally occurring
                          amino acid
REGION                    15996..15997
                          note = misc_feature - Xaa can be any naturally occurring
                          amino acid
```

| | | |
|---|---|---|
| SITE | 16008 | |
| | note = misc_feature - Xaa can be any naturally occurring amino acid | |
| SITE | 16015 | |
| | note = misc_feature - Xaa can be any naturally occurring amino acid | |
| SITE | 16017 | |
| | note = misc_feature - Xaa can be any naturally occurring amino acid | |
| SITE | 16021 | |
| | note = misc_feature - Xaa can be any naturally occurring amino acid | |
| SITE | 16025 | |
| | note = misc_feature - Xaa can be any naturally occurring amino acid | |
| SITE | 16034 | |
| | note = misc_feature - Xaa can be any naturally occurring amino acid | |
| SITE | 16037 | |
| | note = misc_feature - Xaa can be any naturally occurring amino acid | |
| SITE | 16040 | |
| | note = misc_feature - Xaa can be any naturally occurring amino acid | |
| SITE | 16046 | |
| | note = misc_feature - Xaa can be any naturally occurring amino acid | |
| SITE | 16051 | |
| | note = misc_feature - Xaa can be any naturally occurring amino acid | |
| REGION | 16053..16055 | |
| | note = misc_feature - Xaa can be any naturally occurring amino acid | |
| SITE | 16058 | |
| | note = misc_feature - Xaa can be any naturally occurring amino acid | |
| REGION | 16062..16063 | |
| | note = misc_feature - Xaa can be any naturally occurring amino acid | |
| SITE | 16065 | |
| | note = misc_feature - Xaa can be any naturally occurring amino acid | |
| SITE | 16072 | |
| | note = misc_feature - Xaa can be any naturally occurring amino acid | |
| REGION | 16075..16076 | |
| | note = misc_feature - Xaa can be any naturally occurring amino acid | |
| SITE | 16078 | |
| | note = misc_feature - Xaa can be any naturally occurring amino acid | |
| SITE | 16088 | |
| | note = misc_feature - Xaa can be any naturally occurring amino acid | |
| REGION | 16268..16269 | |
| | note = misc_feature - Xaa can be any naturally occurring amino acid | |
| SITE | 16278 | |
| | note = misc_feature - Xaa can be any naturally occurring amino acid | |
| REGION | 16280..16281 | |
| | note = misc_feature - Xaa can be any naturally occurring amino acid | |
| REGION | 16373..16374 | |
| | note = misc_feature - Xaa can be any naturally occurring amino acid | |
| SITE | 16376 | |
| | note = misc_feature - Xaa can be any naturally occurring amino acid | |
| SITE | 16383 | |
| | note = misc_feature - Xaa can be any naturally occurring amino acid | |
| REGION | 16386..16387 | |
| | note = misc_feature - Xaa can be any naturally occurring amino acid | |
| SITE | 16389 | |
| | note = misc_feature - Xaa can be any naturally occurring amino acid | |
| SITE | 16399 | |

-continued

```
                       note = misc_feature - Xaa can be any naturally occurring
                         amino acid
REGION                 16409..16410
                       note = misc_feature - Xaa can be any naturally occurring
                         amino acid
SITE                   16412
                       note = misc_feature - Xaa can be any naturally occurring
                         amino acid
REGION                 16424..16425
                       note = misc_feature - Xaa can be any naturally occurring
                         amino acid
SITE                   16434
                       note = misc_feature - Xaa can be any naturally occurring
                         amino acid
REGION                 16436..16437
                       note = misc_feature - Xaa can be any naturally occurring
                         amino acid
REGION                 16439..16441
                       note = misc_feature - Xaa can be any naturally occurring
                         amino acid
SITE                   16445
                       note = misc_feature - Xaa can be any naturally occurring
                         amino acid
SITE                   16449
                       note = misc_feature - Xaa can be any naturally occurring
                         amino acid
SITE                   16451
                       note = misc_feature - Xaa can be any naturally occurring
                         amino acid
REGION                 16457..16461
                       note = misc_feature - Xaa can be any naturally occurring
                         amino acid
REGION                 16463..16464
                       note = misc_feature - Xaa can be any naturally occurring
                         amino acid
REGION                 16841..16842
                       note = misc_feature - Xaa can be any naturally occurring
                         amino acid
SITE                   16844
                       note = misc_feature - Xaa can be any naturally occurring
                         amino acid
SITE                   16851
                       note = misc_feature - Xaa can be any naturally occurring
                         amino acid
REGION                 16854..16855
                       note = misc_feature - Xaa can be any naturally occurring
                         amino acid
SITE                   16857
                       note = misc_feature - Xaa can be any naturally occurring
                         amino acid
SITE                   16867
                       note = misc_feature - Xaa can be any naturally occurring
                         amino acid
REGION                 16877..16878
                       note = misc_feature - Xaa can be any naturally occurring
                         amino acid
SITE                   16880
                       note = misc_feature - Xaa can be any naturally occurring
                         amino acid
REGION                 16892..16893
                       note = misc_feature - Xaa can be any naturally occurring
                         amino acid
SITE                   16902
                       note = misc_feature - Xaa can be any naturally occurring
                         amino acid
REGION                 16904..16905
                       note = misc_feature - Xaa can be any naturally occurring
                         amino acid
REGION                 16907..16909
                       note = misc_feature - Xaa can be any naturally occurring
                         amino acid
SITE                   16913
                       note = misc_feature - Xaa can be any naturally occurring
                         amino acid
SITE                   16917
                       note = misc_feature - Xaa can be any naturally occurring
                         amino acid
SITE                   16919
                       note = misc_feature - Xaa can be any naturally occurring
```

-continued

| | | |
|---|---|---|
| REGION | 16925..16929 | note = misc_feature - Xaa can be any naturally occurring amino acid |
| REGION | 16931..16932 | note = misc_feature - Xaa can be any naturally occurring amino acid |
| REGION | 17465..17466 | note = misc_feature - Xaa can be any naturally occurring amino acid |
| SITE | 17468 | note = misc_feature - Xaa can be any naturally occurring amino acid |
| SITE | 17475 | note = misc_feature - Xaa can be any naturally occurring amino acid |
| REGION | 17478..17479 | note = misc_feature - Xaa can be any naturally occurring amino acid |
| SITE | 17481 | note = misc_feature - Xaa can be any naturally occurring amino acid |
| SITE | 17491 | note = misc_feature - Xaa can be any naturally occurring amino acid |
| REGION | 17501..17502 | note = misc_feature - Xaa can be any naturally occurring amino acid |
| SITE | 17504 | note = misc_feature - Xaa can be any naturally occurring amino acid |
| REGION | 17516..17517 | note = misc_feature - Xaa can be any naturally occurring amino acid |
| SITE | 17526 | note = misc_feature - Xaa can be any naturally occurring amino acid |
| REGION | 17528..17529 | note = misc_feature - Xaa can be any naturally occurring amino acid |
| REGION | 17531..17533 | note = misc_feature - Xaa can be any naturally occurring amino acid |
| SITE | 17537 | note = misc_feature - Xaa can be any naturally occurring amino acid |
| SITE | 17541 | note = misc_feature - Xaa can be any naturally occurring amino acid |
| SITE | 17543 | note = misc_feature - Xaa can be any naturally occurring amino acid |
| REGION | 17549..17553 | note = misc_feature - Xaa can be any naturally occurring amino acid |
| REGION | 17555..17556 | note = misc_feature - Xaa can be any naturally occurring amino acid |
| SITE | 17567 | note = misc_feature - Xaa can be any naturally occurring amino acid |
| SITE | 17574 | note = misc_feature - Xaa can be any naturally occurring amino acid |
| SITE | 17576 | note = misc_feature - Xaa can be any naturally occurring amino acid |
| SITE | 17580 | note = misc_feature - Xaa can be any naturally occurring amino acid |
| SITE | 17584 | note = misc_feature - Xaa can be any naturally occurring amino acid |
| SITE | 17593 | note = misc_feature - Xaa can be any naturally occurring amino acid |
| SITE | 17596 | note = misc_feature - Xaa can be any naturally occurring amino acid |

-continued

| | | |
|---|---|---|
| SITE | 17599 | |
| | note = misc_feature - Xaa can be any naturally occurring amino acid | |
| SITE | 17605 | |
| | note = misc_feature - Xaa can be any naturally occurring amino acid | |
| SITE | 17610 | |
| | note = misc_feature - Xaa can be any naturally occurring amino acid | |
| REGION | 17612..17614 | |
| | note = misc_feature - Xaa can be any naturally occurring amino acid | |
| SITE | 17617 | |
| | note = misc_feature - Xaa can be any naturally occurring amino acid | |
| REGION | 17621..17622 | |
| | note = misc_feature - Xaa can be any naturally occurring amino acid | |
| SITE | 17624 | |
| | note = misc_feature - Xaa can be any naturally occurring amino acid | |
| SITE | 17631 | |
| | note = misc_feature - Xaa can be any naturally occurring amino acid | |
| REGION | 17777..17778 | |
| | note = misc_feature - Xaa can be any naturally occurring amino acid | |
| SITE | 17780 | |
| | note = misc_feature - Xaa can be any naturally occurring amino acid | |
| SITE | 17787 | |
| | note = misc_feature - Xaa can be any naturally occurring amino acid | |
| REGION | 17790..17791 | |
| | note = misc_feature - Xaa can be any naturally occurring amino acid | |
| SITE | 17793 | |
| | note = misc_feature - Xaa can be any naturally occurring amino acid | |
| SITE | 17803 | |
| | note = misc_feature - Xaa can be any naturally occurring amino acid | |
| REGION | 17813..17814 | |
| | note = misc_feature - Xaa can be any naturally occurring amino acid | |
| SITE | 17816 | |
| | note = misc_feature - Xaa can be any naturally occurring amino acid | |
| REGION | 17828..17829 | |
| | note = misc_feature - Xaa can be any naturally occurring amino acid | |
| SITE | 17838 | |
| | note = misc_feature - Xaa can be any naturally occurring amino acid | |
| REGION | 17840..17841 | |
| | note = misc_feature - Xaa can be any naturally occurring amino acid | |
| REGION | 17843..17845 | |
| | note = misc_feature - Xaa can be any naturally occurring amino acid | |
| SITE | 17849 | |
| | note = misc_feature - Xaa can be any naturally occurring amino acid | |
| SITE | 17853 | |
| | note = misc_feature - Xaa can be any naturally occurring amino acid | |
| SITE | 17855 | |
| | note = misc_feature - Xaa can be any naturally occurring amino acid | |
| REGION | 17861..17865 | |
| | note = misc_feature - Xaa can be any naturally occurring amino acid | |
| REGION | 17867..17868 | |
| | note = misc_feature - Xaa can be any naturally occurring amino acid | |
| SITE | 17879 | |
| | note = misc_feature - Xaa can be any naturally occurring amino acid | |
| SITE | 17886 | |

-continued

```
                        note = misc_feature - Xaa can be any naturally occurring
                           amino acid
SITE                    17888
                        note = misc_feature - Xaa can be any naturally occurring
                           amino acid
SITE                    17892
                        note = misc_feature - Xaa can be any naturally occurring
                           amino acid
SITE                    17896
                        note = misc_feature - Xaa can be any naturally occurring
                           amino acid
SITE                    17905
                        note = misc_feature - Xaa can be any naturally occurring
                           amino acid
SITE                    17908
                        note = misc_feature - Xaa can be any naturally occurring
                           amino acid
SITE                    17911
                        note = misc_feature - Xaa can be any naturally occurring
                           amino acid
SITE                    17917
                        note = misc_feature - Xaa can be any naturally occurring
                           amino acid
SITE                    17922
                        note = misc_feature - Xaa can be any naturally occurring
                           amino acid
REGION                  17924..17926
                        note = misc_feature - Xaa can be any naturally occurring
                           amino acid
SITE                    17929
                        note = misc_feature - Xaa can be any naturally occurring
                           amino acid
REGION                  17933..17934
                        note = misc_feature - Xaa can be any naturally occurring
                           amino acid
SITE                    17936
                        note = misc_feature - Xaa can be any naturally occurring
                           amino acid
SITE                    17943
                        note = misc_feature - Xaa can be any naturally occurring
                           amino acid
REGION                  17946..17947
                        note = misc_feature - Xaa can be any naturally occurring
                           amino acid
SITE                    17949
                        note = misc_feature - Xaa can be any naturally occurring
                           amino acid
SITE                    17959
                        note = misc_feature - Xaa can be any naturally occurring
                           amino acid
REGION                  18089..18090
                        note = misc_feature - Xaa can be any naturally occurring
                           amino acid
SITE                    18092
                        note = misc_feature - Xaa can be any naturally occurring
                           amino acid
SITE                    18099
                        note = misc_feature - Xaa can be any naturally occurring
                           amino acid
REGION                  18102..18103
                        note = misc_feature - Xaa can be any naturally occurring
                           amino acid
SITE                    18105
                        note = misc_feature - Xaa can be any naturally occurring
                           amino acid
SITE                    18115
                        note = misc_feature - Xaa can be any naturally occurring
                           amino acid
REGION                  18125..18126
                        note = misc_feature - Xaa can be any naturally occurring
                           amino acid
SITE                    18128
                        note = misc_feature - Xaa can be any naturally occurring
                           amino acid
REGION                  18140..18141
                        note = misc_feature - Xaa can be any naturally occurring
                           amino acid
SITE                    18150
                        note = misc_feature - Xaa can be any naturally occurring
```

|        |            |
|--------|------------|
| REGION | 18152..18153<br>note = misc_feature - Xaa can be any naturally occurring amino acid |
| REGION | 18155..18157<br>note = misc_feature - Xaa can be any naturally occurring amino acid |
| SITE   | 18161<br>note = misc_feature - Xaa can be any naturally occurring amino acid |
| SITE   | 18165<br>note = misc_feature - Xaa can be any naturally occurring amino acid |
| SITE   | 18167<br>note = misc_feature - Xaa can be any naturally occurring amino acid |
| REGION | 18173..18177<br>note = misc_feature - Xaa can be any naturally occurring amino acid |
| REGION | 18179..18180<br>note = misc_feature - Xaa can be any naturally occurring amino acid |
| SITE   | 18191<br>note = misc_feature - Xaa can be any naturally occurring amino acid |
| SITE   | 18198<br>note = misc_feature - Xaa can be any naturally occurring amino acid |
| SITE   | 18200<br>note = misc_feature - Xaa can be any naturally occurring amino acid |
| SITE   | 18204<br>note = misc_feature - Xaa can be any naturally occurring amino acid |
| SITE   | 18208<br>note = misc_feature - Xaa can be any naturally occurring amino acid |
| SITE   | 18217<br>note = misc_feature - Xaa can be any naturally occurring amino acid |
| SITE   | 18220<br>note = misc_feature - Xaa can be any naturally occurring amino acid |
| SITE   | 18223<br>note = misc_feature - Xaa can be any naturally occurring amino acid |
| SITE   | 18229<br>note = misc_feature - Xaa can be any naturally occurring amino acid |
| SITE   | 18234<br>note = misc_feature - Xaa can be any naturally occurring amino acid |
| REGION | 18236..18238<br>note = misc_feature - Xaa can be any naturally occurring amino acid |
| SITE   | 18241<br>note = misc_feature - Xaa can be any naturally occurring amino acid |
| REGION | 18245..18246<br>note = misc_feature - Xaa can be any naturally occurring amino acid |
| SITE   | 18248<br>note = misc_feature - Xaa can be any naturally occurring amino acid |
| SITE   | 18255<br>note = misc_feature - Xaa can be any naturally occurring amino acid |
| REGION | 18258..18259<br>note = misc_feature - Xaa can be any naturally occurring amino acid |
| SITE   | 18261<br>note = misc_feature - Xaa can be any naturally occurring amino acid |
| SITE   | 18271<br>note = misc_feature - Xaa can be any naturally occurring amino acid |
| REGION | 18401..18402<br>note = misc_feature - Xaa can be any naturally occurring amino acid |

-continued

| | |
|---|---|
| SITE | 18404 |
| | note = misc_feature - Xaa can be any naturally occurring amino acid |
| SITE | 18411 |
| | note = misc_feature - Xaa can be any naturally occurring amino acid |
| REGION | 18414..18415 |
| | note = misc_feature - Xaa can be any naturally occurring amino acid |
| SITE | 18417 |
| | note = misc_feature - Xaa can be any naturally occurring amino acid |
| SITE | 18427 |
| | note = misc_feature - Xaa can be any naturally occurring amino acid |
| REGION | 18437..18438 |
| | note = misc_feature - Xaa can be any naturally occurring amino acid |
| SITE | 18440 |
| | note = misc_feature - Xaa can be any naturally occurring amino acid |
| REGION | 18452..18453 |
| | note = misc_feature - Xaa can be any naturally occurring amino acid |
| SITE | 18462 |
| | note = misc_feature - Xaa can be any naturally occurring amino acid |
| REGION | 18464..18465 |
| | note = misc_feature - Xaa can be any naturally occurring amino acid |
| REGION | 18467..18469 |
| | note = misc_feature - Xaa can be any naturally occurring amino acid |
| SITE | 18473 |
| | note = misc_feature - Xaa can be any naturally occurring amino acid |
| SITE | 18477 |
| | note = misc_feature - Xaa can be any naturally occurring amino acid |
| SITE | 18479 |
| | note = misc_feature - Xaa can be any naturally occurring amino acid |
| REGION | 18485..18489 |
| | note = misc_feature - Xaa can be any naturally occurring amino acid |
| REGION | 18491..18492 |
| | note = misc_feature - Xaa can be any naturally occurring amino acid |
| SITE | 18503 |
| | note = misc_feature - Xaa can be any naturally occurring amino acid |
| SITE | 18510 |
| | note = misc_feature - Xaa can be any naturally occurring amino acid |
| SITE | 18512 |
| | note = misc_feature - Xaa can be any naturally occurring amino acid |
| SITE | 18516 |
| | note = misc_feature - Xaa can be any naturally occurring amino acid |
| SITE | 18520 |
| | note = misc_feature - Xaa can be any naturally occurring amino acid |
| SITE | 18529 |
| | note = misc_feature - Xaa can be any naturally occurring amino acid |
| SITE | 18532 |
| | note = misc_feature - Xaa can be any naturally occurring amino acid |
| SITE | 18535 |
| | note = misc_feature - Xaa can be any naturally occurring amino acid |
| SITE | 18541 |
| | note = misc_feature - Xaa can be any naturally occurring amino acid |
| SITE | 18546 |
| | note = misc_feature - Xaa can be any naturally occurring amino acid |
| REGION | 18548..18550 |

-continued

```
                    note = misc_feature - Xaa can be any naturally occurring
                       amino acid
SITE                18553
                    note = misc_feature - Xaa can be any naturally occurring
                       amino acid
REGION              18557..18558
                    note = misc_feature - Xaa can be any naturally occurring
                       amino acid
SITE                18560
                    note = misc_feature - Xaa can be any naturally occurring
                       amino acid
SITE                18567
                    note = misc_feature - Xaa can be any naturally occurring
                       amino acid
REGION              18570..18571
                    note = misc_feature - Xaa can be any naturally occurring
                       amino acid
SITE                18573
                    note = misc_feature - Xaa can be any naturally occurring
                       amino acid
SITE                18583
                    note = misc_feature - Xaa can be any naturally occurring
                       amino acid
REGION              18713..18714
                    note = misc_feature - Xaa can be any naturally occurring
                       amino acid
SITE                18716
                    note = misc_feature - Xaa can be any naturally occurring
                       amino acid
SITE                18723
                    note = misc_feature - Xaa can be any naturally occurring
                       amino acid
REGION              18726..18727
                    note = misc_feature - Xaa can be any naturally occurring
                       amino acid
SITE                18729
                    note = misc_feature - Xaa can be any naturally occurring
                       amino acid
SITE                18739
                    note = misc_feature - Xaa can be any naturally occurring
                       amino acid
REGION              18749..18750
                    note = misc_feature - Xaa can be any naturally occurring
                       amino acid
SITE                18752
                    note = misc_feature - Xaa can be any naturally occurring
                       amino acid
REGION              18764..18765
                    note = misc_feature - Xaa can be any naturally occurring
                       amino acid
SITE                18774
                    note = misc_feature - Xaa can be any naturally occurring
                       amino acid
REGION              18776..18777
                    note = misc_feature - Xaa can be any naturally occurring
                       amino acid
REGION              18779..18781
                    note = misc_feature - Xaa can be any naturally occurring
                       amino acid
SITE                18785
                    note = misc_feature - Xaa can be any naturally occurring
                       amino acid
SITE                18789
                    note = misc_feature - Xaa can be any naturally occurring
                       amino acid
SITE                18791
                    note = misc_feature - Xaa can be any naturally occurring
                       amino acid
REGION              18797..18801
                    note = misc_feature - Xaa can be any naturally occurring
                       amino acid
REGION              18803..18804
                    note = misc_feature - Xaa can be any naturally occurring
                       amino acid
SITE                18815
                    note = misc_feature - Xaa can be any naturally occurring
                       amino acid
SITE                18822
                    note = misc_feature - Xaa can be any naturally occurring
```

| | | |
|---|---|---|
| SITE | 18824 | note = misc_feature - Xaa can be any naturally occurring amino acid |
| SITE | 18828 | note = misc_feature - Xaa can be any naturally occurring amino acid |
| SITE | 18832 | note = misc_feature - Xaa can be any naturally occurring amino acid |
| SITE | 18841 | note = misc_feature - Xaa can be any naturally occurring amino acid |
| SITE | 18844 | note = misc_feature - Xaa can be any naturally occurring amino acid |
| SITE | 18847 | note = misc_feature - Xaa can be any naturally occurring amino acid |
| SITE | 18853 | note = misc_feature - Xaa can be any naturally occurring amino acid |
| SITE | 18858 | note = misc_feature - Xaa can be any naturally occurring amino acid |
| REGION | 18860..18862 | note = misc_feature - Xaa can be any naturally occurring amino acid |
| SITE | 18865 | note = misc_feature - Xaa can be any naturally occurring amino acid |
| REGION | 18869..18870 | note = misc_feature - Xaa can be any naturally occurring amino acid |
| SITE | 18872 | note = misc_feature - Xaa can be any naturally occurring amino acid |
| SITE | 18879 | note = misc_feature - Xaa can be any naturally occurring amino acid |
| REGION | 18882..18883 | note = misc_feature - Xaa can be any naturally occurring amino acid |
| SITE | 18885 | note = misc_feature - Xaa can be any naturally occurring amino acid |
| SITE | 18895 | note = misc_feature - Xaa can be any naturally occurring amino acid |
| REGION | 19091..19093 | note = misc_feature - Xaa can be any naturally occurring amino acid |
| SITE | 19097 | note = misc_feature - Xaa can be any naturally occurring amino acid |
| SITE | 19101 | note = misc_feature - Xaa can be any naturally occurring amino acid |
| SITE | 19103 | note = misc_feature - Xaa can be any naturally occurring amino acid |
| REGION | 19109..19113 | note = misc_feature - Xaa can be any naturally occurring amino acid |
| REGION | 19115..19116 | note = misc_feature - Xaa can be any naturally occurring amino acid |
| SITE | 19127 | note = misc_feature - Xaa can be any naturally occurring amino acid |
| SITE | 19134 | note = misc_feature - Xaa can be any naturally occurring amino acid |
| SITE | 19136 | note = misc_feature - Xaa can be any naturally occurring amino acid |
| SITE | 19140 | note = misc_feature - Xaa can be any naturally occurring amino acid |

-continued

| | |
|---|---|
| SITE | 19144 |
| | note = misc_feature - Xaa can be any naturally occurring amino acid |
| SITE | 19153 |
| | note = misc_feature - Xaa can be any naturally occurring amino acid |
| SITE | 19156 |
| | note = misc_feature - Xaa can be any naturally occurring amino acid |
| SITE | 19159 |
| | note = misc_feature - Xaa can be any naturally occurring amino acid |
| SITE | 19165 |
| | note = misc_feature - Xaa can be any naturally occurring amino acid |
| SITE | 19170 |
| | note = misc_feature - Xaa can be any naturally occurring amino acid |
| REGION | 19172..19174 |
| | note = misc_feature - Xaa can be any naturally occurring amino acid |
| SITE | 19177 |
| | note = misc_feature - Xaa can be any naturally occurring amino acid |
| REGION | 19181..19182 |
| | note = misc_feature - Xaa can be any naturally occurring amino acid |
| SITE | 19184 |
| | note = misc_feature - Xaa can be any naturally occurring amino acid |
| SITE | 19191 |
| | note = misc_feature - Xaa can be any naturally occurring amino acid |
| REGION | 19194..19195 |
| | note = misc_feature - Xaa can be any naturally occurring amino acid |
| SITE | 19197 |
| | note = misc_feature - Xaa can be any naturally occurring amino acid |
| SITE | 19207 |
| | note = misc_feature - Xaa can be any naturally occurring amino acid |
| REGION | 19337..19338 |
| | note = misc_feature - Xaa can be any naturally occurring amino acid |
| SITE | 19340 |
| | note = misc_feature - Xaa can be any naturally occurring amino acid |
| SITE | 19347 |
| | note = misc_feature - Xaa can be any naturally occurring amino acid |
| REGION | 19350..19351 |
| | note = misc_feature - Xaa can be any naturally occurring amino acid |
| SITE | 19353 |
| | note = misc_feature - Xaa can be any naturally occurring amino acid |
| SITE | 19363 |
| | note = misc_feature - Xaa can be any naturally occurring amino acid |
| REGION | 19373..19374 |
| | note = misc_feature - Xaa can be any naturally occurring amino acid |
| SITE | 19376 |
| | note = misc_feature - Xaa can be any naturally occurring amino acid |
| REGION | 19388..19389 |
| | note = misc_feature - Xaa can be any naturally occurring amino acid |
| SITE | 19398 |
| | note = misc_feature - Xaa can be any naturally occurring amino acid |
| REGION | 19400..19401 |
| | note = misc_feature - Xaa can be any naturally occurring amino acid |
| REGION | 19403..19405 |
| | note = misc_feature - Xaa can be any naturally occurring amino acid |
| SITE | 19409 |

-continued

| | |
|---|---|
| | note = misc_feature - Xaa can be any naturally occurring amino acid |
| SITE | 19413 |
| | note = misc_feature - Xaa can be any naturally occurring amino acid |
| SITE | 19415 |
| | note = misc_feature - Xaa can be any naturally occurring amino acid |
| REGION | 19421..19425 |
| | note = misc_feature - Xaa can be any naturally occurring amino acid |
| REGION | 19427..19428 |
| | note = misc_feature - Xaa can be any naturally occurring amino acid |
| SITE | 19439 |
| | note = misc_feature - Xaa can be any naturally occurring amino acid |
| SITE | 19446 |
| | note = misc_feature - Xaa can be any naturally occurring amino acid |
| SITE | 19448 |
| | note = misc_feature - Xaa can be any naturally occurring amino acid |
| SITE | 19452 |
| | note = misc_feature - Xaa can be any naturally occurring amino acid |
| SITE | 19456 |
| | note = misc_feature - Xaa can be any naturally occurring amino acid |
| SITE | 19465 |
| | note = misc_feature - Xaa can be any naturally occurring amino acid |
| SITE | 19468 |
| | note = misc_feature - Xaa can be any naturally occurring amino acid |
| SITE | 19471 |
| | note = misc_feature - Xaa can be any naturally occurring amino acid |
| SITE | 19477 |
| | note = misc_feature - Xaa can be any naturally occurring amino acid |
| SITE | 19482 |
| | note = misc_feature - Xaa can be any naturally occurring amino acid |
| REGION | 19484..19486 |
| | note = misc_feature - Xaa can be any naturally occurring amino acid |
| SITE | 19489 |
| | note = misc_feature - Xaa can be any naturally occurring amino acid |
| REGION | 19493..19494 |
| | note = misc_feature - Xaa can be any naturally occurring amino acid |
| SITE | 19496 |
| | note = misc_feature - Xaa can be any naturally occurring amino acid |
| SITE | 19503 |
| | note = misc_feature - Xaa can be any naturally occurring amino acid |
| REGION | 19506..19507 |
| | note = misc_feature - Xaa can be any naturally occurring amino acid |
| SITE | 19509 |
| | note = misc_feature - Xaa can be any naturally occurring amino acid |
| SITE | 19519 |
| | note = misc_feature - Xaa can be any naturally occurring amino acid |
| REGION | 19649..19650 |
| | note = misc_feature - Xaa can be any naturally occurring amino acid |
| SITE | 19652 |
| | note = misc_feature - Xaa can be any naturally occurring amino acid |
| SITE | 19659 |
| | note = misc_feature - Xaa can be any naturally occurring amino acid |
| REGION | 19662..19663 |
| | note = misc_feature - Xaa can be any naturally occurring |

-continued

| | |
|---|---|
| SITE | 19665<br>note = misc_feature - Xaa can be any naturally occurring amino acid |
| SITE | 19675<br>note = misc_feature - Xaa can be any naturally occurring amino acid |
| REGION | 19685..19686<br>note = misc_feature - Xaa can be any naturally occurring amino acid |
| SITE | 19688<br>note = misc_feature - Xaa can be any naturally occurring amino acid |
| REGION | 19700..19701<br>note = misc_feature - Xaa can be any naturally occurring amino acid |
| SITE | 19710<br>note = misc_feature - Xaa can be any naturally occurring amino acid |
| REGION | 19712..19713<br>note = misc_feature - Xaa can be any naturally occurring amino acid |
| REGION | 19715..19717<br>note = misc_feature - Xaa can be any naturally occurring amino acid |
| SITE | 19721<br>note = misc_feature - Xaa can be any naturally occurring amino acid |
| SITE | 19725<br>note = misc_feature - Xaa can be any naturally occurring amino acid |
| SITE | 19727<br>note = misc_feature - Xaa can be any naturally occurring amino acid |
| REGION | 19733..19737<br>note = misc_feature - Xaa can be any naturally occurring amino acid |
| REGION | 19739..19740<br>note = misc_feature - Xaa can be any naturally occurring amino acid |
| SITE | 19751<br>note = misc_feature - Xaa can be any naturally occurring amino acid |
| SITE | 19758<br>note = misc_feature - Xaa can be any naturally occurring amino acid |
| SITE | 19760<br>note = misc_feature - Xaa can be any naturally occurring amino acid |
| SITE | 19764<br>note = misc_feature - Xaa can be any naturally occurring amino acid |
| SITE | 19768<br>note = misc_feature - Xaa can be any naturally occurring amino acid |
| SITE | 19777<br>note = misc_feature - Xaa can be any naturally occurring amino acid |
| SITE | 19780<br>note = misc_feature - Xaa can be any naturally occurring amino acid |
| SITE | 19783<br>note = misc_feature - Xaa can be any naturally occurring amino acid |
| SITE | 19789<br>note = misc_feature - Xaa can be any naturally occurring amino acid |
| SITE | 19794<br>note = misc_feature - Xaa can be any naturally occurring amino acid |
| REGION | 19796..19798<br>note = misc_feature - Xaa can be any naturally occurring amino acid |
| SITE | 19801<br>note = misc_feature - Xaa can be any naturally occurring amino acid |
| REGION | 19805..19806<br>note = misc_feature - Xaa can be any naturally occurring amino acid |

-continued

| | | |
|---|---|---|
| SITE | 19808 | |
| | note = misc_feature - Xaa can be any naturally occurring amino acid | |
| SITE | 19815 | |
| | note = misc_feature - Xaa can be any naturally occurring amino acid | |
| REGION | 19818..19819 | |
| | note = misc_feature - Xaa can be any naturally occurring amino acid | |
| SITE | 19821 | |
| | note = misc_feature - Xaa can be any naturally occurring amino acid | |
| SITE | 19831 | |
| | note = misc_feature - Xaa can be any naturally occurring amino acid | |
| REGION | 19960..19961 | |
| | note = misc_feature - Xaa can be any naturally occurring amino acid | |
| SITE | 19963 | |
| | note = misc_feature - Xaa can be any naturally occurring amino acid | |
| SITE | 19970 | |
| | note = misc_feature - Xaa can be any naturally occurring amino acid | |
| REGION | 19973..19974 | |
| | note = misc_feature - Xaa can be any naturally occurring amino acid | |
| SITE | 19976 | |
| | note = misc_feature - Xaa can be any naturally occurring amino acid | |
| SITE | 19986 | |
| | note = misc_feature - Xaa can be any naturally occurring amino acid | |
| REGION | 19996..19997 | |
| | note = misc_feature - Xaa can be any naturally occurring amino acid | |
| SITE | 19999 | |
| | note = misc_feature - Xaa can be any naturally occurring amino acid | |
| REGION | 20011..20012 | |
| | note = misc_feature - Xaa can be any naturally occurring amino acid | |
| SITE | 20021 | |
| | note = misc_feature - Xaa can be any naturally occurring amino acid | |
| REGION | 20023..20024 | |
| | note = misc_feature - Xaa can be any naturally occurring amino acid | |
| REGION | 20026..20028 | |
| | note = misc_feature - Xaa can be any naturally occurring amino acid | |
| SITE | 20032 | |
| | note = misc_feature - Xaa can be any naturally occurring amino acid | |
| SITE | 20036 | |
| | note = misc_feature - Xaa can be any naturally occurring amino acid | |
| SITE | 20038 | |
| | note = misc_feature - Xaa can be any naturally occurring amino acid | |
| REGION | 20044..20048 | |
| | note = misc_feature - Xaa can be any naturally occurring amino acid | |
| REGION | 20050..20051 | |
| | note = misc_feature - Xaa can be any naturally occurring amino acid | |
| SITE | 20062 | |
| | note = misc_feature - Xaa can be any naturally occurring amino acid | |
| SITE | 20069 | |
| | note = misc_feature - Xaa can be any naturally occurring amino acid | |
| SITE | 20071 | |
| | note = misc_feature - Xaa can be any naturally occurring amino acid | |
| SITE | 20075 | |
| | note = misc_feature - Xaa can be any naturally occurring amino acid | |
| SITE | 20079 | |

```
                        note = misc_feature - Xaa can be any naturally occurring
                           amino acid
SITE                    20088
                        note = misc_feature - Xaa can be any naturally occurring
                           amino acid
SITE                    20091
                        note = misc_feature - Xaa can be any naturally occurring
                           amino acid
SITE                    20094
                        note = misc_feature - Xaa can be any naturally occurring
                           amino acid
SITE                    20100
                        note = misc_feature - Xaa can be any naturally occurring
                           amino acid
SITE                    20105
                        note = misc_feature - Xaa can be any naturally occurring
                           amino acid
REGION                  20107..20109
                        note = misc_feature - Xaa can be any naturally occurring
                           amino acid
SITE                    20112
                        note = misc_feature - Xaa can be any naturally occurring
                           amino acid
REGION                  20116..20117
                        note = misc_feature - Xaa can be any naturally occurring
                           amino acid
SITE                    20119
                        note = misc_feature - Xaa can be any naturally occurring
                           amino acid
SITE                    20126
                        note = misc_feature - Xaa can be any naturally occurring
                           amino acid
REGION                  20129..20130
                        note = misc_feature - Xaa can be any naturally occurring
                           amino acid
SITE                    20132
                        note = misc_feature - Xaa can be any naturally occurring
                           amino acid
SITE                    20142
                        note = misc_feature - Xaa can be any naturally occurring
                           amino acid
REGION                  20272..20273
                        note = misc_feature - Xaa can be any naturally occurring
                           amino acid
SITE                    20275
                        note = misc_feature - Xaa can be any naturally occurring
                           amino acid
SITE                    20282
                        note = misc_feature - Xaa can be any naturally occurring
                           amino acid
REGION                  20285..20286
                        note = misc_feature - Xaa can be any naturally occurring
                           amino acid
SITE                    20288
                        note = misc_feature - Xaa can be any naturally occurring
                           amino acid
SITE                    20298
                        note = misc_feature - Xaa can be any naturally occurring
                           amino acid
REGION                  20308..20309
                        note = misc_feature - Xaa can be any naturally occurring
                           amino acid
SITE                    20311
                        note = misc_feature - Xaa can be any naturally occurring
                           amino acid
REGION                  20323..20324
                        note = misc_feature - Xaa can be any naturally occurring
                           amino acid
SITE                    20333
                        note = misc_feature - Xaa can be any naturally occurring
                           amino acid
REGION                  20335..20336
                        note = misc_feature - Xaa can be any naturally occurring
                           amino acid
REGION                  20806..20808
                        note = misc_feature - Xaa can be any naturally occurring
                           amino acid
SITE                    20812
                        note = misc_feature - Xaa can be any naturally occurring
```

```
                    amino acid
SITE                20816
                    note = misc_feature - Xaa can be any naturally occurring
                    amino acid
SITE                20818
                    note = misc_feature - Xaa can be any naturally occurring
                    amino acid
REGION              20824..20828
                    note = misc_feature - Xaa can be any naturally occurring
                    amino acid
REGION              20830..20831
                    note = misc_feature - Xaa can be any naturally occurring
                    amino acid
source              1..22152
                    mol_type = protein
                    organism = Homo sapiens
SEQUENCE: 43
MLKPSGLPGS SSPTRSLMTG SRSTKATPEM DSGLTGATLS PKTSTGAIVV TEHTLPFTSP    60
DKTLASPTSS VVGRTTQSLG VMSSALPEST SRGMTHSEQR TSPSLSPQVN GTPSRNYPAT   120
SMVSGLSSPR TRTSSTEGNF TKEASTYTLT VETTSGPVTE KYTVPTETST TEGDSTETPW   180
DTRYIPVKIT SPMKTFADST ASKENAPVSM TPAETTVTDS HTPGRTNPSF GTLYSSFLDL   240
SPKGTPNSRG ETSLELILST TGYPFSSPEP GSAGHSRIST SAPLSSSASV LDNKISETSI   300
FSGQSLTSPL SPGVPEARAS TMPNSAIPFS MTLSNAETSA ERVRSTISSL GTPSISTKQT   360
AETILTFPHAF AETMDIPSTH IAKTLASEWL GSPGTLGGTS TSALTTTSPS TTLVSEETNT   420
HHSTSGKETE GTLNTSMTPL ETSAPGEESE MTATLVPTLG FTTLDSKIRS PSQVSSSHPT   480
RELRTTGSTS GRQSSSTAAH GSSDILRATT SSTSKASSWT SESTAQQFSE PQHTQWVETS   540
PSMKTERPPA STSVAAPITT SVPSVVSGFT TLKTSSTKGI WLEETSADTL IGESTAGPTT   600
HQFAVPTGIS MTGGSSTRGS QGTTHLLTRA TASSETSADL TLATNGVPVS VSPAVSKTAA   660
GSSPPGGTKP SYTMVSSVIP ETSSLQSSAF REGTSLGLTP LNTRHPFSSP EPDSAGHTKI   720
STSIPLLSSA SVLEDKVSAT STFSHHKATS SITTGTPEIS TKTKPSSAVL SSMTLSNAAT   780
SPERVRNATS PLTHPSPSGE ETAGSVLTLS TSAETTDSPN IHPTGTLTSE SSESPSTLSL   840
PSVSGVKTTF SSSTPSTHLF TSGEETEETS NPSVSQPETS VSRVRTTLAS TSVPTPVFPT   900
MDTWPTRSAQ FSSSHLVSEL RATSSTSVTN STGSALPKIS HLTGTATMSQ TNRDTFNDSA   960
APQSTTWPET SPRFKTGLPS ATTTVSTSAT SLSATVMVSK FTSPATSSME ATSIREPSTT  1020
ILTTETTNGP GSMAVASTNI PIGKGYITEG RLDTSHLPIG TTASSETSMD FTMAKESVSM  1080
SVSPSQSMDA AGSSTPGRTS QFVDTFSDDV YHLTSREITI PRDGTSSALT PQMTATHPPS  1140
PDPGSARSTW LGILSSSPSS PTPKVTMSST FSTQRVTTSM IMDTVETSRW NMPNLPSTTS  1200
LTPSNIPTSG AIGKSTLVPL DTPSPATSLE ASEGGLPTLS TYPESTNTPS IHLGAHASSE  1260
SPSTIKLTMA SVVKPGSYTP LTFPSIETHI HVSTARMAYS SGSSPEMTAP GETNTGSTWD  1320
PTTYITTTDP KDTSSAQVST PHSVRTLRTT ENHPKTESAT PAAYSGSPKI SSSPNLTSPA  1380
TKAWTITDTT EHSTQLHYTK LAEKSSGFET QSAPGPVSVV IPTSPTIGSS TLELTSDVPG  1440
EPLVLAPSEQ TTITLPMATW LSTSLTEEMA STDLDISSPS SPMSTFAIFP PMSTPSHELS  1500
KSEADTSAIR NTDSTTLDQH LGIRSLGRTG DLTTVPITPL TTTWTSVIEH STQAQDTLSA  1560
TMSPTHVTQS LKDQTSIPAS ASPSHLTEVY PELGTQGRSS SEATTFWKPS TDTLSREIET  1620
GPTNIQSTPP MDNTTTGSSS SGVTLGIAHL PIGTSSPAET STNMALERRS STATVSMAGT  1680
MGLLVTSAPG RSISQSLGRV SSVLSESTTE GVTDSSKGSS PRLNTQGNTA LSSSLEPSYA  1740
EGSQMSTSIP LTSSPTTPDV EFIGGSTFWT KEVTTVMTSD ISKSSARTES SSATLMSTAL  1800
GSTENTGKEK LRTASMDLPS PTPSMEVTPW ISLTLSNAPN TTDSLDLSHG VHTSSAGTLA  1860
TDRSLNTGVT RASRLENGSD TSSKSLSMGN STHTSMTDTE KSEVSSSIHP RPETSAPGAE  1920
TTLTSTPGNR AISLTLPFSS IPVEEVISTG ITSGPDINSA PMTHSPITPP TIVWTSTGTI  1980
EQSTQPLHAV SSEKVSVQTQ STPYVNSVAV SASPTHENSV SSGSSTSSPY SSASLESLDS  2040
TISRRNAITS WLWDLTTSLP TTTWPSTSLS EALSSGHSGV SNPSSTTTEF PLFSAASTSA  2100
AKQRNPETET HGPQNTAAST LNTDASSVTG LSETPVGASI SSEVPLPMAI TSRSDVSGLT  2160
SESTANPSLG TASSAGTKLT RTISLPTSES LVSFRMNKDP WTVSIPLGSH PTTNTETSIP  2220
VNSAGPPGLS TVASDVIDTP SDGAESIPTV SFSPSPDTEV TTISHFPEKT THSFRTISSL  2280
THELTSRVTP IPGDWMSSAM STKPTGASPS ITLGERRTIT SAAPTTSPIV LTASFTETST  2340
VSLDNETTVK TSDILDARKT NELPSDSSSS SDLINTSIAS STMDVTKTAS ISPTSISGMT  2400
ASSSPSLFSS DRPQVPTSTT ETNTATSPSV SSNTYSLDGG SNVGGTPSTL PPFTITHPVE  2460
TSSALLAWSR PVRTFSTMVS TDTASGENPT SSNSVVTSVP APGTWASVGS TTDLPAMGFL  2520
KTSPAGEAHS LLASTIEPAT AFTPHLSAAV VTGSSATSEA SLLTTSESKA IHSSPQTPTT  2580
PTSGANWETS ATPESLLVVT ETSDTTLTSK ILVTDTILFS TVSTPPSKFP STGTLSGASF  2640
PTLLPDTPAI PLTATEPTSS LATSFDSTPL VTIASDSLGT VPETTLTMSE TSNGDALVLK  2700
TVSNPDRSIP GITIQGVTES PLHPSSTSPS KIVAPRNTTY EGSITVALST LPAGTTGSLT  2760
FSQSSENSET TALVDSSAGL ERASVMPLTT GSQGMASSGG IRSGSTHSTG TKTFSSLPLT  2820
MNPGEVTAMS EITTNRLTAT QSTAPKGIPV KPTSAESGLL TPVSASSSPS KAFASLTTAP  2880
PSTWGIPQST LTFEFSEVPS LDTKSASLPT PGQSLNTIPD SDASTASSSL SKSPEKNPRA  2940
RMMTSTKAIS ASSFQSTGFT ETPEGSASPS MAGHEPRVPT SGTGDPRYAS ESMSYPDPSK  3000
ASSAMTSTSL ASKLTTLFST GQAARSGSSS SPISLSTEKE TSFLSPTAST SRKTSLFLGP  3060
SMARQPNILV HLQTSALTLS PTSTLNMSQE EPPELTSSQT IAEEEGTTAE TQTLTFTPSE  3120
TPTSLLPVSS PTEPTARRKS SPETWASSSIS VPAKTSLVET TDGTLVTTIK MSSQAAQGNS  3180
TWPAPAEETG TSPAGTSPGS PEVSTTLKIM SSKEPSISPE IRSTVRNSPW KTPETTVPME  3240
TTVEPVTLQS TALGSGSTSI SHLPTGTTSP TKSPTENMLA TERVSLSPSP PEAWTNLYSG  3300
TPGGTRQSLA TMSSVSLESP TARSITGTGQ QSSPELVSKT TGMEFSMWHG STGGTTGDTH  3360
VSLSTSSNIL EDPVTSPNSV SSLTDKSKHK TETWVSTTAI PSTVLNNKIM AAEQQTSRSV  3420
DEAYSSTSSW SDQTSGSDIT LGASPDVTNT LYITSTAQTT SLVSLPSGDQ GITSLTNPSG  3480
GKTSSASSVT SPSIGLETLR ANVSAVKSDI APTAGHLSQT SSPAEVSILD VTTAPTPGIS  3540
TTITTMGTNS ISTTTPNPEV GMSTMDSTPA TERRTTSTEH PSTWSSTAAS DSWTVTDMTS  3600
NLKVARSPGT ISTMHTTSFL ASSTELDSMS TPHGRITVIG TSLVTPSSDA SAVKTETSTS  3660
ERTLSPSDTT ASTPISTFSR VQRMSISVPD ILSTSWTPSS TEAEDVPVSM VSTDHASTKT  3720
```

```
DPNTPLSTFL FDSLSTLDWD TGRSLSSATA TTSAPQGATT PQELTLETMI SPATSQLPFS  3780
IGHITSAVTP AAMARSSGVT FSRPDPTSKK AEQTSTQLPT TTSAHPGQVP RSAATTLDVI  3840
PHTAKTPDAT FQRQGQTALT TEARATSDSW NEKEKSTPSA PWITEMMNSV SEDTIKEVTS  3900
SSSVLKDPEY AGHKLGIWDD FIPKFGKAAH MRELPLLSPP QDKEAIHPST NTVETTGWVT  3960
SSEHASHSTI PAHSASSKLT SPVVTTSTRE QAIVSMSTTT WPESTRARTE PNSFLTIELR  4020
DVSPYMDTSS TTQTSIISSP GSTAITKGPR TEITSSKRIS SSFLAQSMRS SDSPSEAITR  4080
LSNFPAMTES GGMILAMQTS PPGATSLSAP TLDTSATASW TGTPLATTQR FTYSEKTTLF  4140
SKGPEDTSQP SPPSVEETSS SSSLVPIHAT TSPSNILLTS QGHSPSSTPP VTSVFLSETS  4200
GLGKTTDMSR ISLEPGTSLP PNLSSTAGEA LSTYEASRDT KAIHHSADTA VTNMEATSSE  4260
YSPIPGHTKP SKATSPLVTS HIMGDITSST SVFGSSETTE IETVSSVNQG LQERSTSQVA  4320
SSATETSTVI THVSSGDATT HVTKTQATFS SGTSISSPHQ FITSTNTFTD VSTNPSTSLI  4380
MTESSGVTIT TQTGPTGAAT QGPYLLDTST MPYLTETPLA VTPDFMQSEK TTLISKGPKD  4440
VTWTSPPSVA ETSYPSSLTP FLVTTIPPAT STLQGQHTSS PVSATSVLTS GLVKTTDMLN  4500
TSMEPVTNSP QNLNNPSNEI LATLAATTDI ETIHPSINKA VTNMGTASSA HVLHSTLPVS  4560
SEPSTATSPM VPASSMGDAL ASISIPGSET TDIEGEPTSS LTAGRKENST LQEMNSTTES  4620
NIILSNVSVG AITEATKMEV PSFDATFIPT PAQSTKFPDI FSVASSRLSN SPPMTISTHM  4680
TTTQTGSSGA TSKIPLALDT STLETSAGTP SVVTEGFAHS KITTAMNNDV KDVSQTNPPF  4740
QDEASSPSSQ APVLVTTLPS SVAFTPQWHS TSSPVSMSSV LTSSLVKTAG KVDTSLETVT  4800
SSPQSMSNTL DDISVTSAAT TDIETTHPSI NTVVTNVGTT GSAFESHSTV SAYPEPSKVT  4860
SPNVTTSTME DTTISRSIPK SSKTTRTETE TTSSLTPKLR ETSISQEITS STETSTVPYK  4920
ELTGATTEVS RTDVTSSSST SFPGPDQSTV SLDISTETNT RLSTSPIMTE SAEITITTQT  4980
GPHGATSQDT FTMDPSNTTP QAGIHSAMTH GFSQLDVTTL MSRIPQDVSW TSPPSVDTS  5040
SPSSFLSSPA MTTPSLISST LPEDKLSSPM TSLLTSGLVK ITDILRTRLE PVTSSLPNFS  5100
STSDKILATS KDSKDTKEIF PSINTEETNV KANNSGHESH SPALADSETP KATTQMVITT  5160
TVGDPAPSTS MPVHGSSETT NIKREPTYFL TPRLRETSTS QESSFPTDTS FLLSKVPTGT  5220
ITEVSSTGVN SSSKISTPDH DKSTVPPDTF TGEIPRVFTS SIKTKSAEMT ITTQASPPES  5280
ASHSTLPLDT STTLSQGGTH STVTQGFPYS EVTTLMGMGP GNVSWMTTPP VEETSSVSSL  5340
MSSPAMTSPS PVSSTSPQSI PSSPLPVTAL PTSVLVTTTD VLGTTSPESV TSSPPNLSSI  5400
THERPATYKD TAHTEAAMHH STNTAVTNVG TSGSGHKSQS SVLADSETSK ATPLMSTTST  5460
LGDTSVSTST PNISQTNQIQ TEPTASLSPR LRESSTSEKT SSTTETNTAF SYVPTGAITQ  5520
ASRTEISSSR TSISDLDRPT IAPDISTGMI TRLFTSPIMT KSAEMTVTTQ TTTPGATSQG  5580
ILPWDTSTTL FQGGTHSTVS QGFPHSEITT LRSRTPGDVS WMTTPPVEET SSGFSLMSPS  5640
MTSPSPVSST SPESIPSSPL PVTALLTSVL VTTTNVLGTT SPETVTSSPP NLSSPTQERL  5700
TTYKDTAHTE AMHASMHTNT AVANVGTSIS GHESQSSVPA DSHTSKATSP MGITFAMGDT  5760
SVSTSTPAFF ETRIQTESTS SLIPGLRDTR TSEEINTVTE TSTVLSEVPT TTTTEVSRTE  5820
VITSSRTTIS GPDHSKMSPY ISTETITRLS TFPPVTGSTE MAITNQTGPI GTISQATLTL  5880
DTSSTASWEG THSPVTQRFP HSEETTTMSR STKGVSWQSP PSVEETSSPS SPVPLPAITS  5940
HSSLYSAVSG SSPTSALPVT SLLTSGRRKT IDMLDTHSEL VTSSLPSASS FSGEILTSEA  6000
STNTETIHFS ENTAETNMGT TNSMHKLHSS VSIHSQPSGH TPPKVTGSMM EDAIVSTSTP  6060
GSPETKNVDR DSTSPLTPEL KEDSTALVMN STTESNTVFS SVSLDAATEV SRAEVTYYDP  6120
TFMPASAQST KSPDISPEAS SSHSNSPPLT ISTHKTIATQ TGPSGVTSLG QLTLDTSTIA  6180
TSAGTPSART QDFVDSETTS VMNNDLNDVL KTSPFSAEEA NSLSSQAPLL VTTSPSPVTS  6240
TLQEHSTSSL VSVTSVPTPT LAKITDMDTN LEPVTRSPQN LRNTLATSEA TTDTHTMHPS  6300
INTAMANVGT TSSPNEFYFT VSPDSDPYKA TSAVVITSTS GDSIVTSSMP RSSAMKKIES  6360
ETTFSLIFRL RETSTSQKIG SSSDTSTVFD KAFTAATTEV SRTELTSSSR TSIQGTEKPT  6420
MSPDTSTRSV TMLSTFAGLT KSEERTIATQ TGPHRATSQG TLTWDTSITT SQAGTHSAMT  6480
HGFSQLDLST LTSRVPEYIS GTSPPSVEKT SSSSSLLSLP AITSPSPVPT TLPESRPSSP  6540
VHLTSLPTSG LVKTTDMLAS VASLPPNLGS TSHKIPTTSE DIKDTEKMYP STNIAVTNVG  6600
TTTSEKESYS SVPAYSEPPK VTSPMVTSFN IRDTIVSTSM PGSSEITRIE MESTFSVAHG  6660
LKGTSTSQDP IVSTEKSAVL HKLTTGATET SRTEVASSRR TSIPGPDHST ESPDISTEVI  6720
PSLPISLGIT ESSNMTIITR TGPPLGSTSQ GTFTLDTPTT SSRAGTHSMA TQEFPHSEMT  6780
TVMNKDPEIL SWTIPPSIEK TSFSSSLMPS PAMTSPPVSS TLPKTIHTTP SPMTSLLTPS  6840
LVMTTDDTLGT SPEPTTSSPP NLSSTSHVIL TTDEDTTAIE AMHPSTSTAA TNVETTCSGH  6900
GSQSSVLTDS EKTKATAPMD TTSTMGHTTV STSMSVSSET TKIKRESTYS LTPGLRETSI  6960
SQNASFSTDT SIVLSEVPTG TTAEVSRTEV TSSGRTSIPG PSQSTVLPEI STRTMTRLFA  7020
SPTMTESAEM TIPTQTGPSG STSQDTLTLD TSTTKSQAKT HSTLTQRFPH SEMTTLMSRG  7080
PGDMSWQSSP SLENPSSLPS LLLSLPATTSP PPISSTLPVT ISSSPLPVTS LLTSSPVTTT  7140
DMLHTSPELV TSSPPKLSHT SDERLTTGKD TTNTEAVHPS TNTAASNVEI PSFGHESPSS  7200
ALADSETSKA TSPMFITSTQ EDTTVAISTP HFLETSRIQK ESISSLSPKL RETGSSVETS  7260
SAIETSAVLS EVSIGATTEI SRTEVTSSSR TSISGSAEST MLPEISTTRK IIKFPTSPIL  7320
AESSEMTIKT QTSPPGSTSE STFTLDTSTT PSLVITHSTM TQRLPHSEIT TLVSRGAGDV  7380
PRPSSLPVEE TSPPSSQLSL SAMISPSPVS STLPASSHSS SASVTSPLTP GQVKTTEVLD  7440
ASAEPETSSP PSLSSTSVEI LATSEVTTDT EKIHPFPNTA VTKVGTSSSG HESPSSVLPD  7500
SETTKATSAM GTISIMGDTS VSTLTPALSN TRKIQSEPAS SLTTRLRETS TSEETSLATE  7560
ANTVLSKVST GATTEVSRTE AISFSRTSMS GPEQSTMSQD ISIGTIPRIS ASSVLTESAK  7620
MTITTQTGPS ESTLESTLNL NTATTPSWVE THSIVIQGFP HPEMTTSMGR GPGGVSWPSP  7680
PFVKETSPPS SPLSLPAVTS PHPVSTTFLA HIPPSPLPVT SLLTSGPATT TDILGTSTEP  7740
GTSSSSLST TSHERLTTYK DTAHTEAVHP STNTGGTNVA TTSSGYKSQS SVLADSSPMC  7800
TTSTMGDTSV LTSTPAFLET RRIQTELASS LTPGLRESSG SEGTSSGTKM STVLSKVPTG  7860
ATTEISKEDV TSIPGPAQST ISPDISTRTV SWFSTSPVMT ESAEITMNTH TSPLGATTQG  7920
TSTLATSSTT SLTMTHSTIS QGFSHSQMST LMRRGPEDVS WMSPPLLEKT RPSFSLMSSP  7980
ATTSPSPVSS TLPESISSSP LPVTSLLTSG LAKTTDMLHK SSEPVTNSPA NLSSTSVEIL  8040
ATSEVTTDTE KTHPSSNRTV TDVGTSSSGH ESTSFVLADS QTSKVSPMV ITSTMEDTSV  8100
STSTPGFFET SRIQTEPTSS LTLGLRKTSS SEGTSLATEM STVLSGVPTG ATAEVSRTEV  8160
TSSSRTSISG FAQLTVSPET STETITRLPT SSIMTESAEM MIKTQTDPPG STPESTHTVD  8220
ISTTPNWVET HSTVTQRFSH SEMTTLVSRS PGDMLWPSQS SVEETSSASS LLSLPATTSP  8280
SPVSSTLVED FPSASLPVTS LLTPGLVITT DRMGISREPG TSSTSNLSST SHERLTTLED  8340
TVDTEDMQPS THTAVTNVRT SISGHESQSS VLSDSETPKA TSPMGTTYTM GETSVSISTS  8400
DFFETSRIQI EPTSSLTSGL RETSSSERIS SATEGSTVLS EVPSGATTEV SRTEVISSRG  8460
```

```
TSMSGPDQFT ISPDISTEAI TRLSTSPIMT ESAESAITIE TGSPGATSEG TLTLDTSTTT   8520
FWSGTHSTAS PGFSHSEMTT LMSRTPGDVP WPSLPSVEEA SSVSSSLSSP AMTSTSFFSA   8580
LPESISSSPH PVTALLTLGP VKTTDMLRTS SEPETSSPPN LSSTSAEILA TSEVTKDREK   8640
IHPSSNTPVV NVGTVIYKHL SPSSVLADLV TTKPTSPMAT TSTLGNTSVS TSTPAFPETM   8700
MTQPTSSLTS GLREISTSQE TSSATERSAS LSGMPTGATT KVSRTEALSL GRTSTPGPAQ   8760
STISPEISTE TITRISTPLT TTGSAEMTIT PKTGHSGASS QGTFTLDTSS RASWPGTHSA   8820
ATHRSPHSGM TTPMSRGPED VSWPSRPSVE KTSPPSSLVS LSAVTSPSPL YSTPSESSHS   8880
SPLRVTSLFT PVMMKTTDML DTSLEPVTTS PPSMNITSDE SLATSKATME TEAIQLSENT   8940
AVTQMGTISA RQEFYSSYPG LPEPSKVTSP VVTSSTIKDI VSTTIPASSE ITRIEMESTS   9000
TLTPTPRETS TSQEIHSATK PSTVPYKALT SATIEDSMTQ VMSSSRGPSP DQSTMSQDIS   9060
SEVITRLSTS PIKAESTEMT ITTQTGSPGA TSRGTLTLDT STTFMSGTHS TASQGFSHSQ   9120
MTALMSRTPG DVPWLSHPSV EEASSASFSL SSPVMTSSSP VSSTLPDSIH SSSLPVTSLL   9180
TSGLVKTTEL LGTSSEPETS SPPNLSSTSA EILATTEVTT DTEKLEMTNV VTSGYTHESP   9240
SSVLADSVTT KATSSMGITY PTGDTNVLTS TPAFSDTSRI QTKSKLSLTP GLMETSISEE   9300
TSSATEKSTV LSSVPTGATT EVSRTEAISS SRTSIPGPAQ STMSSDTSME TITRISTPLT   9360
RKESTDMAIT PKTGPSGATS QGTFTLDSSS TASWPGTHSA TTQRFPQSVV TTPMSRGPED   9420
VSWPSPLSVE KNSPPSSLVS SSSVTSPSPL YSTPSGSSHS SPVPVTSLFT SIMMKATDML   9480
DASLEPETTS APNMNITSDE SLATSKATTE TEAIHVFENT AASHVETTSA TEELYSSSPG   9540
FSEPTKVISP VVTSSSIRDN MVSTTMPGSS GITRIEIESM SSLTPGLRET RTSQDITSST   9600
ETSTVLYKMS SGATPEVSRT EVMPSSRTSI PGPAQSTMSL DISDEVVTRL STSPIMTESA   9660
EITITTQTGY SLATSQVTLP LGTSMTFLSG THSTMSQGLS HSEMTNLMSR GPESLSWTSP   9720
RFVETTRSSS SLTSLPLTTS LSPVSSTLLD SSPSSPLVKT TEVLDTSSEP KTSSSPNLSS   9780
KTSSSPNLSS TSVEIPATSE IMTDTEKIHP SSNTAVAKVR TSSSVHESHS SVLADSETTI   9840
TIPSMGITSA VDDTTVFTSN PAFSETRRIP TEPTFSLTPG FRETSTSEET TSITETSAVL   9900
YGVPTSATTE VSMTEIMSSN RTHIPDSDQS TMSPDIITEV ITRLSSSSMM SESTQMTITT   9960
QKSSPGATAQ STLTLATTTA PLARTHSTVP PRFLHSEMTT LMSRSPENPS WKSSPFVEKT  10020
SSSSSLLSLP VTTSPSVSST LPQSIPSSSF SVTSLLTPGM VKTTDTSTEP GTSLSPNLSG  10080
TSVEILAASE VTTDTEKIHP SSSMAVTNVG TTSSGHELYS SVSIHSEPSK ATYPVGTPSS  10140
MAETSISTSM PANFETTGFE AEPFSHLTSG FRKTNMSLDT SSVTPTNTPS SPGSTHLLQS  10200
SKTDFTSSAK TSSPDWPPAS QYTEIPVDII TPFNASPSIT ESTGITSFPE SRFTMSVTES  10260
THHLSTDLLP SAETISTGTV MPSLSEAMTS FATTGVPRAI SGSGSPFSRT ESGPGDATLS  10320
TIAESLPSST PVPFSSSTFT TDSSSTIPAL HEITSSSATP YRVDTSLGTE SSTTEGRLVM  10380
VSTLDTSSQP GRTSSTPILD TRMTESVELG TVTSAYQVPS LSTRLTRTDG IMEHITKIPN  10440
EAAHRGTIRP VKGPQTSTSP ASPKGLHTGG TKRMETTTTA LKTTTTALKT TSRATLTTSV  10500
YTPTLGTLTP LNASRQMAST ILTEMMITTP YVFPDVPETT SSLATSLGAE TSTALPRTTP  10560
SVLNRESETT ASLVSRSGAE RSPVIQTLDV SSSEPDTTAS WVIHPAETIP TVSKTTPNFF  10620
HSELDTVSST ATSHGADVSS AIPTNISPSE LDALTPLVTI SGTDTSTTFP TLTKSPHETE  10680
TRTTWLTHPA ETSSTIPRTI PNFSHHESDA TPSIATSPGA ETSSAIPIMT VSPGAEDLVT  10740
SQVTSSGTDR NMTIPTLTLS PGEPKTIASL VTHPEAQTSS AIPTSTISPA VSRLVTSMVT  10800
SLAAKTSTTN RALTNSPGEP ATTVSLVTHP AQTSPTVPWT TSIFFHSKSD TTPSMTTSHG  10860
AESSSAVPTP TVSTEVPGVV TPLVTSSSRAV ISTTIPILTL SPGEPETTPS MATSHGEEAS  10920
SAIPTPTVSP GVPGVVTSLV TSSRAVTSTT IPILTFSLGE PETTPSMATS HGTEAGSAVP  10980
TVLPEVPGMV TSLVASSRAV TSTTLPTLTL SPGEPETTPS MATSHGAEAS STVPTVSPEV  11040
PGVVTSLVTS SSGVNSTSIP TLILSPGELE TTPSMATSHG AEASSAVPTP TVSPGVSGVV  11100
TPLVTSSRAV TSTTIPILTL SSSEPETTPS MATSHGVEAS SAVLTVSPEV PGMVTSLVTS  11160
SRAVTSTTIP TLTISSDEPE TTTSLVTHSE AKMISAIPTL AVSPTVQGLV TSLVTSSGSE  11220
TSAFSNLTVA SSQPETIDSW VAHPGTEASS VVPTLTVSTG EPPTNISLVT HPAESSSTLP  11280
RTTSRFSHSE LDTMPSTVTS PEAESSSAIS TTISPGIPGV LTSLVTSSGR DISATFPTVP  11340
ESPHESEATA SWVTHPAVTS TTVPRTTPNY SHSEPDTTPS IATSPGAEAT SDFPTITVSP  11400
DVPDMVTSQV TSSGTDTSIT IPTLTLSSGE PETTTSFITY SETHTSSAIP TLPVSPGASK  11460
MLTSLVISSG TDSTTTFPTL TETPYEPETT AIQLIHPAET NTMVPKTTPK FSHSKSDTTL  11520
PVAITSPGPE ASSAVSTTTI SPDMSDLVTS LVPSSGTDTS TTFPTLSETP YEPETTVTWL  11580
THPAETSTTV SGTIPNFSHR GSDTAPSMVT SPGAVDTRSGV PTTTIPPSIP GVVTSQVTSS  11640
ATDTSTAIPT LTPSPGEPET TASSATHPGT QTGFTVPIRT VPSSEPDTMA SWVTHPPQTS  11700
TPVSRTTSSF SHSSPDATPV MATSPRTEAS SAVLTTISPG APEMVTSQIT SSGAATSTTV  11760
PTLTHSPGMP ETTALLSTHP RTGTSKTFPA STVFPQVSET TASLTIRPGA ETSSTALPTQT  11820
TSSLFTLLVT GTSRVDLSPT ASPGVSAKTA PLSTHPGTET STMIPTSTLS LGLLETTGLL  11880
ATSSSAETST STLTLTVSPA VSGLSSASIT TDKPQTVTSW NTETSPSVTS VGPPEFSRTV  11940
TGTTMTLIPS EMPTPPKTSH GEGVSPTTIL RTTMVEATNL ATTGSSPTVA KTTTTFNTLA  12000
GSLFTPLTTP GMSTLASESV TSRTSYNHRS WISTTSSYNR RYWTPATSTP VTSTFSPGIS  12060
TSSIPSSTAA TVPFMVPFTL NFTITNLQYE EDMRHPGSRK FNATERELQG LLKPLFRNSS  12120
LEYLYSGCRL ASLRPEKDSS AMAVDAICTH RPDPEDLGLD RERLYWELSN LTNGIQELGP  12180
YTLDRNSLYV NGFTHRSSMP TTSTPGTSTV DVGTSGTPSS SPSPTAAGPL LMPFTLNFTI  12240
TNLQYEEDMR RTGSRKFNTM ESVLQGLLKP LFKNTSVGPL YSGCRLTLLR PEKDGAATGV  12300
DAICTHRLDP KSPGLNREQL YWELSKLTND IEELGPYTLD RNSLYVNGFT HQSSVSTTST  12360
PGTSTVDLRT SGTPSSLSSP TIMAAGPLLV PFTLNFTITN LQYGEDMGHP GSRKFNTTER  12420
VLQGLLPGIF KNTSVGPLYS GCRLTSLRSE KDGAATGVDA ICIHHLDPKS PGLNRERLYW  12480
ELSQLTNGIK ELGPYTLDRN SLYVNGFTHR TSVPTTSTPG TSTVDLGTSG TPFSLPSPAT  12540
AGPLLVLFTL NFTITNLKYE EDMRHPGSRK FNTTERVLQT LLGPMFKNTS VGLLYSGCRL  12600
TLLRSEKDGA ATGVDAICTH RLDPKSPGLD REQLYWELSQ LTNGIKELGP YTLDRNSLYV  12660
NGFTHWIPVP TSSTPGTSTV DLGSGTPSSL PSPTAAGPLL VPFTLNFTIT NLQYEEDMHH  12720
PGSRKFNTTE RVLQGLLPGM FKNTSVGLLY SGCRLTLLRS EKDGAATGVD AICTHRLDPK  12780
SPGVDREQLY WELSQLTNGI KELGPYTLDR NSLYVNGFTH QTSAPNTSTP GTSTVDLGTS  12840
GTPSSLSSPT SAGPLLVPFT LNFTITNLQY EEDMRHPGSR KFNTTERVLQ GLLKPLFKST  12900
SVGPLYSGCR LTLLRSEKDG AATGVDAICT HRLDPKSPGV DREQLYWELS QLTNGIKELG  12960
PYTLDRNSLY VNGFTHQTSA PNTSTPGTST VDLGTSGTPS SLPSPTSAGP LLVPFTLNFT  13020
ITNLQYEEDM HHPGSRKFNT TERVLQGLLG PMFKNTSVGL LYSGCRLTLL RPEKNGAATG  13080
MDAICSHRLD PKSPGLNREQ LYWELSQLTH GIKELGPYTL DRNSLYVNGF THRSSVAPTS  13140
TPGTSTVDLG TSGTPSSLPS PTTAVPLLVP FTLNFTITNL QYGEDMRHPG SRKFNTTERV  13200
```

```
LQGLLGPLFK NSSVGPLYSG CRLISLRSEK DGAATGVDAI CTHHLNPQSP GLDREQLYWQ   13260
LSQMTNGIKE LGPYTLDRNS LYVNGFTHRS SGLTTSTPWT STVDLGTSGT PSPVPSPTTA   13320
GPLLVPFTLN FTITNLQYEE DMHRPGSRKF NTTERVLQGL LSPIFKNSSV GPLYSGCRLT   13380
SLRPEKDGAA TGMDAVCLYH PNPKRPGLDR EQLYWELSQL THNITELGPY SLDRDSLYVN   13440
GFTHQNSVPT TSTPGTSTVY WATTGTPSSF PGHTEPGPLL IPPTFNFTIT NLHYEENMQH   13500
PGSRKFNTTE RVLQGLLKPL FKNTSVGPLY SGCRLTSLRP EKDGAATGMD AVCLYHPNPK   13560
RPGLDREQLY WELSQLTHNI TELGPYSLDR DSLYVNGFTH QNSVPTTSTP GTSTVYWATT   13620
GTPSSFPGHT EPGPLLIPFT FNFTITNLHY EENMQHPGSR KFNTTERVLQ GLLKPLFKNT   13680
SVGPLYSGCR LTLLRPEKHE AATGVDTICT HRVDPIGPGL DRERLYWELS QLTNSITELG   13740
PYTLDRDSLY VNGFNPRSSV PTTSTPGTST VHLATSGTPS SLPGHTAPVP LLIPFTLNFT   13800
ITNLHYEENM QHPGSRKFNT TERVLQGLLK PLFKNTSVGP LYSGCRLTLL RPEKHEAATG   13860
VDTICTHRVD PIGPGLXXEX LYWELSXLTX XIXELGPYTL DRXSLYVNGF THXXSXPTTS   13920
TPGTSTVXXG TSGTPSSSPX XTSAGPLLVP FTLNFTITNL QYEEDMHHPG SRKFNTTERV   13980
LQGLLGPMFK NTSVGLLYSG CRLTLLRPEK NGAATGMDAI CSHRLDPKSP GLDREQLYWE   14040
LSQLTHGIKE LGPYTLDRNS LYVNGFTHRS SVAPTSTPGT STVDLGTSGT PSSLPSPTTA   14100
VPLLVPFTLN FTITNLQYGE DMRHPGSRKF NTTERVLQGL LGPLFKNSSV GPLYSGCRLI   14160
SLRSEKDGAA TGVDAICTHH LNPQSPGLDR EQLYWQLSQM TNGIKELGPY TLDRNSLYVN   14220
GFTHRSSGLT TSTPWTSTVD LGTSGTPSPV PSPTTAGPLL VPFTLNFTIT NLQYEEDMHR   14280
PGSRKFNATE RVLQGLLSPI FKNSSVGPLY SGCRLTSLRP EKDGAATGMD AVCLYHPNPK   14340
RPGLDREQLY WELSQLTHNI TELGPYSLDR DSLYVNGFTH QSSMTTTRTP DTSTMHLATS   14400
RTPASLSGPT TASPLLVLFT INCTITNLQY EEDMRRTGSR KFNTMESVLQ GLLKPLFKNT   14460
SVGPLYSGCR LTLLRPKKDG AATGVDAICT HRLDPKSPGL NREQLYWELS KLTNDIEELG   14520
PYTLDRNSLY VNGFTHQSSV STTSTPGTST VDLRTSGTPS SLSSPTIMXX XPLLXPFTXN   14580
XTITNLXXXX XMXXPGSRKF NTTERVLQGL LRPLFKNTSV SSLYSGCRLT LLRPEKDGAA   14640
TRVDAACTYR PDPKSPGLDR EQLYWELSQL THSITELGPY TLDRVSLYVN GFNPRSSVPT   14700
TSTPGTSTVH LATSGTPSSL PGHTXXXPLL XPFTXNXTIT NLXXXXXMXX PGSRKFNTTE   14760
RVLQGLLKPL FRNSSLEYLY SGCRLASLRP EKDSSAMAVD AICTHRPDPE DLGLDRERLY   14820
WELSNLTNGI QELGPYTLDR NSLYVNGFTH RSSGLTTSTP WTSTVDLGTS GTPSPVPSPT   14880
TAGPLLVPFT LNFTITNLQY EEDMHRPGSR RFNTTERVLQ GLLTPLFKNT SVGPLYSGCR   14940
LTLLRPEKQE AATGVDTICT HRVDPIGPGL DRERLYWELS QLTNSITELG PYTLDRDSLY   15000
VNGFNPWSSV PTTSTPGTST VHLATSGTPS SLPGHTAPVP LLIPFTLNFT ITDLHYEENM   15060
QHPGSRKFNT TERVLQGLLK PLFKSTSVGP LYSGCRLTLL RPEKHGAATG VDAICTLRLD   15120
PTGPGLDRER LYWELSQLTN SVTELGPYTL DRDSLYVNGF THRSSVPTTS IPGTSAVHLE   15180
TSGTPASLPG HTAPGPLLVP FTLNFTITNL QYEEDMRHPG SRKFSTTERV LQGLLKPLFK   15240
NTSVSSLYSG CRLTLLRPEK DGAATRVDAV CTHRPDPKSP GLDRERLYWK LSQLTHGITE   15300
LGPYTLDRHS LYVNGFTHQS SMTTTRTPDT STMHLATSRT PASLSGPTTA SPLLVLFTIN   15360
FTITNLRYEE NMHHPGSRKF NTTERVLQGL LRPVFKNTSV GPLYSGCRLT TLRPKKDGAA   15420
TKVDAICTYR PDPKSPGLDR EQLYWELSQL THSITELGPY TQDRDSLYVN GFTHRSSVPT   15480
TSIPGTSAVH LETSGTPASL PGHTAPGPLL VPFTLNFTIT NLQYEEDMRH PGSRKFNTTE   15540
RVLQGLLKPL FKSTSVGPLY SGCRLTLLRP EKRGAATGVD TICTHRLDPL NPGLDREQLY   15600
WELSKLTRGI IELGPYLLDR GSLYVNGFTH RTSVPTTSTP GTSTVDLGTS GTPFSLPSPA   15660
XXXPLLXPFT XNXTITNLXX XXXMXXPGSR KFNTTERVLQ TLLGPMFKNT SVGLLYSGCR   15720
LTLLRSEKDG AATGVDAICT HRLDPKSPGV DREQLYWELS QLTNGIKELG PYTLDRNSLY   15780
VNGFTHWIPV PTSSTPGTST VDLGSGTPSS LPSPTTAGPL LVPFTLNFTI TNLKYEEDMH   15840
CPGSRKFNTT ERVLQSLLGP MFKNTSVGPL YSGCRLTLLR SEKDGAATGV DAICTHRLDP   15900
KSPGVDREQL YWELSQLTNG IKELGPYTLD RNSLYVNGFT HQTSAPNTST PGTSTVDLGT   15960
SGTPSSLPSP TXXXPLLXPF TXNXTITNLX XXXXMXXPGS RKFNTTEXVL QGLLXPXFKN   16020
XSVGXLYSGC RLTXLRXEKX GAATGXDAIC XHXXXXPKXP GLXXEXLYWEL SXLTXXIXEL   16080
GPYTLDRXSL YVNGFTHWIP VPTSSTPGTS TVDLGSGTPS SLPSPTTAGP LLVPFTLNFT   16140
ITNLKYEEDM HCPGSRKFNT TERVLQSLLG PMFKNTSVGP LYSGCRLTSL RSEKDGAATG   16200
VDAICTHRVD PKSPGVDREQ LYWELSQLTN GIKELGPYTL DRNSLYVNGF THQTSAPNTS   16260
TPGTSTVXXG TSGTPSSXPX XTSAGPLLVP FTLNFTITNL QYEEDMHHPG SRKFNTTERV   16320
LQGLLGPMFK NTSVGLLYSG CRLTLLRPEK NGATTGMDAI CTHRLDPKSP GLXXEXLYWE   16380
LSXLTXXIXE LGPYTLDRXS LYVNGFTHXX SXPTTSTPGT STVXXGTSGT PSSXPXXTXX   16440
XPLLXPFTXN XTITNLXXXX XMXXPGSRKF NTTERVLQGL LKPLFRNSSL EYLYSGCRLA   16500
SLRPEKDSSA MAVDAICTHR PDPEDLGLDR ERLYWELSNL TNGIQELGPY TLDRNSLYVN   16560
GFTHRSSMPT TSTPGTSTVD VGTSGTPSSS PSPTTAGPLL IPPLNFTIT NLQYGEDMGH   16620
PGSRKFNTTE RVLQGLLGPI FKNTSVGPLY SGCRLTSLRS EKDGAATGVD AICIHHLDPK   16680
SPGLNRERLY WELSQLTNGI KELGPYTLDR NSLYVNGFTH RTSVPTTSTP GTSTVDLGTS   16740
GTPFSLPSPA TAGPLLVLFT LNFTITNLKY EEDMHRPGSR KFNTTERVLQ TLLGPMFKNT   16800
SVGLLYSGCR LTLLRSEKDG AATGVDAICT HRLDPKSPGL XXEXLYWELS XLTXXIXELG   16860
PYTLDRXSLY VNGFTHXXSX PTTSTPGTST VXXGTSGTPS SXPXXTXXXP LLXPFTXNXT   16920
ITNLXXXXXM XXPGSRKFNT TERVLQGLLR PVFKNTSVGP LYSGCRLTLL RPKKDGAATK   16980
VDAICTYRPD PKSPGLDREQ LYWELSQLTH SITELGPYTQ DRDSLYVNGF THRSSVPTTS   17040
IPGTSAVHLE TTGTPSSFPG HTEPGPLLIP FTFNFTITNL RYEENMQHPG SRKFNTTERV   17100
LQGLLTPLFK NTSVGPLYSG CRLTLLRPEK QEAATGVDTI CTHRVDPIGP GLDRERLYWE   17160
LSQLTNSITE LGPYTLDRDS LYVDGFNPWS SVPTTSTPGT STVHLATSGT PSPLPGHTAP   17220
VPLLIPFTLN FTITDLHYEE NMQHPGSRKF NLLFKSTSVG PLYSGCRLT   17280
LLRPEKHGAA TGVDAICTLR LDPTGPGLDR ERLYWELSQL TNSITELGPY TLDRDSLYVN   17340
GFNPWSSVPT TSTPGTSTVH LATSGTPSSL PGHTTAGPLL VPFTLNFTIT NLKYEEDMHC   17400
PGSRKFNTTE RVLQSHGPM FKNTSVGPLY SGCRLTLLRS EKDGAATGVD AICTHRLDPK   17460
SPGLXXEXLY WELSXLTXXI XELGPYTLDR XSLYVNGFTH XXSXPTTSTP GTSTVXXGTS   17520
GTPSSXPXXT XXXPLLXPFT XNXTITNLXX XXXMXXPGSR KFNTTERVLQ GLLXPXFKNX   17580
SVGXLYSGCR LTXLRXEKXG AATGXDAICX HXXXXPKXPGL XXEXLYWELS XLTNSITELG   17640
PYTLDRDSLY VNGFTHRSSM PTTSIPGTSA VHLETSGTPA SLPGHTAPGP LLVPFTLNFT   17700
ITNLQYEEDM RHPGSRKFNT TERVLQGLLK PLFKSTSVGP LYSGCRLTLL RPEKRGAATG   17760
VDTICTHRLD PLNPGLXXEX LYWELSXLTX XIXELGPYTL DRXSLYVNGF THXXSXPTTS   17820
TPGTSTVXXG TSGTPSSXPX XTXXXPLLXP FTXNXTITNL XXXXXMXXPG SRKFNTTEXV   17880
LQGLLXPXFK NXSVGXLYSG CRLTXLRXEK XGAATGXDAI CXHXXXXPKX PGLXXEXLYWE   17940
```

```
LSXLTXXIXE LGPYTLDRXS LYVNGFHPRS SVPTTSTPGT STVHLATSGT PSSLPGHTAP  18000
VPLLIPFTLN FTITNLHYEE NMQHPGSRKF NTTERVLQGL LGPMFKNTSV GLLYSGCRLT  18060
LLRPEKNGAA TGMDAICSHR LDPKSPGLXX EXLYWELSXL TXXIXELGPY TLDRXSLYVN  18120
GFTHXXSXPT TSTPGTSTVX XGTSGTPSSX PXXTXXXPLL XPFTXNXTIT NLXXXXXXMXX  18180
PGSRKFNTTE XVLQGLLPX FKNXSVGXLY SGCRLTXLRX EKXGAATGXD AICXHXXXPK  18240
XPGLXXEXLY WELSXLTXXI XELGPYTLDR XSLYVNGFTH QNSVPTTSTP GTSTVYWATT  18300
GTPSSFPGHT EPGPLLIPFT FNFTITNLHY EENMQHPGSR KFNTTERVLQ GLLTPLFKNT  18360
SVGPLYSGCR LTLLRPEKQE AATGVDTICT HRVDPIGPGL XXEXLYWELS XLTXXIXELG  18420
PYTLDRXSLY VNGFTHXXSX PTTSTPGTST VXXGTSGTPS SXPXXTXXXP LLXPFTXNXT  18480
ITNLXXXXXM XXPGSRKFNT TEXVLQGLLX PXFKNXSVGX LYSGCRLTXL RXEKXGAATG  18540
XDAICXHXXX PKXPGLXXEX LYWELSXLTX XIXELGPYTL DRXSLYVNGF THRSSVPTTS  18600
SPGTSTVHLA TSGTPSSLPG HTAPVPLLIP FTLNFTITNL HYEENMQHPG SRKFNTTERV  18660
LQGLLKPLFK STSVGPLYSG CRLTLLRPEK HGAATGVDAI CTLRLDPTGP GLXXEXLYWE  18720
LSXLTXXIXE LGPYTLDRXS LYVNGFTHXX SXPTTSTPGT STVXXGTSGT PSSXPXXTXX  18780
XPLLXPFTXN XTITNLXXXX XMXXPGSRKF NTTEXVLQGL LXPXFKNXSV GXLYSGCRLT  18840
XLRXEKXGAA TGXDAICXHX XXPKXPGLXX EXLYWELSXL TXXIXELGPY TLDRXSLYVN  18900
GFTHRTSVPT TSTPGTSTVH LATSGTPSSL PGHTAPVPLL IPFTLNFTIT NLQYEEDMHR  18960
PGSRKFNTTE RVLQGLLSPI FKNSSVGPLY SGCRLTSLRP EKDGAATGMD AVCLYHPNPK  19020
RPGLDREQLY CELSQLTHNI TELGPYSLDR DSLYVNGFTH QNSVPTTSTP GTSTVYWATT  19080
GTPSSFPGHT XXXPLLXPFT XNXTITNLXX XXXMXXPGSR KFNTTEXVLQ GLLXPXFKNX  19140
SVGXLYSGCR LTXLRXEKXG AATGXDAICX HXXXPKXPGL XXEXLYWELS XLTXXIXELG  19200
PYTLDRXSLY VNGFTHWSSG LTTSTPWTST VDLGTSGTPS PVPSPTTAGP LLVPFTLNFT  19260
ITNLQYEEDM HRPGSRKFNA TERVLQGLLS PIFKNTSVGP LYSGCRLTLL RPEKQEAATG  19320
VDTICTHRVD PIGPGLXXEX LYWELSXLTX XIXELGPYTL DRXSLYVNGF THXXSXPTTS  19380
TPGTSTVXXG TSGTPSSXPX XTXXXPLLXP FTXNXTITNL XXXXXMXXPG SRKFNTTEXV  19440
LQGLLXPXFK NXSVGXLYSG CRLTXLRXEK XGAATGXDAI CXHXXXPKXP GLXXEXLYWE  19500
LSXLTXXIXE LGPYTLDRXS LYVNGFTHRS FGLTTSTPWT STVDLGTSGT PSPVPSPTTA  19560
GPLLVPFTLN FTITNLQYEE DMHRPGSRKF NTTERVLQGL LTPLFRNTSV SSLYSGCRLT  19620
LLRPEKDGAA TRVDAVCTHR PDPKSPGLXX EXLYWELSXL TXXIXELGPY TLDRXSLYVN  19680
GFTHXXSXPT TSTPGTSTVX XGTSGTPSSX PXXTXXXPLL XPFTXNXTIT NLXXXXXXMXX  19740
PGSRKFNTTE XVLQGLLPX FKNXSVGXLY SGCRLTXLRX EKXGAATGXD AICXHXXXPK  19800
XPGLXXEXLY WELSXLTXXI XELGPYTLDR XSLYVNGFTH WIPVPTSSTP GTSTVDLGSG  19860
TPSSLPPTT AGPLLVPFTL NFTITNLQYG EDMGHPGSRK FNTTERVLQG LLGPIFKNTS  19920
VGPLYSGCRL TSLRSEKDGA ATGVDAICIH HLDPKSPGLX XEXLYWELSX LTXXIXELGP  19980
YTLDRXSLYV NGFTHXXSXP TTSTPGTSTV XXGTSGTPSS XPXXTXXXPL LXPFTXNXTI  20040
TNLXXXXXMX XPGSRKFNTT EXVLQGLLXP XFKNXSVGXL YSGCRLTXLR XEKXGAATGX  20100
DAICXHXXXP KXPGLXXEXL YWELSXLTXX IXELGPYTLD RXSLYVNGFT HQTFAPNTST  20160
PGTSTVDLGT SGTPSSLPSP TSAGPLLVPF TLNFTITNLQ YEEDMHHPGS RKFNTTERVL  20220
QGLLGPMFKN TSVGLLYSGC RLTLLRPEKN GAATRVDAVC THRPDPKSPG LXXEXLYWEL  20280
SXLTXXIXEL GPYTLDRXSL YVNGFTHXXS XPTTSTPGTS TVXXGTSGTP SSXPXXTAPV  20340
PLLIPFTLNF TITNLHYEEN MQHPGSRKFN TTERVLQGLL KPLFKSTSVG PLYSGCRLTL  20400
LRPEKHGAAT GVDAICTLRL DPTGPGLDRE RLYWELSQLT NSVTELGPYT LDRDSLYVNG  20460
FTQRSSVPTT SIPGTSAVHL ETSGTPASLP GHTAPGPLLV PFTLNFTITN LQYEVDMRHP  20520
GSRKFNTTER VLQGLLKPLF KSTSVGPLYS GCRLTLLRPE KRGAATGVDT ICTHRLDPLN  20580
PGLDREQLYW ELSKLTRGII ELGPYLLDRG SLYVNGFTHR NFVPITSTPG TSTVHLGTSE  20640
TPSSLPRIV PGPLLVPFTL NFTITNLQYE EAMRHPGSRK FNTTERVLQG LLRPLFKNTS  20700
IGPLYSSCRL TLLRPEKDKA ATRVDAICTH HPDPQSPGLN RLYWELSQ LTHGITELGP  20760
YTLDRDSLYV DGFTHWSPIP TTSTPGTSIV NLGTSGIPPS LPETTXXXPL LXPFTXNXTI  20820
TNLXXXXXMX XPGSRKFNTT ERVLQGLLKP LFKSTSVGPL YSGCRLTLLR PEKDGVATRV  20880
DAICTHRPDP KIPGLDRQQL YWELSQLTHS ITELGPYTLD RDSLYVNGFT QRSSVPTTST  20940
PGTFTVQPET SETPSSLPGP TATGPVLLPF TLNFTITNLQ YEEDMHRPGS RKFNTTERVL  21000
QGLLMPLFKN TSVSSLYSGC RLTLLRPEKD GAATRVDAVC THRPDPKSPG LDRERLYWKL  21060
SQLTHGITEL GPYTLDRHSL YVNGFTHQSS MTTTRTPDTS TMHLATSRTP ASLSGPTTAS  21120
PLLVLFTINF TITNLRYEEN MHHPGSRKFN TTERVLQGLL RPVFKNTSVG PLYSGCRLTL  21180
LRPKDGAAT KVDAICTYRP DPKSPGLDRE QLYWELSQLT HSITELGPYT LDRDSLYVNG  21240
FTQRSSVPTT SIPGTPTVDL GTSGTPVSKP GPSAASPLLV LFTLNFTITN LRYEENMQHP  21300
GSRKFNTTER VLQGLLRSLF KSTSVGPLYS GCRLTLLRPE KDGTATGVDA ICTHHPDPKS  21360
PRLDREQLYW ELSQLTHNIT ELGHYALDND SLFVNGFTHR SSVSTTSTPG TPTVYLGASK  21420
TPASIFGPSA ASHLLILFTL NFTITNLRYE ENMWPGSRKF NTTERVLQGL LRPLFKNTSV  21480
GPLYSGSRLT LLRPEKDGEA TGVDAICTHR PDPTGPGLDR EQLYLELSQL THSITELGPY  21540
TLDRDSLYVN GFTHRSSVPT TSTGVVSEEP FTLNFTINNL RYMADMGQPG SLKFNITDNV  21600
MKHLLSPLFQ RSSLGARYTG CRVIALRSVK NGAETRVDLL CTYLQPLSGP GLPIKQVFHE  21660
LSQQTHGITR LGPYSLDKDS LYLNGYNEPG LDEPPTTPKP ATTFLPPLSE ATTAMGYHLK  21720
TLTLNFTISN LQYSPDMGKG SATFNSTEGV LQHLLRPLFQ KSSMGPFYLG CQLISLRPEK  21780
DGAATGVDTT CTYHPDPVGP GLDIQQLYWE LSQLTHGVTQ LGFYVLDRDS LFINGYAPQN  21840
LSIRGEYQIN PHIVNWNLSN PDPTSSEYIT LLRDIQDKVT TLYKGSQLHD TFRFCLVTNL  21900
TMDSVLVTVK ALFSSNLDPS LVEQVFLDKT LNASFHWLGS TYQLVDIHVT EMESSVYQPT  21960
SSSSTQHFYL NFTITNLPYS QDKAQPGTTN YQRNKRNIED ALNQLFRNSS IKSYFSDCQV  22020
STFRSVPNRH HTGVDSLCNF SPLARRVDRV AIYEEFLRMT RNGTQLQNFT LDRSSVLVDG  22080
YSPNRNEPLT GNSDLPFWAV ILIGLAGLLG LITCLICGVL VTTRRRKKEG EYNVQQQCPG  22140
YYQSHLDLED LQ                                                     22152

SEQ ID NO: 44         moltype = AA  length = 255
FEATURE               Location/Qualifiers
source                1..255
                      mol_type = protein
                      organism = Homo sapiens
SEQUENCE: 44
MTPGTQSPFF LLLLLTVLTV VTGSGHASST PGGEKETSAT QRSSVPSSTE KNAFNSSLED  60
```

```
PSTDYYQELQ RDISEMFLQI YKQGGFLGLS NIKFRPGSVV VQLTLAFREG TINVHDVETQ    120
FNQYKTEAAS RYNLTISDVS VSDVPFPFSA QSGAGVPGWG IALLVLVCVL VALAIVYLIA    180
LAVCQCRRKN YGQLDIFPAR DTYHPMSEYP TYHTHGRYVP PSSTDRSPYE KVSAGNGGSS    240
LSYTNPAVAA TSANL                                                    255

SEQ ID NO: 45          moltype = AA   length = 560
FEATURE                Location/Qualifiers
source                 1..560
                       mol_type = protein
                       organism = Homo sapiens
SEQUENCE: 45
MECLYYFLGF LLLAARLPLD AAKRFHDVLG NERPSAYMRE HNQLNGWSSD ENDWNEKLYP     60
VWKRGDMRWK NSWKGGRVQA VLTSDSPALV GSNITFAVNL IFPRCQKEDA NGNIVYEKNC    120
RNEAGLSADP YVYNWTAWSE DSDGENGTGQ SHHNVFPDGK PFPHHPGWRR WNFIYVFHTL    180
GQYFQKLGRC SVRVSVNTAN VTLGPQLMEV TVYRRHGRAY VPIAQVKDVY VVTDQIPVFV    240
TMFQKNDRNS SDETFLKDLP IMFDVLIHDP SHFLNYSTIN YKWSFGDNTG LFVSTNHTVN    300
HTYVLNGTFS LNLTVKAAAP GPCPPPPPPP RPSKPTPSLG PAGDNPLELS RIPDENCQIN    360
RYGHFQATIT IVEGILEVNI IQMTDVLMPV PWPESSLIDF VVTCQGSIPT EVCTIISDPT    420
CEITQNTVCS PVDVDEMCLL TVRRTFNGSG TYCVNLTLGD DTSLALTSTL ISVPDRDPAS    480
PLRMANSALI SVGCLAIFVT VISLLVYKKH KEYNPIENSP GNVVRSKGLS VFLNRAKAVF    540
FPGNQEKDPL LKNQEFKGVS                                                560

SEQ ID NO: 46          moltype = AA   length = 551
FEATURE                Location/Qualifiers
source                 1..551
                       mol_type = protein
                       organism = Homo sapiens
SEQUENCE: 46
MAAPALSWRL PLLILLLPLA TSWASAAVNG TSQFTCFYNS RANISCVWSQ DGALQDTSCQ     60
VHAWPDRRRW NQTCELLPVS QASWACNLIL GAPDSQKLTT VDIVTLRVLC REGVRWRVMA    120
IQDFKPFENL RLMAPISLQV VHVETHRCNI SWEISQASHY FERHLEFEAR TLSPGHTWEE    180
APLLTLKQKQ EWICLETLTP DTQYEFQVRV KPLQGEFTTW SPWSQPLAFR TKPAALGKDT    240
IPWLGHLLVG LSGAFGFIIL VYLLINCRNT GPWLKKVLKC NTPDPSKFFS QLSSEHGGDV    300
QKWLSSPFPS SSFSPGGLAP EISPLEVLER DKVTQLLLQD DKVPEPASLS SNHSLTSCFT    360
NQGYFFFHLP DALEIEACQV YFTYDPYSEE DPDEGVAGAP TGSSPQPLQP LSGEDDAYCT    420
FPSRDDLLLF SPSLLGGPSP PSTAPGGSGA GEERMPPSLQ ERVPRDWDPQ PLGPPTPGVP    480
DLVDFQPPPE LVLREAGEEV PDAGPREGVS FPWSRPPGQG EFRALNARLP LNTDAYLSLQ    540
ELQGQDPTHL V                                                         551

SEQ ID NO: 47          moltype = AA   length = 427
FEATURE                Location/Qualifiers
source                 1..427
                       mol_type = protein
                       organism = Homo sapiens
SEQUENCE: 47
MEWPARLCGL WALLLCAGGG GGGGGAAPTE TQPPVTNLSV SVENLCTVIW TWNPPEGASS     60
NCSLWYFSHF GDKQDKKIAP ETRRSIEVPL NERICLQVGS QCSTNESEKP SILVEKCISP    120
PEGDPESAVT ELQCIWHNLS YMKCSWLPGR NTSPDTNYTL YYWHRSLEKI HQCENIFREG    180
QYFGCSFDLT KVKDSSFEQH SVQIMVKDNA GKIKPSFNIV PLTSRVKPDP PHIKNLSFHN    240
DDLYVQWENP QNFISRCLFY EVEVNNSQTE THNVFYVQEA KCENPEFERN VENTSCFMVP    300
GVLPDTLNTV RIRVKTNKLC YEDDKLWSNW SQEMSIGKKR NSTLYITMLL IVPVIVAGAI    360
IVLLLYLKRL KIIIFPPPIPD PGKIFKEMFG DQNDDTLHWK KYDIYEKQTK EETDSVVLIE    420
NLKKASQ                                                              427

SEQ ID NO: 48          moltype = AA   length = 323
FEATURE                Location/Qualifiers
source                 1..323
                       mol_type = protein
                       organism = Homo sapiens
SEQUENCE: 48
MARGPGLAPP PLRLPLLLLV LAAVTGHTAA QDNCTCPTNK MTVCSPDGPG GRCQCRALGS     60
GMAVDCSTLT SKCLLLKARM SAPKNARTLV RPSEHALVDN DGLYDPDCDP EGRFKARQCN    120
QTSVCWCVNS VGVRRTDKGD LSLRCDELVR THHILIDLRH RPTAGAFNHS DLDAELRRLF    180
RERYRLHPKF VAAVHYEQPT IQIELRQNTS QKAAGDVDIG DAAYYFERDI KGESLFQGRG    240
GLDLRVRGEP LQVERTLIYY LDEIPPKFSM KRLTAGLIAV IVVVVVALVA GMAVLVITNR    300
RKSGKYKKVE IKELGELRKE PSL                                            323

SEQ ID NO: 49          moltype = AA   length = 257
FEATURE                Location/Qualifiers
source                 1..257
                       mol_type = protein
                       organism = Homo sapiens
SEQUENCE: 49
MAQRMTTQLL LLLVWVAVVG EAQTRIAWAR TELLNVCMNA KHHKEKPGPE DKLHEQCRPW     60
RKNACCSTNT SQEAHKDVSY LYRFNWNHCG EMAPACKRHF IQDTCLYECS PNLGPWIQQV    120
DQSWRKERVL NVPLCKEDCE QWWEDCRTSY TCKSNWHKGW NWTSGFNKCA VGAACQPFHF    180
YFPTPTVLCN EIWTHSYKVS NYSRGSGRCI QMWFDPAQGN PNEEVARFYA AAMSGAGPWA    240
AWPFLLSLAL MLLWLLS                                                   257
```

```
SEQ ID NO: 50           moltype = AA   length = 4130
FEATURE                 Location/Qualifiers
source                  1..4130
                        mol_type = protein
                        organism = Homo sapiens
SEQUENCE: 50
MLKPSGLPGS SSPTRSLMTG SRSTKATPEM DSGLTGATLS PKTSTGAIVV TEHTLPFTSP    60
DKTLASPTSS VVGRTTQSLG VMSSALPEST SRGMTHSEQR TSPSLSPQVN GTPSRNYPAT   120
SMVSGLSSPR TRTSSTEGNF TKEASTYTLT VETTSGPVTE KYTVPTETST TEGDSTETPW   180
DTRYIPVKIT SPMKTFADST ASKENAPVSM TPAETTVTDS HTPGRTNPSF GTLYSSFLDL   240
SPKGTPNSRG ETSLELILST TGYPFSSPEP GSAGHSRIST SAPLSSSASV LDNKISETSI   300
FSGQSLTSPL SPGVPEARAS TMPNSAIPFS MTLSNAETSA ERVRSTISSL GTPSISTKQT   360
AETILTFHAF AETMDIPSTH IAKTLASEWL GSPGTLGGTS TSALTTTSPS TTLVSEETNT   420
HHSTSGKETE GTLNTSMTPL ETSAPGEESE MTATLVPTLG FTTLDSKIRS PSQVSSSHPT   480
RELRTTGSTS GRQSSSTAAH GSSDILRATT SSTSKASSWT SESTAQQFSE PQHTQWVETS   540
PSMKTERPPA STSVAAPITT SVPSVVSGFT TLKTSSTKGI WLEETSADTL IGESTAGPTT   600
HQFAVPTGIS MTGGSSTRGS QGTTHLLTRA TASSETSADL TLATNGVPVS VSPAVSKTAA   660
GSSPPGGTKP SYTMVSSVIP ETSSLQSSAF REGTSLGLTP LNTRHPFSSP EPDSAGHTKI   720
STSIPLLSSA SVLEDKVSAT STFSHHKATS SITTGTPEIS TKTKPSSAVL SSMTLSNAAT   780
SPERVRNATS PLTHPSPSGE ETAGSVLTLS TSAETTDSPN IHPTGTLTSE SSESPSTLSL   840
PSVSGVKTTF SSSTPSTHLF TSGEETEETS NPSVSQPETS VSRVRTTLAS TSVPTPVFPT   900
MDTWPTRSAQ FSSSHLVSEL RATSSTSVTN STGSALPKIS HLTGTATMSQ TNRDTFNDSA   960
APQSTTWPET SPRFKTGLPS ATTTVSTSAT SLSATVMVSK FTSPATSSME ATSIREPSTT  1020
ILTTTETTNGP GSMAVASTNI PIGKGYITEG RLDTSHLPIG TTASSETSMD FTMAKESVSM  1080
SVSPSQSMDA AGSSTPGRTS QFVDTFSDDV YHLTSREITI PRDGTSSALT PQMTATHPPS  1140
PDPGSARSTW LGILSSSPSS PTPKVTMSST FSTQRVTTSM IMDTVETSRW NMPNLPSTTS  1200
LTPSNIPTSG AIGKSTLVPL DTPSPATSLE ASEGGLPTLS TYPESTNTPS IHLGAHASSE  1260
SPSTIKLTMA SVVKPGSYTP LTFPSIETHI HVSTARMAYS SGSSPEMTAP GETNTGSTWD  1320
PTTYITTTDP KDTSSAQVST PHSVRTLRTT ENHPKTESAT PAAYSGSPKI SSSPNLTSPA  1380
TKAWTITDTT EHSTQLHYTK LAEKSSGFET QSAPGPVSVV IPTSPTIGSS TLELTSDVPG  1440
EPLVLAPSEQ TTITLPMATW LSTSLTEEMA STDLDISSPS SPMSTFAIFP PMSTPSHELS  1500
KSEADTSAIR NTDSTTLDQH LGIRSLGRTG DLTTVPITPL TTTWTSVIEH STQAQDTLSA  1560
TMSPTHVTQS LKDQTSIPAS ASPSHLTEVY PELGTQGRSS SEATTFWKPS TDTLSREIET  1620
GPTNIQSTPP MDNTTTGSSS SGVTLGIAHL PIGTSSPAET STNMALERRS STATVSMAGT  1680
MGLLVTSAPG RSISQSLGRV SSVLSESTTE GVTDSSKGSS PRLNTQGNTA LSSSSLEPSYA  1740
EGSQMSTSIP LTSSPTTPDV EFIGGSTFWT KEVTTVMTSD ISKSSARTES SSATLMSTAL  1800
GSTENTGKEK LRTASMDLPS PTPSMEVTPW ISLTLSNAPN TTDSLDLSHG VHTSSAGTLA  1860
TDRSLNTGVT RASRLENGSD TSSKSLSMGN STHTSMTYTE KSEVSSSIHP RPETSAPGAE  1920
TTLTSTPGNR AISLTLPFSS IPVEEVISTG ITSGPDINSA PMTHSPITPP TIVWTSTGTI  1980
EQSTQPLHAV SSEKVSVQTQ STPYVNSVAV SASPTHENSV SSGSSTSSPY SSASLESLDS  2040
TISRRNAITS WLWDLTTSLP TTTWPSTSLS EALSSGHSGV SNPSSTTTEF PLFSAASTSA  2100
AKQRNPETET HGPQNTAAST LNTDASSVTG LSETPVGASI SSEVPLPMAI TSRSDVSGLT  2160
SESTANPSLG TASSAGTKLT RTISLPTSES LVSFRMNKDP WTVSIPLGSH PTTNTETSIP  2220
VNSAGPPGLS TVASDVIDTP SDGAESIPTV SFSPSPDTEV TTISHFPEKT THSFRTISSL  2280
THELTSRVTP IPGDWMSSAM STKPTGASPS ITLGERRTIT SAAPTTSPIV LTASFTETST  2340
VSLDNETTVK TSDILDARKT NELPSDSSSS SDLINTSIAS STMDVTKTAS ISPTSISGMT  2400
ASSSPSLFSS DRPQVPTSTT ETNATSPSV SSNTYSLDGG SVNVGGTPSTL PPFTITHPVE  2460
TSSALLAWSR PVRTFSTMVS TDTASGENPT SSNVVTSVP APGTWTSVGS TTDLPAMGFL  2520
KTSPAGEAHS LLASTIEPAT AFTPHLSAAV VTGSSATSEA SLLTTSESKA IHSSPQTPTT  2580
PTSGANWETS ATPESLLVVT ETSDTTLSK ILVTDTILFS TVSTPPSKFP STGTLSGASF  2640
PTLLPDTPAI PLTATEPTSS LATSFDSTPL VTIASDSLGT VPETTLTMSE TSNGDALVSL  2700
TVSNPDRSIP GITIQGVTES PLHPSSTSPS KIVAPRNTTY EGSITVALST LPAGTTGSLV  2760
FSQSSENSET TALVDSSAGL ERASVMPLTT GSQGMASSGG IRSGSTHSTG TKTFSSLPLT  2820
MNPGEVTAMS EITTNRLTAT QSTAPKGIPV KPTSAESGLL TPVSASSSPS KAFASLTTAP  2880
PTWGIPQSTL TFEFSEVPSL DTKSASLPTP GQSLNTIPDS DASTASSSLS KSPEKNPRAR  2940
MMTSTKAISA SSFQSTGFTE TPEGSASPSM AGHEPRVPTS GTGDPRYASE SMSYPDPSKA  3000
SSAMTSTSLA SKLTTLFSTG QAARSGSSSS PISLSTEKET SFLSPTASTS RKTSLFLGPS  3060
MARQPNILVH LQTSALTLSP TSTLNMSQEE PPELTSSQTI AEEEGTTAET QTLTFTPSET  3120
PTSLLPVSSP TEPTARRKSS PETWASSISV PAKTSLVETT DGTLVTTIKM SSQAAQGNST  3180
WPAPAEETGS SPAGTSPGSP EMSTTLKIMS SKEPSISPEI RSTVRNSPWK TPETTVPMET  3240
TVEPVTLQST ALGSGSTSIS HLPTGTTSPT KSPTENMLAT ERVSLSPSPP EAWTNLYSGT  3300
PGGTRQSLAT MSSVSLESPT ARSITGTGQQ SSPELVSKTT GMEFSMWHGS TGGTTGDTHV  3360
SLSTSSNILE DPVTSPNSVS SLTDKSKHKT ETWVSTTAIP TVLVNNKIMA AEQQTSRSVD  3420
EAYSSTSSWS DQTSGSDITL GASPDVTNTL YITSTAQTTS LVSLPSGDQG ITSLTNPSGG  3480
KTSSASSVTS PSIGLETLRA NVSAVKSDIA PTAGHLSQTS SPAEVSILDV TTAPTPGIST  3540
TITTMGTNSI STTTPNPEVG MSTMDSTPAT ERRTTSTEHP STWSSTAASD SWTVTDMTSN  3600
LKVARSPGTI STMHTTSFLA SSTELDSMST PHGRITVIGT SLVTPSSDAS AVKTETSTSE  3660
RTLSPSDTTA STPISTFSRV QRMSISVPDI LSTSWTPSST EADDVPVSMV STDHASTKTD  3720
PNTPLSTFLF DSLSTLDWDT GRSLSSATAT TSAPQGATTP QELTLETMIS PATSQLPFSI  3780
GHITSAVTPA AMARSSGVTF SRPDPTSKKA EQTSTQLPTT TSAHPGQVPR SAATTLDVIP  3840
HTAKTPDATF QRQGQTALTT EARATSDSWN EKEKSTPSAP WITEMMNSVS EDTIKEVTSS  3900
SSVLRTLNTL DINLESGTTS SPSWKSSPYE RIAPSESTTD KEAIHPSTNT VETTGWVTSS  3960
EHASHSTIPA HSASSKLTSP VVTTSTREQA IVSMSTTTWP ESTRARTEPN SFLTIELRDV  4020
SPSSTT QTSIISSPGS TAITKGPRTE ITSSKRISS FLAQSMRSSD SPSEAITRLS  4080
NFPPAMTESGG MILAMQTSPP GATSLSAPTL DTSATASWTG TPLATTQRFT          4130

SEQ ID NO: 51           moltype = AA   length = 442
FEATURE                 Location/Qualifiers
source                  1..442
```

```
                        mol_type = protein
                        organism = Homo sapiens
SEQUENCE: 51
MQPPPSLCGR  ALVALLLACG  LLGVWGEERG  FPPDKATPLL  QTAEIMTPPT  KTLWPKGSNA   60
SLARSLAPAE  VPKGDRTAGS  PPRTISPPPC  QGPIEIKETF  KYINTVVSCL  VFVLGIIGNS  120
TLLRIIYKNK  CMRNGPNILV  ASLALGDLLH  IVIDIPINVY  KLLAEDWPFG  AEMCKLVPFI  180
QKASVGITVL  SLCALSIDRY  RAVASWSRIK  GIGVPKWTAV  EIVLIWVVSV  VLAVPEAIGF  240
DIITMDYKGS  YLRICLLHPV  QKTAFMQFYK  TAKDWWLFSF  YFCLPLAITA  FFYTLMTCEM  300
LRKKSGMQIA  LNDHLKQRRE  VAKTVFCLVL  VFALCWLPLH  LSRILKLTLY  NQNDPNRCEL  360
LSFLLVLDYI  GINMASLNSC  INPIALYLVS  KRFKNCFKSC  LCCWCQSFEE  KQSLEEKQSC  420
LKFKANDHGY  DNFRSSNKYS  SS                                             442

SEQ ID NO: 52           moltype = AA  length = 339
FEATURE                 Location/Qualifiers
source                  1..339
                        mol_type = protein
                        organism = Homo sapiens
SEQUENCE: 52
MESRKDITNQ  EELWKMKPRR  NLEEDDYLHK  DTGETSMLKR  PVLLHLHQTA  HADEFDCPSE   60
LQHTQELFPQ  WHLPIKIAAI  IASLTFLYTL  LREVIHPLAT  SHQQYFYKIP  ILVINKVLPM  120
VSITLLALVY  LPGVIAAIVQ  LHNGTKYKKF  PHWLDKWMLT  RKQFGLLSFF  FAVLHAIYSL  180
SYPMRRSYRY  KLLNWAYQQV  QQNKEDAWIE  HDVWRMEIYV  SLGIVGLAIL  ALLAVTSIPS  240
VSDSLTWREF  HYIQSKLGIV  SLLLGTIHAL  IFAWNKWIDI  KQFVWYTPPT  FMIAVFLPIV  300
VLIFKSILFL  PCLRKKILKI  RHGWEDVTKI  NKTEICSQL                           339

SEQ ID NO: 53           moltype = AA  length = 710
FEATURE                 Location/Qualifiers
source                  1..710
                        mol_type = protein
                        organism = Homo sapiens
SEQUENCE: 53
MGGKQRDEDD  EAYGKPVKYD  PSFRGPIKNR  SCTDVICCVL  FLLFILGYIV  VGIVAWLYGD   60
PRQVLYPRNS  TGAYCGMGEN  KDKPYLLYFN  IFSCILSSNI  ISVAENGLQC  PTPQVCVSSC  120
PEDPWTVGKN  EFSQTVGEVF  YTKNRNFCLP  GVPWNMTVIT  SLQQELCPSF  LLPSAPALGR  180
CFPWTNVTPP  ALPGITNDTT  IQQGISGLID  SLNARDISVK  IFEDFAQSWY  WILVALGVAL  240
VLSLLFILLL  RLVAGPLVLV  LILGVLGVLA  YGIYYCWEEY  RVLRDKGASI  SQLGFTTNLS  300
AYQSVQETWL  AALIVLAVLE  AILLLMLIFL  RQRIRIAIAL  LKEASKAVGQ  MMSTMFYPLV  360
TFVLLICIA   YWAMTALYLA  TSGQPQYVLW  ASNISSPGCA  KVPINTSCNP  TAHLVNSSCP  420
GLMCVFQGYS  SKGLIQRSVF  NLQIYGVLGL  FWTLNWVLAL  GQCVLAGAFA  SFYWAFHKPQ  480
DIPTFPLISA  FIRTLRYHTG  SLAFGALILT  LVQIARVILE  YIDHKLRGVQ  NPVARCIMCC  540
FKCCLWCLEK  FIKFLNRNAY  IMIAIYGKNF  CVSAKNAFML  LMRNIVRVVV  LDKVTDLLLF  600
FGKLLVVGGV  GVLSFFFFSG  RIPGLGKDFK  SPHLNYYWLP  IMTSILGAYV  IASGFFSVFG  660
MCVDTLFLCF  LEDLERNNGS  LDRPYYMSKS  LLKILGKKNE  APPDNKKRKK              710

SEQ ID NO: 54           moltype = AA  length = 441
FEATURE                 Location/Qualifiers
source                  1..441
                        mol_type = protein
                        organism = Yersinia pestis
SEQUENCE: 54
MKERSTELVQ  GFRHSVPYIN  AHRGKTFVVM  LGGEAIEHEN  FSSIVNDIGL  LHSLGIRLVV   60
VYGARPQIDS  NLADHNYEPI  YHKHTRVTDA  RTLEMVKQAA  GLLQLDITAR  LSMSLNNTPL  120
QGAHINVVSG  NFIIAQPLGV  DDGVDYCHSG  RIRRIDEEAI  HRQLDNGAIV  LLGPVAVSVT  180
GESFNLTSEE  VATQLAIKLK  AEKMIGFCSS  QGVTDSEGNI  ISELFPNDAQ  KRIEDLEQDG  240
DYNSGTVRFL  RGAVKACRSG  VRRSHLLSYQ  EDGALIQELF  SRDGIGTQIV  MESAEQVRRA  300
TINDIGGILE  LIRPLEQQGI  LVRRSREQLE  MEIDKFTIIE  RDNLTIACAA  LYPFPDEHIG  360
EMACVAVHPD  YRSSSRGEML  LNRITNQARQ  MGLKKLFVLT  TRSIHWFQER  GFTPAEVDVL  420
PIQKQELYNY  QRRSKILLAD  L                                              441

SEQ ID NO: 55           moltype = AA  length = 1073
FEATURE                 Location/Qualifiers
source                  1..1073
                        mol_type = protein
                        organism = Homo sapiens
SEQUENCE: 55
MKTLLLDLAL  WSLLFQPGWL  SFSSQVSQNC  HNGSYEISVL  MMGNSAFAEP  LKNLEDAVNE   60
GLEIVRGRLQ  NAGLNVTVNA  TFMYSDGLIH  NSGDCRSSTC  EGLDLRKIS   NAQRMGCVLI  120
GPSCTYSTFQ  MYLDTELSYP  MISAGSFGLS  CDYKETLTRL  MSPARKLMYF  LVNFWKTNDL  180
PFKTYSWSTS  YVYKNGTETE  DCFWYLNALE  ASVSYFSHEL  GFKVVLRQDK  EFQDILMDHN  240
RKSNVIIMCG  GPEFLYKLKG  DRAVAEDIVI  ILVDLFNDQY  FEDNVTAPDY  MKNVLVLTLS  300
PGNSLLNSSF  SRNLSPTKRD  FALAYLNGIL  LFGHMLKIFL  ENGENITTPK  FAHAFRNLTF  360
EGYDGPVTLD  DWGDVDSTMV  LLYTSVDTKK  YKVLLTYDTH  VNKTYPVDMS  PTFTWKNSKL  420
PNDITGRGPQ  ILMIAVFTLT  GAVVLLLLVA  LLMLRKYRLD  YELRQKKWSH  IPPENIFPLE  480
TNETNHVSLK  IDDDKRRDTI  QRLRQCKYDK  KRVILKDLKH  NDGNFTEKQK  IELNKLLQID  540
YYNLTKFYGT  VKLDTMIFGV  IEYCERGSLR  EVLNDTISYP  DGTFMDWEFK  ISVLYDIAKG  600
MSYLHSSKTE  VHGRLKSTNC  VVDSRMVVKI  TDFGCNSILP  PKKDLWTAPE  HLRQANISQK  660
GDVYSYGIIA  QEIILRKETF  YTLSCRDRNE  KIFRVENSNG  MKPFRPDLFL  ETAEEKELEV  720
YLLVKNCWEE  DPEKRPDFKK  IETTLAKIFG  LFHDQKNESY  MDTLIRRLQL  YSRNLEHLVE  780
ERTQLYKAER  DRADRLNFML  LPRLVVKSLK  EKGFVEPELY  EEVTIYFSDI  VGFTTICKYS  840
```

```
TPMEVVDMLN DIYKSFDHIV DHHDVYKVET IGDAYMVASG LPKRNGNRHA IDIAKMALEI   900
LSFMGTFELE HLPGLPIWIR IGVHSGPCAA GVVGIKMPRY CLFGDTVNTA SRMESTGLPL   960
RIHVSGSTIA ILKRTECQFL YEVRGETYLK GRGNETTYWL TGMKDQKFNL PTPPTVENQQ  1020
RLQAEFSDMI ANSLQKRQAA GIRSQKPRRV ASYKKGTLEY LQLNTTDKES TYF         1073

SEQ ID NO: 56          moltype = AA   length = 239
FEATURE                Location/Qualifiers
source                 1..239
                       mol_type = protein
                       organism = Homo sapiens
SEQUENCE: 56
MAHAGRTGYD NREIVMKYIH YKLSQRGYEW DAGDVGAAPP GAAPAPGIFS SQPGHTPHPA    60
ASRDPVARTS PLQTPAAPGA AAGPALSPVP PVVHLTLRQA GDDFSRRYRR DPAEMSSQLH   120
LTPFTARGRF ATVVEELFRD GVNWGRIVAF FEFGGVMCVE SVNREMSPLV DNIALWMTEY   180
LNRHLHTWIQ DNGGWDAFVE LYGPSMRPLF DFSWLSLKTL LSLALVGACI TLGAYLGHK    239

SEQ ID NO: 57          moltype = AA   length = 393
FEATURE                Location/Qualifiers
source                 1..393
                       mol_type = protein
                       organism = Homo sapiens
SEQUENCE: 57
MEEPQSDPSV EPPLSQETFS DLWKLLPENN VLSPLPSQAM DDLMLSPDDI EQWFTEDPGP    60
DEAPRMPEAA PRVAPAPAAP TPAAPAPAPS WPLSSSVPSQ KTYQGSYGFR LGFLHSGTAK   120
SVTCTYSPAL NKMFCQLAKT CPVQLWVDST PPPGTRVRAM AIYKQSQHMT EVVRRCPHHE   180
RCSDSDGLAP PQHLIRVEGN LRVEYLDDRN TFRHSVVVPY EPPEVGSDCT TIHYNYMCNS   240
SCMGGMNRRP ILTIITLEDS SGNLLGRNSF EVHVCACPGR DRRTEEENLR KKGEPHHELP   300
PGSTKRALSN NTSSSPQPKK KPLDGEYFTL QIRGRERFEM FRELNEALEL KDAQAGKEPG   360
GSRAHSSHLK SKKGQSTSRH KKLMFKTEGP DSD                                393

SEQ ID NO: 58          moltype = AA   length = 164
FEATURE                Location/Qualifiers
source                 1..164
                       mol_type = protein
                       organism = Homo sapiens
SEQUENCE: 58
MSEPAGDVRQ NPCGSKACRR LFGPVDSEQL SRDCDALMAG CIQEARERWN FDFVTETPLE    60
GDFAWERVRG LGLPKLYLPT GPRRGRDELG GGRRPGTSPA LLQGTAEEDH VDLSLSCTLV   120
PRSGEQAEGS PGGPGDSQGR KRRQTSMTDF YHSKRRLIFS KRKP                    164

SEQ ID NO: 59          moltype = AA   length = 110
FEATURE                Location/Qualifiers
source                 1..110
                       mol_type = protein
                       organism = Homo sapiens
SEQUENCE: 59
MALWMRLLPL LALLALWGPD PAAAFVNQHL CGSHLVEALY LVCGERGFFY TPKTRREAED    60
LQVGQVELGG GPGAGSLQPL ALEGSLQKRG IVEQCCTSIC SLYQLENYCN              110

SEQ ID NO: 60          moltype = AA   length = 267
FEATURE                Location/Qualifiers
source                 1..267
                       mol_type = protein
                       organism = Homo sapiens
SEQUENCE: 60
MPRSCCSRSG ALLLALLLQA SMEVRGWCLE SSQCQDLTTE SNLLECIRAC KPDLSAETPM    60
FPGNGDEQPL TENPRKYVMG HFRWDRFGRR NSSSSGSSGA GQKREDVSAG EDCGPLPEGG   120
PEPRSDGAKP GPREGKRSYS MEHFRWGKPV GKKRRPVKVY PNGAEDESAE AFPLEFKREL   180
TGQRLREGDG PDGPADDGAG AQADLEHSLL VAAEKKDEGP YRMEHFRWGS PPKDKRYGGF   240
MTSEKSQTPL VTLFKNAIIK NAYKKGE                                       267

SEQ ID NO: 61          moltype = AA   length = 462
FEATURE                Location/Qualifiers
source                 1..462
                       mol_type = protein
                       organism = Homo sapiens
SEQUENCE: 61
MASNSSSCPT PGGGHLNGYP VPPYAFFFPP MLGGLSPPGA LTTLQHQLPV SGYSTPSPAT    60
IETQSSSSEE IVPSPPSPPP LPRIYKPCFV CQDKSSGYHY GVSACEGCKG FFRRSIQKNM   120
VYTCHRDKNC IINKVTRNRC QYCRLQKCFE VGMSKESVRN DRNKKKKEVP KPECSESYTL   180
TPEVGELIEK VRKAHQETFP ALCQLGKYTT NNSSEQRVSL DIDLWDKFSE LSTKCIIKTV   240
EFAKQLPGFT TLTIADQITL LKAACLDILI LRICTRYTPE QDTMTFSDGL TLNRTQMHNA   300
GFGPLTDLVF AFANQLLPLE MDDAETGLLS AICLICGDRQ DLEQPDRVDM LQEPLLEALK   360
VYVRKRRPSR PHMFPKMLMK ITDLRSISAK GAERVITLKM EIPGSMPPLI QEMLENSEGL   420
DTLSGQPGGG GRDGGGLAPP PGSCSPSLSP SSNRSSPATH SP                      462

SEQ ID NO: 62          moltype = AA   length = 455
FEATURE                Location/Qualifiers
source                 1..455
```

```
                        mol_type = protein
                        organism = Homo sapiens
SEQUENCE: 62
MTTSGHACPV  PAVNGHMTHY  PATPYPLLFP  PVIGGLSLPP  LHGLHGHPPP  SGCSTPSPAT   60
IETQSTSSEE  LVPSPPSPLP  PPRVYKPCFV  CQDKSSGYHY  GVSACEGCKG  FFRRSIQKNM  120
IYTCHRDKNC  VINKVTRNRC  QYCRLQKCFE  VGMSKESVRN  DRNKKKKETS  KQECTESYEM  180
TAELDDLTEK  IRKAHQETFP  SLCQLGKYTT  NSSADHRVRL  DLGLWDKFSE  LATKCIIKIV  240
EFAKRLPGFT  GLTIADQITL  LKAACLDILI  LRICTRYTPE  QDTMTFSDGL  TLNRTQMHNA  300
GFGPLTDLVF  TFANQLLPLE  MDDTETGLLS  AICLICGDRQ  DLEEPTKVDK  LQEPLLEALK  360
IYIRKRRPSK  PHMFPKILMK  ITDLRSISAK  GAERVITLKM  EIPGSMPPLI  QEMLENSEGH  420
EPLTPSSSGN  TAEHSPSISP  SSVENSGVSQ  SPLVQ                                455

SEQ ID NO: 63           moltype = AA  length = 455
FEATURE                 Location/Qualifiers
source                  1..455
                        mol_type = protein
                        organism = Homo sapiens
SEQUENCE: 63
MTTSGHACPV  PAVNGHMTHY  PATPYPLLFP  PVIGGLSLPP  LHGLHGHPPP  SGCSTPSPAT   60
IETQSTSSEE  LVPSPPSPLP  PPRVYKPCFV  CQDKSSGYHY  GVSACEGCKG  FFRRSIQKNM  120
IYTCHRDKNC  VINKVTRNRC  QYCRLQKCFE  VGMSKESVRN  DRNKKKKETS  KQECTESYEM  180
TAELDDLTEK  IRKAHQETFP  SLCQLGKYTT  NSSADHRVRL  DLGLWDKFSE  LATKCIIKIV  240
EFAKRLPGFT  GLTIADQITL  LKAACLDILI  LRICTRYTPE  QDTMTFSDGL  TLNRTQMHNA  300
GFGPLTDLVF  TFANQLLPLE  MDDTETGLLS  AICLICGDRQ  DLEEPTKVDK  LQEPLLEALK  360
IYIRKRRPSK  PHMFPKILMK  ITDLRSISAK  GAERVITLKM  EIPGSMPPLI  QEMLENSEGH  420
EPLTPSSSGN  TAEHSPSISP  SSVENSGVSQ  SPLVQ                                455

SEQ ID NO: 64           moltype = AA  length = 462
FEATURE                 Location/Qualifiers
source                  1..462
                        mol_type = protein
                        organism = Homo sapiens
SEQUENCE: 64
MDTKHFLPLD  FSTQVNSSLT  SPTGRGSMAA  PSLHPSLGPG  IGSPGQLHSP  ISTLSSPING   60
MGPPFSVISS  PMGPHSMSVP  TTPTLGFSTG  SPQLSSPMNP  VSSSEDIKPP  LGLNGVLKVP  120
AHPSGNMASF  TKHICAICGD  RSSGKHYGVY  SCEGCKGFFK  RTVRKDLTYT  CRDNKDCLID  180
KRQRNRCQYC  RYQKCLAMGM  KREAVQEERQ  RGKDRNENEV  ESTSSANEDM  PVERILEAEL  240
AVEPKTETYV  EANMGLNPSS  PNDPVTNICQ  AADKQLFTLV  EWAKRIPHFS  ELPLDDQVIL  300
LRAGWNELLI  ASFSHRSIAV  KDGILLATGL  HVHRNSAHSA  GVGAIFDRVL  TELVSKMRDM  360
QMDKTELGCL  RAIVLFNPDS  KGLSNPAEVE  ALREKVYASL  EAYCKHKYPE  QPGRFAKLLL  420
RLPALRSIGL  KCLEHLFFFK  LIGDTPIDTF  LMEMLEAPHQ  MT                       462

SEQ ID NO: 65           moltype = AA  length = 533
FEATURE                 Location/Qualifiers
source                  1..533
                        mol_type = protein
                        organism = Homo sapiens
SEQUENCE: 65
MSWAARPPFL  PQRHAAGQCG  PVGVRKEMHC  GVASRWRRRR  PWLDPAAAAA  AAVAGGEQQT   60
PEPEPGEAGR  DGMGDSGRDS  RSPDSSSPNP  LPQGVPPPSP  PGPPLPPSTA  PSLGGSAPPS  120
PPPMPPPPLG  SPFPVISSSM  GSPGLPPPAP  PGFSGPVSSP  QINSTVSLPG  GGSGPPEDVK  180
PPVLGVRGLH  CPPPPGGPGA  GKRLCAICGD  RSSGKHYGVY  SCEGCKGFFK  RTIRKDLTYS  240
CRDNKDCTVD  KRQRNRCQYC  RYQKCLATGM  KREAVQEERQ  RGKDKDGDGE  GAGGAPEEMP  300
VDRILEAELA  VEQKSDQGVE  GPGGTGGSGS  SPNDPVTNIC  QAADKQLFTL  VEWAKRIPHF  360
SSLPLDDQVI  LLRAGWNELL  IASFSHRSID  VRDGILLATG  LHVHRNSAHS  AGVGAIFDRV  420
LTELVSKMRD  MRMDKTELGC  LRAIILFNPD  AKGLSNPSEV  EVLREKVYAS  LETYCKQKYP  480
EQQGRFAKLL  LRLPALRSIG  LKCLEHLFFF  KLIGDTPIDT  FLMEMLEAPH  QLA          533

SEQ ID NO: 66           moltype = AA  length = 463
FEATURE                 Location/Qualifiers
source                  1..463
                        mol_type = protein
                        organism = Homo sapiens
SEQUENCE: 66
MYGNYSHFMK  FPAGYGGSPG  HTGSTSMSPS  AALSTGKPMD  SHPSYTDTPV  SAPRTLSAVG   60
TPLNALGSPY  RVITSAMGPP  SGALAAPPGI  NLVAPPSSQL  NVVNSVSSSE  DIKPLPGLPG  120
IGNMNYPSTS  PGSLVKHICA  ICGDRSSGKH  YGVYSCEGCK  GFFKRTIRKD  LIYTCRDNKD  180
CLIDKRQRNR  CQYCRYQKCL  VMGMKREAVQ  EERQRSRERA  ESEAECATSG  HEDMPVERIL  240
EAELAVEPKT  ESYGDMNMEN  STNDPVTNIC  HAADKQLFTL  VEWAKRIPHF  SDLTLEDQVI  300
LLRAGWNELL  IASFSHRSVS  VQDGILLATG  LHVHRSSAHS  AGVGSIFDRV  LTELVSKMKD  360
MQMDKSELGC  LRAIVLFNPD  AKGLSNPSEV  ETLREKVYAT  LEAYTKQKYP  EQPGRFAKLL  420
LRLPALRSIG  LKCLEHLFFF  KLIGDTPIDT  FLMEMLETPL  QIT                      463

SEQ ID NO: 67           moltype = AA  length = 493
FEATURE                 Location/Qualifiers
source                  1..493
                        mol_type = protein
                        organism = Homo sapiens
SEQUENCE: 67
```

```
MLAATVLTLA LLGNAHACSK GTSHEAGIVC RITKPALLVL NHETAKVIQT AFQRASYPDI   60
TGEKAMMLLG QVKYGLHNIQ ISHLSIASSQ VELVEAKSID VSIQNVSVVF KGTLKYGYTT  120
AWWLGIDQSI DFEIDSAIDL QINTQLTCDS GRVRTDAPDC YLSFHKLLLH LQGEREPGWI  180
KQLFTNFISF TLKLVLKGQI CKEINVISNI MADFVQTRAA SILSDGDIGV DISLTGDPVI  240
TASYLESHHK GHFIYKNVSE DLPLPTFSPT LLGDSRMLYF WFSERVFHSL AKVAFQDGRL  300
MLSLMGDEFK AVLETWGFNT NQEIFQEVVG GFPSQAQVTV HCLKMPKISC QNKGVVVNSS  360
VMVKFLFPRP DQQHSVAYTF EEDIVTTVQA SYSKKKLFLS LLDFQITPKT VSNLTESSSE  420
SVQSFLQSMI TAVGIPEVMS RLEVVFTALM NSKGVSLFDI INPEIITRDG FLLLQMDFGF  480
PEHLLVDFLQ SLS                                                    493

SEQ ID NO: 68            moltype = AA  length = 185
FEATURE                  Location/Qualifiers
source                   1..185
                         mol_type = protein
                         organism = Homo sapiens
SEQUENCE: 68
MKLVSVALMY LGSLAFLGAD TARLDVASEF RKKWNKWALS RGKRELRMSS SYPTGLADVK   60
AGPAQTLIRP QDMKGASRSP EDSSPDAARI RVKRYRQSMN NFQGLRSFGC RFGTCTVQKL  120
AHQIYQFTDK DKDNVAPRSK ISPQGYGRRR RRSLPEAGPG RTLVSSKPQA HGAPAPPSGS  180
APHFL                                                             185

SEQ ID NO: 69            moltype = AA  length = 498
FEATURE                  Location/Qualifiers
source                   1..498
                         mol_type = protein
                         organism = Homo sapiens
SEQUENCE: 69
MTVFLSFAFL AAILTHIGCS NQRRSPENSG RRYNRIQHGQ CAYTFILPEH DGNCRESTTD   60
QYNTNALQRD APHVEPDFSS QKLQHLEHVM ENYTQWLQKL ENYIVENMKS EMAQIQQNAV  120
QNHTATMLEI GTSLLSQTAE QTRKLTDVET QVLNQTSRLE IQLLENSLST YKLEKQLLQQ  180
TNEILKIHEK NSLLEHKILE MEGKHKEELD TLKEEKENLQ GLVTRQTYII QELEKQLNRA  240
TTNNSVLQKQ QLELMDTVHN LVNLCTKEGV LLKGGKREEE KPFRDCADVY QAGFNKSGIY  300
TIYINNMPEP KKVFCNMDVN GGGWTVIQHR EDGSLDFQRG WKEYKMGFGN PSGEYWLGNE  360
FIFAITSQRQ YMLRIELMDW EGNRAYSQYD RFHIGNEKQN YRLYLKGHTG TAGKQSSLIL  420
HGADFSTKDA DNDNCMCKCA LMLTGGWWFD ACGPSNLNGM FYTAGQNHGK LNGIKWHYFK  480
GPSYSLRSTT MMIRPLDF                                               498

SEQ ID NO: 70            moltype = AA  length = 558
FEATURE                  Location/Qualifiers
source                   1..558
                         mol_type = protein
                         organism = Homo sapiens
SEQUENCE: 70
MAALTRDPQF QKLQQWYREH RSELNLRRLF DANKDRFNHF SLTLNTNHGH ILVDYSKNLV   60
TEDVMRMLVD LAKSRGVEAA RERMFNGEKI NYTEGRAVLH VALRNRSNTP ILVDGKDVMP  120
EVNKVLDKMK SFCQRVRSGD WKGYTGKTIT DVINIGIGGS DLGPLMVTEA LKPYSSGGPR  180
VWYVSNIDGT HIAKTLAQLN PESSLFIIAS KTFTTQETIT NAETAKEWFL QAAKDPSAVA  240
KHFVALSTNT TKVKEFGIDP QNMFEFWDWV GGRYSLWSAI GLSIALHVGF DNFEQLLSGA  300
HWMDQHFRTT PLEKNAPVLL ALLGIWYINC FGCETHAMLP YDQYLHRFAA YFQQGDMESN  360
GKYITKSGTR VDHQTGPIVW GEPGTNGQHA FYQLIHQGTK MIPCDFLIPV QTQHPIRKGL  420
HHKILLANFL AQTEALMRGK STEEARKELQ AAGKSPEDLE RLLPHKVFEG NRPTNSIVFT  480
KLTPFMLGAL VAMYEHKIFV QGIIWDINSF DQWGVELGKQ LAKKIEPELD GSAQVTSHDA  540
STNGLINFIK QQREARVQ                                               558

SEQ ID NO: 71            moltype = AA  length = 307
FEATURE                  Location/Qualifiers
source                   1..307
                         mol_type = protein
                         organism = Homo sapiens
SEQUENCE: 71
MPGQELRTVN GSQMLLVLLV LSWLPHGGAL SLAEASRASF PGPSELHSED SRFRELRKRY   60
EDLLTRLRAN QSWEDSNTDL VPAPAVRILT PEVRLGSGGH LHLRISRAAL PEGLPEASRL  120
HRALFRLSPT ASRSWDVTRP LRRQLSLARP QAPALHLRLS PPPSQSDQLL AESSSARPQL  180
ELHLRPQAAR GRRRARARNG DHCPLGPGRC CRLHTVRASL EDLGWADWVL SPREVQTMC  240
IGACPSQFRA ANMHAQIKTS LHRLKPDTVP APCCVPASYN PMVLIQKTDT GVSLQTYDDL  300
LAKDCHC                                                           307

SEQ ID NO: 72            moltype = AA  length = 247
FEATURE                  Location/Qualifiers
source                   1..247
                         mol_type = protein
                         organism = Homo sapiens
SEQUENCE: 72
MTILFLTMVI SYFGCMKAAP MKEANIRGQG GLAYPGVRTH GTLESVNGPK AGSRGLTSLA   60
DTFEHVIEEL LDEDHKVRPN EENNKDADLY TSRVMLSSQV PLEPPLLFLL EEYKNYLDAA  120
NMSMMVLRHS DPARRGELSV CDSISEWVTA ADKKTAVDMS GGTVTVLEKV PVSKGQLKQY  180
FYETKCNPMG YTKEGCRGID KRHWNSQCRT TQSYVRALTM DSKKRIGWRF IRIDTSCVCT  240
LTIKRGR                                                           247
```

```
SEQ ID NO: 73            moltype = AA  length = 1754
FEATURE                  Location/Qualifiers
source                   1..1754
                         mol_type = protein
                         organism = Homo sapiens
SEQUENCE: 73
MAPYPCGCHI LLLLFCCLAA ARANLLNLNW LWFNNEDTSH AATTIPEPQG PLPVQPTADT     60
TTHVTPRNGS TEPATAPGSP EPPSELLEDG QDTPTSAESP DAPEENIAGV GAEILNVAKG    120
IRSFVQLWND TVPTESLARA ETLVLETPVG PLALAGPSST PQENGTTLWP SRGIPSSPGA    180
HTTEAGTLPA PTPSPPSLGR PWAPLTGPSV PPPSSGRASL SSLLGGAPPW GSLQDPDSQG    240
LSPAAAAPSQ QLQRPDVRLR TPLLHPLVMG SLGKHAAPSA FSSGLPGALS QVAVTTLTRD    300
SGAWVSHVAN SVGPGLANNS ALLGADPEAP AGRCLPLPPS LPVCGHLGIS RFWLPNHLHH    360
ESGEQVRAGA RAWGGLLQTH CHPFLAWFFC LLLVPPCGSV PPPAPPPCCQ FCEALQDACW    420
SRLGGGRLPV ACASLPTQED GYCVLIGPAA ERISEEVGLL QLLGDPPPQQ VTQTDDPDVG    480
LAYVFGPDAN SGQVARYHFP SLFFRDFSLL FHIRPATEGP GVLFAITDSA QAMVLLGVKL    540
SGVQDGHQDI SLLYTEPGAG QTHTAASFRL PAFVGQWTHL ALSVAGGFVA LYVDCEEFQR    600
MPLARSSRGL ELEPGAGLFV AQAGGADPDK FQGVIAELKV RRDPQVSPMH CLDEEGDDSD    660
GASGDSGSGL GDARELLREE TGAALKPRLP APPPVTTPPL AGGSSTEDSR SEEVEEQTTV    720
ASLGAQTLPG SDSVSTWDGS VRTPGGRVKE GGLKGQKGEP GVPGPPGRAG PPGSPCLPGP    780
PGLPCPVSPL GPAGPALQTV PGPQGPPGPP GRDGTPGRDG EPGDPGEDGK PGDTGPQGFP    840
GTPGDVGPKG DKGDPGVGER GPPGPQGPPG PPGPSFRHDK LTFIDMEGSG FGGDLEALRG    900
PRGFPGPPGP PGVPGLPGEP GRFGVNSSDV PGPAGLPGVP GREGPPGPPG LPGPPGPPGR    960
EGPPGRTGQK GSLGEAGAPG HKGSKGAPGR AGARGESGLA GAPGPAGPPG PPGPPGPPGP   1020
GLPAGFDDME GSGGPFWSTA RSADGPQGPP GLPGLKGDPG VPGLPGAKGE VGADGVPGFP   1080
GLPGREGIAG PQGPKGDRGS RGEKDPGPKD GVGQPGLPGP PGPPGPVVYV SEQDGSVLSV   1140
PGPEGRPGFA GFPGPAGPKG NLGSKGERGS PGPKGEKGEP GSIFSPDGGA LGPAQKGAKG   1200
EPGFRGPPGP YGRPGYKGEI GFPGRPGRPG MNGLKGEKGE PGDASLGFGM RGMPGPPGPP   1260
GPPGPPGTPV YDSNVFAESS RPGPPGLPGN QGPPGPKGAK GEVGPPGPPG QPFPFDFLQLE   1320
AEMKGEKGDR GDAGQKGERG EPGGGFFGS  SLPGPPGPPG PPGPRGYPGI PGPKGESIRG   1380
QPGPPGPQGP PGIGYEGRQG PPGPPGPPG  PSFPGPHRQT ISVPGPPGPP GPPGPPGTMG   1440
ASSGVRLWAT RQAMLGQVHE VPEGWLIFVA EQEELYVRVQ NGFRKVQLEA RTPLPRGTDN   1500
EVAALQPPVV QLHDSNPYPR REHPHPTARP WRADDILASP PRLPEPQPYP GAPHHSSYVH   1560
LRPARPTSPP AHSRDFQPV  LHLVALNSPL SGGMRGIRGA DFQCFQQARA VGLAGTFRAF   1620
LSSRLQDLYS IVRRADRAAV PIVNLKDELL FPSWEALFSG SEGPLKPGAR IFSFDGKDVL   1680
RHPTWPQKSV WHGSDPNGRR LTESYCETWR TEAPSATGQA SSLLGGRLLG QSAASCHHAY   1740
IVLCIENSFM TASK                                                    1754

SEQ ID NO: 74            moltype = AA  length = 1763
FEATURE                  Location/Qualifiers
source                   1..1763
                         mol_type = protein
                         organism = Homo sapiens
SEQUENCE: 74
MAPYPCGCHI LLLLFCCLAA ARANLLNLNW LWFNNEDTSH AATTIPEPQG PLPVQPTADT     60
TTHVTPRNGS TEPATAPGSP EPPSELLEDG QDTPTSAESP DAPEENIAGV GAEILNVAKG    120
IRSFVQLWND TVPTESLARA ETLVLETPVG PLALAGPSST PQENGTTLWP SRGIPSSPGA    180
HTTEAGTLPA PTPSPPSLGR PWAPLTGPSV PPPSSGRASL SSLLGGAPPW GSLQDPDSQG    240
LSPAAAAPSQ QLQRPDVRLR TPLLHPLVMG SLGKHAAPSA FSSGLPGALS QVAVTTLTRD    300
SGAWVSHVAN SVGPGLANNS ALLGADPEAP AGRCLPLPPS LPVCGHLGIS RFWLPNHLHH    360
ESGEQVRAGA RAWGGLLQTH CHPFLAWFFC LLLVPPCGSV PPPAPPPCCQ FCEALQDACW    420
SRLGGGRLPV ACASLPTQED GYCVLIGPAA ERISEEVGLL QLLGDPPPQQ VTQTDDPDVG    480
LAYVFGPDAN SGQVARYHFP SLFFRDFSLL FHIRPATEGP GVLFAITDSA QAMVLLGVKL    540
SGVQDGHQDI SLLYTEPGAG QTHTAASFRL PAFVGQWTHL ALSVAGGFVA LYVDCEEFQR    600
MPLARSSRGL ELEPGAGLFV AQAGGADPDK FQGVIAELKV RRDPQVSPMH CLDEEGDDSD    660
GASGDSGSGL GDARELLREE TGAALKPRLP APPPVTTPPL AGGSSTEDSR SEEVEEQTTV    720
ASLGAQTLPG SDSVSTWDGS VRTPGGRVKE GGLKGQKGEP GVPGPPGRAG PPGSPCLPGP    780
PGLPCPVSPL GPAGPALQTV PGPQGPPGPP GRDGTPGRDG EPGDPGEDGK PGDTGPQGFP    840
GTPGDVGPKG DKGDPGVGER GPPGPQGPPG PPGPSFRHDK LTFIDMEGSG FGGDLEALRG    900
PRGFPGPPGP PGVPGLPGEP GRFGVNSSDV PGPAGLPGVP GREGPPGPPG LPGPPGPPGR    960
EGPPGRTGQK GSLGEAGAPG HKGSKGAPGR AGARGESGLA GAPGPAGPPG PPGPPGPPGP   1020
GLPAGFDDME GSGGPFWSTA RSADGPQGPP GLPGLKGDPG VPGLPGAKGE VGADGVPGFP   1080
GLPGREGIAG PQGPKGDRGS RGEKDPGPKD GVGQPGLPGP PGPPGPVVYV SEQDGSVLSV   1140
PGPEGRPGFA GFPGPAGPKG NLGSKGERGS PGPKGEKGEP GSIFSPDGGA LGPAQKGAKG   1200
EPGFRGPPGP YGRPGYKGEI GFPGRPGRPG MNGLKGEKGE PGDASLGFGM RGMPGPPGPP   1260
GPPGPPGTPV YDSNVFAESS RPGPPGLPGN QGPPGPKGAK GEVGPPGPPG QPFPFDFLQLE   1320
AEMKGEKGDR GDAGQKGERG EPGGGFFGS  SLPGPPGPPG PPGPRGYPGI PGPKGESIRG   1380
QPGPPGPQGP PGIGYEGRQG PPGPPGPPG  PSFPGPHRQT ISVPGPPGPP GPPGPPGTMG   1440
ASSGVRLWAT RQAMLGQVHE VPEGWLIFVA EQEELYVRVQ NGFRKVQLEA RTPLPRGTDN   1500
EVAALQPPVV QLHDSNPYPR REHPHPTARP WRADDILASP PRLPEPQPYP GAPHHSSYVH   1560
LRPARPTSPP AHSRDFQPV  LHLVALNSPL SGGMRGIRGA DFQCFQQARA VGLAGTFRAF   1620
LSSRLQDLYS IVRRADRAAV PIVNLKDELL FPSWEALFSG SEGPLKPGAR IFSFDGKDVL   1680
RHPTWPQKSV WHGSDPNGRR LTESYCETWR TEAPSATGQA SSLLGGRLLG QSAASCHHAY   1740
IVLCIENSFM TASKMGGSHH HHH                                          1763

SEQ ID NO: 75            moltype = AA  length = 1166
FEATURE                  Location/Qualifiers
source                   1..1166
                         mol_type = protein
                         organism = Homo sapiens
```

```
SEQUENCE: 75
MLLTLIILLP VVSKFSFVSL SAPQHWSCPE GTLAGNGNST CVGPAPFLIF SHGNSIFRID    60
TEGTNYEQLV VDAGVSVIMD FHYNEKRIYW VDLERQLLQR VFLNGSRQER VCNIEKNVSG   120
MAINWINEEV IWSNQQEGII TVTDMKGNNS HILLSALKYP ANVAVDPVER FIFWSSEVAG   180
SLYRADLDGV GVKALLETSE KITAVSLDVL DKRLFWIQYN REGSNSLICS CDYDGGSVHI   240
SKHPTQHNLF AMSLFGDRIF YSTWKMKTIW IANKHTGKDM VRINLHSSFV PLGELKVVHP   300
LAQPKAEDDT WEPEQKLCKL RKGNCSSTVC GQDLQSHLCM CAEGYALSRD RKYCEDVNEC   360
AFWNHGCTLG CKNTPGSYYC TCPVGFVLLP DGKRCHQLVS CPRNVSECSH DCVLTSEGPL   420
CFCPEGSVLE RDGKTCSGCS SPDNGGCSQL CVPLSPVSWE CDCFPGYDLQ LDEKSCAASG   480
PQPFLLFANS QDIRHMHFDG TDYGTLLSQQ MGMVYALDHD PVENKIYFAH TALKWIERAN   540
MDGSQRERLI EEGVDVPEGL AVDWIGRRFY WTDRGKSLIG RSDLNGKRSK IITKENISQP   600
RGIAVHPMAK RLFWTDTGIN PRIESSSLQG LGRLVIASSD LIWPSGITID FLTDKLYWCD   660
AKQSVIEMAN LDGSKRRRLT QNDVGHPFAV AVFEDYVWFS DWAMPSVMRV NKRTGKDRVR   720
LQGSMLKPSS LVVVHPLAKP GADPCLYQNG GCEHICKKRL GTAWCSCREG FMKASDGKTC   780
LALDGHQLLA GGEVDLKNQV TPLDILSKTR VSEDNITESQ HMLVAEIMVS DQDDCAPVGC   840
SMYARCISEG EDATCQCLKG FAGDKLCSD IDECEMGVPV CPPASSKCIN TEGGYVCRCS    900
EGYQGDGIHC LDSTPPPHLR EDDHHYSVRN SDSECPLSHD GYCLHDGVCM YIEALDKYAC   960
NCVVGYIGER CQYRDLKWWE LRHAGHGQQQ KVIVVAVCVV VLVMLLLLSL WGAHYYRTQK  1020
LLSKNPKNPY EESSRDVRSR RPADTEDGMS SCPQPWFVVI KEHQDLKNGG QPVAGEDGQA  1080
ADGSMQPTSW RQEPQLCGMG TEQGCWIPVS SDKGSCPQVM ERSFHMPSYG TQTLEGGVEK  1140
PHSLLSANPL WQQRALDPPH QMELTQ                                      1166

SEQ ID NO: 76           moltype = AA  length = 193
FEATURE                 Location/Qualifiers
source                  1..193
                        mol_type = protein
                        organism = Homo sapiens
SEQUENCE: 76
MGVHECPAWL WLLLSLLSLP LGLPVLGAPP RLICDSRVLQ RYLLEAKEAE NITTGCAEHC    60
SLNENITVPD TKVNFYAWKR MEVGQQAVEV WQGLALLSEA VLRGQALLVN SSQPWEPLQL   120
HVDKAVSGLR SLTTLLRALG AQKEAISPPD AASAAPLRTI TADTFRKLFR VYSNFLRGKL   180
KLYTGEACRT GDR                                                     193

SEQ ID NO: 77           moltype = AA  length = 288
FEATURE                 Location/Qualifiers
source                  1..288
                        mol_type = protein
                        organism = Homo sapiens
SEQUENCE: 77
MVGVGGGDVE DVTPRPGGCQ ISGRGARGCN GIPGAAAWEA ALPRRRPRRH PSVNPRSRAA    60
GSPRTRGRRT EERPSGSRLG DRGRGRALPG GRLGGRGRGR APERVGGRGR GRGTAAPRAA   120
PAARGSRPGP AGTMAAGSIT TLPALPEDGG SGAFPPGHFK DPKRLYCKNG GFFLRIHPDG   180
RVDGVREKSD PHIKLQLQAE ERGVVSIKGV CANRYLAMKE DGRLLASKCV TDECFFFERL   240
ESNNYNTYRS RKYTSWYVAL KRTGQYKLGS KTGPGQKAIL FLPMSAKS                288

SEQ ID NO: 78           moltype = AA  length = 211
FEATURE                 Location/Qualifiers
source                  1..211
                        mol_type = protein
                        organism = Homo sapiens
SEQUENCE: 78
MKLWDVVAVC LVLLHTASAF PLPAGKRPPE APAEDRSLGR RRAPFALSSD SNMPEDYPDQ    60
FDDVMDFIQA TIKRLKRSPD KQMAVLPRRE RNRQAAAANP ENSRGKGRRG QRGKNRGCVL   120
TAIHLNVTDL GLGYETKEEL IFRYCSGSCD AAETTYDKIL KNLSRNRRLV SDKVGQACCR   180
PIAFDDDLSF LDDNLVYHIL RKHSAKRCGC I                                  211

SEQ ID NO: 79           moltype = AA  length = 204
FEATURE                 Location/Qualifiers
source                  1..204
                        mol_type = protein
                        organism = Homo sapiens
SEQUENCE: 79
MAGPATQSPM KLMALQLLLW HSALWTVQEA TPLGPASSLP QSFLLKCLEQ VRKIQGDGAA    60
LQEKLCATYK LCHPEELVLL GHSLGIPWAP LSSCPSQALQ LAGCLSQLHG LFLYQGLLQ   120
ALEGISPELG PTLDTLQLDV ADFATTIWQQ MEELGMAPAL QPTQGAMPAF ASAFQRRAGG   180
VLVASHLQSF LEVSYRVLRH LAQP                                         204

SEQ ID NO: 80           moltype = AA  length = 144
FEATURE                 Location/Qualifiers
source                  1..144
                        mol_type = protein
                        organism = Homo sapiens
SEQUENCE: 80
MWLQSLLLLG TVACSISAPA RSPSPSTQPW EHVNAIQEAR RLLNLSRDTA AEMNETVEVI    60
SEMFDLQEPT CLQTRLELYK QGLRGSLTKL KGPLTMMASH YKQHCPPTPE TSCATQIITF   120
ESFKENLKDF LLVIPFDCWE PVQE                                         144

SEQ ID NO: 81           moltype = AA  length = 454
FEATURE                 Location/Qualifiers
```

```
source                  1..454
                        mol_type = protein
                        organism = Homo sapiens
SEQUENCE: 81
MARPNKFLLW FCCFAWLCFP ISLGSQASGG EAQIAASAEL ESGAMPWSLL QHIDERDRAG    60
LLPALFKVLS VGRGGSPRLQ PDSRALHYMK KLYKTYATKE GIPKSNRSHL YNTVRLFTPC   120
TRHKQAPGDQ VTGILPSVEL LFNLDRITTV EHLLKSVLLY NINNSVSFSS AVKCVCNLMI   180
KEPKSSSRTL GRAPYSFTFN SQFEFGKKHK WIQIDVTSLL QPLVASNKRS IHMSINFTCM   240
KDQLEHPSAQ NGLFNMTLVS PSLILYLNDT SAQAYHSWYS LHYKRRPSQG PDQERSLSAY   300
PVGEEAAEDG RSSHHRHRRG QETVSSELKK PLGPASFNLS EYFRQFLLPQ NECELHDFRL   360
SFSQLKWDNW IVAPHRYNPR YCKGDCPRAV GHRYGSPVHT MVQNIIYEKL DSSVPRPSCV   420
PAKYSPLSVL TIEPDGSIAY KEYEDMIATK CTCR                              454

SEQ ID NO: 82           moltype = AA  length = 728
FEATURE                 Location/Qualifiers
source                  1..728
                        mol_type = protein
                        organism = Homo sapiens
SEQUENCE: 82
MWVTKLLPAL LLQHVLLHLL LLPIAIPYAE GQRKRRNTIH EFKKSAKTTL IKIDPALKIK    60
TKKVNTADQC ANRCTRNKGL PFTCKAFVFD KARKQCLWFP FNSMSSGVKK EFGHEFDLYE   120
NKDYIRNCII GKGRSYKGTV SITKSGIKCQ PWSSMIPHEH SFLPSSYRGK DLQENYCRNP   180
RGEEGGPWCF TSNPEVRYEV CDIPQCSEVE CMTCNGESYR GLMDHTESGK ICQRWDHQTP   240
HRHKFLPERY PDKGFDDNYC RNPDGQPRPW CYTLDPHTRW EYCAIKTCAD NTMNDTDVPL   300
ETTECIQGQG EGYRGTVNTI WNGIPCQRWD SQYPHEHDMT PENFKCKDLR ENYCRNPDGS   360
ESPWCFTTDP NIRVGYCSQI PNCDMSHGQD CYRGNGKNYM GNLSQTRSGL TCSMWDKNME   420
DLHRHIFWEP DASKLNENYC RNPDDDAHGP WCYTGNPLIP WDYCPISRCE GDTTPTIVNL   480
DHPVISCAKT KQLRVVNGIP TRTNIGWMVS LRYRNKHICG GSLIKESWVL TARQCFPSRD   540
LKDYEAWLGI HDVHGRGDEK CKQVLNVSQL VYGPEGSDLV LMKLARPAVL DDFVSTIDLP   600
NYGCTIPEKT SCSVYGWGYT GLINYDGLLR VAHLYIMGNE KCSQHHRGKV TLNESEICAG   660
AEKIGSGPCE GDYGGPLVCE QHKMRMVLGV IVPGRGCAIP NRPGIFVRVA YYAKWIHKII   720
LTYKVPQS                                                          728

SEQ ID NO: 83           moltype = AA  length = 240
FEATURE                 Location/Qualifiers
source                  1..240
                        mol_type = protein
                        organism = Homo sapiens
SEQUENCE: 83
MSRSNRQKEY KCGDLVFAKM KGYPHWPARI DEMPEAAVKS TANKYQVFFF GTHETAFLGP    60
KDLFPYEESK EKFGKPNKRK GFSEGLWEIE NNPTVKASGY QSSQKKSCVE EPEPEPEAAE   120
GDGDKKGNAE GSSDEEGKLV IDEPAKEKNE KGALKRRAGD LLEDSPKRPK EAENPEGEEK   180
EAATLEVERP LPMEVEKNST PSEPGSGRGP PQEEEEEEDE EEEATKEDAE APGIRDHESL   240

SEQ ID NO: 84           moltype = AA  length = 153
FEATURE                 Location/Qualifiers
source                  1..153
                        mol_type = protein
                        organism = Homo sapiens
SEQUENCE: 84
MGKISSSLPTQ LFKCCFCDFL KVKMHTMSSS HLFYLALCLL TFTSSATAGP ETLCGAELVD    60
ALQFVCGDRG FYFNKPTGYG SSSRRAPQTG IVDECCFRSC DLRRLEMYCA PLKPAKSARS   120
VRAQRHTDMP KTQKEVHLKN ASRGSAGNKN YRM                               153

SEQ ID NO: 85           moltype = AA  length = 657
FEATURE                 Location/Qualifiers
source                  1..657
                        mol_type = protein
                        organism = Homo sapiens
SEQUENCE: 85
MLRGPGPGLL LLAVQCLGTA VPSTGASKSK RQAQQMVQPQ SPVAVSQSKP GCYDNGKHYQ    60
INQQWERTYL GNALVCTCYG GSRGFNCESK PEAEETCFDK YTGNTYRVGD TYERPKDSMI   120
WDCTCIGAGR GRISCTIANR CHEGGQSYKI GDTWRRPHET GGYMLECVCL GNGKGEWTCK   180
PIAEKCFDHA AGTSYVVGET WEKPYQGWMM VDCTCLGEGS GRITCTSRNR CNDQDTRTSY   240
RIGDTWRKKD NRGNLLQCIC TGNRGEWKC  ERHTSVQTTS SGSGPFTDVR AAVYQPQPHP   300
QPPPYGHCVT DSGVVYSVGM QWLKTQGNKQ MLCTCLGNGV SCQETAVTQT YGGNSNGEPC   360
VLPFTYNGRT FYSCTTEGRQ DGHLWCSTTS NYEQDQKYSF CTDHTVLVQT RGGNSNGALC   420
HPPFLYNNHN YTDCTSEGRR DNMKWCGTTQ NYDADQKFGF CPMAAHEEIC TTNEGVMYRI   480
GDQWDKQHDM GHMMRCTCVG NGRGEWTCIA YSQLRDQCIV DDITYNVNDT FHKRHEEGHM   540
LNCTCFGQGR GRWKCDPVDQ CQDSETGTFY QIGDSWEKYV HGVRYQCYCY GRGIGEWHCQ   600
PLQTYPSSSG PVEVFITETP SQPNSHPIQW NAPQPSHISK YILRWRPVSI PPRNLGY     657

SEQ ID NO: 86           moltype = AA  length = 375
FEATURE                 Location/Qualifiers
source                  1..375
                        mol_type = protein
                        organism = Homo sapiens
SEQUENCE: 86
MQKLQLCVYI YLFMLIVAGP VDLNENSEQK ENVEKEGLCN ACTWRQNTKS SRIEAIKIQI    60
```

```
LSKLRLETAP NISKDVIRQL LPKAPPLREL IDQYDVQRDD SSDGSLEDDD YHATTETIIT    120
MPTESDFLMQ VDGKPKCCFF KFSSKIQYNK VVKAQLWIYL RPVETPTTVF VQILRLIKPM    180
KDGTRYTGIR SLKLDMNPGT GIWQSIDVKT VLQNWLKQPE SNLGIEIKAL DENGHDLAVT    240
FPGPGEDGLN PFLEVKVTDT PKRSRRDFGL DCDEHSTESR CCRYPLTVDF EAFGWDWIIA    300
PKRYKANYCS GECEFVFLQK YPHTHLVHQA NPRGSAGPCC TPTKMSPINM LYFNGKEQII    360
YGKIPAMVVD RCGCS                                                    375

SEQ ID NO: 87           moltype = AA  length = 257
FEATURE                 Location/Qualifiers
source                  1..257
                        mol_type = protein
                        organism = Homo sapiens
SEQUENCE: 87
MSILFYVIFL AYLRGIQGNN MDQRSLPEDS LNSLIIKLIQ ADILKNKLSK QMVDVKENYQ     60
STLPKAEAPR EPERGGPAKS AFQPVIAMDT ELLRQQRRYN SPRVLLSDST PLEPPPLYLM    120
EDYVGSPVVA NRTSRRKRYA EHKSHRGEYS VCDSESLWVT DKSSAIDRG  HQVTVLGEIK    180
TGNSPVKQYF YETRCKEARP VKNGCRGIDD KHWNSQCKTS QTYVRALTSE NNKLVGWRWI    240
RIDTSCVCAL SRKIGRT                                                  257

SEQ ID NO: 88           moltype = AA  length = 211
FEATURE                 Location/Qualifiers
source                  1..211
                        mol_type = protein
                        organism = Homo sapiens
SEQUENCE: 88
MRTLACLLLL GCGYLAHVLA EEAEIPREVI ERLARSQIHS IRDLQRLLEI DSVGSEDSLD     60
TSLRAHGVHA TKHVPEKRPL PIRRKRSIEE AVPAVCKTRT VIYEIPRSQV DPTSANFLIW    120
PPCVEVKRCT GCCNTSSVKC QPSRVHHRSV KVAKVEYVRK KPKLKEVQVR LEEHLECACA    180
TTSLNPDYRE EDTGRPRESG KKRKRKRLKP T                                  211

SEQ ID NO: 89           moltype = AA  length = 353
FEATURE                 Location/Qualifiers
source                  1..353
                        mol_type = protein
                        organism = Homo sapiens
SEQUENCE: 89
MELTELLLVV MLLPTARLTL SSPAPPACDL RVLSKLLRDS HVLHSKLSQC PEVHPLPTPV     60
LLPAVDFSLG EWKTQMEETK AQDILGAVTL LLEGVMAARG QLGPTCLSSL LGQLSEQVRL    120
LLGALQSLLG TQLPPQGRTT AHKDPNAIFL SFQHLLRGKV RFLMLVGGST LCVRRAPPTT    180
AVPSRTSLVL TLNELPNRTS GLLETNFTAS ARTTGSGLLK WQQGFRAKIP GLLNQTSRSL    240
DQIPGYLNRI HELLNGTRGL FPGPSRRTLG APDISSGTSD TGSLPPNLQP GYSPSPTHPP    300
TGQYTLFPLP PTLPTPVVQL HPLLPDPSAP TPTPTSPLLN TSYTHSQNLS QEG           353

SEQ ID NO: 90           moltype = AA  length = 159
FEATURE                 Location/Qualifiers
source                  1..159
                        mol_type = protein
                        organism = Homo sapiens
SEQUENCE: 90
MVPSAGQLAL FALGIVLAAC QALENSTSPL SDPPVAAAVV SHFNDCPDSH TQFCFHGTCR     60
FLVQEDKPAC VCHSGYVGAR CEHADLLAVV AASQKKQAIT ALVVVSIVAL AVLIITCVLI    120
HCCQVRKHCE WCRALICRHE KPSALLKGRT ACCHSETVV                          159

SEQ ID NO: 91           moltype = AA  length = 390
FEATURE                 Location/Qualifiers
source                  1..390
                        mol_type = protein
                        organism = Homo sapiens
SEQUENCE: 91
MPPSGLRLLL LLLPLLWLLV LTPGRPAAGL STCKTIDMEL VKRKRIEAIR GQILSKLRLA     60
SPPSQGEVPP GPLPEAVLAL YNSTRDRVAG ESAEPEPEPE ADYYAKEVTR VLMVETHNEI    120
YDKFKQSTHS IYMFFNTSEL REAVPEPVLL SRAELRLLRL KLKVEQHVEL YQKYSNNSWR    180
YLSNRLLAPS DSPEWLSFDV TGVVRQWLSR GGEIEGFRLS AHCSCDSRDN TLQVDINGFT    240
TGRRGDLATI HGMNRPFLLL MATPLERAQH LQSSRHRRAL DTNYCFSSTE KNCCVRQLYI    300
DFRKDLGWKW IHEPKGYHAN FCLGPCPYIW SLDTQYSKVL ALYNQHNPGA SAAPCCVPQA    360
LEPLPIVYYV GRKPKVEQLS NMIVRSCKCS                                    390

SEQ ID NO: 92           moltype = AA  length = 233
FEATURE                 Location/Qualifiers
source                  1..233
                        mol_type = protein
                        organism = Homo sapiens
SEQUENCE: 92
MSTESMIRDV ELAEEALPKK TGGPQGSRRC LFLSLFSFLI VAGATTLFCL LHFGVIGPQR     60
EEFPRDLSLI SPLAQAVRSS SRTPSDKPVA HVVANPQAEG QLQWLNRRAN ALLANGVELR    120
DNQLVVPSEG LYLIYSQVLF KGQGCPSTHV LLTHTISRIA VSYQTKVNLL SAIKSPCQRE    180
TPEGAEAKPW YEPIYLGGVF QLEKGDRLSA EINRPDYLDF AESGQVYFGI IAL           233

SEQ ID NO: 93           moltype = AA  length = 191
```

```
FEATURE                 Location/Qualifiers
source                  1..191
                        mol_type = protein
                        organism = Homo sapiens
SEQUENCE: 93
MNFLLSWVHW SLALLLYLHH AKWSQAAPMA EGGGQNHHEV VKFMDVYQRS YCHPIETLVD    60
IFQEYPDEIE YIFKPSCVPL MRCGGCCNDE GLECVPTEES NITMQIMRIK PHQGQHIGEM   120
SFLQHNKCEC RPKKDRARQE NPCGPCSERR KHLFVQDPQT CKCSCKNTDS RCKARQLELN   180
ERTCRCDKPR R                                                        191

SEQ ID NO: 94           moltype = AA   length = 170
FEATURE                 Location/Qualifiers
source                  1..170
                        mol_type = protein
                        organism = Homo sapiens
SEQUENCE: 94
MPVMRLFPCF LQLLAGLALP AVPPQQWALS AGNGSSEVEV VPFQEVWGRS YCRALERLVD    60
VVSEYPSEVE HMFSPSCVSL LRCTGCCGDE NLHCVPVETA NVTMQLLKIR SGDRPSYVEL   120
TFSQHVRCEC RPLREKMKPE RRRPKGRGKR RREKQRPTDC HLCGDAVPRR              170

SEQ ID NO: 95           moltype = AA   length = 270
FEATURE                 Location/Qualifiers
source                  1..270
                        mol_type = protein
                        organism = Ricinus communis
SEQUENCE: 95
DNNIFPKQYP IINFTTAGAT VQSYTNFIRA VRGRLTTGAD VRHEIPVLPN RVGLPINQRF    60
ILVELSNHAE LSVTLALDVT NAYVVGYRAG NSAYFFHPDN QEDAEAITHL FTDVQNRYTF   120
AFGGNYDRLE QLAGNLRENI ELGNGPLEEA ISALYYYSTG GTQLPTLARS FIICIQMISE   180
AARFQYIEGE MRTRIRYNRR SAPDPSVITL ENSWGRLSTA IQESNQGAFA SPIQLQRRNG   240
SKFSVYDVSI LIPIIALMVY RCAPPPSSQF                                    270

SEQ ID NO: 96           moltype = AA   length = 262
FEATURE                 Location/Qualifiers
source                  1..262
                        mol_type = protein
                        organism = Ricinus communis
SEQUENCE: 96
ADVCMDPEPI VRIVGRNGLC VDVRDGRFHN GNAIQLWPCK SNTDANQLWT LKRDNTIRSN    60
GKCLTTYGYS PGVYVMIYDC NTAATDATRW QIWDNGTIIN PRSSLVLAAT SGNSGTTLTV   120
QTNIYAVSQG WLPTNNTQPF VTTIVGLYGL CLQANSGQVW IEDCSSEKAE QQWALYADGS   180
IRPQQNRDNC LTSDSNIRET VVKILSCGPA SSGQRWMFKN DGTILNLYSG LVLDVRASDP   240
SLKQIILYPL HGDPNQIWLP LF                                            262

SEQ ID NO: 97           moltype = AA   length = 560
FEATURE                 Location/Qualifiers
SITE                    9
                        note = misc_feature - Xaa can be any naturally occurring
                          amino acid
SITE                    139
                        note = misc_feature - Xaa can be any naturally occurring
                          amino acid
SITE                    149
                        note = misc_feature - Xaa can be any naturally occurring
                          amino acid
SITE                    510
                        note = misc_feature - Xaa can be any naturally occurring
                          amino acid
SITE                    525
                        note = misc_feature - Xaa can be any naturally occurring
                          amino acid
SITE                    558
                        note = misc_feature - Xaa can be any naturally occurring
                          amino acid
source                  1..560
                        mol_type = protein
                        organism = Corynebacterium diphtheriae
SEQUENCE: 97
MSRKLFASXL IGALLGIGAP PSAHAGADDV VDSSKSFVME NFSSYHGTKP GYVDSIQKGI    60
QKPKSGTQRN YDDDWKGFYS TDNKYDAAGY SVDNENPLSG KAGDVVKVTY PGLTKVLALK   120
VDNAETIKKE LGLSLTEPXM EQVGTEEFXK RFGDGASRVV LSLPFAEGSS SVEYINNWEQ   180
AKALSVKLEI NFETRGKRGQ DAMYEYMAQA CAGNRVRRSV GRSLSCINLD WDVIRDKTKT   240
KIESLKEHGP IKNKMSESPN KTVSQEKAKQ YLEEFHQTAL EHPQLSELKT VTGTNPLFAG   300
ANYAAWAVNV AQVIDSETAD NLEKTTAALS ILPGIGSVMG IADGAVHHNT EEIVAQSIAL   360
SSLMVAQAIP LVGELVDIGF APYNFVESII NLFQVVHNSY NRSAYSPGHK TQPFLHDGYA   420
VSWNTVEDSI IRTGFQGESG HDIKITAENT PLPIASVLLP TIPGKLDVNK SKTHISVNGR   480
KIRMRCRAID GDVTFCRPKS PVYVGNGVHX NLHVAFHRSS SEKIXSNEIS SDSIGVLGYQ   540
KTVDHTKVNS KLSLFFEXKS                                               560
```

```
SEQ ID NO: 98            moltype = AA  length = 638
FEATURE                  Location/Qualifiers
source                   1..638
                         mol_type = protein
                         organism = Pseudomonas aeruginosa
SEQUENCE: 98
MHLTPHWIPL VASLGLLAGG SFASAAEEAF DLWNECAKAC VLDLKDGVRS SRMSVDPAIA    60
DTNGQGVLHY SMVLEGGNDA LKLAIDNALS ITSDGLTIRL EGGVEPNKPV RYSYTRQARG   120
SWSLNWLVPI GHEKPSNIKV FIHELNAGNQ LSHMSPIYTI EMGDELLAKL ARDATFFVRA   180
HESNEMQPTL AISHAGVSVV MAQAQPRREK RWSEWASGKV LCLLDPLDGV YNYLAQQRCN   240
LDDTWEGKIY RVLAGNPAKH DLDIKPTVIS HRLHFPEGGS LAALTAHQAC HLPLETFTRH   300
RQPRGWEQLE QCGYPVQRLV ALYLAARLSW NQVDQVIRNA LASPGSGGDL GEAIREQPEQ   360
ARLALTLAAA ESERFVRQGT GNDEAGAASA DVVSLTCPVA AGECAGPADS GDALLERNYP   420
TGAEFLGDGG DISFSTRGTQ NWTVERLLQA HRQLEERGYV FVGYHGTFLE AAQSIVFGGV   480
RARSQDLDAI WRGFYIAGDP ALAYGYAQDQ EPDARGRIRN GALLRVYVPR SSLPGFYRTG   540
LTLAAPEAAG EVERLIGHPL PLRLDAITGP EEEGGRLETI LGWPLAERTV VIPSAIPTDP   600
RNVGGDLDPS SIPDKEQAIS ALPDYASQPG KPPREDLK                            638

SEQ ID NO: 99            moltype = AA  length = 316
FEATURE                  Location/Qualifiers
source                   1..316
                         mol_type = protein
                         organism = Gelonium multiflorum
SEQUENCE: 99
MKGNMKVYWI KIAVATWFCC TTIVLGSTAR IFSLPTNDEE ETSKTLGLDT VSFSTKGATY    60
ITYVNFLNEL RVKLKPEGNS HGIPLLRKKC DDPGKCFVLV ALSNDNGQLA EIAIDVTSVY   120
VVGYQVRNRS YFFKDAPDAA YEGLFKNTIK TRLHFGGSYP SLEGEKAYRE TTDLGIEPLR   180
IGIKKLDENA IDNYKPTEIA SSLLVVIQMV SEAARFTFIE NQIRNNFQQR IRPANNTISL   240
ENKWGKLSFQ IRTSGANGMF SEAVELERAN GKKYYVTAVD QVKPKIALLK FVDKDPKTSL   300
AAELIIQNYE SLVGFD                                                    316

SEQ ID NO: 100           moltype = AA  length = 292
FEATURE                  Location/Qualifiers
source                   1..292
                         mol_type = protein
                         organism = Saponaria officinalis
SEQUENCE: 100
MKIYVVATIA WILLQFSAWT TTDAVTSITL DLVNPTAGQY SSFVDKIRNN VKDPNLKYGG    60
TDIAVIGPPS KDKFLRINFQ SSRGTVSLGL KRDNLYVVAY LAMDNTNVNR AYYFKSEITS   120
AELTALFPEA TTANQKALEY TEDYQSIEKN AQITQGDKSR KELGLGIDLL LTFMEAVNKK   180
ARVVKNEARF LLIAIQMTAE VARFRYIQNL VTKNFPNKFD SDNKVIQFEV SWRKISTAIY   240
GDAKNGVFNK DYDFGFGKVR QVKDLQMGLL MYLGKPKSSN EANSTAYATT VL            292

SEQ ID NO: 101           moltype = AA  length = 386
FEATURE                  Location/Qualifiers
source                   1..386
                         mol_type = protein
                         organism = Pseudomonas aeruginosa
SEQUENCE: 101
LAGNPAKHDL DIKPTVISHR LHFPEGGSLA ALTAHQACHL PLETFTRHRQ PRGWEQLEQC    60
GYPVQRLVAL YLAARLSWNQ VDQVIRNALA SPGSGGDLGE AIREQPEQAR LALTLAAAES   120
ERFVRQGTGN DEAGAASADV VSLTCPVAAG ECAGPADSGD ALLERNYPTG AEFLGDGGDI   180
SFSTRGTQNW TVERLLQAHR QLEERGYVFV GYHGTFLEAA QSIVFGGVRA RSQDLDAIWR   240
GFYIAGDPAL AYGYAQDQEP DARGRIRNGA LLRVYVPRSS LPGFYRTGLT LAAPEAAGEV   300
ERLIGHPLPL RLDAITGPEE EGGRLETILG WPLAERTVVI PSAIPTDPRN VGGDLDPSSI   360
PDKEQAISAL PDYASQPGKP PREDLK                                         386

SEQ ID NO: 102           moltype = AA  length = 370
FEATURE                  Location/Qualifiers
source                   1..370
                         mol_type = protein
                         organism = Pseudomonas aeruginosa
SEQUENCE: 102
LAGNPAKHDL DIKPTVISHR LHFPEGGSLA ALTAHQACHL PLETFTRHRQ PRGWEQLEQC    60
GYPVQRLVAL YLAARLSWNQ VDQVIRNALA SPGSGGDLGE AIREQPEQAR LAGNDEAGAA   120
SADVVSLTCP VAAGECAGPA DSGDALLERN YPTGAEFLGD GGDISFSTRG TQNWTVERLL   180
QAHRQLEERG YVFVGYHGTF LEAAQSIVFG GVRARSQDLD AIWRGFYIAG DPALAYGYAQ   240
DQEPDARGRI RNGALLRVYV PRSSLPGFYR TGLTLAAPEA AGEVERLIGH PLPLRLDAIT   300
GPEEEGGRLE TILGWPLAER TVVIPSAIPT DPRNVGGDLD PSSIPDKEQA ISALPDYASQ   360
PGKPPREDLK                                                           370

SEQ ID NO: 103           moltype = AA  length = 1620
FEATURE                  Location/Qualifiers
source                   1..1620
                         mol_type = protein
                         organism = Homo sapiens
SEQUENCE: 103
MGAIGLLWLL PLLLSTAAVG SGMGTGQRAG SPAAGPPLQP REPLSYSRLQ RKSLAVDFVV    60
PSLFRVYARD LLLPPSSSEL KAGRPEARGS LALDCAPLLR LLGPAPGVSW TAGSPAPAEA   120
```

| | | | | | |
|---|---|---|---|---|---|
| RTLSRVLKGG | SVRKLRRAKQ | LVLELGEEAI | LEGCVGPPGE | AAVGLLQFNL | SELFSWWIRQ | 180
| GEGRLRIRLM | PEKKASEVGR | EGRLSAAIRA | SQPRLLFQIF | GTGHSSLESP | TNMPSPSPDY | 240
| FTWNLTWIMK | DSFPFLSHRS | RYGLECSFDF | PCELEYSPPL | HDLRNQSWSW | RRIPSEEASQ | 300
| MDLLDGPGAE | RSKEMPRGSF | LLLNTSADSK | HTILSPWMRS | SSEHCTLAVS | VHRHLQPSGR | 360
| YIAQLLPHNE | AAREILLMPT | PGKHGWTVLQ | GRIGRPDNPF | RVALEYISSG | NRSLSAVDFF | 420
| ALKNCSEGTS | PGSKMALQSS | FTCWNGTVLQ | LGQACDFHQD | CAQGEDESQM | CRKLPVGFYC | 480
| NFEDGFCGWT | QGTLSPHTPQ | WQVRTLKDAR | FQDHQDHALL | LSTTDVPASE | SATVTSATFP | 540
| APIKSSPCEL | RMSWLIRGVL | RGNVSLVLVE | NKTGKEQGRM | VWHVAAYEGL | SLWQWMVLPL | 600
| LDVSDRFWLQ | MVAWWGQGSR | AIVAFDNISI | SLDCYLTISG | EDKILQNTAP | KSRNLFERNP | 660
| NKELKPGENS | PRQTPIFDPT | VHWLFTTCGA | SGPHGPTQAQ | CNNAYQNSNL | SVEVGSEGPL | 720
| KGIQIWKVPA | TDTYSISGYG | AAGGKGGKNT | MMRSHGVSVL | GIFNLEKDDM | LYILVGQQGE | 780
| DACPSTNQLI | QKVCIGENNV | IEEEIRVNRS | VHEWAGGGGG | GGGATYVFKM | KDGVPVPLII | 840
| AAGGGGRAYG | AKTDTFHPER | LENNSSVLGL | NGNSGAAGGG | GGWNDNTSLL | WAGKSLQEGA | 900
| TGGHSCPQAM | KKWGWETRGG | FGGGGGGCSS | GGGGGGYIGG | NAASNNDPEM | DGEDGVSFIS | 960
| PLGILYTPAL | KVMEGHGEVN | IKHYLNCSHC | EVDECHMDPE | SHKVICFCDH | GTVLAEDGVS | 1020
| CIVSPTPEPH | LPLSLILSVV | TSALVAALVL | AFSGIMIVYR | RKHQELQAMQ | MELQSPEYKL | 1080
| SKLRTSTIMT | DYNPNYCFAG | KTSSISDLKE | VPRKNITLIR | GLGHGAFGEV | YEGQVSGMPN | 1140
| DPSPLQVAVK | TLPEVCSEQD | ELDFLMEALI | ISKFNHQNIV | RCIGVSLQSL | PRFILLELMA | 1200
| GGDLKSFLRE | TRPRPSQPSS | LAMLDLLHVA | RDIACGCQYL | EENHFIHRDI | AARNCLLTCP | 1260
| GPGRVAKIGD | FGMARDIYRA | SYYRKGGCAM | LPVKWMPPEA | FMEGIFTSKT | DTWSFGVLLW | 1320
| EIFSLGYMPY | PSKSNQEVLE | FVTSGGRMDP | PKNCPGPVYR | IMTQCWQHQP | EDRPNFAIIL | 1380
| ERIEYCTQDP | DVINTALPIE | YGPLVEEEEK | VPVRPKDPEG | VPPLLVSQQA | KREEERSPAA | 1440
| PPPLPTTSSG | KAAKKPTAAE | ISVRVPRGPA | VEGGHVNMAF | SQSNPPSELH | KVHGSRNKPT | 1500
| SLWNPTYGSW | FTEKPTKKNN | PIAKKEPHDR | GNLGLEGSCT | VPPNVATGRL | PGASLLLEPS | 1560
| SLTANMKEVP | LFRLRHFPCG | NVNYGYQQQG | LPLEAATAPG | AGHYEDTILK | SKNSMNQPGP | 1620

```
SEQ ID NO: 104         moltype = AA  length = 6
FEATURE                Location/Qualifiers
REGION                 1..6
                       note = Synthetic polypeptide PSA derived peptide
source                 1..6
                       mol_type = protein
                       organism = synthetic construct
SEQUENCE: 104
HSSKLQ                                                                   6

SEQ ID NO: 105         moltype = AA  length = 1255
FEATURE                Location/Qualifiers
source                 1..1255
                       mol_type = protein
                       organism = Homo sapiens
SEQUENCE: 105
```

| | | | | | |
|---|---|---|---|---|---|
| MTPGTQSPFF | LLLLLTVLTV | VTGSGHASST | PGGEKETSAT | QRSSVPSSTE | KNAVSMTSSV | 60
| LSSHSPGSGS | STTQGQDVTL | APATEPASGS | AATWGQDVTS | VPVTRPALGS | TTPPAHDVTS | 120
| APDNKPAPGS | TAPPAHGVTS | APDTRPAPGS | TAPPAHGVTS | APDTRPAPGS | TAPPAHGVTS | 180
| APDTRPAPGS | TAPPAHGVTS | APDTRPAPGS | TAPPAHGVTS | APDTRPAPGS | TAPPAHGVTS | 240
| APDTRPAPGS | TAPPAHGVTS | APDTRPAPGS | TAPPAHGVTS | APDTRPAPGS | TAPPAHGVTS | 300
| APDTRPAPGS | TAPPAHGVTS | APDTRPAPGS | TAPPAHGVTS | APDTRPAPGS | TAPPAHGVTS | 360
| APDTRPAPGS | TAPPAHGVTS | APDTRPAPGS | TAPPAHGVTS | APDTRPAPGS | TAPPAHGVTS | 420
| APDTRPAPGS | TAPPAHGVTS | APDTRPAPGS | TAPPAHGVTS | APDTRPAPGS | TAPPAHGVTS | 480
| APDTRPAPGS | TAPPAHGVTS | APDTRPAPGS | TAPPAHGVTS | APDTRPAPGS | TAPPAHGVTS | 540
| APDTRPAPGS | TAPPAHGVTS | APDTRPAPGS | TAPPAHGVTS | APDTRPAPGS | TAPPAHGVTS | 600
| APDTRPAPGS | TAPPAHGVTS | APDTRPAPGS | TAPPAHGVTS | APDTRPAPGS | TAPPAHGVTS | 660
| APDTRPAPGS | TAPPAHGVTS | APDTRPAPGS | TAPPAHGVTS | APDTRPAPGS | TAPPAHGVTS | 720
| APDTRPAPGS | TAPPAHGVTS | APDTRPAPGS | TAPPAHGVTS | APDTRPAPGS | TAPPAHGVTS | 780
| APDTRPAPGS | TAPPAHGVTS | APDTRPAPGS | TAPPAHGVTS | APDTRPAPGS | TAPPAHGVTS | 840
| APDTRPAPGS | TAPPAHGVTS | APDTRPAPGS | TAPPAHGVTS | APDTRPAPGS | TAPPAHGVTS | 900
| APDTRPAPGS | TAPPAHGVTS | APDTRPAPGS | TAPPAHGVTS | APDNRPALGS | TAPPVHNVTS | 960
| ASGSASGSAS | TLVHNGTSAR | ATTTPASKST | PFSIPSHHSD | TPTTLASHST | KTDASSTHHS | 1020
| SVPPLTSSNH | STSPQLSTGV | SFFFLSFHIS | NLQFNSSLED | PSTDYYQELQ | RDISEMFLQI | 1080
| YKQGGFLGLS | NIKFRPGSVV | VQLTLAFREG | TINVHDVETQ | FNQYKTEAAS | RYNLTISDVS | 1140
| VSDVPFPFSA | QSGAGVPGWG | IALLVLVCVL | VALAIVYLIA | LAVCQCRRKN | YGQLDIFPAR | 1200
| DTYHPMSEYP | TYHTHGRYVP | PSSTDRSPYE | KVSAGNGGSS | LSYTNPAVAA | TSANL | 1255

```
SEQ ID NO: 106         moltype = AA  length = 7
FEATURE                Location/Qualifiers
REGION                 1..7
                       note = Synthetic polypeptide PSA PEPTIDE FRAGMENT
source                 1..7
                       mol_type = protein
                       organism = synthetic construct
SEQUENCE: 106
HSSKLQK                                                                  7

SEQ ID NO: 107         moltype = AA  length = 202
FEATURE                Location/Qualifiers
source                 1..202
                       mol_type = protein
                       organism = Homo sapiens
```

```
-continued

SEQUENCE: 107
MCYGKCARCI  GHSLVGLALL  CIAANILLYF  PNGETKYASE  NHLSRFVWFF  SGIVGGGLLM   60
LLPAFVFIGL  EQDDCCGCCG  HENCGKRCAM  LSSVLAALIG  IAGSGYCVIV  AALGLAEGPL  120
CLDSLGQWNY  TFASTEGQYL  LDTSTWSECT  EPKHIVEWNV  SLFSILLALG  GIEFILCLIQ  180
VINGVLGGIC  GFCCSHQQQY  DC                                              202

SEQ ID NO: 108           moltype = AA  length = 7
FEATURE                  Location/Qualifiers
REGION                   1..7
                         note = Synthetic polypeptide PSA PEPTIDE FRAGMENT
SITE                     6
                         note = X - ETHANYL-D-ALANINE
source                   1..7
                         mol_type = protein
                         organism = synthetic construct
SEQUENCE: 108
HSSKLXK                                                                    7

SEQ ID NO: 109           moltype = AA  length = 530
FEATURE                  Location/Qualifiers
source                   1..530
                         mol_type = protein
                         organism = Homo sapiens
SEQUENCE: 109
MRRLWGAARK  PSGAGWEKEW  AEAPQEAPGA  WSGRLGPGRS  GRKGRAVPGW  ASWPAHLALA   60
ARPARHLGGA  GQGPRPLHSG  TAPFHSRASG  ERQRRLEPQL  QHESRCRSST  PADAWRAEAA  120
LPVRAMGAPW  GSPTAAAGGR  RGWRRGRGLP  WTVCVLAAAG  LTCTALITYA  CWGQLPPLPW  180
ASPTPSRPVG  VLLWWEPFGG  RDSAPRPPPD  CRLRFNISGC  RLLTDRASYG  EAQAVLFHHR  240
DLVKGPPDWP  PPWGIQAHTA  EEVDLRVLDY  EEAAAAAEAL  ATSSPRPPGQ  RWVWMNFESP  300
SHSPGLRSLA  SNLFNWTLSY  RADSDVFVPY  GYLYPRSHPG  DPPSGLAPPL  SRKQGLVAWV  360
VSHWDERQAR  VRYYHQLSQH  VTVDVFGRGG  PGQPVPEIGL  LHTVARYKFY  LAFENSQHLD  420
YITEKLWRNA  LLAGAVPVVL  GPDRANYERF  VPRGAFIHVD  DFPSASSLAS  YLLFLDRNPA  480
VYRRYFHWRR  SYAVHITSFW  DEPWCRVCQA  VQRAGDRPKS  IRNLASWFER              530

SEQ ID NO: 110           moltype = AA  length = 609
FEATURE                  Location/Qualifiers
source                   1..609
                         mol_type = protein
                         organism = Homo sapiens
SEQUENCE: 110
MKWVESIFLI  FLLNFTESRT  LHRNEYGIAS  ILDSYQCTAE  ISLADLATIF  FAQFVQEATY   60
KEVSKMVKDA  LTAIEKPTGD  EQSSGCLENQ  LPAFLEELCH  EKEILEKYGH  SDCCSQSEEG  120
RHNCFLAHKK  PTPASIPLFQ  VPEPVTSCEA  YEEDRETFMN  KFIYEIARRH  PFLYAPTILL  180
WAARYDKIIP  SCCKAENAVE  CFQTKAATVT  KELRESSLLN  QHACAVMKNF  GTRTFQAITV  240
TKLSQKFTKV  NFTEIQKLVL  DVAHVHEHCC  RGDVLDCLQD  GEKIMSYICS  QQDTLSNKIT  300
ECCKLTTLER  GQCIIHAEND  EKPEGLSPNL  NRFLGDRDFN  QFSSGEKNIF  LASFVHEYSR  360
RHPQLAVSVI  LRVAKGYQEL  LEKCFQTENP  LECQDKGEEE  LQKYIQESQA  LAKRSCGLFQ  420
KLGEYYLQNA  FLVAYTKKAP  QLTSSELMAI  TRKMAATAAT  CCQLSEDKLL  ACGEGAADII  480
IGHLCIRHEM  TPVNPGVGQC  CTSSYANRRP  CFSSLVVDET  YVPPAFSDDK  FIFHKDLCQA  540
QGVALQTMKQ  EFLINLVKQK  PQITEEQLEA  VIADFSGLLE  KCCQGQEQEV  CFAEEGQKLI  600
SKTRAALGV                                                               609

SEQ ID NO: 111           moltype = AA  length = 6
FEATURE                  Location/Qualifiers
REGION                   1..6
                         note = Synthetic polypeptide PSA PEPTIDE FRAGMENT
SITE                     1
                         note = B - 4-HYDROXYPROLINE
SITE                     4
                         note = X - CYCLOHEXYL GLYCINE
source                   1..6
                         mol_type = protein
                         organism = synthetic construct
SEQUENCE: 111
BASXQS                                                                     6

SEQ ID NO: 112           moltype = AA  length = 550
FEATURE                  Location/Qualifiers
source                   1..550
                         mol_type = protein
                         organism = Homo sapiens
SEQUENCE: 112
MPRIPASPLS  CCPPDMLGPC  MLLLLLLLGL  RLQLSLGIIP  VEEENPDFWN  REAAEALGAA   60
KKLQPAQTAA  KNLIIFLGDG  MGVSTVTAAR  ILKGQKKDKL  GPEIPLAMDR  FPYVALSKTY  120
NVDKHVPDSG  ATATAYLCGV  KGNFQTIGLS  AAARFNQCNT  TRGNEVISVM  NRAKKAGKSV  180
GVVTTTRVQH  ASPAGTYAHT  VNRNWYSDAD  VPASARQEGC  QDIATQLISN  MDIDVILGGG  240
RKYMFRMGTP  DPEYPDDYSQ  GGTRLDGKNL  VQEWLAKRQG  ARYVWNRTEL  MQASLDPSVT  300
HLMGLFEPGD  MKYEIHRDST  LDPSLMEMTE  AALRLLSRNP  RGFFLFVEGG  RIDHGHHESR  360
AYRALTETIM  FDDAIERAGQ  LTSEEDTLSL  VTADHSHVFS  FGGYPLRGSS  IFGLAPGKAR  420
```

```
DRKAYTVLLY GNGPGYVLKD GARPDVTESE SGSPEYRQQS AVPLDEETHA GEDAVVFARG    480
PQAHLVHGVQ EQTFIAHVMA FAACLEPYTA CDLAPPAGTT DAAHPGRSVV PALLPLLAGT    540
LLLLETATAP                                                          550

SEQ ID NO: 113          moltype = AA  length = 261
FEATURE                 Location/Qualifiers
source                  1..261
                        mol_type = protein
                        organism = Homo sapiens
SEQUENCE: 113
MWVPVVFLTL SVTWIGAAPL ILSRIVGGWE CEKHSQPWQV LVASRGRAVC GGVLVHPQWV    60
LTAAHCIRNK SVILLGRHSL FHPEDTGQVF QVSHSFPHPL YDMSLLKNRF LRPGDDSSHD    120
LMLLRLSEPA ELTDAVKVMD LPTQEPALGT TCYASGWGSI EPEEFLTPKK LQCVDLHVIS    180
NDVCAQVHPQ KVTKFMLCAG RWTGGKSTCS GDSGGPLVCN GVLQGITSWG SEPCALPERP    240
SLYTKVVHYR KWIKDTIVAN P                                             261

SEQ ID NO: 114          moltype = AA  length = 750
FEATURE                 Location/Qualifiers
source                  1..750
                        mol_type = protein
                        organism = Homo sapiens
SEQUENCE: 114
MWNLLHETDS AVATARRPRW LCAGALVLAG GFFLLGFLFG WFIKSSNEAT NITPKHNMKA    60
FLDELKAENI KKFLYNFTQI PHLAGTEQNF QLAKQIQSQW KEFGLDSVEL AHYDVLLSYP    120
NKTHPNYISI INEDGNEIFN TSLFEPPPPG YENVSDIVPP FSAFSPQGMP EGDLVYVNYA    180
RTEDFFKLER DMKINCSGKI VIARYGKVFR GNKVKNAQLA GAKGVILYSD PADYFAPGVK    240
SYPDGWNLPG GGVQRGNILN LNGAGDPLTP GYPANEYAYR RGIAEAVGLP SIPVHPIGYY    300
DAQKLLEKMG GSAPPDSSWR GSLKVPYNVG PGFTGNFSTQ KVKMHIHSTN EVTRIYNVIG    360
TLRGAVEPDR YVILGGHRDS WVFGGIDPQS GAAVVHEIVR SFGTLKKEGW RPRRTILFAS    420
WDAEEFGLLG STEWAEENSR LLQERGVAYI NADSSIEGNY TLRVDCTPLM YSLVHNLTKE    480
LKSPDEGFEG KSLYESWTKK SPSPEFSGMP RISKLGSGND FEVFFQRLGI ASGRARYTKN    540
WETNKFSGYP LYHSVYETYE LVEKFYDPMF KYHLTVAQVR GGMVFELANS IVLPFDCRDY    600
AVVLRKYADK IYSISMKHPQ EMKTYSVSFD SLFSAVKNFT EIASKFSERL QDFDKSNPIV    660
LRMMNDQLMF LERAFIDPLG LPDRPFYRHV IYAPSSHNKY AGESFPGIYD ALFDIESKVD    720
PSKAWGEVKR QIYVAAFTVQ AAAETLSEVA                                    750

SEQ ID NO: 115          moltype = AA  length = 386
FEATURE                 Location/Qualifiers
source                  1..386
                        mol_type = protein
                        organism = Homo sapiens
SEQUENCE: 115
MRAAPLLLAR AASLNLGFLF LLFFWLDRSV LAKELKFVTL VFRHGDRSPI DTFPTDPIKE    60
SSWPQGFGQL TQLGMEQHYE LGEYIRKRYR KFLNESYKHE QVYIRSTDVD RTLMSAMTNL    120
AALVPPEGVS IWNPILLWQP IPVHTVPLSE DQLLYLPFRN CPRFQELESE TLKSEEFQKR    180
LHPYKDFIAT LGKLSGLHGQ DLFGIWSKVY DPLYCESVHN FTLPSRATED TMTKLRELSE    240
LSLLSLYGIH KQKEKSRLQG GVLVMNEILNH MKRATQIPSY KKLIMYSAHD TTVSGLQMAL    300
DVYNGLLPPY ASCHLTELYF EKGEYFVEMY YRNETQHEPY PLMLPGCSPS CPLERFAELV    360
GPVIPQDWST ECMTTNSHQG TEDSTD                                        386

SEQ ID NO: 116          moltype = AA  length = 7
FEATURE                 Location/Qualifiers
REGION                  1..7
                        note = Synthetic polypeptide PSA PEPTIDE FRAGMENT
SITE                    1
                        note = B - 4-HYDROXYPROLINE
SITE                    4
                        note = X - CYCLOHEXYL GLYCINE
source                  1..7
                        mol_type = protein
                        organism = synthetic construct
SEQUENCE: 116
BASXQSL                                                             7

SEQ ID NO: 117          moltype = AA  length = 309
FEATURE                 Location/Qualifiers
source                  1..309
                        mol_type = protein
                        organism = Homo sapiens
SEQUENCE: 117
MSLEQRSLHC KPEEALEAQQ EALGLVCVQA ATSSSSPLVL GTLEEVPTAG STDPPQSPQG    60
ASAFPTTINF TRQRQPSEGS SSREEEGPST SCILESLFRA VITKKVADLV GFLLLKYRAR    120
EPVTKAEMLE SVIKNYKHCF PEIFGKASES LQLVFGIDVK EADPTGHSYV LVTCLGLSYD    180
GLLGDNQIMP KTGFLIIVLV MIAMEGGHAP EEEIWEELSV MEVYDGREHS AYGEPRKLLT    240
QDLVQEKYLE YRQVPDSDPA RYEFLWGPRA LAETSYVKVL EYVIKVSARV RFFFPSLREA    300
ALREEEEGV                                                           309

SEQ ID NO: 118          moltype = AA  length = 314
FEATURE                 Location/Qualifiers
```

```
source                         1..314
                               mol_type = protein
                               organism = Homo sapiens
SEQUENCE: 118
MPLEQRSQHC KPEEGLEARG EALGLVGAQA PATEEQQTAS SSSTLVEVTL GEVPAADSPS    60
PPHSPQGASS FSTTINYTLW RQSDEGSSNQ EEEGPRMFPD LESEFQAAIS RKMVELVHFL   120
LLKYRAREPV TKAEMLESVL RNCQDFFPVI FSKASEYLQL VFGIEVVEVV PISHLYILVT   180
CLGLSYDGLL GDNQVMPKTG LLIIVLAIIA IEGDCAPEEK IWEELSMLEV FEGREDSVFA   240
HPRKLLMQDL VQENYLEYRQ VPGSDPACYE FLWGPRALIE TSYVKVLHHT LKIGGEPHIS   300
YPPLHERALR EGEE                                                    314

SEQ ID NO: 119                 moltype = AA  length = 314
FEATURE                        Location/Qualifiers
source                         1..314
                               mol_type = protein
                               organism = Homo sapiens
SEQUENCE: 119
MPLEQRSQHC KPEEGLEARG EALGLVGAQA PATEEQEAAS SSSTLVEVTL GEVPAAESPD    60
PPQSPQGASS LPTTMNYPLW SQSYEDSSNQ EEEGPSTFPD LESEFQAALS RKVAELVHFL   120
LLKYRAREPV TKAEMLGSVV GNWQYFFPVI FSKASSSLQL VFGIELMEVD PIGHLYIFAT   180
CLGLSYDGLL GDNQIMPKAG LLIIVLAIIA REGDCAPEEK IWEELSVLEV FEGREDSILG   240
DPKKLLTQHF VQENYLEYRQ VPGSDPACYE FLWGPRALVE TSYVKVLHHM VKISGGPHIS   300
YPPLHEWVLR EGEE                                                    314

SEQ ID NO: 120                 moltype = AA  length = 317
FEATURE                        Location/Qualifiers
source                         1..317
                               mol_type = protein
                               organism = Homo sapiens
SEQUENCE: 120
MSLEQKSQHC KPEEGVEAQE EALGLVGAQA PTTEEQEAAV SSSSPLVLGT LEKVPAAESA    60
DPPQSPQGAS ALPTTISFTC WRQPNEGSSS QEEEEASTSP DAESLFREAL SNKVDELAHF   120
LLRKYRAKEL VTKAEMLERV IKNYKRCFPV IFGKASESLK MIFGIDVKEV DPASNTYTLV   180
TCLGLSYDGL LGNNQIFPKT GLLIIVLGTI AMEGDSASEE EIWEELVMG VYDGREHTVY    240
GEPRKLLTQD WVQENYLEYR QVPGSNPARY EFLWGPRALA ETSYVKVLEH VVRVNARVRI   300
AYPSLREAAL LEEEEGV                                                 317

SEQ ID NO: 121                 moltype = AA  length = 760
FEATURE                        Location/Qualifiers
source                         1..760
                               mol_type = protein
                               organism = Homo sapiens
SEQUENCE: 121
MMDQARSAFS NLFGGEPLSY TRFSLARQVD GDNSHVEMKL AVDEEENADN NTKANVTKPK    60
RCSGSICYGT IAVIVFFLIG FMIGYLGYCK GVEPKTECER LAGTESPVRE EPGEDFPAAR   120
RLYWDDLKRK LSEKLDSTDF TGTIKLLNEN SYVPREAGSQ KDENLALYVE NQFREFKLSK   180
VWRDQHFVKI QVKDSAQNSV IIVDKNGRLV YLVENPGGYV AYSKAATVTG KLVHANFGTK   240
KDFEDLYTPV NGSIVIVRAG KITFAEKVAN AESLNAIGVL IYMDQTKFPI VNAELSFFGH   300
AHLGTGDPYT PGFPSFNHTQ FPPSRSSGLP NIPVQTISRA AAEKLFGNME GDCPSDWKTD   360
STCRMVTSES KNVKLTVSNV LKEIKILNIF GVIKGFVEPD HYVVVGAQRD AWGPGAAKSG   420
VGTALLLKLA QMFSDMVLKD GFQPSRSIIF ASWSAGDFGS VGATEWLEGY LSSLHLKAFT   480
YINLDKAVLG TSNFKVSASP LLYTLIEKTM QNVKHPVTGQ FLYQDSNWAS KVEKLTLDNA   540
AFPFLAYSGI PAVSFCFCED TDYPYLGTTM DTYKELIERI PELNKVARAA AEVAGQFVIK   600
LTHDVELNLD YERYNSQLLS FVRDLNQYRA DIKEMGLSLQ WLYSARGDFF RATSRLTTDF   660
GNAEKTDRFV MKKLNDRVMR VEYHFLSPYV SPKESPFRHV FWGSGSHTLP ALLENLKLRK   720
QNNGAFNETL FRNQLALATW TIQGAANALS GDVWDIDNEF                        760

SEQ ID NO: 122                 moltype = AA  length = 1058
FEATURE                        Location/Qualifiers
source                         1..1058
                               mol_type = protein
                               organism = Homo sapiens
SEQUENCE: 122
MDLGPLNICE EMTILHGGFL LAEQLFHPKA LAELTKSDWE RVGRPIVEAL REISSAAAHS    60
QPFAWKKKAL IIIWAKVLQP HPVTPSDTET RWQEDLFFSV GNMIPTINHT ILFELLKSLE   120
ASGLFIQLLM ALPTTICHAE LERFLEHVTV DTSAEDVAFF LDVWWEVMKH KGHPQDPLLS   180
QFSAMAHKYL PALDEFPHPP KRLRSDPDAC PTMPLLAMLL RGLTQIQSRI LGPGRKCCAL   240
ANLADMLTVF ALTEDDPQEV SATVYLDKLA TVISVWNSDT QNPYHQQALA EKVKEAERDV   300
SLTSLAKLPS ETIFVGCEFL HHLLREWGEE LQAVLRSSQG TSYDSYRLCD SLTSFSQNAT   360
LYLNRTSLSK EDRQVVSELA ECVRDFLRKT STVLKNRALE DITASIAMAV IQQKMDRHME   420
VCYIFASEKK WAFSDEWVAC LGSNRALFRQ PDLVLRLLET VIDVSTADRA IPESQIRQVI   480
HLILECYADL SLPGKNKVLA GILRSWGRKG LSEKLLAYVE GFQEDLNTTF NQLTQSASEQ   540
GLAKAVASVA RLVIVHPEVT VKKMCSLAVV NLGTHKFLAQ ILTAFPALRF VEEQGPNSSA   600
TFMVSCLKET VWMKFSTPKE EKQFLELLNC LMSPVKPQGI PVAALLEPDE VLKEFVLPFL   660
RLDVEEVDLS LRIFIQTLEA NACREEYWLQ TCSPFPLLFS LCQLLDRFSK YWQLPKEKRC   720
LSLDRKDLAI HILELLCEIV SANAETFSPD VWIKSLSWLH RKLEQLDWTV GLRLKSFFEG   780
HFKCEVPATL FEICKLSEDE WTSQAHPGYG AGTGLLAWME CCCVSSGISE RMLSLLVVDV   840
GNPEEVRLFS KGFLVALVQV MPWCSPQEWQ RLHQLTRRLL EKQLLHVPYS LEYIQFVPLL   900
NLKPFAQELQ LSVLFLRTFQ FLCSHSCRDW LPLEGWNHVV KLLCGSLTRL LDSVRAIQAA   960
```

```
GPWVQGPEQD LTQEALFVYT QVFCHALHIM AMLHPEVCEP LYVLALETLT CYETLSKTNP   1020
SVSSLLQRAH EQRFLKSIAE GIGPEERRQT LLQKMSSF                          1058

SEQ ID NO: 123          moltype = AA  length = 255
FEATURE                 Location/Qualifiers
source                  1..255
                        mol_type = protein
                        organism = Homo sapiens
SEQUENCE: 123
MTPGTQSPFF LLLLLTVLTV VTGSGHASST PGGEKETSAT QRSSVPSSTE KNAFNSSLED    60
PSTDYYQELQ RDISEMFLQI YKQGGFLGLS NIKFRPGSVV VQLTLAFREG TINVHDVETQ   120
FNQYKTEAAS RYNLTISDVS VSDVPFPFSA QSGAGVPGWG IALLVLVCVL VALAIVYLIA   180
LAVCQCRRKN YGQLDIFPAR DTYHPMSEYP TYHTHGRYVP PSSTDRSPYE KVSAGNGGSS   240
LSYTNPAVAA TSANL                                                   255

SEQ ID NO: 124          moltype = AA  length = 702
FEATURE                 Location/Qualifiers
source                  1..702
                        mol_type = protein
                        organism = Homo sapiens
SEQUENCE: 124
MESPSAPPHR WCIPWQRLLL TASLLTFWNP PTTAKLTIES TPFNVAEGKE VLLLVHNLPQ    60
HLFGYSWYKG ERVDGNRQII GYVIGTQQAT PGPAYSGREI IYPNASLLIQ NIIQNDTGFY   120
TLHVIKSDLV NEEATGQFRV YPELPKPSIS SNNSKPVEDK DAVAFTCEPE TQDATYLWWV   180
NNQSLPVSPR LQLSNGNRTL TLFNVTRNDT ASYKCETQNP VSARRSDSVI LNVLYGPDAP   240
TISPLNTSYR SGENLNLSCH AASNPPAQYS WFVNGTFQQS TQELFIPNIT VNNSGSYTCQ   300
AHNSDTGLNR TTVTTITVYA EPPKPFITSN NSNPVEDEDA VALTCEPEIQ NTTYLWWVNN   360
QSLPVSPRLQ LSNDNRTLTL LSVTRNDVGP YECGIQNELS VDHSDPVILN VLYGPDDPTI   420
SPSYTYYRPG VNLSLSCHAA SNPPAQYSWL IDGNIQQHTQ ELFISNITEK NSGLYTCQAN   480
NSASGHSRTT VKTITVSAEL PKPSISSNNS KPVEDKDAVA FTCEPEAQNT TYLWWVNGQS   540
LPVSPRLQLS NGNRTLTLFN VTRNDARAYV CGIQNSVSAN RSDPVTLDVL YGPDTPIISP   600
PDSSYLSGAN LNLSCHSASN PSPQYSWRIN GIPQQHTQVL FIAKITPNNN GTYACFVSNL   660
ATGRNNSIVK SITVSASGTS PGLSAGATVG IMIGVLVGVA LI                      702

SEQ ID NO: 125          moltype = AA  length = 661
FEATURE                 Location/Qualifiers
source                  1..661
                        mol_type = protein
                        organism = Homo sapiens
SEQUENCE: 125
MDLVLKRCLL HLAVIGALLA VGATKVPRNQ DWLGVSRQLR TKAWNRQLYP EWTEAQRLDC    60
WRGGQVSLKV SNDGPTLIGA NASFSIALNF PGSQKVLPDG QVIWVNNTII NGSQVWGGQP   120
VYPQETDDAC IFPDGGPCPS GSWSQKRSFV YVWKTWGQYW QVLGGPVSGL SIGTGRAMLG   180
THTMEVTVYH RRGSRSYVPL AHSSSAFTIT DQVPFSVSVS QLRALDGGNK HFLRNQPLTF   240
ALQLHDPSGY LAEADLSYTW DFGDSSGTLI SRALVVTHTY LEPGPVTAQV VLQAAIPLTS   300
CGSSPVPGTT DGHRPTAEAP NTTAGQVPTT EVVGTTPGQA PTAEPSGTTS VQVPTTEVIS   360
TAPVQMPTAE STGMTPEKVP VSEVMGTTLA EMSTPEATGM PTAEVSIVVL SGTTAAQVTT   420
TEWVETTARE LPIPEPEGPD ASSIMSTESI TGSLGPLLDG TATLRLVKRQ VPLDCVLYRY   480
GSFSVTLDIV QGIESAEILQ AVPSGEGDAF ELTVSCQGGL PKEACMEISS PGCQPPAQRL   540
CQPVLPSPAC QLVLHQILKG GSGTYCLNVS LADTNSLAVV STQLIMPGQE AGLGQVPLIV   600
GILLVLMAVV LASLIYRRRL MKQDFSVPQL PHSSSHWLRL PRIFCSCPIG ENSPLLSGQQ   660
V                                                                   661

SEQ ID NO: 126          moltype = AA  length = 118
FEATURE                 Location/Qualifiers
source                  1..118
                        mol_type = protein
                        organism = Homo sapiens
SEQUENCE: 126
MPREDAHFIY GYPKKGHGHS YTTAEEAAGI GILTVILGVL LLIGCWYCRR RNGYRALMDK    60
SLHVGTQCAL TRRCPQEGFD HRDSKVSLQE KNCEPVVPNA PPAYEKLSAE QSPPPYSP     118

SEQ ID NO: 127          moltype = AA  length = 8
FEATURE                 Location/Qualifiers
REGION                  1..8
                        note = Synthetic polypeptide PSA PEPTIDE FRAGMENT
SITE                    1
                        note = B - 4-HYDROXYPROLINE
SITE                    4
                        note = X - CYCLOHEXYL GLYCINE
source                  1..8
                        mol_type = protein
                        organism = synthetic construct
SEQUENCE: 127
BSSXQSSP                                                             8

SEQ ID NO: 128          moltype = AA  length = 351
FEATURE                 Location/Qualifiers
source                  1..351
```

```
                        mol_type = protein
                        organism = Homo sapiens
SEQUENCE: 128
MSFPCKFVAS FLLIFNVSSK GAVSKEITNA LETWGALGQD INLDIPSFQM SDDIDDIKWE    60
KTSDKKKIAQ FRKEKETFKE KDTYKLFKNG TLKIKHLKTD DQDIYKVSIY DTKGKNVLEK   120
IFDLKIQERV SKPKISWTCI NTTLTCEVMN GTDPELNLYQ DGKHLKLSQR VITHKWTTSL   180
SAKFKCTAGN KVSKESSVEP VSCPEKGLDI YLIIGICGGG SLLMVFVALL VFYITKRKKQ   240
RSRRNDEELE TRAHRVATEE RGRKPHQIPA STPQNPATSQ HPPPPPGHRS QAPSHRPPPP   300
GHRVQHQPQK RPPAPSGTQV HQQKGPPLPR PRVQPKPPHG AAENSLSPSS N            351

SEQ ID NO: 129          moltype = AA  length = 297
FEATURE                 Location/Qualifiers
source                  1..297
                        mol_type = protein
                        organism = Homo sapiens
SEQUENCE: 129
MTTPRNSVNG TFPAEPMKGP IAMQSGPKPL FRRMSSLVGP TQSFFMRESK TLGAVQIMNG    60
LPHIALGGLL MIPAGIYAPI CVTVWYPLWG GIMYIISGSL LAATEKNSRK CLVKGKMIMN   120
SLSLFAAISG MILSIMDILN IKISHFLKME SLNPIRAHTP YINIYNCEPA NPSEKNSPST   180
QYCYSIQSLF LGILSVMLIF AFFQELVIAG IVENEWKRTC SRPKSNIVLL SAEEKKEQTI   240
EIKEEVVGLT ETSSQPKNEE DIEIIPIQEE EEEETETNFP EPPQDQESSP IENDSSP      297

SEQ ID NO: 130          moltype = AA  length = 61
FEATURE                 Location/Qualifiers
source                  1..61
                        mol_type = protein
                        organism = Homo sapiens
SEQUENCE: 130
MKRFLFLLLT ISLLVMVQIQ TGLSGQNDTS QTSSPSASSS MSGGIFLFFV ANAIIHLFCF    60
S                                                                   61

SEQ ID NO: 131          moltype = AA  length = 8
FEATURE                 Location/Qualifiers
REGION                  1..8
                        note = Synthetic polypeptide PSA PEPTIDE FRAGMENT
SITE                    1
                        note = Z - 4-O-ACETYL-HYDROXYPROLINE
SITE                    4
                        note = X - CYCLOHEXYL GLYCINE
source                  1..8
                        mol_type = protein
                        organism = synthetic construct
SEQUENCE: 131
ZSSXQSSP                                                             8

SEQ ID NO: 132          moltype = AA  length = 8
FEATURE                 Location/Qualifiers
REGION                  1..8
                        note = Synthetic polypeptide PSA PEPTIDE FRAGMENT
source                  1..8
                        mol_type = protein
                        organism = synthetic construct
SEQUENCE: 132
RRSSYYSG                                                             8

SEQ ID NO: 133          moltype = AA  length = 164
FEATURE                 Location/Qualifiers
source                  1..164
                        mol_type = protein
                        organism = Homo sapiens
SEQUENCE: 133
EMLQGLLLLL LLSMGGTWAS KEPLRPRCRP INATLAVEKE GCPVCITVNT TICAGYCPTM    60
TRVLQGVLPA LPQVVCNYRD VRFESIRLPG CPRGVNPVVS YAVALSCQCA LCRRSTTDCG   120
GPKDHPLTCD DPRFQDSSSS KAPPPSLPSP SRLPGPSDTP ILPQ                    164

SEQ ID NO: 134          moltype = AA  length = 300
FEATURE                 Location/Qualifiers
source                  1..300
                        mol_type = protein
                        organism = Homo sapiens
SEQUENCE: 134
MANCEFSPVS GDKPCCRLSR RAQLCLGVSI LVLILVVVLA VVVPRWRQQW SGPGTTKRFP    60
ETVLARCVKY TEIHPEMRHV DCQSVWDAFK GAFISKHPCN ITEEDYQPLM KLGTQTVPCN   120
KILLWSRIKD LAHQFTQVQR DMFTLEDTLL GYLADDLTWC GEFNTSKINY QSCPDWRKDC   180
SNNPVSVFWK TVSRRFAEAA CDVVHVMLNG SRSKIFDKNS TFGSVEVHNL QPEKVQTLEA   240
WVIHGGREDS RDLCQDPTIK ELESIISKRN IQFSCKNIYR PDKFLQCVKN PEDSSCTSEI   300

SEQ ID NO: 135          moltype = AA  length = 277
FEATURE                 Location/Qualifiers
```

```
source                  1..277
                        mol_type = protein
                        organism = Homo sapiens
SEQUENCE: 135
MVRLPLQCVL WGCLLTAVHP EPPTACREKQ YLINSQCCSL CQPGQKLVSD CTEFTETECL    60
PCGESEFLDT WNRETHCHQH KYCDPNLGLR VQQKGTSETD TICTCEEGWH CTSEACESCV   120
LHRSCSPGFG VKQIATGVSD TICEPCPVGF FSNVSSAFEK CHPWTSCETK DLVVQQAGTN   180
KTDVVCGPQD RLRALVVIPI IFGILFAILL VLVFIKKVAK KPTNKAPHPK QEPQEINFPD   240
DLPGSNTAAP VQETLHGCQP VTQEDGKESR ISVQERQ                            277

SEQ ID NO: 136          moltype = AA  length = 6
FEATURE                 Location/Qualifiers
REGION                  1..6
                        note = Synthetic polypeptide PSA FRAGMRNT PEPTIDE
source                  1..6
                        mol_type = protein
                        organism = synthetic construct
SEQUENCE: 136
SSKYQL                                                               6

SEQ ID NO: 137          moltype = AA  length = 7
FEATURE                 Location/Qualifiers
REGION                  1..7
                        note = Synthetic polypeptide PSA FRAGMENT PEPTIDE
SITE                    1
                        note = B - N-GLUTARYL-4 HYDROXYPROLINE
SITE                    4
                        note = X - CYCLOHEXYL GLYCINE
source                  1..7
                        mol_type = protein
                        organism = synthetic construct
SEQUENCE: 137
BASXQSL                                                              7

SEQ ID NO: 138          moltype = AA  length = 5
FEATURE                 Location/Qualifiers
REGION                  1..5
                        note = Synthetic polypeptide CASPASE-3 PEPTIDE FRAGMENT
source                  1..5
                        mol_type = protein
                        organism = synthetic construct
SEQUENCE: 138
DEVDP                                                                5

SEQ ID NO: 139          moltype = AA  length = 8
FEATURE                 Location/Qualifiers
REGION                  1..8
                        note = Synthetic polypeptide CASPASE-3 PEPTIDE FRAGMENT
source                  1..8
                        mol_type = protein
                        organism = synthetic construct
SEQUENCE: 139
KGSGDVEG                                                             8

SEQ ID NO: 140          moltype = AA  length = 646
FEATURE                 Location/Qualifiers
source                  1..646
                        mol_type = protein
                        organism = Homo sapiens
SEQUENCE: 140
MGLPRLVCAF LLAACCCCPR VAGVPGEAEQ PAPELVEVEV GSTALLKCGL SQSQGNLSHV    60
DWFSVHKEKR TLIFRVRQGQ GQSEPGEYEQ RLSLQDRGAT LALTQVTPQD ERIFLCQGKR   120
PRSQEYRIQL RVYKAPEEPN IQVNPLGIPV NSKEPEEVAT CVGRNGYPIP QVIWYKNGRP   180
LKEEKNRVHI QSSQTVESSG LYTLQSILKA QLVKEDKDAQ FYCELNYRLP SGNHMKESRE   240
VTVPVFYPTE KVWLEVEPVG MLKEGDRVEI RCLADGNPPP HFSISKQNPS TREAEEETTN   300
DNGVLVLEPA RKEHSGRYEC QAWNLDTMIS LLSEPQELLV NYVSDVRVSP AAPERQEGSS   360
LTLTCEAESS QDLEFQWLRE ETDQVLERGP VLQLHDLKRE AGGGYRCVAS VPSIPGLNRT   420
QLVKLAIFGP PWMAFKERKV WVKENMVLNL SCEASGHPRP TISWNVNGTA SEQDQDPQRV   480
LSTLNVLVTP ELLETGVECT ASNDLGKNTS ILFLELVNLT TLTPDSNTTT GLSTSTASPH   540
TRANSTSTER KLPEPESRGV VIVAVIVCIL VLAVLGAVLY FLYKKGKLPC RRSGKQEITL   600
PPSRKTELVV EVKSDKLPEE MGLLQGSSGD KRAPGDQGEK YIDLRH                  646

SEQ ID NO: 141          moltype = AA  length = 4
FEATURE                 Location/Qualifiers
REGION                  1..4
                        note = Synthetic polypeptide CATHEPSIN B PEPTIDE FRAGMENT
source                  1..4
                        mol_type = protein
                        organism = synthetic construct
```

```
SEQUENCE: 141
GFLG                                                                         4

SEQ ID NO: 142           moltype = AA  length = 4
FEATURE                  Location/Qualifiers
REGION                   1..4
                         note = Synthetic polypeptide CATHEPSIN B PEPTIDE FRAGMENT
source                   1..4
                         mol_type = protein
                         organism = synthetic construct
SEQUENCE: 142
KKFA                                                                         4

SEQ ID NO: 143           moltype = AA  length = 1210
FEATURE                  Location/Qualifiers
source                   1..1210
                         mol_type = protein
                         organism = Homo sapiens
SEQUENCE: 143
MRPSGTAGAA LLALLAALCP ASRALEEKKV CQGTSNKLTQ LGTFEDHFLS LQRMFNNCEV   60
VLGNLEITYV QRNYDLSFLK TIQEVAGYVL IALNTVERIP LENLQIIRGN MYYENSYALA  120
VLSNYDANKT GLKELPMRNL QEILHGAVRF SNNPALCNVE SIQWRDIVSS DFLSNMSMDF  180
QNHLGSCQKC DPSCPNGSCW GAGEENCQKL TKIICAQQCS GRCRGKSPSD CCHNQCAAGC  240
TGPRESDCLV CRKFRDEATC KDTCPPLMLY NPTTYQMDVN PEGKYSFGAT CVKKCPRNYV  300
VTDHGSCVRA CGADSYEMEE DGVRKCKKCE GPCRKVCNGI GIGEFKDSLS INATNIKHFK  360
NCTSISGDLH ILPVAFRGDS FTHTPPLDPQ ELDILKTVKE ITGFLLIQAW PENRTDLHAF  420
ENLEIIRGRT KQHGQFSLAV VSLNITSLGL RSLKEISDGD VIISGNKNLC YANTINWKKL  480
FGTSGQKTKI ISNRGENSCK ATGQVCHALC SPEGCWGPEP RDCVSCRNVS RGRECVDKCK  540
LLEGEPREFV ENSECIQCHP ECLPQAMNIT CTGRGPDNCI QCAHYIDGPH CVKTCPAGVM  600
GENNTLVWKY ADAGHVCHLC HPNCTYGCTG PGLEGCPTNG PKIPSIATGM VGALLLLLVV  660
ALGIGLFMRR RHIVRKRTLR RLLQERELVE PLTPSGEAPN QALLRILKET EFKKIKVLGS  720
GAFGTVYKGL WIPEGEKVKI PVAIKELREA TSPKANKEIL DEAYVMASVD NPHVCRLLGI  780
CLTSTVQLIT QLMPFGCLLD YVREHKDNIG SQYLLNWCVQ IAKGMNYLED RRLVHRDLAA  840
RNVLVKTPQH VKITDFGLAK LLGAEEKEYH AEGGKVPIKW MALESILHRI YTHQSDVWSY  900
GVTVWELMTF GSKPYDGIPA SEISSILEKG ERLPQPPICT IDVYMIMVKC WMIDADSRPK  960
FRELIIEFSK MARDPQRYLV IQGDERMHLP SPTDSNFYRA LMDEEDMDDV VDADEYLIPQ 1020
QGFFSSPSTS RTPLLSSLSA TSNNSTVACI DRNGLQSCPI KEDSFLQRYS SDPTGALTED 1080
SIDDTFLPVP EYINQSVPKR PAGSVQNPVY HNQPLNPAPS RDPHYQDPHS TAVGNPEYLN 1140
TVQPTCVNST FDSPAHWAQK GSHQISLDNP DYQQDFFPKE AKPNGIFKGS TAENAEYLRV 1200
APQSSEFIGA                                                        1210

SEQ ID NO: 144           moltype = AA  length = 4
FEATURE                  Location/Qualifiers
REGION                   1..4
                         note = Synthetic polypeptide CATHEPSIN B PEPTIDE FRAGMENT
source                   1..4
                         mol_type = protein
                         organism = synthetic construct
SEQUENCE: 144
AFKK                                                                         4

SEQ ID NO: 145           moltype = AA  length = 4
FEATURE                  Location/Qualifiers
REGION                   1..4
                         note = Synthetic polypeptide CATHEPSIN B PEPTIDE FRAGMENT
source                   1..4
                         mol_type = protein
                         organism = synthetic construct
SEQUENCE: 145
GFLG                                                                         4

SEQ ID NO: 146           moltype = AA  length = 9
FEATURE                  Location/Qualifiers
REGION                   1..9
                         note = Synthetic polypeptide FAP PEPTIDE FRAGMENT
source                   1..9
                         mol_type = protein
                         organism = synthetic construct
SEQUENCE: 146
KQEQNPGST                                                                    9

SEQ ID NO: 147           moltype = AA  length = 11
FEATURE                  Location/Qualifiers
REGION                   1..11
                         note = Synthetic polypeptide
source                   1..11
                         mol_type = protein
                         organism = synthetic construct
SEQUENCE: 147
```

```
ACDCRGDCFC G                                                              11

SEQ ID NO: 148          moltype = AA   length = 13
FEATURE                 Location/Qualifiers
REGION                  1..13
                        note = Synthetic polypeptide
source                  1..13
                        mol_type = protein
                        organism = synthetic construct
SEQUENCE: 148
DGARYCRGDC FDG                                                            13

SEQ ID NO: 149          moltype = AA   length = 5
FEATURE                 Location/Qualifiers
REGION                  1..5
                        note = Synthetic polypeptide Cathepsin B fragment
source                  1..5
                        mol_type = protein
                        organism = synthetic construct
SEQUENCE: 149
RGDYK                                                                      5

SEQ ID NO: 150          moltype = AA   length = 5
FEATURE                 Location/Qualifiers
source                  1..5
                        mol_type = protein
                        organism = Homo sapiens
SEQUENCE: 150
RGDFK                                                                      5

SEQ ID NO: 151          moltype = AA   length = 10
FEATURE                 Location/Qualifiers
source                  1..10
                        mol_type = protein
                        organism = Homo sapiens
SEQUENCE: 151
RGDYKKYDGR                                                                10

SEQ ID NO: 152          moltype = AA   length = 14
FEATURE                 Location/Qualifiers
REGION                  1..14
                        note = Synthetic polypeptide Cathepsin B fragment
source                  1..14
                        mol_type = protein
                        organism = synthetic construct
SEQUENCE: 152
CAGKNFFWKT FTSC                                                           14

SEQ ID NO: 153          moltype = AA   length = 5
FEATURE                 Location/Qualifiers
REGION                  1..5
                        note = Synthetic polypeptide Cathepsin B fragment
SITE                    5
                        note = X - N-methyl valine
source                  1..5
                        mol_type = protein
                        organism = synthetic construct
SEQUENCE: 153
RGDFX                                                                      5

SEQ ID NO: 154          moltype = AA   length = 5
FEATURE                 Location/Qualifiers
source                  1..5
                        mol_type = protein
                        organism = Homo sapiens
SEQUENCE: 154
PHSCN                                                                      5

SEQ ID NO: 155          moltype = AA   length = 5
FEATURE                 Location/Qualifiers
SITE                    1
                        note = X - Acetylated PRO
SITE                    5
                        note = Z - Amidated ASN
source                  1..5
                        mol_type = protein
                        organism = Homo sapiens
SEQUENCE: 155
XHSCZ                                                                      5
```

```
SEQ ID NO: 156            moltype = AA  length = 25
FEATURE                   Location/Qualifiers
source                    1..25
                          mol_type = protein
                          organism = Homo sapiens
SEQUENCE: 156
TMPFLFCNVN DVCNFASRND YSYWL                                              25

SEQ ID NO: 157            moltype = AA  length = 4
FEATURE                   Location/Qualifiers
REGION                    1..4
                          note = Synthetic polypeptide Cathepsin B fragment
source                    1..4
                          mol_type = protein
                          organism = synthetic construct
SEQUENCE: 157
YSNS                                                                      4

SEQ ID NO: 158            moltype = AA  length = 5
FEATURE                   Location/Qualifiers
REGION                    1..5
                          note = Synthetic polypeptide Cathepsin B fragment
source                    1..5
                          mol_type = protein
                          organism = synthetic construct
SEQUENCE: 158
YSNSG                                                                     5

SEQ ID NO: 159            moltype = AA  length = 20
FEATURE                   Location/Qualifiers
REGION                    1..20
                          note = Synthetic polypeptide Cathepsin B fragment
source                    1..20
                          mol_type = protein
                          organism = synthetic construct
SEQUENCE: 159
FLSSRLQDLY SIVRRADRAA                                                    20

SEQ ID NO: 160            moltype = AA  length = 11
FEATURE                   Location/Qualifiers
REGION                    1..11
                          note = Synthetic polypeptide Cathepsin B fragment
source                    1..11
                          mol_type = protein
                          organism = synthetic construct
SEQUENCE: 160
IVRRADRAAV P                                                             11

SEQ ID NO: 161            moltype = AA  length = 13
FEATURE                   Location/Qualifiers
REGION                    1..13
                          note = Synthetic polypeptide Cathepsin B fragment
source                    1..13
                          mol_type = protein
                          organism = synthetic construct
SEQUENCE: 161
RQVFQVAYII IKA                                                           13

SEQ ID NO: 162            moltype = AA  length = 12
FEATURE                   Location/Qualifiers
REGION                    1..12
                          note = Synthetic polypeptide Cathepsin B fragment
source                    1..12
                          mol_type = protein
                          organism = synthetic construct
SEQUENCE: 162
KAFDITYVRL KF                                                            12

SEQ ID NO: 163            moltype = AA  length = 12
FEATURE                   Location/Qualifiers
REGION                    1..12
                          note = Synthetic polypeptide Laminin Peptide C16S
source                    1..12
                          mol_type = protein
                          organism = synthetic construct
SEQUENCE: 163
DFKLFAVTIK YR                                                            12
```

```
SEQ ID NO: 164            moltype = AA  length = 8
FEATURE                   Location/Qualifiers
REGION                    1..8
                          note = Synthetic polypeptide Cathepsin B fragment
source                    1..8
                          mol_type = protein
                          organism = synthetic construct
SEQUENCE: 164
CPQPRPLC                                                                   8

SEQ ID NO: 165            moltype = AA  length = 503
FEATURE                   Location/Qualifiers
source                    1..503
                          mol_type = protein
                          organism = Homo sapiens
SEQUENCE: 165
MLSQLAMLQG SLLLVVATMS VAQQTRQEAD RGCETLVVQH GHCSYTFLLP KSEPCPPGPE          60
VSRDSNTLQR ESLANPLHLG KLPTQQVKQL EQALQNNTQW LKKLERAIKT ILRSKLEQVQ         120
QQMAQNQTAP MLELGTSLLN QTTAQIRKLT DMEAQLLNQT SRMDAQMPET FLSTNKLENQ         180
LLLQRQKLQQ LQGQNSALEK RLQALETKQQ EELASILSKK AKLLNTLSRQ SAALTNIERG         240
LRGVRHNSSL LQDQQHSLRQ LLVLLRHLVQ ERANASAPAF IMAGEQVFQD CAEIQRSGAS         300
ASGVYTIQVS NATKPRKVFC DLQSSGGRWT LIQRRENGTV NFQRNWKDYK QGFGDPAGEH         360
WLGNEVVHQL TRRAAYSLRV ELQDWEGHEA YAQYEHFHLG SENQLYRLSV VGYSGSAGRQ         420
SSLVLQNTSF STLDSDNDHC LCKCAQVMSG GWWFDACGLS NLNGVYYHAP DNKYKMDGIR         480
WHYFKGPSYS LRASRMMIRP LDI                                                503

SEQ ID NO: 166            moltype = AA  length = 369
FEATURE                   Location/Qualifiers
source                    1..369
                          mol_type = protein
                          organism = Homo sapiens
SEQUENCE: 166
MLKPSLPFTS LLFLQLPLLG VGLNTTILTP NGNEDTTADF FLTTMPTDSL SVSTLPLPEV          60
QCFVFNVEYM NCTWNSSSEP QPTNLTLHYW YKNSDNDKVQ KCSHYLFSEE ITSGCQLKK         120
EIHLYQTFVV QLQDPREPRR QATQMLKLQN LVIPWAPENL TLHKLSESQL ELNWNNRFLN         180
HCLEHLVQYR TDWDHSWTEQ SVDYRHKFSL PSVDGQKRYT FRVRSRFNPL CGSAQHWSEW         240
SHPIHWGSNT SKENPFLFAL EAVVISVGSM GLIISLLCVY FWLERTMPRI PTLKNLEDLV         300
TEYHGNFSAW SGVSKGLAES LQPDYSERLC LVSEIPPKGG ALGEGPGASP CNQHSPYWAP         360
PCYTLKPET                                                                369

SEQ ID NO: 167            moltype = AA  length = 196
FEATURE                   Location/Qualifiers
source                    1..196
                          mol_type = protein
                          organism = Homo sapiens
SEQUENCE: 167
MRTLACLLLL GCGYLAHVLA EEAEIPREVI ERLARSQIHS IRDLQRLLEI DSVGSEDSLD          60
TSLRAHGVHA TKHVPEKRPL PIRRKRSIEE AVPAVCKTRT VIYEIPRSQV DPTSANFLIW         120
PPCVEVKRCT GCCNTSSVKC QPSRVHHRSV KVAKVEYVRK KPKLKEVQVR LEEHLECACA         180
TTSLNPDYRE EDTDVR                                                        196

SEQ ID NO: 168            moltype = AA  length = 226
FEATURE                   Location/Qualifiers
source                    1..226
                          mol_type = protein
                          organism = Homo sapiens
SEQUENCE: 168
MFIMGLGDPI PEELYEMLSD HSIRSFDDLQ RLLHGDPGEE DGAELDLNMT RSHSGGELES          60
LARGRRSLGS LTIAEPAMIA ECKTRTEVFE ISRRLIDRTN ANFLVWPPCV EVQRCSGCCN         120
NRNVQCRPTQ VQLRPVQVRK IEIVRKKPIF KKATVTLEDH LACKCETVAA ARPVTRSPGG         180
SQEQRAKTPQ TRVTIRTVRV RRPPKGKHRK FKHTHDKTAL KETLGA                        226

SEQ ID NO: 169            moltype = AA  length = 322
FEATURE                   Location/Qualifiers
source                    1..322
                          mol_type = protein
                          organism = Homo sapiens
SEQUENCE: 169
MRTSKCFLKT ASSQRNGVQD PQHERIITVS TNGSIHSPRF PHTYPRNTVL VWRLVAVEEN          60
VWIQLTFDER FGLEDPEDDI CKYDFVEVEE PSDGTILGRW CGSGTVPGKQ ISKGNQIRIR         120
FVSDEYFPSE PGFCIHYNIV MPQFTEAVSP SVLPPSALPL DLLNNAITAF STLEDLIRYL         180
EPERWQLDLE DLYRPTWQLL GKAFVFGRKS RVVDLNLLTE EVRLYSCTPR NFSVSIREEL         240
KRTDTIFWPG CLLVKRCGGN CACCLHNCNE CQCVPSKVTK KYHEVLQLRP KTGVRGLHKS         300
LTDVALEHHE ECDCVCRGST GG                                                 322

SEQ ID NO: 170            moltype = AA  length = 364
FEATURE                   Location/Qualifiers
source                    1..364
                          mol_type = protein
```

-continued

```
                        organism = Homo sapiens
SEQUENCE: 170
MHRLIFVYTL ICANFCSCRD TSATPQSASI KALRNANLRR DDLYRRDETI QVKGNGYVQS    60
PRFPNSYPRN LLLTWRLHSQ ENTRIQLVFD NQFGLEEAEN DICRYDFVEV EDISETSTII   120
RGRWCGHKEV PPRIKSRTNQ IKITPKSDDY FVAKPGFKIY YSLLEDFQPA AASETNWESV   180
TSSISGVSYN SPSVTDPTLI ADALDKKIAE FDTVEDLLKY FNPESWQEDL ENMYLDTPRY   240
RGRSYHDRKS KVDLDRLNDD AKRYSCTPRN YSVNIREELK LANVVFFPRC LLVQRCGGNC   300
GCGTVNWRSC TCNSGKTVKK YHEVLQFEPG HIKRRGRAKT MALVDIQLDH HERCDCICSS   360
RPPR                                                                364

SEQ ID NO: 171          moltype = AA  length = 6
FEATURE                 Location/Qualifiers
REGION                  1..6
                        note = Synthetic polypeptide KALLIKREIN 2 PEPTIDE FRAGMENT
source                  1..6
                        mol_type = protein
                        organism = synthetic construct
SEQUENCE: 171
GKAFRR                                                                6

SEQ ID NO: 172          moltype = AA  length = 7
FEATURE                 Location/Qualifiers
REGION                  1..7
                        note = Synthetic polypeptide MMP-2/-9/ PEPTIDE FRAGMENT
SITE                    3
                        note = Z - CITRULLINE
SITE                    5
                        note = X - HOMOPHENYLALANINE
source                  1..7
                        mol_type = protein
                        organism = synthetic construct
SEQUENCE: 172
EPZGXYL                                                               7

SEQ ID NO: 173          moltype = AA  length = 6
FEATURE                 Location/Qualifiers
REGION                  1..6
                        note = Synthetic polypeptide MMP-2/-9/ PEPTIDE FRAGMENT
source                  1..6
                        mol_type = protein
                        organism = synthetic construct
SEQUENCE: 173
GILGVP                                                                6

SEQ ID NO: 174          moltype = AA  length = 8
FEATURE                 Location/Qualifiers
REGION                  1..8
                        note = Synthetic polypeptide MMP-2/-9/ PEPTIDE FRAGMENT
source                  1..8
                        mol_type = protein
                        organism = synthetic construct
SEQUENCE: 174
GPLGIAGQ                                                              8

SEQ ID NO: 175          moltype = AA  length = 8
FEATURE                 Location/Qualifiers
REGION                  1..8
                        note = Synthetic polypeptide MMP-7 PEPTIDE FRAGMENT
source                  1..8
                        mol_type = protein
                        organism = synthetic construct
SEQUENCE: 175
KRALGLPG                                                              8

SEQ ID NO: 176          moltype = AA  length = 8
FEATURE                 Location/Qualifiers
REGION                  1..8
                        note = Synthetic polypeptide MMP-7 PEPTIDE FRAGMENT
source                  1..8
                        mol_type = protein
                        organism = synthetic construct
SEQUENCE: 176
RPLALWRS                                                              8
```

```
SEQ ID NO: 177        moltype =    length =
SEQUENCE: 177
000

SEQ ID NO: 178        moltype =    length =
SEQUENCE: 178
000

SEQ ID NO: 179        moltype = AA  length = 4
FEATURE               Location/Qualifiers
REGION                1..4
                      note = Synthetic polypeptide PLASMIN PEPTIDE FRAGMENT
source                1..4
                      mol_type = protein
                      organism = synthetic construct
SEQUENCE: 179
AFKK                                                                    4

SEQ ID NO: 180        moltype = AA  length = 11
FEATURE               Location/Qualifiers
REGION                1..11
                      note = Synthetic polypeptide THROMBIN PEPTIDE FRAGMENT
SITE                  1
                      note = X - POLY-L-LYSINE
SITE                  4
                      note = Z - PIPERIDINE
source                1..11
                      mol_type = protein
                      organism = synthetic construct
SEQUENCE: 180
XGFZRSGGGG G                                                           11

SEQ ID NO: 181        moltype = AA  length = 8
FEATURE               Location/Qualifiers
REGION                1..8
                      note = Synthetic polypeptide TRYPSIN PEPTIDE FRAGMENT
SITE                  1
                      note = X - POLY-L-LYSINE
source                1..8
                      mol_type = protein
                      organism = synthetic construct
SEQUENCE: 181
XGASRFTG                                                                8
```

What is claimed is:

1. A compound of the formula I

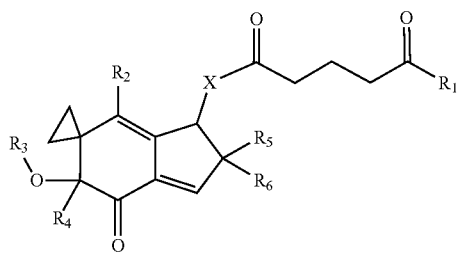

(I)

or a pharmaceutically acceptable salt thereof, where X is selected from a first group consisting of —S— and —O—; $R_1$ represents an antibody affinity moiety; $R_3$ is —H; $R_2$, $R_4$ and $R_5$ are —CH$_3$; and $R_6$ is selected from a second group consisting of —CH$_3$, —CH$_2$—OH, —CH$_2$—O(—(C=O)—CH$_3$, —O—(C=O)—CH$_2$—CH$_2$—CH$_2$—(C=O)—OH, —O(C=O)—C$_6$H$_3$(NO$_2$)$_2$, and —CH$_2$—(C=O)—(CH$_3$)$_2$.

2. A composition comprising an R-enantiomer of the compound of claim 1.

3. A composition comprising an S-enantiomer of the compound of claim 1.

4. A composition comprising enantiomers and racemic mixtures of the compound of claim 1.

5. A composition comprising the compound of claim 1, and a physiologically compatible carrier.

6. A composition comprising the compound of claim 1, in the form of a liposomal particle, a nanoparticle, or a PEGylated compound.

7. The compound of claim 1, where the antibody affinity moiety is directed against an antigen selected from a group consisting of Alk (SEQ ID: 103), CA125 (SEQ ID: 104), CA15-3 (SEQ ID: 105), CA19-9, L6 (SEQ ID: 107), Lewis Y (SEQ ID: 108), Lewis X (SEQ ID: 109), alpha fetoprotein (SEQ ID: 110), CA 242, placental alkaline phosphatase (SEQ ID: 112), prostate specific antigen (SEQ ID: 113), prostate specific membrane antigen (SEQ ID: 114), prostatic acid phosphatase (SEQ ID: 115), epidermal growth factor, MAGE-1 (SEQ ID: 117), MAGE-2 (SEQ ID: 118), MAGE-3 (SEQ ID: 119), MAGE-4 (SEQ ID: 120), anti-transferrin receptor (SEQ ID: 121), p97 (SEQ ID: 121), MUC1 (SEQ ID: 123), CEA (SEQ ID: 124), gp100 (SEQ ID: 125), MART-1 (SEQ ID: 126), IL-2 receptor, CD2 (SEQ ID: 128), CD20 (SEQ ID: 129), CD52 (SEQ ID: 130), CD33, CD22, beta human chorionic gonadotropin (SEQ ID: 133), CD38 (SEQ ID: 134), CD40 (SEQ ID: 135), CD80, CD86, mucin, P21, and MPG (SEQ ID: 140).

8. A compound of the formula II

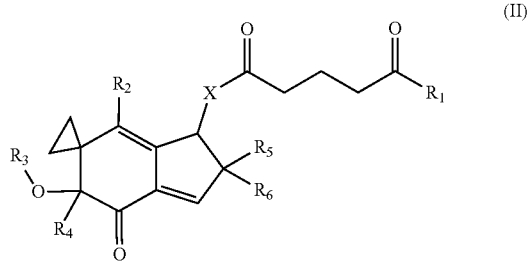

(II)

or a pharmaceutically acceptable salt thereof, where X is selected from a first group consisting of —S— and —O—; $R_1$ represents a peptide growth factor affinity moiety;
$R_3$ is —H;
$R_2$, $R_4$ and $R_5$ are —$CH_3$; and
$R_6$ is selected from a second group consisting of —$CH_3$, —$CH_2$—OH, —$CH_2$—O(—(C=O)—$CH_3$, —O—(C=O)—$CH_2$—$CH_2$—$CH_2$—(C=O)—OH, —O(C=O)—$C_6H_3(NO_2)_2$, and —$CH_2$—(C=O)—$(CH_3)_2$.

9. A composition comprising an R-enantiomer of the compound of claim 8.

10. A composition comprising an S-enantiomer of the compound of claim 8.

11. A composition comprising enantiomers and racemic mixtures of the compound of claim 8.

12. A composition comprising the compound of claim 8, and a physiologically compatible carrier.

13. A composition comprising the compound of claim 8, in the form of a liposomal particle, a nanoparticle, or a PEGylated compound.

14. A compound of the formula III

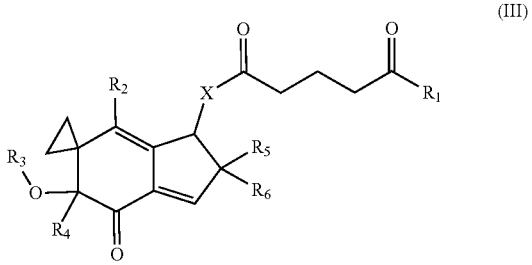

(III)

or a pharmaceutically acceptable salt thereof, where X is selected from a first group consisting of —S— and —O—; $R_1$ represents a steroid;
$R_3$ is —H;
$R_2$, $R_4$ and $R_5$ are —$CH_3$; and
$R_6$ is selected from a second group consisting of —$CH_3$, —$CH_2$—OH, —$CH_2$—O(—(C=O)—$CH_3$, —O—(C=O)—$CH_2$—$CH_2$—$CH_2$—(C=O)—OH, —O(C=O)—$C_6H_3(NO_2)_2$, and —$CH_2$—(C=O)—$(CH_3)_2$.

15. A composition comprising either an R-enantiomer or an S-enantiomer of the compound of claim 14.

16. A composition comprising enantiomers and racemic mixtures of the compound of claim 14.

17. A composition comprising the compound of claim 14, and a physiologically compatible carrier.

18. A composition comprising the compound of claim 14, in the form of a liposomal particle, a nanoparticle, or a PEGylated compound.

19. The compound of claim 8, where the peptide growth factor affinity moiety is selected from a group consisting of adrenomedullin (SEQ ID: 68), angiopoietin (SEQ ID: 69, 106, 111, and 145), autocrine motility factor (SEQ ID: 70), bone morphogenetic proteins (SEQ ID: 71), brain-derived neurotrophic factor (SEQ ID: 72), endostatin (SEQ ID: 73), endostar (SEQ ID: 74), epidermal growth factor (SEQ ID: 75), erythropoietin (SEQ ID: 76), fibroblast growth factor (FGF) (SEQ ID: 77), glial cell line-derived neurotrophic factor (SEQ ID: 78), granulocyte colony-stimulating factor (SEQ ID: 79), granulocyte macrophage colony-stimulating factor (SEQ ID: 80), growth differentiation factor-9 (SEQ ID: 81), hepatocyte growth factor (SEQ ID: 82), hepatoma-derived growth factor (SEQ ID: 83), insulin-like growth factor (SEQ ID: 84), migration-stimulating factor (SEQ ID: 85), myostatin (SEQ ID: 86), nerve growth factor (SEQ ID: 87), neurotrophins (SEQ ID: 144), platelet-derived growth factor (SEQ ID: 88), platelet-derived growth factor B (SEQ ID: 168), platelet-derived growth factor C, platelet-derived growth factor D (SEQ ID: 37), thrombopoietin (SEQ ID: 89), transforming growth factor alpha (SEQ ID: 90), transforming growth factor beta (SEQ ID: 91), tumor necrosis factor-alpha (SEQ ID: 92), vascular endothelial growth factor (SEQ ID: 93), and placental growth factor (SEQ ID: 94).

20. The compound of claim 14, where the steroid is selected from a group consisting of cholesterol (5-cholesten-3beta-ol), pregnenolone (3beta-hydroxy-5-pregnen-20-one), 17-hydroxyprenenolone (3-beta, 17-dihydroxy-5-pregnen-20-one), progesterone (4-pregnene-3,20-dione), 17-hydroxyprogesterone (17-hydroxy-4-pregnene-3,20-dione), androstenedione (4-androstene-3,17-dione), 4-hydroxyandrostenedione (4-hydroxy-4-androstene-3,17-dione), 11-beta-hydroxyandostenedione (11beta-4-androstene-3,17-dione), androstanediol (3-beta, 17-beta-Androstanediol), estrogen, estrone (3-hydroxy-1,3,5 (10)-estratrien-17-one), estradiol (1,3,5 (10)-estratriene-3,17beta-diol), estriol (1,3,5 (10)-estratriene-3,16alpha, 17beta-triol)), corticosterone (11-beta,21-dihydroxy-4-pregnene-3,20-dione), deoxycorticosterone (21-hydroxy-4-pregnene-3,20-dione), cortisol (11-beta, 17,21-trihydroxy-4-pregnene-3,20-dione), 11-deoxycortisol (17,21-dihydroxy-4-pregnene-3,20-dione), cortisone (17,21-dihydroxy-4-pregnene-3,11,20-trione), 18-hydroxycorticosterone (11-beta, 18,21-trihydroxy-4-pregnene-3,20-dione), 1-alpha-hydroxycorticosterone (1-alpha, 11-beta,21-trihydroxy-4-pregnene-3,20-dione), aldosterone (18,11-hemiacetal of 11beta,21-dihydroxy-3,20-dioxo-4-pregnen-18-al), testosterone (17beta-hydroxy-4-androsten-3-one), epitestosterone (17-alpha-hydroxy-4-androsten-3-one), 5-alpha-dihydrotesterone (17-beta-hydroxy-5alpha-androstan-3-one), 5-beta-dihydrotestosterone (17-beta-hydroxy-5beta-androstan-3-one), 11-beta-hydroxytesosterone (11-beta, 17beta-dihydroxy-4-androsten-3-one), 11-ketotesosterone (17-beta-hydroxy-4-androsten-3,17-dione), and androsterone, androsterone (3-alpha-hydroxy-5alpha-androstan-17-one), epiandrosterone (3-beta-hydroxy-5alpha-androstan-17-one), adrenosterone (4-androstene-3,11,17-trione), dehydroepiandrosterone (3beta-hydroxy-5-androsten-17-one), and dehydroepiandrosterone sulfate (3-beta-sulfooxy-5-androsten-17-one).

* * * * *